US012516099B2

(12) United States Patent
Westoby et al.

(10) Patent No.: US 12,516,099 B2
(45) Date of Patent: Jan. 6, 2026

(54) PROCESSES FOR GENERATING ENGINEERED CELLS AND COMPOSITIONS THEREOF

(71) Applicant: Juno Therapeutics, Inc., Seattle, WA (US)

(72) Inventors: Matthew Westoby, Seattle, WA (US); Adrian Wrangham Briggs, Seattle, WA (US); David G. Kugler, Seattle, WA (US); Lothar Germeroth, Munich (DE); Christian Stemberger, Munich (DE); Mateusz Pawel Poltorak, Munich (DE); Divya Varun, Seattle, WA (US); Keenan Bashour, Seattle, WA (US); Robert Guy Caspary, Seattle, WA (US); Calvin Chan, Seattle, WA (US)

(73) Assignee: Juno Therapeutics, Inc., Seattle, WA (US)

( * ) Notice: Subject to any disclaimer, the term of this patent is extended or adjusted under 35 U.S.C. 154(b) by 1223 days.

(21) Appl. No.: 17/267,000

(22) PCT Filed: Aug. 9, 2019

(86) PCT No.: PCT/US2019/046062

§ 371 (c)(1),
(2) Date: Feb. 8, 2021

(87) PCT Pub. No.: WO2020/033927

PCT Pub. Date: Feb. 13, 2020

(65) Prior Publication Data

US 2021/0163893 A1 Jun. 3, 2021

Related U.S. Application Data

(60) Provisional application No. 62/861,308, filed on Jun. 13, 2019, provisional application No. 62/842,402,
(Continued)

(51) Int. Cl.
*C07K 14/725* (2006.01)
*A61K 40/11* (2025.01)
(Continued)

(52) U.S. Cl.
CPC .......... *C07K 14/7051* (2013.01); *A61K 40/11* (2025.01); *A61K 40/31* (2025.01); *A61K 40/4211* (2025.01); *A61K 40/4215* (2025.01); *A61P 35/00* (2018.01); *C07K 14/70521* (2013.01); *C12N 5/0636* (2013.01); *A61K 2239/48* (2023.05); *A61K 2300/00* (2013.01); *C07K 2317/622* (2013.01);
(Continued)

(58) Field of Classification Search
CPC .......... C07K 14/7051; C07K 14/70521; C07K 14/70578; C07K 16/2878; C07K 2317/622; C07K 16/2818; C07K 16/2809; C07K 2319/02; A61K 40/11; A61K 40/31; A61K 40/4211; A61K 40/4215; A61K 2239/31; A61K 2239/38; A61K 2239/48; A61K 48/00; A61K 35/17; A61K 2121/00; A61K 2300/00; A61P 35/00; C12N 5/0636; C12N 2501/2302; C12N 2501/2307; C12N 2501/2315; C12N 2510/00; C12N 2531/00; C12N 2501/998
See application file for complete search history.

(56) References Cited

U.S. PATENT DOCUMENTS

| | | | |
|---|---|---|---|
| 4,235,871 | A | 11/1980 | Papahadjopoulos et al. |
| 4,361,549 | A | 11/1982 | Kung et al. |

(Continued)

FOREIGN PATENT DOCUMENTS

| | | | |
|---|---|---|---|
| CN | 101 226 118 | A | 7/2008 |
| CN | 101 446 576 | | 6/2009 |

(Continued)

OTHER PUBLICATIONS

US 8,252,592 B2, 08/2012, Sadelain (withdrawn)
Anastasov et al. (2016). Optimized Lentiviral Transduction Protocols by Use of a Poloxamer Enhancer, Spinoculation, and scFv-Antibody Fusions to VSV-G. In: Federico, M. (eds) Lentiviral Vectors and Exosomes as Gene and Protein Delivery Tools. Methods in Molecular Biology, vol. 1448. Humana Press, NY (Year: 2016).*

(Continued)

*Primary Examiner* — Janet L Andres
*Assistant Examiner* — Carol Ann Chase
(74) *Attorney, Agent, or Firm* — Morrison & Foerster LLP

(57) ABSTRACT

The present disclosure provides processes for genetically engineering T cells, such as primary CD4+ T cells and/or CD8+ T cells, for use in cell therapy that does not involve expanding the cells. In particular aspects, the provided processes successfully generate compositions of engineered T cells, such as containing populations of engineered T cells, that express a chimeric antigen receptor (CAR) within a shortened amount of time as compared to alternative engineering processes, such as processes that involve expanding the cells. In certain aspects, the provided processes successfully generate a composition of engineered T cells suitable for use in cell therapy within 4 days from when the process to stimulate or activate the cells is initiated. In some aspects, the resulting engineered cell compositions are composed of cell population that are less differentiated, less exhausted, and more potent than engineered T cell compositions generated by other means, such as by processes that involve expanding the cells. Also provided are compositions of T cells generated by the provided methods and their uses for treating subjects.

34 Claims, 77 Drawing Sheets

Specification includes a Sequence Listing.

Related U.S. Application Data filed on May 2, 2019, provisional application No. 62/798,433, filed on Jan. 29, 2019, provisional application No. 62/742,249, filed on Oct. 5, 2018, provisional application No. 62/716,981, filed on Aug. 9, 2018.

(51) Int. Cl.

| | |
|---|---|
| ***A61K 40/31*** | (2025.01) |
| ***A61K 40/42*** | (2025.01) |
| ***A61P 35/00*** | (2006.01) |
| ***C07K 14/705*** | (2006.01) |
| ***C12N 5/0783*** | (2010.01) |

(52) U.S. Cl.

CPC ................ *C12N 2501/2302* (2013.01); *C12N 2501/2307* (2013.01); *C12N 2501/2315* (2013.01); *C12N 2510/00* (2013.01)

(56) References Cited

U.S. PATENT DOCUMENTS 4,452,773 A 6/1984 Molday
4,690,915 A 9/1987 Rosenberg
4,795,698 A 1/1989 Owen
4,835,263 A 5/1989 Nguyen et al.
4,851,341 A 7/1989 Hopp
5,087,616 A 2/1992 Myers
5,168,049 A 12/1992 Meade et al.
5,200,084 A 4/1993 Liberti
5,219,740 A 6/1993 Miller
5,506,121 A 4/1996 Skerra et al.
5,773,224 A 6/1998 Grandics et al.
5,801,115 A 9/1998 Albers et al.
5,840,306 A 11/1998 Hofmann et al.
5,985,658 A 11/1999 Colinas
6,022,951 A 2/2000 Sano et al.
6,040,177 A 3/2000 Riddell et al.
6,060,273 A 5/2000 Dirks et al.
6,103,493 A 8/2000 Skerra et al.
6,123,655 A 9/2000 Fell
6,156,493 A 12/2000 Stayton
6,165,750 A 12/2000 Stayton et al.
6,207,453 B1 3/2001 Maass
6,352,694 B1 3/2002 June et al.
6,368,813 B1 4/2002 Reznik et al.
6,410,319 B1 6/2002 Raubitschek
6,451,995 B1 9/2002 Cheung
6,531,127 B2 3/2003 Mujller et al.
6,534,055 B1 3/2003 June et al.
6,733,433 B1 5/2004 Fell
7,033,834 B2 4/2006 Valerio et al.
7,070,995 B2 7/2006 Jensen
7,265,209 B2 9/2007 Jensen
7,354,762 B2 4/2008 Jensen
7,446,179 B2 11/2008 Jensen
7,446,190 B2 11/2008 Sadelain
7,446,191 B2 11/2008 Jensen
7,482,000 B2 1/2009 DeVaux et al.
7,494,656 B2 2/2009 Bachmann
7,704,708 B2 4/2010 Wu et al.
7,776,562 B2 8/2010 Busch et al.
7,837,871 B2 11/2010 Gjerde et al.
7,981,632 B2 7/2011 Schmidt
8,298,782 B2 10/2012 Busch et al.
8,324,353 B2 12/2012 Jensen
8,339,645 B2 12/2012 Nakawaki
8,361,473 B2 1/2013 Makler et al.
8,389,282 B2 3/2013 Sadelain et al.
8,449,874 B2 5/2013 Bachmann
8,479,118 B2 7/2013 Lyndersay et al.
8,735,330 B2 5/2014 Geir
8,735,540 B2 5/2014 Schmidt et al.
8,772,008 B2 7/2014 Doyon
8,802,374 B2 8/2014 Jensen
8,911,993 B2 12/2014 June et al.
9,023,604 B2 5/2015 Schmidt et al.
9,233,125 B2 1/2016 Davila et al.
9,599,590 B2 3/2017 Sabin et al.
10,131,882 B2 11/2018 Matthew et al.
10,228,312 B2 3/2019 Stadler
10,273,300 B2 * 4/2019 Bedoya .............. C07K 16/2803
10,428,351 B2 * 10/2019 Crisman ................ A61K 35/17
10,752,668 B2 8/2020 Agaugue et al.
11,028,143 B2 * 6/2021 Zhao ...................... C07K 14/54
11,248,238 B2 2/2022 Bashour et al.
11,274,278 B2 3/2022 Germeroth et al.
11,400,115 B2 8/2022 Ramsbourg et al.
11,466,253 B2 10/2022 Germeroth et al.
11,851,678 B2 * 12/2023 Mujacic ........... A61K 39/39558
11,866,465 B2 1/2024 Schmidt et al.
11,913,024 B2 2/2024 Germeroth et al.
12,066,365 B2 8/2024 Stadler
12,129,477 B2 10/2024 Bashour et al.
12,135,265 B2 11/2024 Stadler
12,208,137 B2 1/2025 Ramsborg et al.
12,258,580 B2 3/2025 Lee et al.
12,296,010 B2 5/2025 Ramsborg et al.
2002/0131960 A1 9/2002 Sadelain
2002/0150914 A1 10/2002 Anderse et al.
2003/0170238 A1 9/2003 Gruenberg et al.
2003/0175850 A1 9/2003 Ross et al.
2003/0223994 A1 12/2003 Hoogenboom et al.
2004/0082012 A1 4/2004 Busch et al.
2004/0191260 A1 9/2004 Reiter et al.
2006/0019319 A1 1/2006 Billadeau et al.
2006/0034850 A1 2/2006 Weidanz et al.
2006/0058226 A1 3/2006 Ishikawa et al.
2006/0106199 A1 5/2006 Erdmann et al.
2007/0092530 A1 4/2007 Weidanz et al.
2007/0099248 A1 5/2007 Ting et al.
2007/0116690 A1 5/2007 Yang et al.
2007/0238169 A1 10/2007 Abilez et al.
2007/0241061 A1 10/2007 Engstrom et al.
2008/0085532 A1 4/2008 Gorlach et al.
2008/0171951 A1 7/2008 Fell
2008/0255004 A1 10/2008 Neurauter et al.
2009/0226474 A1 9/2009 Weidanz et al.
2009/0233360 A1 9/2009 Baghbaderani et al.
2009/0304679 A1 12/2009 Weidanz
2010/0068738 A1 3/2010 Kawamura et al.
2010/0267057 A1 10/2010 Rakestraw et al.
2011/0003380 A1 1/2011 Miltenyi
2011/0070581 A1 3/2011 Gupta
2011/0236411 A1 9/2011 Scholler et al.
2011/0293667 A1 12/2011 Baksh et al.
2012/0214187 A1 8/2012 Lees et al.
2012/0308580 A1 12/2012 Bertoletti et al.
2012/0321665 A1 12/2012 Bollyky et al.
2013/0029418 A1 1/2013 Angel et al.
2013/0115588 A1 5/2013 Davis et al.
2013/0149337 A1 6/2013 Cooper et al.
2013/0196375 A1 8/2013 Strobbe
2013/0287748 A1 10/2013 June
2014/0255993 A1 9/2014 Follstad et al.
2014/0286987 A1 9/2014 Spencer et al.
2014/0294841 A1 10/2014 Scheinberg et al.
2014/0295458 A1 10/2014 Schmidt
2015/0266973 A1 9/2015 Jarjour et al.
2015/0283178 A1 10/2015 June et al.
2015/0301046 A1 10/2015 Schmidt
2016/0046700 A1 2/2016 Foster et al.
2016/0272688 A1 9/2016 Schmidt
2016/0362472 A1 12/2016 Bitter et al.
2017/0037369 A1 2/2017 Ramsborg et al.
2017/0051035 A1 2/2017 Payne et al.
2017/0051252 A1 2/2017 Morgan et al.
2017/0052176 A1 2/2017 Carl et al.
2017/0209492 A1 7/2017 June et al.
2017/0240882 A1 8/2017 Abrams et al.
2017/0240920 A1 8/2017 Pule et al.
2017/0254774 A1 9/2017 Sabin et al.
2018/0064627 A1 3/2018 Lange et al.
2018/0296602 A1 10/2018 Riddell et al.

(56) References Cited

U.S. PATENT DOCUMENTS

| | | | |
|---|---|---|---|
| 2019/0112576 A1 | 4/2019 | Germeroth et al. | |
| 2019/0136186 A1 | 5/2019 | Germeroth et al. | |
| 2019/0226951 A1 | 7/2019 | Stadler | |
| 2019/0234844 A1 | 8/2019 | Stadler | |
| 2020/0017880 A1 | 1/2020 | Bashour et al. | |
| 2020/0239910 A1* | 7/2020 | Bonyhadi | A61K 39/464417 |
| 2020/0354677 A1 | 11/2020 | Lee et al. | |
| 2020/0384025 A1 | 12/2020 | Mujacic et al. | |
| 2021/0017249 A1* | 1/2021 | Sather | A61K 2239/38 |
| 2021/0032297 A1 | 2/2021 | Schmidt et al. | |
| 2021/0163893 A1 | 6/2021 | Westoby et al. | |
| 2021/0207080 A1 | 7/2021 | Beauchesne et al. | |
| 2021/0230671 A1 | 7/2021 | Briggs | |
| 2022/0002669 A1 | 1/2022 | Germeroth et al. | |
| 2022/0195388 A1 | 6/2022 | Germeroth et al. | |
| 2022/0243223 A1 | 8/2022 | Bashour et al. | |
| 2023/0087953 A1 | 3/2023 | Westoby et al. | |
| 2023/0090117 A1* | 3/2023 | Haig | C12N 5/0636 435/372.3 |
| 2023/0090176 A1 | 3/2023 | Ramsborg et al. | |
| 2023/0190798 A1 | 6/2023 | Westoby et al. | |
| 2023/0190814 A1 | 6/2023 | Ramsborg et al. | |
| 2023/0295567 A1 | 9/2023 | Germeroth et al. | |
| 2024/0076617 A1* | 3/2024 | Mujacic | A61K 2239/48 |
| 2024/0101613 A1 | 3/2024 | Schmidt et al. | |
| 2024/0191188 A1 | 6/2024 | Germeroth et al. | |
| 2025/0019723 A1 | 1/2025 | Bashour et al. | |
| 2025/0020556 A1 | 1/2025 | Stadler | |
| 2025/0152712 A1 | 5/2025 | Ramsborg et al. | |
| 2025/0161449 A1 | 5/2025 | Ramsborg et al. | |
| 2025/0161450 A1 | 5/2025 | Ramsborg et al. | |
| 2025/0171739 A1 | 5/2025 | Lee et al. | |

FOREIGN PATENT DOCUMENTS

| | | |
|---|---|---|
| CN | 103 305 464 | 9/2013 |
| CN | 103 502 438 | 1/2014 |
| CN | 104450614 | 3/2015 |
| CN | 106635955 | 5/2017 |
| CN | 106754670 | 5/2017 |
| CN | 106801032 | 6/2017 |
| CN | 106834218 | 6/2017 |
| DE | 19641876 | 4/1998 |
| EP | 0452342 | 10/1991 |
| EP | 0700430 | 3/1996 |
| EP | 2468860 | 6/2012 |
| EP | 2537416 | 12/2012 |
| EP | 3372670 | 9/2018 |
| EP | 4219687 | 8/2024 |
| JP | 2006-516197 | 6/2006 |
| JP | 2016-063803 | 4/2016 |
| RU | 2249039 | 3/2005 |
| RU | 2469044 | 12/2012 |
| WO | WO 1986/002077 | 1/1985 |
| WO | WO 1992/008796 | 5/1992 |
| WO | WO 1994/028143 | 12/1994 |
| WO | WO 1996/013593 | 5/1996 |
| WO | WO 1996/018105 | 6/1996 |
| WO | WO 1996/020014 | 7/1996 |
| WO | WO 1996/24606 | 8/1996 |
| WO | WO 1998/040396 | 9/1998 |
| WO | WO 1999/018129 | 4/1999 |
| WO | WO 1999/060120 | 11/1999 |
| WO | WO 2000/014257 | 3/2000 |
| WO | WO 2000/038762 | 7/2000 |
| WO | WO 2000/043551 | 7/2000 |
| WO | WO 2002/054065 | 7/2002 |
| WO | WO 2002/077018 | 10/2002 |
| WO | WO 2002/077029 | 10/2002 |
| WO | WO 2003/020763 | 3/2003 |
| WO | WO 2003/068201 | 8/2003 |
| WO | WO 2003/090781 | 11/2003 |
| WO | WO 2004/029221 | 4/2004 |
| WO | WO 2004/033685 | 4/2004 |
| WO | WO 2004/096975 | 11/2004 |
| WO | WO 2004/104185 | 12/2004 |
| WO | WO 2005/050209 | 6/2005 |
| WO | WO 2006/000830 | 1/2006 |
| WO | WO 2006/037960 | 4/2006 |
| WO | WO 2006/044650 | 4/2006 |
| WO | WO 2006/058226 | 6/2006 |
| WO | WO 2007/112012 | 10/2007 |
| WO | WO 2007/117602 | 10/2007 |
| WO | WO 2008/011486 | 1/2008 |
| WO | WO 2008/035631 | 3/2008 |
| WO | WO 2008/100122 | 8/2008 |
| WO | WO 2008/140573 | 11/2008 |
| WO | WO 2009/003493 | 1/2009 |
| WO | WO 2009/072003 | 6/2009 |
| WO | WO 2009/072006 | 6/2009 |
| WO | WO 2009/091826 | 7/2009 |
| WO | WO 2009/092068 | 7/2009 |
| WO | WO 2009/095447 | 8/2009 |
| WO | WO 2010/080032 | 7/2010 |
| WO | WO 2010/104949 | 9/2010 |
| WO | WO 2011/044186 | 4/2011 |
| WO | WO 2011/107489 | 9/2011 |
| WO | WO 2012/017081 | 2/2012 |
| WO | WO 2012/058627 | 5/2012 |
| WO | WO 2012/079000 | 6/2012 |
| WO | WO 2012/081650 | 6/2012 |
| WO | WO 2012/114978 | 8/2012 |
| WO | WO 2012/129514 | 9/2012 |
| WO | WO 2012/137538 | 10/2012 |
| WO | WO 2013/011011 | 1/2013 |
| WO | WO 2013/038272 | 3/2013 |
| WO | WO 2013/062365 | 5/2013 |
| WO | WO 2013/071154 | 5/2013 |
| WO | WO 2013/123061 | 8/2013 |
| WO | WO 2013/124474 | 8/2013 |
| WO | WO 2013/126726 | 8/2013 |
| WO | WO 2013/163171 | 10/2013 |
| WO | WO 2013/166321 | 11/2013 |
| WO | WO 2013/188427 | 12/2013 |
| WO | WO 2013/192294 | 12/2013 |
| WO | WO 2014/011489 | 1/2014 |
| WO | WO 2014/011996 | 1/2014 |
| WO | WO 2014/012001 | 1/2014 |
| WO | WO 2014/031687 | 2/2014 |
| WO | WO 2014/048920 | 4/2014 |
| WO | WO- 2014/055668 | 4/2014 |
| WO | WO 2014/076277 | 5/2014 |
| WO | WO 2014/127261 | 8/2014 |
| WO | WO 2014/186469 | 11/2014 |
| WO | WO 2015/009604 | 1/2015 |
| WO | WO 2015/009606 | 1/2015 |
| WO | WO 2015/184228 | 3/2015 |
| WO | WO 2015/095895 | 6/2015 |
| WO | WO 2015/142675 | 9/2015 |
| WO | WO 2015/157252 | 10/2015 |
| WO | WO 2015/157384 | 10/2015 |
| WO | WO 2015/158868 | 10/2015 |
| WO | WO 2015/162211 | 10/2015 |
| WO | WO 2015/164675 | 10/2015 |
| WO | WO 2015/181253 | 12/2015 |
| WO | WO 2016/019300 | 2/2016 |
| WO | WO 2016/030414 | 3/2016 |
| WO | WO 2016/061416 | 4/2016 |
| WO | WO 2016/073602 | 5/2016 |
| WO | WO 2016/090190 | 6/2016 |
| WO | WO 2016/090312 | 6/2016 |
| WO | WO 2016/090320 | 6/2016 |
| WO | WO 2016/090327 | 6/2016 |
| WO | WO 2016/090329 | 6/2016 |
| WO | WO 2016/090369 | 6/2016 |
| WO | WO 2016/094304 | 6/2016 |
| WO | WO 2016/109410 | 7/2016 |
| WO | WO 2016/164580 | 10/2016 |
| WO | WO 2016/164731 | 10/2016 |
| WO | WO 2016/166568 | 10/2016 |
| WO | WO 2017/015427 | 1/2017 |
| WO | WO 2017/015490 | 1/2017 |
| WO | WO 2017/023803 | 2/2017 |

(56) References Cited

FOREIGN PATENT DOCUMENTS

| | | |
|---|---|---|
| WO | WO 2017/027291 | 2/2017 |
| WO | WO 2017/050884 | 3/2017 |
| WO | WO 2017/068419 | 4/2017 |
| WO | WO 2017/068421 | 4/2017 |
| WO | WO 2017/068425 | 4/2017 |
| WO | WO 2017/070337 | 4/2017 |
| WO | WO 2015/164745 | 6/2017 |
| WO | WO 2017/096329 | 6/2017 |
| WO | WO 2017/156479 | 9/2017 |
| WO | WO 2017/157505 | 9/2017 |
| WO | WO 2017/161353 | 9/2017 |
| WO | WO 2017/173256 | 10/2017 |
| WO | WO 2017/177137 | 10/2017 |
| WO | WO 2017/214207 | 12/2017 |
| WO | WO 2018/106595 | 6/2018 |
| WO | WO 2018/106732 | 6/2018 |
| WO | WO 2018/134691 | 7/2018 |
| WO | WO 2018/162352 | 9/2018 |
| WO | WO 2018/170188 | 9/2018 |
| WO | WO 2018/191723 | 10/2018 |
| WO | WO 2018/197949 | 11/2018 |
| WO | WO 2018/204427 | 11/2018 |
| WO | WO 2018/223101 | 12/2018 |
| WO | WO 2019/018603 | 1/2019 |
| WO | WO 2019/089855 | 5/2019 |
| WO | WO 2019/090004 | 5/2019 |
| WO | WO 2019/090364 | 5/2019 |
| WO | WO 2019/113556 | 6/2019 |
| WO | WO 2019/113557 | 6/2019 |
| WO | WO 2019/140425 | 7/2019 |
| WO | WO 2020/014333 | 1/2020 |
| WO | WO 2020/033916 | 2/2020 |
| WO | WO 2020/089343 | 5/2020 |
| WO | WO 2021/163389 | 8/2021 |
| WO | WO 2021/163391 | 8/2021 |

OTHER PUBLICATIONS

Boyman, O., Cho, JH., Sprent, J. (2010). The Role of Interleukin-2 in Memory CD8 Cell Differentiation. Chapter 3 in: Zanetti, M., Schoenberger, S.P. (eds) Memory T Cells. Advances in Experimental Medicine and Biology, vol. 684. Springer, New York, NY. (Year: 2010).*

Krug, C., Wiesinger, M., Abken, H et al. A GMP-compliant protocol to expand and transfect cancer patient T cells with mRNA encoding a tumor-specific chimeric antigen receptor. Cancer Immunol Immunother 63, 999-1008 (2014). (Year: 2014).*

Braun et al., "Rapid separation of T cell subpopulations with monoclonal antibodies and affinity chromatography," J Immunol Methods. (1982) 54(2):251-8.

Casati et al., "Clinical-scale selection and viral transduction of human naïve and central memory CD8+ T cells for adoptive cell therapy of cancer patients," Cancer Immunology (2013) 62(10): 1563-1573.

Davis et al., "Assessment of a positive selection technique using an avidin column to isolate human peripheral blood T cell subsets," J Immunol Methods. (1994) 175(2):247-57.

Fernandes et al., "Kinetics of class II MHC expression on cytotoxic T cells generated by skin allograft," Tissue Antigens. (1990) 36(3):93-9.

Gunzer et al,, "Two-step negative enrichment of CD4+ and CD8+ T cells from murine spleen via nylon wool adherence and an optimized antibody cocktail," J Immunol Methods. (2001) 258(1-2): 55-63.

Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese) English Translation provided.

Kaikkonen et al., "(Strept)avidin-displaying lentiviruses as versatile tools for targeting and dual imaging of gene delivery," Gene Ther (2009) 16:894-904.

Lada et al., Measurement of Integrated HIV DNA by Pulse-Field Gel Electrophoresis and ddPCR. CROI 2016 Boston, Feb. 22-25, 2016, Poster #362. https://www.croiconference.org/wp-content/uploads/sites/2/posters/2016/362.pdf.

Mak et al., "Glutathione Primes T Cell Metabolism for Inflammation," Immunity. (2017) 46(4):675-689.

Medvec et al., "Improved Expansion and In Vivo Function of Patient T Cells by a Serum-free Medium," Mol Ther Methods Clin Dev. (2017) 8:65-74.

Milone et al., "Chimeric Receptors Containing CD137 Signal Transduction Domains Mediate Enhanced Survival of T Cells and Increased Antileukemic Efficacy In Vivo," Mol Ther (2009) 17(8):1453-64.

Moeller et al., "Adoptive transfer of gene-engineered CD4+ helper T cells induces potent primary and secondary tumor rejection," Blood (2005) 106(9):2995-3003.

Nascimbeni et al., "Peripheral CD4+CD8+ T cells are differentiated effector memory cells with antiviral functions," Blood (2004) 104(2):478-86.

Powell et al., "Sequence and structural determinants required for priming of plus-strand DNA synthesis by the human immunodeficiency virus type 1 polypurine tract," J Viral (1996) 70(8):5288-5296.

Pullagurla et al., "Parallel affinity-based isolation of leukocyte subsets using microfluidics: application for stroke diagnosis," Analytical chemistry (2014) 86(8):4058-4065.

Purification Technical Handbook (2010 retrieved from https://at.vwr.com/assetsvc/asset/de AT/id/20551553/contents).

Sabatino et al., "Generation of clinical-grade CD19-specific CAR-modified CD8+ memory stem cells for the treatment of human B-cell malignancies," Blood. Jul. 28, 2016;128(4):519-28.

Skea et al., "The selective expansion of functional T cell subsets," J Hematother Stem Cell Res. (1999) 8(5): 525-38.

Smith et al., "Redirected infection of directly biotinylated recombinant adenovirus vectors through cell surface receptors and antigens," Proc Natl Acad Sci USA (1999) 8855-8860.

Tarantula, Explanatory Biotechnological Dictionary (English translation only).

Akron Biotech "Exceptional purity, consistency and performance. Expand T-Cells and NK-Cells with Akron's cGMP IL-15," (2023): 1-9.

Al-Shanti et al., "Human purified CD8+ T cells: Ex vivo expansion model to generate a maximum yield of functional cytotoxic cells," Immunol Invest. (2007);36(1):85-104.

Amos et al., "The role of caspase 3 and BclxL in the action of interleukin 7 (IL-7): a survival factor in activated human T cells," Cytokine. (1998) 10(9):662-8.

Barrett et al., "The length and mode of termination of individual muscle fibers in the human Sartorius and posterior femoral muscles," Cell Tissues Organs (1962) 48(3):242-257.

Berger et al., "Adoptive transfer of effector CD8 T cells derived from central memory cells establishes persistent T cell memory in primates." J Clin Invest (2008) 118(1): 294-305.

Berthois et al., "Phenol red in tissue culture media is a weak estrogen: implications concerning the study of estrogen-responsive cells in culture," Proc Natl Acad Sci U S A. (1986);83(8):2496-500.

Bondanza et al., "IL-7 receptor expression identifies suicide gene-modified allospecific CD8+ T cells capable of self-renewal and differentiation into antileukemia effectors," Blood. (2011) 117(24):6469-78.

Bostrom et al., "High affinity antigen recognition of the dual specific variants of herceptin is entropy-driven in spite of structural plasticity," PLoS One. (2011) 6(4):e17887, 12 pages.

Chai et al., "Single-molecule protein arrays enabled by scanning probe block copolymer lithography," Proc Natl Acad Sci USA. (2011) 108(49): 19521-5.

Chang et al., "Investigation of interfacial properties of pure and mixed poloxamers for surfactant-mediated shear protection of mammalian cells," Colloids Surf B Biointerfaces. (2017) 156:358-365.

Chen et al., "Biotin IgM Antibodies in Human Blood: A Previously Unknown Factor Eliciting False Results in Biotinylation-Based Immunoassays," Plos One (2012); 7(8); e42376, pp. 1-8.

(56) References Cited

OTHER PUBLICATIONS

Dong, Modern Biology, Beijing Institute of Technology Press, 1st edition, p. 328, Jul. 31, 2016 (Article in Chinese; English translation provided).
Dufait et al., "Retroviral and lentiviral vectors for the induction of immunological tolerance," Scientifica (Cairo) (Dec. 2012) 2012:694137, 14 pages.
Dupont et al., "Comparative dose-responses of recombinant human IL-2 and IL-7 on STAT5 phosphorylation in CD4+FOXP3-cells versus regulatory T cells: a whole blood perspective," Cytokine. (2014) 69(1):146-9.
Finney et al., "Activation of resting human primary T cells with chimeric receptors: costimulation from CD28, inducible costimulator, CD134, and CD137 in series with signals from the TCR zeta chain," J Immunol. (2004) 172(1):104-13.
Gattinoni et al., "A human memory T cell subset with stem cell-like properties," Nat Med. (2011) 17(10):1290-7.
Gattinoni L et al., "Acquisition of full effector function in vitro paradoxically impairs the in vivo antitumor efficacy of adoptively transferred CDS+ T cells," J Clin Invest. (2005) 115(6):1616-26.
Ghassemi et al., "Rapid manufacturing of non-activated potent CAR T cells," Nat Biomed Eng. (2022) 6(2):118-128.
Hinrichs et al., "Adoptively transferred effector cells derived from naive rather than central memory CD8+ T cells mediate superior antitumor immunity," Proc Natl Acad Sci U S A. (2009) 106(41):17469-74.
Hinrichs et al., "Human effector CD8+ T cells derived from naive rather than memory subsets possess superior traits for adoptive immunotherapy," Blood. (2011) 117(3):808-14.
Hirakawa et al., "IL-2, IL-7, IL-15 and IL-6 Induce Differential Activation of Naive and Memory T Cell Subsets," Blood (2015) 126(23):3425, 4 pages.
Hou et al., "Tutorial on Animal Cell Culture Techniques," Gansu Science and Technology Press (2009) 520, Chapter 9, p. 105. (Article in Chinese; English translation provided).
Iyer et al., "Industrializing Autologous Adoptive Immunotherapies: Manufacturing Advances and Challenges," Front Med (Lausanne). (2018) 5:150, 9 pages.
Jarmoskaite et al., "How to measure and evaluate binding affinities," Elife (2020) 9:e57264, 34 pages.
Jethwa et al., "Use of gene-modified regulatory T-cells to control autoimmune and alloimmune pathology: is now the right time?," Clin Immunol. (2014) 150(1):51-63.
Jiang Bo, Fundamentals and Clinics of Apoptosis, People's Military Medical Press, p. 141, Jul. 1999 (Reference in Chinese; English translation provided).
Kaartinen et al., "Low interleukin-2 concentration favors generation of early memory T cells over effector phenotypes during chimeric antigen receptor T-cell expansion," Cytotherapy (2017) 19(6):689-702.
Kato et al., "Development of Rous sarcoma Virus-like Particles Displaying hVV49 scFv for specific targeted drug delievery to human colon carcinoma cells," Pharm Res (2015) 32:3699-3707.
Katz et al., "Therapeutic targeting of CD19 in hematological malignancies: past, present, future and beyond." Leuk Lymphoma. (2014) 55(5):999-1006.
Kemper et al., "Label-free quantitative cell division monitoring of endothelial cells by digital holographic microscopy," J Biomed Opt. (2010) 15(3):036009, 6 pages.
Levine et al., "Global manufacturing of CAR T cell therapy" Mol. Ther. Methods & Clin. Dev. (2016) 4: 92-101.
Li, Experiment of Biochemistry and Molecular Biology, edited by Weifang Li, Hefei: China University of Science and Technology Press, Jan. 2012, pp. 95-109. (English machine translation provided).
Life Technologies Corporation (2013) OpTmizerTM CTSTM T-cell Expansion SFM Technical information; pp. 1-2 (Year: 2013).
Lv, Clinical Immunological Test (2nd Edition), edited by Lv Shijing, Beijing: China Medical Science and Technology Press, Jan. 2010, p. 110, (II) avidin and streptavidin. (English machine translation provided).
Mackensen et al., "Anti-CD19 CAR T cell therapy for refractory systemic lupus erythematosus," Nat Med (2022) 28(10):2124-2132 and Supplementary Materials.
Marenghi et al., "The role of perfusion in maintaining high density T-cell cultures," GE (2014):1-2.
Marthandan et al., "An investigation of the effects of the antioxidants, ebselen or N-acetyl cysteine on human peripheral blood mononuclear cells and T cells," Immun Ageing. (2013) 10(1):7, 16 pages.
Mei et al., "Rationale of anti-CD19 immunotherapy: an option to target autoreactive plasma cells in autoimmunity," Arthritis Res Ther. (2012) 14 Suppl 5(Suppl 5):S1, 16 pages.
Mougiakakos et al., "CD19-Targeted CAR T Cells in Refractory Systemic Lupus Erythematosus," N Engl J Med (2021) 385(6):567-569 and Supplementary Appendix.
Navarro et al., "Estrogen Stimulation Differentially Impacts Human Male and Female Antigen-Specific T Cell Anti-Tumor Function and Polyfunctionality," Gender and the Genome. (2017) 1(4):167-179.
Nesbeth et al., "Metabolic Biotinylation of Lentiviral Pseudotypes for Scalable Paramagnetic Microparticle-Dependent Manipulation," Mol Ther (2006) 13(4):814-822.
Okern et al., "CTS™ immune cell SR for serum free culture and expansion of human T cells," J Immunother Cancer. (2015); 3(Suppl 2): P1.
Parrott et al., "Metabolically biotinylated adenovirus for cell targeting, ligand screening, and vector purification," Mol Ther (2003) 8(4):688-700.
Poltorak et al., "Expamers: a new technology to control T cell activation," Sci Rep. (2020) 10(1):17832, 15 pages.
Ponnazhagan et al., "Conjugate-based targeting of recombinant adeno-associated virus type 2 vectors by using avidin-linked ligands," J Virol. (2002) 76(24):12900-7.
Prospec, Streptavidin Protein, catalogue No. PRO-283, retrieved from: https://www.prospecbio.com/streptavidin [Dec. 28, 2022] (Year: 2016) 3 pages.
Qian et al., "Advances in the Development of Interleukin-2 and its Analogues," Chinese Journal of Pharmaceuticals. (2020) 947-955. (Article in Chinese; English abstract provided).
Saligrama et al., "IL-15 maintains T-cell survival via S-nitrosylation-mediated inhibition of caspase-3," Cell Death Differ. (2014) 21(6):904-14.
Salmon, "Arming T cells against B cells in systemic lupus erythematosus," Nat Med (2022) 28(10):2009-2010.
Sun et al., "Plug-and-go strategy to manipulate streptavidin valencies," Bioconjugate Chem (2014) 25:1375-1380.
Takahashi et al., "Non-destructive on-chip cell sorting system with real-time microscopic image processing," Journal of Nanobiotechnology (2004) 2(5), 8 pages.
ThermoFisher Scientific, Avidin-Biotein Interaction, retrieved from https://www.thermofisher.com/us/en/home/life-science/protein-biology/protein-biology-learning-center/protein-biology-resource-library/pierce-protein-methods/avidin-biotin-interaction.html on Apr. 9, 2019, pp. 1-7.
Van Loenen et al., "A Good Manufacturing Practice procedure to engineer donor virus-specific T cells into potent anti-leukemic effector cells," Haematologica. (2014) 99(4):759-68.
Wang et al., "Detection of integration of plasmid DNA into host genomic DNA following intramuscular injection and electroporation," Gene Ther (2004) 11(8):711-21.
Weigmann, "Cell Isolation of Spleen Mononuclear Cells," Bio-Protocol (2013) 3(9):4 pages.
Xu et al., "Effects of cryopreservation on chimeric antigen receptor T cell functions," Cryobiology (2018) 83:40-47.
Zhang et al., "Novel CD19 chimeric antigen receptor T cells manufactured next-day for acute lymphoblastic leukemia," Blood Cancer J. Jun. 24, 2022;12(6):96, 9 pages.
Abate-Daga et al., "CAR models: next-generation CAR modifications for enhanced T cell function," Mol Ther Oncolytics (2016) 3:16014.

(56) References Cited

OTHER PUBLICATIONS

Addo et al., "Fully Differentiated HIV-1 Specific CD8+ T Effector Cells Are More Frequently Detectable in Controlled than in Progressive HIV-1 Infection," PLoS One. (2007) 2(3): e321.
Aksoy et al., "Human primary T cells: A practical guide," dated Jun. 19, 2018. Retrieved from https://peerj.com/preprints/26993.html.
Alonso-Camino et al., "CARbodies: Human Antibodies Against Cell Surface Tumor Antigens Selected From Repertoires Displayed on T Cell Chimeric Antigen Receptors," Mol Ther Nucl Acids (2013) 2: e93.
Anikeeva et al., "Evidence that the density of self peptide-MHC ligands regulates T-cell receptor signaling," PLoS One (2012) 7(8): e41466.
Anonymous, "Scientists helping scientists™ | WWW Optimization of Human T Cell Expansion Protocol: Effects of Early Cell Dilution," (2018).
Anonymous, "Cross-linking reagents introduction to cross-linking single-step vs. multi-step reactions," Published on Jan. 1, 2005. Retrieved from http://www.korambiotech.com/upload/bbs/2/Cross-LinkingTechHB.pdf. Retrieved on Nov. 30, 2018.
Anonymous, "SMCC and Sulfo-SMCC," Published Jan. 1, 2018. Retrieved on https://assets.thermofisher.com/TFS-Assets/LSG/manuals/MAN0011295_SMCC_SulfoSMCC_UG.pdf. Retrieved on Dec. 3, 2018.
Anonymous, "Traut's reagent," Published on Jan. 1, 2012. Retrieved from https://assets.thermofisher.com/TFS-Assets/LSG/manuals/MAN0011238_Trauts_Reag_UG.pdf. Retrieved on Dec. 3, 2018.
Arakawa et al. "Cloning and sequencing of the VH and V kappa genes of an anti-CD3 monoclonal antibody, and construction of a mouse/human chimeric antibody," J Biochem. (1996) 120(3): 657-662.
Argarana et al., "Molecular cloning and nucleotide sequence of the streptavidin gene," Nucl Acids Res (1986) 14(4):1871-1882.
Bambauer et al., "LDL-apheresis: technical and clinical aspects," The Scientific World Journal (2012) 2012: 314283.
Barrett et al., "Chimeric Antigen Receptor Therapy for Cancer," Annu Rev Med (2014) 65:333-347.
Baum et al., "Retrovirus Vectors: Toward the plentivirus," Mol Ther (2006) 13:1050-1063.
Bes et al. (2003). "Mapping the Paratope of Anti-CD4 Recombinant Fab 13B8.2 by Combining Parallel Peptide Synthesis and Site-directed Mutagenesis", The Journal of Biological Chemistry (2003) 278(16):14266-14273.
Boris-Lawrie et al., "Recent advances in retrovirus vector technology," Cur. Opin. Genet. Develop. (1993) 3:102-109.
Brash et al., "Strontium phosphate transfection of human cells in primary culture: stable expression of the simian virus 40 large-T-antigen gene in primary human bronchial epithelial cells," Mol. Cell Biol. (1987) 7: 2031-2034.
Brentjens et al., "CD19-targeted T cells rapidly induce molecular remissions in adults with chemotherapy-refractory acute lymphoblastic leukemia," Sci Transl Med. (2013) 5(177):177ra38.
Bulek et al., "Structural basis for the killing of human beta cells by CD8(+) T cells in type 1 diabetes," Nat Immunol. (2012) 13(3): 283-289.
Burns et al., "Vesicular stomatitis virus G glycoprotein pseudotyped retroviral vectors: concentration to very high titer and efficient gene transfer into mammalian and nonmammalian cells," Proc. Natl. Acad. Sci. USA (1993) 90:8033-8037.
Carlens et al., "Ex vivo T lymphocyte expansion for retroviral transduction: influence of serum-free media on variations in cell expansion rates and lymphocyte subset distribution," Exp Hematol (2000) 28(10): 1137-1146.
Carpenter et al., "B-cell maturation antigen is a promising target for adoptive T-cell therapy of multiple myeloma," Clin Cancer Res. (2013) 19:2048-2060.
Carrillo et al., "The multiple sequence alighment problem in biology," SIAM Journal of Applied Mathematics (1988) 48(5):1073-1082.
Casalegno-Garduño et al., Multimer technologies for detection and adoptive transfer of antigen-specific T cells. Cancer Immunol Immunother. Feb. 2010;59(2):195-202.
Cavalieri et al., "Human T lymphocytes transduced by lentiviral vectors in the absence of TCR activation maintain an intact immune competence," Blood (2003) 102(2): 497-505.
Chaara et al., "RepSeq Data Representativeness and Robustness Assessment by Shannon Entropy," Front Immunol. (2018) 9:1038.
Challita et al., "Multiple Modifications in Cis Elements of the Long Terminal Repeat of Retroviral Vectors Lead to Increased Expression and Decreased DNA Methylation in Embryonic Carcinoma Cells," J Virol (1995) 69(2): 748-55.
Cheadle et al., "Chimeric antigen receptors for T-cell based therapy," Methods Mol Biol (2012) 907:645-666.
Cheever et al., "The prioritization of cancer antigens: a national cancer institute pilot project for the acceleration of translational research." Clin Cancer Res. Sep. 1, 2009;15(17):5323-37.
Chervin et al., "Engineering higher affinity T cell receptors using a T cell display system," J Immunol Methods. (2008) 339(2): 175-84.
Chicaybam et al., "An efficient low cost method for gene transfer to T lymphocytes," PLoS One (2013) 8(3): e60298.
Cho et al., "Targeting B Cell Maturation Antigen (BCMA) in Multiple Myeloma: Potential Uses of BCMA-Based Immunotherapy," Front Immunol. (2018) 9:1821.
Chothia et al.,. "The outline structure of the T-cell alpha beta receptor," EMBO J. (1988) 7(12): 3745-55.
Chu et al., "CS1-specific chimeric antigen receptor (CAR)-engineered natural killer cells enhance in vitro and in vivo antitumor activity against human multiple myeloma," Leukemia (2014) 28(4):917-927.
Clackson et al., "Making antibody fragments using phage display libraries," Nature (1991) 352(6336):624-628.
Clackson et al., "Redesigning an FKBP-ligand interface to generate chemical dimerizers with novel specificity," Proc Natl Acad Sci U S A. (1998) 95(18): 10437-10442.
Cohen et al., "Recognition of Fresh Human Tumor by Human Peripheral Blood Lymphocytes Transduced with a Bicistronic Retroviral Vector Encoding a Murine Anti-p53 TCR," J Immunol (2005) 175(9):5799-5808.
Cohen et al., "Recombinant antibodies with MHC-restricted, peptide-specific, T-cell receptor-like specificity: new tools to study antigen presentation and TCR-peptide-MHC interactions," J Mol RecogN (2003) 16:324-332.
Cooper et al., "T-cell clones can be rendered specific for CD19: toward the selective augmentation of the graft-versus-B-lineage leukemia effect," Blood. (2003) 101:1637-1644.
Corces et al., "An improved ATAC-seq protocol reduces background and enables interrogation of frozen tissues," Nat Methods. (2017) 14(10): 959-962.
Davila et al., "CD19 CAR-targeted T cells induce long-term remission and B Cell Aplasia in an immunocompetent mouse model of B cell acute lymphoblastic leukemia," PLoS One (2013) 8(4): e61338.
De Felipe et al., "Targeting of proteins derived from self-processing polyproteins containing multiple signal sequences," Trafic (2004) 5(8):616-626.
De Felipe, "Skipping the co-expression problem: the new 2A "Chysel" technology," Genetics Vaccines and Therapy (2004) 2:13.
Di Stasi et al., "Inducible apoptosis as a safety switch for adoptive cell therapy," N Engl J Med. (2011) 365(18):1673-83.
Dubel et al., "Bifunctional and multimeric complexes of streptavidin fused to single chain antibodies (scFv)," J Immunol Methods (1995) 178(2):201-209.
Entschladen et al., "Differential requirement of protein tyrosine kinases and protein kinase C in the regulation of T cell locomotion in three-dimensional collagen matrices," J Immunol. (1997) 159(7): 3203-3210.
Erhart et al., "Chemical development of intracellular protein heterodimerizers," Chem Biol. (2013) 20(4): 549-57.
Fairhead et al., "Plug-and-Play Pairing via Defined Divalent Streptavidins," J Mol Biol (2014) 426(1):199-214.
Farrar et al., "Activation of the Raf-1 kinase cascade by coumermycin-induced dimerization," Nature. (1996) 383(6596): 178-81.

(56) References Cited

OTHER PUBLICATIONS

Fedorov et al., "PD-1- and CTLA-4-Based Inhibitory Chimeric Antigen Receptors (iCARs) Divert Off-Target Immunotherapy Responses," Sci Transl Medicine (2013) 5(215):215ra172.
Fesnak et al., "Engineered T cells: the promise and challenges of cancer immunotherapy," Nat Rev Cancer. (2016) 16(9): 566-581.
Foon et al., "Immunologic classification of leukemia and lymphoma," Blood (1986) 68(1):1-31.
Fraietta et al., "Determinants of response and resistance to CD19 chimeric antigen receptor (CAR) T cell therapy of chronic lymphocytic leukemia," Nat Med. (May 2018) 24(5):563-571. Epub Apr. 30, 2018.
Frecha et al., "Advances in the field of lentivector-based transduction of T and B lymphocytes for gene therapy," Mol Ther (2010) 18(10):1748-1757.
Friedl et al., "T lymphocyte locomotion in a three-dimensional collagen matrix: Expression and function of cell adhesion molecules," J Immunol. (1995) 154: 4973-4985.
Galbiati et al., "N-terminal fatty acylation of the alpha-subunit of the G-protein Gi1: only the myristoylated protein is a substrate for palmitoylation," Biochem J. (1994) 303 ( Pt 3)(Pt 3):697-700.
Garfall et al., "Posterior Reversible Encephalopathy Syndrome (PRES) after infusion of anti-Bcma CAR T cells (CART_BCMA) for multiple myeloma: Successful Treatment with Cyclophophamide," Blood (2016) 128(22):5702.
Gargett et al., "Different cytokine and stimulation conditions influence the expansion and immune phenotype of third-generation chimeric antigen receptor T cells specific for tumor antigen GD2," Cytotherapy (2015) 17(4):487-495.
Gauthier-Campbell et al., "Regulation of Dendritic Branching and Filopodia Formation in Hippocampal Neurons by Specific Acylated Protein Motifs□D□V," Mol Biol Cell. (2004) 15(5): 2205-2217.
Gearing et al., "The international standard for human interleukin-2. Calibration by international collaborative study," J Immunological Methods (1988) 114(1-2):3-9.
Germeroth "IBA T-catch cell isolation in pipette tips" Apr. 23, 2014 Retrieved from the internet: URL:http://x.ymcdn.com/sites/www.celltherapysociety.org/resource/resmgr/2014_AnnualMtgPresentations/T2_L.Germeroth.pdf [Retrieved on Jan. 23, 2017].
Ghassemi et al., "Reducing Ex Vivo Culture Improves the Antileukemic Activity of Chimeric Antigen Receptor (CAR) T Cells", Cancer Immunol Res. (Sep. 2018) 6(9):1100-1109. Epub Jul. 20, 2018.
Ghassemi S., "Ultra-Short Manufacturing of Quiescent Chimeric Antigen Receptor T Cells for Adoptive Immunotherapy," Molecular Therapy vol. 27 No. 4S1 Apr. 2019, p. 86.
Godawat et al., "Period counter-current chromatography—design and operational considerations for integrated and continuous purification of proteins," Biotechnology journal (2012) 7(12):1496-1508.
Gust et al., "Endothelial Activation and Blood-Brain Barrier Disruption in Neurotoxicity after Adoptive Immunotherapy with CD19 CAR-T Cells," Cancer Discov. (2017) 7(12): 1404-1419.
Hackett et al., "A transposon and transposase system for human application," Molecular Therapy: The Journal of the American Society of Gene Therapy (2010) 18:674-683.
Harkiolaki et al., "T cell-mediated autoimmune disease due to low-affinity crossreactivity to common microbial peptides," Immunity. (2009) 30(3): 348-57.
Hermans et al., "The VITAL assay: a versatile fluorometric technique for assessing CTL- and NKT-mediated cytotoxicity against multiple targets in vitro and in vivo," J Immunol Methods (2004) 285(1):25-40.
Hindson, B. et al. "High-Throughput Droplet Digital PCR System for Absolute Quantitation of DNA Copy Number," Analytical Chemistry (2011) 83(22):8604-8610.
Holler et al., "In vitro evolution of a T cell receptor with high affinity for peptide/MHC," Proc Natl Acad Sci U S A. (2000) 97(10): 5387-5392.
Holler et al., "TCRs with high affinity for foreign pMHC show self-reactivity," Nat Immunol. Jan. 2003;4(1):55-62.
Holliger, P. et al., "Specific killing of lymphoma cells by cytotoxic T-cells mediated by a bispecific diabody," Protein Engineering Design and Selection (1996) 9(3):299-305.
Holliger, P. et al., "Diabodies': Small Bivalent and Bispecific Antibody Fragments," (1993) Proc. Natl. Acad. Sci. USA 90:6444-6448.
Holt et al., "Domain Antibodies: Proteins For Therapy," Trends in Biotechnology (2003) 21(11): 484-490.
Howarth et al., "A monovalent streptavidin with a single femtomolar biotin binding site," Nature Methods (2006) 3:267-273.
Huang et al., "DNA transposons for modification of human primary T lymphocytes," Methods Mol Biol (2009) 506: 115-126.
Hudecek et al., "Receptor affinity and extracellular domain modifications affect tumor recognition by ROR1-specific chimeric antigen receptor T cells," Clin Cancer Res (2013) 19(12):3153-3164.
Hudecek et al., "The nonsignaling extracellular spacer domain of chimeric antigen receptors is decisive for in vivo antitumor activity," Cancer Immunol Res (2015) 3(2):125-135.
Huggett et al., "Digital PCR as a novel technology and its potential implications for molecular diagnostics," Clin Chem. (2013) 59(12): 1691-1693.
Hunziker et al., "Exhaustion of cytotoxic T cells during adoptive immunotherapy of virus carrier mice can be prevented by B cells or CD4+ T cells," Eur J Immunol (2002) 32(2):374-382.
Hutten et al., "New magnetic nanoparticles for biotechnology," J. Biotechnol. (2004), 112(1-2); 47-63.
Iliades et al., "Triabodies: single chain Fv fragments without a linker form trivalent trimers," FEBS Lett. (1997) 409(3): 437-441.
Ill et al., "Design and construction of a hybrid immunoglobulin domain with properties of both heavy and light chain variable regions," Protein Eng. (1997) 10(8):949-957.
Imadome, "The clinical condition and diagnosis of EBV-T/NK-LPD (CAEBV, EBV-HLH etc.)," [Rinsho Ketsueki] Japanese J Clin Hematol (2013) 54(10):1992-98. (Reference in Japanese).
Janeway et al., Immunobiology: The Immune System in Health and Disease, 3rd ED., Current Biology Publications (1997), p. 4:33.
Johnston, et al., "Biolistic transformation: microbes to mice," Nature (1990) 346: 776-777.
Jores et al., "Resolution of hypervariable regions in T-cell receptor beta chains by a modified Wu-Kabat index of amino acid diversity.," PNAS (1990) 87(23):9138-9142.
Kindt et al., "Antigens and Antibodies," in Chapter 4 of Kuby Immunology, 6th ed., W.H. Freeman and Co., N.Y, (2007) pp. 91, 14 pages.
Kipriyanov et al., "Bispecific tandem diabody for tumor therapy with improved antigen binding and pharmacokinetics," J Mol Biol (1999) 293(1):41-56.
Klebanoff et al., "Sorting through subsets: which T-cell populations mediate highly effective adoptive immunotherapy?," J Immunother. (2012) 35(9): 651-660.
Klooster et al., "Targeting and localized signalling by small GTPases," Biol Cell. (2007) 99(1): 1-12.
Knabel et al., "Reversible MHC multimer staining for functional isolation of T-cell populations and effective adoptive transfer," Nat Med. Jun. 2002;8(6):631-637.
Kochenderfer et al., "Construction and preclinical evaluation of an anti-CD19 chimeric antigen receptor," J. Immunotherapy (2009) 32(7): 689-702.
Kochenderfer et al., "Treating B-cell cancer with T cells expressing anti-CD19 chimeric antigen receptors," Nature Reviews Clinical Oncology (2013) 10:267-276.
Kohanski, R.A., Lane, M.D. "Monovalent avidin affinity columns" Methods Enzymol. 1990;184:194-200.
Kong et al., "Isolation of breast cancer stem cell and screening of specific polypeptide bonding to it," Chinese Journal of Cancer Prevention and Control (2013) 20(24):1892-1895.
Koste et al., "T-cell receptor transfer into human T cells with ecotropic retroviral vectors," Gene Therapy (2014) 21: 533-538.
Kotb, "Bacterial pyrogenic exotoxins as superantigens," Clin Microbiol Rev. (1995) 8(3):411-426.
Kuball et al., "Facilitating matched pairing and expression of TCR chains introduced into human T cells," Blood, (2007) 109:2331-2338.

(56) References Cited

OTHER PUBLICATIONS

Kumar et al., "Cell separation using cryogel-based affinity chromatography", Nature Protocols, Nature Publishing Group, GB, vol. 5, No. 11, Nov. 1, 2010, pp. 1737-1747.
Kumar et al., "Integrated bioprocess for the production and isolation of urokinase from animal cell culture using supermacroporous cryogel matrices," Biotechnology and Bioengineering (2006) 93(4):636-646.
Kurucz et al., "A bacterially expressed single-chain Fv construct from the 2B4 T-cell receptor," Proc Natl Acad Sci U S A. (1993) 90(9): 3830-3834.
Larvor et al., Measurement of the dissociation rate constant of antigen/antibody complexes in solution by enzyme-linked immunosorbent assay. J Immunol Methods. Apr. 15, 1994;170(2):167-175.
Lefranc et al., "IMGT unique numbering for immunoglobulin and T cell receptor variable domains and Ig superfamily V-like domains," Dev Comp Immunol (2003) 27(1):55-77.
Li et al., "Directed evolution of human T-cell receptors with picomolar affinities by phage display," Nature Biotechnology (2005) 23:349-354.
Li et al., "Negative enrichment of target cells by microfluidic affinity chromatography," Analytical Chemistry (2011) 83(20):7863-7869.
Li et al., "Multiparameter cell affinity chromatography: Separation and analysis in a single microfluidic channel," Anal Chem (2012) 84(19):8140-8148.
Lim et al., "Engineered streptavidin monomer and dimer with improved stability and function," Biochemistry (2010) 50:8682-8691.
Ling et al., "B-cell and plasma cell antigens: new and previously defined clusters," Leucocyte typing III. (1987) 302-355.
Liu et al., "Inclusion of Strep-tag II in design of antigen receptors for T-cell immunotherapy," Nature Biotechnology (2016) 34(4):430-434.
Lupton et al., "Dominant positive and negative selection using a hygromycin phosphotransferase-Thymidine kinase dusion gene," Molecular and cellular biology (1991) 11(6):3374-3378.
Manuri et al., "piggyBac transposon/transposase system to generate CD19-specific T cells for the treatment of B-lineage malignancies," Hum Gene Ther (2010) 21(4): 427-437.
Marin-Acevedo et al., "Cancer immunotherapy beyond immune checkpoint inhibitors," Journal of Hematology & Oncology (2018) 11:8; 25 pgs.
Martin et al., "The affinity-selection of a minibody polypeptide inhibitor of human interleukin-6," EMBO J. (1994) 13(22): 5303-5309.
Martin et al., "Modeling antibody hypervariable loops: a combined algorithm," PNAS (1989) 86(23):9268-9272.
Methods in Molecular Medicine, vol. 58: Metastasis Research Protocols, vol. 2: Cell Behavior In Vitro and In Vivo, p. 17-25 Edited by: S. A. Brooks and U. Schumacher © Humana Press Inc., Totowa, NJ.
Miller et al., "Improved retroviral vectors for gene transfer and expression," BioTechniques (1989) 7:980-990.
Miller et al., "Retrovirus packaging cells," Human Gene Therapy (1990) 1:5-14.
Miltenyi et al., High Gradient Magnetic Cell Separation With MACS. Cytometry. 1990;11(2):231-238.
Mirzaei et al., "Chimeric Antigen Receptors T Cell Therapy in Solid Tumor: Challenges and Clinical Applications," Front Immunol. (2017) 8:1850.
Miyamoto et al., "Rapid and orthogonal logic gating with a gibberellin-induced dimerization system," Nat Chem Biol. (2012) 8(5): 465-470.
Morsut et al., "Engineering Customized Cell Sensing and Response Behaviors Using Synthetic Notch Receptors," Cell. (2016) 164(4): 780-791.
Nagorsen et al., "Immunomodulatory therapy of cancer with T cell-engaging BiTE antibody blinatumomab," Exp Cell Res (2011) 317(9):1255-1260.
Naldini et al., "Lentiviruses as gene transfer agents for delivery to non-dividing cells", Curr Opin Biotechnol., Oct. 9, 1998; 5:457-63.
Neeson et al., "Ex vivo culture of chimeric antigen receptor T cells generates functional CD8+ T cells with effector and central memory-like phenotype," Gene Therapy (2010) 17(9):1105-1116.
Padmanabhan et al., Purification of Transiently Transfected Cells by Magnetic Affinity Cell Sorting. J Immunogenet. Apr. 1989;16(2):91-102.
Park et al., "Treating cancer with genetically engineered T cells," Trends Biotechnol. (2011) 29(11): 550-557.
Parkhurst et al., "Characterization of genetically modified T-cell receptors that recognize the CEA:691-699 peptide in the context of HLA-A2.1 on human colorectal cancer cells," Clin Cancer Res (2009) 15:169-180.
Pinheiro et al., "Evaluation Of A Droplet Digital Polymerase Chain Reaction Format For DNA Copy Number Quantification," Anal. Chem. (2012) 84(2):1003-1011.
Plieva et al., "Characterization of supermacroporous monolithic polyacrylamide based matrices designed for chromatography of bioparticles," Journal of Chromatography (2004) 807(1):129-137.
Pohl et al., "Principle and Applications Of Digital PCR," Expert Rev Mol. Diagn. (2004) 4:41-47.
Pont et al., "γ-Secretase inhibition increases efficacy of BCMA-specific chimeric antigen receptor T cells in multiple myeloma," Blood. (2019) 134(19): 1585-1597.
Portolano et al., "Lack of promiscuity in autoantigen-specific H and L chain combinations as revealed by human H and L chain "roulette"," J Immunol (1993) 150(3):880-887.
Qiagen: "Strep-tagged Protein Purification Handbook For expressing, purifying, and detecting proteins carrying a Strep-tag II or a 6xHis tag and a Strep-tag II Two-step protein purification system His.Strep pQE-TriSystem Vector Set pQE-TriSystem Strep Vector Strep-Tactin Superflow and Superflow Cartridge", Apr. 1, 2007 (Apr. 1, 2007.
Riddell et al., "The Fred Hutchinson Cancer Research Center and the University of Washington School of Medicine, Department of Medicine, Division of Oncology Oct. 7, 1991," Human Gene Therapy (1992) 3:319-338.
Rosenberg, et al., "Cell transfer immunotherapy for metastatic solid cancer—what clinicians need to know," Nat Rev Clin Oncol. (2011) 8(10):577-85.
Roybal et al., "Precision Tumor Recognition by T Cells With Combinatorial Antigen-Sensing Circuits," Cell. (2016) 164(4): 770-779.
Rybak et al., "Purification of biotinylated proteins on streptavidin resin: a protocol for quantitative elution," Proteomics. 2004 4(8): 2296-2299.
Sadelain, "Chimeric antigen receptors: driving immunology towards synthetic biology," Curr Opin Immunol. (2016) 41:68-76.
Sadelain et al., "The basic principles of chimeric antigen receptor design," Cancer Discov. (2013) 3(4): 388-398.
Scarpa et al., "Characterization of recombinant helper retroviruses from Moloney-based vectors in ecotropic and amphotropic packaging cell lines," Virology (1991) 180:849-852.
Schlueter et al., "Specificity and Binding Properties of a Single-chain T Cell Receptor," J Mol Biol (1996) 859-869.
Schmidt and Skerra, The Strep-tag system for one-step purification and high-affinity detection or capturing of proteins. Nat Protoc. 2007;2(6):1528-1535.
Schmitt et al., "Adoptive transfer and selective reconstitution of streptamer-selected cytomegalovirus-specific CD8+ T cells leads to virus clearance in patients after allogeneic peripheral blood stem cell transplantation," Transfusion. Mar. 2011;51(3):591-9.
Schroeder, Nach Zellen Angeln. Faszination Forschung Jun. 30, 2010:28-37 Retrieved from the Internet: URL:http://portal.mytum.de/pressestelle/faszination-forschung/2010nr6/index html [retrieved on Nov. 16, 2012]—p. 34-p. 37 (English translation provided).
Schuler et al., SYFPEITHI, Database for Searching and T-Cell Epitope Prediction. in Immunoinformatics Methods in Molecular Biology, (2007) 409(1): 75-93.

(56) References Cited

OTHER PUBLICATIONS

Seimetz et al., "Development and approval of the trifunctional antibody catumaxomab (anti-EpCAM x anti-CD3) as a targeted cancer immunotherapy," Cancer Treat Rev (2010) 36:458-467.
Serra et al., "Modulation of oat arginine decarboxylase gene expression and genome organization in transgenic Trypanosoma cruzi epimastigotes," FEBS J. (2006) 273(3): 628-637.
Sharma et al., "Efficient sleeping beauty DNA transposition from DNA minicircles," Molec Ther Nucl Acids (2013) 2, e74.
Shooshtari et al., "Correlation analysis of intracellular and secreted cytokines via the generalized integrated mean fluorescence intensity," Cytometry A. (2010) 77(9): 873-80.
Shuga et al., "Single molecule quantitation and sequencing of rare translocations using microfluidic nested digital PCR," Nucleic Acids Research (2013) 41(16): e159.
Singh et al., "ProPred: prediction of HLA-DR binding sites," Bioinformatics. (2001) 17(12): 1236-1237.
Skerra et al., "Applications of a peptide ligand for streptavidin: the Strep-tag," Biomolecular Engineer (1999) 16(1-4):79-86.
Skowera et al., "CTLs are targeted to kill beta cells in patients with type 1 diabetes through recognition of a glucose-regulated preproinsulin epitope," J Clin Invest. (2008) 118(10): 3390-3402.
Smith et al., "Ex vivo expansion of human T cells for adoptive immunotherapy using the novel xeno-free CTS immune cell serum replacement," Clin Transl Immunol (2015) 4:e31.
Soman et al., "MTS dye based colorimetric CTLL-2 cell proliferation assay for product release and stability monitoring of interleukin-15: assay qualification, standardization and statistical analysis," J Immunol Methods (2009) 348(1-2):83-94.
Soo Hoo et al., "Characterization of a single-chain T-cell receptor expressed in *Escherichia coli*," Proc Natl Acad Sci U S A. (1992) 89(10): 4759-4763.
Spencer et al., "Controlling Signal Transduction with Synthetic Ligands," Science (1993) 262(5136):1019-1024.
Stemberger et al., "Novel Serial Positive Enrichment Technology Enables Clinical Multiparameter Cell Sorting," PLoS One (2012) 7(4): e35798.
Stone et al., "The assembly of single domain antibodies into bispecific decavalent molecules," J Immunol Methods. (2007) 318(1-2): 88-94.
Tamada et al., "Redirecting Gene-Modified T Cells Toward Various Cancer Types Using Tagged Antibodies," Clin Cancer Res (2012) 18(23): 6436-6445.
Terakura et al., "Generation of CD19-chimeric antigen receptor modified CD8+ T cells derived from virus-specific central memory T cells," Blood (2012) 1:72-82.
Themeli et al., "Generation of tumor-targeted human T lymphocytes from induced pluripotent stem cells for cancer therapy," Nat Biotechnol. (2013) 31(10): 928-933.
Traunecker et al., "Bispecific single chain molecules (Janusins) target cytotoxic lymphocytes on HIV infected cells," EMBO j. (1991) 10(12):3655-3659.
Traunecker et al., "Bispecific single chain molecules (Janusins) target cytotoxic lymphocytes on HIV infected cells," EMBO J. Dec. 1991;10(12):3655-9.
Trickett et al., "T cell stimulation and expansion using anti-CD3/CD28 beads" J. Immunol Methods (2003) 275(102):251-255.
Tsomides et al., "Naturally processed viral peptides recognized by cytotoxic T lymphocytes on cells chronically infected by human immunodeficiency virus type 1," J Exp Med. (1994) 180(4):1 283-1293.
Tsukahara et al., "CD19 target-engineered T-cells accumulate at tumor lesions in human B-cell lymphoma xenograft mouse models," Biochem Biophys Res Commun (2013) 438(1): 84-89.
Turtle et al., "Anti-CD19 Chimeric Antigen Receptor-Modified T Cell Therapy for B Cell Non-Hodgkin Lyphoma and Chronic Lyphocytic Leukemia: Fludarabine and Cyclophosphamide Lyphodepletion Imprives In Vivo Expansion and Persistence of CAR-T Cells and Clinical Outcomes," Blood (2015) 126:184.
Turtle et al., "Engineered T cells for anti-cancer therapy," Curr. Opin. Immunol. (2012) 24(5): 633-39.
Turtle et al., "Immunotherapy of non-Hodgkin's lymphoma with a defined ratio of CD8+ and CD4+ CD19-specific chimeric antigen receptor-modified T cells," Sci Transl Med (2016) 8(355):355ra116.
Urbanska et al., "A Universal Strategy for Adoptive Immunotherapy of Cancer Through Use of a Novel T-cell Antigen Receptor," Cancer Res (2012) 72(7): 1844-52.
Utz et al., "Analysis of the T-cell receptor repertoire of human T-cell leukemia virus type 1 (HTLV-1) Tax-specific CD8+ cytotoxic T lymphocytes from patients with HTLV-1-associated disease: evidence for oligoclonal expansion," J Virol. (1996) 70(2): 843-851.
Van Tendeloo et al., "High-level transgene expression in primary human T lymphocytes and adult bone marrow CD34+ cells via electroporation-mediated gene delivery," Gene Therapy (2000) 7(16): 1431-1437.
Vanhove et al., "Selective blockade of CD28 and not CTLA-4 with a single-chain Fv-alpha1-antitrypsin fusion antibody," Blood. (2003) 102(2): 564-570.
Varela-Rohena et al., "Control of HIV-1 immune escape by CD8 T cells expressing enhanced T-cell receptor," Nature Medicine (2008) 14(12):1390-1395.
Verhoeyen et al., "Lentiviral vector gene transfer into human T cells," Methods Mol Biol. (2009) 506: 97-114.
Vigneron et al., "Database of T cell-defined human tumor antigens: the 2013 update," Cancer Immun. Jul. 15 2013;13:15.
Vincent et al., "Targeting of proteins to membranes through hedgehog auto-processing," Nat Biotechnol. (2003) 21(8): 936-940.
Voss et al. "Mutagenesis of a flexible loop in Streptavidin Leads to Higher Affinity for the Strep-tag II Peptide and Improved Performance in Recombinant Protein Purification", Protein Engineering (1997) 10(8): 975-982.
Wadhwa et al., "Receptor mediated glycotargeting," J. Drug Targeting (1995) 3: 111.
Wadhwa et al., "Strategies for detection, measurement and characterization of unwanted antibodies induced by therapeutic biologicals," J Immunol Methods (2003) 278(1-2):1-17.
Wang et al., "Open-tubular capillary cell affinity chromatography: single and tandem blood cell separation," Anal Chem (2008) 80(6):2118-2124.
Wang et al., "New Chimeric Antigen Receptor Design for Solid Tumors," Front Immunol. (2017) 8:1934, 9 pages.
Wang et al., Generation of leukaemia antigen-specific donor lymphocyte infusions powered by streptamer-based selection. Bone Marrow Transplantation Mar. 2009;43(Suppl1):S73.
Wang et al., "Streptamer-based selection of WT1-specific CD8+ T cells for specific donor lymphocyte infusions", Experimental Hematology, vol. 38, No. 11, Nov. 1, 2010 (Nov. 1, 2010 ), pp. 1066-1073.
Whale et al., "Methods for applying accurate digital PCR analysis on low copy DNA samples," PLoS One. (2013) 8(3): e58177.
White et al., "Comparison of the glycosyl-phosphatidylinositol cleavage/attachment site between mammalian cells and parasitic protozoa," J Cell Sci. (2000) 113 (Pt 4): 721-727.
Wu et al., "Adoptive T-cell therapy using autologous tumor-infiltrating lymphocytes for metastatic melanoma: current status and future outlook," Cancer (2012) 18(2): 160-175.
Wu et al., "Engineering soluble monomeric streptavidin with reversible biotin binding capability," J Biol Chem (2005) 280(24):23225-23231.
Wulfing et al., "Correctly folded T-cell receptor fragments in the periplasm of *Escherichia coli*. Influence of folding catalysts," J Mol Biol. (1994) 242(5): 655-669.
Xia et al., "Enrichment of haploid spermatids in mice by flow sorting," Natl Journal of Andrology (2014) 20(2):106-110.
Xu et al., "Cytokine release syndrome in cancer immunotherapy with chimeric antigen receptor engineered T cells," Cancer Letters (2014) 343(2):172-178.
Xu et al., Aptamer-Based Microfluidic Device for Enrichment, Sorting, and Detection of Multiple Cancer Cells. Anal Chem. Sep. 1, 2009;81(17):7436-7442.

(56) References Cited

OTHER PUBLICATIONS

Yan et al., "A combination of humanised anti-CD19 and anti-BCMA CAR T cells in patients with relapsed or refractory multiple myeloma: a single-arm, phase 2 trial," Lancet Haematol. (2019) 6(10): e521-e529.
Yarilin, "Immunology principles," M. Medicine (1999) 184-195, 339-347 (English Translation included).
Ye et al., "Tobacco (*Nicotiana tobaccum*) nuclear transgenics with high copy number can express NPTII driven by the chloroplast psbA promoter," Plant Cell Rep. (1996) 15(7):479-83.
Zhang et al., "A novel approach to make homogeneous protease-stable monovalent streptavidin," Biochem Biophys Res Commun (2015) 463(4):1059-1063.
Zlatkine et al., "Retargeting of cytosolic proteins to the plasma membrane by the Lck protein tyrosine kinase dual acylation motif," J Cell Sci. (1997) 110 (5): 673-679.
U.S. Appl. No. 17/850,875, filed Jun. 27, 2022, by Ramsborg et al.
U.S. Appl. No. 17/799,254 , filed Aug. 11, 2022, by Westoby et al.
U.S. Appl. No. 17/799,239, filed Aug. 11, 2022, by Westoby et al.
Abramson et al., "Transcend NHL 001: Immunotherapy with the CD19-Directed CAR T-Cell Product JCAR017 Results in High Complete Response Rates in Relapsed or Refractory B-Cell Non-Hodgkin Lymphoma," Blood (2016) 128(22):4192.
Al-Hujaily et al., "Development of novel immunotherapies for multiple myeloma," Int J Mol Sci. (2016) 17:1506.
Ali et al., "T cells expressing an anti-B-cell maturation antigen chimeric antigen receptor cause remissions of multiple myeloma," Blood (2016) 128 (13): 1688-1700.
Applikon Biotechnology/BioPharma-Reporter (2016) How automation has changed the way we count cells BioPharma-Reporter.com; 1-4 (Year: 2016).
Bashour et al., "Functional Characterization of a T Cell Stimulation Reagent for the Production of Therapeutic Chimeric Antigen Receptor T Cells," Presentation of Poster, presented at American Society of Hematology Annual Meeting, Orlando, FL (Dec. 5, 2015).
Chang et al., "Identification and selective expansion of functionally superior T cells expressing chimeric antigen receptors," J Transl Med (2015) 13(1):161.
Church et al., "Tumor-specific CD4+ T cells maintain effector and memory tumor-specific CD8+ T cells," Eur J Immunol (2014) 44: 69-79.
Corada et al., "Monoclonal antibodies directed to different regions of vascular endothelial cadherin extracellular domain affect adhesion and clustering of the protein and modulate endothelial permeability," Blood. (2001) 97(6):1679-84.
Dainiak et al., Methods in Cell Separations. Adv Biochem Eng Biotechnol. 2007;106:1-18.
Eaker et al., "Concise review: guidance in developing commercializable autologous/patient-specific cell therapy manufacturing," Stem Cells Transl Med. (2013) 2(11): 871-83.
Fraietta et al., "Biomarkers of Response to Anti-CD19 Chimeric Antigen Receptor (CAR) T-Cell Therapy in Patients with Chronic Lymphocytic Leukemia," Blood (2016) 128(22):57.
Frayer et al., "Mean Body Weight, Height, Waist Circumference, and Body Mass Index Among Adults: United States, 1999-2000 Through 2015-2016," Natl Health Stat Report. (2018) (122):1-16.
Hobson et al., "In situ transduction of target cells on solid surfaces by immobilized viral vectors," BMC Biotechnol (2003) 3(4): 1-10.
Hudson et al., "Engineered Antibodies," Nature Medicine (2003) 9(1):129-133.
Imamoto et al., "Advantages of AlaGln as an additive to cell culture medium: use with anti-CD20 chimeric antibody-producing Potelligent™ CHO cell lines," Cytotechnology (2013) 65:135-143.
Invitrogen. Healthy cells in = good data out. Cell isolation and Activation. p. 1-12 (Year: 2010).
Janas et al., "Perfusion's role in maintenance of high-density T-cell cultures," BioProcesses International. (2015) pp. 1-12.
Kahn et al., "Optimization of retroviral vector-mediated gene transfer into endothelial cells in vitro," Circ Res. (1992) 71(6):1508-17.
Kisielow et al., "Ly antigens as markers for functionally distinct subpopulations of thymus-derived lymphocytes of the mouse," Nature (1975) 253: 219-20.
Klaver et al., "T Cell Maturation Stage Prior to and During GMP Processing Informs on CAR T Cell Expansion in Patients," Front Immunol. (2016) 7:648.
Klebanoff et al., "IL-15 enhances the in vivo antitumor activity of tumor-reactive CD8+ T cells," Proc Natl Acad Sci USA (2004) 101: 1969-74.
Korndorfer et al., "Improved affinity of engineered streptavidin for the Strep-tag II peptide is due to a fixed open conformation of the lid-like loop at the binding site," Protein Sci. (2002) 11(4):883-893.
Kubben et al., "Identification of differential protein interactors of lamin A and progerin," Nucleus. (2010) 1(6):513-25.
Kumar et al., Affinity binding of cells to cryogel adsorbents with immobilized specific ligands: effect of ligand coupling and matrix architecture. J Mol Recognit. Jan.-Feb. 2005;18(1):84-93.
Lada et al., "Quantitation of integrated HIV provirus by pulsed-field gel electrophoresis and droplet digital PCR," J Clin Microbiol (2018) 56(12):e01158.
Larson et al., "Defined cell composition and precise control over JCAR017 dose enables identification of relationships between chimeric antigen receptor T cell product attributes, pharmacokinetics, and clinical endpoints in NHL", Cancer Res (Jul. 1, 2018) 78(13 Supplement): 960.
Levin et al., "Optimizing the affinity and specificity of proteins with molecular display," Mol BioSyst (2006) 2:49-57.
Li et al., "Comparison of anti-CD3 and anti-CD28-coated beads with soluble anti-CD3 for expanding human T cells: Differing impact on CD8 T cell phenotype and responsiveness to restimulation," J Transl Med (2010) 8(1):104.
Li et al., "Comparison of inlet geometry in microfluidic cell affinity chromatography," Analytical chemistry (2011) 83(3):774-781.
Lu et al., "A Rapid Cell Expansion Process for Production of Engineered Autologous CAR-T Cell Therapies," Human Gene Therapy Methods (2016) 27(6):209-218.
Matic et al., "Fine tuning and efficient T cell activation with stimulatory aCD3 nanoarrays," Nano Lett. (2013) 13(11):5090-5097.
Maude et al., "Tisagenlecleucel in Children and Young Adults with B-Cell Lymphoblastic Leukemia," New Engl J Med (2018) 378(5):439-448.
Morizono et al., "A versatile targeting system with lentiviral vectors bearing the biotin-adaptor peptide," J Gene Med. Aug. 2009;11(8):655-63.
Okamoto et al., "A promising vector for TCR gene therapy: differential effect of siRNA, 2A peptide, and disulfide bond on the introduced TCR expression," Mol Ther Nucl Acids (2012) 1(12):1-11.
Padlan,"X-Ray Crystallography of Antibodies," Adv Prot Chem (1996) 49:57-133.
Poirier et al. "CD28-specific immunomodulating antibodies: what can be learned from experimental models?" American Journal of Transplantation. Jul. 2012;12(7):1682-90.
Qureshi et al., "Development and characterization of a series of soluble tetrameric and monomeric streptavidin muteins with differential biotin binding affinities," The Journal of Biological Chemistry (2001) 276(49):46422-46428.
Sano et al., "A streptavidin-protein a chimera that allows one-step production of a variety of specific antibody conjugates," Nature (1991) 9:1378-1381.
Sawai et al., "A novel method of cell-specific mRNA transfection," Molecular Genetics of Metabolim (1998) 64:44-51.
Sun et al., "Early transduction produces highly functional chimeric antigen receptor-modified virus-specific T-cells with central memory markers: a Production Assistant for Cell Therapy (PACT) translational application," J Immunother Cancer. (2015) 3:5.
Tai et al., "Antibody-Based Therapies in Multiple Myeloma," Bone Marrow Research (2010) vol. 2011. Article ID 924058.
Tai et al., "Targeting B-cell maturation antigen in multiple myeloma," Immunotherapy (2015) 7:1187-1199.
Tumaini et al., "Simplified process for the production of anti-CD19-CAR-engineered T cells," Cytotherapy. Nov. 2013;15(11):1406-15.

(56) References Cited

OTHER PUBLICATIONS

Turka et al., "CD28 is an inducible T cell surface antigen that transduces a proliferative signal in CD3+ mature thymocytes," J Immunol. (1990) 144(5):1646-53.
Turtle et al., "CD19 CAR-T cells of defined CD4+:CD8+ composition in adult B cell All patients," J. Clin. Invest. (2016) 126(6):2123-38.
Vormittag et al., "A guide to manufacturing CAR T cell therapies," Curr Opin in Biotechnology (2018) 53:164-181.
Walter et al., "Cutting edge: Predetermined Avidity of Human CD8 T cells expanded on calibrated MHC/Anti-CD28-Coated Microspheres," J Immunol (2003) 171:4973-4978.
Wang et al., "Clinical manufacturing of CAR T cells: foundation of a promising therapy," Molecular Therapy—Oncolytics (2016) 3:16015.
Wang et al., "Phenotypic and functional attributes of lentivirus-modified CD19-specific human CD8+ central memory T cells manufactured at clinical scale," J Immunother. (2012) 35(9):689-701.
Williams et al., "Affinity recovery of moloney murine leukaemia virus," J Chromatography B (2005) 820(1):111-119.
Woolridge et al. "Anti-CD8 antibodies can inhibit or enhance peptide-MHC class I (pMHCI) multimer binding: this is paralleled by their effects on CTL activation and occurs in the absence of an interaction between pMHCI and CD8 on the cell surface." The Journal of Immunology (2003) 171.12: 6650-6660.
Xu et al., "Closely related T-memory stem cells correlate with in vivo expansion of CAR.CD19-T cells and are preserved by IL-7 and IL-15," Blood (2014) 123(24):3750-3759.
Xu et al., "Multiparameter comparative analysis reveals differential impacts of various cytokines on CART cell phenotype and function ex vivo and in vivo," Oncotarget (2016) 7(50):82354-82368.
Zhao et al., "Development of the First World Health Organization Lentiviral Vector Standard: Toward the production control and standardization of lentivirus-based gene therapy products," Human Gene Therapy Methods (2017) 28(4):205-214.
U.S. Appl. No. 18/895,272, filed Sep. 24, 2024, by Bashour et al.
U.S. Appl. No. 18/904,030, filed Oct. 1, 2024, by Stadler.
Teschner et al., "In Vitro Stimulation and Expansion of Human Tumour-Reactive CD8+ Cytotoxic T Lymphocytes by Anti-CD3/CD28/CD137 Magnetic Beads," Scandinavian Journal of Immunology (Apr. 2011) 74(2):155-164.
U.S. Appl. No. 19/221,239, filed May 28, 2025, by Germeroth et al.
Alvarez-Fernandez et al., "A short CD3/CD28 costimulation combined with IL-21 enhance the generation of human memory stem T cells for adoptive immunotherapy," J Transl Med. (Jul. 2016) 14(1):214, 10 pages.
Berger et al., "Safety of targeting ROR1 in primates with chimeric antigen receptor-modified T cells," Cancer Immunol Res (Feb. 2015, e-pub. Oct. 29, 2014) 3(2):206-216, 24 pages.
Boonpiyathad et al., "Immunologic mechanisms in asthma," Semin Immunol (Dec. 2019, e-pub. Nov. 6, 2019) 46:101333, 9 pages.
Brentjens et al., "Genetically targeted T cells eradicate systemic acute lymphoblastic leukemia xenografts," Clin Cancer Res (Sep. 15, 2007) 13(18):5426-5435.
Brentjens et al. "Safety and persistence of adoptively transferred autologous CD19-targeted T cells in patients with relapsed or chemotherapy refractory B-cell leukemias," Blood (Nov. 3, 2011, e-pub. Aug. 17, 2011) 118(18):4817-4828.
Carter, "B cells in health and disease," Mayo Clin Proc (Mar. 2006) 81(3):377-384.
Casati et al., "Enrichment, stimulation, and viral transduction of naive and central memory CD8+ T cells under GMP conditions for translational research towards the development of adoptive cell therapy of cancer patients," Excerpt from MACS&more (Feb. 2013) 15:20-24.
Celgene, "Understanding CAR T-cell Therapy as a Treatment Option for Blood Cancer Patients," Leukemia & Lymphoma Society (Jun. 21, 2019), Presentation, Hilton Nashville Downtown, Nashville, TN, 177 pages, retrieved from https://m.teamintraining.org/sites/default/files/National/USA/Pdf/Slides_Transcipts/P19065_CAR%20T%20Nashville_Combined%20Decks_FINAL pdf.
Chatot et al., "An improved culture medium supports development of random-bred 1-cell mouse embryos in vitro," J Reprod Fertil (Jul. 1989) 86(2):679-688.
Christodoulou et al., "Measurement of lentiviral vector titre and copy number by cross-species duplex quantitative PCR," Gene Ther (Jan. 2016, e-pub. Jun. 30, 2015) 23(1):113-118.
Cohen et al., "B-cell maturation antigen-specific CAR T cells are clinically active in multiple myeloma," J Clin Invest (Mar. 21, 2019) 129(6):2210-2221.
Drechsel et al., "739. Towards Automated Manufacturing of Clinical Scale Gene-Modified T Cells," Next Generation RNA Virus Vectors (May 2014) 22(Supplement 1):S286.
EP 19197801.4 Application as filed on Apr. 23, 2015, by Juno Therapeutics Inc, "Methods for isolating, culturing, and genetically engineering immune cell populations for adoptive therapy," PCT/US2015/027401, 150 pages. D3.
EP 23164036.8 Application as filed on Apr. 23, 2015, by Juno Therapeutics Inc, "Methods for isolating, culturing, and genetically engineering immune cell populations for adoptive therapy," PCT/US2015/027401, 149 pages. D2.
Ex-Cell 302. Serum-Free Medium for CHO Cells. Material Safety Data Sheet. SAFC Bioscience, 2 pages. (Year: 2006).
Gardner et al., "Intent to treat leukemia remission by CD19 CAR T cells of defined formulation and dose in children and young adults," Blood (Jun. 22, 2017, e-pub. Apr. 13, 2017) 129(25):3322-3331.
Gattinoni et al., "T memory stem cells in health and disease," Nat Med (Jan. 2017) 23(1): 18-27.
Gattinoni et al., "Paths to stemness: building the ultimate antitumour T cell," Nat Rev Cancer (Oct. 2012, e-pub. Sep. 21, 2012) 12(10):671-684. Advanced Online Publication, pp. 1-14.
Ghassemi et al., "Reducing Ex Vivo Culture Improves the Antileukemic Activity of Chimeric Antigen Receptor (CAR) T Cells," Cancer Immunol Res (Sep. 2018, e-pub. Jul. 20, 2018) 6(9):1100-1109, supplemental pp. 1-10.
GlutaMAX-I (100X). GIBCO invitrogen cell culture. Form No. 3960 (Sep. 2010), 1 page.
Haghikia et al., "Anti-CD19 CAR T cells for refractory myasthenia gravis," Lancet Neurol (Dec. 2023) 22(12):1104-1105.
Han et al., "Masked Chimeric Antigen Receptor for Tumor-Specific Activation," Mol Ther (Jan. 2017) 25(1):274-284.
Harrington et al., "Development of JCARH125: Optimization of a Fully Human Anti-Bcma CAR for Use in the Treatment of Multiple Myeloma," Blood (Dec. 7, 2017) 130(Suppl_1):1813, 3 pages.
Isakov, "Immunoreceptor tyrosine-based activation motif (ITAM), a unique module linking antigen and Fc receptors to their signaling cascades," Leukoc Biol (Jan. 1997) 61(1):6-16.
Jackson et al., "Driving CAR T-cells forward," Nat Rev Clin Oncol (Jun. 2016, e-pub. Mar. 22, 2016) 13(6):370-383. Author Manuscript, 31 pages.
Jeon et al., "Development of a serum-free medium for in vitro expansion of human cytotoxic T lymphocytes using a statistical design," BMC Biotechnology (Sep. 21, 2010) 10:70, 9 pages.
Kaegi et al., "Systematic Review of Safety and Efficacy of Rituximab in Treating Immune-Mediated Disorders," Front Immunol (Sep. 6, 2019) 10:1990, 18 pages.
Kalos et al., "T cells with chimeric antigen receptors have potent antitumor effects and can establish memory in patients with advanced leukemia," Sci Transl Med (Aug. 10, 2011) 3(95):95ra73, 21 pages.
Karnieli et al., "A consensus introduction to serum replacements and serum-free media for cellular therapies," Cytotherapy (Feb. 2017, e-pub. Dec. 22, 2016) 19(2):155-169.
Kim, "Systemic autoinflammatory disorders: autoinflammatory and autoimmune disordersm," Clin Exp Pediatr (Oct. 2023, e-pub. Jul. 4, 2023) 66(10):439-440.
Kishton et al., "Metabolic Regulation of T Cell Longevity and Function in Tumor Immunotherapy," Cell Metab (Jul. 5, 2017) 26(1):94-109.
Kochenderfer et al., "Adoptive transfer of syngeneic T cells transduced with a chimeric antigen receptor that recognizes murine CD19 can eradicate lymphoma and normal B cells", Blood (Nov. 11, 2010, e-pub. Jul. 14, 2010) 116(19):3875-3886.

(56) References Cited

OTHER PUBLICATIONS

Kochenderfer et al., "B-cell depletion and remissions of malignancy along with cytokine-associated toxicity in a clinical trial of anti-CD19 chimeric-antigen-receptor-transduced T cells," Blood (Mar. 22, 2012) 119(12):2709-2720. Including supplementary information, 21 pages.
Krainer et al., "Systemic autoinflammatory diseases," J Autoimmun (May 2020, e-pub. Feb. 1, 2020) 109:102421, 10 pages.
Kueberuwa et al., "CCR7+ selected gene-modified T cells maintain a central memory phenotype and display enhanced persistence in peripheral blood in vivo," J Immunother Cancer (Feb. 21, 2017) 5(14):1-14.
Laport et al., "Adoptive transfer of costimulated T cells induces lymphocytosis in patients with relapsed/refractory non-Hodgkin lymphoma following CD34+-selected hematopoietic cell transplantation," Blood (Sep. 15, 2003, e-pub. May 22, 2003) 102(6):2004-2013.
Leiper et al., "Randomised placebo-controlled trial of rituximab (anti-CD20) in active ulcerative colitis," Gut (Nov. 2011, e-pub. Apr. 6, 2011) 60(11):1520-1526.
Litvinova et al., "The influence of immunoregulatory cytokines IL-2, IL-7, and IL-15 upon activation, proliferation, and apoptosis of immune memory T-cells in vitro," Cell and Tissue Biology (Dec. 11, 2013) 7(6):539-544.
Love et al., "ITAM-mediated signaling by the T-cell antigen receptor," Cold Spring Harb Perspect Biol (Jun. 2010, e-pub. Apr. 28, 2010) 2(6):a002485, 11 pages.
Mailankody et al., "JCARH125, Anti-BCMA CAR T-cell Therapy for Relapsed/Refractory Multiple Myeloma: Initial Proof of Concept Results from a Phase 1/2 Multicenter Study (Evolve)," Blood (Nov. 29, 2018) 132(Supplement 1):957, 4 pages.
Marcus et al., "Allogeneic chimeric antigen receptor-modified cells for adoptive cell therapy of cancer," Expert Opin Biol Ther (Jul. 2014, e-pub. Mar. 24, 2014) 14(7):947-954.
Mcgonagle et al., "A proposed classification of the immunological diseases," PLoS Med (Aug. 2006) 3(8):e297, pp. 1242-1248.
Moeller et al., "Sustained antigen-specific antitumor recall response mediated by gene-modified CD4+ T helper-1 and CD8+ T cells," Cancer Res (Dec. 1, 2007) 67(23):11428-11437.
Muller et al., "CD19-targeted CAR T cells in refractory antisynthetase syndrome," The Lancet (Mar. 11, 2023, e-pub. Feb. 15, 2023) 401(10379):815-818.
Muller et al., "CD19 CAR T-Cell Therapy in Autoimmune Disease—A Case Series with Follow-up," N Engl J Med (Feb. 22, 2024) 390(8):687-700.
Muller et al., "CD19 CAR T-Cell Therapy in Autoimmune Disease—A Case Series with Follow-up," N Engl J Med (Feb. 22, 2024) 390(8):687-700. Supplementary Appendix, 20 pages.
Pecher et al., "CD19-Targeting CAR T Cells for Myositis and Interstitial Lung Disease Associated With Antisynthetase Syndrome," JAMA (Jun. 27, 2023) 329(24):2154-2162.
Porter et al., "Chimeric Antigen Receptor-Modified T Cells in Chronic Lymphoid Leukemia," N Engl J Med (Aug. 2011) 365(8):725-733.
Ramos et al., "CD19-CAR trials," Cancer J (Mar.-Apr. 2014) 20(2):112-118, 12 pages.
Ramos et al., "CD19-CAR trials," Cancer J (Mar.-Apr. 2014) 20(2):112-118. Screenshot of Cancer Journal webpage, 1 page.
Riddell et al., "Adoptive therapy with chimeric antigen receptor-modified T cells of defined subset composition," Cancer J (Mar.-Apr. 2014) 20(2):141-144, 10 pages.
RPMI 1640. catalog #32404, downloaded from https://www.thermofisher.com/us/en/home/technical-resources/media-formulation.192.html. p. 1-2 (Year: 2023).
RPMI-1640 medium. Sigma-Aldrich. p. 1-2 (Year: 2007).
R&D systems, "The Heat Is On: Detecting Chemokine Receptors on Live Cells," Jun. 15, 2018, Downloaded from: https://www.rndsystems.com/blog/heat-detecting-chemokine-receptors-live-cells, 2 pages.
Schett et al., "CAR T-cell therapy in autoimmune diseases," Lancet (Nov. 25, 2023, e-pub. Sep. 22, 2023.) 402(10416):2034-2044.
Schett et al., "Advancements and challenges in CAR T cell therapy in autoimmune diseases," Nat Rev Rheumatol (Sep. 2024, e-pub. Aug. 6, 2024) 20(9):531-544.
Shen et al., "Chimeric antigen receptor containing ICOS signaling domain mediates specific and efficient antitumor effect of T cells against EGFRvIII expressing glioma," J Hematol Oncol (May 9, 2013) 6:33, 7 pages.
Sommermeyer et al., "Chimeric antigen receptor-modified T cells derived from defined CD8+ and CD4+ subsets confer superior antitumor reactivity in vivo," Leukemia (Feb. 2016, e-pub. Sep. 15, 2015) 30: 492-500.
Taubmann et al., "Rescue therapy of antisynthetase syndrome with CD19-targeted CAR-T cells after failure of several B-cell depleting antibodies," Rheumatology (Oxford) (Jan. 4, 2024, e-pub. Jul. 11, 2023) 63(1):e12-e14.
Technical Bulletin, "Animal-Component Free Recombinant Human Insulin is Suitable for Use in Serum-Free Media," SAFC Biosciences. p. 1-4 (Year: 2006).
Thermo Fisher Scientific, Inc. "DynabeadsTM Human T-Activator CD3/CD28 for T Cell Expansion and Activation," Catalog No. 11131D; Downloaded from: https://www.thermofisher.com/order/catalog/product/11131D, Date Unknown, 8 pages.
Turtle, "Chimeric antigen receptor modified T cell therapy for B cell malignancies," Int J Hematol (Feb. 2014, e-pub. Dec. 14, 2013) 99(2):132-140.
U.S. Appl. No. 61/983,415, filed Apr. 23, 2014, by Juno Therapeutics, Inc., "Methods For Isolating, Culturing, And Genetically Engineering Immune Cell Populations For Adoptive Therapy," 71 pages.
U.S. Appl. No. 61/823,253, filed May 14, 2013, Certified priority document; related PCT Application No. PCT/US2014/038005, Date of receipt at the International Bureau Jun. 5, 2014, 171 pages.
Walpole et al., "The weight of nations: an estimation of adult human biomass," BMC Public Health (Jun. 18, 2012) 12:439, 6 pages.
Wang et al., "Adoptive transfer of tumor-primed, in vitro-activated, CD4+ T effector cells (TEs) combined with CD8+ TEs provides intratumoral TE proliferation and synergistic antitumor response," Blood (Jun. 1, 2007, e-pub. Feb. 6, 2007) 109(11):4865-4872.
Who Unit Chart. PeproTech. downloaded from https://www.peprotech.com/en/who-unit-chart. p. 1-2 (Year: 2023).
Zynda et al., "Optimization of a Phenol Red-Free T Cell Expansion Medium to Improve Performance and Workflow Flexibility," Thermo Fisher Scientific, Poster, presented at International Society for Cellular Therapy (ISCT) Melbourne Annual Meeting, May 29-Jun. 1, 2019, one page.

* cited by examiner

CD8+ CAR+

CD4+ CAR+

% Caspase + CAR-T cells

%Subset of CD8 CAR-T cells
CD27+CCR7+
CD27+CCR7-
CD27-CCR7+
CD27-CCR7-

% Cytokine + CD8 CAR-T cells
IL2
IFNγ
TNF
IL2+IFNγ
IL2+TNF
IL2+IFNγ+TNF

%Subset of CD4 CAR-T cells

%Cytokine+ CD4 CAR-T cells
% Cytokine + CD4 CAR-T cells total live cells/well
Day 0
Day 3
Day 6
Day 8
Day 12
Chronic stim AUC
Without Compound 63
With Compound 63

SEQUENCE LISTING

<160> NUMBER OF SEQ ID NOS: 123

<210> SEQ ID NO 1
<211> LENGTH: 12
<212> TYPE: PRT
<213> ORGANISM: Artificial Sequence
<220> FEATURE:
<223> OTHER INFORMATION: spacer (IgG4hinge)

<400> SEQUENCE: 1

Glu Ser Lys Tyr Gly Pro Pro Cys Pro Pro Cys Pro
1               5                   10

<210> SEQ ID NO 2
<211> LENGTH: 36
<212> TYPE: DNA
<213> ORGANISM: Artificial Sequence
<220> FEATURE:
<223> OTHER INFORMATION: spacer (IgG4hinge)

<400> SEQUENCE: 2
gaatctaagt acggaccgcc ctgcccccct tgccct 36

<210> SEQ ID NO 3
<211> LENGTH: 119
<212> TYPE: PRT
<213> ORGANISM: Artificial Sequence
<220> FEATURE:
<223> OTHER INFORMATION: Hinge-CH3 spacer

<400> SEQUENCE: 3

Glu Ser Lys Tyr Gly Pro Pro Cys Pro Pro Cys Pro Gly Gln Pro Arg
1               5                   10                  15

Glu Pro Gln Val Tyr Thr Leu Pro Pro Ser Gln Glu Glu Met Thr Lys
            20                  25                  30

Asn Gln Val Ser Leu Thr Cys Leu Val Lys Gly Phe Tyr Pro Ser Asp
        35                  40                  45

Ile Ala Val Glu Trp Glu Ser Asn Gly Gln Pro Glu Asn Asn Tyr Lys
    50                  55                  60

Thr Thr Pro Pro Val Leu Asp Ser Asp Gly Ser Phe Phe Leu Tyr Ser
65                  70                  75                  80

Arg Leu Thr Val Asp Lys Ser Arg Trp Gln Glu Gly Asn Val Phe Ser
                85                  90                  95

```
Cys Ser Val Met His Glu Ala Leu His Asn His Tyr Thr Gln Lys Ser
            100                 105                 110

Leu Ser Leu Ser Leu Gly Lys
        115


<210> SEQ ID NO 4
<211> LENGTH: 229
<212> TYPE: PRT
<213> ORGANISM: Artificial Sequence
<220> FEATURE:
<223> OTHER INFORMATION: Hinge-CH2-CH3 spacer

<400> SEQUENCE: 4

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 5
<211> LENGTH: 282
<212> TYPE: PRT
<213> ORGANISM: Artificial Sequence
<220> FEATURE:
<223> OTHER INFORMATION: IgD-hinge-Fc

<400> SEQUENCE: 5

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30
```

Thr Thr Arg Asn Thr Gly Arg Gly Gly Glu Glu Lys Lys Lys Glu Lys
35 40 45

Glu Lys Glu Glu Gln Glu Glu Arg Glu Thr Lys Thr Pro Glu Cys Pro
50 55 60

Ser His Thr Gln Pro Leu Gly Val Tyr Leu Leu Thr Pro Ala Val Gln
65 70 75 80

Asp Leu Trp Leu Arg Asp Lys Ala Thr Phe Thr Cys Phe Val Val Gly
85 90 95

Ser Asp Leu Lys Asp Ala His Leu Thr Trp Glu Val Ala Gly Lys Val
100 105 110

Pro Thr Gly Gly Val Glu Glu Gly Leu Leu Glu Arg His Ser Asn Gly
115 120 125

Ser Gln Ser Gln His Ser Arg Leu Thr Leu Pro Arg Ser Leu Trp Asn
130 135 140

Ala Gly Thr Ser Val Thr Cys Thr Leu Asn His Pro Ser Leu Pro Pro
145 150 155 160

Gln Arg Leu Met Ala Leu Arg Glu Pro Ala Ala Gln Ala Pro Val Lys
165 170 175

Leu Ser Leu Asn Leu Leu Ala Ser Ser Asp Pro Pro Glu Ala Ala Ser
180 185 190

Trp Leu Leu Cys Glu Val Ser Gly Phe Ser Pro Pro Asn Ile Leu Leu
195 200 205

Met Trp Leu Glu Asp Gln Arg Glu Val Asn Thr Ser Gly Phe Ala Pro
210 215 220

Ala Arg Pro Pro Pro Gln Pro Gly Ser Thr Thr Phe Trp Ala Trp Ser
225 230 235 240

Val Leu Arg Val Pro Ala Pro Pro Ser Pro Gln Pro Ala Thr Tyr Thr
245 250 255

Cys Val Val Ser His Glu Asp Ser Arg Thr Leu Leu Asn Ala Ser Arg
260 265 270

Ser Leu Glu Val Ser Tyr Val Thr Asp His
275 280

<210> SEQ ID NO 6
<211> LENGTH: 24
<212> TYPE: PRT
<213> ORGANISM: Artificial Sequence
<220> FEATURE:
<223> OTHER INFORMATION: T2A

<400> SEQUENCE: 6

Leu Glu Gly Gly Gly Glu Gly Arg Gly Ser Leu Leu Thr Cys Gly Asp
1 5 10 15

Val Glu Glu Asn Pro Gly Pro Arg
20

<210> SEQ ID NO 7
<211> LENGTH: 357
<212> TYPE: PRT
<213> ORGANISM: Artificial Sequence
<220> FEATURE:
<223> OTHER INFORMATION: tEGFR

<400> SEQUENCE: 7

Met Leu Leu Leu Val Thr Ser Leu Leu Leu Cys Glu Leu Pro His Pro
1 5 10 15

```
Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80

Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
    130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
    210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
    290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Leu Val Val Ala Leu Gly
            340                 345                 350

Ile Gly Leu Phe Met
        355


<210> SEQ ID NO 8
<211> LENGTH: 27
<212> TYPE: PRT
<213> ORGANISM: Homo sapiens
<220> FEATURE:
<223> OTHER INFORMATION: CD28 (amino acids 153-179 of Accession No.
      P10747)
```

<400> SEQUENCE: 8

Phe Trp Val Leu Val Val Val Gly Gly Val Leu Ala Cys Tyr Ser Leu
1 5 10 15

Leu Val Thr Val Ala Phe Ile Ile Phe Trp Val
20 25

<210> SEQ ID NO 9
<211> LENGTH: 66
<212> TYPE: PRT
<213> ORGANISM: Homo sapiens
<220> FEATURE:
<223> OTHER INFORMATION: CD28 (amino acids 114-179 of Accession No. P10747)

<400> SEQUENCE: 9

Ile Glu Val Met Tyr Pro Pro Pro Tyr Leu Asp Asn Glu Lys Ser Asn
1 5 10 15

Gly Thr Ile Ile His Val Lys Gly Lys His Leu Cys Pro Ser Pro Leu
20 25 30

Phe Pro Gly Pro Ser Lys Pro Phe Trp Val Leu Val Val Val Gly Gly
35 40 45

Val Leu Ala Cys Tyr Ser Leu Leu Val Thr Val Ala Phe Ile Ile Phe
50 55 60

Trp Val
65

<210> SEQ ID NO 10
<211> LENGTH: 41
<212> TYPE: PRT
<213> ORGANISM: Homo sapiens
<220> FEATURE:
<223> OTHER INFORMATION: CD28 (amino acids 180-220 of P10747)

<400> SEQUENCE: 10

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 11
<211> LENGTH: 41
<212> TYPE: PRT
<213> ORGANISM: Artificial Sequence
<220> FEATURE:
<223> OTHER INFORMATION: CD28 (LL to GG)

<400> SEQUENCE: 11

Arg Ser Lys Arg Ser Arg Gly Gly His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 12
<211> LENGTH: 42
<212> TYPE: PRT
<213> ORGANISM: Homo sapiens
<220> FEATURE:

<223> OTHER INFORMATION: 4-1BB (amino acids 214-255 of Q07011.1)

<400> SEQUENCE: 12

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 13
<211> LENGTH: 112
<212> TYPE: PRT
<213> ORGANISM: Homo sapiens
<220> FEATURE:
<223> OTHER INFORMATION: CD3 zeta

<400> SEQUENCE: 13

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 14
<211> LENGTH: 112
<212> TYPE: PRT
<213> ORGANISM: Homo sapiens
<220> FEATURE:
<223> OTHER INFORMATION: CD3 zeta

<400> SEQUENCE: 14

```
Arg Val Lys Phe Ser Arg Ser Ala Glu Pro Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 15
<211> LENGTH: 112
<212> TYPE: PRT

<213> ORGANISM: Homo sapiens
<220> FEATURE:
<223> OTHER INFORMATION: CD3 zeta

<400> SEQUENCE: 15

Arg Val Lys Phe Ser Arg Ser Ala Asp Ala Pro Ala Tyr Lys Gln Gly
1 5 10 15

Gln Asn Gln Leu Tyr Asn Glu Leu Asn Leu Gly Arg Arg Glu Glu Tyr
20 25 30

Asp Val Leu Asp Lys Arg Arg Gly Arg Asp Pro Glu Met Gly Gly Lys
35 40 45

Pro Arg Arg Lys Asn Pro Gln Glu Gly Leu Tyr Asn Glu Leu Gln Lys
50 55 60

Asp Lys Met Ala Glu Ala Tyr Ser Glu Ile Gly Met Lys Gly Glu Arg
65 70 75 80

Arg Arg Gly Lys Gly His Asp Gly Leu Tyr Gln Gly Leu Ser Thr Ala
85 90 95

Thr Lys Asp Thr Tyr Asp Ala Leu His Met Gln Ala Leu Pro Pro Arg
100 105 110

<210> SEQ ID NO 16
<211> LENGTH: 335
<212> TYPE: PRT
<213> ORGANISM: Artificial Sequence
<220> FEATURE:
<223> OTHER INFORMATION: tEGFR

<400> SEQUENCE: 16

Arg Lys Val Cys Asn Gly Ile Gly Ile Gly Glu Phe Lys Asp Ser Leu
1 5 10 15

Ser Ile Asn Ala Thr Asn Ile Lys His Phe Lys Asn Cys Thr Ser Ile
20 25 30

Ser Gly Asp Leu His Ile Leu Pro Val Ala Phe Arg Gly Asp Ser Phe
35 40 45

Thr His Thr Pro Pro Leu Asp Pro Gln Glu Leu Asp Ile Leu Lys Thr
50 55 60

Val Lys Glu Ile Thr Gly Phe Leu Leu Ile Gln Ala Trp Pro Glu Asn
65 70 75 80

Arg Thr Asp Leu His Ala Phe Glu Asn Leu Glu Ile Ile Arg Gly Arg
85 90 95

Thr Lys Gln His Gly Gln Phe Ser Leu Ala Val Val Ser Leu Asn Ile
100 105 110

Thr Ser Leu Gly Leu Arg Ser Leu Lys Glu Ile Ser Asp Gly Asp Val
115 120 125

Ile Ile Ser Gly Asn Lys Asn Leu Cys Tyr Ala Asn Thr Ile Asn Trp
130 135 140

Lys Lys Leu Phe Gly Thr Ser Gly Gln Lys Thr Lys Ile Ile Ser Asn
145 150 155 160

Arg Gly Glu Asn Ser Cys Lys Ala Thr Gly Gln Val Cys His Ala Leu
165 170 175

Cys Ser Pro Glu Gly Cys Trp Gly Pro Glu Pro Arg Asp Cys Val Ser
180 185 190

Cys Arg Asn Val Ser Arg Gly Arg Glu Cys Val Asp Lys Cys Asn Leu
195 200 205

Leu Glu Gly Glu Pro Arg Glu Phe Val Glu Asn Ser Glu Cys Ile Gln
210 215 220

Cys His Pro Glu Cys Leu Pro Gln Ala Met Asn Ile Thr Cys Thr Gly
225 230 235 240

Arg Gly Pro Asp Asn Cys Ile Gln Cys Ala His Tyr Ile Asp Gly Pro
245 250 255

His Cys Val Lys Thr Cys Pro Ala Gly Val Met Gly Glu Asn Asn Thr
260 265 270

Leu Val Trp Lys Tyr Ala Asp Ala Gly His Val Cys His Leu Cys His
275 280 285

Pro Asn Cys Thr Tyr Gly Cys Thr Gly Pro Gly Leu Glu Gly Cys Pro
290 295 300

Thr Asn Gly Pro Lys Ile Pro Ser Ile Ala Thr Gly Met Val Gly Ala
305 310 315 320

Leu Leu Leu Leu Leu Val Val Ala Leu Gly Ile Gly Leu Phe Met
325 330 335

<210> SEQ ID NO 17
<211> LENGTH: 18
<212> TYPE: PRT
<213> ORGANISM: Artificial Sequence
<220> FEATURE:
<223> OTHER INFORMATION: T2A

<400> SEQUENCE: 17

Glu Gly Arg Gly Ser Leu Leu Thr Cys Gly Asp Val Glu Glu Asn Pro
1 5 10 15

Gly Pro

<210> SEQ ID NO 18
<211> LENGTH: 22
<212> TYPE: PRT
<213> ORGANISM: Artificial Sequence
<220> FEATURE:
<223> OTHER INFORMATION: P2A

<400> SEQUENCE: 18

Gly Ser Gly Ala Thr Asn Phe Ser Leu Leu Lys Gln Ala Gly Asp Val
1 5 10 15

Glu Glu Asn Pro Gly Pro
20

<210> SEQ ID NO 19
<211> LENGTH: 19
<212> TYPE: PRT
<213> ORGANISM: Artificial Sequence
<220> FEATURE:
<223> OTHER INFORMATION: P2A

<400> SEQUENCE: 19

Ala Thr Asn Phe Ser Leu Leu Lys Gln Ala Gly Asp Val Glu Glu Asn
1 5 10 15

Pro Gly Pro

<210> SEQ ID NO 20
<211> LENGTH: 20
<212> TYPE: PRT
<213> ORGANISM: Artificial Sequence
<220> FEATURE:
<223> OTHER INFORMATION: E2A

<400> SEQUENCE: 20

Gln Cys Thr Asn Tyr Ala Leu Leu Lys Leu Ala Gly Asp Val Glu Ser
1 5 10 15

Asn Pro Gly Pro
20

<210> SEQ ID NO 21
<211> LENGTH: 22
<212> TYPE: PRT
<213> ORGANISM: Artificial Sequence
<220> FEATURE:
<223> OTHER INFORMATION: F2A

<400> SEQUENCE: 21

Val Lys Gln Thr Leu Asn Phe Asp Leu Leu Lys Leu Ala Gly Asp Val
1 5 10 15

Glu Ser Asn Pro Gly Pro
20

<210> SEQ ID NO 22
<211> LENGTH: 10
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (5)...(9)
<223> OTHER INFORMATION: SGGGG is repeated 5 times

<400> SEQUENCE: 22

Pro Gly Gly Gly Ser Gly Gly Gly Gly Pro
1 5 10

<210> SEQ ID NO 23
<211> LENGTH: 17
<212> TYPE: PRT
<213> ORGANISM: Artificial Sequence
<220> FEATURE:
<223> OTHER INFORMATION: Linker

<400> SEQUENCE: 23

Gly Ser Ala Asp Asp Ala Lys Lys Asp Ala Ala Lys Lys Asp Gly Lys
1 5 10 15

Ser

<210> SEQ ID NO 24
<211> LENGTH: 66
<212> TYPE: DNA
<213> ORGANISM: Artificial Sequence
<220> FEATURE:
<223> OTHER INFORMATION: GMCSFR alpha chain signal sequence

<400> SEQUENCE: 24
atgcttctcc tggtgacaag ccttctgctc tgtgagttac cacacccagc attcctcctg 60
atccca 66

<210> SEQ ID NO 25
<211> LENGTH: 22
<212> TYPE: PRT
<213> ORGANISM: Artificial Sequence
<220> FEATURE:
<223> OTHER INFORMATION: GMCSFR alpha chain signal sequence

<400> SEQUENCE: 25

Met Leu Leu Leu Val Thr Ser Leu Leu Leu Cys Glu Leu Pro His Pro
1 5 10 15

```
Ala Phe Leu Leu Ile Pro
            20


<210> SEQ ID NO 26
<211> LENGTH: 18
<212> TYPE: PRT
<213> ORGANISM: Artificial Sequence
<220> FEATURE:
<223> OTHER INFORMATION: CD8 alpha signal peptide

<400> SEQUENCE: 26

Met Ala Leu Pro Val Thr Ala Leu Leu Leu Pro Leu Ala Leu Leu Leu
1               5                   10                  15

His Ala


<210> SEQ ID NO 27
<211> LENGTH: 15
<212> TYPE: PRT
<213> ORGANISM: Artificial Sequence
<220> FEATURE:
<223> OTHER INFORMATION: Hinge

<400> SEQUENCE: 27

Glu Pro Lys Ser Cys Asp Lys Thr His Thr Cys Pro Pro Cys Pro
1               5                   10                  15


<210> SEQ ID NO 28
<211> LENGTH: 12
<212> TYPE: PRT
<213> ORGANISM: Artificial Sequence
<220> FEATURE:
<223> OTHER INFORMATION: Hinge

<400> SEQUENCE: 28

Glu Arg Lys Cys Cys Val Glu Cys Pro Pro Cys Pro
1               5                   10


<210> SEQ ID NO 29
<211> LENGTH: 61
<212> TYPE: PRT
<213> ORGANISM: Artificial Sequence
<220> FEATURE:
<223> OTHER INFORMATION: Hinge

<400> SEQUENCE: 29

Glu Leu Lys Thr Pro Leu Gly Asp Thr His Thr Cys Pro Arg Cys Pro
1               5                   10                  15

Glu Pro Lys Ser Cys Asp Thr Pro Pro Pro Cys Pro Arg Cys Pro Glu
            20                  25                  30

Pro Lys Ser Cys Asp Thr Pro Pro Pro Cys Pro Arg Cys Pro Glu Pro
        35                  40                  45

Lys Ser Cys Asp Thr Pro Pro Pro Cys Pro Arg Cys Pro
    50                  55                  60


<210> SEQ ID NO 30
<211> LENGTH: 12
<212> TYPE: PRT
<213> ORGANISM: Artificial Sequence
<220> FEATURE:
<223> OTHER INFORMATION: Hinge

<400> SEQUENCE: 30

Glu Ser Lys Tyr Gly Pro Pro Cys Pro Ser Cys Pro
1               5                   10
```

<210> SEQ ID NO 31
<211> LENGTH: 5
<212> TYPE: PRT
<213> ORGANISM: Artificial Sequence
<220> FEATURE:
<223> OTHER INFORMATION: Hinge
<220> FEATURE:
<221> NAME/KEY: VARIANT
<222> LOCATION: 1
<223> OTHER INFORMATION: Xaa is glycine, cysteine or arginine
<220> FEATURE:
<221> NAME/KEY: VARIANT
<222> LOCATION: 4
<223> OTHER INFORMATION: Xaa is cysteine or threonine

<400> SEQUENCE: 31

Xaa Pro Pro Xaa Pro
1               5

<210> SEQ ID NO 32
<211> LENGTH: 9
<212> TYPE: PRT
<213> ORGANISM: Artificial Sequence
<220> FEATURE:
<223> OTHER INFORMATION: Hinge

<400> SEQUENCE: 32

Tyr Gly Pro Pro Cys Pro Pro Cys Pro
1               5

<210> SEQ ID NO 33
<211> LENGTH: 10
<212> TYPE: PRT
<213> ORGANISM: Artificial Sequence
<220> FEATURE:
<223> OTHER INFORMATION: Hinge

<400> SEQUENCE: 33

Lys Tyr Gly Pro Pro Cys Pro Pro Cys Pro
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Hinge

<400> SEQUENCE: 34

Glu Val Val Val Lys Tyr Gly Pro Pro Cys Pro Pro Cys Pro
1               5                   10

<210> SEQ ID NO 35
<211> LENGTH: 11
<212> TYPE: PRT
<213> ORGANISM: Artificial Sequence
<220> FEATURE:
<223> OTHER INFORMATION: FMC63 CDR L1

<400> SEQUENCE: 35

Arg Ala Ser Gln Asp Ile Ser Lys Tyr Leu Asn
1               5                   10

<210> SEQ ID NO 36
<211> LENGTH: 7
<212> TYPE: PRT
<213> ORGANISM: Artificial Sequence
<220> FEATURE:

<223> OTHER INFORMATION: FMC63 CDR L2

<400> SEQUENCE: 36

Ser Arg Leu His Ser Gly Val
1 5

<210> SEQ ID NO 37
<211> LENGTH: 9
<212> TYPE: PRT
<213> ORGANISM: Artificial Sequence
<220> FEATURE:
<223> OTHER INFORMATION: FMC63 CDR L3

<400> SEQUENCE: 37

Gly Asn Thr Leu Pro Tyr Thr Phe Gly
1 5

<210> SEQ ID NO 38
<211> LENGTH: 5
<212> TYPE: PRT
<213> ORGANISM: Artificial Sequence
<220> FEATURE:
<223> OTHER INFORMATION: FMC63 CDR H1

<400> SEQUENCE: 38

Asp Tyr Gly Val Ser
1 5

<210> SEQ ID NO 39
<211> LENGTH: 16
<212> TYPE: PRT
<213> ORGANISM: Artificial Sequence
<220> FEATURE:
<223> OTHER INFORMATION: FMC63 CDR H2

<400> SEQUENCE: 39

Val Ile Trp Gly Ser Glu Thr Thr Tyr Tyr Asn Ser Ala Leu Lys Ser
1 5 10 15

<210> SEQ ID NO 40
<211> LENGTH: 7
<212> TYPE: PRT
<213> ORGANISM: Artificial Sequence
<220> FEATURE:
<223> OTHER INFORMATION: FMC63 CDR H3

<400> SEQUENCE: 40

Tyr Ala Met Asp Tyr Trp Gly
1 5

<210> SEQ ID NO 41
<211> LENGTH: 120
<212> TYPE: PRT
<213> ORGANISM: Artificial Sequence
<220> FEATURE:
<223> OTHER INFORMATION: FMC63 VH

<400> SEQUENCE: 41

Glu Val Lys Leu Gln Glu Ser Gly Pro Gly Leu Val Ala Pro Ser Gln
1 5 10 15

Ser Leu Ser Val Thr Cys Thr Val Ser Gly Val Ser Leu Pro Asp Tyr
20 25 30

Gly Val Ser Trp Ile Arg Gln Pro Pro Arg Lys Gly Leu Glu Trp Leu
35 40 45

```
Gly Val Ile Trp Gly Ser Glu Thr Thr Tyr Tyr Asn Ser Ala Leu Lys
    50                  55                  60

Ser Arg Leu Thr Ile Ile Lys Asp Asn Ser Lys Ser Gln Val Phe Leu
65                  70                  75                  80

Lys Met Asn Ser Leu Gln Thr Asp Asp Thr Ala Ile Tyr Tyr Cys Ala
                85                  90                  95

Lys His Tyr Tyr Tyr Gly Gly Ser Tyr Ala Met Asp Tyr Trp Gly Gln
            100                 105                 110

Gly Thr Ser Val Thr Val Ser Ser
        115                 120


<210> SEQ ID NO 42
<211> LENGTH: 107
<212> TYPE: PRT
<213> ORGANISM: Artificial Sequence
<220> FEATURE:
<223> OTHER INFORMATION: FMC63 VL

<400> SEQUENCE: 42

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr
            100                 105


<210> SEQ ID NO 43
<211> LENGTH: 245
<212> TYPE: PRT
<213> ORGANISM: Artificial Sequence
<220> FEATURE:
<223> OTHER INFORMATION: FMC63 scFv

<400> SEQUENCE: 43

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Ser Thr Ser Gly
            100                 105                 110
```

```
Ser Gly Lys Pro Gly Ser Gly Glu Gly Ser Thr Lys Gly Glu Val Lys
        115                 120                 125

Leu Gln Glu Ser Gly Pro Gly Leu Val Ala Pro Ser Gln Ser Leu Ser
    130                 135                 140

Val Thr Cys Thr Val Ser Gly Val Ser Leu Pro Asp Tyr Gly Val Ser
145                 150                 155                 160

Trp Ile Arg Gln Pro Pro Arg Lys Gly Leu Glu Trp Leu Gly Val Ile
                165                 170                 175

Trp Gly Ser Glu Thr Thr Tyr Tyr Asn Ser Ala Leu Lys Ser Arg Leu
            180                 185                 190

Thr Ile Ile Lys Asp Asn Ser Lys Ser Gln Val Phe Leu Lys Met Asn
        195                 200                 205

Ser Leu Gln Thr Asp Asp Thr Ala Ile Tyr Tyr Cys Ala Lys His Tyr
    210                 215                 220

Tyr Tyr Gly Gly Ser Tyr Ala Met Asp Tyr Trp Gly Gln Gly Thr Ser
225                 230                 235                 240

Val Thr Val Ser Ser
                245


<210> SEQ ID NO 44
<211> LENGTH: 11
<212> TYPE: PRT
<213> ORGANISM: KASQNVGTNVAArtificial Sequence
<220> FEATURE:
<223> OTHER INFORMATION: SJ25C1 CDR L1

<400> SEQUENCE: 44

Lys Ala Ser Gln Asn Val Gly Thr Asn Val Ala
1               5                   10


<210> SEQ ID NO 45
<211> LENGTH: 7
<212> TYPE: PRT
<213> ORGANISM: Artificial Sequence
<220> FEATURE:
<223> OTHER INFORMATION: SJ25C1 CDR L2

<400> SEQUENCE: 45

Ser Ala Thr Tyr Arg Asn Ser
1               5


<210> SEQ ID NO 46
<211> LENGTH: 9
<212> TYPE: PRT
<213> ORGANISM: Artificial Sequence
<220> FEATURE:
<223> OTHER INFORMATION: SJ25C1 CDR L3

<400> SEQUENCE: 46

Gln Gln Tyr Asn Arg Tyr Pro Tyr Thr
1               5


<210> SEQ ID NO 47
<211> LENGTH: 5
<212> TYPE: PRT
<213> ORGANISM: Artificial Sequence
<220> FEATURE:
<223> OTHER INFORMATION: SJ25C1 CDR H1

<400> SEQUENCE: 47

Ser Tyr Trp Met Asn
1               5
```

<210> SEQ ID NO 48
<211> LENGTH: 17
<212> TYPE: PRT
<213> ORGANISM: Artificial Sequence
<220> FEATURE:
<223> OTHER INFORMATION: SJ25C1 CDR H2

<400> SEQUENCE: 48

```
Gln Ile Tyr Pro Gly Asp Gly Asp Thr Asn Tyr Asn Gly Lys Phe Lys
1               5                   10                  15

Gly
```

<210> SEQ ID NO 49
<211> LENGTH: 13
<212> TYPE: PRT
<213> ORGANISM: Artificial Sequence
<220> FEATURE:
<223> OTHER INFORMATION: SJ25C1 CDR H3

<400> SEQUENCE: 49

```
Lys Thr Ile Ser Ser Val Val Asp Phe Tyr Phe Asp Tyr
1               5                   10
```

<210> SEQ ID NO 50
<211> LENGTH: 122
<212> TYPE: PRT
<213> ORGANISM: Artificial Sequence
<220> FEATURE:
<223> OTHER INFORMATION: SJ25C1 VH

<400> SEQUENCE: 50

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser
        115                 120
```

<210> SEQ ID NO 51
<211> LENGTH: 108
<212> TYPE: PRT
<213> ORGANISM: Artificial Sequence
<220> FEATURE:
<223> OTHER INFORMATION: SJ25C1 VL

<400> SEQUENCE: 51

```
Asp Ile Glu Leu Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30
```

-continued

```
Val Ala Trp Tyr Gln Gln Lys Pro Gly Gln Ser Pro Lys Pro Leu Ile
        35                  40                  45

Tyr Ser Ala Thr Tyr Arg Asn Ser Gly Val Pro Asp Arg Phe Thr Gly
    50                  55                  60

Ser Gly Ser Gly Thr Asp Phe Thr Leu Thr Ile Thr Asn Val Gln Ser
65                  70                  75                  80

Lys Asp Leu Ala Asp Tyr Phe Cys Gln Gln Tyr Asn Arg Tyr Pro Tyr
                85                  90                  95

Thr Ser Gly Gly Gly Thr Lys Leu Glu Ile Lys Arg
            100                 105
```

<210> SEQ ID NO 52
<211> LENGTH: 15
<212> TYPE: PRT
<213> ORGANISM: Artificial Sequence
<220> FEATURE:
<223> OTHER INFORMATION: Linker

<400> SEQUENCE: 52

```
Gly Gly Gly Gly Ser Gly Gly Gly Gly Ser Gly Gly Gly Gly Ser
1               5                   10                  15
```

<210> SEQ ID NO 53
<211> LENGTH: 245
<212> TYPE: PRT
<213> ORGANISM: Artificial Sequence
<220> FEATURE:
<223> OTHER INFORMATION: SJ25C1 scFv

<400> SEQUENCE: 53

```
Glu Val Lys Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Gly Asp Thr Asn Tyr Asn Gly Lys Phe
    50                  55                  60

Lys Gly Gln Ala Thr Leu Thr Ala Asp Lys Ser Ser Ser Thr Ala Tyr
65                  70                  75                  80

Met Gln Leu Ser Gly Leu Thr Ser Glu Asp Ser Ala Val Tyr Phe Cys
                85                  90                  95

Ala Arg Lys Thr Ile Ser Ser Val Val Asp Phe Tyr Phe Asp Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Glu Leu Thr Gln Ser
    130                 135                 140

Pro Lys Phe Met Ser Thr Ser Val Gly Asp Arg Val Ser Val Thr Cys
145                 150                 155                 160

Lys Ala Ser Gln Asn Val Gly Thr Asn Val Ala Trp Tyr Gln Gln Lys
                165                 170                 175

Pro Gly Gln Ser Pro Lys Pro Leu Ile Tyr Ser Ala Thr Tyr Arg Asn
            180                 185                 190

Ser Gly Val Pro Asp Arg Phe Thr Gly Ser Gly Ser Gly Thr Asp Phe
        195                 200                 205

Thr Leu Thr Ile Thr Asn Val Gln Ser Lys Asp Leu Ala Asp Tyr Phe
    210                 215                 220
```

Cys Gln Gln Tyr Asn Arg Tyr Pro Tyr Thr Ser Gly Gly Gly Thr Lys
225 230 235 240

Leu Glu Ile Lys Arg
245

<210> SEQ ID NO 54
<211> LENGTH: 12
<212> TYPE: PRT
<213> ORGANISM: Artificial Sequence
<220> FEATURE:
<223> OTHER INFORMATION: FMC63 HC-CDR3

<400> SEQUENCE: 54

His Tyr Tyr Tyr Gly Gly Ser Tyr Ala Met Asp Tyr
1 5 10

<210> SEQ ID NO 55
<211> LENGTH: 7
<212> TYPE: PRT
<213> ORGANISM: Artificial Sequence
<220> FEATURE:
<223> OTHER INFORMATION: FMC63 LC-CDR2

<400> SEQUENCE: 55

His Thr Ser Arg Leu His Ser
1 5

<210> SEQ ID NO 56
<211> LENGTH: 9
<212> TYPE: PRT
<213> ORGANISM: Artificial Sequence
<220> FEATURE:
<223> OTHER INFORMATION: FMC63 LC-CDR3

<400> SEQUENCE: 56

Gln Gln Gly Asn Thr Leu Pro Tyr Thr
1 5

<210> SEQ ID NO 57
<211> LENGTH: 735
<212> TYPE: DNA
<213> ORGANISM: Artificial Sequence
<220> FEATURE:
<223> OTHER INFORMATION: Sequence encoding scFv

<400> SEQUENCE: 57
gacatccaga tgacccagac cacctccagc ctgagcgcca gcctgggcga ccgggtgacc 60
atcagctgcc gggccagcca ggacatcagc aagtacctga actggtatca gcagaagccc 120
gacggcaccg tcaagctgct gatctaccac accagccggc tgcacagcgg cgtgcccagc 180
cggtttagcg gcagcggctc cggcaccgac tacagcctga ccatctccaa cctggaacag 240
gaagatatcg ccacctactt ttgccagcag ggcaacacac tgccctacac ctttggcggc 300
ggaacaaagc tggaaatcac cggcagcacc tccggcagcg gcaagcctgg cagcggcgag 360
ggcagcacca agggcgaggt gaagctgcag gaaagcggcc ctggcctggt ggccccccagc 420 cagagcctga gcgtgacctg caccgtgagc ggcgtgagcc tgcccgacta cggcgtgagc 480
tggatccggc agccccccag gaagggcctg gaatggctgg gcgtgatctg gggcagcgag 540
accacctact acaacagcgc cctgaagagc cggctgacca tcatcaagga caacagcaag 600
agccaggtgt tcctgaagat gaacagcctg cagaccgacg acaccgccat ctactactgc 660
gccaagcact actactacgg cggcagctac gccatggact actggggcca gggcaccagc 720
gtgaccgtga gcagc 735

<210> SEQ ID NO 58
<211> LENGTH: 18
<212> TYPE: PRT
<213> ORGANISM: Artificial Sequence
<220> FEATURE:
<223> OTHER INFORMATION: Linker

<400> SEQUENCE: 58

Gly Ser Thr Ser Gly Ser Gly Lys Pro Gly Ser Gly Glu Gly Ser Thr
1 5 10 15

Lys Gly

<210> SEQ ID NO 59
<211> LENGTH: 326
<212> TYPE: PRT
<213> ORGANISM: Homo sapiens
<220> FEATURE:
<223> OTHER INFORMATION: Human IgG2 Fc (Uniprot P01859)

<400> SEQUENCE: 59

Ala Ser Thr Lys Gly Pro Ser Val Phe Pro Leu Ala Pro Cys Ser Arg
1 5 10 15

Ser Thr Ser Glu Ser Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Asn Phe Gly Thr Gln Thr
65 70 75 80

Tyr Thr Cys Asn Val Asp His Lys Pro Ser Asn Thr Lys Val Asp Lys
85 90 95

Thr Val Glu Arg Lys Cys Cys Val Glu Cys Pro Pro Cys Pro Ala Pro
100 105 110

Pro Val Ala Gly Pro Ser Val Phe Leu Phe Pro Pro Lys Pro Lys Asp
115 120 125

Thr Leu Met Ile Ser Arg Thr Pro Glu Val Thr Cys Val Val Val Asp
130 135 140

Val Ser His Glu Asp Pro Glu Val Gln Phe Asn Trp Tyr Val Asp Gly
145 150 155 160

Val Glu Val His Asn Ala Lys Thr Lys Pro Arg Glu Glu Gln Phe Asn
165 170 175

Ser Thr Phe Arg Val Val Ser Val Leu Thr Val Val His Gln Asp Trp
180 185 190

Leu Asn Gly Lys Glu Tyr Lys Cys Lys Val Ser Asn Lys Gly Leu Pro
195 200 205

Ala Pro Ile Glu Lys Thr Ile Ser Lys Thr Lys Gly Gln Pro Arg Glu
210 215 220

Pro Gln Val Tyr Thr Leu Pro Pro Ser Arg Glu Glu Met Thr Lys Asn
225 230 235 240

Gln Val Ser Leu Thr Cys Leu Val Lys Gly Phe Tyr Pro Ser Asp Ile
245 250 255

```
Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325


<210> SEQ ID NO 60
<211> LENGTH: 327
<212> TYPE: PRT
<213> ORGANISM: Homo sapiens
<220> FEATURE:
<223> OTHER INFORMATION: Human IgG4 Fc (Uniprot P01861

<400> SEQUENCE: 60

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

```
Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325


<210> SEQ ID NO 61
<211> LENGTH: 159
<212> TYPE: PRT
<213> ORGANISM: Streptomyces avidinii
<220> FEATURE:
<223> OTHER INFORMATION: UniProt No. P22629

<400> SEQUENCE: 61

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155


<210> SEQ ID NO 62
<211> LENGTH: 126
<212> TYPE: PRT
<213> ORGANISM: Streptomyces avidinii
<220> FEATURE:
<223> OTHER INFORMATION: Minimal streptavidin

<400> SEQUENCE: 62

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Glu Ser
            20                  25                  30

Ala Val Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95
```

```
Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125


<210> SEQ ID NO 63
<211> LENGTH: 126
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 63

Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Ile Gly
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110

Gly His Asp Thr Phe Thr Lys Val Lys Pro Ser Ala Ala Ser
        115                 120                 125


<210> SEQ ID NO 64
<211> LENGTH: 8
<212> TYPE: PRT
<213> ORGANISM: Artificial Sequence
<220> FEATURE:
<223> OTHER INFORMATION: Strep-tag

<400> SEQUENCE: 64

Trp Ser His Pro Gln Phe Glu Lys
1               5


<210> SEQ ID NO 65
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 65

Trp Ser His Pro Gln Phe Glu Lys Gly Gly Gly Ser Gly Gly Gly Ser
1               5                   10                  15

Gly Gly Gly Ser Trp Ser His Pro Gln Phe Glu Lys
            20                  25


<210> SEQ ID NO 66
<211> LENGTH: 24
<212> TYPE: PRT
<213> ORGANISM: Artificial Sequence
<220> FEATURE:
<223> OTHER INFORMATION: Twin-Strep-tag
```

<400> SEQUENCE: 66

```
Trp Ser His Pro Gln Phe Glu Lys Gly Gly Gly Ser Gly Gly Gly Ser
1               5                   10                  15

Trp Ser His Pro Gln Phe Glu Lys
            20
```

<210> SEQ ID NO 67
<211> LENGTH: 28
<212> TYPE: PRT
<213> ORGANISM: Artificial Sequence
<220> FEATURE:
<223> OTHER INFORMATION: Twin-Strep-tag

<400> SEQUENCE: 67

```
Trp Ser His Pro Gln Phe Glu Lys Gly Gly Gly Ser Gly Gly Gly Ser
1               5                   10                  15

Gly Gly Ser Ala Trp Ser His Pro Gln Phe Glu Lys
            20                  25
```

<210> SEQ ID NO 68
<211> LENGTH: 127
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 68

```
Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Ile
            20                  25                  30

Gly Ala Arg Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125
```

<210> SEQ ID NO 69
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is Gly or Glu
<220> FEATURE:
<221> NAME/KEY: VARIANT
<222> LOCATION: 8
<223> OTHER INFORMATION: Xaa is Gly, Lys or Arg

<400> SEQUENCE: 69

Trp Xaa His Pro Gln Phe Xaa Xaa
1               5

<210> SEQ ID NO 70
<211> LENGTH: 8
<212> TYPE: PRT
<213> ORGANISM: Artificial Sequence
<220> FEATURE:
<223> OTHER INFORMATION: Streptavidin binding peptide, Strep-tag

<400> SEQUENCE: 70

Trp Arg His Pro Gln Phe Gly Gly
1               5

<210> SEQ ID NO 71
<211> LENGTH: 28
<212> TYPE: PRT
<213> ORGANISM: Artificial Sequence
<220> FEATURE:
<223> OTHER INFORMATION: Sequential modules of streptavidin-binding peptide
<220> FEATURE:
<221> NAME/KEY: VARIANT
<222> LOCATION: 9
<223> OTHER INFORMATION: Xaa is any amino acid.
<220> FEATURE:
<221> NAME/KEY: VARIANT
<222> LOCATION: 10
<223> OTHER INFORMATION: Xaa is any amino acid.
<220> FEATURE:
<221> NAME/KEY: VARIANT
<222> LOCATION: 11
<223> OTHER INFORMATION: Xaa is any amino acid.
<220> FEATURE:
<221> NAME/KEY: VARIANT
<222> LOCATION: 12
<223> OTHER INFORMATION: Xaa is any amino acid.
<220> FEATURE:
<221> NAME/KEY: VARIANT
<222> LOCATION: 13
<223> OTHER INFORMATION: Xaa is any amino acid.
<220> FEATURE:
<221> NAME/KEY: VARIANT
<222> LOCATION: (14)...(14)
<223> OTHER INFORMATION: Xaa is any amino acid.
<220> FEATURE:
<221> NAME/KEY: VARIANT
<222> LOCATION: (15)...(15)
<223> OTHER INFORMATION: Xaa is any amino acid.
<220> FEATURE:
<221> NAME/KEY: VARIANT
<222> LOCATION: (16)...(16)
<223> OTHER INFORMATION: Xaa is any amino acid.
<220> FEATURE:
<221> NAME/KEY: VARIANT
<222> LOCATION: (17)...(17)
<223> OTHER INFORMATION: Xaa is any amino acid or null.
<220> FEATURE:
<221> NAME/KEY: VARIANT
<222> LOCATION: (18)...(18)
<223> OTHER INFORMATION: If Xaa at position 17 is any amino acid, then Xaa at position 18 is any amino acid. If Xaa at position 17 is null, then Xaa at position 18 is null.
<220> FEATURE:
<221> NAME/KEY: VARIANT
<222> LOCATION: (19)...(19)
<223> OTHER INFORMATION: If Xaa at position 17 is any amino acid, then Xaa at position 19 is any amino acid. If Xaa at position 17 is null, then Xaa at position 19 is null.
<220> FEATURE:
<221> NAME/KEY: VARIANT
<222> LOCATION: (20)...(20)

```
<223> OTHER INFORMATION: If Xaa at position 17 is any amino acid, then
      Xaa at position 20 is any amino acid. If Xaa at
      position 17 is null, then Xaa at position 20 is
      null.

<400> SEQUENCE: 71

Trp Ser His Pro Gln Phe Glu Lys Xaa Xaa Xaa Xaa Xaa Xaa Xaa Xaa
1               5                   10                  15

Xaa Xaa Xaa Xaa Trp Ser His Pro Gln Phe Glu Lys
            20                  25


<210> SEQ ID NO 72
<211> LENGTH: 28
<212> TYPE: PRT
<213> ORGANISM: Artificial Sequence
<220> FEATURE:
<223> OTHER INFORMATION: Sequential modules of streptavidin-binding
      peptide
<220> FEATURE:
<221> NAME/KEY: VARIANT
<222> LOCATION: 17
<223> OTHER INFORMATION: Xaa is Gly or null.
<220> FEATURE:
<221> NAME/KEY: VARIANT
<222> LOCATION: 18
<223> OTHER INFORMATION: If Xaa at position 17 is Gly, then Xaa at
      position 18 is Gly. If Xaa at position 17 is null, then Xaa
      at position 18 is null.
<220> FEATURE:
<221> NAME/KEY: VARIANT
<222> LOCATION: 19
<223> OTHER INFORMATION: If Xaa at position 17 is Gly, then Xaa at
      position 19 is Gly. If Xaa at position 17 is null, then Xaa
      at position 19 is null.
<220> FEATURE:
<221> NAME/KEY: VARIANT
<222> LOCATION: 20
<223> OTHER INFORMATION: If Xaa at position 17 is Gly, then Xaa at
      position 20 is Ser. If Xaa at position 17 is null, then Xaa
      at position 20 is null.

<400> SEQUENCE: 72

Trp Ser His Pro Gln Phe Glu Lys Gly Gly Gly Ser Gly Gly Gly Ser
1               5                   10                  15

Xaa Xaa Xaa Xaa Trp Ser His Pro Gln Phe Glu Lys
            20                  25


<210> SEQ ID NO 73
<211> LENGTH: 30
<212> TYPE: PRT
<213> ORGANISM: Artificial Sequence
<220> FEATURE:
<223> OTHER INFORMATION: Twin-Strep-tag

<400> SEQUENCE: 73

Ser Ala Trp Ser His Pro Gln Phe Glu Lys Gly Gly Gly Ser Gly Gly
1               5                   10                  15

Gly Ser Gly Gly Gly Ser Trp Ser His Pro Gln Phe Glu Lys
            20                  25                  30


<210> SEQ ID NO 74
<211> LENGTH: 30
<212> TYPE: PRT
<213> ORGANISM: Artificial Sequence
<220> FEATURE:
<223> OTHER INFORMATION: Twin-Strep-tag
```

<400> SEQUENCE: 74

```
Ser Ala Trp Ser His Pro Gln Phe Glu Lys Gly Gly Gly Ser Gly Gly
1               5                   10                  15

Gly Ser Gly Gly Ser Ala Trp Ser His Pro Gln Phe Glu Lys
            20                  25                  30
```

<210> SEQ ID NO 75
<211> LENGTH: 159
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 75

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

<210> SEQ ID NO 76
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 76

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Ala Asn Ala Trp Lys Ser Thr Leu Val
            100                 105                 110
```

```
Gly His Asp Thr Phe Thr Lys Val Lys Pro Ser Ala Ala Ser
        115                 120                 125


<210> SEQ ID NO 77
<211> LENGTH: 127
<212> TYPE: PRT
<213> ORGANISM: Streptomyces avidinii
<220> FEATURE:
<223> OTHER INFORMATION: Mutein Streptavidin Val44-Thr45-Ala46-Arg47

<400> SEQUENCE: 77

Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Val
            20                  25                  30

Thr Ala Arg Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125


<210> SEQ ID NO 78
<211> LENGTH: 4
<212> TYPE: PRT
<213> ORGANISM: Artificial Sequence
<220> FEATURE:
<223> OTHER INFORMATION: Streptavidin-binding peptide

<400> SEQUENCE: 78

His Pro Gln Phe
1


<210> SEQ ID NO 79
<211> LENGTH: 8
<212> TYPE: PRT
<213> ORGANISM: Artificial Sequence
<220> FEATURE:
<223> OTHER INFORMATION: Streptavidin-binding peptide
<220> FEATURE:
<221> NAME/KEY: VARIANT
<222> LOCATION: 1
<223> OTHER INFORMATION: Xaa is Trp, Lys or Arg
<220> FEATURE:
<221> NAME/KEY: VARIANT
<222> LOCATION: 2
<223> OTHER INFORMATION: Xaa is any amino acid
<220> FEATURE:
<221> NAME/KEY: VARIANT
<222> LOCATION: 7
<223> OTHER INFORMATION: Xaa is Gly or Glu
<220> FEATURE:
<221> NAME/KEY: VARIANT
<222> LOCATION: 8
<223> OTHER INFORMATION: Xaa is Gly, Lys or Arg

<400> SEQUENCE: 79

Xaa Xaa His Pro Gln Phe Xaa Xaa
1               5
```

<210> SEQ ID NO 80
<211> LENGTH: 159
<212> TYPE: PRT
<213> ORGANISM: Streptomyces avidinii
<220> FEATURE:
<223> OTHER INFORMATION: Mutein Streptavidin Ile44-Gly45-Ala-46-Arg47

<400> SEQUENCE: 80

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Ile Gly Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155
```

<210> SEQ ID NO 81
<211> LENGTH: 126
<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 81

```
Glu Ala Gly Ile Thr Gly Thr Trp Tyr Asn Gln Leu Gly Ser Thr Phe
1               5                   10                  15

Ile Val Thr Ala Gly Ala Asp Gly Ala Leu Thr Gly Thr Tyr Val Thr
            20                  25                  30

Ala Arg Gly Asn Ala Glu Ser Arg Tyr Val Leu Thr Gly Arg Tyr Asp
        35                  40                  45

Ser Ala Pro Ala Thr Asp Gly Ser Gly Thr Ala Leu Gly Trp Thr Val
    50                  55                  60

Ala Trp Lys Asn Asn Tyr Arg Asn Ala His Ser Ala Thr Thr Trp Ser
65                  70                  75                  80

Gly Gln Tyr Val Gly Gly Ala Glu Ala Arg Ile Asn Thr Gln Trp Leu
                85                  90                  95

Leu Thr Ser Gly Thr Thr Glu Glu Asn Ala Gly Tyr Ser Thr Leu Val
            100                 105                 110

Gly His Asp Thr Phe Thr Lys Val Lys Pro Ser Ala Ala Ser
        115                 120                 125
```

<210> SEQ ID NO 82
<211> LENGTH: 139

<212> TYPE: PRT
<213> ORGANISM: Streptomyces avidinii
<220> FEATURE:
<223> OTHER INFORMATION: Mutein Streptavidin Val44-Thr45-Ala46-Arg47 and
      Glu117, Gly120, Try121 (mutein m1-9)

<400> SEQUENCE: 82

```
Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Val Thr Ala Arg Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Glu Asn Ala Gly Tyr Ser Thr Leu Val Gly His Asp
        115                 120                 125

Thr Phe Thr Lys Val Lys Pro Ser Ala Ala Ser
    130                 135
```

<210> SEQ ID NO 83
<211> LENGTH: 127
<212> TYPE: PRT
<213> ORGANISM: Streptomyces avidinii
<220> FEATURE:
<223> OTHER INFORMATION: Minimal streptavidin

<400> SEQUENCE: 83

```
Met Glu Ala Gly Ile Thr Gly Thr Trp Tyr Asn Gln Leu Gly Ser Thr
1               5                   10                  15

Phe Ile Val Thr Ala Gly Ala Asp Gly Ala Leu Thr Gly Thr Tyr Glu
            20                  25                  30

Ser Ala Val Gly Asn Ala Glu Ser Arg Tyr Val Leu Thr Gly Arg Tyr
        35                  40                  45

Asp Ser Ala Pro Ala Thr Asp Gly Ser Gly Thr Ala Leu Gly Trp Thr
    50                  55                  60

Val Ala Trp Lys Asn Asn Tyr Arg Asn Ala His Ser Ala Thr Thr Trp
65                  70                  75                  80

Ser Gly Gln Tyr Val Gly Gly Ala Glu Ala Arg Ile Asn Thr Gln Trp
                85                  90                  95

Leu Leu Thr Ser Gly Thr Thr Glu Ala Asn Ala Trp Lys Ser Thr Leu
            100                 105                 110

Val Gly His Asp Thr Phe Thr Lys Val Lys Pro Ser Ala Ala Ser
        115                 120                 125
```

<210> SEQ ID NO 84
<211> LENGTH: 107
<212> TYPE: PRT
<213> ORGANISM: Artificial Sequence
<220> FEATURE:
<223> OTHER INFORMATION: FKBP

<400> SEQUENCE: 84

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Met Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 85
<211> LENGTH: 107
<212> TYPE: PRT
<213> ORGANISM: Artificial Sequence
<220> FEATURE:
<223> OTHER INFORMATION: FKBP12v36

<400> SEQUENCE: 85

```
Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Val Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu
            100                 105
```

<210> SEQ ID NO 86
<211> LENGTH: 16
<212> TYPE: PRT
<213> ORGANISM: Artificial Sequence
<220> FEATURE:
<223> OTHER INFORMATION: Modified acylation motif

<400> SEQUENCE: 86

```
Met Gly Ser Asn Lys Ser Lys Pro Lys Asp Ala Ser Gln Arg Arg Arg
1               5                   10                  15
```

<210> SEQ ID NO 87
<211> LENGTH: 5
<212> TYPE: PRT
<213> ORGANISM: Artificial Sequence
<220> FEATURE:
<223> OTHER INFORMATION: Dual acylation motif
<220> FEATURE:
<221> NAME/KEY: VARIANT
<222> LOCATION: 4
<223> OTHER INFORMATION: Xaa is any amino acid

<400> SEQUENCE: 87

Met Gly Cys Xaa Cys
1 5

<210> SEQ ID NO 88
<211> LENGTH: 4
<212> TYPE: PRT
<213> ORGANISM: Artificial Sequence
<220> FEATURE:
<223> OTHER INFORMATION: acylation region
<220> FEATURE:
<221> NAME/KEY: VARIANT
<222> LOCATION: 4
<223> OTHER INFORMATION: Xaa is any amino acid

<400> SEQUENCE: 88

Cys Ala Ala Xaa
1

<210> SEQ ID NO 89
<211> LENGTH: 119
<212> TYPE: PRT
<213> ORGANISM: Artificial Sequence
<220> FEATURE:
<223> OTHER INFORMATION: Variable Heavy chain of anti-CD3 antibody OKT3

<400> SEQUENCE: 89

Gln Val Gln Leu Gln Gln Ser Gly Ala Glu Leu Ala Arg Pro Gly Ala
1 5 10 15

Ser Val Lys Met Ser Cys Lys Ala Ser Gly Tyr Thr Phe Thr Arg Tyr
20 25 30

Thr Met His Trp Val Lys Gln Arg Pro Gly Gln Gly Leu Glu Trp Ile
35 40 45

Gly Tyr Ile Asn Pro Ser Arg Gly Tyr Thr Asn Tyr Asn Gln Lys Phe
50 55 60

Lys Asp Lys Ala Thr Leu Thr Thr Asp Lys Ser Ser Ser Thr Ala Tyr
65 70 75 80

Met Gln Leu Ser Ser Leu Thr Ser Glu Asp Ser Ala Val Tyr Tyr Cys
85 90 95

Ala Arg Tyr Tyr Asp Asp His Tyr Cys Leu Asp Tyr Trp Gly Gln Gly
100 105 110

Thr Thr Leu Thr Val Ser Ser
115

<210> SEQ ID NO 90
<211> LENGTH: 106
<212> TYPE: PRT
<213> ORGANISM: Artificial Sequence
<220> FEATURE:
<223> OTHER INFORMATION: Variable Light chain of anti-CD3 antibody OKT3

<400> SEQUENCE: 90

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Val Ser Tyr Met
20 25 30

Asn Trp Tyr Gln Gln Lys Ser Gly Thr Ser Pro Lys Arg Trp Ile Tyr
35 40 45

Asp Thr Ser Lys Leu Ala Ser Gly Val Pro Ala His Phe Arg Gly Ser
50 55 60

```
Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105


<210> SEQ ID NO 91
<211> LENGTH: 116
<212> TYPE: PRT
<213> ORGANISM: Artificial Sequence
<220> FEATURE:
<223> OTHER INFORMATION: Variable Heavy chain of anti-CD28 antibody
      CD28.3

<400> SEQUENCE: 91

Leu Gln Gln Ser Gly Ala Glu Leu Val Lys Pro Gly Ala Ser Val Arg
1               5                   10                  15

Leu Ser Cys Lys Ala Ser Gly Tyr Thr Phe Thr Glu Tyr Ile Ile His
            20                  25                  30

Trp Ile Lys Leu Arg Ser Gly Gln Gly Leu Glu Trp Ile Gly Trp Phe
        35                  40                  45

Tyr Pro Gly Ser Asn Asp Ile Gln Tyr Asn Ala Lys Phe Lys Gly Lys
    50                  55                  60

Ala Thr Leu Thr Ala Asp Lys Ser Ser Ser Thr Val Tyr Met Glu Leu
65                  70                  75                  80

Thr Gly Leu Thr Ser Glu Asp Ser Ala Val Tyr Phe Cys Ala Arg Arg
                85                  90                  95

Asp Asp Phe Ser Gly Tyr Asp Ala Leu Pro Tyr Trp Gly Gln Gly Thr
            100                 105                 110

Met Val Thr Val
        115


<210> SEQ ID NO 92
<211> LENGTH: 108
<212> TYPE: PRT
<213> ORGANISM: Artificial Sequence
<220> FEATURE:
<223> OTHER INFORMATION: Variable Light chain of anti-CD28 antibody
      CD28.3

<400> SEQUENCE: 92

Asp Ile Gln Met Thr Gln Ser Pro Ala Ser Leu Ser Val Ser Val Gly
1               5                   10                  15

Glu Thr Val Thr Ile Thr Cys Arg Thr Asn Glu Asn Ile Tyr Ser Asn
            20                  25                  30

Leu Ala Trp Tyr Gln Gln Lys Gln Gly Lys Ser Pro Gln Leu Leu Ile
        35                  40                  45

Tyr Ala Ala Thr His Leu Val Glu Gly Val Pro Ser Arg Phe Ser Gly
    50                  55                  60

Ser Gly Ser Gly Thr Gln Tyr Ser Leu Lys Ile Thr Ser Leu Gln Ser
65                  70                  75                  80

Glu Asp Phe Gly Asn Tyr Tyr Cys Gln His Phe Trp Gly Thr Pro Cys
                85                  90                  95

Thr Phe Gly Gly Gly Thr Lys Leu Glu Ile Lys Arg
            100                 105


<210> SEQ ID NO 93
<211> LENGTH: 3
```

<212> TYPE: PRT
<213> ORGANISM: Artificial Sequence
<220> FEATURE:
<223> OTHER INFORMATION: Streptavidin Binding peptide
<220> FEATURE:
<221> NAME/KEY: VARIANT
<222> LOCATION: 3
<223> OTHER INFORMATION: Xaa is Gln, Asp, or Met

<400> SEQUENCE: 93

His Pro Xaa
1

<210> SEQ ID NO 94
<211> LENGTH: 9
<212> TYPE: PRT
<213> ORGANISM: Artificial Sequence
<220> FEATURE:
<223> OTHER INFORMATION: HA-tag

<400> SEQUENCE: 94

Tyr Pro Tyr Asp Val Pro Asp Tyr Ala
1 5

<210> SEQ ID NO 95
<211> LENGTH: 11
<212> TYPE: PRT
<213> ORGANISM: Artificial Sequence
<220> FEATURE:
<223> OTHER INFORMATION: VSV-G-tag

<400> SEQUENCE: 95

Tyr Thr Asp Ile Glu Met Asn Arg Leu Gly Lys
1 5 10

<210> SEQ ID NO 96
<211> LENGTH: 11
<212> TYPE: PRT
<213> ORGANISM: Artficial Sequence
<220> FEATURE:
<223> OTHER INFORMATION: HSV-tag

<400> SEQUENCE: 96

Gln Pro Glu Leu Ala Pro Glu Asp Pro Glu Asp
1 5 10

<210> SEQ ID NO 97
<211> LENGTH: 10
<212> TYPE: PRT
<213> ORGANISM: Artificial Sequence
<220> FEATURE:
<223> OTHER INFORMATION: T7 epitope

<400> SEQUENCE: 97

Ala Ser Met Thr Gly Gly Gln Gln Met Gly
1 5 10

<210> SEQ ID NO 98
<211> LENGTH: 11
<212> TYPE: PRT
<213> ORGANISM: Artificial Sequence
<220> FEATURE:
<223> OTHER INFORMATION: HSV epitope

<400> SEQUENCE: 98

Gln Pro Glu Leu Ala Pro Glu Asp Pro Glu Asp
1 5 10

<210> SEQ ID NO 99
<211> LENGTH: 10
<212> TYPE: PRT
<213> ORGANISM: Artificial Sequence
<220> FEATURE:
<223> OTHER INFORMATION: Myc epitope

<400> SEQUENCE: 99

Glu Gln Lys Leu Ile Ser Glu Glu Asp Leu
1 5 10

<210> SEQ ID NO 100
<211> LENGTH: 14
<212> TYPE: PRT
<213> ORGANISM: Artificial Sequence
<220> FEATURE:
<223> OTHER INFORMATION: V5-tag

<400> SEQUENCE: 100

Gly Lys Pro Ile Pro Asn Pro Leu Leu Gly Leu Asp Ser Thr
1 5 10

<210> SEQ ID NO 101
<211> LENGTH: 253
<212> TYPE: PRT
<213> ORGANISM: Artificial Sequence
<220> FEATURE:
<223> OTHER INFORMATION: Variable Heavy chain of Fab fragment m13B8.2

<400> SEQUENCE: 101

Ala Met Gln Val Gln Leu Lys Gln Ser Gly Pro Gly Leu Val Gln Pro
1 5 10 15

Ser Gln Ser Leu Ser Ile Thr Cys Thr Val Ser Gly Phe Ser Leu Thr
20 25 30

Thr Phe Gly Val His Trp Val Arg Gln Ser Pro Gly Lys Gly Leu Glu
35 40 45

Trp Leu Gly Val Ile Trp Ala Ser Gly Ile Thr Asp Tyr Asn Val Pro
50 55 60

Phe Met Ser Arg Leu Ser Ile Thr Lys Asp Asn Ser Lys Ser Gln Val
65 70 75 80

Phe Phe Lys Leu Asn Ser Leu Gln Pro Asp Asp Thr Ala Ile Tyr Tyr
85 90 95

Cys Ala Lys Asn Asp Pro Gly Thr Gly Phe Ala Tyr Trp Gly Gln Gly
100 105 110

Thr Leu Val Thr Val Ser Ala Gly Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Gly Ser
210 215 220

```
Ala Trp Ser His Pro Gln Phe Glu Lys Gly Gly Gly Ser Gly Gly Gly
225                 230                 235                 240

Ser Gly Gly Ser Ala Trp Ser His Pro Gln Phe Glu Lys
                245                 250


<210> SEQ ID NO 102
<211> LENGTH: 218
<212> TYPE: PRT
<213> ORGANISM: Artificial Sequence
<220> FEATURE:
<223> OTHER INFORMATION: Variable Light chain of Fab Fragment m13B8.2

<400> SEQUENCE: 102

Ala Met Asp Ile Gln Met Thr Gln Ser Pro Ala Ser Leu Ser Ala Ser
1               5                   10                  15

Val Gly Glu Thr Val Thr Phe Thr Cys Arg Ala Ser Glu Met Ile Tyr
            20                  25                  30

Ser Tyr Leu Ala Trp Tyr Gln Gln Lys Gln Gly Lys Ser Pro Gln Leu
        35                  40                  45

Leu Val His Asp Ala Lys Thr Leu Ala Glu Gly Val Pro Ser Arg Phe
    50                  55                  60

Ser Gly Gly Gly Ser Gly Thr Gln Phe Ser Leu Lys Ile Asn Thr Leu
65                  70                  75                  80

Gln Pro Glu Asp Phe Gly Thr Tyr Tyr Cys Gln Ala His Tyr Gly Asn
                85                  90                  95

Pro Pro Thr Phe Gly Gly Gly Thr Lys Leu Glu Ile Lys Arg Gly Ile
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Ser
    210                 215


<210> SEQ ID NO 103
<211> LENGTH: 11
<212> TYPE: PRT
<213> ORGANISM: Artificial Sequence
<220> FEATURE:
<223> OTHER INFORMATION: MAT tag

<400> SEQUENCE: 103

His Asn His Arg His Lys His Gly Gly Gly Cys
1               5                   10


<210> SEQ ID NO 104
<211> LENGTH: 118
<212> TYPE: PRT
<213> ORGANISM: Artificial Sequence
<220> FEATURE:
<223> OTHER INFORMATION: Variable Heavy chain of huOKT8
```

<400> SEQUENCE: 104

Gln Val Gln Leu Val Gln Ser Gly Ala Glu Val Lys Lys Pro Gly Ala
1               5                   10                  15

Thr Val Lys Ile Ser Cys Lys Val Ser Gly Phe Asn Ile Lys Asp Thr
            20                  25                  30

Tyr Ile His Trp Val Gln Gln Ala Pro Gly Lys Gly Leu Glu Trp Met
        35                  40                  45

Gly Arg Ile Asp Pro Ala Asn Asp Asn Thr Leu Tyr Ala Ser Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Tyr Gly Tyr Tyr Val Phe Asp His Trp Gly Gln Gly Thr
            100                 105                 110

Leu Val Thr Val Ser Ser
        115

<210> SEQ ID NO 105
<211> LENGTH: 107
<212> TYPE: PRT
<213> ORGANISM: Artificial Sequence
<220> FEATURE:
<223> OTHER INFORMATION: Variable Light chain of huOKT8

<400> SEQUENCE: 105

Asp Val Gln Ile Thr Gln Ser Pro Ser Ser Leu Ser Ala Ser Val Gly
1               5                   10                  15

Asp Arg Val Thr Ile Thr Cys Arg Thr Ser Arg Ser Ile Ser Gln Tyr
            20                  25                  30

Leu Ala Trp Tyr Gln Gln Lys Pro Gly Lys Val Pro Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln His Asn Glu Asn Pro Leu
                85                  90                  95

Thr Phe Gly Gly Gly Thr Lys Val Glu Ile Lys
            100                 105

<210> SEQ ID NO 106
<211> LENGTH: 118
<212> TYPE: PRT
<213> ORGANISM: Artificial Sequence
<220> FEATURE:
<223> OTHER INFORMATION: Variable heavy (VH) Anti-BCMA

<400> SEQUENCE: 106

Glu Val Gln Leu Val Gln Ser Gly Ala Glu Met Lys Lys Pro Gly Ala
1               5                   10                  15

Ser Leu Lys Leu Ser Cys Lys Ala Ser Gly Tyr Thr Phe Ile Asp Tyr
            20                  25                  30

Tyr Val Tyr Trp Met Arg Gln Ala Pro Gly Gln Gly Leu Glu Ser Met
        35                  40                  45

Gly Trp Ile Asn Pro Asn Ser Gly Gly Thr Asn Tyr Ala Gln Lys Phe
    50                  55                  60

```
Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Met Tyr Tyr Cys
                85                  90                  95

Ala Arg Ser Gln Arg Asp Gly Tyr Met Asp Tyr Trp Gly Gln Gly Thr
            100                 105                 110

Leu Val Thr Val Ser Ser
        115


<210> SEQ ID NO 107
<211> LENGTH: 105
<212> TYPE: PRT
<213> ORGANISM: Artificial Sequence
<220> FEATURE:
<223> OTHER INFORMATION: Variable light (VL) Anti-BCMA

<400> SEQUENCE: 107

Gln Ser Ala Leu Thr Gln Pro Ala Ser Val Ser Ala Ser Pro Gly Gln
1               5                   10                  15

Ser Ile Ala Ile Ser Cys Thr Gly Thr Ser Ser Asp Val Gly Trp Tyr
            20                  25                  30

Gln Gln His Pro Gly Lys Ala Pro Lys Leu Met Ile Tyr Glu Asp Ser
        35                  40                  45

Lys Arg Pro Ser Gly Val Ser Asn Arg Phe Ser Gly Ser Lys Ser Gly
    50                  55                  60

Asn Thr Ala Ser Leu Thr Ile Ser Gly Leu Gln Ala Glu Asp Glu Ala
65                  70                  75                  80

Asp Tyr Tyr Cys Ser Ser Asn Thr Arg Ser Ser Thr Leu Val Phe Gly
                85                  90                  95

Gly Gly Thr Lys Leu Thr Val Leu Gly
            100                 105


<210> SEQ ID NO 108
<211> LENGTH: 228
<212> TYPE: PRT
<213> ORGANISM: Homo sapiens
<220> FEATURE:
<223> OTHER INFORMATION: Hinge-CH2-CH3 spacer

<400> SEQUENCE: 108

Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125
```

```
Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225


<210> SEQ ID NO 109
<211> LENGTH: 117
<212> TYPE: PRT
<213> ORGANISM: Artificial Sequence
<220> FEATURE:
<223> OTHER INFORMATION: Variable heavy (VH) Anti-BCMA

<400> SEQUENCE: 109

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Ile Asn Trp Val Lys Arg Ala Pro Gly Lys Gly Leu Lys Trp Met
        35                  40                  45

Gly Trp Ile Asn Thr Glu Thr Arg Glu Pro Ala Tyr Ala Tyr Asp Phe
    50                  55                  60

Arg Gly Arg Phe Ala Phe Ser Leu Glu Thr Ser Ala Ser Thr Ala Tyr
65                  70                  75                  80

Leu Gln Ile Asn Asn Leu Lys Tyr Glu Asp Thr Ala Thr Tyr Phe Cys
                85                  90                  95

Ala Leu Asp Tyr Ser Tyr Ala Met Asp Tyr Trp Gly Gln Gly Thr Ser
            100                 105                 110

Val Thr Val Ser Ser
        115


<210> SEQ ID NO 110
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 110

Asp Ile Val Leu Thr Gln Ser Pro Pro Ser Leu Ala Met Ser Leu Gly
1               5                   10                  15

Lys Arg Ala Thr Ile Ser Cys Arg Ala Ser Glu Ser Val Thr Ile Leu
            20                  25                  30

Gly Ser His Leu Ile His Trp Tyr Gln Gln Lys Pro Gly Gln Pro Pro
        35                  40                  45

Thr Leu Leu Ile Gln Leu Ala Ser Asn Val Gln Thr Gly Val Pro Ala
    50                  55                  60
```

Arg Phe Ser Gly Ser Gly Ser Arg Thr Asp Phe Thr Leu Thr Ile Asp
65 70 75 80

Pro Val Glu Glu Asp Asp Val Ala Val Tyr Tyr Cys Leu Gln Ser Arg
85 90 95

Thr Ile Pro Arg Thr Phe Gly Gly Gly Thr Lys Leu Glu Ile Lys
100 105 110

<210> SEQ ID NO 111
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 111

Gln Ile Gln Leu Val Gln Ser Gly Pro Asp Leu Lys Lys Pro Gly Glu
1 5 10 15

Thr Val Lys Leu Ser Cys Lys Ala Ser Gly Tyr Thr Phe Thr Asn Phe
20 25 30

Gly Met Asn Trp Val Lys Gln Ala Pro Gly Lys Gly Phe Lys Trp Met
35 40 45

Ala Trp Ile Asn Thr Tyr Thr Gly Glu Ser Tyr Phe Ala Asp Asp Phe
50 55 60

Lys Gly Arg Phe Ala Phe Ser Val Glu Thr Ser Ala Thr Thr Ala Tyr
65 70 75 80

Leu Gln Ile Asn Asn Leu Lys Thr Glu Asp Thr Ala Thr Tyr Phe Cys
85 90 95

Ala Arg Gly Glu Ile Tyr Tyr Gly Tyr Asp Gly Gly Phe Ala Tyr Trp
100 105 110

Gly Gln Gly Thr Leu Val Thr Val Ser Ala
115 120

<210> SEQ ID NO 112
<211> LENGTH: 107
<212> TYPE: PRT
<213> ORGANISM: Artificial Sequence
<220> FEATURE:
<223> OTHER INFORMATION: Variable light (VL) Anti-BCMA

<400> SEQUENCE: 112

Asp Val Val Met Thr Gln Ser His Arg Phe Met Ser Thr Ser Val Gly
1 5 10 15

Asp Arg Val Ser Ile Thr Cys Arg Ala Ser Gln Asp Val Asn Thr Ala
20 25 30

Val Ser Trp Tyr Gln Gln Lys Pro Gly Gln Ser Pro Lys Leu Leu Ile
35 40 45

Phe Ser Ala Ser Tyr Arg Tyr Thr Gly Val Pro Asp Arg Phe Thr Gly
50 55 60

Ser Gly Ser Gly Ala Asp Phe Thr Leu Thr Ile Ser Ser Val Gln Ala
65 70 75 80

Glu Asp Leu Ala Val Tyr Tyr Cys Gln Gln His Tyr Ser Thr Pro Trp
85 90 95

Thr Phe Gly Gly Gly Thr Lys Leu Asp Ile Lys
100 105

<210> SEQ ID NO 113
<211> LENGTH: 116
<212> TYPE: PRT

-continued

<213> ORGANISM: Artificial Sequence
<220> FEATURE:
<223> OTHER INFORMATION: Variable heavy (VH) Anti-BCMA

<400> SEQUENCE: 113

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Tyr Ser Gly Ser Phe Asp Asn Trp Gly Gln Gly Thr Leu Val
            100                 105                 110

Thr Val Ser Ser
        115
```

<210> SEQ ID NO 114
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 114

```
Ser Tyr Glu Leu Thr Gln Pro Pro Ser Ala Ser Gly Thr Pro Gly Gln
1               5                   10                  15

Arg Val Thr Met Ser Cys Ser Gly Thr Ser Ser Asn Ile Gly Ser His
            20                  25                  30

Ser Val Asn Trp Tyr Gln Gln Leu Pro Gly Thr Ala Pro Lys Leu Leu
        35                  40                  45

Ile Tyr Thr Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ala Trp Asp Gly Ser Leu
                85                  90                  95

Asn Gly Leu Val Phe Gly Gly Gly Thr Lys Leu Thr Val Leu Gly
            100                 105                 110
```

<210> SEQ ID NO 115
<211> LENGTH: 5
<212> TYPE: PRT
<213> ORGANISM: Artificial Sequence
<220> FEATURE:
<223> OTHER INFORMATION: Linker

<400> SEQUENCE: 115

```
Gly Gly Gly Gly Ser
1               5
```

<210> SEQ ID NO 116
<211> LENGTH: 4
<212> TYPE: PRT
<213> ORGANISM: Artificial Sequence
<220> FEATURE:
<223> OTHER INFORMATION: Linker

<400> SEQUENCE: 116

Gly Gly Gly Ser
1

<210> SEQ ID NO 117
<211> LENGTH: 21
<212> TYPE: PRT
<213> ORGANISM: Artificial Sequence
<220> FEATURE:
<223> OTHER INFORMATION: Linker

<400> SEQUENCE: 117

Ser Arg Gly Gly Gly Gly Ser Gly Gly Gly Gly Ser Gly Gly Gly Gly
1 5 10 15

Ser Leu Glu Met Ala
20

<210> SEQ ID NO 118
<211> LENGTH: 122
<212> TYPE: PRT
<213> ORGANISM: Artificial Sequence
<220> FEATURE:
<223> OTHER INFORMATION: Variable heavy (VH) Anti-BCMA

<400> SEQUENCE: 118

Glu Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Ile Ala Asn Tyr Ala Gln Lys Phe
50 55 60

Gln Gly Arg Val Thr Met Thr Glu Asp Thr Ser Thr Asp Thr Ala Tyr
65 70 75 80

Met Glu Leu Ser Ser Leu Arg Ser Glu Asp Thr Ala Val Tyr Tyr Cys
85 90 95

Ala Arg Ser Gly Tyr Ser Lys Ser Ile Val Ser Tyr Met Asp Tyr Trp
100 105 110

Gly Gln Gly Thr Leu Val Thr Val Ser Ser
115 120

<210> SEQ ID NO 119
<211> LENGTH: 111
<212> TYPE: PRT
<213> ORGANISM: Artificial Sequence
<220> FEATURE:
<223> OTHER INFORMATION: Variable light (VL) Anti-BCMA

<400> SEQUENCE: 119

Leu Pro Val Leu Thr Gln Pro Pro Ser Thr Ser Gly Thr Pro Gly Gln
1 5 10 15

Arg Val Thr Val Ser Cys Ser Gly Ser Ser Ser Asn Ile Gly Ser Asn
20 25 30

Val Val Phe Trp Tyr Gln Gln Leu Pro Gly Thr Ala Pro Lys Leu Val
35 40 45

Ile Tyr Arg Asn Asn Gln Arg Pro Ser Gly Val Pro Asp Arg Phe Ser
50 55 60

Val Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Ser Gly Tyr Val Phe Gly Thr Gly Thr Lys Val Thr Val Leu Gly
100 105 110

<210> SEQ ID NO 120
<211> LENGTH: 120
<212> TYPE: PRT
<213> ORGANISM: Artificial Sequence
<220> FEATURE:
<223> OTHER INFORMATION: Variable heavy (VH) Anti-BCMA

<400> SEQUENCE: 120

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Ser Tyr
20 25 30

Ala Ile Ser Trp Val Arg Gln Ala Pro Gly Gln Gly Leu Glu Trp Met
35 40 45

Gly Arg Ile Ile Pro Ile Leu Gly Thr Ala Asn Tyr Ala Gln Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Val Tyr Tyr Cys
85 90 95

Ala Arg Ser Gly Tyr Gly Ser Tyr Arg Trp Glu Asp Ser Trp Gly Gln
100 105 110

Gly Thr Leu Val Thr Val Ser Ser
115 120

<210> SEQ ID NO 121
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 121

Gln Ala Val Leu Thr Gln Pro Pro Ser Ala Ser Gly Thr Pro Gly Gln
1 5 10 15

Arg Val Thr Ile Ser Cys Ser Gly Ser Ser Ser Asn Ile Gly Ser Asn
20 25 30

Tyr Val Phe Trp Tyr Gln Gln Leu Pro Gly Thr Ala Pro Lys Leu Leu
35 40 45

Ile Tyr Ser Asn Asn Gln Arg Pro Ser Gly Val Pro Asp Arg Phe Ser
50 55 60

Gly Ser Lys Ser Gly Thr Ser Ala Ser Leu Ala Ile Ser Gly Leu Arg
65 70 75 80

Ser Glu Asp Glu Ala Asp Tyr Tyr Cys Ala Ala Trp Asp Asp Ser Leu
85 90 95

Ser Ala Ser Tyr Val Phe Gly Thr Gly Thr Lys Val Thr Val Leu Gly
100 105 110

<210> SEQ ID NO 122
<211> LENGTH: 118
<212> TYPE: PRT

-continued

```
<213> ORGANISM: Artificial Sequence
<220> FEATURE:
<223> OTHER INFORMATION: Variable heavy (VH) Anti-BCMA

<400> SEQUENCE: 122

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Tyr Met His Trp Val Arg Gln Ala Pro Gly Gln Arg Leu Glu Trp Met
        35                  40                  45

Gly Trp Ile Asn Pro Asn Ser Gly Gly Thr Asn Tyr Ala Gln Lys Phe
    50                  55                  60

Gln Asp Arg Ile Thr Val Thr Arg Asp Thr Ser Ser Asn Thr Gly Tyr
65                  70                  75                  80

Met Glu Leu Thr Arg Leu Arg Ser Asp Asp Thr Ala Val Tyr Tyr Cys
                85                  90                  95

Ala Arg Ser Pro Tyr Ser Gly Val Leu Asp Lys Trp Gly Gln Gly Thr
            100                 105                 110

Leu Val Thr Val Ser Ser
        115


<210> SEQ ID NO 123
<211> LENGTH: 112
<212> TYPE: PRT
<213> ORGANISM: Artificial Sequence
<220> FEATURE:
<223> OTHER INFORMATION: Variable light (VL) Anti-BCMA

<400> SEQUENCE: 123

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Phe Asp Val His Trp Tyr Gln Gln Leu Pro Gly Thr Ala Pro Lys Leu
        35                  40                  45

Leu Ile Tyr Gly Asn Ser Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Gly Tyr Val Phe Gly Thr Gly Thr Lys Val Thr Val Leu Gly
            100                 105                 110
```

PROCESSES FOR GENERATING ENGINEERED CELLS AND COMPOSITIONS THEREOF

CROSS-REFERENCE TO RELATED APPLICATIONS

This application is a National Stage application under 35 U.S.C. § 371 of International Application No. PCT/US2019/046062, filed on Aug. 9, 2019, which claims priority from U.S. provisional application No. 62/716,981 filed Aug. 9, 2018, entitled "Processes for Generating Engineered Cells and Compositions Thereof," U.S. provisional application No. 62/742,249 filed Oct. 5, 2018, entitled "Processes for Generating Engineered Cells and Compositions Thereof," U.S. provisional application No. 62/798,433 filed Jan. 29, 2019, entitled "Processes for Generating Engineered Cells and Compositions Thereof," U.S. provisional application No. 62/842,402 filed May 2, 2019, entitled "Processes for Generating Engineered Cells and Compositions Thereof," and U.S. provisional application No. 62/861,308 filed Jun. 13, 2019, entitled "Processes for Generating Engineered Cells and Compositions Thereof," the contents of which are incorporated by reference in their entirety.

INCORPORATION BY REFERENCE OF SEQUENCE LISTING

The present application is being filed with a Sequence Listing in electronic format. The Sequence Listing is provided as a file entitled 735042017400SeqList.txt, created on Feb. 8, 2021, which is 92,988 bytes in size. The information in electronic format of the Sequence Listing is incorporated by reference in its entirety.

FIELD

The present disclosure provides processes for genetically engineering T cells, such as primary CD4+ T cells and/or CD8+ T cells, for use in cell therapy that does not involve expanding the cells. In particular aspects, the provided processes successfully generate compositions of engineered T cells, such as populations of engineered T cells, which express a chimeric antigen receptor (CAR) within a shortened amount of time as compared to alternative engineering processes, such as processes that involve expanding the cells. In certain aspects, the provided processes successfully generate a composition of engineered T cells suitable for use in cell therapy within 4 days from when the process to stimulate or activate the cells is initiated. In some aspects, the resulting engineered cell compositions are composed of cell population that are less differentiated, less exhausted, and more potent than engineered T cell compositions generated by other means, such as by processes that involve expanding the cells. Also provided are compositions of T cells generated by the provided methods and their uses for treating subjects.

BACKGROUND

Various cell therapy methods are available for treating diseases and conditions. Among cell therapy methods are methods involving immune cells, such as T cells, genetically engineered with a recombinant receptor, such as chimeric antigen receptors. However, in some cases, some of the existing processes for generating genetically engineered cell compositions may be time consuming or may vary in the amount of time required for successful completion. In certain cases, some of the existing processes may result in a composition in which the cell population has a low potency or persistence in vivo. Improved methods for manufacturing and/or engineering such cell therapies are needed, including to provide for a more efficient process and/or an improved cell composition product.

SUMMARY

Provided herein is a method for producing a composition of engineered T cells, the method comprising: (a) exposing an input composition comprising primary T cells with a stimulatory reagent under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out: (i) at a time between 24 and 120 hours, or between 1 day and 5 days, or between about 1 day and about 5 days, inclusive, after the exposing to the stimulatory reagent is initiated; (ii) at a time when integrated vector is detected in the genome but prior to achieving a stable integrated vector copy number (iVCN) per diploid genome; (iii) at a time before the total number of viable cells at the harvesting is more than or more than about three times, two times, or the same or about the same as the number of total viable cells of the stimulated population; and/or (iv) at a time when the percentage of CD27+CCR7+ is greater than or greater than about 60% among total T cells in the population, total CD3+ T cells in the population, total CD4+ T cells in the population, or total CD8+ T cells, or of recombinant protein-expressing cells thereof, in the population; thereby producing a composition of engineered cells.

In some embodiments, the input composition comprises at least $300\times10^6$ viable primary T cells. In certain embodiments, the stimulatory reagent is capable of activating one or more intracellular signaling domains of one or more components of a TCR complex and one or more intracellular signaling domains of one or more costimulatory molecules.

Provided herein is a method for producing a composition of engineered T cells, the method comprising: (a) exposing an input composition comprising at least $300\times10^6$ viable primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out: (i) at a time between 48 and 120 hours, or between 2 days and 5 days, or between about 2 days and about 5 days, inclusive, after the exposing to the stimulatory reagent is initiated; (ii) at a time when integrated vector is detected in the genome but prior to achieving a stable integrated vector copy number (iVCN) per diploid genome; (iii) at a time before the total number of viable cells at the harvesting is more than or more than about three times, two times, or the same or about the same as the number of total viable cells of the stimulated population; and/or (iv) at a time when the percentage of naïve-like T cells is greater than or greater than about 60% among total T cells in the population, total CD3+ cells in the population, total CD4+ T cells in the population, or total CD8+ T cells, or of recombinant protein-expressing cells thereof, in the population; thereby producing a composition of engineered cells.

In some embodiments, the harvesting is carried out at a time when integrated vector is detected in the genome but prior to achieving stable iVCN per diploid genome. In certain embodiments, stable iVCN per diploid genome is achieved when the iVCN peaks and remains unchanged, or unchanged within a tolerated error, for a period of time greater than 24 hours or one day, or greater than about 24 hours or about one day. In particular embodiments, stable iVCN per diploid genome is achieved when the fraction of iVCN to total vector copy number (VCN) in the diploid genome of the population of transformed cells, on average, is or is about 1.0 or is within a tolerated error thereof. In some embodiments, the harvesting is carried out at a time when the fraction of integrated vector copy number (iVCN) to total VCN in the population of transformed cells, on average, is less than 0.8.

In some embodiments, T cells are harvested at a time when the percentage of naïve-like T cells is greater than or greater than about 60% among total T cells in the population, total CD3+ cells in the population, total CD4+ T cells in the population, or total CD8+ T cells, or of recombinant protein-expressing cells thereof, in the population. In certain embodiments, the naïve-like T cells comprise CD27+ CCR7+ T cells.

Provided herein is a method for producing a composition of engineered T cells, the method comprising: (a) exposing an input composition comprising primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous-polynucleotide encoding a recombinant protein, thereby generating a population of transformed cells; and (c) harvesting T cells of the transformed population, wherein the harvesting is carried out at a time between 48 and 120 hours, or between 2 days and 5 days, or between about 2 days and about 5 days, inclusive, after the exposing to the stimulatory reagent is initiated, wherein at the time of harvesting the integrated vector copy number (iVCN) of the population of transformed cells, on average, is between or between about 0.4 copies per diploid genome and 2.0 copies per diploid genome; thereby producing a composition of engineered cells.

In some embodiments, the harvesting is carried out at a time when the iVCN of the population of transformed cells, on average, is less than or less than about 2.0 copies per diploid genome. In certain embodiments, the harvesting is carried out at a time when the iVCN of the population of transformed cells, on average, is less than or less than about 1.5 copies per diploid genome. In particular embodiments, the harvesting is carried out at a time when the iVCN of the population of transformed cells, on average, is less than or less than about 1.0 copy per diploid genome. In some embodiments, the harvesting is carried out at a time when the iVCN of the population of transformed cells, on average, is less than or less than about 0.75 copies per diploid genome. In certain embodiments, the harvesting is carried out at a time when the iVCN of the population of transformed cells, on average, is less than or less than about 0.5 copies per diploid genome.

Provided herein is a method for producing a composition of engineered T cells, the method comprising: (a) exposing an input composition comprising primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, or between 2 days and 5 days, or between about 2 days and about 5 days, inclusive, after the exposing to the stimulatory reagent is initiated, wherein at the time of harvesting the percentage of naïve-like cells is greater than or greater than about 60% among total T cells in the population, total CD4+ T cells in the population or total CD8+ T cells, or of recombinant protein-expressing cells thereof, in the population; thereby producing a composition of engineered cells.

In some embodiments, at the time of harvesting in provided methods, the percentage of central memory T cells is greater than or greater than about 60% among total T cells in the population, total CD4+ T cells in the population or total CD8+ T cells, or of recombinant protein-expressing cells thereof, in the population. In particular embodiments, central memory T cells are CCR7+CD45RA−.

Provided herein is a method for producing a composition of engineered T cells, the method comprising: (a) exposing an input composition comprising primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, or between 2 days and 5 days, or between about 2 days and about 5 days, inclusive, after the exposing to the stimulatory reagent is initiated, wherein at the time of harvesting the percentage of naïve-like cells and/or central memory cells is greater than or greater than about 60% among total T cells in the population, total CD4+ T cells in the population or total CD8+ T cells, or of recombinant protein-expressing cells thereof, in the population, thereby producing a composition of engineered cells.

In some embodiments, at the time of harvesting: the percentage of naïve-like T cells is greater than or greater than about 60% among total recombinant protein-expressing cells in the population, such as greater than or greater than about 65%, 70%, 80%, 90% or 95% total recombinant protein-expressing T cells in the population. In some embodiments, at the time of harvesting: the percentage of naïve-like T cells is greater than or greater than about 60% among total recombinant protein-expressing CD4+ T cells in the population, such as greater than or greater than about 65%, 70%, 80%, 90% or 95% total recombinant protein-expressing CD4+ cells in the population. In some embodiments, at the time of harvesting: the percentage of naïve-like T cells is greater than or greater than about 60% among total recombinant protein-expressing CD8+ T cells in the population, such as greater than or greater than about 65%, 70%, 80%, 90% or 95% total recombinant protein-expressing CD8+ cells in the population. In some embodiments, the naïve-like T cells or the T cells that are surface positive for a marker expressed on naïve-like T cells are CCR7+ CD45RA+, CD27+CCR7+ or CD62L− CCR7+. In some embodiments, the naïve-like T cells comprise CCR7+ CD45RA+. In particular embodiments, the naïve-like T cells comprise CD27+CCR7+ cells.

In some embodiments, at the time of harvesting: the percentage of CD27+CCR7+ is greater than or greater than about 60% among total recombinant protein-expressing cells in the population, such as greater than or greater than about 65%, 70%, 80%, 90% or 95% total recombinant protein-expressing T cells in the population. In some embodiments, at the time of harvesting: the percentage of CD27+CCR7+ is greater than or greater than about 40% among total recombinant protein-expressing CD4+ T cells in the population, such as greater than or greater than about 50%, 60%, 70%, 80%, 90% or 95% total recombinant protein-expressing CD4+ cells in the population. In some embodiments, at the time of harvesting: the percentage of CD27+CCR7+ is greater than or greater than about 40% among total recombinant protein-expressing CD8+ T cells in the population, such as greater than or greater than about 50%, 60%, 70%, 80%, 90% or 95% total recombinant protein-expressing CD8+ cells in the population.

In some embodiments, at the time of harvesting: the percentage of naïve-like T cells and/or central memory T cells is greater than or greater than about 60% among total recombinant protein-expressing cells in the population, such as greater than or greater than about 65%, 70%, 80%, 90% or 95% total recombinant protein-expressing T cells in the population. In some embodiments, at the time of harvesting: the percentage of naïve-like T cells and/or central memory T cells is greater than or greater than about 40% among total recombinant protein-expressing CD4+ T cells in the population, such as greater than or greater than about 50%, 60%, 70%, 80%, 90% or 95% total recombinant protein-expressing CD4+ cells in the population. In some embodiments, at the time of harvesting, the percentage of naïve-like T cells and/or central memory T cells is greater than or greater than about 40% among total recombinant protein-expressing CD8+ T cells in the population, such as greater than or greater than about 50%, 60%, 70%, 80%, 90% or 95% total recombinant protein-expressing CD8+ cells in the population. In some embodiments, the naïve-like T cells or the T cells that are surface positive for a marker expressed on naïve-like T cells are CCR7+CD45RA+, CD27+CCR7+ or CD62L−CCR7+. In some embodiments, the naïve-like T cells comprise CCR7+CD45RA+. In particular embodiments, the naïve-like T cells comprise CD27+CCR7+ cells. In particular embodiments, central memory T cells are CCR7+CD45RA−.

In some embodiments, subsequent to the introducing and prior to the harvesting, the method further comprises incubating the population of transformed cells for up to 96 hours or 4 days. In particular embodiments, the incubation is carried out at a temperature of about 37° C. In certain embodiments, the incubating is carried out for up to 72 hours or 3 days subsequent to the introducing. In particular embodiments, the incubating is carried out for up to 48 hours or 2 days subsequent to the introducing. In some embodiments, the incubating is carried out for up to 24 hours or one day subsequent to the introducing. In certain embodiments, the incubation is carried out for at least 18 hours. In particular, embodiments, the incubation is performed under static conditions. In particular embodiments, static conditions are conditions that do not involve centrifugation, shaking, rotating, rocking, or perfusion, e.g., continuous or semi-continuous perfusion of the media.

In particular embodiments, the harvesting is carried out within 96 hours or 4 days after the exposing to the stimulatory agent is initiated. In some embodiments, the harvesting is carried out within 72 hours or 3 days after the exposing to the stimulatory agent is initiated. In certain embodiments, the harvesting is carried out within 48 hours or 2 days after the exposing to the stimulatory agent is initiated.

In particular embodiments, one or both of the exposing and the introducing is carried out in the presence of one or more recombinant cytokines. In some embodiments, the incubating is carried out in the presence of one or more recombinant cytokines. In certain embodiments, the incubating is carried out in basal media lacking one or more recombinant cytokines.

Provided herein is a method for producing a composition of engineered T cells, the method comprising: (a) exposing an input composition comprising primary T cells with a stimulatory reagent under conditions to stimulate T cells, said conditions comprising the presence of one or more recombinant cytokines, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours or 4 days, optionally wherein the incubation is carried out at a temperature of about 37° C., wherein the incubating is carried out in basal media lacking one or more recombinant cytokines; and (c) subsequent to the incubating, harvesting T cells of the transformed population, thereby producing a composition of engineered cells, wherein the harvesting is carried out at a time between 48 and 120 hours, or between 2 days and 5 days, inclusive, after the exposing to the stimulatory reagent is initiated; thereby producing a composition of engineered cells.

In some embodiments, the one or more recombinant cytokines are human. In certain embodiments, the one or more recombinant cytokines are selected from recombinant IL-2, recombinant IL-7 and recombinant IL-15. In particular embodiments, the one or more recombinant cytokines include between 10 and 200 IU/mL recombinant IL-2; between 100 IU/mL and 1,000 IU/mL recombinant IL-7; and/or between 10 and 200 IU/mL recombinant IL-15. In particular embodiments, the one or more recombinant cytokines are or comprise recombinant IL-2, recombinant IL-7 and recombinant IL-15. For example, in some cases, the one or more recombinant cytokines include between 10 and 200 IU/mL recombinant IL-2; between 100 IU/mL and 1,000 IU/mL recombinant IL-7; and between 10 and 200 IU/mL recombinant IL-15.

In some embodiments, one or both of the exposing and the introducing is carried out in serum free media.

In certain embodiments, the stimulatory reagent comprises (i) a primary agent that specifically binds to a member of a TCR complex, optionally that specifically binds to CD3 and (ii) a secondary agent that specifically binds to a T cell costimulatory molecule, optionally wherein the costimulatory molecule is selected from CD28, CD137 (4-1-BB), OX40, or ICOS. In particular embodiments, the one or both of the primary and secondary agents comprise an antibody or an antigen-binding fragment thereof. In some embodiments, the primary and secondary agents comprise an antibody or an antigen-binding fragment thereof. In particular embodiments, the stimulatory reagent comprises an anti-CD3 antibody and an anti-CD28 antibody.

In some embodiments, the primary agent and secondary agent are present or attached on the surface of a solid support. In certain embodiments, the solid support is or comprises a bead. In particular embodiments, the ratio of beads to cells is less than 3:1.

Provided herein is a method for producing a composition of engineered T cells, the method comprising: (a) exposing an input composition comprising primary T cells with a stimulatory reagent comprising a bead having attached thereto (i) a primary agent that specifically binds to a member of a TCR complex, optionally that specifically binds to CD3 and (ii) a secondary agent that specifically binds to a T cell costimulatory molecule, wherein the ratio of beads to cells is less than 3:1 and the exposing is carried out under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, or between 2 days and 5 days, inclusive, after the exposing to the stimulatory reagent is initiated; thereby producing a composition of engineered cells.

In some embodiments, the ratio of beads to cells is or is about 1:1. In certain embodiments, the bead has attached thereto an anti-CD3 antibody and an anti-CD28 antibody, or an antigen-binding fragment thereof.

In particular embodiments, the primary agent and secondary agent are reversibly bound on the surface of an oligomeric particle reagent comprising a plurality of streptavidin or streptavidin mutein molecules.

Provided herein is a method for producing a composition of engineered T cells, the method comprising: (a) exposing an input composition comprising primary T cells with a stimulatory reagent comprising an oligomeric particle reagent comprising a plurality of streptavidin or streptavidin mutein molecules, the oligomeric particle reagent having reversibly bound thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, or between 2 days and 5 days, inclusive, after the exposing to the stimulatory reagent is initiated, thereby producing a composition of engineered cells.

In some embodiments, the exposing is carried out with an amount of the stimulatory reagent, such as the oligomeric particle reagent comprising a plurality of streptavidin or streptavidin mutein molecules, that is between or between about 0.1 μg and 20 μg, inclusive, per $10^6$ cells in the input composition.

Provided herein is a method for stimulating T cells, the method comprising exposing an input composition comprising T cells with a stimulatory reagent in an amount between or between about 0.1 μg and 20 μg, inclusive, per $10^6$ cells in the input composition, said stimulatory reagent comprising an oligomeric particle reagent comprising a plurality of streptavidin or streptavidin mutein molecules, wherein the exposing is carried out under conditions to stimulate T cells, thereby generating a stimulated population. In some embodiments, the input composition comprises primary T cells.

Provided herein is a method for stimulating T cells, the method comprising exposing an input composition comprising T cells with a stimulatory reagent in an amount between or between about 0.1 μg and 20 μg, inclusive, per $10^6$ cells in the input composition, said stimulatory reagent comprising an oligomeric particle reagent comprising a plurality of streptavidin or streptavidin mutein molecules having attached thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells, thereby generating a stimulated population. In some embodiments, the input composition comprises primary T cells.

In some embodiments, subsequent to the introducing and prior to the harvesting, the method further comprises incubating the population of transformed cells for up to 96 hours or 4 days. In some embodiments, the incubation is carried out at a temperature of about 37° C. In certain embodiments, the incubating is carried out for up to 72 hours or 3 days subsequent to the introducing. In particular embodiments, the incubating is carried out for up to 48 hours or 2 days subsequent to the introducing. In some embodiments, the incubating is carried out for up to 24 hours or one day subsequent to the introducing. In particular embodiments, the incubation is performed under static conditions. In particular embodiments, static conditions are conditions that do not involve centrifugation, shaking, rotating, rocking, or perfusion, e.g., continuous or semi-continuous perfusion of the media.

In certain embodiments, the harvesting is carried out within 96 hours or 4 days after the exposing the input composition with the stimulatory agent is initiated. In particular embodiments, the harvesting is carried out within 72 hours or 3 days after the exposing the input composition with the stimulatory agent is initiated. In some embodiments, the harvesting is carried out within 48 hours or 2 days after the exposing the input composition with the stimulatory agent is initiated.

In certain embodiments, one or both of the exposing and the introducing is carried out in the presence of one or more recombinant cytokines.

In some embodiments, the incubating is carried out in the presence of one or more recombinant cytokines. In particular embodiments, the incubating is carried out in basal media lacking one or more recombinant cytokines.

Provided herein is a method for producing a composition of engineered T cells, the method comprising: (a) exposing an input composition comprising primary T cells with a stimulatory reagent comprising a bead having attached thereto (i) a primary agent that specifically binds to a member of a TCR complex, optionally that specifically binds to CD3 and (ii) a secondary agent that specifically binds to a T cell costimulatory molecule, wherein the ratio of beads to cells is less than 3:1 and the exposing is carried out under conditions to stimulate T cells comprising the presence of one or more recombinant cytokines, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours or 4 days, optionally wherein the incubation is carried out at a temperature of about 37° C., wherein the incubating is carried out in basal media lacking one or more recombinant cytokines; and (d) subsequent to the incubating, harvesting T cells of the transformed population, thereby producing a composition of engineered cells, wherein the harvesting is carried out at a time between 48 and 120 hours, or between 2 days and 5 days, inclusive, after the exposing to the stimulatory reagent is initiated; thereby producing a composition of engineered cells.

Provided herein is a method for producing a composition of engineered T cells, the method comprising: (a) exposing an input composition comprising primary T cells with a stimulatory reagent comprising an oligomeric particle reagent comprising a plurality of streptavidin or streptavidin mutein molecules, the oligomeric particle reagent having attached thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells comprising the presence of one or more recombinant cytokines, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours or 4 days, optionally wherein the incubation is carried out at a temperature of about 37° C., wherein the incubating is carried out in basal media lacking one or more recombinant cytokines; and (d) subsequent to the incubating, harvesting T cells of the transformed population, thereby producing a composition of engineered cells, wherein the harvesting is carried out at a time between 48 and 120 hours, or between 2 days and 5 days, inclusive, after the exposing to the stimulatory reagent is initiated; thereby producing a composition of engineered cells.

In some embodiments, the exposing with the oligomeric particle stimulatory reagent comprising a plurality of streptavidin or streptavidin mutein molecules is carried out with an amount of the stimulatory reagent that is between or between about 0.4 μg and 8 μg, inclusive, per $10^6$ cells in the input composition. In certain embodiments, the exposing is carried out with an amount of the stimulatory reagent that is between or between about 0.8 μg and 4 μg, inclusive, per $10^6$ cells in the input composition. In particular embodiments, the exposing is carried out with an amount of the stimulatory reagent that is or is about 0.8 μg per $10^6$ cells in the input composition.

In some embodiments, the one or more recombinant cytokines are human. In some embodiments, the one or more recombinant cytokines are selected from recombinant IL-2, recombinant IL-7 and/or recombinant IL-15. For example, in some cases, the one or more recombinant cytokines include between 10 and 200 IU/mL recombinant IL-2; between 100 IU/mL and 1,000 IU/mL recombinant IL-7; and/or between 10 and 200 IU/mL recombinant IL-15. In certain embodiments, the one or more recombinant cytokines are or comprise recombinant IL-2, recombinant IL-7 and recombinant IL-15. For example, in some cases, the one or more recombinant cytokines include between 10 and 200 IU/mL recombinant IL-2; between 100 IU/mL and 1,000 IU/mL recombinant IL-7; and between 10 and 200 IU/mL recombinant IL-15. In particular embodiments, one or both of the exposing and the introducing is carried out in serum free media. In some embodiments, the incubating is carried out in serum free media.

In certain embodiments, the stimulatory reagent is one in which the primary agent and secondary agent, such as an anti-CD3 and anti-CD28 antibody or antigen-binding fragment thereof, are present or attached on the surface of a bead. In certain embodiments, the ratio of beads to cells is from or from about 2:1 to 0.5:1. In particular embodiments, the ratio of beads to cells is at or at about 1:1. In some embodiments, the bead comprises a diameter of greater than or greater than about 3.5 μm but no more than about 9 μm or no more than about 8 μm or no more than about 7 μm or no more than about 6 μm or no more than about 5 μm. In certain embodiments, the bead comprises a diameter of or about 4.5 μm. In some embodiments, the bead is inert. In particular embodiments, the bead is or comprises a polystyrene surface. In some embodiments, the bead is paramagnetic or superparamagnetic. For example, in some cases the bead is one that is attracted to a magnetic field. In some embodiments, prior to the harvesting, the method further comprises exposing the cells to a magnetic field either subsequent to or during the incubation, thereby removing the stimulatory reagent from the cells.

In some embodiments, the stimulatory reagent is one in which the primary agent and secondary agent, such as an anti-CD3 and anti-CD28 antibody or antigen-binding fragment thereof, are reversibly bound to an oligomeric particle reagent comprising a plurality of streptavidin or streptavidin mutein molecules. In certain embodiments, the streptavidin or streptavidin mutein molecules bind to or are capable of binding to biotin, avidin, a biotin analog or mutein, an avidin analog or mutein, and/or a biologically active fragment thereof. In particular embodiments, each of the plurality of streptavidin mutein molecules comprise the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO: 61.

In some embodiments, each of the plurality of the streptavidin mutein molecules comprises: a) the sequence of amino acids set forth in any of SEQ ID NOS: 62, 63, 68, 75-77, or 80-83; b) a sequence of amino acids that exhibit at least 85%, 86%, 87%, 88%, 89%, 89%, 90%, 91%, 92%, 93%, 94%, 95%, 96%, 97%, 98%, 99% or more sequence identity to any of SEQ ID NOS: 62, 63, 68, 75-77, or 80-83 and contain the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ and/or reversibly bind to biotin, a biotin analog or a streptavidin-binding peptide; or c) a functional fragment of a) or b) that reversibly binds to biotin, a biotin analog, or a streptavidin-binding peptide. In certain embodiments, the plurality of streptavidin mutein molecules comprise the sequence of amino acids set forth in SEQ ID NO: 63 or 68.

In particular embodiments, the primary agent and the secondary agent that are reversibly bound on the surface of the oligomeric particle reagent each comprise a streptavidin-binding peptide. In some embodiments, the streptavidin-binding peptide is selected from the group consisting of Trp-Ser-His-Pro-Gln-Phe-Glu-Lys (SEQ ID NO: 64), Ser-Ala-Trp-Ser-His-Pro-Gln-Phe-Glu-Lys-$(GlyGlyGlySer)_3$-Trp-Ser-His-Pro-Gln-Phe-Glu-Lys (SEQ ID NO:73), Trp-Ser-His-Pro-Gln-Phe-Glu-Lys-$(GlyGlyGlySer)_3$-Trp-Ser-His-Pro-Gln-Phe-Glu-Lys (SEQ ID NO: 65), Trp-Ser-His-Pro-Gln-Phe-Glu-Lys-$(GlyGlyGlySer)_2$-Trp-Ser-His-Pro-Gln-Phe-Glu-Lys (SEQ ID NO: 66) and Trp-Ser-His-Pro-Gln-Phe-Glu-Lys-$(GlyGlyGlySer)_2$Gly-Gly-Ser-Ala-Trp-Ser-His-Pro-Gln-Phe-Glu-Lys (SEQ ID NO: 67).

In certain embodiments, the one or both of the primary and secondary agents comprise an antibody or an antigen-binding fragment thereof. In particular embodiments, the one or more agents is or comprises a monovalent antibody fragment. In some embodiments, one or both of the primary and secondary agent is or comprises a Fab.

In some embodiments, the oligomeric particle reagent comprises: a radius of greater than 60 nm, greater than 70 nm, greater than 80 nm, or greater than 90 nm. In some embodiments, the oligomeric particle reagent comprises: a radius of between 50 nm and 150 nm, between 75 nm and 125 nm, between 80 nm and 115 nm, or between 90 nm and 110 nm, inclusive; or a radius of 90 nm±15 nm, or 95 nm±20-25 nm.

In some embodiments, the oligomeric particle reagent comprises a molecular weight of: at least $5\times10^7$ g/mol, or at least $1\times10^8$ g/mol; and/or between $5\times10^7$ g/mol and $5\times10^8$ g/mol, between $1\times10^8$ g/mol and $5\times10^8$ g/mol, or between $1\times10^8$ g/mol and $2\times10^8$ g/mol.

In certain embodiments, the oligomeric particle reagent comprises at least 500 streptavidin or streptavidin mutein tetramers, at least 1,000 streptavidin or streptavidin mutein tetramers, at least 1,500 streptavidin or streptavidin mutein tetramers, or at least 2,000 streptavidin or streptavidin mutein tetramers; and/or; between 1,000 and 20,000 streptavidin or streptavidin mutein tetramers, between 1,000 and 10,000 streptavidin or streptavidin mutein tetramers, or between 2,000 and 5,000 streptavidin or streptavidin mutein tetramers.

In some embodiments, the method further comprises adding a substance to the cells either subsequent to or during at least a portion of the incubating, wherein the substance is capable of reversing the bond between the primary and secondary agent, such as as an anti-CD3 and anti-CD28 antibody or antigen-binding fragment thereof, and the oligomeric particle reagent. In certain embodiments, the substance is a free binding partner and/or is a competition agent. In particular embodiments, the presence of the substance terminates or lessens the signal induced or modulated by the primary and secondary agent in the T cells. In some embodiments, the substance is or comprises a streptavidin-binding peptide, biotin or a biologically active fragment, or a biotin analog or biologically active fragment. In certain embodiments, the substance is or comprises a streptavidin-binding peptide and the streptavidin-binding peptide is selected from the group consisting of Trp-Ser-His-Pro-Gln-Phe-Glu-Lys (SEQ ID NO: 64), Ser-Ala-Trp-Ser-His-Pro-Gln-Phe-Glu-Lys-$(GlyGlyGlySer)_3$-Trp-Ser-His-Pro-Gln-Phe-Glu-Lys (SEQ ID NO: 73), Trp-Ser-His-Pro-Gln-Phe-Glu-Lys-$(GlyGlyGlySer)_3$-Trp-Ser-His-Pro-Gln-Phe-Glu-Lys (SEQ ID NO: 65), Trp-Ser-His-Pro-Gln-Phe-Glu-Lys-$(GlyGlyGlySer)_2$-Trp-Ser-His-Pro-Gln-Phe-Glu-Lys (SEQ ID NO: 66) and Trp-Ser-His-Pro-Gln-Phe-Glu-Lys-$(GlyGlyGlySer)_2$Gly-Gly-Ser-Ala-Trp-Ser-His-Pro-Gln-Phe-Glu-Lys (SEQ ID NO: 67). In some embodiments, the substance is or comprises biotin or a biologically active fragment, or a biotin analog or biologically active fragment.

In certain embodiments, the substance is added between or between about 42 hours and 120 hours, inclusive, after the exposing to the stimulatory reagent comprising the oligomeric particle is initiated. In certain embodiments, the substance is added between or between about 48 hours and 120 hours, or between or between about 2 days and 5 days, inclusive, after the exposing to the oligomeric particle reagent is initiated. In particular embodiments, the substance is added between or between about 72 hours and 96 hours, or between or between about 3 days and 4 days, after the exposing to the oligomeric particle reagent is initiated. In some embodiments, the substance is added or is added about 48 hours or about 2 days after the exposing to the oligomeric particle reagent is initiated. In certain embodiments, the substance is added or is added about 72 hours or about 3 days after the exposing to the oligomeric particle reagent is initiated. In particular embodiments, the substance is added or is added about 96 hours or about 4 days after the exposing to the oligomeric particle reagent is initiated.

In some embodiments, the substance is added subsequent to the incubation and prior to the harvesting. In certain embodiments, the substance is added during at least a portion of the incubating, and wherein the incubating continues after the substance is added. In particular embodiments, after the substance is added, the incubating is performed in the presence of basal media lacking recombinant cytokines.

Provided herein is a method for producing a composition of engineered T cells, the method comprising: (a) exposing an input composition comprising primary T cells with between or between about 0.02 μg and 8 μg per $10^6$ cells of a stimulatory reagent comprising an oligomeric particle reagent comprising a plurality of streptavidin or streptavidin mutein molecules, the oligomeric particle reagent having attached thereto (i) a primary agent that specifically binds to CD3 and (ii) a secondary agent that specifically binds CD28, wherein the exposing is carried out in the presence of serum free media with recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for between 24 hours and 96 hours or between one day and 4 days, optionally wherein the incubation is carried out at a temperature of about 37° C., and adding a substance comprising biotin or a biologically active fragment thereof, optionally a D-biotin, or a biotin analog or biologically active fragment thereof during at least a portion of the incubating; and (d) subsequent to the incubating, harvesting T cells of the transformed population, thereby producing a composition of engineered cells, wherein the harvesting is carried out at a time between 72 and 96 hours, or between 3 days and 4 days, inclusive, after the exposing to the stimulatory reagent is initiated; thereby producing a composition of engineered cells.

In some embodiments, the input composition comprises at least $300\times10^6$ viable primary T cells. In some embodiments, the number of primary T cells in the input composition is at or about 450×$10^6$ viable primary T cells, at or about 500×$10^6$ viable primary T cells, at or about 550×$10^6$ viable primary T cells, at or about 600×$10^6$ viable primary T cells, at or about 700×$10^6$ viable primary T cells, at or about 800×$10^6$ viable primary T cells, at or about 900×$10^6$ viable primary T cells, or at or about 1,000×$10^6$ viable primary T cells, or any value between any of the foregoing. In certain embodiments, the input composition comprises or comprises at or about 600×$10^6$ viable primary T cells. In particular embodiments, the number of cells in the input composition is up to 900×$10^6$ viable primary T cells or is or is about 900×$10^6$ viable primary T cells.

In some embodiments, primary T cells in the input compositions include primary CD3+ T cells, or include primary CD4+ T cells, and/or primary CD8+ T cells. In some embodiments, the cells in the input composition are enriched, such as by selection or isolation, from a biological sample from a subject. In some embodiments, the primary T cells are enriched in primary CD3+ T cells isolated or selected from a biological sample, such as by immunoaffinity-based selection for CD3+ T cells. In some embodiments, the primary T cells are enriched in primary CD4+ T cells isolated or selected from a biological sample, such as by immunoaffinity-based selection for CD4+ T cells. In some embodiments, the primary T cells are enriched primary CD8+ T cells isolated or selected from a biological sample, such as by immunoaffinity-based selection for CD8+ T cells. In some embodiments, the primary T cells are enriched primary CD4+ and enriched primary CD8+ T cells isolated or selected from a biological sample, such as by immunoaffinity-based selection for CD4+ T cells and CD8+ T cells.

In particular embodiments, the input composition comprises a ratio of between 1.5:1 and 2.0 to 1 CD4+ to CD8+ cells. In some embodiments, the input composition comprises a ratio of between 1.2:1 and 0.8:1 CD4+ to CD8+ cells. In some embodiments, the ratio is at or about 1:1 CD4+ to CD8+ T cells.

Provided herein is a method for producing a composition of engineered T cells, the method comprising: (a) exposing an input composition comprising primary T cells with between or between about 0.4 μg and 8 μg per $10^6$ cells of a stimulatory reagent comprising an oligomeric particle reagent comprising a plurality of streptavidin or streptavidin mutein molecules, the oligomeric particle reagent having attached thereto (i) a primary agent that specifically binds to CD3 and (ii) a secondary agent that specifically binds CD28, wherein the input composition comprises a ratio of between 2:1 and 1:2 CD4+ to CD8+ T cells and comprises at least 300×$10^6$ primary T cells that are CD4+ and CD8+ T cells, and wherein the exposing is carried out in the presence of serum free media comprising recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for between or between about 24 hours to 72 hours, between or between about one day to 3 days, optionally wherein the incubation is carried out at a temperature of about 37° C.; and adding a substance comprising biotin or a biologically active fragment thereof, optionally a D-biotin, or a biotin analog or biologically active fragment thereof during at least a portion of the incubation, wherein the adding is carried out at a time between 48 and 72 hours or between 2 and 3 days, inclusive, after the exposing to the stimulatory reagent is initiated; and (d) subsequent to the incubating, harvesting T cells of the transformed population, thereby producing a composition of engineered cells, wherein the harvesting is carried out at a time between 72 and 96 hours or between 3 and 4 days, inclusive, after the exposing to the stimulatory reagent is initiated; thereby producing a composition of engineered cells. In some embodiments, said primary T cells comprise a ratio of or of about 1:1 CD4+ T cells to CD8+ T cells. In some embodiments, the substance is added or is added about 48 hours or about 2 days after the exposing to the oligomeric particle reagent is initiated. In certain embodiments, the substance is added or is added about 72 hours or about 3 days after the exposing to the oligomeric particle reagent is initiated. In particular embodiments, the substance is added or is added about 96 hours or about 4 days after the exposing to the oligomeric particle reagent is initiated.

Provided herein is a method for producing a composition of engineered T cells, the method comprising: (a) exposing an input composition comprising at least 300×$10^6$ primary T cells a stimulatory reagent comprising a paramagnetic bead at a ratio of beads to cells is from or from about 2:1 to 0.5:1, wherein the bead is an inert paramagnetic bead comprising a polystyrene coating and a diameter of or of about 4.5 μm, the bead having attached thereto (i) an anti-CD3 antibody or antigen-binding fragment thereof and an anti-CD28 antibody or antigen-binding fragment thereof, wherein the input composition comprises a ratio of between 2:1 and 1:2 CD4+ to CD8+ T cells and comprises at least 300×$10^6$ primary T cells that are CD4+ and CD8+ T cells, and wherein the exposing is carried out in the presence of serum free media comprising recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for between 48 hours and 72 hours, or between 2 days and 3 days, inclusive, optionally wherein the incubation is carried out at a temperature of about 37° C.; (d) subsequent to the incubating, exposing the cells to a magnetic field to remove the stimulatory reagent from the cells and then harvesting the T cells, thereby producing a composition of engineered cells, wherein the harvesting is carried out at a time between 72 and 96 hours, or between about 3 days and 4 days, inclusive, after the exposing to the stimulatory reagent is initiated; thereby producing a composition of engineered cells. In some embodiments, the primary T cells comprising a ratio of or of about 1:1 CD4+ T cells to CD8+ T cells.

In some embodiments, the number of primary T cells in the input composition is at or about 450×$10^6$ viable primary T cells, at or about 500×$10^6$ viable primary T cells, at or about 550×$10^6$ viable primary T cells, at or about 600×$10^6$ viable primary T cells, at or about 700×$10^6$ viable primary T cells, at or about 800×$10^6$ viable primary T cells, at or about 900×$10^6$ viable primary T cells, or at or about 1,000×$10^6$ viable primary T cells, or any value between any of the foregoing. In certain embodiments, the input composition comprises or comprises at or about 600×$10^6$ viable primary T cells. In particular embodiments, the number of cells in the input composition is up to 900×$10^6$ viable primary T cells or is or is about 900×$10^6$ viable primary T cells.

In some embodiments, at least a portion of the incubating is performed in the presence of serum free media comprising recombinant IL-2, IL-7, and IL-15. In certain embodiments, the incubating is carried out in basal media lacking recombinant cytokines. In particular embodiments, the incubating is carried out for or for about 24 hours or for or for about one day subsequent to the introducing. In some embodiments, the incubating is carried out for or for about 48 hours or for or for about 2 days subsequent to the introducing. In certain embodiments, the incubating is carried out for or for about 72 hours or for or for about 3 days subsequent to the introducing.

In some embodiments, prior to the exposing to the stimulatory reagent, the method includes enriching CD3+ T cells from a biological sample, wherein the enriching comprises selection in a closed system for cells that are CD3+, thereby generating a selected population. In some cases, the enrichment is a first selection and cells and the first selection are further selected for cells that are CD3+ to further enrich the selection, thereby generating a second selected population. In some embodiments, the input composition comprises the enriched CD3+ cells. In some embodiments, the input composition comprises enriched CD3+ cells from the first selection. In some embodiments, the input composition comprises enriched CD3+ cells from the second selection.

In certain embodiments, the enriching cells comprise immunoaffinity-based selection. In some embodiments, the immunoaffinity-based selection is effected by contacting cells with an antibody immobilized on or attached to an affinity chromatography matrix, said antibody capable of specifically binding to a cell surface marker on the cell. In some embodiments, the immunoaffinity-based selection is a positive selection of CD3+ T cells. In certain embodiments, the method further comprises after contacting cells in the sample to the affinity chromatography matrix, eluting the cells having bound to the antibody, thereby recovering the selected cells from the matrix.

In some embodiments, prior to the exposing to the stimulatory reagent, the method includes enriching CD4+ or CD8+ T cells from a biological sample, wherein the enriching comprises: (a) performing a first selection in a closed system, said first selection comprising enriching for one of (i) CD4+ cells and (ii) CD8+ cells from a sample containing primary human T cells, the enrichment thereby generating a first selected population and a non-selected population; and (b) performing a second selection in the closed system, said second selection comprising enriching for the other of (i) CD4+ cells and (ii) CD8+ cells from the non-selected population, the enrichment thereby generating a second selected population, wherein the enriching produces separate enriched populations of CD4+ T cells and for CD8+ T cells, wherein the separate enriched populations each comprise cells from one of the of the first selected population or the second selected population, and wherein the input composition comprises cells from one or more of the enriched population of CD4+ T cells and the enriched population of CD8+ T cells.

In some embodiments, the separate enriched populations of CD4+ T cells and CD8+ T cells are combined, thereby producing the input composition. In certain embodiments, said combining is performed in the closed system, optionally wherein the closed system is automated. In particular embodiments, enriching cells in the first and/or second selection comprises performing positive selection or negative selection based on expression of a cell surface marker. In some embodiments, enriching cells in the first or second selection comprises performing a plurality of positive or negative selection steps based on expression of a cell surface marker or markers to enrich for CD4+ or CD8+ cells.

In certain embodiments, the enriching cells in the first and/or second selection comprise immunoaffinity-based selection. In some embodiments, the immunoaffinity-based selection is effected by contacting cells with a n antibody, immobilized on or attached to an affinity chromatography matrix, said antibody, capable of specifically binding to a a cell surface marker on the cell, to effect positive or negative selection of CD4+ or CD8+ cells. In certain embodiments, the method further comprises after contacting cells in the sample to an affinity chromatography matrix in the first selection and/or second selection, eluting the cells having bound to the antibody, thereby recovering the selected cells from the matrix. In particular embodiments, enriching CD4+ or CD8+ T cells from the biological sample comprises: (a) the enriching for the CD4+ cells by positive selection based on surface expression of CD4; (b) enriching for the CD8+ cells by positive selection based on surface expression of CD8. In some embodiments, the or both (a) and (b).

In some embodiments, the immunoaffinity-based selection on an affinity chromatography matrix is carried out using an antibody that further comprises one or more binding partners capable of forming a reversible bond with a binding reagent immobilized on the matrix, whereby the antibody is reversibly bound to said chromatography matrix during said contacting. In such embodiments, cells expressing the cell surface marker specifically bound by the antibody on said matrix are capable of being recovered from the matrix by disruption of the reversible binding between the binding reagent and binding partner. In some embodiments, the binding partner is selected from among biotin, a biotin analog, and a peptide capable of binding to the binding reagent and the binding reagent is selected from among streptavidin, a streptavidin analog or mutein, avidin and an avidin analog or mutein. In some embodiments, the binding partner comprises a sequence of amino acids set forth in SEQ ID NO:64; and/or the binding reagent is a streptavidin mutein comprising the sequence of amino acids set forth in SEQ ID NO: 75, 80, 76 or 63. In some embodiments, after contacting cells in the sample to an affinity chromatography matrix, the methods for enriching cells includes applying a competition reagent to disrupt the bond between the binding partner and binding reagent, thereby recovering the selected cells from the matrix. In some embodiments, the competition reagent is biotin or a biotin analog. In some embodiments, the antibody or antibodies in the selection or selections has a dissociation rate constant ($k_{off}$) for binding and the cell surface marker of greater than or greater than about $3\times10^{-5}$ $sec^{-1}$. In some embodiments, the antibody or antibodies in the selection or selections has an affinity for the cell surface marker of a dissociation constant ($K_d$) in the range of about $10^{-3}$ to $10^{-7}$ or in the range of about $10^{-7}$ to about $10^{-10}$. In some embodiments, the chromatography matrix of the selection or selections is packed in a separation vessel, which is a column.

In some embodiments, prior to the exposing to the stimulatory reagent, enriching CD4+ or CD8+ T cells from a biological sample, wherein the enriching comprises contacting cells of said sample with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample; and recovering cells bound to the first and/or the second immunoaffinity reagent, thereby generating an enriched composition comprising CD4+ cells and CD8+ cells, and wherein the input composition comprises cells of the enriched composition comprising CD4+ cells and CD8+ cells. In some embodiments, each of the immunoaffinity reagents comprises an antibody or antigen-binding fragment thereof. In certain embodiments, the immunoaffinity reagents are immobilized on the outside surface of a bead. In particular embodiments, the bead is a magnetic bead. In some embodiments, the recovering cells bound to the first or the second immunoaffinity reagent comprises exposing the cells to a magnetic field.

In certain embodiments, the biological sample comprises primary T cells obtained from a subject, optionally a human subject. In certain embodiments, the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product. In some embodiments, the biological sample is an apheresis or leukapheresis product that has been previously cryofrozen prior to the enriching.

In particular embodiments, the harvesting is carried out at or at about 48 hours or at or at about 2 days after the exposing to the stimulatory reagent is initiated. In some embodiments, the harvesting is carried out at or at about 72 hours or at or at about 3 days after the exposing to the stimulatory reagent is initiated. In certain embodiments, the harvesting is carried out at or at about 48 hours or at or at about 2 days after the exposing to the stimulatory reagent is initiated.

In particular embodiments, the harvesting is carried out at a time when integrated vector is detected in the genome but prior to achieving stable iVCN per diploid genome. In some embodiments, the harvesting is carried out at a time when the fraction of integrated vector copy number (iVCN) to total VCN in the population of transformed cells, on average, is less than 0.8. In certain embodiments, the harvesting is carried out at a time when the iVCN of the population of transformed cells, on average, is less than or less than about 2.0 copies per diploid genome.

In some embodiments, the harvesting is carried out at a time when the iVCN of the population of transformed cells, on average, is less than or less than about 1.5 copies per diploid genome. In certain embodiments, the harvesting is carried out at a time when the iVCN of the population of transformed cells, on average, is less than or less than about 1.0 copy per diploid genome. In particular embodiments, the harvesting is carried out at a time when the iVCN of the population of transformed cells, on average, is less than or less than about 0.75 copies per diploid genome. In some embodiments, the harvesting is carried out at a time when the iVCN of the population of transformed cells, on average, is less than or less than about 0.5 copies per diploid genome. In certain embodiments, harvesting the cells comprises removing cellular debris by rinsing or washing the cells. In particular embodiments, the cells are harvested at a time when the percentage of naïve-like cells is greater than or greater than about 60% among total T cells in the population, total CD4+ T cells in the population or total CD8+ T cells, or of recombinant protein-expressing cells thereof, in the population. In some embodiments, the cells are harvested at a time when the percentage of naïve like T cells and/or central memory T cells is greater than or greater than about 60% among total T cells in the population, total CD4+ T cells in the population or total CD8+ T cells, or of recombinant protein-expressing cells thereof, in the population. In some embodiments, at the time of harvesting: the percentage of naïve-like T cells is greater than or greater than about 60% among total recombinant protein-expressing cells in the population, such as greater than or greater than about 65%, 70%, 80%, 90% or 95% total recombinant protein-expressing T cells in the population. In some embodiments, at the time of harvesting, the percentage of naïve-like T cells is greater than or greater than about 60% among total recombinant protein-expressing CD4+ T cells in the population, such as greater than or greater than about 65%, 70%, 80%, 90% or 95% total recombinant protein-expressing CD4+ cells in the population. In some embodiments, at the time of harvesting, the percentage of naïve-like T cells is greater than or greater than about 60% among total recombinant protein-expressing CD8+ T cells in the population, such as greater than or greater than about 65%, 70%, 80%, 90% or 95% total recombinant protein-expressing CD8+ cells in the population. In some embodiments, the naïve-like T cells or the T cells that are surface positive for a marker expressed on naïve-like T cells are CCR7+CD45RA+, CD27+CCR7+ or CD62L−CCR7+. In some embodiments, the naïve-like T cells comprise CCR7+CD45RA+. In particular embodiments, the naïve-like T cells comprise CD27+CCR7+ cells.

In some embodiments, at the time of harvesting, the percentage of naïve-like T cells and/or central memory T cells is greater than or greater than about 60% among total recombinant protein-expressing cells in the population, such as greater than or greater than about 65%, 70%, 80%, 90% or 95% total recombinant protein-expressing T cells in the population. In some embodiments, the percentage of naïve-like T cells and/or central memory T cells is greater than or greater than about 60% among total recombinant protein-expressing CD4+ T cells in the population, such as greater than or greater than about 65%, 70%, 80%, 90% or 95% total recombinant protein-expressing CD4+ cells in the population. In some embodiments, the percentage of naïve-like T cells and/or central memory T cells is greater than or greater than about 60% among total recombinant protein-expressing CD8+ T cells in the population, such as greater than or greater than about 65%, 70%, 80%, 90% or 95% total recombinant protein-expressing CD8+ cells in the population. In some embodiments, the naïve-like T cells or the T cells that are surface positive for a marker expressed on naïve-like T cells are CCR7+CD45RA+, CD27+CCR7+ or CD62L−CCR7+. In some embodiments, the naïve-like T cells comprise CCR7+CD45RA+. In particular embodiments, the naïve-like T cells comprise CD27+CCR7+ cells. In particular embodiments, central memory T cells are CCR7+CD45RA−.

In certain embodiments, the method further comprises formulating cells of the output composition for cryopreservation and/or administration to a subject. In some embodiments, the cells are formulated in the presence of a pharmaceutically acceptable excipient. In particular embodiments, the cells of the output composition are formulated in the presence of a cryoprotectant. In some embodiments, the cryoprotectant comprises DMSO. In some cases, a DMSo may prevent intracellular crystals from forming during the freezing process.

In some embodiments, the cells of the output composition are formulated in a container, optionally a vial or a bag. In certain embodiments, the recombinant protein is a recombinant receptor capable of binding to a target antigen that is associated with, specific to, and/or expressed on a cell or tissue of a disease, disorder or condition. In particular embodiments, the disease, disorder or condition is an infectious disease or disorder, an autoimmune disease, an inflammatory disease, or a tumor or a cancer.

In some embodiments, the target antigen is a tumor antigen. In certain embodiments, the target antigen is selected from among $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G protein-coupled receptor class C group 5 member D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha(IL-22R$\alpha$), IL-13 receptor alpha 2 (IL-13R$\alpha$2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.

In certain embodiments, the recombinant protein is or comprises a functional non-TCR antigen receptor or a TCR or antigen-binding fragment thereof. In particular embodiments, the recombinant protein is a chimeric antigen receptor (CAR). In some embodiments, the recombinant receptor is an anti-BCMA CAR. In certain embodiments, the recombinant protein is an anti-CD19 CAR.

In particular embodiments, the chimeric antigen receptor comprises an extracellular domain comprising an antigen-binding domain, a spacer and/or a hinge region, a transmembrane domain, and an intracellular signaling domain comprising a costimulatory signaling region. In some embodiments, the extracellular domain comprising an antigen-binding domain comprises an scFv. In certain embodiments, the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In particular embodiments, the intracellular signaling domain is or comprises an intracellular signaling domain of a CD3 chain, optionally a CD3-zeta (CD35) chain, or a signaling portion thereof. In some embodiments, the costimulatory signaling region comprises an intracellular signaling domain of a CD28, a 4-1BB or an ICOS or a signaling portion thereof.

In certain embodiments, the serum free media comprises: 0.5 mM to 5 mM of a dipeptide form of L-glutamine in a basal media; 0.5 mM to 5 mM L-glutamine; and at least one protein, wherein the media is free of serum.

In some embodiments, the basal media lacking one or more recombinant cytokines comprises L-glutamine. In some embodiments, the L-glutamine is present at a concentration of from about 0.5 mM to about 5 mM. In some embodiments, the L-glutamine is present at a concentration of about 2 mM.

In some embodiments, the basal media lacking one or more recombinant cytokines is free of serum.

In some embodiments, the basal media further comprises at least one protein selected from one or more of albumin, insulin or transferrin, optionally one or more of a human or recombinant albumin, insulin or transferrin.

In some embodiments, any of the methods described herein can be carried out using a non-viral method of genetic engineering, e.g., for introduction of a heterologous polynucleotide encoding the recombinant protein into a cell, e.g., a T cell. Any of the provided embodiments of the method described herein can be carried out using a non-viral method for introduction of a heterologous polynucleotide encoding the recombinant protein into a primary T cell for the manufacture of a cell therapy. In particular aspects, the non-viral method is a method that facilitates integration of the polynucleotide or a portion thereof encoding the recombinant receptor into a genome in a cell. Various methods of non-viral introduction can be used, including any method of non-viral introduction as described herein.

In one aspect, provided herein is a composition comprising engineered cells produced by any method provided herein. In some embodiments, the composition is a therapeutic composition. Provided herein is a therapeutic T cell composition produced by any method provided herein.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are naïve-like T cells or are T cells that are surface positive for a marker expressed on naïve-like T cells. In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are central memory T cells or are T cells that are surface positive for a marker expressed on central memory T cells. In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are naïve-like T cells or central memory T cells, or are T cells that are surface positive for a marker expressed on naïve-like T cells or central memory T cells. In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are CD27+CCR7+ T cells.

In some embodiments, the naïve-like T cells are surface positive for a T cell activation marker selected from the group consisting of CD45RA, CD27, CD28, and CCR7; and/or are surface negative for a marker selected from the group consisting of CD25, CD45RO, CD56, CD62L, KLRG1; and/or have low expression of CD95; and/or have low expression of CD95; and/or are negative for intracellular expression of a cytokine selected from the group consisting of IL-2, IFN-γ, IL-4, IL-10.

In some embodiments, the marker expressed on naïve-like T cell is selected from the group consisting of CD45RA, CD27, CD28, and CCR7. In some embodiments, the naïve-like T cells or the T cells that are surface positive for a marker expressed on naïve-like T cells are CCR7+CD45RA+, CD27+CCR7+ or CD62L−CCR7+. In some embodiments, the naïve-like T cells or the T cells that are surface positive for a marker expressed on naïve-like T cells include CD27+CCR7+ T cells, wherein at least 70%, 80%, 85%, or 90% of the total receptor$^+$/CD8+ cells in the composition are CD27+CCR7+. In some embodiments, the naïve-like T cells or the T cells that are surface positive for a marker expressed on naïve-like T cells include CD27+CCR7+ T cells, wherein at least 50%, 60%, 70%, 80%, 85%, or 90% of the total receptor$^+$/CD4+ cells in the composition are CD27+CCR7+.

In some embodiments, the naïve-like T cells or the T cells that are surface positive for a marker expressed on naïve-like T cells include CD27+CCR7+ T cells, wherein at least 50%, 60%, 70%, 80%, 85%, or 90% of the total receptor$^+$/CD8+ cells in the composition are CD27+CCR7+ and at least 50%, 60%, 70%, 80%, 85%, or 90% of the total receptor$^+$/CD4+ cells in the composition are CD27+CCR7+. In some embodiments, at least 50%, 60%, 70%, 80% or 90% of the total receptor$^+$/CD8$^+$ cells in the composition are naïve-like T cells or are surface positive for a marker expressed on naïve-like T cells and at least 15%, 20%, 30%, 40%, 50%, 60%, 70%, 80% or 90% of the total receptor$^+$/CD4$^+$ cells in the composition are naïve-like T cells or are surface positive for a marker expressed on naïve-like T cells.

In some embodiments, at least 20%, 25%, 30%, 40%, 50%, 60%, 70%, 80% or 90% of the total receptor$^+$/CD8$^+$ cells in the composition are central memory T cells or are surface positive for a marker expressed on central memory T cells and at least 50%, 60%, 70%, 80% or 90% of the total receptor$^+$/CD4$^+$ cells in the composition are central memory T cells or are surface positive for a marker expressed on central memory T cells. In some embodiments, at least 40%, 50%, 60%, 70%, 80% or 90% of the total receptor$^+$/CD8$^+$ cells in the composition are naïve-like T cells or central memory T cells or are surface positive for a marker expressed on naïve-like T cells or central memory T cells and at least 50%, 60%, 70%, 80% or 90% of the total receptor$^+$/CD4$^+$ cells in the composition are naïve-like T cells or central memory T cells or are surface positive for a marker expressed on naïve-like T cells or central memory T cells.

In some embodiments, on average in a plurality of T cell compositions produced by the method disclosed herein, at least at or about, or at or about, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are naïve-like T cells or are T cells that are surface positive for a marker expressed on naïve-like T cells. In some embodiments, on average in a plurality of T cell compositions produced by the method disclosed herein, at least at or about, or at or about, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are central memory T cells or are T cells that are surface positive for a marker expressed on central memory T cells. In some embodiments, on average in a plurality of T cell compositions produced by the method disclosed herein, at least at or about, or at or about, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are naïve-like T cells or central memory T cells, or are T cells that are surface positive for a marker expressed on naïve-like T cells or central memory T cells. In some embodiments, on average in a plurality of T cell compositions produced by the method disclosed herein, at least at or about, or at or about, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are CD27+CCR7+ T cells. In any of the preceding embodiments, on average in a plurality of T cell compositions produced by the method disclosed herein, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition can be CD4+ T cells and CD8+ T cells. In any of the preceding embodiments, on average in a plurality of T cell compositions produced by the method disclosed herein, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition can be CD3+ T cells.

In one aspect, provided herein is a therapeutic T cell composition including CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are naïve-like T cells or are surface positive for a marker expressed on naïve-like T cells and at least 30%, 40%, 50%, 60%, 70%, 80% or 90% of the total receptor$^+$/CD4$^+$ cells in the composition are naïve-like T cells or are surface positive for a marker expressed on naïve-like T cells.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are naïve-like T cells or are T cells that are surface positive for a marker expressed on naïve-like T cells. In some embodiments, at least 60% of the total receptor$^+$/CD8$^+$ cells in the composition are naïve-like T cells or are surface positive for a marker expressed on naïve-like T cells and 30% of the total receptor$^+$/CD4$^+$ cells in the composition are naïve-like T cells or are surface positive for a marker expressed on naïve-like T cells. In some embodiments, at least 70% of the total receptor$^+$/CD8$^+$ cells in the composition are naïve-like T cells or are surface positive for a marker expressed on naïve-like T cells and 40% of the total receptor$^+$/CD4$^+$ cells in the composition are naïve-like T cells or are surface positive for a marker expressed on naïve-like T cells. In some embodiments, at least 70% of the total receptor$^+$/CD8$^+$ cells in the composition are naïve-like T cells or are surface positive for a marker expressed on naïve-like T cells and 50% of the total receptor$^+$/CD4$^+$ cells in the composition are naïve-like T cells or are surface positive for a marker expressed on naïve-like T cells. In some embodiments, at least 70% of the total receptor$^+$/CD8$^+$ cells in the composition are naïve-like T cells or are surface positive for a marker expressed on naïve-like T cells and 60% of the total receptor$^+$/CD4$^+$ cells in the composition are naïve-like T cells or are surface positive for a marker expressed on naïve-like T cells. In some embodiments, at least 70% of the total receptor$^+$/CD8$^+$ cells in the composition are naïve-like T cells or are surface positive for a marker expressed on naïve-like T cells and 70% of the total receptor$^+$/CD4$^+$ cells in the composition are naïve-like T cells or are surface positive for a marker expressed on naïve-like T cells.

In one aspect, provided herein is a therapeutic T cell composition including CD4+ T cells expressing a recombinant receptor and CD8+ T cells expressing a recombinant receptor, wherein at least 20%, 25%, 30%, 40%, 50%, 60%, 70%, 80% or 90% of the total receptor$^+$/CD8$^+$ cells in the composition are central memory T cells or are surface positive for a marker expressed on central memory T cells and at least 50%, 60%, 70%, 80% or 90% of the total receptor$^+$/CD4$^+$ cells in the composition are central memory T cells or are surface positive for a marker expressed on central memory T cells.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are central memory T cells or are T cells that are surface positive for a marker expressed on central memory T cells. In some embodiments, at least 25% of the total receptor$^+$/CD8$^+$ cells in the composition are central memory T cells or are surface positive for a marker expressed on central memory T cells and at least 60% of the total receptor$^+$/CD4$^+$ cells in the composition are central memory T cells or are surface positive for a marker expressed on central memory T cells. In some embodiments, at least 65% of the total receptor$^+$/CD8$^+$ cells in the composition are central memory T cells or are surface positive for a marker expressed on central memory T cells and at least 60% of the total receptor$^+$/CD4$^+$ cells in the composition are central memory T cells or are surface positive for a marker expressed on central memory T cells. In some embodiments, at least 70% of the total receptor$^+$/CD8$^+$ cells in the composition are central memory T cells or are surface positive for a marker expressed on central memory T cells and 65% of the total receptor$^+$/CD4$^+$ cells in the composition are central memory T cells or are surface positive for a marker expressed on central memory T cells. In some embodiments, at least 70% of the total receptor$^+$/CD8$^+$ cells in the composition are central memory T cells or are surface positive for a marker expressed on central memory T cells and 70% of the total receptor$^+$/CD4$^+$ cells in the composition are central memory T cells or are surface positive for a marker expressed on central memory T cells.

In one aspect, provided herein is a therapeutic T cell composition including CD4+ T cells expressing a recombinant receptor and CD8+ T cells expressing a recombinant receptor, wherein at least 40%, 50%, 60%, 70%, 80% or 90% of the total receptor$^+$/CD8$^+$ cells in the composition are naïve-like T cells or central memory T cells or are surface positive for a marker expressed on naïve-like T cells or central memory T cells and at least 50%, 60%, 70%, 80% or 90% of the total receptor$^+$/CD4$^+$ cells in the composition are naïve-like T cells or central memory T cells or are surface positive for a marker expressed on naïve-like T cells or central memory T cells.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are naïve-like T cells or central memory T cells or are T cells that are surface positive for a marker expressed on naïve-like T cells or central memory T cells. In some embodiments, at least 50% of the total receptor$^+$/CD8$^+$ cells in the composition are naïve-like T cells or central memory T cells or are surface positive for a marker expressed on naïve-like T cells or central memory T cells and at least 65% of the total receptor$^+$/CD4$^+$ cells in the composition are naïve-like T cells or central memory T cells or are surface positive for a marker expressed on naïve-like T cells or central memory T cells. In some embodiments, at least 70% of the total receptor$^+$/CD8$^+$ cells in the composition are naïve-like T cells or central memory T cells or are surface positive for a marker expressed on naïve-like T cells or central memory T cells and at least 70% of the total receptor$^+$/CD4$^+$ cells in the composition are naïve-like T cells or central memory T cells or are surface positive for a marker expressed on naïve-like T cells or central memory T cells. In some embodiments, at least 75% of the total receptor$^+$/CD8$^+$ cells in the composition are naïve-like T cells or central memory T cells or are surface positive for a marker expressed on naïve-like T cells or central memory T cells and at least 75% of the total receptor$^+$/CD4$^+$ cells in the composition are naïve-like T cells or central memory T cells or are surface positive for a marker expressed on naïve-like T cells or central memory T cells.

In some embodiments, the naïve-like T cells are surface positive for a T cell activation marker selected from the group consisting of CD45RA, CD27, CD28, and CCR7; and/or are surface negative for a marker selected from the group consisting of CD25, CD45RO, CD56, CD62L, KLRG1; and/or have low expression of CD95. In some embodiments, the marker expressed on naïve-like T cell is selected from the group consisting of CD45RA, CD27, CD28, and CCR7. In some embodiments, the receptor$^+$/CD4$^+$ T cells or the receptor$^+$/CD4$^+$ T cells that are naïve-like T cells or that are surface positive for a marker expressed on naïve-like T cells are CCR7+CD45RA+, CD27+CCR7+ or CD62L−CCR7+. In some embodiments, wherein the receptor$^+$/CD4$^+$ T cells or the receptor$^+$/CD4$^+$ T cells that are naïve-like T cells or that are surface positive for a marker expressed on naïve-like T cells are CD27+CCR7+. In some embodiments, the receptor$^+$/CD8$^+$ T cells or the receptor$^+$/CD8$^+$ T cells that are naïve-like T cells or that are surface positive for a marker expressed on naïve-like T cells are CCR7+CD45RA+, CD27+CCR7+ or CD62L−CCR7+. In some embodiments, the receptor$^+$/CD8$^+$ T cells or the receptor$^+$/CD8$^+$ T cells that are naïve-like T cells or that are surface positive for a marker expressed on naïve-like T cells are CD27+CCR7+.

In one aspect, provided herein is a therapeutic T cell composition including CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are CD27+

CCR7+ and at least 30%, 40%, 50%, 60%, 70%, 80% or 90% of the total receptor$^+$/CD4$^+$ cells in the composition are CD27+CCR7+.

In one aspect, provided herein is a therapeutic T cell composition including CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are CD27+CCR7+ and at least 50%, 60%, 70%, 80% or 90% of the total receptor$^+$/CD4$^+$ cells in the composition are CD27+CCR7+.

In some embodiments, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells. In some embodiments, at least or at least about 90% of the cells in the composition are CD4+ T cells and CD8+ T cells, at least or at least about 60% of the total receptor$^+$/CD8$^+$ cells in the composition are CD27+CCR7+, and at least or at least about 40% of the total receptor$^+$/CD4$^+$ cells in the composition are CD27+CCR7+. In some embodiments, at least or at least about 95% of the cells in the composition are CD4+ T cells and CD8+ T cells, at least or at least about 65% of the total receptor$^+$/CD8$^+$ cells in the composition are CD27+CCR7+, and at least or at least about 45% of the total receptor$^+$/CD4$^+$ cells in the composition are CD27+CCR7+. In some embodiments, at least or at least about 98% of the cells in the composition are CD4+ T cells and CD8+ T cells, at least or at least about 70%, at least or at least about 75%, at least or at least about 80%, or at least or at least about 85% of the total receptor$^+$/CD8$^+$ cells in the composition are CD27+CCR7+, and at least or at least about 50%, at least or at least about 55%, at least or at least about 60%, or at least or at least about 65% of the total receptor$^+$/CD4$^+$ cells in the composition are CD27+CCR7+. In some embodiments, at least or at least about 98% of the cells in the composition are CD4+ T cells and CD8+ T cells, at least or at least about 75% of the total receptor$^+$/CD8$^+$ cells in the composition are CD27+CCR7+, and at least or at least about 55% of the total receptor$^+$/CD4$^+$ cells in the composition are CD27+CCR7+. In some embodiments, at least or at least about 98% of the cells in the composition are CD4+ T cells and CD8+ T cells, at least or at least about 80% of the total receptor$^+$/CD8$^+$ cells in the composition are CD27+CCR7+, and at least or at least about 60% of the total receptor$^+$/CD4$^+$ cells in the composition are CD27+CCR7+. In some embodiments, at least or at least about 98% of the cells in the composition are CD4+ T cells and CD8+ T cells, at least or at least about 85% of the total receptor$^+$/CD8$^+$ cells in the composition are CD27+CCR7+, and at least or at least about 65% of the total receptor$^+$/CD4$^+$ cells in the composition are CD27+CCR7+. In some embodiments, at least or at least about 98% of the cells in the composition are CD4+ T cells and CD8+ T cells, at least or at least about 90% of the total receptor$^+$/CD8$^+$ cells in the composition are CD27+CCR7+, and at least or at least about 70% of the total receptor$^+$/CD4$^+$ cells in the composition are CD27+CCR7+. In some embodiments, at least 90% of the cells in the composition are CD4+ T cells and CD8+ T cells, at least 60% of the total receptor$^+$/CD8$^+$ cells in the composition are CD27+CCR7+ and at least 40% of the total receptor$^+$/CD4$^+$ cells in the composition are CD27+CCR7+. In some embodiments, at least 90% of the cells in the composition are CD4+ T cells and CD8+ T cells, at least 70% of the total receptor$^+$/CD8$^+$ cells in the composition are CD27+CCR7+ and at least 50% of the total receptor$^+$/CD4$^+$ cells in the composition are CD27+CCR7+. In some embodiments, at least 90% of the cells in the composition are CD4+ T cells and CD8+ T cells, at least 70% of the total receptor$^+$/CD8$^+$ cells in the composition are CD27+CCR7+ and at least 60% of the total receptor$^+$/CD4$^+$ cells in the composition are CD27+CCR7+. In some embodiments, wherein at least 95% of the cells in the composition are CD4+ T cells and CD8+ T cells, at least 70% of the total receptor$^+$/CD8$^+$ cells in the composition are CD27+CCR7+ and at least 70% of the total receptor$^+$/CD4$^+$ cells in the composition are CD27+CCR7+. In some embodiments, at least 95% of the cells in the composition are CD4+ T cells and CD8+ T cells, at least 80% of the total receptor$^+$/CD8$^+$ cells in the composition are CD27+CCR7+ and at least 80% of the total receptor$^+$/CD4$^+$ cells in the composition are CD27+CCR7+.

In some embodiments, at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are CD27+CCR7+.

In some embodiments, the ratio of receptor+/CD4+ T cells to receptor+/CD8+ T cells in the composition is between about 1:3 and about 3:1. In some embodiments, the ratio of receptor+/CD4+ T cells to receptor+/CD8+ T cells in the composition is between about 1:2 and about 2:1. In some embodiments, the ratio of receptor+/CD4+ T cells to receptor+/CD8+ T cells in the composition is at or about 1:1.

In some embodiments, the composition includes one or more unit doses of cells. In some embodiments, the unit dose includes between or between about $1\times10^4$ and $50\times10^6$ T cells.

In some embodiments, the recombinant protein is or comprises a chimeric receptor and/or a recombinant antigen receptor. In some embodiments, the recombinant receptor is capable of binding to a target protein that is associated with, specific to, and/or expressed on a cell or tissue of a disease, disorder or condition. In some embodiments, the disease, disorder or condition is an infectious disease or disorder, an autoimmune disease, an inflammatory disease, or a tumor or a cancer. In some embodiments, the target antigen is a tumor antigen. In some embodiments, the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.

In some embodiments, wherein the recombinant protein is or comprises a functional non-TCR antigen receptor or a TCR or antigen-binding fragment thereof.

In some embodiments, wherein the recombinant protein comprises an extracellular domain comprising an antigen-binding domain. In some embodiments, wherein the antigen-binding domain is or comprises an antibody or an antibody fragment thereof, which in some embodiments is a single chain fragment. In some embodiments, the fragment includes antibody variable regions joined by a flexible linker. In some embodiments, the fragment includes an scFv.

In some embodiments, the recombinant protein includes an intracellular signaling region. In some embodiments, wherein the intracellular signaling region includes an intracellular signaling domain. In some embodiments, the intracellular signaling domain is or includes a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM). In some embodiments, the intracellular signaling domain is or includes an intracellular signaling domain of a CD3 chain. In some embodiments, the CD3 chain is a CD3-zeta (CD3ζ) chain, or a signaling portion thereof.

In some embodiments, the recombinant protein further includes a transmembrane domain disposed between the extracellular domain and the intracellular signaling region. In some embodiments, the intracellular signaling region further includes a costimulatory signaling domain. In some embodiments, the costimulatory signaling domain includes an intracellular signaling domain of a T cell costimulatory molecule or a signaling portion thereof. In some embodiments, the costimulatory signaling domain includes an intracellular signaling domain of a CD28, a 4-1BB or an ICOS or a signaling portion thereof. In some embodiments, the costimulatory signaling domain is between the transmembrane domain and the intracellular signaling domain.

In some embodiments, the T cells are primary T cells obtained from a subject: In some embodiments, the T cells are autologous to the subject. In some embodiments, the T cells are allogeneic to the subject.

In some embodiments, the composition includes a pharmaceutically acceptable excipient. In particular embodiments, the composition further comprises a pharmaceutically acceptable carrier. In certain embodiments, the composition further comprises a cryoprotectant. In some embodiments, the cryoprotectant is DMSO.

In certain embodiments, at least 60% of total T cells, total CD4+ T cells, or total CD8+ T cells of the composition, of recombinant protein-expressing cells thereof are CD27+ CCR7+. In some embodiments, at least 65%, 70%, 80%, 90% or 95% of total recombinant protein-expressing cells of the composition are CD27+CCR7+, at least 65%, 70%, 80%, 90% or 95% of recombinant protein-expressing CD4+ T cells of the composition are CD27+CCR7+, or at least 65%, 70%, 80%, 90% or 95% of recombinant protein-expressing CD8+ T cells of the composition are CD27+ CCR7+.

In one aspect, provided herein is an article of manufacture, comprising the composition of the methods or composition provided herein, and instructions for administering the output composition to a subject.

In certain embodiments, the subject has a disease or condition. In some embodiments, the recombinant receptor specifically recognizes or specifically binds to an antigen associated with, or expressed or present on cells of, the disease or condition.

In one aspect, provided herein is a method of treating a subject having or suspected of having a disease or condition, the method comprising administering to the subject a dose of T cells from any composition provided herein.

In certain embodiments, the dose of T cells is administered to the subject as a single dose or is administered only one time within a period of two weeks, one month, three months, six months, 1 year or more. In some embodiments, the dose of T cells comprises between at or about $1\times10^4$ and $50\times10^6$ T cells, inclusive. In particular embodiments, the dose of T cells comprises less than $50\times10^6$ T cells, $10\times10^6$ T cells, $5\times10^6$ T cells, $1\times10^6$ T cells, $0.5\times10^6$ T cells, or $1\times10^5$ T cells. In certain embodiments, the dose of T cells comprises or comprises about $20\times10^6$ T cells. In some embodiments, wherein the dose of T cells comprises or comprises about $10\times10^6$ T cells.

In certain embodiments, the dose of T cells comprises or comprises about $2\times10^6$ T cells. In particular embodiments, the dose of T cells comprises or comprises about $1\times10^6$ T cells.

In some embodiments, the T cells of the dose of T cells are total T cells, total viable T cells, total viable recombinant receptor expressing T cells, total viable recombinant receptor expressing CD4+ T cells, or total viable recombinant receptor expressing CD8+ T cells. In certain embodiments, the disease or condition is a cancer. In particular embodiments, the disease or condition is a myeloma, leukemia or lymphoma. In some embodiments, the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

BRIEF DESCRIPTION OF THE DRAWINGS

FIG. 1A summarizes WST metabolic activity for all tested batches (pooled) compared to reference batches containing anti-CD3/anti-CD28 multimerized on an oligomeric backbone with an average hydrodynamic radius of 36 nm or 101 nm. The average WST metabolic activity among T cells from the different donors for individual tested batches and reference reagents is shown in FIG. 1B.

FIG. 4A depicts the percentage of CD4+ and CD8+ T cells positive for both CCR7 and CD27. FIG. 4B depicts the percentage of CCR7+ CD27+ cells for CD4+CAR+T cells. FIG. 4C depicts the percentage of CCR7+CD27+ cells for CD8+CAR+T cells. FIG. 4D displays the percentage of CCR7+CD27+ cells generated from a representative donor from an expanded process at various days during the process of manufacture, including activation at day 1 (d1 AMAT), transduction at day 2 (d2 XMAT), and at various times after initiation of cultivation (d4 INOC+2, d6 INOC+4, d7 INOC+5).

FIG. 5A depicts tumor burden means per each group. FIGS. 5B-5F display results for individual mice in each assessed treatment group: FIG. 5B (control), FIG. 5C (Expanded process), FIG. 5D (non-expanded oligomer process), FIG. 5E (non-expanded bead process) and FIG. 5F (non-expanded bead process, basal media).

FIG. 9A shows the percentage of viable cells and the total number of CAR+ T cells from anti-CD19 CAR-T cell compositions generated using an expanded or a non-expanded process. FIG. 9B shows the percentage of viable cells and the total number of CAR+ T cells from anti-CD19 CAR-T cell compositions generated from T cells that were either stimulated directly after selection (non-frozen) or cryopreserved prior to stimulation (frozen).

FIG. 11A depicts the number of viable anti-CD19 CAR-T cells assessed at various time points over the long term stimulation. ND—Not detectable. FIG. 11B depicts the percentage of positively stained cells from samples collected at days 11 and 19 from the long term stimulation cultures and stained with antibodies against surface proteins including CD25, CD69, PD-1, LAG-3, TIM-3, CD45RA, and TIGIT, as well as for a surrogate marker of CAR expression.

FIG. 12A depicts quantifications of tumor presence measured as average radiance of tumor associated bioluminescent signal, and the percentage of tumor cells in blood samples collected at different time points during the study. FIG. 12B depicts the percentage of both total T cells and CAR-T cells in blood samples collected at different time points during the study. FIG. 12C depicts the percent survival of mice up to 60 days after injection.

FIG. 13A depicts the percentage of CCR7+CD27+ cells of CD4+CAR+T cells. FIG. 13B depicts the percentage of CD4+CAR+ T cells and CD8+ CAR+ T cells.

FIG. 15A shows the total number of live cells observed during the course of the long-term stimulation. FIG. 15B shows the expansion of the different T cell compositions as quantified as the area under the curve for total viable cells measured from day 1 to day 6 of the incubation. FIG. 15C shows the percent of viable cells (viability %) across the T cells produced from the different engineering processes observed at different time points during the course of the long-term stimulation.

FIG. 16A shows the percent of CD4/CAR+ and CD8/CAR+ T cells stained positive for cytokines TNFa, IFN-g, and IL-2 at day 0 of long-term stimulation. FIG. 16B shows the percent of CD4/CAR+ and CD8/CAR+ T cells stained positive for cytokines TNFa, IFN-g, and IL-2 at day 6 of long-term stimulation. FIG. 16C shows the polyfunctional and IL-2 inclusive scores from cumulative levels of cytokines as determined in CD8+ cells, normalized by scaling with donor.

FIG. 19A) or day 4 (D4; FIG. 19B) of the process. Controls mice injected with tumor cells only (Tumor no TX) and mice injected tumor cells and mock transduced T cell compositions (Mock).

FIG. 30A shows pS6 expression in live CD8+ T cells by memory subset. FIG. 30B shows the mean florescence intensity (mfi) of total CD8 T cells by treatment as indicated. FIGS. 30C-30D show viability and total T cell numbers, respectively, over time (as indicated by days; d1, etc) in culture after initiation of stimulation ("input").

FIG. 31A shows intracellular expression of Caspase at the time of thaw. FIGS. 31B-31D show CD8 CAR-T cell and CD4 CAR-T cell phenotypic profiles, respectively, by subset expression of CD27 and/or CCR7. FIGS. 31C-31E show intracellular IL-2, IFNγ, or TNF (left panels) or combinations of IL-2 and/or IFNγ or TNF (right panels) among CD8 CAR-T cells and CD4 CAR-T cells, respectively, stimulated with antigen-bearing targets. FIG. 31F shows expansion and survival over 12 days (left panel) and total expansion metric calculated by area under the curve (right panel) for CAR-T cells stimulated with anti-CAR beads.

FIGS. 32D-32F show exemplary mean percentages of CAR+ cells of CD3+aCas3− cells (FIG. 32D, top panel), CAR+ cells of aCas3−CD4+ cells (FIG. 32D, bottom left panel), CAR+ cells of aCas3−CD8+ cells (FIG. 32D, bottom right panel), harvested product (HRPO) total nucleated CAR+ cells of CD3+aCas3− cells (FIG. 32E), CAR+CD25+ cells of aCas3−CD4+ cells (FIG. 32F, left panel), and CAR+CD25+ cells of aCas3−CD8+ cells (FIG. 32F, right panel).

FIG. 34A shows percentages of CD3+CD8+ and CD3+ CD4+ cells of live CD45+ cells (left panel), and percentages of CD8+CAR+ and CD4+CAR+ cells of CD45+ cells (right panel). FIG. 34B shows ratios of CD4+CAR+ to CD+CAR+ cells and CD4+ to CD8+ cells.

FIGS. 36A-36B show exemplary percentages of CD45RA+CCR7+ cells of aCAS-CD8+CAR+ and aCAS-CD4+CAR+ cells (FIG. 36A, left top panel), CD45RA−CCR7+ cells of aCAS-CD8+ CAR+ and aCas-CD4+CAR+ cells (FIG. 36A, right top panel), CD45RA−CCR7-cells of aCas-CD8+CAR+ and aCas-CD4+CAR+ cells (FIG. 36A, left bottom panel), CD45RA+CCR7-cells of aCAS-CD8+CAR+ and aCas-CD4+CAR+ cells (FIG. 36A, right bottom panel), and CD27+CCR7+ cells of aCAS-CD8+CAR+ and aCas-CD4+ CAR+ cells (FIG. 36B).

FIG. 38 shows total live cell counts and AUC for cells engineered to express an anti-CD19 CAR. FIG. 39 shows total live cell counts and AUC for cells engineered to express an anti-BCMA CAR.

FIG. 42A (right panel) shows tumor growth from Day-1 (before treatment) to Day 50 post-treatment calculated from area under the curve (AUC) of BLI for each group.

DETAILED DESCRIPTION

Figure 1A:
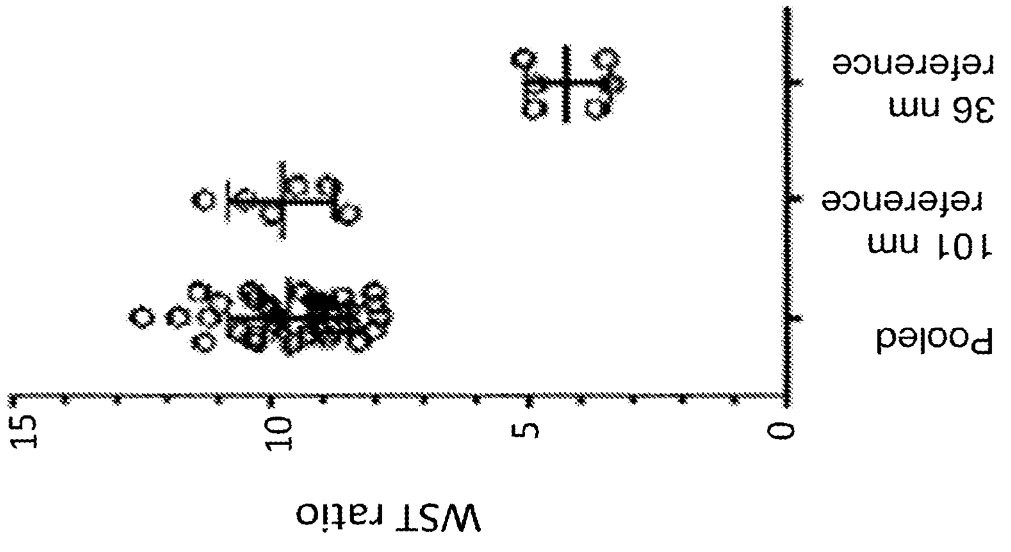
FIGS. 1A and 1B show results of a WST metabolic assay of T cells from three different donors incubated with anti-CD3/anti-CD28 multimerized on different batches of oligomeric reagents.

Provided herein are methods for generating or producing compositions of engineered cells, such as engineered T cells, that express a recombinant protein, e.g., a recombinant receptor such as a chimeric antigen receptor (CAR) or a recombinant T cell receptor (TCR). In some embodiments, the methods are or include one or more steps of incubating an input population of the cells (also referred to herein as an input composition), such as populations of primary T cells, under stimulatory conditions and then introducing a polynucleotide encoding a recombinant protein into the cells. In particular embodiments, the methods are used in connection with a process that is completed within a set amount of time, such as within four or fewer days after the initiation of stimulation of cells in an input composition.

Different processes are available for generating compositions containing genetically engineered T cell populations, including for generating engineered T cells that express a CAR. However, in particular aspects, some of these processes may require a long or a relatively long amount of time to generate the engineered cells. In addition, in various aspects, some existing processes may vary in the amount of time required to successfully produce engineered T cells suitable for cell therapy, making it difficult to coordinate that administration of the cell therapy. In certain aspects, some of these processes may produce populations of cells that include a relatively high percentage or amount of exhausted cells, differentiated cells, or cells with a low potency. Additional methods for generating engineered T cells are needed.

In particular embodiments, the provided methods are used in connection with a process for efficiently producing or generating engineered cells that are suitable for use in a cell therapy. In some embodiments, the provided processes for generating engineered cells contain one or more steps for stimulating and genetically engineering (e.g., transforming, transducing or transfecting) T cells produce a population of engineered T cells that may be collected or formulated for use as a composition for cell therapy. In some aspects, the processes provided herein successfully generate engineered cells without the need for any additional steps for expanding the cells, e.g. without an expansion unit operation and/or that includes steps intended to cause expansion of cells. In some aspects, the provided methods generate engineered T cells with enhanced potency as compared to engineered T cell compositions produced from alternative processes, such as those that involve expanding the cells.

In particular aspects, the durations of the provided processes can be measured from when cells, e.g., T cells of an input cell population or input composition, are first contacted or exposed to stimulating conditions (e.g., as described herein such as in Section I-B), referred to herein as the initiation of the stimulation or stimulating and also referred to herein as the exposing to the stimulatory reagent, e.g., as in when the exposing to the stimulatory reagent is initiated. In some embodiments, the duration of time required to harvest or collect an output population (also referred to herein as an output composition or as a composition of engineered cells, e.g., engineered T cells) containing engineered cells is measured from initiation of the stimulation. In particular embodiments, the duration of the process is, is about, or is less than 120 hours, 108 hours, 96 hours, 84 hours, 72 hours, 60 hours, 48 hours, 36 hours, or 30 hours. In particular embodiments, the duration of the process is, is about, or is less than 5 days, 4 days, 3 days, 2 days, or one day. In particular embodiments, the engineered cells, e.g., the cells of the output composition or population, are more potent, persistent or naïve-like than cells that are engineered with processes that require longer amounts of time. In some aspects, the duration, e.g., the amount of time required to generate or produce an engineered population of T cells, of the provided processes are shorter than those of some existing processes by, by about, or by at least 2 days, 3 days, 4 days, 5 days, 6 days, 7 days, or more than 7 days. In some embodiments, the duration of the provided process is, is about, or is less than 75%, 60%, 50%, 40%, 30%, 25%, 15%, or 10% of alternative or existing processes.

In certain embodiments, the provided processes are performed on a population of cells, e.g., CD3+, CD4+, and/or CD8+ T cells, that are isolated, enriched, or selected from a biological sample. In some aspects, the provided methods can produce or generate a composition of engineered T cells from when a biological sample is collected from a subject within a shortened amount of time as compared to other methods or processes. In some embodiments, the provided methods can produce or generate engineered T cells, including any or all times where biological samples, or enriched, isolated, or selected cells are cryopreserved and stored, within or within about 10 days, 9 days, 8 days, 7 days, 6 days, 5 days, 4 days, 3 days, or 2 days, or within or within about 120 hours, 96 hours, 72 hours, or 48 hours, from when a biological sample is collected from a subject to when the engineered T cells are collected, harvested, or formulated (e.g., for cryopreservation or administration).

In certain embodiments, the engineered T cells, e.g., output composition or populations of T cells containing T cells expressing a recombinant receptor, such as a chimeric antigen receptor, produced or generated by the provided processes are particularly effective or potent when utilized as cells for a cell therapy. For example, in some aspects, an output composition containing engineered T cells, e.g., CAR+ T cells, that are generated from the provided processes have a much higher degree of potency and/or proliferative capacity than engineered T cells generated or produced by alternative existing processes. In some aspects, an output composition containing engineered T cells, e.g., CAR+ T cells, produced by the provided processes have enhanced anti-tumor or anti-cancer cell activity than engineered T cells, e.g., CAR+ T cells, produced by alternative or existing methods.

Particular embodiments contemplate that a population of engineered T cells, e.g., CAR+ T cells, produced by the provided processes, e.g., processes that do not include or require expansion of the T cells during the process, would not, in some aspects, have been predicted to attain the high degree of potency or efficacy attained. Existing methods of manufacturing T cells for cell therapy include processes for expanding cells or require expansion of cells such as to a threshold density, e.g. processes that include an expansion unit operation and/or include steps intended to cause expansion of cells. Certain embodiments contemplate that expansion would have been predicted to be necessary to generate a sufficient amount of vector integration into the engineered T cells that would have been expected to be required for generating a potent or efficacious population of CAR+ T cells. Here, it is demonstrated that processes lacking steps or conditions for expansion (e.g. processes that lack an expansion unit operation and/or that do not include steps intended to cause expansion of cells), e.g., as in the provided processes, can produce potent or efficacious CAR+ T cell compositions. In some aspects, the engineered cells that are harvested, collected, or formulated prior to stable integration of the vector, e.g., the viral vector, still result in potent or efficacious compositions of CAR+ T cells. In certain aspects, CAR+ T cells produced by the provided methods are more potent, persistent, or efficacious than CAR+ T cells produced or generated from alternative processes that include expansion ((e.g. processes that include an expansion unit operation and/or include steps intended to cause expansion of cells). Certain embodiments contemplate that that vector integration may continue to occur during or even after the cells are collected, harvested, or formulated.

Also provided herein are processes for producing or engineering T cell populations that include stimulating the cells with an oligomeric stimulatory reagent. Existing reagents for use in stimulating T cells in vitro, such as in the absence of exogenous growth factors or low amounts of exogenous growth factors, are known (see e.g. U.S. Pat. No. 6,352,694 B1 and European Patent EP 0 700 430 B1). In general, such reagents may employ beads, e.g., magnetic beads, of greater than 1 μm in diameter to which various binding agents (e.g. anti-CD3 antibody and/or anti-CD28 antibody) are immobilized. However, in some cases, such magnetic beads are, for example, difficult to integrate into methods for stimulating cells under conditions required for clinical trials or therapeutic purposes since it has to be made sure that these magnetic beads are completely removed before administering the expanded T cells to a subject. In some aspects, such removal, such as by exposing the cells to a magnetic field, may decrease the yield of viable cells available for the cell therapy. In certain cases, such reagents, e.g., stimulatory reagents containing magnetic beads, must be incubated with the cells for a minimal amount of time to allow a sufficient amount of detachment of the T cells from the stimulatory reagent.

The provided processes utilizing oligomeric stimulatory reagents overcome such potential limitations. For example, in some embodiments, the provided processes avoid or reduce risk of residual stimulatory reagent, e.g., reagents containing magnetic beads, in the output cells generated or produced by the processes. In some embodiments, this also means that a process that is compliant with GMP standards can be more easily established compared to other methods, such as those where additional measures have to be taken to ensure that the final engineered T cell population is free of beads. In some embodiments, this may be readily accomplished in the present embodiments by the addition of a substance, e.g., a competition reagent, that dissociates the oligomeric stimulatory reagents from the cells, e.g., by simply rinsing or washing the cells. e.g., by centrifugation. Thus, in some aspects, removal or separation of oligomeric stimulatory reagent from cells, such as by the addition of a substance or competition reagent, results in little or no cell loss as compared to removal or separation of bead based stimulatory reagents. In some aspects, the timing of the oligomeric stimulatory reagent removal or separation is not limited or is less limited than the removal or separation of bead based stimulatory reagents. Thus, in some aspects, the oligomeric stimulatory reagent may be removed or separated from the cells at any time or stage during the provided processes.

In some aspects of the provided processes, cells are transduced or subjected to transduction with a process that involves incubation, e.g., an incubation of the T cells introduced with a viral vector encoding a heterologous or recombinant protein (e.g. CAR), in the presence of basal media. In certain aspects, the basal media does not contain additional additives (e.g., nutrients, vitamins, or amino acids) or any additional recombinant cytokines or growth factors. In certain aspects, the basal media does not contain recombinant cytokines or growth factors. In certain aspects, the basal media may contain certain essential amino acids, such as L-glutamine, but not contain other further additional additives or recombinant cytokines. In some aspects, the incubation in the presence of basal media, e.g., as compared to incubation in the presence of supplemented, complete, serum containing, or serum replacement containing media, reduces differentiation that may take place during an engineering process. Thus, in some aspects, incubation in the presence of basal media, e.g., following transduction or spinoculation, increases the portions of less differentiated and naïve-like cells in the output composition, e.g., the composition of cells produced containing a population of cells containing CAR+ T cells.

Among the findings provided herein is the observation that weak or reduced stimulation, such as with reduced amounts of stimulatory reagents that are typically utilized for stimulating T cells, can generate engineered CAR+ T cells that are as, or even more, potent, persistent, or efficacious as CAR+ T cells generated by processes that involve stronger stimulatory conditions or higher amounts or concentrations of stimulatory reagent. For example, in some embodiments, stimulating cells with a lower amount or relatively low amount of oligomeric stimulatory reagents may increase the potency, efficacy, or persistency of the resulting engineered cell population, as compared to processes using higher amounts of oligomeric stimulatory reagent. Such embodiments contemplate that such effects may persist even at doses sufficiently low enough to reduce the expression of activation markers or the portion of cells positive for the activation markers during and after the process.

In particular embodiments, the provided methods do not expand cells or contain steps where the cells are expanded to a threshold amount or concentration. In some aspects, protocols that do not rely on expanding the cells to increase the number or concentration of cells from a starting cell population, e.g., an input population, do not require incubations or cultivations that may vary between cell populations. For example, some embodiments contemplate that cell populations obtained from different subjects, such as subjects having different diseases or disease subtypes, may divide or expand at different rates. In certain aspects, eliminating potentially variable steps requiring cell expansion allows for the duration of the whole process to be tightly controlled. In certain embodiments, the variability of the process duration is reduced or eliminated which may, in some aspects, allow for improved coordination for appointments and treatment between doctors, patients, and technicians to facilitate autologous cell therapies.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Process for Generating Engineering Cells

Provided herein are methods for generating an output population of engineered cells, such as engineered CD4+ T and CD8+ T cells, that express a recombinant protein, e.g., a recombinant receptor such as a T cell receptor (TCR) or a chimeric antigen receptor (CAR). In certain embodiments, the methods provided herein are used in connection with manufacturing, generating, or producing a cell therapy, and may be used in connection with additional processing steps, such as steps for the isolation, separation, selection, activation or stimulation, transduction, washing, suspension, dilution, concentration, and/or formulation of the cells. In some embodiments, the methods of generating or producing engineered cells, e.g., engineered T cells, include one or more of steps for isolating cells from a subject, incubating the cells under stimulatory conditions, and genetically engineering the cells. In some embodiments, the method includes processing steps carried out in an order in which input cells, e.g. primary CD3+ T cells, CD4+ T cells, and/or CD8+ T cells, are first isolated, such as selected or separated, from a biological sample, incubated under stimulating conditions, genetically engineered to introduce a recombinant polynucleotide encoding a recombinant receptor into the cells such as by transduction or transfection; and then collected, harvested, or filled into a container, e.g., a bag or vial, as an output population. In some aspects of the methods, the biological sample can be a cryopreserved biological sample, such as a cryopreserved apheresis product. In some embodiments, the cells of the output population are re-introduced into the same subject, optionally after cryopreserving and storing the cells. In some embodiments, the output populations of engineered cells are suitable for use in a therapy, e.g., an autologous cell therapy.

In particular embodiments, the provided methods are used in connection with generating an output population of cells expressing a recombinant receptor from an initial or input population of cells. In certain embodiments, the input population is produced, generated, and/or made by combining, mixing, and/or pooling cells including from a population of cells containing enriched T cells, enriched CD3+ T cells, enriched CD4+ T cells, and/or enriched CD8+ T cells (herein after also referred to as populations of enriched T cells, populations of enriched CD3+ T cells, populations of enriched CD4+ T cells, and populations of enriched CD8+ T cells, respectively). In some embodiments, the input population of cells is a population of CD3+ T cells, e.g., without CD4+ and/or CD8+ selection. In some embodiments, the input population of cells is a population enriched in CD3+ T cells from a starting sample, such as PBMCs or a leukaphresis sample, wherein the starting sample has not been subjected to CD4+ and/or CD8+ selection. In some embodiments, the starting sample is selected for CD3 without any previous, concurrent, or subsequent selection for another marker (e.g., CD4 and/or CD8) in order to generate an input population enriched in CD3+ T cells. In some embodiments, the input population of cells is enriched in CD3+ T cells, which input population is not subjected to a further selection, e.g., CD4+ and/or CD8+ selection, before being subjected to a step of the manufacturing process such as activating or stimulating the input population or engineering. In some embodiments, the input population of cells is a population of combined, mixed, and/or pooled CD4+ and CD8+ T cells. In certain embodiments, the provided methods are used in connection with one or more of: activating or stimulating cells, e.g., cells of an input population; genetically engineering the activated or stimulated cells, e.g., to introduce a polynucleotide encoding a recombinant protein by transduction or transfection. In certain embodiments, the methods may also be used in connection with isolating or selecting cells from a biological sample to generate an input population of enriched T cells, such as from a biological sample taken, collected, and/or obtained from a subject. In particular embodiments, the provided methods may be used in connection with harvesting, collecting, and/or formulating populations of enriched T cells after the cells have been incubated, activated, stimulated, engineered, transduced, and/or cultured.

In certain embodiments, the provided methods do not contain any steps, stages, or conditions that result in expansion of the cells. In particular embodiments, the cells of the input population, e.g., a starting population of enriched CD3+ T cells (e.g., without previous or concurrent selection for the CD4 and/or CD8 markers), a starting sample of CD4+ T cells (e.g., with substantially no CD8+ T cells), a starting sample of CD8+ T cells (e.g., with substantially no CD4+ T cells), or a starting population of CD4+ T cells and CD8+ T cells, do not expand while undergoing the provided methods for generating populations of engineered cells. In particular embodiments, the cells of the output population, e.g., an output population of cells that were genetically engineered by the provided processes, is the same, about the same, reduced, or decreased as compared to the amount of cells in the input population, such as at the start of the culturing under stimulating conditions. In some aspects, protocols that do not rely on expanding the cells to increase the number or concentration of cells from a starting cell population, e.g., an input population, do not require incubations or cultivations that may vary between cell populations. For example, some embodiments contemplate that cell populations obtained from different subjects, such as subjects having different diseases or disease subtypes, may divide or expand at different rates. In certain aspects, eliminating potentially variable steps requiring cell expansion allows for the duration of the whole process to be tightly controlled.

In some embodiments, the methods are used in conjunction with one or more steps for stimulating the cells, such as by incubating cells under stimulating conditions. In some aspects, such stimulating conditions are or include culturing the cells with a stimulatory reagent, e.g., a stimulatory reagent described herein such as in Section I-B-1. In particular embodiments, a set or fixed amount of cells are stimulated, such as at a set or fixed concentration. In certain embodiments, the stimulating, e.g., culturing the cells under stimulating conditions, is performed for a set or fixed amount of time, such as an amount of time under 2 days or for an amount of time between 18 hours and 30 hours. In some aspects, the stimulating with the stimulatory reagent is carried out for at or about 20 hours±4 hours.

In certain embodiments, methods provided herein are performed in connection with introducing a heterologous or recombinant polynucleotide into the cells, e.g., transducing or transfecting the cells, such as by a method described herein, e.g., in Section I-C. In particular embodiments, the cells are incubated either during or after genetically engineering the cells, for example, for an amount of time sufficient to allow for integration of a heterologous or recombinant polynucleotide encoding a recombinant protein or to allow for the expression of the recombinant protein. In certain embodiments, the cells are incubated for a set or fixed amount of time, such as an amount of time greater than 18 hours or less than 4 days, e.g., 72 hours±6 hours. In any of the provided embodiments, the introducing can be carried out on cells after they have been stimulated with the stimulatory reagent. In some embodiments, 1 the engineering step is started or initiated within a set amount of time from when the stimulating is started or initiated, such as within 30 hours from when the stimulatory reagent is added, cultured, or contacted to the cells. In particular embodiments, the engineering step is started or initiated between 18 hours and 30 hours, such as 20 hours±4 hours, after the stimulatory reagent is added, cultured, or contacted to the cells.

In some embodiments, the one or more process steps are carried out, at least in part, in serum free media. In some embodiments, the serum free media is a defined or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the provided methods are carried out such that one, more, or all steps in the preparation of cells for clinical use, e.g., in adoptive cell therapy, are carried out without exposing the cells to non-sterile conditions. In some embodiments, the cells are isolated, separated or selected, transduced, washed, optionally activated or stimulated and formulated, all within a closed, sterile system or device. In some embodiments, the one or more of the steps are carried out apart from the closed system or device. In some such embodiments, the cells are transferred apart from the closed system or device under sterile conditions, such as by sterile transfer to a separate closed system.

In particular embodiments, the populations of enriched T cells may be collected, formulated for cryoprotection, frozen (e.g., cryoprotected), and/or stored below 0° C., below −20° C., or at or below −70 C or −80° C. prior to, during, or after any stage or step of the process for generating output populations of enriched T cells expressing recombinant receptors. In some embodiments, the cells may be stored for an amount of time under 1, 2, 3, 4, 5, 6, 7, 8, 9, or 10 days, or an amount of time under 1, 2, 3, 4, 5, 6, 7, 8 weeks, or for an amount of time at least 1, 2, 3, 4, 5, 6, 7, or 8 weeks, or for more than 8 weeks. After storage, the populations of enriched T cells may be thawed and the processing may be resumed from the same point in the process. In some embodiments, input populations of enriched T cells are cryoprotected and stored prior to further processing, e.g., incubation under stimulating conditions. In particular embodiments, cultivated and/or formulated populations of enriched T cells are cryoprotected and stored prior to being administered to as subject, e.g., as an autologous cell therapy.

In certain embodiments, the methods provided herein are used in connection with a process whereby engineered cells are generated by a process that includes steps for stimulating the cells and then introducing a polynucleotide encoding a recombinant receptor, e.g., a CAR, into the cells. In particular embodiments, the stimulating is performed for between 18 and 30 hours, such as for about 24 hours, and the introduction of the polynucleotide is subsequently performed. In certain embodiments, the cells are harvested or collected, such as to be formulated for cryopreservation or administrated to a subject, within 3 days after the introduction of the polynucleotide is initiated. In various embodiments, the cells are harvested or collected, such as to be formulated for cryopreservation or administered to a subject, within 4 days after the incubation under stimulatory conditions is initiated.

In particular embodiments, at any stage or step in the process, a portion of the cells may be sampled or collected, e.g., cells may be taken from the population of T cells (such as a population of enriched T cells) while the population remains in the closed system, such as during the isolation, incubation, engineering, cultivation, and/or formulation. In certain embodiments, such cells may be analyzed for makers, features, or characteristics including but not limited to viability, apoptosis, activation, stimulation, growth, and/or exhaustion. In some embodiments, the cells are sampled or collected by an automated process while the population of enriched T cells remains in the closed system. In some embodiments, the analysis of sampled or collected cells is automated. In particular embodiments, the analysis is performed in a closed system under sterile conditions.

In some embodiments, cells or populations of cells that are produced and/or processed by the provided methods may be compared to cells or populations of cells processed or produced by an exemplary and/or alternative process. In certain embodiments, the alternative and/or exemplary process may differ in one or more specific aspects, but otherwise contains similar or the same features, aspects, steps, stages, reagents, or conditions of the embodiment or aspect of the provided methods that be compared to an exemplary or alternative process. For example, engineered cells generated by the provided methods, e.g., an output population of non-expanded cells, may be compared to cells that were generated with a process that involved one or more steps of expanding the cells. In some embodiments, unless otherwise specified, the provided methods and the exemplary or alternative process would have been otherwise similar and/or identical, such as with similar or identical steps for isolating, selecting, enriching, activating, stimulating, engineering, transfecting, transducing, cultivating, and/or formulating. In some embodiments, unless otherwise specified, the provided methods and the alternative process isolate, select, and/or enrich cells from the same or similar types of biological samples, and/or process cells and/or input cells of the same cell type.

Also provided are cells and populations prepared by the methods, including pharmaceutical populations and formulations, and kits, systems, and devices for carrying out the methods. Further provided are methods for use of the cells and populations prepared by the methods, including therapeutic methods, such as methods for adoptive cell therapy, and pharmaceutical populations for administration to subjects.

A. Samples and Cell Preparation

In particular embodiments, the provided methods are used in connection with isolating, selecting, or enriching cells from a biological sample to generate one or more input populations of enriched cells, e.g., T cells. In some embodiments, the provided methods include isolation of cells or populations thereof from biological samples, such as those obtained from or derived from a subject, such as one having a particular disease or condition or in need of a cell therapy or to which cell therapy will be administered. In some aspects, the subject is a human, such as a subject who is a patient in need of a particular therapeutic intervention, such as the adoptive cell therapy for which cells are being isolated, processed, and/or engineered. Accordingly, the cells in some embodiments are primary cells, e.g., primary human cells. The samples include tissue, fluid, and other samples taken directly from the subject. The biological sample can be a sample obtained directly from a biological source or a sample that is processed. Biological samples include, but are not limited to, body fluids, such as blood, plasma, serum, cerebrospinal fluid, synovial fluid, urine and sweat, tissue and organ samples, including processed samples derived therefrom.

In some aspects, the sample is blood or a blood-derived sample, or is derived from an apheresis or leukapheresis product. Exemplary samples include whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g., adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contains cells other than red blood cells and platelets.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{++}/Mg^{++}$ free PBS. In certain embodiments, components of a blood cell sample are removed and the cells directly resuspended in culture media.

In some embodiments, the sample containing cells (e.g., an apheresis product or a leukapheresis product) is washed in order to remove one or more anti-coagulants, such as heparin, added during apheresis or leukapheresis.

In some embodiments, the sample containing cells (e.g., a whole blood sample, a buffy coat sample, a peripheral blood mononuclear cells (PBMC) sample, an unfractionated T cell sample, a lymphocyte sample, a white blood cell sample, an apheresis product, or a leukapheresis product) is cryopreserved and/or cryoprotected (e.g., frozen) and then thawed and optionally washed prior to any steps for isolating, selecting, activating, stimulating, engineering, transducing, transfecting, incubating, culturing, harvesting, formulating a population of the cells, and/or administering the formulated cell population to a subject.

In some embodiments, a sample containing autologous Peripheral Blood Mononuclear Cells (PBMCs) from a subject is collected in a method suitable to ensure appropriate quality for manufacturing. In one aspect, the sample containing PBMCs is derived from fractionated whole blood. In some embodiments, whole blood from a subject is fractionated by leukapheresis using a centrifugal force and making use of the density differences between cellular phenotypes, when autologous mononuclear cells (MNCs) are preferentially enriched while other cellular phenotypes, such as red blood cells, are reduced in the collected cell composition. In some embodiments, autologous plasma is concurrently collected during the MNC collection, which in some aspects can allow for extended leukapheresis product stability. In one aspect, the autologous plasma is added to the leukapheresis product to improve the buffering capacity of the leukapheresis product matrix. In some aspects, a total volume of whole blood processed in order to generate the leukapheresis product is or is about 2 L, 4 L, 6 L, 8 L, 10 L, 12 L, 14 L, 16 L, 18 L, or 20 L, or is any value between any of the foregoing. In some embodiments, the volume of autologous plasma collected is or is about 10 mL, 50 mL, 100 mL, 150 mL, 200 mL, 250 mL, or 300 mL, or more, or is a volume between any of the foregoing. In some embodiments, the leukapheresis product is subjected to a procedure, e.g., washing and formulation for in-process cryopreservation, within about 48 hours of the leukapheresis collection completion. In some embodiments, the leukapheresis product is subjected to one or more wash steps, e.g., within about 2 hours, 6 hours, 12 hours, 18 hours, 24 hours, 36 hours, or 48 hours of the leukapheresis collection completion. In some aspects, the one or more wash step removes the anticoagulant during leukapheresis collection, cellular waste that may have accumulated in the leukapheresis product, residual platelets and/or cellular debris. In some embodiments, one or more buffer exchange is performed during the one or more wash step.

In particular embodiments, an apheresis product or a leukapheresis product is cryopreserved and/or cryoprotected (e.g., frozen) and then thawed before being subject to a cell selection or isolation step (e.g., a T cell selection or isolation step) as described infra. In some embodiments, after a cryopreserved and/or cryoprotected apheresis product or leukapheresis product is subject to a T cell selection or isolation step, no additional cryopreservation and/or cryoprotection step is performed during or between any of the subsequent steps, such as the steps of activating, stimulating, engineering, transducing, transfecting, incubating, culturing, harvesting, formulating a population of the cells, and/or administering the formulated cell population to a subject. For example, T cells selected from a thawed cryopreserved and/or cryoprotected apheresis product or leukapheresis product are not again cryopreserved and/or cryoprotected before being thawed and optionally washed for a downstream process, such as T cell activation/stimulation or transduction.

In particular embodiments, an apheresis product or a leukapheresis product is cryopreserved and/or cryoprotected (e.g., frozen) at a density of, of about, or at least $5\times10^6$ cells/mL, $10\times10^6$ cells/mL, $20\times10^6$ cells/mL, $30\times10^6$ cells/mL, $40\times10^6$ cells/mL, $50\times10^6$ cells/mL, $60\times10^6$ cells/mL, $70\times10^6$ cells/mL, $80\times10^6$ cells/mL, $90\times10^6$ cells/mL, $100\times10^6$ cells/mL, $110\times10^6$ cells/mL, $120\times10^6$ cells/mL, $130\times10^6$ cells/mL, $140\times10^6$ cells/mL, or $150\times10^6$ cells/mL, or any value between any of the foregoing, in a cryopreservation solution or buffer. In some embodiments, the cryopreservation solution or buffer is or contains, for example, a DMSO solution optionally comprising human serum albumin (HSA), or other suitable cell freezing media.

In particular embodiments, the cryopreserved and/or cryoprotected apheresis product or leukapheresis product is banked (e.g., without T cell selection before freezing the sample), which, in some aspects, can allow more flexibility for subsequent manufacturing steps. In some aspects, the cryopreserved and/or cryoprotected apheresis product or leukapheresis product is aliquoted into multiple cryopreservation container such as bags, which can each individually or in combination be used in processing of the product. For example, when the total number of viable cells in the apheresis product or leukapheresis product is less than $15\times10^9$ cells, the cryopreserved and/or cryoprotected apheresis product or leukapheresis product is aliquoted into four cryopreservation container such as bags. In some embodiments, when the total number of viable cells in the apheresis product or leukapheresis product is $15\text{-}30\times10^9$ cells, the cryopreserved and/or cryoprotected apheresis product or leukapheresis product is aliquoted into eight cryopreservation container such as bags.

In one aspect, banking cells before selection increases cell yields for a downstream process, and banking cells earlier may mean they are healthier and may be easier to meet manufacturing success criteria. In another aspect, once thawed, the cryopreserved and/or cryoprotected apheresis product or leukapheresis product can be subject to one or more different selection methods. Advantages of this approach are, among other things, to enhance the availability, efficacy, and/or other aspects of cells of a cell therapy for treatment of a disease or condition of a subject, such as in the donor of the sample and/or another recipient.

In some embodiments, the sample (e.g. apheresis or leukapheresis sample) is collected and cryopreserved and/or cryoprotected prior to or without prior cell selection (e.g., without prior T cell selection, such as selection by chromatography), at a time after the donor is diagnosed with a disease or condition. In some aspects, the time of cryopreservation also is before the donor has received one or more of the following: any initial treatment for the disease or condition, any targeted treatment or any treatment labeled for treatment for the disease or condition, or any treatment other than radiation and/or chemotherapy. In some embodiments, the sample is collected after a first relapse of a disease following initial treatment for the disease, and before the donor or subject receives subsequent treatment for the disease. The initial and/or subsequent treatments may be a therapy other than a cell therapy. In some embodiments, the collected cells may be used in a cell therapy following initial and/or subsequent treatments. In one aspect, the cryopreserved and/or cryoprotected sample without prior cell selection may help reduce up-front costs, such as those associated with non-treatment patients in a randomized clinic trial who may crossover and require treatment later.

In some embodiments, the sample (e.g. apheresis or leukapheresis sample) is collected and cryopreserved and/or cryoprotected prior to or without prior cell selection (e.g., without prior T cell selection, such as selection by chromatography), at a time after a second relapse of a disease following a second line of treatment for the disease, and before the donor or subject receives subsequent treatment for the disease. In some embodiments, patients are identified as being likely to relapse after a second line of treatment, for example, by assessing certain risk factors. In some embodiments, the risk factors are based on disease type and/or genetics, such as double-hit lymphoma, primary refractory cancer, or activated B-cell lymphoma. In some embodiments, the risk factors are based on clinical presentation, such as early relapse after first-line treatment, or other poor prognostic indicators after treatment (e.g., IPI (International Prognostic Index)>2).

In some embodiments, the sample (e.g. apheresis or leukapheresis sample) is collected and cryopreserved and/or cryoprotected prior to or without prior cell selection (e.g., without prior T cell selection, such as selection by chromatography), at a time before the donor or subject is diagnosed with a disease. In some aspects, the donor or subject may be determined to be at risk for developing a disease. In some aspects, the donor or subject may be a healthy subject. In certain cases, the donor or subject may elect to bank or store cells without being deemed at risk for developing a disease or being diagnosed with a disease in the event that cell therapy is required at a later stage in life. In some embodiments, a donor or subject may be deemed at risk for developing a disease based on factors such as genetic mutations, genetic abnormalities, genetic disruptions, family history, protein abnormalities (such as deficiencies with protein production and/or processing), and lifestyle choices that may increase the risk of developing a disease. In some embodiments, the cells are collected as a prophylactic.

In some embodiments, the cryopreserved and/or cryoprotected sample of cells (e.g. apheresis or leukapheresis sample), such as a sample of cells that has not been subjected to a prior cell selection (e.g., without prior T cell selection, such as selection by chromatography) is stored, or banked, for a period of time greater than or equal to 12 hours, 24 hours, 36 hours, or 48 hours, or greater than or equal to 0.5 days, one day, 1.5 days, or two days. In some embodiments, the sample is stored or banked for a period of time greater than or equal to 1 week, 2 weeks, 3 weeks, or 4 weeks. In some embodiments, the sample is placed into long-term storage or long-term banking. In some aspects, the sample is stored for a period of time greater than or equal to 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 11 years, 12 years, 13 years, 14 years, 15 years, 16 years, 17 years, 18 years, 19 years, 20 years, 25 years, 30 years, 35 years, 40 years, or more.

In some embodiments, an apheresis or leukapheresis sample taken from a donor is shipped in a cooled environment to a storage or processing facility, and/or cryogenically stored at the storage facility or processed at the processing facility. In some embodiments, before shipping, the sample is processed, for example, by selecting T cells, such as CD3+ T cells, CD4+ T cells, and/or CD8+ T cells. In some embodiments, such processing is performed after shipping and before cryogenically storing the sample. In some embodiments, the processing is performed after thawing the sample following cryogenically storage.

By allowing donors to store their cells at a stage when the donors, and thus their cells, have not undergone extensive treatment for a disease and/or prior to contracting of a disease or condition or diagnosis thereof, such cells may have certain advantages for use in cell therapy compared to cells harvested after one or after multiple rounds of treatment. For example, cells harvested before one or more rounds of treatment may be healthier, may exhibit higher levels of certain cellular activities, may grow more rapidly, and/or may be more receptive to genetic manipulation than cells that have undergone several rounds of treatment. Another example of an advantage according to embodiments described herein may include convenience. For example, by collecting, optionally processing, and storing a donor's cells before they are needed for cell therapy, the cells would be readily available if and when a recipient later needs them. This could increase apheresis lab capacity, providing technicians with greater flexibility for scheduling the apheresis collection process.

Exemplary methods and systems for cryogenic storage and processing of cells from a sample, such as an apheresis sample, can include those described in WO2018170188. In some embodiments, the method and systems involve collecting apheresis before the patient needs cell therapy, and then subjecting the apheresis sample to cryopreservation for later use in a process for engineering the cells, e.g. T cells, with a recombinant receptor (e.g. CAR). In some cases, such processes can include those described herein. In some embodiments, an apheresis sample is collected from a subject and cryopreserved prior to subsequent T cell selection, activation, stimulation, engineering, transduction, transfection, incubation, culturing, harvest, formulation of a population of the cells, and/or administration of the formulated cell population to a subject. In such examples, the cryopreserved apheresis sample is thawed prior to subjecting the sample to one or more selection steps, such as any as described herein.

In some embodiments, the cryopreserved and/or cryoprotected sample of cells (e.g. apheresis or leukapheresis sample), such as a sample of cells that has not been subject to a prior cell selection (e.g., without prior T cell selection, such as selection by chromatography) is thawed prior to its use for downstream processes for manufacture of a cell population for cell therapy, for example, a T cell population containing CAR+ T cells. In some embodiments, such a cryopreserved and/or cryoprotected sample of cells (e.g. apheresis or leukapheresis sample) is used in connection with the process provided herein for engineered a T cell therapy, such as a CAR+ T cell therapy. In particular examples, no further step of cryopreservation is carried out prior to or during the harvest/formulation steps.

1. T Cell Selection

In some embodiments, selection, isolation, or enrichment of the cells or populations includes one or more preparation and/or non-affinity based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components. In some embodiments, the methods include density-based cell separation methods, such as the preparation of white blood cells from peripheral blood by lysing the red blood cells and centrifugation through a Percoll or Ficoll gradient. In certain embodiments, methods, techniques, and reagents for selection, isolation, and enrichment are described, for example, in WO2013124474 and WO2015164675, which are hereby incorporated by reference in their entirety.

In some embodiments, a cryopreserved and/or cryoprotected apheresis product or leukapheresis product is thawed. In some embodiments, the thawed cell composition is subjected to dilution (e.g., with a serum-free medium) and/or wash (e.g., with a serum-free medium), which in some cases can remove or reduce unwanted or undesired components. In some cases, the dilution and/or wach removes or reduces the presence of a cryoprotectant, e.g. DMSO, contained in the thawed sample, which otherwise may negatively impact cellular viability, yield, recovery upon extended room temperature exposure. In some embodiments, the dilution and/or wash allows media exchange of a thawed cryopreserved product into a serum-free medium, e.g. one described herein in Section II or in PCT/US2018/064627 incorporated herein by reference.

In some embodiments, the serum-free medium comprises a basal medium (e.g. OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4 (1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

In some embodiments, at least a portion of the selection step includes incubation of cells with a selection reagent. The incubation with a selection reagent or reagents, e.g., as part of selection methods which may be performed using one or more selection reagents for selection of one or more different cell types based on the expression or presence in or on the cell of one or more specific molecules, such as surface markers, e.g., surface proteins, intracellular markers, or nucleic acid. In some embodiments, any known method using a selection reagent or reagents for separation based on such markers may be used. In some embodiments, the selection reagent or reagents result in a separation that is affinity- or immunoaffinity-based separation. For example, the selection in some aspects includes incubation with a reagent or reagents for separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner.

In some aspects of such processes, a volume of cells is mixed with an amount of a desired affinity-based selection reagent. The immunoaffinity-based selection can be carried out using any system or method that results in a favorable energetic interaction between the cells being separated and the molecule specifically binding to the marker on the cell, e.g., the antibody or other binding partner on the solid surface, e.g., particle. In some embodiments, methods are carried out using particles such as beads, e.g. magnetic beads, that are coated with a selection agent (e.g. antibody) specific to the marker of the cells. The particles (e.g. beads) can be incubated or mixed with cells in a container, such as a tube or bag, while shaking or mixing, with a constant cell density-to-particle (e.g., bead) ratio to aid in promoting energetically favored interactions. In other cases, the methods include selection of cells in which all or a portion of the selection is carried out in the internal cavity of a centrifugal chamber, for example, under centrifugal rotation. In some embodiments, incubation of cells with selection reagents, such as immunoaffinity-based selection reagents, is performed in a centrifugal chamber. In certain embodiments, the isolation or separation is carried out using a system, device, or apparatus described in International Patent Application, Publication Number WO2009/072003, or US20110003380 A1, which are hereby incorporated by reference in their entirety. In one example, the system is a system as described in International Publication Number WO2016/073602, which is hereby incorporated by reference in its entirety.

In some embodiments, by conducting such selection steps or portions thereof (e.g., incubation with antibody-coated particles, e.g., magnetic beads) in the cavity of a centrifugal chamber, the user is able to control certain parameters, such as volume of various solutions, addition of solution during processing and timing thereof, which can provide advantages compared to other available methods. For example, the ability to decrease the liquid volume in the cavity during the incubation can increase the concentration of the particles (e.g. bead reagent) used in the selection, and thus the chemical potential of the solution, without affecting the total number of cells in the cavity. This in turn can enhance the pairwise interactions between the cells being processed and the particles used for selection. In some embodiments, carrying out the incubation step in the chamber, e.g., when associated with the systems, circuitry, and control as described herein, permits the user to effect agitation of the solution at desired time(s) during the incubation, which also can improve the interaction.

In some embodiments, at least a portion of the selection step is performed in a centrifugal chamber, which includes incubation of cells with a selection reagent. In some aspects of such processes, a volume of cells is mixed with an amount of a desired affinity-based selection reagent that is far less than is normally employed when performing similar selections in a tube or container for selection of the same number of cells and/or volume of cells according to manufacturer's instructions. In some embodiments, an amount of selection reagent or reagents that is/are no more than 5%, no more than 10%, no more than 15%, no more than 20%, no more than 25%, no more than 50%, no more than 60%, no more than 70% or no more than 80% of the amount of the same selection reagent(s) employed for selection of cells in a tube or container-based incubation for the same number of cells and/or the same volume of cells according to manufacturer's instructions is employed.

In some embodiments, for selection, e.g., immunoaffinity-based selection of the cells, the cells are incubated in the cavity of the chamber in a population that also contains the selection buffer with a selection reagent, such as a molecule that specifically binds to a surface marker on a cell that it desired to enrich and/or deplete, but not on other cells in the population, such as an antibody, which optionally is coupled to a scaffold such as a polymer or surface, e.g., bead, e.g., magnetic bead, such as magnetic beads coupled to monoclonal antibodies specific for CD3, CD4, and CD8. In some embodiments, as described, the selection reagent is added to cells in the cavity of the chamber in an amount that is substantially less than (e.g. is no more than 5%, 10%, 20%, 30%, 40%, 50%, 60%, 70% or 80% of the amount) as compared to the amount of the selection reagent that is typically used or would be necessary to achieve about the same or similar efficiency of selection of the same number of cells or the same volume of cells when selection is performed in a tube with shaking or rotation. In some embodiments, the incubation is performed with the addition of a selection buffer to the cells and selection reagent to achieve a target volume with incubation of the reagent of, for example, 10 mL to 200 mL, such as at least or about at least or about or 10 mL, 20 mL, 30 mL, 40 mL, 50 mL, 60 mL, 70 mL, 80 mL, 90 mL, 100 mL, 150 mL or 200 mL. In some embodiments, the selection buffer and selection reagent are pre-mixed before addition to the cells. In some embodiments, the selection buffer and selection reagent are separately added to the cells. In some embodiments, the selection incubation is carried out with periodic gentle mixing condition, which can aid in promoting energetically favored interactions and thereby permit the use of less overall selection reagent while achieving a high selection efficiency.

In some embodiments, the total duration of the incubation with the selection reagent is from or from about 5 minutes to 6 hours, such as 30 minutes to 3 hours, for example, at least or about at least 30 minutes, 60 minutes, 120 minutes or 180 minutes.

In some embodiments, the incubation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In some embodiments, such process is carried out within the entirely closed system to which the chamber is integral. In some embodiments, this process (and in some aspects also one or more additional step, such as a previous wash step washing a sample containing the cells, such as an apheresis sample) is carried out in an automated fashion, such that the cells, reagent, and other components are drawn into and pushed out of the chamber at appropriate times and centrifugation effected, so as to complete the wash and binding step in a single closed system using an automated program.

In some embodiments, after the incubation and/or mixing of the cells and selection reagent and/or reagents, the incubated cells are subjected to a separation to select for cells based on the presence or absence of the particular reagent or reagents. In some embodiments, the separation is performed in the same closed system in which the incubation of cells with the selection reagent was performed. In some embodiments, after incubation with the selection reagents, incubated cells, including cells in which the selection reagent has bound are transferred into a system for immunoaffinity-based separation of the cells. In some embodiments, the system for immunoaffinity-based separation is or contains a magnetic separation column.

Such separation steps can be based on positive selection, in which the cells having bound the reagents, e.g. antibody or binding partner, are retained for further use, and/or negative selection, in which the cells having not bound to the reagent, e.g., antibody or binding partner, are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, the process steps further include negative and/or positive selection of the incubated and cells, such as using a system or apparatus that can perform an affinity-based selection. In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level (marker$^{high}$) on the positively or negatively selected cells, respectively.

The separation need not result in 100% enrichment or removal of a particular cell population or cells expressing a particular marker. For example, positive selection of or enrichment for cells of a particular type, such as those expressing a marker, refers to increasing the number or percentage of such cells, but need not result in a complete absence of cells not expressing the marker. Likewise, negative selection, removal, or depletion of cells of a particular type, such as those expressing a marker, refers to decreasing the number or percentage of such cells, but need not result in a complete removal of all such cells.

In some examples, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types. In certain embodiments, separation steps are repeated and or performed more than once, where the positively or negatively selected fraction from one step is subjected to the same separation step, such as a repeated positive or negative selection. In some examples, a single separation step is repeated and/or performed more than once, for example to increase the purity of the selected cells and/or to further remove and/or deplete the negatively selected cells from the negatively selected fraction. In certain embodiments, one or more separation steps are performed two times, three times, four times, five times, six times, seven times, eight times, nine times, ten times, or more than ten times. In certain embodiments, the one or more selection steps are performed and/or repeated between one and ten times, between one and five times, or between three and five times.

For example, in some aspects, specific subpopulations of T cells, such as cells positive or expressing high levels of one or more surface markers, e.g., CD28+, CD62L+, CCR7+, CD27+, CD127+, CD3+, CD4+, CD8+, CD45RA+, and/or CD45RO+ T cells, are isolated by positive or negative selection techniques. In some embodiments, such cells are selected by incubation with one or more antibody or binding partner that specifically binds to such markers. In some embodiments, the antibody or binding partner can be conjugated, such as directly or indirectly, to a solid support or matrix to effect selection, such as a magnetic bead or paramagnetic bead. For example, CD3+, CD28+ T cells can be positively selected using CD3/CD28 conjugated magnetic beads (e.g., DYNABEADS® M-450 CD3/CD28 T Cell Expander, and/or ExpACT® beads).

In some embodiments, T cells are separated from a PBMC sample by negative selection of markers expressed on non-T cells, such as B cells, monocytes, or other white blood cells, such as CD14. In some aspects, a CD3+ selection step is used to generate a population enriched in CD3+ T cells from a starting sample, such as PBMCs or a leukaphresis sample, wherein the starting sample has not been subjected to positive or negative selection based on another marker such as CD4 and/or CD8. In some embodiments, the starting sample is selected for CD3 without any previous, concurrent, or subsequent selection for another marker (e.g., CD4 and/or CD8) in order to generate an input population enriched in CD3+ T cells. In some embodiments, the input population of cells is enriched in CD3+ T cells, which input population is not subjected to a further selection, e.g., CD4+ and/or CD8+ selection, before being subjected to a step of the manufacturing process such as activating or stimulating the input population or engineering. In certain embodiments, the input population enriched in CD3+ T cells has a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells.

In some embodiments, T cells are separated from a PBMC sample by negative selection of markers expressed on non-T cells, such as B cells, monocytes, or other white blood cells, such as CD14. In some aspects, a CD4+ or CD8+ selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naïve-like, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al., (2012) Blood. 1:72-82; Wang et al. (2012) J Immunother. 35 (9): 689-701. In some embodiments, combining TCM-enriched CD8+ T cells and CD4+ T cells further enhances efficacy.

In embodiments, memory T cells are present in both CD62L+ and CD62L− subsets of CD8+ peripheral blood lymphocytes. PBMC can be enriched for or depleted of CD62L− CD8+ and/or CD62L+CD8+ fractions, such as using anti-CD8 and anti-CD62L antibodies.

In some embodiments, the enrichment for central memory T ($T_{CM}$) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained and used in subsequent steps of the methods, optionally following one or more further positive or negative selection steps. In some embodiments, the selection for the CD4+ cell population and the selection for the CD8+ cell population are carried out simultaneously. In some embodiments, the CD4+ cell population and the selection for the CD8+ cell population are carried out sequentially, in either order. In some embodiments, methods for selecting cells can include those as described in published U.S. App. No. US20170037369, which is hereby incorporated by reference in its entirety. In some embodiments, the selected CD4+ cell population and the selected CD8+ cell population may be combined subsequent to the selecting. In some aspects, the selected CD4+ cell population and the selected CD8+ cell population may be combined in a bioreactor bag as described herein.

In particular embodiments, a biological sample, e.g., a sample of PBMCs or other white blood cells, are subjected to selection of CD4+ T cells, where both the negative and positive fractions are retained. In certain embodiments, CD8+ T cells are selected from the negative fraction. In some embodiments, a biological sample is subjected to selection of CD8+ T cells, where both the negative and positive fractions are retained. In certain embodiments, CD4+ T cells are selected from the negative fraction.

In some aspects, a CD8-based positive selection step is used to generate a population enriched in CD8+ T cells from a starting sample, such as PBMCs or a leukaphresis sample, wherein the starting sample has not been subjected to selection based on another marker such as CD3+ and/or CD4+. In some embodiments, both the negative and positive fractions from the CD8 positive selection step are retained, and the CD8-negative fraction is further subjected to a CD4-based positive selection step in order to generate a population enriched in CD4+ T cells. In some embodiments, cells from the population enriched in CD8+ T cells and cells from the population enriched in CD4+ T cells are mixed, combined, and/or pooled to generate an input population containing CD4+ T cells and CD8+ T cells. In certain embodiments, the population enriched in CD8+ T cells and the population enriched in CD4+ T cells are pooled, mixed, and/or combined prior to stimulating cells, e.g., culturing the cells under stimulating conditions such as described in Section I-B. In certain embodiments, the pooled, mixed, and/or combined cells or populations have a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1, or 1:1 CD4+ T cells to CD8+ T cells. In certain embodiments, the cells or populations are pooled, mixed, and/or combined in order to have a ratio of or of about 1:1 CD4+ T cells to CD8+ T cells in the pooled, mixed, and/or combined cell composition.

In some aspects, a CD4-based positive selection step is used to generate a population enriched in CD4+ T cells from a starting sample, such as PBMCs or a leukaphresis sample, wherein the starting sample has not been subjected to selection based on another marker such as CD3+ and/or CD8+. In some embodiments, both the negative and positive fractions from the CD4 positive selection step are retained, and the CD4-negative fraction is further subjected to a CD8-based positive selection step used to generate a population enriched in CD8+ T cells. In some embodiments, cells from the population enriched in CD4+ T cells and cells from the population enriched in CD8+ T cells are mixed, combined, and/or pooled to generate an input population containing CD8+ T cells and CD4+ T cells. In certain embodiments, the population enriched in CD4+ T cells and the population enriched in CD8+ T cells are pooled, mixed, and/or combined prior to stimulating cells, e.g., culturing the cells under stimulating conditions such as described in Section I-B. In certain embodiments, the pooled, mixed, and/or combined cells or populations have a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1, or 1:1 CD4+ T cells to CD8+ T cells. In certain embodiments, the cells or populations are pooled, mixed, and/or combined in order to have a ratio of or of about 1:1 CD4+ T cells to CD8+ T cells in the pooled, mixed, and/or combined cell composition.

In some embodiments, a selection agent that specifically binds CD4 and a selection agent that specifically binds CD8 are used to generate a population enriched in CD4+ T cells and a population enriched in CD8+ T cells, respectively. In some embodiments, the capacities of the CD4-specific selection agent and the CD8-specific selection agent are the same or substantially the same, for example, a unit volume or unit weight of the selection agents (e.g., ClinicMACS CD4 selection reagent and CD8 selection reagent) can be used to select CD4 or CD8 cells from the same number of total cells. In some embodiments, a greater amount of CD4-specific selection agent can be used than the CD8-specific selection agent with the same or substantially the same capacity. For example, the volumes or weights of the CD4-specific selection agent and the CD8-specific selection agent can be at a ratio of about 5:1, 4:1, 3:1, 2:1, or 1:5:1.

In a particular example, a sample of PBMCs or other white blood cell sample is subjected to selection of CD4+ cells, where both the negative and positive fractions are retained. The negative fraction then is subjected to negative selection based on expression of CD14 and CD45RA or CD19, and positive selection based on a marker characteristic of central memory T cells, such as CD62L or CCR7, where the positive and negative selections are carried out in either order.

CD4+ T helper cells may be sorted into naïve, central memory, and effector cells by identifying cell populations that have cell surface antigens. CD4+ lymphocytes can be obtained by standard methods. In some embodiments, naive CD4+ T lymphocytes are CD45RO−, CD45RA+, CD62L+, or CD4+ T cells. In some embodiments, central memory CD4+ cells are CD62L+ and CD45RO+. In some embodiments, effector CD4+ cells are CD62L− and CD45RO−.

In one example, to enrich for CD4+ cells by negative selection, a monoclonal antibody cocktail typically includes antibodies to CD14, CD20, CD11b, CD16, HLA-DR, and CD8. In some embodiments, the antibody or binding partner is bound to a solid support or matrix, such as a magnetic bead or paramagnetic bead, to allow for separation of cells for positive and/or negative selection. For example, in some embodiments, the cells and cell populations are separated or isolated using immunomagnetic (or affinitymagnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher © Humana Press Inc., Totowa, NJ).

In some aspects, the incubated sample or population of cells to be separated is incubated with a selection reagent containing small, magnetizable or magnetically responsive material, such as magnetically responsive particles or microparticles, such as paramagnetic beads (e.g., Dynalbeads or MACS® beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select.

In some embodiments, the magnetic particle or bead comprises a magnetically responsive material bound to a specific binding member, such as an antibody or other binding partner. Many well-known magnetically responsive materials for use in magnetic separation methods are known, e.g., those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084, which are hereby incorporated by reference, also may be used.

The incubation generally is carried out under conditions whereby the antibodies or binding partners, or molecules, such as secondary antibodies or other reagents, which specifically bind to such antibodies or binding partners, which are attached to the magnetic particle or bead, specifically bind to cell surface molecules if present on cells within the sample.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some aspects, separation is achieved in a procedure in which the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In some embodiments, the affinity-based selection is via magnetic-activated cell sorting (MACS) (Miltenyi Biotech, Auburn, CA). Magnetic Activated Cell Sorting (MACS), e.g., CliniMACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, the suboptimal yield concentration of the affinity reagent is a concentration below a concentration used or required to achieve an optimal or maximal yield of bound cells in a given selection or enrichment involving incubating cells with the reagent and recovering or separating cells having bound to the reagent ("yield," for example, being the number of the cells so-recovered or selected compared to the total number of cells in the incubation that are targeted by the reagent or to which the reagent is specific or that have a marker for which the reagent is specific and capable of binding). The suboptimal yield concentration generally is a concentration or amount of the reagent that in such process or step achieves less than all, e.g., no more than 70% yield of bound cells, e.g., CD4+ and/or CD8+ T cells, upon recovery of the cells having bound to the reagent. In some embodiments, no more than at or about 50%, 45%, 40%, 30%, or 25% yield is achieved by the suboptimal concentration of the affinity reagent. The concentration may be expressed in terms of number or mass of particles or surfaces per cell and/or number of mass or molecules of agent (e.g., antibody, such as antibody fragment) per cell. In particular embodiments, the suboptimal yield concentrations are sufficient to derive or achieve the fixed, controlled, and/or defined ratio of naïve-like CD4+ T cells to naïve-like CD8+ T cells.

In some embodiments, e.g., when operating in a suboptimal yield concentration for each or one or more of two or more selection reagents with affinity to CD4+ and/or CD8+ T cells, one or more of such reagents is used at a concentration that is higher than one or more of the other such reagent(s), in order to bias the ratio of the cell type recognized by that reagent as compared to the cell type(s) recognized by the other(s). For example, the reagent specifically binding to the marker for which it is desired to bias the ratio may be included at a concentration (e.g., agent or mass per cells) that is increased by half, 1-fold, 2-fold, 3-fold, 4-fold, 5-fold, 10-fold, or more, compared to other(s), depending on how much it is desired to increase the ratio.

In some embodiments, when operating in the suboptimal range and/or with enough cells to achieve saturation of reagents, the amount of immunoaffinity reagent is proportional to the approximate yield of enriched cells. In certain embodiments, an appropriate amount or concentration of immunoaffinity reagents that depend on the desired ratio of the generated population containing the enriched or selected CD4+ and CD8+ T cells can be determined as a matter of routine.

In some embodiments, the separation and/or isolation steps are carried out using magnetic beads in which immunoaffinity reagents are reversibly bound, such as via a peptide ligand interaction with a streptavidin mutein as described in WO 2015/164675, hereby incorporated by reference in its entirety. Exemplary of such magnetic beads are Streptamers®. In some embodiments, the separation and/or steps is carried out using magnetic beads, such as those commercially available from Miltenyi Biotec.

In some embodiments, the first selection or enrichment of CD4+ and CD8+ cells from a sample are performed using immunoaffinity-based reagents that include at least a first and second affinity chromatography matrix, respectively, having immobilized thereon an antibody. In some embodiments, one or both of the first and/or second selection can employ a plurality of affinity chromatography matrices and/or antibodies, whereby the plurality of matrices and/or antibodies employed for the same selection, i.e. the first selection or the second selection, are serially connected. In some embodiments, the affinity chromatography matrix or matrices employed in a first and/or second selection adsorbs or is capable of selecting or enriching at least about $50\times10^6$ cells/mL, $100\times10^6$ cells/mL, $200\times10^6$ cells/mL or $400\times10^6$ cells/mL. In some embodiments, the adsorption capacity can be modulated based on the diameter and/or length of the column. In some embodiments, the culture-initiating ratio of the selected or enriched population is achieved by choosing a sufficient amount of matrix and/or at a sufficient relative amount to achieve the culture-initiating ratio assuming based on, for example, the adsorption capacity of the column or columns for selecting cells.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In some embodiments, the isolation and/or selection results in one or more populations of enriched T cells, e.g., CD3+ T cells, CD4+ T cells, and/or CD8+ T cells. In some embodiments, two or more separate population of enriched T cells are isolated, selected, enriched, or obtained from a single biological sample. In some embodiments, separate populations are isolated, selected, enriched, and/or obtained from separate biological samples collected, taken, and/or obtained from the same subject.

In certain embodiments, the isolation and/or selection results in one or more populations of enriched T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD3+ T cells. In particular embodiment, the population of enriched T cells consists essentially of CD3+ T cells.

In certain embodiments, the isolation and/or enrichment results in a populations of enriched CD4+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD4+ T cells. In certain embodiments, the input population of CD4+ T cells includes less than 40%, less than 35%, less than 30%, less than 25%, less than 20%, less than 15%, less than 10%, less than 5%, less than 1%, less than 0.1%, or less than 0.01% CD8+ T cells, and/or contains no CD8+ T cells, and/or is free or substantially free of CD8+ T cells. In some embodiments, the population of enriched T cells consists essentially of CD4+ T cells.

In certain embodiments, the isolation and/or enrichment results in a populations of enriched CD8+ T cells that includes at least 60%, at least 65%, at least 70%, at least 75%, at least 80%, at least 85%, at least 90%, at least 95%, at least 98%, at least 99%, at least 99.5%, at least 99.9%, or at or at about 100% CD8+ T cells. In certain embodiments, the population of CD8+ T cells contains less than 40%, less than 35%, less than 30%, less than 25%, less than 20%, less than 15%, less than 10%, less than 5%, less than 1%, less than 0.1%, or less than 0.01% CD4+ T cells, and/or contains no CD4+ T cells, and/or is free of or substantially free of CD4+ T cells. In some embodiments, the population of enriched T cells consists essentially of CD8+ T cells.

In some embodiments, the one or more populations enriched T cells are frozen, e.g., cryopreserved and/or cryoprotected, after isolation, selection and/or enrichment. In particular embodiments, a population of enriched CD3+ T cells are frozen, e.g., cryopreserved and/or cryoprotected, after isolation, selection and/or enrichment. In particular embodiments, a population of enriched CD4+ T cells are frozen, e.g., cryopreserved and/or cryoprotected, after isolation, selection and/or enrichment. In certain embodiments, a population of enriched CD8+ T cells are frozen, e.g., cryopreserved and/or cryoprotected, after isolation, selection and/or enrichment. In some embodiments, the one or more populations of enriched T cells are frozen e.g., cryopreserved and/or cryoprotected, prior to any steps of incubating, activating, stimulating, engineering, transducing, transfecting, cultivating, expanding, harvesting, and/or formulating the population of cells. In particular embodiments, a population of enriched CD3+ T cells are frozen e.g., cryopreserved and/or cryoprotected, prior to any steps of incubating, activating, stimulating, engineering, transducing, transfecting, cultivating, expanding, harvesting, and/or formulating the population of cells. In particular embodiments, a population of enriched CD4+ T cells are frozen e.g., cryopreserved and/or cryoprotected, prior to any steps of incubating, activating, stimulating, engineering, transducing, transfecting, cultivating, expanding, harvesting, and/or formulating the population of cells. In some embodiments, a population of enriched CD8+ T cells are frozen e.g., cryopreserved and/or cryoprotected, prior to any steps of incubating, activating, stimulating, engineering, transducing, transfecting, cultivating, expanding, harvesting, and/or formulating the population of cells. In some embodiments, the one or more populations of enriched T cells, such as population of enriched CD3+ T cells are frozen e.g., cryopreserved and/or cryoprotected, prior to any steps of activating, stimulating, engineering, transducing, transfecting, incubating, culturing, harvesting, and/or formulating the population of cells. In some embodiments, the one or more populations of enriched T cells, such as population of enriched CD4+ T cells and/or enriched CD8+ cells, are frozen e.g., cryopreserved and/or cryoprotected, prior to any steps of activating, stimulating, engineering, transducing, transfecting, incubating, culturing, harvesting, and/or formulating the population of cells. In particular embodiments, the one or more cryoprotected input populations are stored, e.g., at or at about −80° C., for between 12 hours and 7 days, between 24 hours and 120 hours, or between 2 days and 5 days. In particular embodiments, the one or more cryoprotected input populations are stored at or at about −80° C., for an amount of time of less than 10 days, 9 days, 8 days, 7 days, 6 days, or 5 days, 4 days, 3 days, 2 days, or 1 day. In some embodiments, the one or more cryoprotected input populations are stored at or at about −70° C. or −80° C. for less than 3 days, such as for about 2 days.

a. Selection Agents or Reagents

In certain aspects, the methods provided herein employ a selection agent. In some embodiments, the agent is a selection reagent. In some embodiments, the selection agent binds to a molecule on the surface of a cell, such as a cell surface molecule. In some instances, the cell surface molecule is a selection marker. In some embodiments, the selection agent is capable of specifically binding to a selection marker expressed by one or more of the cells in a sample.

In some embodiments, the cells, e.g., target cells (e.g., T cells), have or express a molecule on the cell surface, e.g., a selection marker, such that the cells to be selected are defined by the presence of at least one common specific molecule. In some embodiments, the sample containing the target cell may also contain additional cells that are devoid of the molecule (e.g., selection marker). For example, in some embodiments, T cells may be selected from a sample containing multiple cells types, e.g., red blood cells or B cells.

In some aspects, the cell surface molecule, e.g., selection marker, may be an antigen defining a desired cell population or subpopulation, for instance a population or subpopulation of blood cells, e. g. lymphocytes (e.g. T cells, T-helper cells, for example, CD3+ T cells, CD8+ Tcells, CD4+ T-helper cells, B cells or natural killer cells), monocytes, or stem cells, e.g. CD34-positive peripheral stem cells or Nanog or Oct-4 expressing stem cells. In some embodiments, the selection marker can be a marker expressed on the surface of T cells or a subset of T cells, such as CD25, CD28, CD62L, CCR7, CD27, CD127, CD3, CD4, CD8, CD45RA, and/or CD45RO. Examples of T-cells include cells such as CMV-specific CD8+ T-lymphocytes, cytotoxic T-cells, memory T-cells and regulatory T-cells (Treg). An illustrative example of Treg includes CD4 CD25 CD45RA Treg cells and an illustrative example of memory T-cells includes CD62L CD8+ specific central memory T-cells.

In some embodiments, the selection marker may be CD4 and the selection agent specifically binds CD4. In some aspects, the selection agent that specifically binds CD4 may be selected from the group consisting of an anti-CD4-antibody, a divalent antibody fragment of an anti-CD4 antibody, a monovalent antibody fragment of an anti-CD4-antibody, and a proteinaceous CD4 binding molecule with antibody-like binding properties. In some embodiments, an anti-CD4-antibody, such as a divalent antibody fragment or a monovalent antibody fragment (e.g. CD4 Fab fragment) can be derived from antibody 13B8.2 or a functionally active mutant of 13B8.2 that retains specific binding for CD4. For example, exemplary mutants of antibody 13B8.2 or m13B8.2 are described in U.S. Pat. Nos. 7,482,000, U.S.

Patent Appl. No. US2014/0295458 or International Patent Application No. WO2013/124474; and Bes, C, et al. J Biol Chem 278, 14265-14273 (2003). The mutant Fab fragment termed "m13B8.2" carries the variable domain of the CD4 binding murine antibody 13B8.2 and a constant domain containing constant human CH1 domain of type gamma for the heavy chain and the constant human light chain domain of type kappa, as described in U.S. Pat. No. 7,482,000. In some embodiments, the anti-CD4 antibody, e.g. a mutant of antibody 13B8.2, contains the amino acid replacement H91A in the variable light chain, the amino acid replacement Y92A in the variable light chain, the amino acid replacement H35A in the variable heavy chain and/or the amino acid replacement R53A in the variable heavy chain, each by Kabat numbering. In some aspects, compared to variable domains of the 13B8.2 Fab fragment in m13B8.2 the His residue at position 91 of the light chain (position 93 in SEQ ID NO: 102) is mutated to Ala and the Arg residue at position 53 of the heavy chain (position 55 in SEQ ID NO: 101) is mutated to Ala. In some embodiments, the reagent that is reversibly bound to anti-CD4 or a fragment thereof is commercially available or derived from a reagent that is commercially available (e.g. catalog No. 6-8000-206 or 6-8000-205 or 6-8002-100; IBA GmbH, Gottingen, Germany). In some embodiments, the selection agent comprises an anti-CD4 Fab fragment. In some embodiments, the anti-CD4 Fab fragment comprises a variable heavy chain having the sequence set forth by SEQ ID NO: 101 and a variable light chain having the sequence set forth by SEQ ID NO: 102. In some embodiments, the anti-CD4 Fab fragment comprises the CDRs of the variable heavy chain having the sequence set forth by SEQ ID NO: 101 and the CDRs of the variable light chain having the sequence set forth by SEQ ID NO:102.

In some embodiments, the selection marker may be CD8 and the selection agent specifically binds CD8. In some aspects, the selection agent that specifically binds CD8 may be selected from the group consisting of an anti-CD8-antibody, a divalent antibody fragment of an anti-CD8 antibody, a monovalent antibody fragment of an anti-CD8-antibody, and a proteinaceous CD8 binding molecule with antibody-like binding properties. In some embodiments, an anti-CD8-antibody, such as a divalent antibody fragment or a monovalent antibody fragment (e.g. CD8 Fab fragment) can be derived from antibody OKT8 (e.g. ATCC CRL-8014) or a functionally active mutant thereof that retains specific binding for CD8. In some embodiments, the reagent that is reversibly bound to anti-CD8 or a fragment thereof is commercially available or derived from a reagent that is commercially available (e.g. catalog No. 6-8003 or 6-8000-201; IBA GmbH, Gottingen, Germany). In some embodiments, the selection agent comprises an anti-CD8 Fab fragment. In some embodiments, the anti-CD8 Fab fragment comprises a variable heavy chain having the sequence set forth by SEQ ID NO:104 and a variable light chain having the sequence set forth by SEQ ID NO: 105. In some embodiments, the anti-CD8 Fab fragment comprises the CDRs of the variable heavy chain having the sequence set forth by SEQ ID NO: 104 and the CDRs of the variable light chain having the sequence set forth by SEQ ID NO: 105.

In some embodiments, the selection marker may be CD3 and the selection agent specifically binds CD3. In some aspects, the selection agent that specifically binds CD3 may be selected from the group consisting of an anti-CD3-antibody, a divalent antibody fragment of an anti-CD3 antibody, a monovalent antibody fragment of an anti-CD3-antibody, and a proteinaceous CD3 binding molecule with antibody-like binding properties. In some embodiments, an anti-CD3-antibody, such as a divalent antibody fragment or a monovalent antibody fragment (e.g. CD3 Fab fragment) can be derived from antibody OKT3 (e.g. ATCC CRL-8001; see e.g., Stemberger et al. PLOS One. 2012; 7 (4): e35798) or a functionally active mutant thereof that retains specific binding for CD3. In some embodiments, the reagent that is reversibly bound to anti-CD3 or a fragment thereof is commercially available or derived from a reagent that is commercially available (e.g. catalog No. 6-8000-201, 6-8001-100; IBA GmbH, Gottingen, Germany). In some embodiments, the selection agent comprises an anti-CD3 Fab fragment. In some embodiments, the anti-CD3 Fab fragment comprises a variable heavy chain having the sequence set forth by SEQ ID NO:89 and a variable light chain having the sequence set forth by SEQ ID NO:90. In some embodiments, the anti-CD3 Fab fragment comprises the CDRs of the variable heavy chain having the sequence set forth by SEQ ID NO:89 and the CDRs of the variable light chain having the sequence set forth by SEQ ID NO:90.

In any of the above examples, the divalent antibody fragment may be an (Fab)2'-fragment, or a divalent single-chain Fv fragment while the monovalent antibody fragment may be selected from the group consisting of a Fab fragment, an Fv fragment, and a single-chain Fv fragment (scFv). In any of the above examples, the proteinaceous binding molecule with antibody-like binding properties may be an aptamer, a mutein based on a polypeptide of the lipocalin family, a glubody, a protein based on the ankyrin scaffold, a protein based on the crystalline scaffold, an adnectin, and an avimer.

2. T Cell Selection by Chromatography

In some embodiments, cells, e.g., T cells, are isolated, selected, or enriched by chromatographic isolation, such as by column chromatography including affinity chromatography or gel permeations chromatography. In some embodiments, the method employs a receptor binding reagent that binds to a receptor molecule that is located on the surface of a target cell, e.g., the cell to be isolated, selected, or enriched. Such methods may be described as (traceless) cell affinity chromatography technology (CATCH) and may include any of the methods or techniques described in PCT Application Nos. WO2013124474 and WO2015164675, which are hereby incorporated by reference in its entirety.

In some embodiments, the cells, e.g., the target cells, have or express a receptor molecule on the cell surface, such that the cells to be isolated, selected, or enriched are defined by the presence of at least one common specific receptor molecule. In some embodiments, the sample containing the target cell may also contain additional cells that are devoid of the receptor molecule. For example, in some embodiments, T cells are isolated, enriched, and or elected from a sample containing multiple cells types, e.g., red blood cells or B cells.

In some embodiments, the selection agent is comprised in a chromatography column, e.g., bound directly or indirectly to the chromatography matrix (e.g., stationary phase). In some embodiments, the selection agent is present on the chromatography matrix (e.g., stationary phase) at the time the sample is added to the column. In some embodiments, the selection agent is capable of being bound indirectly to the chromatography matrix (e.g., stationary phase) through a reagent, e.g., selection reagent. In some embodiments, the selection reagent is bound covalently or non-covalently to the stationary phase of the column. In some embodiments, the selection reagent is reversibly immobilized on the chromatography matrix (e.g., stationary phase). In some cases, the selection reagent is immobilized on the chromatography matrix (e.g., stationary phase) via covalent bonds. In some aspects, the selection reagent is reversibly immobilized on the chromatography matrix (e.g., stationary phase) non-covalently.

In some aspects, a selection agent is added to the sample. In some aspects, a receptor binding reagent is added to the sample. In certain embodiments, the receptor binding reagent has a binding site B, which specifically binds to the receptor molecule (e.g., CD3, CD4, and/or CD8) on the surface of the cell, e.g., the target cell. In some aspects, the receptor binding reagent also includes a binding partner C, which can specifically and reversibly bind to a binding site Z of a selection agent such as an affinity reagent.

In certain aspects, the affinity reagent may also contain two or more binding sites Z that can be bound by the binding partner C, thereby providing a multimerization of the receptor binding reagent. This affinity reagent used herein can thus also be a multimerization reagent. The affinity reagent may, for example, be streptavidin, a streptavidin mutein, avidin, an avidin mutein or a mixture thereof. In some aspects, different chromatography matrices are coupled to different affinity reagents, and may be layered into a column forming a multicomponent system for separation.

In certain embodiments the sample, e.g., the sample containing the cells and the receptor binding reagent, is loaded on or contacted with a chromatography matrix containing an attached or immobilized affinity reagent. In particular aspects, the affinity reagent has a plurality of binding sites Z that specifically bind to the binding partner C of the receptor binding reagent. In certain aspects, the receptor binding reagent binds to the affinity reagent by the interaction between the binding partner C and the binding site Z. Thus, in some embodiments, the cell, e.g., the target cell, is immobilized via the complex that is formed by the one or more binding sites Z of the affinity reagent and the binding partner C of receptor binding reagent on the chromatography matrix. In further aspects, the cells, e.g., the target cells, may be depleted from the sample, such as by rinsing, releasing, or washing the remaining sample from the chromatography matrix. In particular aspects, the receptor binding reagent may either be included in the sample that contains the cells or it may applied or contacted to the chromatography matrix for binding to the attached affinity or multimerization reagent, such as before the sample is added to the chromatography matrix.

In some aspects, a competition reagent is then loaded onto the chromatography column. In particular embodiments, the competition reagent has a binding site that is able to bind to the binding site Z of the affinity reagent. In certain embodiments, the competition reagent forms a complex with the affinity reagent, and is thereby immobilized on the chromatography matrix. As a result of this competitive binding, the binding between the receptor binding reagent and the affinity reagent at binding partner C and binding site Z is displaced. In particular embodiments, adding or loading the competition reagent to a chromatography matrix with an attached complex containing the affinity reagent, receptor binding reagent, and the cell, e.g., the target cell, elutes the cell from the chromatography matrix. In some aspects, the receptor binding reagent has a low affinity towards the receptor molecule of the cell at binding site B, such that the receptor binding reagent dissociates from the cell in the presence of the competition reagent. Thus, in some embodiments, the cells, e.g., the target cells, are eluted from the chromatography matrix free or essentially free of bound receptor binding molecules.

In some embodiments, the selection agent may be present, for example bound directly to (e.g., covalently or non-covalently) or indirectly via a selection reagent, on the chromatography matrix (e.g., stationary phase) at the time the sample is added to the chromatography column (e.g., stationary phase). Thus, upon addition of the sample, target cells can be bound by the selection agent and immobilized on the chromatography matrix (e.g., stationary phase) of the column. Alternatively, in some embodiments, the selection agent can be added to the sample. In this way, the selection agent binds to the target cells (e.g., T cells) in the sample, and the sample can then be added to a chromatography matrix (e.g., stationary phase) comprising the selection reagent, where the selection agent, already bound to the target cells, binds to the selection reagent, thereby immobilizing the target cells on the chromatography matrix (e.g., stationary phase). In some embodiments, the selection agent binds to the selection reagent as described herein via binding partner C, as described herein, comprised in the selection agent.

In some embodiments, two or more selection agents associate with, such as are reversibly or irreversibly bound to, the selection reagent, such as via the one or plurality of binding sites Z present on the selection reagent. In some cases, this results in the selection agents being closely arranged to each other such that an avidity effect can take place if a target cell having (at least two copies of) a cell surface molecule (e.g., selection marker) is brought into contact with the selection agent that is able to bind the particular molecule (e.g., selection marker).

In some embodiments, two or more different selection agents that are the same, i.e. have the same selection marker binding specificity, can be reversibly bound to the selection reagent. In some embodiments, it is possible to use at least two different selection agents, and in some cases, three or four different selection agents that bind to different selection markers. In some aspects, each of the at least two selection agents can bind to a different molecule (e.g., selection marker), such as a first molecule, second molecule and so on. In some cases, the different molecules (e.g., selection markers), such as cell surface molecules, can be present on the same target cell. In other cases, the different molecules (e.g., selection markers), such as cell surface molecules, can be present on different target cells that are present in the same population of cells. In some case, a third, fourth and so on selection agent can be associated with the same reagent, each containing a further different binding site.

In some embodiments, the two or more different selection agents contain the same binding partner C. In some embodiments, the two or more different selection agents contain different binding partners. In some aspects, a first selection agent can have a binding partner C1 that can specifically bind to a binding site Z1 present on the selection reagent and a second selection agent can have a binding partner C2 that can specifically bind to the binding site Z1 or to a binding site Z2 present on the selection reagent. Thus, in some instances, the plurality of binding sites Z comprised by the selection reagent includes binding sites Z1 and 22, which are capable of reversibly binding to binding partners C1 and C2, respectively, comprised by the selection agent. In some embodiments, C1 and C2 are the same, and/or Z1 and Z2 are the same. In other aspects, one or more of the plurality of binding sites Z can be different. In other instances, one or more of the plurality of binding partners C may be different. It is within a level of a skilled artisan to choose any combination of different binding partners C that are compatible with a selection reagent containing the binding sites Z, as long as each of the binding partners C are able to interact, such as specifically bind, with one of the binding sites Z.

In some embodiments, a reversible bond formed between binding partner C and binding site Z can be disrupted by a competition agent and/or free binding agent. In some embodiments, a competition agent and/or free binding agent can be a biotin, a biotin derivative or analog or a streptavidin-binding peptide capable of competing for binding with the binding partner C for the one or more binding sites Z. In some embodiments, the binding partner C and the competition agent and/or free binding agent are different, and the competition agent and/or free binding agent exhibit a higher binding affinity for the one or more binding sites Z compared to the affinity of the binding partner. In particular aspects of any of the methods provided herein, addition of a competition agent and/or free binding agent to the stationary phase of the chromatography column to disrupt the binding of the selection agent to the selection reagent is not required to detach the target cells (e.g., T cells) from the chromatography matrix (e.g., stationary phase).

In some embodiments, the cells, e.g., the target cells of the sample, may be depleted from the sample, such as by rinsing, releasing, or washing the remaining sample from the chromatography matrix (e.g., stationary phase). In some embodiments, one or more (e.g., 2, 3, 4, 5, 6) wash steps are used to remove unbound cells and debris from the chromatography matrix (e.g., stationary phase). In some embodiments, the sample is allowed penetrate the matrix for at least or about 5, 10, 16, 20, 25, 30, 35, 40, 45, 50, 55, 60, 70, 80, 90, 100, or 120 minutes before one or more wash steps are performed.

In some embodiments, an elution sample from the eluate of the first chromatography column, which includes the cells, e.g., the target cells, the competition reagent, and the receptor binding reagent, is collected. In certain embodiments, the elution sample is loaded onto a second chromatography column, which has a suitable stationary phase that is both an affinity chromatography matrix and, at the same time, can act as gel permeation matrix. In particular embodiments, the affinity chromatography matrix has an affinity reagent immobilized thereon. In some aspects, the receptor binding reagent and the competition reagent bind to a binding site Z on the affinity reagent, and are thereby immobilized on the chromatography matrix. As a result, in certain aspects, the elution sample containing the isolated target cells is depleted of the receptor binding reagent and the competition reagent. Thus, in some aspects, the target cells, being freed of any reactants, are now in a condition for further use, for example, for processing by any of the methods described herein.

In some embodiments, multiple rounds of cell selection steps are carried out, where the positively or negatively selected fraction from one step is subjected to another selection step, such as a subsequent positive or negative selection. In certain embodiments, methods, techniques, and reagents for selection, isolation, and enrichment are described, for example, in PCT Application No. WO2015164675, which is hereby incorporated by reference in its entirety.

In some embodiments, a single selection step can be used to isolate target cells (e.g., CD3+ T cells) from a sample. In some embodiments, the single selection step can be performed on a single chromatography column. In some examples, a single selection step can deplete cells expressing multiple markers simultaneously. Likewise, multiple cell types can simultaneously be positively selected. In certain embodiments, selection steps are repeated and or performed more than once, where the positively or negatively selected fraction from one step is subjected to the same selection step, such as a repeated positive or negative selection. In some examples, a single selection step is repeated and/or performed more than once, for example to increase the purity of the selected cells and/or to further remove and/or deplete the negatively selected cells from the negatively selected fraction. In certain embodiments, one or more selection steps are performed two times, three times, four times, five times, six times, seven times, eight times, nine times, ten times, or more than ten times. In certain embodiments, the one or more selection steps are performed and/or repeated between one and ten times, between one and five times, or between three and five times.

Cell selection may be performed using one or more chromatography columns. In some embodiments the one or more chromatography columns are included in a closed system. In some embodiments, the closed system is an automated closed system, for example requiring minimal or no user (e.g., human) input. In some embodiments, cell selection is performed sequentially (e.g., a sequential selection technique). In some embodiments, the one or more chromatography columns are arranged sequentially. For example, a first column may be oriented such that is the output of the column (e.g., eluant) can be fed, e.g., via connected tubing, to a second chromatography column. In some embodiments, a plurality of chromatography columns may be arranged sequentially. In some embodiments, cell selection may be achieved by carrying out sequential positive and negative selection steps, the subsequent step subjecting the negative and/or positive fraction from the previous step to further selection, where the entire process is carried out in the same tube or tubing set. In some embodiments, a sample containing target cells is subjected to a sequential selection in which a first selection is effected to enrich for one of the CD4+ or CD8+ populations, and the non-selected cells from the first selection are used as the source of cells for a second selection to enrich for the other of the CD4+ or CD8+ populations. In some embodiments, a further selection or selections can be effected to enrich for sub-populations of one or both of the CD4+ or CD8+ population, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to a sequential selection in which a first selection is effected to enrich for a CD3+ population, and the selected cells are used as the source of cells for a second selection to enrich for CD3+ populations. In some embodiments, a sample containing target cells is subjected to a sequential selection in which a first selection is effected to enrich for a CD3+ population on a first stationary phase (e.g., in a first chromatograph column), and the flowthrough containing unbound cells is used as the source of cells for a second selection to enrich for a CD3+ population on a second stationary phase (e.g., in a second chromatograph column), wherein the first and second stationary phases are arranged sequentially. In some embodiments, the selection is a positive selection for CD3+ T cells (e.g., by using an antibody or antigen binding fragment thereof that specifically binds to cell surface CD3). In some embodiments, a further selection or selections can be effected to enrich for sub-populations of the CD3+ population, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to sequential selection in which a first selection is effected to enrich for a CD3+ population, and the selected cells are used as the source of cells for a second selection to enrich for CD4+ populations. In some embodiments, a further selection or selections can be effected to enrich for sub-populations of the CD3+CD4+ population, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to sequential selection in which a first selection is effected to enrich for a CD3+ population, and the selected cells are used as the source of cells for a second selection to enrich for CD8+ populations. In some embodiments, a further selection or selections can be effected to enrich for sub-populations of the CD3+CD8+ population, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. It is contemplated that in some aspects, specific subpopulations of T cells (e.g., CD3+ cells), such as cells positive or expressing high levels of one or more surface markers, e.g., CD28+, CD62L+, CCR7+, CD27+, CD127+, CD4+, CD8+, CD45RA+, and/or CD45RO+ T cells, are selected by positive or negative sequential selection techniques. In some embodiments, cell selection is performed in parallel (e.g., parallel selection technique). In some embodiments, the one or more chromatography columns are arranged in parallel. For example, two or more columns may be arranged such that a sample is loaded onto two or more columns at the same time via tubing that allows for the sample to be applied to each column without the need for the sample to traverse through a first column. For example, using a parallel selection technique, cell selection may be achieved by carrying out positive and/or negative selection steps simultaneously, for example in a closed system where the entire process is carried out in the same tube or tubing set. In some embodiments, a sample containing target cells is subjected to a parallel selection in which the sample is load onto two or more chromatography columns, where each column effects selection of a cell population. In some embodiments, the two or more chromatography columns effect selection of CD3+, CD4+, or CD8+ populations individually. In some embodiments, the two or more chromatography columns, including affinity chromatography or gel permeation chromatography, independently effect selection of the same cell population. For example, the two or more chromatography columns may effect selection of CD3+ cells. In some embodiments, the two or more chromatography columns, including affinity chromatography or gel permeation chromatography, independently effect selection of different cell populations. For example, the two or more chromatography columns independently may effect selection of CD3+ cells, CD4+ cells, and CD8+ cells. In some embodiments, a further selection or selections, for example using sequential selection techniques, can be effected to enrich for sub-populations of one or all cell populations selected via parallel selection. For example, selected cells may be further selected for central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to a parallel selection in which parallel selection is effected to enrich for a CD3+ population on the two or more columns. In some embodiments, a further selection or selections can be effected to enrich for sub-populations of the CD3+ population, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to a parallel selection in which a selection is effected to enrich for a CD3+ population and a CD4+ population on the two or more columns, independently. In some embodiments, a further selection or selections can be effected to enrich for sub-populations of the CD3+ and CD4+ populations, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to a parallel selection in which parallel selection is effected to enrich for a CD3+ population and a CD8+ population. In some embodiments, a further selection or selections can be effected to enrich for sub-populations of the CD3+ and CD8+ populations, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. In some embodiments, a sample containing target cells is subjected to a parallel selection in which parallel selection is effected to enrich for a CD4+ population and a CD8+ population. In some embodiments, a further selection or selections can be effected to enrich for sub-populations of the CD4+ and CD8+ populations, for example, central memory T ($T_{CM}$) cells, naïve T cells, and/or cells positive for or expressing high levels of one or more surface markers, e.g., CD28+, CD62L+, CCR7+, CD27+, CD127+, CD4+, CD8+, CD45RA+, and/or CD45RO+. It is contemplated that in some aspects, specific subpopulations of T cells (e.g., CD3+, CD4+, CD8+ T cells), such as cells positive or expressing high levels of one or more surface markers, e.g., CD28+, CD62L+, CCR7+, CD27+, CD127+, CD4+, CD8+, CD45RA+, and/or CD45RO+ T cells, are selected by positive or negative parallel selection techniques. In some embodiments, sequential and parallel selection techniques can be used in combination.

In general, binding capacity of a stationary phase (e.g., selection resin) affects how much stationary phase is needed in order to select a certain number of target moieties, e.g., target cells such as T cells. The binding capacity, e.g., the number of target cells that can be immobilized per mL of the stationary phase (e.g., selection resin), can be used to determine or control the number of captured target cells on one or more columns. One or more chromatography column can be used for the on-column cell selection and stimulation disclosed herein. When multiple columns are used, they can be arranged sequentially, in parallel, or in a suitable combination thereof. Thus, the binding capacity of a stationary phase (e.g., selection resin) can be used to standardize the reagent amount in a single-column approach or the reagent amount for each column in a multiple-column approach.

In some embodiments, the binding capacity of the stationary phase used herein is the maximum number of target cells (e.g., CD3+ T cells, CD4+ T cells, or CD8+ T cells)

bound to the stationary phase at given solvent and cell concentration conditions, when an excess of target cells are loaded onto the stationary phase. In one aspect, the binding capacity of the stationary phase used herein for on-column cell selection and stimulation is a static binding capacity. In some embodiments, the static binding capacity of the stationary phase (e.g., selection resin) disclosed herein ranges between about 50 million and about 100 million target cells per mL of stationary phase. In some embodiments, the static binding capacity of the stationary phase (e.g., selection resin) is between about 10 million and about 20 million, between about 20 million and about 30 million, between about 30 million and about 40 million, between about 40 million and about 50 million, between about 50 million and about 60 million, between about 60 million and about 70 million, between about 70 million and about 80 million, between about 80 million and about 90 million, between about 90 million and about 100 million, between about 110 million and about 120 million, between about 120 million and about 130 million, between about 130 million and about 140 million, between about 140 million and about 150 million, between about 150 million and about 160 million, between about 160 million and about 170 million, between about 170 million and about 180 million, between about 180 million and about 190 million, or between about 190 million and about 200 million cells per mL of stationary phase.

In some embodiments, the binding capacity of the stationary phase used herein is the number of target cells (e.g., CD3+ T cells, CD4+ T cells, or CD8+ T cells) that bind to the stationary phase under given flow conditions before a significant breakthrough of unbound target cells occurs. In one aspect, the binding capacity of the stationary phase used herein for on-column cell selection and stimulation is a dynamic binding capacity, i.e., the binding capacity under operating conditions in a packed chromatography column during sample application. In some embodiments, the dynamic binding capacity is determined by loading a sample containing a known concentration of the target cells and monitoring the flow-through, and the target cells will bind the stationary phase to a certain break point before unbound target cells will flow through the column. In some embodiments, the dynamic binding capacity of the stationary phase (e.g., selection resin) disclosed herein ranges between about 50 million and about 100 million target cells per mL of stationary phase. In some embodiments, the dynamic binding capacity of the stationary phase (e.g., selection resin) is between about 10 million and about 20 million, between about 20 million and about 30 million, between about 30 million and about 40 million, between about 40 million and about 50 million, between about 50 million and about 60 million, between about 60 million and about 70 million, between about 70 million and about 80 million, between about 80 million and about 90 million, between about 90 million and about 100 million, between about 110 million and about 120 million, between about 120 million and about 130 million, between about 130 million and about 140 million, between about 140 million and about 150 million, between about 150 million and about 160 million, between about 160 million and about 170 million, between about 170 million and about 180 million, between about 180 million and about 190 million, or between about 190 million and about 200 million target cells per mL of stationary phase.

Generally, a chromatographic method is a fluid chromatography, typically a liquid chromatography. In some aspects, the chromatography can be carried out in a flow through mode in which a fluid sample containing the cells, e.g., the target cells, is applied, for example, by gravity flow or by a pump on one end of a column containing the chromatography matrix and in which the fluid sample exists the column at the other end of the column. In addition the chromatography can be carried out in an "up and down" mode in which a fluid sample containing the cells to be isolated is applied, for example, by a pipette on one end of a column containing the chromatography matrix packed within a pipette tip and in which the fluid sample enters and exists the chromatography matrix/pipette tip at the other end of the column. Alternatively, the chromatography can also be carried out in a batch mode in which the chromatography material (stationary phase) is incubated with the sample that contains the cells, for example, under shaking, rotating or repeated contacting and removal of the fluid sample, for example, by means of a pipette.

In some aspects, any material may be employed as chromatography matrix in the context of the invention, as long as the material is suitable for the chromatographic isolation of cells. In particular aspects, a suitable chromatography material is at least innocuous or essentially innocuous, e.g., not detrimental to cell viability, when used in a packed chromatography column under desired conditions for cell isolation and/or cell separation. In some aspects, the chromatography matrix remains in a predefined location, typically in a predefined position, whereas the location of the sample to be separated and of components included therein, is being altered. Thus, in some aspects, the chromatography matrix is a "stationary phase."

Typically, the respective chromatography matrix has the form of a solid or semi-solid phase, whereas the sample that contains the target cell to be isolated/separated is a fluid phase. The mobile phase used to achieve chromatographic separation is likewise a fluid phase. The chromatography matrix can be a particulate material (of any suitable size and shape) or a monolithic chromatography material, including a paper substrate or membrane (cf. the Example Section). Thus, the chromatography can be both column chromatography as well as planar chromatography. In addition to standard chromatography columns, columns allowing a bidirectional flow or pipette tips can be used for column based/flow through mode based chromatographic separation of cells as described here. In some aspects, a particulate matrix material is used, and the particulate matrix material may, for example, have a mean particle size of about 5 μm to about 200 μm, or from about 5 μm to about 400 μm, or from about 5 μm to about 600 μm. In some aspects, planar chromatography is used, and the matrix material may be any material suitable for planar chromatography, such as conventional cellulose-based or organic polymer based membranes (for example, a paper membrane, a nitrocellulose membrane or a polyvinylidene difluoride (PVDF) membrane) or silica coated glass plates.

In some aspects, the chromatography matrix/stationary phase is a non-magnetic material or non-magnetisable material. Such material may include derivatized silica or a crosslinked gel. A crosslinked gel (which is typically manufactured in a bead form) may be based on a natural polymer, such as a crosslinked polysaccharide. Suitable examples include but are not limited to agarose gels or a gel of crosslinked dextran(s). A crosslinked gel may also be based on a synthetic polymer, i.e. on a polymer class that does not occur in nature. Usually such a synthetic polymer on which a chromatography stationary phase for cell separation is based is a polymer that has polar monomer units, and which is therefore in itself polar.

Illustrative examples of suitable synthetic polymers are polyacrylamide(s), a styrene-divinylbenzene gel and a copolymer of an acrylate and a diol or of an acrylamide and a diol. An illustrative example is a polymethacrylate gel, commercially available as a Fractogel®. A further example is a copolymer of ethylene glycol and methacrylate, commercially available as a Toyopearl®. In some embodiments a chromatography stationary phase may also include natural and synthetic polymer components, such as a composite matrix or a composite or a co-polymer of a polysaccharide and agarose, e.g. a polyacrylamide/agarose composite, or of a polysaccharide and N,N'-methylenebisacrylamide. An illustrative example of a copolymer of a dextran and N,N'-methylenebisacryl¬amide is the above-mentioned Sephacryl® series of material. A derivatized silica may include silica particles that are coupled to a synthetic or to a natural polymer. Examples of such embodiments include, but are not limited to, polysaccharide grafted silica, polyvinylpyrrolidone grafted silica, polyethylene oxide grafted silica, poly(2-hydroxyethylaspartamide) silica and poly(N-isopropylacrylamide) grafted silica.

A chromatography matrix employed in the present invention is in some embodiments a gel filtration (also known as size exclusion) matrix, for example, when used in a removal cartridge as described herein. A gel filtration can be characterized by the property that it is designed to undergo, at least essentially, no interaction with the cells to be separated. Hence, a gel filtration matrix allows the separation of cells or other biological entities as defined herein largely on the basis of their size. A respective chromatography matrix is typically a particulate porous material as mentioned above. The chromatography matrix may have a certain exclusion limit, which is typically defined in terms of a molecular weight above which molecules are entirely excluded from entering the pores. The respective molecular weight defining the size exclusion limit may be selected to be below the weight corresponding to the weight of a target cell (or biological entity) to be isolated. In such an embodiment the target cell is prevented from entering the pores of the size exclusion chromatography matrix. Likewise, a stationary phase that is an affinity chromatography matrix may have pores that are of a size that is smaller than the size of a chosen target cell. In illustrative embodiments the affinity chromatography matrix and/or the gel filtration matrix has a mean pore size of 0 to about 500 nm.

Other components present in a sample such as receptor binding molecules or a competition reagent may have a size that is below the exclusion limit of the pores and this can enter the pores of the size exclusion chromatography matrix. Of such components that are able to partially or fully enter the pore volume, larger molecules, with less access to the pore volume will usually elute first, whereas the smallest molecules elute last. In some embodiments the exclusion limit of the size exclusion chromatography matrix is selected to be below the maximal width of the target cell. Hence, components that have access to the pore volume will usually remain longer in/on the size exclusion chromatography matrix than target cell. Thus, target cells can be collected in the eluate of a chromatography column separately from other matter/components of a sample. Therefore components such as a receptor binding reagent, or where, applicable a competition reagent, elute at a later point of time from a gel filtration matrix than the target cell. This separation effect will be further increased, if the gel permeation matrix comprises an affinity reagent (usually covalently bound thereon) that comprises binding sites, for example binding sites Z that are able to bind reagents such as a receptor binding reagent and/or a competition reagent present in a sample. The receptor binding reagent and/or the competition reagent will be bound by the binding sites Z of the affinity reagent and thereby immobilized on the gel permeation matrix. This method is usually carried out in a removal cartridge as used in the present invention and in some embodiments a method, a combination and a kit according to the invention include and/or employ such a gel filtration matrix. In a respective method cells are accordingly separated on the basis of size.

A chromatography matrix employed in the present invention may also include magnetically attractable matter such as one or more magnetically attractable particles or a ferrofluid. A respective magnetically attractable particle may comprise a multimerization reagent or an affinity reagent with binding site that is capable of binding a target cell. Magnetically attractable particles may contain diamagnetic, ferromagnetic, paramagnetic or superparamagnetic material. Superparamagnetic material responds to a magnetic field with an induced magnetic field without a resulting permanent magnetization. Magnetic particles based on iron oxide are for example commercially available as Dynabeads® from Dynal Biotech, as magnetic MicroBeads from Miltenyi Biotec, as magnetic porous glass beads from CPG Inc., as well as from various other sources, such as Roche Applied Science, BIOCLON, BioSource International Inc., micromod, AMBION, Merck, Bangs Laboratories, Polysciences, or Novagen Inc., to name only a few. Magnetic nanoparticles based on superparamagnetic Co and FeCo, as well as ferromagnetic Co nanocrystals have been described, for example by Hütten, A. et al. (J. Biotech. (2004), 112, 47-63). However, in some embodiments a chromatography matrix employed in the present invention is void of any magnetically attractable matter.

In some embodiments, the receptor molecule that is located on the cell surface, e.g., the target cell surface may be any molecule as long as it remains covalently or non-covalently bonded to the cell surface during a chromatographic separation process in a method according to the invention. The receptor molecule is a molecule against which a receptor binding reagent may be directed. In some embodiments the receptor is a peptide or a protein, such as a membrane receptor protein. In some embodiments the receptor is a lipid, a polysaccharide or a nucleic acid. A receptor that is a protein may be a peripheral membrane protein or an integral membrane protein. It may in some embodiments have one or more domains that span the membrane. In certain embodiments, the receptor molecule is a surface protein of an immune cell, e.g., CD3, CD4, or CD8. In some embodiments the receptor molecule may be an antigen defining a desired cell population or subpopulation, for instance a population or subpopulation of blood cells, e. g. lymphocytes (e.g. T cells, CD3+ T cells, CD4+ T cells, or CD8+ T cells).

In some embodiments, the receptor binding reagent has or contains a binding site B. In certain embodiments, the binding site B is monovalent. In some aspects, a monovalent binding site B is or contains a monovalent antibody fragment or a proteinaceous binding molecule with immunoglobulin-like functions, an aptamer or an MHC molecule. Examples of monovalent antibody fragments include, but are not limited to a Fab fragment, a Fv fragment, and a single-chain Fv fragment (scFv), including a divalent single-chain Fv fragment. Examples of (recombinant) antibody fragments are Fab fragments, Fv fragments, single-chain Fv fragments (scFv), a divalent antibody fragment such as an (Fab)2'-fragment, diabodies, triabodies (Iliades, P., et al., *FEBS Lett* (1997) 409, 437-441), decabodies (Stone, E., et al., *Journal of Immunological Methods* (2007) 318, 88-94)

and other domain antibodies (Holt, L. J., et al., *Trends Biotechnol.* (2003), 21, 11, 484-490). In some embodiments one or more binding sites of the receptor molecule binding reagent may be a bivalent proteinaceous artificial binding molecule such as a dimeric lipocalin mutein that is also known as "duocalin". In some embodiments the receptor binding reagent may have a single second binding site, i.e., it may be monovalent. Examples of monovalent receptor binding reagents include, but are not limited to, a monovalent antibody fragment, a proteinaceous binding molecule with antibody-like binding properties or an MHC molecule.

Yet further examples of suitable proteinaceous binding molecules are an EGF-like domain, a Kringle-domain, a fibronectin type I domain, a fibronectin type II domain, a fibronectin type III domain, a PAN domain, a G1a domain, a SRCR domain, a Kunitz/Bovine pancreatic trypsin Inhibitor domain, tendamistat, a Kazal-type serine protease inhibitor domain, a Trefoil (P-type) domain, a von Willebrand factor type C domain, an Anaphylatoxin-like domain, a CUB domain, a thyroglobulin type I repeat, LDL-receptor class A domain, a Sushi domain, a Link domain, a Thrombospondin type I domain, an immunoglobulin domain or a an immunoglobulin-like domain (for example, domain antibodies or camel heavy chain antibodies), a C-type lectin domain, a MAM domain, a von Willebrand factor type A domain, a Somatomedin B domain, a WAP-type four disulfide core domain, a F5/8 type C domain, a Hemopexin domain, an SH2 domain, an SH3 domain, a Laminin-type EGF-like domain, a C2 domain, "Kappabodies" (cf. Ill. et al., Protein Eng (1997) 10, 949-57, a so called "minibody" (Martin et al., EMBO J (1994) 13, 5303-5309), a diabody (cf. Holliger et al., PNAS USA (1993) 90, 6444-6448), a so called "Janusis" (cf. Traunecker et al., EMBO J (1991) 10, 3655-3659, or Traunecker et al., Int J Cancer (1992) Suppl 7, 51-52), a nanobody, a microbody, an affilin, an affibody, a knottin, ubiquitin, a zinc-finger protein, an autofluorescent protein or a leucine-rich repeat protein. An example of a nucleic acid molecule with antibody-like functions is an aptamer. An aptamer folds into a defined three-dimensional motif and shows high affinity for a given target structure.

In particular aspects, the receptor binding protein contains a binding partner C. In some aspects, the binding partner C included in the receptor binding reagent may for instance be hydrocarbon-based (including polymeric) and include nitrogen-, phosphorus-, sulphur-, carben-, halogen- or pseudohalogen groups. It may be an alcohol, an organic acid, an inorganic acid, an amine, a phosphine, a thiol, a disulfide, an alkane, an amino acid, a peptide, an oligopeptide, a polypeptide, a protein, a nucleic acid, a lipid, a saccharide, an oligosaccharide, or a polysaccharide. As further examples, it may also be a cation, an anion, a polycation, a polyanion, a polycation, an electrolyte, a polyelectrolyte, a carbon nanotube or carbon nanofoam. Generally, such a binding partner has a higher affinity to the binding site of the multimerization reagent than to other matter. Examples of a respective binding partner include, but are not limited to, a crown ether, an immunoglobulin, a fragment thereof and a proteinaceous binding molecule with antibody-like functions.

In some embodiments the binding partner C that is included in the receptor binding reagent includes biotin and the affinity reagent includes a streptavidin analog or an avidin analog that reversibly binds to biotin. In some embodiments the binding partner C that is included in the receptor binding reagent includes a biotin analog that reversibly binds to streptavidin or avidin, and the affinity reagent includes streptavidin, avidin, a streptavidin analog or an avidin analog that reversibly binds to the respective biotin analog. In some embodiments the binding partner C that is included in the receptor binding reagent includes a streptavidin or avidin binding peptide and the affinity reagent includes streptavidin, avidin, a streptavidin analog or an avidin analog that reversibly binds to the respective streptavidin or avidin binding peptide.

In some embodiments the binding partner that is included in the receptor binding reagent may include a streptavidin-binding peptide In some embodiments, the peptide sequence contains a sequence with the general formula His-Pro-Xaa, where Xaa is glutamine, asparagine, or methionine, such as contains the sequence set forth in SEQ ID NO: 78. In some embodiments, the peptide sequence contains the sequence set forth in SEQ ID NO: 93. In some embodiments, the peptide sequence has the general formula set forth in SEQ ID NO: 79, such as set forth in SEQ ID NO: 69. In one example, the peptide sequence is Trp-Arg-His-Pro-Gln-Phe-Gly-Gly (also called Strep-Tag®, set forth in SEQ ID NO: 70). In one example, the peptide sequence is Trp-Ser-His-Pro-Gln-Phe-Glu-Lys (also called Strep-Tag® II, set forth in SEQ ID NO: 64), which is described in U.S. Pat. No. 6,103,493, for example, and is commercially available under the trademark Strep-Tactin®. The streptavidin binding peptides might, for example, be single peptides such as the "Strep-Tag®" described in U.S. Pat. No. 5,506,121, for example, or streptavidin binding peptides having a sequential arrangement of two or more individual binding modules as described in International Patent Publication WO 02/077018 or U.S. Pat. No. 7,981,632.

In some embodiment the binding partner C of the receptor binding reagent includes a moiety known to the skilled artisan as an affinity tag. In such an embodiment the affinity reagent includes a corresponding binding partner, for example, an antibody or an antibody fragment, known to bind to the affinity tag. As a few illustrative examples of known affinity tags, the binding partner that is included in the receptor binding reagent may include dinitrophenol or digoxigenin, oligohistidine, polyhistidine, an immunoglobulin domain, maltose-binding protein, glutathione-S-transferase (GST), chitin binding protein (CBP) or thioredoxin, calmodulin binding peptide (CBP), FLAG'-peptide, the HA-tag (e.g., SEQ ID NO: 94), the VSV-G-tag (e.g., SEQ ID NO: 95), the HSV-tag (e.g., SEQ ID NO: 96), the T7 epitope (e.g., SEQ ID NO: 97), maltose binding protein (MBP), the HSV epitope (e.g., SEQ ID NO: 98) of the sequence of herpes simplex virus glycoprotein D, the "myc" epitope (e.g., SEQ ID NO: 99) of the transcription factor c-myc of the sequence, the V5-tag (e.g., SEQ ID NO: 100), or glutathione-S-transferase (GST). In such an embodiment the complex formed between the one or more binding sites of the affinity reagent, in this case an antibody or antibody fragment, and the antigen can be disrupted competitively by adding the free antigen, i.e. the free peptide (epitope tag) or the free protein (such as MBP or CBP). The affinity tag might also be an oligonucleotide tag. Such an oligonucleotide tag may, for instance, be used to hybridize to an oligonucleotide with a complementary sequence, linked to or included in the affinity reagent.

Further examples of a suitable binding partner C include, but are not limited to, a lectin, protein A, protein G, a metal, a metal ion, nitrilo triacetic acid derivatives (NT A), RGD-motifs, a dextrane, polyethyleneimine (PEI), a redox polymer, a glycoproteins, an aptamers, a dye, amylose, maltose, cellulose, chitin, glutathione, calmodulin, gelatine, polymyxin, heparin, NAD, NADP, lysine, arginine, benzamidine, poly U, or oligo-dT. Lectins such as Concavalin A are known to bind to polysaccharides and glycosylated proteins.

An illustrative example of a dye is a triazine dye such as Cibacron blue F3G-A (CB) or Red HE-3B, which specifically bind NADH-dependent enzymes. Typically, Green A binds to Co A proteins, human serum albumin, and dehydrogenases. In some cases, the dyes 7-aminoactinomycin D and 4',6-diamidino-2-phenylindole bind to DNA. Generally, cations of metals such as Ni, Cd, Zn, Co, or Cu, are typically used to bind affinity tags such as an oligohistidine containing sequence, including the hexahistidine or the His-Asn-His-Arg-His-Lys-His-Gly-Gly-Gly-Cys tag (MAT tag) (SEQ ID NO: 103), and N-methacryloyl-(L)-cysteine methyl ester.

In line with International Patent Application PCT/EP2012/063969, published as WO 2013/011011, (the entire content of which is incorporated herein by reference for all purpose) the strength of the binding between the receptor binding reagent and a receptor molecule on a target cell may not be not essential for the reversibility of the binding of the target cell to the affinity reagent via the receptor binding reagent. Rather, irrespective of the strength of the binding, meaning whether the dissociation constant (Kd) for the binding between the receptor binding reagent via the binding site B and the receptor molecule is of low affinity, for example, in the range of a Kd of about $10^{-3}$ to about $10^{-7}$ M, or of high affinity, for example, in the range of a Kd of about $10^{-7}$ to about $1\times10^{-10}$ M, a target cell can be reversibly stained as long as the dissociation of the binding of the receptor binding reagent via the binding site B and the receptor molecule occurs sufficiently fast. In this regard the dissociation rate constant ($K_{off}$) for the binding between the receptor binding reagent via the binding site B and the receptor molecule may have a value of about $3\times10^{-5}$ $sec^{-1}$ or greater (this dissociation rate constant is the constant characterizing the dissociation reaction of the complex formed between the binding site B of the receptor binding reagent and the receptor molecule on the surface of the target cell). The association rate constant (kon) for the association reaction between the binding site B of the receptor binding reagent and the receptor molecule on the surface of the target cell may have any value. In order to ensure a sufficiently reversible binding between receptor molecule and receptor binding reagent it is advantageous to select the $k_{off}$ value of the binding equilibrium to have a value of about $3\times10^{-5}$ $sec^{-1}$ or greater, of about $5\times10^{-5}$ $sec^{-1}$ or greater, such as or as about $1\times10^{-4}$ $sec^{-1}$ or greater, $5\times10^{-4}$ $sec^{-1}$ or greater, $1\times10^{-3}$ $sec^{-1}$ or greater, $5\times10^{-3}$ $sec^{-1}$ or greater, a $1\times10^{-2}$ $sec^{-1}$ or greater, $1\times10^{-1}$ $sec^{-1}$ or greater or $5\times10^{-1}$ $sec^{-1}$ or greater. It is noted here that the values of the kinetic and thermodynamic constants as used herein, refer to conditions of atmospheric pressure, i.e. 1.013 bar, and room temperature, i.e. 25° C.

In some embodiments the receptor binding reagent has a single (monovalent) binding site B capable of specifically binding to the receptor molecule. In some embodiments the receptor binding reagent has at least two (i.e., a plurality of binding sites B including three, four or also five identical binding sites B), capable of binding to the receptor molecule. In any of these embodiment the binding of the receptor molecule via (each of) the binding site(s) B may have a $k_{off}$ value of about $3\times10^{-5}$ $sec^{-1}$ or greater. Thus, the receptor binding reagent can be monovalent (for example a monovalent antibody fragment or a monovalent artificial binding molecule (proteinaceous or other) such as a mutein based on a polypeptide of the lipocalin family (also known as "Anticalin®), or a bivalent molecule such as an antibody or a fragment in which both binding sites are retained such as an $F(ab')_2$ fragment. In some embodiments the receptor molecule may be a multivalent molecule such as a pentameric IgE molecule, provided the $k_{off}$ rate is $3\times10^{-5}$ $sec^{-1}$ or greater.

In some embodiments of the invention, it is on a molecular level not the $k_{off}$ rate (of $3\times10^{-5}$ $sec^{-1}$ or greater) of the binding of the receptor binding reagent via the at least binding site B and the receptor molecule on the target cell that provides for the (traceless) isolation of biological material via reversible cell affinity chromatography technology described here. Rather, and as described, for example, in U.S. Pat. No. 7,776,562 or International Patent application WO02/054065, a low affinity binding between the receptor molecule and the binding site B of the binding receptor binding reagent together with an avidity effect mediated via the immobilized affinity reagent allows for a reversibly and traceless isolation of a target cell. In these embodiments a complex between the two or more binding sites Z of the affinity reagent and the binding partner C of at least two receptor binding reagents can form, allowing a reversible immobilization and subsequent elution of the target cells from the affinity chromatography matrix (via addition of the competing agent that will disrupt the binding (complex) formed between the binding partner C and the binding sites Z which in turn leads to the dissociation of the receptor binding reagent from the target cell. As mentioned above, such a low binding affinity may be characterized by a dissociation constant ($K_D$) in the range from about $1.0\times10^{-3}$ M to about $1.0\times10^{-7}$ M for the binding of the receptor binding reagent via the binding site B and the receptor molecule on the target cell surface.

3. Input Compositions

In certain embodiments, the provided methods are used in connection with producing or preparing an input population or composition of cells. In certain embodiments, the input cell composition includes a population of cells for use in genetic engineering, e.g., cells that will be genetically engineered or that will undergo a process to produce genetically engineered cells. In certain embodiments, the cells will be treated with, contacted with, or incubated with a nucleic acid that encodes a recombinant receptor. In certain embodiments, the input composition contains T cells, viable T cells, CD3+ T cells, CD4+ T cells, CD8+ T cells, and/or subpopulations thereof.

In some embodiments, cell viability is assessed with an assay that may include, but is not limited to, dye uptake assays (e.g., calcein AM assays), XTT cell viability assays, and dye exclusion assays (e.g., trypan blue, Eosin, or propidium dye exclusion assays). In particular embodiments, a viable cell has negative expression of one or more apoptotic markers, e.g., Annexin V or active Caspase 3. In some embodiments, the viable cell is negative for the expression of one or more apoptosis marker that may include, but are not limited to, a caspase or an active caspase, e.g., caspase 2, caspase 3, caspase 6, caspase 7, caspase 8, caspase 9, or caspase 10, Bcl-2 family members, e.g., Bax, Bad, and Bid, Annexin V, or TUNEL staining. In particular embodiments, the viable cells are active caspase 3 negative. In certain embodiments, the viable cells are Annexin V negative.

In some embodiments, the input composition comprises a population of enriched CD3+ T cells, e.g., viable CD3+ T cells. In some embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population are CD3+ T cells, e.g., viable CD3+ T cells. In some embodiments, the input population consists essentially of CD3+ T cells, e.g., viable CD3+ T cells.

In certain embodiments, the input population is a population of cells enriched for enriched CD4+ T cells and CD8+ T cells, e.g., CD4+ T cells and CD8+ T cells. In particular embodiments, the input population is or includes at least 60%, at least 65%, at least 70%, at least 75%, at least 80%, at least 85%, at least 90%, at least 95%, at least 98%, at least 99%, at least 99.5%, at least 99.9%, or at or at about 100% cells that are CD4+ or CD8+ T cells. In some embodiments, the input population consists essentially of CD4+ and CD8+ T cells.

In certain embodiments, the input population is a population of enriched CD4+ T cells. In particular embodiments, at least 60%, at least 65%, at least 70%, at least 75%, at least 80%, at least 85%, at least 90%, at least 95%, at least 98%, at least 99%, at least 99.5%, at least 99.9%, or at or at about 100% of the cells of the input population are CD4+ T cells. In some embodiments, the input population consists essentially of CD4+ T cells.

In some embodiments, cells from a population of enriched CD4+ T cells and cells from a population of enriched CD8+ T cells are mixed, combined, and/or pooled to generate an input population containing CD4+ T cells and CD8+ T cells. In certain embodiments, the populations of enriched CD4+ T cells and CD8+ T cells are pooled, mixed, and/or combined prior to stimulating cells, e.g., culturing the cells under stimulating conditions such as described in Section I-B. In certain embodiments, the populations of enriched CD4+ and CD8+ T cells are pooled, mixed, and/or combined subsequent to isolating, enriching, and/or selecting the CD4+ and CD8+ T cells from a biological sample. In particular embodiments, the populations of enriched CD4+ and CD8+ T cells are pooled, mixed, and/or combined subsequent to freezing, e.g., cryopreserving, and thawing the populations of enriched CD4+ and CD8+ T cells.

In certain embodiments, the input population is produced, generated, or made by mixing, pooling, and/or combining cells from a population of enriched CD4+ cells with cells from a population of enriched CD8+ cells. In certain embodiments, the population of enriched CD4+ T cells contains at least 60%, 65%, 70%, 75%, 80%, 85%, 90%, 95%, 98%, 99%, or 99.9% CD4+ T cells. In particular embodiments, the population of enriched CD4+ T cells contains 100% CD4+ T cells or contains about 100% CD4+ T cells. In certain embodiments, the population of enriched T cells includes or contains less than 20%, less than 10%, less than 5%, less than 1%, less than 0.1%, or less than 0.01% CD8+ T cells, and/or contains no CD8+ T cells, and/or is free or substantially free of CD8+ T cells. In some embodiments, the populations of cells consist essentially of CD4+ T cells. In certain embodiments, the population of enriched CD8+ T cells contains at least 75%, 80%, 85%, 90%, 95%, 98%, 99%, or 99.9% CD8+ T cells, or contains or contains about 100% CD8+ T cells. In certain embodiments, the population of enriched CD8+ T cells includes or contains less than 20%, less than 10%, less than 5%, less than 1%, less than 0.1%, or less than 0.01% CD4+ T cells, and/or contains no CD4+ T cells, and/or is free or substantially free of CD4+ T cells. In some embodiments, the populations of cells consist essentially of CD8+ T cells.

In certain embodiments, CD4+ T cells and CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In particular embodiments, viable CD4+ T cells and viable CD8+ T cells are pooled, mixed, and/or combined at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells.

In particular embodiments, the input composition has an amount of, of about, or of at least $50\times10^6$, $100\times10^6$, $150\times10^6$, $200\times10^6$, $250\times 10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, $1,000\times10^6$, $1,100\times10^6$, or $1,200\times10^6$ T cells, such as viable T cells, viable CD3+ T cells, or viable mixed CD4+ and CD8+ T cells. In particular embodiments, the input composition has an amount of, of about, or of at least $50\times10^6$, $100\times10^6$, $150\times10^6$, $200\times10^6$, $250\times 10^6$, $300\times10^6$, $350\times10^6$, $400\times10^6$, $450\times10^6$, $500\times10^6$, $550\times10^6$, $600\times10^6$ CD4+ T cells, e.g., viable CD4+ T cells. In certain embodiments, the input composition has an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$ CD8+ T cells, e.g., viable CD8+ T cells. In some embodiments, the amount of cells is an amount of viable CD4+ and CD8+ T cells pooled, mixed and/or combined together in the same composition. In such embodiments, the CD4+ and CD8+ T cell are present at a ratio of between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1 or 1:1 CD4+ T cells to CD8+ T cells. In some embodiments, the amount of cells is an amount of viable CD4+ and CD8+ T cells pooled, mixed and/or combined together at a ratio of about 1:1 or 1:1 CD4+ T cells to CD8+ T cells.

In particular embodiments, the input composition has an amount of between or between about $300\times10^6$ and $600\times10^6$ T cells, e.g., viable CD3+ cells, or mixed viable CD4+ and viable CD8+ cells (e.g., mixed at or at about a 1:1 ratio). In some embodiments, the input population has an amount of or of about $300\times10^6$, e.g., viable CD3+ cells, or mixed viable CD4+ and viable CD8+ cells (e.g., mixed at or at about a 1:1 ratio). In some embodiments, the input population has an amount of or of about $400\times10^6$, e.g., viable CD3+ cells or mixed viable CD4+ and viable CD8+ cells (e.g., mixed at or at about a 1:1 ratio). In some embodiments, the input population has an amount of or of about $500\times10^6$, e.g., viable CD3+ cells or mixed viable CD4+ and viable CD8+ cells (e.g., mixed at or at about a 1:1 ratio). In some embodiments, the input population has an amount of or of about $600\times10^6$, e.g., viable CD3+ cells or mixed viable CD4+ and viable CD8+ cells (e.g., mixed at or at about a 1:1 ratio). In some embodiments, the input population has an amount of or of about $700\times10^6$, e.g., viable CD3+ cells or mixed viable CD4+ and viable CD8+ cells (e.g., mixed at or at about a 1:1 ratio). In some embodiments, the input population has an amount of or of about $800\times10^6$, e.g., viable CD3+ cells or mixed viable CD4+ and viable CD8+ cells (e.g., mixed at or at about a 1:1 ratio). In some embodiments, the input population has an amount of or of about $900\times10^6$, e.g., viable CD3+ cells or mixed viable CD4+ and viable CD8+ cells (e.g., mixed at or at about a 1:1 ratio). In some embodiments, the input population has an amount of or of about $100\times10^7$, e.g., viable CD3+ cells or mixed viable CD4+ and viable CD8+ cells (e.g., mixed at or at about a 1:1 ratio). In some embodiments, the input population has an amount of or of about $110\times10^7$, e.g., viable CD3+ cells or mixed viable CD4+ and viable CD8+ cells (e.g., mixed at or at about a 1:1 ratio). In some embodiments, the input population has an amount of or of about $120\times10^7$, e.g., viable CD3+ cells or mixed viable CD4+ and viable CD8+ cells (e.g., mixed at or at about a 1:1 ratio).

In certain embodiments, CD4+ T cells and CD8+ T cells are pooled, mixed, and/or combined such that the input composition has up to or up to about a target number (2n) of T cells, such as viable T cells, viable CD3+ T cells, or viable mixed CD4+ and CD8+ T cells. In certain embodiments where a composition comprising enriched CD4+ T cells contains at least n of CD4+ T cells and a composition comprising enriched CD8+ T cells (e.g., derived from the same donor, e.g., from the same aphresis or leukaphresis sample from the donor, as the CD4+ T cell composition) contains at least n of CD8+ T cells, n of CD4+ T cells from the CD4+ T cell composition and n of CD8+ T cells from the CD8+ T cell composition are pooled, mixed, and/or combined (i.e. at 1:1 CD4+ to CD8+ ratio) to generate an input composition containing the target number (2n) of T cells. In certain embodiments where a composition comprising enriched CD4+ T cells contains no more than (e.g., fewer than) n of CD4+ T cells and a composition comprising enriched CD8+ T cells (e.g., derived from the same donor, e.g., from the same aphresis or leukaphresis sample from the donor, as the CD4+ T cell composition) contains no more than (e.g., fewer than) n of CD8+ T cells, all of the cells of the CD4+ T cell composition and all of the cells of the CD8+ T cell composition are pooled, mixed, and/or combined to generate the input composition. In these embodiments, the input composition may contain fewer than the target number (2n) of T cells. In certain embodiments where a composition comprising enriched CD4+ T cells contains fewer than n of CD4+ T cells and a composition comprising enriched CD8+ T cells (e.g., derived from the same donor, e.g., from the same aphresis or leukaphresis sample from the donor, as the CD4+ T cell composition) contains more than n of CD8+ T cells, or vice versa, cells of the CD4+ or CD8+ T cell composition are used to supplement the alternative cell type such that the input composition contains up to the target number (2n) of T cells. In any of the preceding embodiments, the target number 2n can be $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, $1{,}000\times10^6$, $1{,}100\times10^6$, or $1{,}200\times10^6$.

In certain embodiments, $450\times10^6$ CD4+ T cells from a composition comprising enriched CD4+ T cells and $450\times10^6$ CD8+ T cells from a composition comprising enriched CD8+ T cells (e.g., derived from the same donor, e.g., from the same aphresis or leukaphresis sample from the donor, as the CD4+ T cell composition) are pooled, mixed, and/or combined to generate an input composition containing $900\times10^6$ CD4+ and CD8+ T cells. In certain embodiments, when a composition comprising enriched CD4+ T cells contains fewer than $450\times10^6$ CD4+ T cells and a composition comprising enriched CD8+ T cells (e.g., derived from the same donor, e.g., from the same aphresis or leukaphresis sample from the donor, as the CD4+ T cell composition) contains fewer than $450\times10^6$ CD8+ T cells, all of the cells of the CD4+ T cell composition and all of the cells of the CD8+ T cell composition are pooled, mixed, and/or combined to generate the input composition. In certain embodiments, when either of the compositions contains fewer than $450\times10^6$ CD4+ or CD8+ cells while the other composition contains more than $450\times10^6$ CD8+ cells or CD4+ cells, then up to $900\times10^6$ CD4+ T cells and CD8+ T cells are combined to generate an input composition. The total number of CD4+ and CD8+ T cells in the input composition may be lower than $900\times10^6$. In other words, cells of the composition comprising enriched CD4+ T cells may be used to supplement the composition comprising enriched CD8+ T cells, or vice versa, in order to generate an input composition comprising up to the target number (2n) of T cells, e.g., up to $900\times10^6$ T cells to be subjected to stimulation.

Although in the above embodiments, the cell selection, isolation, separation, enrichment, and/or purification processes are discussed in the context of preparing an input composition, it should be understood that the cell selection, isolation, separation, enrichment, and/or purification processes disclosed herein can be used during, prior to, or between any of the subsequent steps (e.g., activation, stimulation, engineering, transduction, transfection, incubation, culturing, harvest, formulation, and/or administering a formulated cell population to a subject), in any suitable combination and/or order. For example, a T cell selection, isolation, separation, enrichment, and/or purification step can be performed between T cell activation/stimulation and T cell transduction. In another example, a T cell selection, isolation, separation, enrichment, and/or purification step can be performed after T cell transduction, but prior to harvesting, prior to collecting, and/or prior to formulating the cells. In a particular example, a T cell selection, isolation, separation, enrichment, and/or purification step can be performed immediately prior to harvesting the cells as a refining or clarification step. In some embodiments, a T cell selection step by chromatography is performed between T cell activation/stimulation and T cell transduction. In some embodiments, a T cell selection step by chromatography is performed after T cell transduction, but prior to harvesting, prior to collecting, and/or prior to formulating the cells. In some embodiments, a T cell selection step by chromatography is performed immediately prior to harvesting the cells.

In some embodiments, the input composition is subjected to one or more dilution and/or wash step, e.g., with a serum-free medium, prior to stimulating the cells, e.g., culturing the cells under stimulating conditions such as described in Section I-B. In some embodiments, the dilution and/or wash step allows media exchange into a serum-free medium, such as one described herein in Section II or in PCT/US2018/064627, which is incorporated herein by reference.

In some embodiments, the serum-free medium comprises a basal medium (e.g. OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology*. 2015 January; 4 (1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

In some embodiments, the input composition is generated by mixing, combining, and/or pooling a population enriched in CD8+ T cells generated from a starting sample, such as PBMCs or a leukaphresis sample, with a population enriched in CD4+ T cells generated from the starting sample. In some embodiments, the population enriched in CD4+ T cells is generated from the CD8-negative fraction generated during the process of generating the population enriched in CD8+ T cells from the starting sample. In particular embodiments, the input composition has a ratio of or of about 1:1 CD4+ T cells to CD8+ T cells, and is subjected to one or more wash step, e.g., with a serum-free medium described herein in Section II or in PCT/US2018/064627, prior to stimulating the cells, e.g., culturing the cells under stimulating conditions such as described in Section I-B. In some embodiments, the one or more wash step allows media exchange from a PBS/EDTA buffer containing albumin into the serum-free medium, which is also used in cell stimulation.

B. Stimulation

In some embodiments, the provided methods are used in connection with stimulating the cells, e.g., culturing the cells under stimulating conditions. In some embodiments, the stimulating conditions include conditions that activate or stimulate, and/or are capable of activating or stimulating a signal in the cell, e.g., a CD4+ or CD8+ T cell, such as a signal generated from a TCR and/or a coreceptor. In some embodiments, the stimulating conditions are or include one or more steps of culturing the cells with or in the presence of a stimulatory reagent, e.g., a reagent that activates or stimulates, or is capable of activing or stimulating a signal in the cell. In some embodiments, the stimulatory reagent stimulates and/or activates a TCR and/or a coreceptor. In particular embodiments, the stimulatory reagent is a reagent provided herein, e.g., as described in Section I-B-1. In certain embodiments, stimulating or culturing a population of cells under stimulating conditions generates or produces a population of stimulated cells (also referred to herein as a stimulated population of cells).

In some embodiments, cells of an input populations, e.g., an input population described herein such as in Section I-A-3, are stimulated. In certain embodiments, the cells of the input population are stimulated or subjected to stimulation prior to introducing a heterologous or recombinant polynucleotide into the cells, such as by a method, step, or technique described herein, e.g., in Section I-C. In particular embodiments, the cells from the input population have been previously frozen, e.g., cryopreserved, and stored, and are thawed and optionally washed prior to stimulating. In particular embodiments, the cells of the input population are selected (e.g., as described in Section I-A-1 and Section I-A-2) from a composition thawed from cryopreserved and/or cryoprotected apheresis product or leukapheresis product, and the cells of the input population are not frozen, e.g., cryopreserved, and stored, prior to stimulating.

In particular aspects, the initiation of the stimulation (also referred to herein as the stimulating) occurs when the input cells are first contacted or exposed to stimulating conditions. In some embodiments, the stimulation is considered to be initiated when the cells of the input population are first stimulated or exposed to conditions that activate or stimulate, and/or are capable of activing or stimulating a signal in the cell, such as a signal generated from a TCR and/or a coreceptor. In some embodiments, the stimulation is initiated when the input cells are first contacted or exposed to a stimulatory reagent, such as a stimulatory reagent described herein, e.g, in section I-B-1.

In some embodiments, the stimulation, e.g. culturing the cells under stimulating conditions, is performed for, for about, or for less than, 48 hours, 42 hours, 36 hours, 30 hours, 24 hours, 22 hours, 20 hours, 18 hours, 16 hours, or 12 hours. In some embodiments, the stimulation, e.g. culturing the cells under stimulating conditions, is performed for 20±4 hours or between or between about 16 hours and 24 hours. In particular embodiments, the stimulation, e.g. culturing the cells under stimulating conditions, is performed for between or between about 36 hours and 12 hours, 30 hours and 18 hours, or for or for about 24 hours, or 22 hours. In some embodiments, the stimulation, e.g. culturing the cells under stimulating conditions, is performed for, for about, or for less than, 2 days or one day.

In particular embodiments, an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, or $1{,}000\times10^6$ cells of the input population are stimulated or subjected to stimulation, e.g., cultured under stimulating conditions. In particular embodiments, the amount of the input population that are stimulated, e.g., cultured under stimulating conditions, is at or about $50\times10^6$ cells, at or about $100\times10^6$ cells, at or about $150\times10^6$ cells, at or about $200\times10^6$ cells, at or about $250\times10^6$ cells, at or about $300\times10^6$ cells, at or about $350\times10^6$ cells, at or about $400\times10^6$ cells, at or about $450\times10^6$ cells, at or about $500\times10^6$ cells, at or about $550\times10^6$ cells, at or about $600\times10^6$ cells, at or about $700\times10^6$ cells, at or about $800\times10^6$ cells, at or about $900\times10^6$ cells, or at or about $1{,}000\times10^6$ cells, or any value between any of the foregoing. In particular embodiments, an amount of or of about $900\times10^6$ cells of the input population are stimulated, e.g., cultured under stimulating conditions.

In particular embodiments, the input composition comprises viable CD4+ T cells and viable CD8+ T cells, at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1, or 1:1 viable CD4+ T cells to viable CD8+ T cells. In particular embodiments, the input composition comprises viable CD4+ T cells and viable CD8+ T cells, at a ratio of about 1:1 or 1:1 viable CD4+ T cells to viable CD8+ T cells. In particular embodiments, an amount of or of about $450\times10^6$ CD4+ cells of the input population are stimulated, e.g., cultured under stimulating conditions. In particular embodiments, an amount of or of about $450\times10^6$ CD8+ cells of the input population are stimulated, e.g., cultured under stimulating conditions. In particular embodiments, an amount of or of about $450\times10^6$ CD4+ T cells and an amount of or of about $450\times10^6$ CD8+ T cells of the input population are stimulated, e.g., cultured under stimulating conditions.

In certain embodiments, the cells, e.g., cells of the input population, are stimulated or subjected to stimulation e.g., cultured under stimulating conditions such as in the presence of a stimulatory reagent, at a density of, of about, or at least $0.01\times10^6$ cells/mL, $0.1\times10^6$ cells/mL, $0.5\times10^6$ cells/mL, $1.0\times10^6$ cells/mL, $1.5\times10^6$ cells/mL, $2.0\times10^6$ cells/mL, $2.5\times10^6$ cells/mL, $3.0\times10^6$ cells/mL, $4.0\times10^6$ cells/mL, $5.0\times10^6$ cells/mL, $10\times10^6$ cells/mL, or $50\times10^6$ cells/mL. In certain embodiments, the cells, e.g., cells of the input population, are stimulated or subjected to stimulation e.g., cultured under stimulating conditions such as in the presence of a stimulatory reagent, at a density of, of about, or at least $3.0\times10^6$ cells/mL. In certain embodiments, the cells of the input are viable cells.

In some embodiments, the conditions for stimulation and/or activation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In particular embodiments, the stimulating conditions include culturing the cells, e.g., cells from an input population, with and/or in the presence of one or more cytokines. In particular embodiments, the one or more cytokines are recombinant cytokines. In some embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes IL-2.

In certain embodiments, the amount or concentration of the one or more cytokines are measured and/or quantified with International Units (IU). International units may be used to quantify vitamins, hormones, cytokines, vaccines, blood products, and similar biologically active substances. In some embodiments, IU are or include units of measure of the potency of biological preparations by comparison to an international reference standard of a specific weight and strength e.g., WHO 1st International Standard for Human IL-2, 86/504. International Units are the only recognized and standardized method to report biological activity units that are published and are derived from an international collaborative research effort. In particular embodiments, the IU for population, sample, or source of a cytokine may be obtained through product comparison testing with an analogous WHO standard product. For example, in some embodiments, the IU/mg of a population, sample, or source of human recombinant IL-2, IL-7, or IL-15 is compared to the WHO standard IL-2 product (NIBSC code: 86/500), the WHO standard IL-17 product (NIBSC code: 90/530) and the WHO standard IL-15 product (NIBSC code: 95/554), respectively.

In some embodiments, the biological activity in IU/mg is equivalent to (ED50 in ng/ml)-1×106. In particular embodiments, the ED50 of recombinant human IL-2 or IL-15 is equivalent to the concentration required for the half-maximal stimulation of cell proliferation (XTT cleavage) with CTLL-2 cells. In certain embodiments, the ED50 of recombinant human IL-7 is equivalent to the concentration required for the half-maximal stimulation for proliferation of PHA-activated human peripheral blood lymphocytes. Details relating to assays and calculations of IU for IL-2 are discussed in Wadhwa et al., Journal of Immunological Methods (2013), 379 (1-2): 1-7; and Gearing and Thorpe, Journal of Immunological Methods (1988), 114 (1-2): 3-9; details relating to assays and calculations of IU for IL-15 are discussed in Soman et al. Journal of Immunological Methods (2009) 348 (1-2): 83-94.

In some embodiments, the cells, e.g., the input cells, are stimulated or subjected to stimulation in the presence of a cytokine, e.g., a recombinant human cytokine, at a concentration of between 1 IU/mL and 1,000 IU/mL, between 10 IU/mL and 50 IU/mL, between 50 IU/mL and 100 IU/mL, between 100 IU/mL and 200 IU/mL, between 100 IU/mL and 500 IU/mL, between 250 IU/mL and 500 IU/mL, or between 500 IU/mL and 1,000 IU/mL.

In some embodiments, the cells, e.g., the input cells, are stimulated or subjected to stimulation in the presence of recombinant IL-2, e.g., human recombinant IL-2, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., cells of the input population, are stimulated or subjected to stimulation in the presence of recombinant IL-2 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In some embodiments, the cells, e.g., the input cells, are stimulated or subjected to stimulation in the presence of or of about 100 IU/mL of recombinant IL-2, e.g., human recombinant IL-2.

In some embodiments, the cells, e.g., the input cells, are stimulated or subjected to stimulation in the presence of recombinant IL-7, e.g., human recombinant IL-7, at a concentration between 100 IU/mL and 2,000 IU/mL, between 500 IU/mL and 1,000 IU/mL, between 100 IU/mL and 500 IU/mL, between 500 IU/mL and 750 IU/mL, between 750 IU/mL and 1,000 IU/mL, or between 550 IU/mL and 650 IU/mL. In particular embodiments, the cells, e.g., the input cells, are stimulated or subjected to stimulation in the presence of IL-7 at a concentration at or at about 50 IU/mL, 100 IU/mL, 150 IU/mL, 200 IU/mL, 250 IU/mL, 300 IU/mL, 350 IU/mL, 400 IU/mL, 450 IU/mL, 500 IU/mL, 550 IU/mL, 600 IU/mL, 650 IU/mL, 700 IU/mL, 750 IU/mL, 800 IU/mL, 750 IU/mL, 750 IU/mL, 750 IU/mL, or 1,000 IU/mL. In particular embodiments, the cells, e.g., the input cells, are stimulated or subjected to stimulation in the presence of or of about 600 IU/mL of recombinant IL-7, e.g., human recombinant IL-7.

In some embodiments, the cells, e.g., the input cells, are stimulated or subjected to stimulation in the presence of recombinant IL-15, e.g., human recombinant IL-15, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., a cell of the input population, are stimulated or subjected to stimulation in the presence of recombinant IL-15 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 200 IU/mL. In some embodiments, the cells, e.g., the input cells, are stimulated or subjected to stimulation in the presence of or of about 100 IU/mL of recombinant IL-15, e.g., human recombinant IL-15.

In particular embodiments, the cells, e.g., cells from the input population, are stimulated or subjected to stimulation under stimulating conditions in the presence of IL-2, IL-7, and/or IL-15. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are stimulated or subjected to stimulation under stimulating conditions in the presence of recombinant IL-2, IL-7, and IL-15. In certain embodiments, the cells are stimulated or subjected to stimulation under stimulating conditions in the presence of recombinant IL-2 of or of about 100 IU/mL, recombinant IL-7 of or of about 600 IU/mL, and recombinant IL-15 of or of about 100 IU/mL.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, stimulation is carried out in accordance with techniques such as those described in U.S. Pat. No. 6,040,177 to Riddell et al., Klebanoff et al. (2012) J Immunother. 35 (9): 651-660, Terakura et al. (2012) Blood. 1:72-82, and/or Wang et al. (2012) J Immunother. 35 (9): 689-701.

In some embodiments, the stimulation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In some embodiments, the stimulation is performed in serum free media described herein in Section II or in PCT/US2018/064627. In some embodiments, the serum-free medium comprises a basal medium (e.g.OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology*. 2015 January; 4 (1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15. In some embodiments, at least a portion of the stimulation in the presence of one or more stimulating conditions or a stimulatory reagent is carried out in the internal cavity of a centrifugal chamber, for example, under centrifugal rotation, such as described in International Publication Number WO2016/073602 which is incorporated by reference. In some embodiments, at least a portion of the stimulation performed in a centrifugal chamber includes mixing with a reagent or reagents to induce stimulation and/or activation. In some embodiments, cells, such as selected cells, are mixed with a stimulating condition or stimulatory agent in the centrifugal chamber. In some aspects of such processes, a volume of cells is mixed with an amount of one or more stimulating conditions or agents that is far less than is normally employed when performing similar stimulations in a cell culture plate or other system.

In some embodiments, the stimulation generally is carried out under mixing conditions, such as in the presence of spinning, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm), such as at an RCF at the sample or wall of the chamber or other container of from or from about 80 g to 100 g (e.g. at or about or at least 80 g, 85 g, 90 g, 95 g, or 100 g). In some embodiments, the spin is carried out using repeated intervals of a spin at such low speed followed by a rest period, such as a spin and/or rest for 1, 2, 3, 4, 5, 6, 7, 8, 9, or 10 seconds, such as a spin at approximately 1 or 2 seconds followed by a rest for approximately 5, 6, 7, or 8 seconds.

In certain embodiments, the stimulation is performed under static conditions, such as conditions that do not involve centrifugation, shaking, rotating, rocking, or perfusion, e.g., continuous or semi-continuous perfusion of the media. In some embodiments, either prior to or shortly after, e.g., within 5, 15, or 30 minutes, the initiation, the cells are transferred (e.g., transferred under sterile conditions) to a container such as a bag or vial, and placed in an incubator. In particular embodiments, incubator is set at, at about, or at least 16° C., 24° C., or 35° C. In some embodiments, the incubator is set at 37° C., at about at 37° C., or at 37° C.±2° C., ±1° C., ±0.5° C., or ±0.1° C. In particular embodiments, the stimulation under static condition is performed in a cell culture bag placed in an incubator. In some embodiments, the culture bag is composed of a single-web polyolefin gas permeable film which enables monocytes, if present, to adhere to the bag surface.

1. Stimulatory Reagents

In particular embodiments, the stimulating conditions include incubating, culturing, and/or cultivating the cells with a stimulatory reagent. In certain embodiments, the stimulatory reagent contains or includes a bead. In certain embodiments, the initiation of the stimulation occurs when the cells are incubated or contacted with the stimulatory reagent. In particular embodiments, the stimulatory reagent contains or includes an oligomeric reagent, e.g., a streptavidin mutein oligomer. In particular embodiments, the stimulatory reagent activates and/or is capable of activating one or more intracellular signaling domains of one or more components of a TCR complex and/or one or more intracellular signaling domains of one or more costimulatory molecules.

In some embodiments, the stimulating conditions or stimulatory reagents include one or more agent, e.g., ligand, which is capable of stimulating or activating an intracellular signaling domain of a TCR complex. In some embodiments, an agent as contemplated herein can include, but is not limited to, RNA, DNA, proteins (e.g., enzymes), antigens, polyclonal antibodies, monoclonal antibodies, antibody fragments, carbohydrates, lipids lectins, or any other biomolecule with an affinity for a desired target. In some embodiments, the desired target is a T cell receptor and/or a component of a T cell receptor. In certain embodiments, the desired target is CD3. In certain embodiment, the desired target is a T cell costimulatory molecule, e.g., CD28, CD137 (4-1-BB), OX40, or ICOS. The one or more agents may be attached directly or indirectly to the bead by a variety of methods known and available in the art. The attachment may be covalent, noncovalent, electrostatic, or hydrophobic and may be accomplished by a variety of attachment means, including for example, a chemical means, a mechanical means, or an enzymatic means. In some embodiments, the agent is an antibody or antigen binding fragment thereof, such as a Fab. In some embodiments, a biomolecule (e.g., a biotinylated anti-CD3 antibody) may be attached indirectly to the bead via another biomolecule (e.g., anti-biotin antibody) that is directly attached to the bead.

In some embodiments, the stimulatory reagent contains one or more agents (e.g. antibody) that is attached to a bead (e.g., a paramagnetic bead) and specifically binds to one or more of the following macromolecules on a cell (e.g., a T cell): CD2, CD3, CD4, CD5, CD8, CD25, CD27, CD28, CD29, CD31, CD44, CD45RA, CD45RO, CD54 (ICAM-1), CD127, MHCI, MHCII, CTLA-4, ICOS, PD-1, OX40, CD27L (CD70), 4-1BB (CD137), 4-1BBL, CD30L, LIGHT, IL-2R, IL-12R, IL-1R, IL-15R; IFN-gammaR, TNF-alphaR, IL-4R, IL-10R, CD18/CD11a (LFA-1), CD62L (L-selectin), CD29/CD49d (VLA-4), Notch ligand (e.g. Delta-like 1/4, Jagged 1/2, etc.), CCR1, CCR2, CCR3, CCR4, CCR5, CCR7, and CXCR3 or fragment thereof including the corresponding ligands to these macromolecules or fragments thereof. In some embodiments, an agent (e.g. antibody) attached to the bead specifically binds to one or more of the following macromolecules on a cell (e.g. a T cell): CD28, CD62L, CCR7, CD27, CD127, CD3, CD4, CD8, CD45RA, and/or CD45RO.

In some embodiments, one or more of the agents attached to the bead is an antibody. The antibody can include a polyclonal antibody, monoclonal antibody (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')2, and Fv). In some embodiments, the stimulatory reagent is an antibody fragment (including antigen-binding fragment), e.g., a Fab, Fab'-SH, Fv, scFv, or (Fab')2 fragment. It will be appreciated that constant regions of any isotype can be used for the antibodies contemplated herein, including IgG, IgM, IgA, IgD, and IgE constant regions, and that such constant regions can be obtained from any human or animal species (e.g., murine species). In some embodiments, the agent is an antibody that binds to and/or recognizes one or more components of a T cell receptor. In particular embodiments, the agent is an anti-CD3 antibody. In certain embodiments, the agent is an antibody that binds to and/or recognizes a co-receptor. In some embodiments, the stimulatory reagent comprises an anti-CD28 antibody.

In some embodiments, the cells, e.g., cells of the input population, are stimulated or subjected to stimulation in the presence of a ratio of stimulatory reagent to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of stimulatory reagent to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of stimulatory reagent to cells is about 1:1 or is 1:1.

In some embodiments, the cells are stimulated or subjected to stimulation in the presence of, of about, or of at least 0.01 μg, 0.02 μg, 0.03 μg, 0.04 μg, 0.05 μg, 0.1 μg, 0.2 μg, 0.3 μg, 0.4 μg, 0.5 μg, 0.75 μg, 1 μg, 1.2 μg, 1.4 μg, 1.6 μg, 1.8 μg, 2 μg, 3 μg, 4 μg, 5 μg, 6 μg, 7 μg, 8 μg, 9 μg, or 10 μg of the stimulatory reagent per $10^6$ cells. In some embodiments, the cells are stimulated or subjected to stimulation in the presence of or of about 4 μg per $10^6$ cells. In particular embodiments, the cells are stimulated or subjected to stimulation in the presence of or of about 0.8 μg per $10^6$ cells. In various embodiments, the cells are stimulated or subjected to stimulation in the presence of or of about 0.8 μg per $10^6$ cells. In particular embodiments, the cells are stimulated or subjected to stimulation in the presence of or of about 1.2 μg per $10^6$ cells. In particular embodiments, the cells are stimulated or subjected to stimulation in the presence of or of about 1.8 μg per $10^6$ cells.

a. Bead Reagents

In certain embodiments, the stimulatory reagent contains a particle, e.g., a bead, that is conjugated or linked to one or more agents, e.g., biomolecules, that are capable of activating and/or expanding cells, e.g., T cells. In some embodiments, the one or more agents are bound to a bead. In some embodiments, the bead is biocompatible, i.e., composed of a material that is suitable for biological use. In some embodiments, the beads are non-toxic to cultured cells, e.g., cultured T cells. In some embodiments, the beads may be any particles which are capable of attaching agents in a manner that permits an interaction between the agent and a cell.

In some embodiments, the stimulatory reagent contains a bead and one or more agents that directly interact with a macromolecule on the surface of a cell. In certain embodiments, the bead (e.g., a paramagnetic bead) interacts with a cell via one or more agents (e.g., an antibody) specific for one or more macromolecules on the cell (e.g., one or more cell surface proteins). In certain embodiments, the bead (e.g., a paramagnetic bead) is labeled with a first agent described herein, such as a primary antibody (e.g., an anti-biotin antibody) or other biomolecule, and then a second agent, such as a secondary antibody (e.g., a biotinylated anti-CD3 antibody) or other second biomolecule (e.g., streptavidin), is added, whereby the secondary antibody or other second biomolecule specifically binds to such primary antibodies or other biomolecule on the particle.

In some embodiments, the bead has a diameter of greater than about 0.001 μm, greater than about 0.01 μm, greater than about 0.1 μm, greater than about 1.0 μm, greater than about 10 μm, greater than about 50 μm, greater than about 100 μm or greater than about 1000 μm and no more than about 1500 μm. In some embodiments, the bead has a diameter of about 1.0 μm to about 500 μm, about 1.0 μm to about 150 μm, about 1.0 μm to about 30 μm, about 1.0 μm to about 10 μm, about 1.0 μm to about 5.0 μm, about 2.0 μm to about 5.0 μm, or about 3.0 μm to about 5.0 μm. In some embodiments, the bead has a diameter of about 3 μm to about 5 μm. In some embodiments, the bead has a diameter of at least or at least about or about 0.001 μm, 0.01 μm, 0.1 μm, 0.5 μm, 1.0 μm, 1.5 μm, 2.0 μm, 2.5 μm, 3.0μ, 3.5 μm, 4.0 μm, 4.5 μm, 5.0 μm, 5.5 μm, 6.0 μm, 6.5 μm, 7.0 μm, 7.5μ, 8.0 μm, 8.5 μm, 9.0 μm, 9.5 μm, 10 μm, 12 μm, 14 μm, 16 μm, 18 μm or 20 μm. In certain embodiments, the bead has a diameter of or about 4.5 μm. In certain embodiments, the bead has a diameter of or about 2.8 μm.

In some embodiments, the beads have a density of greater than 0.001 $g/cm^3$, greater than 0.01 $g/cm^3$, greater than 0.05 $g/cm^3$, greater than 0.1 $g/cm^3$, greater than 0.5 $g/cm^3$, greater than 0.6 $g/cm^3$, greater than 0.7 $g/cm^3$, greater than 0.8 $g/cm^3$, greater than 0.9 $g/cm^3$, greater than 1 $g/cm^3$, greater than 1.1 $g/cm^3$, greater than 1.2 $g/cm^3$, greater than 1.3 $g/cm^3$, greater than 1.4 $g/cm^3$, greater than 1.5 $g/cm^3$, greater than 2 $g/cm^3$, greater than 3 $g/cm^3$, greater than 4 $g/cm^3$, or greater than 5 $g/cm^3$. In some embodiments, the beads have a density of between about 0.001 $g/cm^3$ and about 100 $g/cm^3$, about 0.01 $g/cm^3$ and about 50 $g/cm^3$, about 0.1 $g/cm^3$ and about 10 $g/cm^3$, about 0.1 $g/cm^3$ and about 0.5 $g/cm^3$, about 0.5 $g/cm^3$ and about 1 $g/cm^3$, about 0.5 $g/cm^3$ and about 1.5 $g/cm^3$, about 1 $g/cm^3$ and about 1.5 $g/cm^3$, about 1 $g/cm^3$ and about 2 $g/cm^3$, or about 1 $g/cm^3$ and about 5 $g/cm^3$. In some embodiments, the beads have a density of about 0.5 $g/cm^3$, about 0.5 $g/cm^3$, about 0.6 $g/cm^3$, about 0.7 $g/cm^3$, about 0.8 $g/cm^3$, about 0.9 $g/cm^3$, about 1.0 $g/cm^3$, about 1.1 $g/cm^3$, about 1.2 $g/cm^3$, about 1.3 $g/cm^3$, about 1.4 $g/cm^3$, about 1.5 $g/cm^3$, about 1.6 $g/cm^3$, about 1.7 $g/cm^3$, about 1.8 $g/cm^3$, about 1.9 $g/cm^3$, or about 2.0 $g/cm^3$. In certain embodiments, the beads have a density of about 1.6 $g/cm^3$. In particular embodiments, the beads or particles have a density of about 1.5 $g/cm^3$. In certain embodiments, the particles have a density of about 1.3 $g/cm^3$ In certain embodiments, a plurality of the beads has a uniform density. In certain embodiments, a uniform density comprises a density standard deviation of less than 10%, less than 5%, or less than 1% of the mean bead density.

In some embodiments, the bead contains at least one material at or near the bead surface that can be coupled, linked, or conjugated to an agent. In some embodiments, the bead is surface functionalized, i.e. comprises functional groups that are capable of forming a covalent bond with a binding molecule, e.g., a polynucleotide or a polypeptide. In particular embodiments, the bead comprises surface-exposed carboxyl, amino, hydroxyl, tosyl, epoxy, and/or chloromethyl groups. In particular embodiments, the beads comprise surface exposed agarose and/or sepharose. In certain embodiments, the bead surface comprises attached stimulatory reagents that can bind or attach binding molecules. In particular embodiments, the biomolecules are polypeptides. In some embodiments, the beads comprise surface exposed protein A, protein G, or biotin.

In some embodiments, the bead reacts in a magnetic field. In some embodiments, the bead is a magnetic bead. In some embodiments, the magnetic bead is paramagnetic. In particular embodiments, the magnetic bead is superparamagnetic. In certain embodiments, the beads do not display any magnetic properties unless they are exposed to a magnetic field.

In particular embodiments, the bead comprises a magnetic core, a paramagnetic core, or a superparamagnetic core. In some embodiments, the magnetic core contains a metal. In some embodiments, the metal can be, but is not limited to, iron, nickel, copper, cobalt, gadolinium, manganese, tantalum, zinc, zirconium or any combinations thereof. In certain embodiments, the magnetic core comprises metal oxides (e.g., iron oxides), ferrites (e.g., manganese ferrites, cobalt ferrites, nickel ferrites, etc.), hematite and metal alloys (e.g., CoTaZn). In some embodiments, the magnetic core comprises one or more of a ferrite, a metal, a metal alloy, an iron oxide, or chromium dioxide. In some embodiments, the magnetic core comprises elemental iron or a compound thereof. In some embodiments, the magnetic core comprises one or more of magnetite (Fe3O4), maghemite (γFe2O3), or greigite (Fe3S4). In some embodiments, the inner core comprises an iron oxide (e.g., $Fe_3O_4$).

In certain embodiments, the bead contains a magnetic, paramagnetic, and/or superparamagnetic core that is covered by a surface functionalized coat or coating. In some embodiments, the coat can contain a material that can include, but is not limited to, a polymer, a polysaccharide, a silica, a fatty acid, a protein, a carbon, agarose, sepharose, or a combination thereof. In some embodiments, the polymer can be a polyethylene glycol, poly (lactic-co-glycolic acid), polyglutaraldehyde, polyurethane, polystyrene, or a polyvinyl alcohol. In certain embodiments, the outer coat or coating comprises polystyrene. In particular embodiments, the outer coating is surface functionalized.

In some embodiments, the stimulatory reagent comprises a bead that contains a metal oxide core (e.g., an iron oxide core) and a coat, wherein the metal oxide core comprises at least one polysaccharide (e.g., dextran), and wherein the coat comprises at least one polysaccharide (e.g., amino dextran), at least one polymer (e.g., polyurethane) and silica. In some embodiments the metal oxide core is a colloidal iron oxide core. In certain embodiments, the one or more agents include an antibody or antigen-binding fragment thereof. In particular embodiments, the one or more agents include an anti-CD3 antibody and an anti-CD28 antibody. In some embodiments, the stimulatory reagent comprises an anti-CD3 antibody, anti-CD28 antibody, and an anti-biotin antibody. In some embodiments, the stimulatory reagent comprises an anti-biotin antibody. In some embodiments, the bead has a diameter of about 3 μm to about 10 μm. In some embodiments, the bead has a diameter of about 3 μm to about 5 μm. In certain embodiments, the bead has a diameter of about 3.5 μm.

In some embodiments, the stimulatory reagent comprises one or more agents that are attached to a bead comprising a metal oxide core (e.g., an iron oxide inner core) and a coat (e.g., a protective coat), wherein the coat comprises polystyrene. In certain embodiments, the beads are monodisperse, paramagnetic (e.g., superparamagnetic) beads comprising a paramagnetic (e.g., superparamagnetic) iron core, e.g., a core comprising magnetite ($Fe_3O_4$) and/or maghemite ($\gamma Fe_2O_3$) c and a polystyrene coat or coating. In some embodiments, the bead is non-porous. In some embodiments, the beads contain a functionalized surface to which the one or more agents are attached. In certain embodiments, the one or more agents are covalently bound to the beads at the surface. In some embodiments, the one or more agents include an antibody or antigen-binding fragment thereof. In some embodiments, the one or more agents include an anti-CD3 antibody and an anti-CD28 antibody. In some embodiments, the one or more agents include an anti-CD3 antibody and/or an anti-CD28 antibody, and an antibody or antigen fragment thereof capable of binding to a labeled antibody (e.g., biotinylated antibody), such as a labeled anti-CD3 or anti-CD28 antibody. In certain embodiments, the beads have a density of about 1.5 $g/cm^3$ and a surface area of about 1 $m^2/g$ to about 4 $m^2/g$. In particular embodiments; the beads are monodisperse superparamagnetic beads that have a diameter of about 4.5 μm and a density of about 1.5 $g/cm^3$. In some embodiments, the beads the beads are monodisperse superparamagnetic beads that have a mean diameter of about 2.8 μm and a density of about 1.3 $g/cm^3$.

In some embodiments, the population of enriched T cells is incubated with stimulatory reagent a ratio of beads to cells at or at about 3:1, 2.5:1, 2:1, 1.5:1, 1.25:1, 1.2:1, 1.1:1, 1:1, 0.9:1, 0.8:1, 0.75:1, 0.67:1, 0.5:1, 0.3:1, or 0.2:1. In particular embodiments, the ratio of beads to cells is between 2.5:1 and 0.2:1, between 2:1 and 0.5:1, between 1.5:1 and 0.75:1, between 1.25:1 and 0.8:1, between 1.1:1 and 0.9:1. In particular embodiments, the ratio of beads to cells is about 1:1 or is 1:1.

b. Oligomeric Streptavidin Mutein Reagents

In particular embodiments, the stimulatory reagent contains an oligomeric reagent, e.g., a streptavidin mutein reagent, that is conjugated, linked, or attached to one or more agent, e.g., ligand, which is capable of activating an intracellular signaling domain of a TCR complex. In some embodiments, the one or more agents have an attached binding domain or binding partner (e.g., a binding partner C) that is capable of binding to oligomeric reagent at a particular binding sites (e.g., binding site Z). In some embodiments, a plurality of the agent is reversibly bound to the oligomeric reagent. In various embodiments, the oligomeric reagent has a plurality of the particular binding sites which, in certain embodiments, are reversibly bound to a plurality of agents at the binding domain (e.g., binding partner C). In some embodiments, the amount of bound agents are reduced or decreased in the presence of a competition reagent, e.g., a reagent that is also capable of binding to the particular binding sites (e.g., binding site Z).

In some embodiments, the stimulatory reagent is or includes a reversible systems in which at least one agent (e.g., an agent that is capable of producing a signal in a cell such as a T cell) is associated, e.g., reversibly associated, with the oligomeric reagent. In some embodiments, the reagent contains a plurality of binding sites capable of binding, e.g., reversibly binding, to the agent. In some cases, the reagent is a oligomeric particle reagent having at least one attached agent capable of producing a signal in a cell such as a T cell. In some embodiments, the agent contains at least one binding site, e.g., a binding site B, that can specifically bind an epitope or region of the molecule and also contains a binding partner, also referred to herein as a binding partner C, that specifically binds to at least one binding site of the reagent, e.g., binding site Z of the reagent. In some embodiments, the binding interaction between the binding partner C and the at least one binding site Z is a non-covalent interaction. In some cases, the binding interaction between the binding partner C and the at least one binding site Z is a covalent interaction. In some embodiments, the binding interaction, such as non-covalent interaction, between the binding partner C and the at least one binding site Z is reversible.

Substances that may be used as oligomeric reagents in such reversible systems are known, see e.g., U.S. Pat. Nos. 5,168,049; 5,506,121; 6,103,493; 7,776,562; 7,981,632; 8,298,782; 8,735,540; 9,023,604; and International published PCT Appl. Nos. WO2013/124474 and WO2014/076277. Non-limiting examples of reagents and binding partners capable of forming a reversible interaction, as well as substances (e.g. competition reagents) capable of reversing such binding, are described below.

In some embodiments, the oligomeric reagent is an oligomer of streptavidin, streptavidin mutein or analog, avidin, an avidin mutein or analog (such as neutravidin) or a mixture thereof, in which such oligomeric reagent contains one or more binding sites for reversible association with the binding domain of the agent (e.g., a binding partner C). In some embodiments, the binding domain of the agent can be a biotin, a biotin derivative or analog, or a streptavidin-binding peptide or other molecule that is able to specifically bind to streptavidin, a streptavidin mutein or analog, avidin or an avidin mutein or analog.

In certain embodiments, one or more agents (e.g., agents that are capable of producing a signal in a cell such as a T cell) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent.

In some embodiments, the oligomeric reagent is a streptavidin oligomer, a streptavidin mutein oligomer, a streptavidin analog oligomer, an avidin oligomer, an oligomer composed of avidin mutein or avidin analog (such as neutravidin) or a mixture thereof. In particular embodiments, the oligomeric reagents contain particular binding sites that are capable of binding to a binding domain (e.g., the binding partner C) of an agent. In some embodiments, the binding domain can be a biotin, a biotin derivative or analog, or a streptavidin-binding peptide or other molecule that is able to specifically bind to streptavidin, a streptavidin mutein or analog, avidin or an avidin mutein or analog. In some embodiments, the streptavidin can be wild-type streptavidin, streptavidin muteins or analogs, such as streptavidin-like polypeptides. Likewise, avidin, in some aspects, includes wild-type avidin or muteins or analogs of avidin such as neutravidin, a deglycosylated avidin with modified arginines that typically exhibits a more neutral pi and is available as an alternative to native avidin. Generally, deglycosylated, neutral forms of avidin include those commercially available forms such as "Extravidin", available through Sigma Aldrich, or "NeutrAvidin" available from Thermo Scientific or Invitrogen, for example In some embodiments, the reagent is a streptavidin or a streptavidin mutein or analog. In some embodiments, wild-type streptavidin (wt-streptavidin) has the amino acid sequence disclosed by Argarana et al, Nucleic Acids Res. 14 (1986) 1871-1882 (SEQ ID NO: 61). In general, streptavidin naturally occurs as a tetramer of four identical subunits, i.e. it is a homo-tetramer, where each subunit contains a single binding site for biotin, a biotin derivative or analog or a biotin mimic. An exemplary sequence of a streptavidin subunit is the sequence of amino acids set forth in SEQ ID NO: 61, but such a sequence also can include a sequence present in homologs thereof from other *Streptomyces* species. In particular, each subunit of streptavidin may exhibit a strong binding affinity for biotin with a dissociation constant ($K_d$) on the order of about $10^{-14}$ M. In some cases, streptavidin can exist as a monovalent tetramer in which only one of the four binding sites is functional (Howarth et al. (2006) Nat. Methods, 3:267-73; Zhang et al. (2015) Biochem. Biophys. Res. Commun., 463:1059-63)), a divalent tetramer in which two of the four binding sites are functional (Fairhead et al. (2013) J. Mol. Biol., 426:199-214), or can be present in monomeric or dimeric form (Wu et al. (2005) J. Biol. Chem., 280:23225-31; Lim et al. (2010) Biochemistry, 50:8682-91).

In some embodiments, streptavidin may be in any form, such as wild-type or unmodified streptavidin, such as a streptavidin from a *Streptomyces* species or a functionally active fragment thereof that includes at least one functional subunit containing a binding site for biotin, a biotin derivative or analog or a biotin mimic, such as generally contains at least one functional subunit of a wild-type streptavidin from *Streptomyces avidinii* set forth in SEQ ID NO: 61 or a functionally active fragment thereof. For example, in some embodiments, streptavidin can include a fragment of wild-type streptavidin, which is shortened at the N- and/or C-terminus. Such minimal streptavidins include any that begin N-terminally in the region of amino acid positions 10 to 16 of SEQ ID NO: 61 and terminate C-terminally in the region of amino acid positions 133 to 142 of SEQ ID NO:

61. In some embodiments, a functionally active fragment of streptavidin contains the sequence of amino acids set forth in SEQ ID NO: 62. In some embodiments, streptavidin, such as set forth in SEQ ID NO: 62, can further contain an N-terminal methionine at a position corresponding to Ala13 with numbering set forth in SEQ ID NO: 61. Reference to the position of residues in streptavidin or streptavidin muteins is with reference to numbering of residues in SEQ ID NO: 61.

Examples of streptavidins or streptavidin muteins are mentioned, for example, in WO 86/02077, DE 19641876 A1, U.S. Pat. No. 6,022,951, WO 98/40396 or WO 96/24606. Examples of streptavidin muteins are known in the art, see e.g., U.S. Pat. Nos. 5,168,049; 5,506,121; 6,022,951; 6,156,493; 6,165,750; 6,103,493; or 6,368,813; or International published PCT App. No. WO2014/076277.

In some embodiments, a streptavidin mutein can contain amino acids that are not part of an unmodified or wild-type streptavidin or can include only a part of a wild-type or unmodified streptavidin. In some embodiments, a streptavidin mutein contains at least one subunit that can have one more amino acid substitutions (replacements) compared to a subunit of an unmodified or wild-type streptavidin, such as compared to the wild-type streptavidin subunit set forth in SEQ ID NO: 61 or a functionally active fragment thereof, e.g. set forth in SEQ ID NO: 62.

In some embodiments, the binding affinity, such as dissociation constant ($K_d$), of streptavidin or a streptavidin mutein for a binding domain is less than $1\times10^{-4}$M, $5\times10^{-4}$ M, $1\times10^{-5}$ M, $5\times10^{-5}$ M, $1\times10^{-6}$ M, $5\times10^{-6}$ M or $1\times10^{-7}$ M, but generally greater than $1\times10^{-13}$ M, $1\times10^{-12}$ M or $1\times10^{-11}$ M. For example, peptide sequences (e.g., Strep-tags), such as disclosed in U.S. Pat. No. 5,506,121, can act as biotin mimics and demonstrate a binding affinity for streptavidin, e.g., with a $K_d$ of approximately between $10^{-4}$ and $10^{-5}$ M. In some cases, the binding affinity can be further improved by making a mutation within the streptavidin molecule, see e.g. U.S. Pat. No. 6,103,493 or WO2014/076277. In some embodiments, binding affinity can be determined by methods known in the art, such as any described herein.

In some embodiments, the reagent, such as a streptavidin or streptavidin mutein, exhibits binding affinity for a peptide ligand binding partner, which peptide ligand binding partner can be the binding partner C present in the agent (e.g., receptor-binding agent or selection agent). In some embodiments, the peptide sequence contains a sequence with the general formula His-Pro-Xaa, where Xaa is glutamine, asparagine, or methionine, such as contains the sequence set forth in SEQ ID NO: 78. In some embodiments, the peptide sequence contains a sequence set forth in SEQ ID NO: 93. In some embodiments, the peptide sequence has the general formula set forth in SEQ ID NO: 79, such as set forth in SEQ ID NO: 69. In one example, the peptide sequence is Trp-Arg-His-Pro-Gln-Phe-Gly-Gly (also called Strep-Tag®, set forth in SEQ ID NO: 70). In one example, the peptide sequence is Trp-Ser-His-Pro-Gln-Phe-Glu-Lys (also called Strep-Tag® II, set forth in SEQ ID NO: 64). In some embodiments, the peptide ligand contains a sequential arrangement of at least two streptavidin-binding modules, wherein the distance between the two modules is at least 0 and not greater than 50 amino acids, wherein one binding module has 3 to 8 amino acids and contains at least the sequence His-Pro-Xaa, where Xaa is glutamine, asparagine, or methionine, and wherein the other binding module has the same or different streptavidin peptide ligand, such as set forth in SEQ ID NO: 79 (see e.g. International Published PCT Appl. No. WO02/077018; U.S. Pat. No. 7,981,632). In some embodiments, the peptide ligand contains a sequence having the formula set forth in any of SEQ ID NO: 71 or 72. In some embodiments, the peptide ligand has the sequence of amino acids set forth in any of SEQ ID NOS: 65-67, 73-74. In most cases, all these streptavidin binding peptides bind to the same binding site, namely the biotin binding site of streptavidin. If one or more of such streptavidin binding peptides is used as binding partners C, e.g. C1 and C2, the multimerization reagent and/or oligomeric particle reagents bound to the one or more agents via the binding partner C is typically composed of one or more streptavidin muteins.

In some embodiments, the streptavidin mutein is a mutant as described in U.S. Pat. No. 6,103,493. In some embodiments, the streptavidin mutein contains at least one mutation within the region of amino acid positions 44 to 53, based on the amino acid sequence of wild-type streptavidin, such as set forth in SEQ ID NO: 61. In some embodiments, the streptavidin mutein contains a mutation at one or more residues 44, 45, 46, and/or 47. In some embodiments, the streptavidin mutein contains a replacement of Glu at position 44 of wild-type streptavidin with a hydrophobic aliphatic amino acid, e.g. Val, Ala, Ile or Leu, any amino acid at position 45, an aliphatic amino acid, such as a hydrophobic aliphatic amino acid at position 46 and/or a replacement of Val at position 47 with a basic amino acid, e.g. Arg or Lys, such as generally Arg. In some embodiments, Ala is at position 46 and/or Arg is at position 47 and/or Val or Ile is at position 44. In some embodiments, the streptavidin mutant contains residues Val44-Thr45-Ala46-Arg47, such as set forth in exemplary streptavidin muteins containing the sequence of amino acids set forth in SEQ ID NO: 75 or SEQ ID NO: 76 or 77 (also known as streptavidin mutant 1, SAM1). In some embodiments, the streptavidin mutein contains residues Ile44-Gly45-Ala46-Arg47, such as set forth in exemplary streptavidin muteins containing the sequence of amino acids set forth in SEQ ID NO: 80, 63, or 68 (also known as SAM2). In some cases, such streptavidin mutein are described, for example, in U.S. Pat. No. 6,103,493, and are commercially available under the trademark Strep-Tactin®. In some embodiments, the mutein streptavidin contains the sequence of amino acids set forth in SEQ ID NO: 81 or SEQ ID NO: 82. In particular embodiments, the molecule is a tetramer of streptavidin or a streptavidin mutein comprising a sequence set forth in any of SEQ ID NOS: 62, 76, 63, 81, 83, 77 or 68, which, as a tetramer, is a molecule that contains 20 primary amines, including 1 N-terminal amine and 4 lysines per monomer.

In some embodiments, streptavidin mutein exhibits a binding affinity characterized by a dissociation constant ($K_d$) that is or is less than $3.7\times10^{-5}$ M for the peptide ligand (Trp-Arg-His-Pro-Gln-Phe-Gly-Gly; also called Strep-Tag®, set forth in SEQ ID NO: 70) and/or that is or is less than $7.1\times10^{-5}$ M for the peptide ligand (Trp-Ser-His-Pro-Gln-Phe-Glu-Lys; also called Strep-Tag® II, set forth in SEQ ID NO: 64) and/or that is or is less than $7.0\times10^{-5}$ M, $5.0\times10^{-5}$ M, $1.0\times10^{-5}$ M, $5.0\times10^{-6}$ M, $1.0\times10^{-6}$ M, $5.0\times10^{-7}$ M, or $1.0\times10^{-7}$ M, but generally greater than $1\times10^{-13}$ M, $1\times10^{-12}$ M or $1\times10^{-11}$ M for any of the peptide ligands set forth in any of SEQ ID NOS: 64, 71-74, 65-67, 69, 70, 78, 79.

In some embodiments, the resulting streptavidin mutein exhibits a binding affinity characterized by an association constant ($K_a$) that is or is greater than $2.7\times10^{4}$ $M^{-1}$ for the peptide ligand (Trp-Arg-His-Pro-Gln-Phe-Gly-Gly; also called Strep-Tag®, set forth in SEQ ID NO: 70) and/or that is or is greater than $1.4\times10^{4}$ $M^{-1}$ for the peptide ligand (Trp-Ser-His-Pro-Gln-Phe-Glu-Lys; also called Strep-Tag®

II, set forth in SEQ ID NO: 64) and/or that is or is greater than $1.43\times10^4$ $M^{-1}$, $1.67\times10^4$ $M^{-1}$, $2\times10^4$ $M^{-1}$, $3.33\times10^4$ $M^{-1}$, $5\times10^4$ $M^{-1}$, $1\times10^5$ $M^{-1}$, $1.11\times10^5$ $M^{-1}$, $1.25\times10^5$ $M^{-1}$, $1.43\times10^5$ $M^{-1}$, $1.67\times10^5$ $M^{-1}$, $2\times10^5$ $M^{-1}$, $3.33\times10^5$ $M^{-1}$, $5\times10^5$ $M^{-1}$, $1\times10^6$ $M^{-1}$, $1.11\times10^6$ $M^{-1}$, $1.25\times10^6$ $M^{-1}$, $1.43\times10^6$ $M^{-1}$, $1.67\times10^6$ $M^{-1}$, $2\times10^6$ $M^{-1}$, $3.33\times10^6$ $M^{-1}$, $5\times10^6$ $M^{-1}$, $1\times10^7$ $M^{-1}$, but generally less than $1\times10^{13}$ $M^{-1}$, $1\times10^{12}$ $M^{-1}$ or $1\times10^{11}$ $M^{-1}$ for any of the peptide ligands set forth in any of SEQ ID NOS: 64, 71-74, 65-67, 69, 70, 78, 79.

In particular embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 70 nm and 125 nm, inclusive; a molecular weight of between $1\times10^7$ g/mol and $1\times10^9$ g/mol, inclusive; and/or between 1,000 and 5,000 streptavidin or streptavidin mutein tetramers, inclusive. In some embodiments, the oligomeric particle reagent is bound, e.g., reversibly bound, to one or more agents such as an agent that binds to a molecule, e.g. receptor, on the surface of a cell. In certain embodiments, the one or more agents are agents described herein, e.g., in Section I-B-1-a. In some embodiments, the agent is an anti-CD3 and/or an anti-CD28 antibody or antigen binding fragment thereof, such as an antibody or antigen fragment thereof that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II. In particular embodiments, the one or more agents comprise a streptavidin-based oligomer, such as a streptavidin mutein oligomer, conjugated to Strep-tagged anti-CD3 and Strep-tagged anti-CD28 Fabs. In some embodiments, the oligomeric particle reagent is any as described in WO2015/158868 or WO2018/197949.

In some embodiments, provided herein is an oligomeric particle reagent that is composed of and/or contains a plurality of streptavidin or streptavidin mutein tetramers. In certain embodiments, the oligomeric particle reagent provided herein contains a plurality of binding sites that reversibly bind or are capable of reversibly binding to one or more agents, e.g., a stimulatory agent and/or a selection agent. In some embodiments, the oligomeric particle has a radius, e.g., an average radius, of between 80 nm and 120 nm, inclusive; a molecular weight, e.g., an average molecular weight of between $7.5\times10^6$ g/mol and $2\times10^8$ g/mol, inclusive; and/or an amount, e.g., an average amount, of between 500 and 10,000 streptavidin or streptavidin mutein tetramers, inclusive. In some embodiments, the oligomeric particle reagent is bound, e.g., reversibly bound, to one or more agents, such as an agent that binds to a molecule, e.g. receptor, on the surface of a cell. In certain embodiments, the one or more agents are agents described herein, e.g., in Section I-B-1-a. In some embodiments, the agent is an anti-CD3 and/or an anti-CD28 Fab, such as a Fab that contains a binding partner, e.g., a streptavidin binding peptide, e.g. Strep-Tag® II. In particular embodiments, the one or more agents is an anti-CD3 and/or an anti CD28 Fab containing a binding partner, e.g., a streptavidin binding peptide, e.g. Strep-Tag® II.

In some embodiments, the cells are stimulated or subjected to stimulation in the presence of, of about, or of at least 0.01 μg, 0.02 μg, 0.03 μg, 0.04 μg, 0.05 μg, 0.1 μg, 0.2 μg, 0.3 μg, 0.4 μg, 0.5 μg, 0.75 μg, 1 μg, 1.2 μg, 1.4 μg, 1.6 μg, 1.8 μg, 2 μg, 3 μg, 4 μg, 5 μg, 6 μg, 7 μg, 8 μg, 9 μg, or 10 μg of the oligomeric stimulatory reagent (e.g., the streptavidin-based oligomer, such as a streptavidin mutein oligomer, conjugated to Strep-tagged anti-CD3 and Strep-tagged anti-CD28 Fabs) per $10^6$ cells. In some embodiments, the cells are stimulated or subjected to stimulation in the presence of or of about 4 μg of the oligomeric stimulatory reagent (e.g., the streptavidin-based oligomer, such as a such as a streptavidin mutein oligomer, conjugated to Strep-tagged anti-CD3 and Strep-tagged anti-CD28 Fabs) per $10^6$ cells. In particular embodiments, the cells are stimulated or subjected to stimulation in the presence of or of about 1.2 μg of the oligomeric stimulatory reagent (e.g., the streptavidin-based oligomer, such as a streptavidin mutein oligomer, conjugated to Strep-tagged anti-CD3 and Strep-tagged anti-CD28 Fabs) per $10^6$ cells. In particular embodiments, the cells are stimulated or subjected to stimulation in the presence of or of about 0.8 μg of the oligomeric stimulatory reagent (e.g., the streptavidin-based oligomer, such as a streptavidin mutein oligomer, conjugated to Strep-tagged anti-CD3 and Strep-tagged anti-CD28 Fabs) per $10^6$ cells. In particular embodiments, the cells are stimulated or subjected to stimulation in the presence of or of about 1.8 μg of the oligomeric stimulatory reagent (e.g., the streptavidin-based oligomer, such as a streptavidin mutein oligomer, conjugated to Strep-tagged anti-CD3 and Strep-tagged anti-CD28 Fabs) per $10^6$ cells. In certain aspects, within the oligomeric stimulatory reagent, the mass ratio between the oligomeric particles and the attached agents is about 3:1. In certain aspects, within the oligomeric stimulatory reagent, the mass ratio among the oligomeric particles, the attached anti-CD3 Fabs, and the attached anti-CD28 Fabs is about 3:0.5:0.5. In certain aspects, 4 μg of the oligomeric stimulatory reagent is or includes 3 μg of oligomeric particles and 1 μg of attached agents, e.g., 0.5 μg of anti-CD3 Fabs and 0.5 μg of anti-CD28 Fabs. In other examples, 1.2 μg of the oligomeric stimulatory reagent per $10^6$ cells is or includes 0.9 μg of oligomeric particles and 0.3 μg of attached agents, e.g., 0.15 μg of anti-CD3 Fabs and 0.15 μg of anti-CD28 Fabs, per $10^6$ cells. In some embodiments, the oligomeric stimulatory reagent is added to a serum-free medium and the stimulation is performed in the serum free medium, e.g., as described herein in Section II or in PCT/US2018/064627.

In particular embodiments, an amount of or of about $900\times10^6$ T cells (e.g., $900\times10^6$ CD3+ T cells, or $450\times10^6$ CD4+ T cells and $450\times10^6$ CD8+ T cells) of the input population are subjected to stimulation, e.g., cultured under stimulating conditions, in the presence of the oligomeric stimulatory reagent (e.g., the streptavidin-based oligomer, such as a streptavidin mutein oligomer, conjugated to Strep-tagged anti-CD3 and Strep-tagged anti-CD28 Fabs). In certain embodiments, the cells, e.g., cells of the input population, are stimulated or subjected to stimulation e.g., cultured under stimulating conditions such as in the presence of a stimulatory reagent, at a density of, of about, or at least $0.01\times10^6$ cells/mL, $0.1\times10^6$ cells/mL, $0.5\times10^6$ cells/mL, $1.0\times10^6$ cells/mL, $1.5\times10^6$ cells/mL, $2.0\times10^6$ cells/mL, $2.5\times10^6$ cells/mL, $3.0\times10^6$ cells/mL, $4.0\times10^6$ cells/mL, $5.0\times10^6$ cells/mL, $10\times10^6$ cells/mL, or $50\times10^6$ cells/mL. In certain embodiments, the cells, e.g., cells of the input population, are stimulated or subjected to stimulation e.g., cultured under stimulating conditions such as in the presence of a stimulatory reagent, at a density of, of about, or at least $3.0\times10^6$ cells/mL.

In some embodiments, the serum-free medium comprises a basal medium (e.g.OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4 (1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2 (e.g., 100 IU/mL), recombinant human IL-7 (e.g., 600 IU/mL), and/or recombinant human IL-15 (e.g., 100 IU/mL).

C. Genetic Engineering

In some embodiments, the provided methods include genetically engineering the cells, e.g., introducing a heterologous or recombinant polynucleotide encoding a recombinant protein. Such recombinant proteins may include recombinant receptors, such as any described in Section III. Any method of introducing a heterologous or recombinant polynucleotide that would result in integration of the polynucleotide encoding the recombinant receptor into the genome of a cell such as a T cell may be used, including viral and non-viral methods of genetic engineering. Introduction of the polynucleotides, e.g., heterologous or recombinant polynucleotides, encoding the recombinant protein into the cell may be carried out using any of a number of known vectors. Such vectors include viral, including lentiviral and gammaretroviral, systems. Exemplary methods include those for transfer of heterologous polynucleotides encoding the receptors, including via viral, e.g., retroviral or lentiviral, transduction. In some embodiments, a population of stimulated cells is genetically engineered, such as to introduce a heterologous or recombinant polynucleotide encoding a recombinant receptor, thereby generating a population of transformed cells (also referred to herein as a transformed population of cells).

In some embodiments, the provided methods include genetically engineering the cells, e.g., introducing a heterologous or recombinant polynucleotide encoding a recombinant protein, using a non-viral method, such as electroporation, calcium phosphate transfection, protoplast fusion, cationic liposome-mediated transfection, nanoparticles such as lipid nanoparticles, tungsten particle-facilitated microparticle bombardment, strontium phosphate DNA co-precipitation, and other approaches described in, e.g., WO 2014055668, and U.S. Pat. No. 7,446,190. Transposon-based systems also are contemplated.

In particular embodiments, the cells are genetically engineered, transformed, or transduced after the cells have been stimulated, activated, and/or incubated under stimulating conditions, such as by any of the methods provided herein, e.g., in Section I-B. In particular embodiments, the one or more stimulated populations have been previously cryoprotected and stored, and are thawed and optionally washed prior to genetically engineering, transforming, transfecting, or transducing the cells.

In particular embodiments, the cells are genetically engineered, transformed, or transduced after the cells are stimulated or subjected to stimulation or cultured under stimulatory conditions. In particular embodiments, the cells are genetically engineered, transformed, or transduced at, at about, or within 72 hours, 60 hours, 48 hours, 36 hours, 24 hours, or 12 hours, inclusive, from the initiation of the stimulation. In particular embodiments, the cells are genetically engineered, transformed, or transduced at, at about, or within 3 days, two days, or one day, inclusive, from the initiation of the stimulation. In certain embodiments, the cells are genetically engineered, transformed, or transduced between or between about 12 hours and 48 hours, 16 hours and 36 hours, or 18 hours and 30 hours after the initiation of the stimulation. In particular embodiments, the cells are genetically engineered, transformed, or transduced between or between about 18 hours and 30 hours after the initiation of the stimulation. In particular embodiments, the cells are genetically engineered, transformed, or transduced at or at about 16 hours, 18 hours, 20 hours, 22 hours, or 24 hours after the initiation of the stimulation.

In certain embodiments, methods for genetic engineering are carried out by contacting or introducing one or more cells of a population with a nucleic acid molecule or polynucleotide encoding the recombinant protein, e.g. a recombinant receptor. In certain embodiments, the nucleic acid molecule or polynucleotide is heterologous to the cells. In particular embodiments, heterologous nucleic acid molecule or heterologous polynucleotide is not native to the cells. In certain embodiments, the heterologous nucleic acid molecule or heterologous polynucleotide encodes a protein, e.g., a recombinant protein, that is not natively expressed by the cell. In particular embodiments, the heterologous nucleic acid molecule or polynucleotide is or contains a nucleic acid sequence that is not found in the cell prior to the contact or introduction.

In some embodiments, the cells, e.g., stimulated cells, are engineered, e.g., transduced or in the presence of a transduction adjuvant. Exemplary transduction adjuvants include, but are not limited to, polycations, fibronectin or fibronectin-derived fragments or variants, and RetroNectin. In certain embodiments, the cells are engineered in the presence of polycations, fibronectin or fibronectin-derived fragments or variants, and/or RetroNectin. In particular embodiments, the cells are engineered in the presence of a polycation that is polybrene, DEAE-dextran, protamine sulfate, poly-L-lysine, or a cationic liposome. In particular embodiments, the cells are engineered in the presence of protamine sulfate. In some embodiments, the presence of an oligomeric stimulatory reagent, e.g., as described in Section I-B-1 can act as a transduction adjuvant, see, e.g., WO/2017/068419 which is incorporated herein by reference.

In some embodiments, the genetic engineering, e.g., transduction, is carried out in serum free media, e.g, as described herein in Section II or in PCT/US2018/064627. In some embodiments, the serum free media is a defined or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In particular embodiments, the cells are engineered in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In particular embodiments, cells, e.g., stimulated cells are engineered under stimulating conditions in the presence of IL-2, IL-7, and/or IL-15. In certain embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are engineered, e.g., transduced or under stimulating conditions in the presence of recombinant IL-2, IL-7, and IL-15, such as recombinant human IL-2 (e.g., 100 IU/mL), recombinant human IL-7 (e.g., 600 IU/mL), and/or recombinant human IL-15 (e.g., 100 IU/mL).

In some embodiments, the cells are genetically engineered, transformed, or transduced in the presence of the same or similar media as was present during the stimulation. In some embodiments, the cells are genetically engineered, transformed, or transduced in media having the same cytokines as the media present during stimulation. In certain embodiments, the cells are genetically engineered, transformed, or transduced, in media having the same cytokines at the same concentrations as the media present during stimulation.

1. Transduction

In some embodiments, genetically engineering the cells is or includes introducing the polynucleotide, e.g., the heterologous or recombinant polynucleotide, into the cells by transduction. In some embodiments, the cells are transduced or subjected to transduction with a viral vector. In particular embodiments, the cells are transduced or subjected to transduction with a viral vector. In some embodiments, the virus is a retroviral vector, such as a gammaretroviral vector or a lentiviral vector. Methods of lentiviral transduction are known. Exemplary methods are described in, e.g., Wang et al. (2012) J. Immunother. 35 (9): 689-701; Cooper et al. (2003) Blood. 101:1637-1644; Verhoeyen et al. (2009) Methods Mol Biol. 506:97-114; and Cavalieri et al. (2003) Blood. 102 (2): 497-505.

In some embodiments, the transduction is carried out by contacting one or more cells of a population with a nucleic acid molecule encoding the recombinant protein, e.g. recombinant receptor. In some embodiments, the contacting can be effected with centrifugation, such as spinoculation (e.g. centrifugal inoculation). Such methods include any of those as described in International Publication Number WO2016/073602. Exemplary centrifugal chambers include those produced and sold by Biosafe SA, including those for use with the Sepax® and Sepax® 2 system, including an A-200/F and A-200 centrifugal chambers and various kits for use with such systems. Exemplary chambers, systems, and processing instrumentation and cabinets are described, for example, in U.S. Pat. Nos. 6,123,655, 6,733,433 and Published U.S. Patent Application, Publication No.: US 2008/0171951, and published international patent application, publication no. WO 00/38762, the contents of each of which are incorporated herein by reference in their entirety. Exemplary kits for use with such systems include, but are not limited to, single-use kits sold by BioSafe SA under product names CS-430.1, CS-490.1, CS-600.1 or CS-900.2.

In particular embodiments, an amount of, of about, or of at least $50\times10^6$, $100\times10^6$, $150\times10^6$, $200\times10^6$, $250\times10^6$, $300\times10^6$, $350\times10^6$, $400\times10^6$, $450\times10^6$, $500\times10^6$, $550\times10^6$, $600\times10^6$, $700\times10^6$, $800\times10^6$, $900\times10^6$, or $1,000\times10^6$ cells of the composition that has been subjected to stimulation, e.g., cultured under stimulating conditions, are subjected to genetic engineering, e.g., transduction. In particular embodiments, the total number of cells, e.g., viable T cells comprising both CD4+ T cells and CD8+ T cells, that have been subjected to stimulation and are subsequently subjected to transduction is at or about $50\times10^6$ cells, at or about $100\times10^6$ cells, at or about $150\times10^6$ cells, at or about $200\times10^6$ cells, at or about $250\times10^6$ cells, at or about $300\times10^6$ cells, at or about $350\times10^6$ cells, at or about $400\times10^6$ cells, at or about $450\times10^6$ cells, at or about $500\times10^6$ cells, at or about $550\times10^6$ cells, at or about $600\times10^6$ cells, at or about $700\times10^6$ cells, at or about $800\times10^6$ cells, at or about $900\times10^6$ cells, or at or about $1,000\times10^6$ cells, or any value between any of the foregoing. In particular embodiments, up to $900\times10^6$ cells of the input population are subjected to stimulation, and an amount of, of about, or up to $600\times10^6$ cells of the cells that have been subjected to stimulation are subjected to genetic engineering, e.g., transduction. In particular embodiments, the cell composition subjected to genetic engineering, e.g., transduction, comprises viable CD4+ T cells and viable CD8+ T cells, at a ratio of between 1:10 and 10:1, between 1:5 and 5:1, between 4:1 and 1:4, between 1:3 and 3:1, between 2:1 and 1:2, between 1.5:1 and 1:1.5, between 1.25:1 and 1:1.25, between 1.2:1 and 1:1.2, between 1.1:1 and 1:1.1, or about 1:1, or 1:1 viable CD4+ T cells to viable CD8+ T cells.

In some embodiments, the provided methods are used in connection with transducing a viral vector containing a polynucleotide encoding a recombinant receptor into, into about, or into less than $300\times10^6$ cells, e.g., viable T cells of a stimulated cell population. In certain embodiments, at or about $100\times10^6$ cells, e.g., viable T cells of a stimulated cell population are transduced or subjected to transduction.

In some embodiments, the provided methods are used in connection with transducing a viral vector containing a polynucleotide encoding a recombinant receptor into, into about, or into less than $600\times10^6$ cells, e.g., viable T cells of a stimulated cell population. In certain embodiments, at or about $600\times10^6$ cells, e.g., viable T cells of a stimulated cell population are transduced or subjected to transduction. In some embodiments, up to $900\times10^6$ cells (e.g., viable CD3+ cells or mixed viable CD4+ and viable CD8+ cells (e.g., mixed at or at about a 1:1 ratio)) are subjected to stimulation, and an amount of, of about, or up to $600\times10^6$ cells of the cells that have been subjected to stimulation are subjected to transduction.

In some embodiments, the transduction is performed in serum free media. In some embodiments, the transduction is performed in the presence of IL-2, IL-7, and IL-15. In some embodiments, the viral vector for transduction is frozen and thawed prior to use, and the thawed viral vector is diluted with serum free media. In some embodiments, the serum free media for diluting the viral vector and for transduction are as described herein in Section II or in PCT/US2018/064627.

In some embodiments, the serum-free medium comprises a basal medium (e.g.OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with one or more additional components for the maintenance, expansion, and/or activation of a cell (e.g., a T cell), such as provided by an additional supplement (e.g. OpTmizer™ T-Cell Expansion Supplement (ThermoFisher)). In some embodiments, the serum-free medium further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4 (1): c31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free medium further comprises one or more recombinant cytokines, such as recombinant human IL-2, recombinant human IL-7, and/or recombinant human IL-15.

In particular embodiments, the cells, e.g., the cells of the stimulated cell population contain at least 80%, at least 85%, at least 90%, or at least 95% cells that are CD4+ T cells or CD8+ T cells. In some embodiments, the transduction, including post-transduction incubation, is performed for between 24 and 48 hours, between 36 and 12 hours, between 18 and 30 hours, or for or for about 24 hours. In some embodiments, the transduction, including post-transduction incubation, is performed for or for about 24 hours, 48 hours, or 72 hours, or for or for about 1 day, 2 days, or 3 days, respectively. In particular embodiments, the transduction, including post-transduction incubation, is performed for or for about 24 hours±6 hours, 48 hours±6 hours, or 72 hours±6 hours. In particular embodiments, the transduction, including post-transduction incubation, is performed for or for about 72 hours, 72±4 hours, or for or for about 3 days.

In certain embodiments, the transduction step is initiated within two days, within 36 hours, within 30 hours, within 24 hours, within 18 hours, within 16 hours, within 14 hours, or within 12 hours of the start or initiation of the incubation, e.g., the incubation under stimulating conditions. In certain embodiments, the transduction step is initiated at about 20 hours of the start or initiation of the incubation, e.g., the incubation under stimulating conditions. In certain embodiments, the transduction step is initiated at 20±4 hours of the start or initiation of the incubation, e.g., the incubation under stimulating conditions.

In some embodiments, the system is included with and/or placed into association with other instrumentation, including instrumentation to operate, automate, control and/or monitor aspects of the transduction step and one or more various other processing steps performed in the system, e.g. one or more processing steps that can be carried out with or in connection with the centrifugal chamber system as described herein or in International Publication Number WO2016/073602. This instrumentation in some embodiments is contained within a cabinet. In some embodiments, the instrumentation includes a cabinet, which includes a housing containing control circuitry, a centrifuge, a cover, motors, pumps, sensors, displays, and a user interface. An exemplary device is described in U.S. Pat. Nos. 6,123,655, 6,733,433 and US 2008/0171951.

In some embodiments, the system comprises a series of containers, e.g., bags, tubing, stopcocks, clamps, connectors, and a centrifuge chamber. In some embodiments, the containers, such as bags, include one or more containers, such as bags, containing the cells to be transduced and the viral vector particles, in the same container or separate containers, such as the same bag or separate bags. In some embodiments, the system further includes one or more containers, such as bags, containing medium, such as diluent and/or wash solution, which is pulled into the chamber and/or other components to dilute, resuspend, and/or wash components and/or populations during the methods. The containers can be connected at one or more positions in the system, such as at a position corresponding to an input line, diluent line, wash line, waste line and/or output line.

In some embodiments, the chamber is associated with a centrifuge, which is capable of effecting rotation of the chamber, such as around its axis of rotation. Rotation may occur before, during, and/or after the incubation in connection with transduction of the cells and/or in one or more of the other processing steps. Thus, in some embodiments, one or more of the various processing steps is carried out under rotation, e.g., at a particular force. The chamber is typically capable of vertical or generally vertical rotation, such that the chamber sits vertically during centrifugation and the side wall and axis are vertical or generally vertical, with the end wall(s) horizontal or generally horizontal.

In some embodiments, the population containing cells and population containing viral vector particles, and optionally air, can be combined or mixed prior to providing the populations to the cavity. In some embodiments, the population containing cells and population containing viral vector particles, and optionally air, are provided separately and combined and mixed in the cavity. In some embodiments, a population containing cells, a population containing viral vector particles, and optionally air, can be provided to the internal cavity in any order. In any of such some embodiments, a population containing cells and viral vector particles is the input population once combined or mixed together, whether such is combined or mixed inside or outside the centrifugal chamber and/or whether cells and viral vector particles are provided to the centrifugal chamber together or separately, such as simultaneously or sequentially.

In some embodiments, intake of the volume of gas, such as air, occurs prior to the incubating the cells and viral vector particles, such as rotation, in the transduction method. In some embodiments, intake of the volume of gas, such as air, occurs during the incubation of the cells and viral vector particles, such as rotation, in the transduction method.

In some embodiments, the liquid volume of the cells or viral vector particles that make up the transduction population, and optionally the volume of air, can be a predetermined volume. The volume can be a volume that is programmed into and/or controlled by circuitry associated with the system.

In some embodiments, intake of the transduction population, and optionally gas, such as air, is controlled manually, semi-automatically and/or automatically until a desired or predetermined volume has been taken into the internal cavity of the chamber. In some embodiments, a sensor associated with the system can detect liquid and/or gas flowing to and from the centrifuge chamber, such as via its color, flow rate and/or density, and can communicate with associated circuitry to stop or continue the intake as necessary until intake of such desired or predetermined volume has been achieved. In some aspects, a sensor that is programmed or able only to detect liquid in the system, but not gas (e.g. air), can be made able to permit passage of gas, such as air, into the system without stopping intake. In some such embodiments, a non-clear piece of tubing can be placed in the line near the sensor while intake of gas, such as air, is desired. In some embodiments, intake of gas, such as air, can be controlled manually.

In aspects of the provided methods, the internal cavity of the centrifuge chamber is subjected to high speed rotation. In some embodiments, rotation is effected prior to, simultaneously, subsequently or intermittently with intake of the liquid input population, and optionally air. In some embodiments, rotation is effected subsequent to intake of the liquid input population, and optionally air. In some embodiments, rotation is by centrifugation of the centrifugal chamber at a relative centrifugal force at the inner surface of side wall of the internal cavity and/or at a surface layer of the cells of at or about or at least at or about 200 g, 300 g, 400 g, 500 g, 600 g, 700 g, 800 g, 1000 g, 1100 g, 1500, 1600 g, 1800 g, 2000 g, 2200 g, 2500 g, 3000 g, 3200 g, 3500 g or 4000 g. In some embodiments, rotation is by centrifugation at a force that is greater than or about 1100 g, such as by greater than or about 1200 g, greater than or about 1400 g, greater than or about 1600 g, greater than or about 1800 g, greater than or about 2000 g, greater than or about 2400 g, greater than or about 2800 g, greater than or about 3000 g or greater than or about 3200 g. In particular embodiments, the rotation by centrifugation is at a force between 600 g and 800 g. In particular embodiments, the rotation by centrifugation is at a force of or of about 693 g. In some embodiments, rotation is by centrifugation at a force that is or is about 1600 g.

In some embodiments, the gas, such as air, in the cavity of the chamber is expelled from the chamber. In some embodiments, the gas, such as air, is expelled to a container that is operably linked as part of the closed system with the centrifugal chamber. In some embodiments, the container is a free or empty container. In some embodiments, the air, such as gas, in the cavity of the chamber is expelled through a filter that is operably connected to the internal cavity of the chamber via a sterile tubing line. In some embodiments, the air is expelled using manual, semi-automatic or automatic processes. In some embodiments, air is expelled from the chamber prior to, simultaneously, intermittently or subsequently with expressing the output population containing incubated cells and viral vector particles, such as cells in which transduction has been initiated or cells have been transduced with a viral vector, from the cavity of the chamber.

In some embodiments, the transduction and/or other incubation is performed as or as part of a continuous or semi-continuous process. In some embodiments, a continuous process involves the continuous intake of the cells and viral vector particles, e.g., the transduction composition (either as a single pre-existing composition or by continuously pulling into the same vessel, e.g., cavity, and thereby mixing, its parts), and/or the continuous expression or expulsion of liquid, and optionally expelling of gas (e.g. air), from the vessel, during at least a portion of the incubation, e.g., while centrifuging. In some embodiments, the continuous intake and continuous expression are carried out at least in part simultaneously. In some embodiments, the continuous intake occurs during part of the incubation, e.g., during part of the centrifugation, and the continuous expression occurs during a separate part of the incubation. The two may alternate. Thus, the continuous intake and expression, while carrying out the incubation, can allow for a greater overall volume of sample to be processed, e.g., transduced.

In some embodiments, the incubation is part of a continuous process, the method including, during at least a portion of the incubation, effecting continuous intake of said transduction composition into the cavity during rotation of the chamber and during a portion of the incubation, effecting continuous expression of liquid and, optionally expelling of gas (e.g. air), from the cavity through the at least one opening during rotation of the chamber.

In some embodiments, the semi-continuous incubation is carried out by alternating between effecting intake of the composition into the cavity, incubation, expression of liquid from the cavity and, optionally expelling of gas (e.g. air) from the cavity, such as to an output container, and then intake of a subsequent (e.g., second, third, etc.) composition containing more cells and other reagents for processing, e.g., viral vector particles, and repeating the process. For example, in some embodiments, the incubation is part of a semi-continuous process, the method including, prior to the incubation, effecting intake of the transduction composition into the cavity through said at least one opening, and subsequent to the incubation, effecting expression of fluid from the cavity; effecting intake of another transduction composition comprising cells and the viral vector particles into said internal cavity; and incubating the another transduction composition in said internal cavity under conditions whereby said cells in said another transduction composition are transduced or subjected to transduction with said vector. The process may be continued in an iterative fashion for a number of additional rounds. In this respect, the semi-continuous or continuous methods may permit production of even greater volume and/or number of cells.

In some embodiments, a portion of the transduction incubation is performed in the centrifugal chamber, which is performed under conditions that include rotation or centrifugation.

In particular embodiments, transduction of the cells with the viral vector is or includes spinoculation, e.g., centrifugation of a mixture containing the cells and the viral particles. In some embodiments, the composition containing cells and viral particles can be rotated, generally at relatively low force or speed, such as speed lower than that used to pellet the cells, such as from or from about 600 rpm to 1700 rpm (e.g. at or about or at least 600 rpm, 1000 rpm, or 1500 rpm or 1700 rpm). In some embodiments, the rotation is carried at a force, e.g., a relative centrifugal force, of from or from about 100 g to 4000 g (e.g. at or about or at least at or about 100 g, 200 g, 300 g, 400 g, 500 g, 600 g, 700 g, 800 g, 900 g, 1000 g, 1500 g, 2000 g, 2500 g, 3000 g or 3500 g), as measured for example at an internal or external wall of the chamber or cavity.

In some embodiments, the cells are spinoculated with the viral vector at a force, e.g., a relative centrifugal force, of between or between about 100 g and 4000 g, 200 g and 1,000 g, 500 g and 1200 g, 1000 g and 2000 g, 600 g and 800 g, 1200 g and 1800 g, or 1500 g and 1800 g. In certain embodiments, the cells are spinoculated with the viral vector particle for, for at least, or for about 100 g, 200 g, 300 g, 400 g, 500 g, 600 g, 700 g, 800 g, 900 g, 1000 g, 1200 g, 1500 g, 1600 g, 2000 g, 2500 g, 3000 g, 3200 g, or 3500 g. In some embodiments, the cells are transduced or subjected to transduction with the viral vector at a force of or of about 692 g or 693 g. In particular embodiments, the cells are transduced or subjected to transduction with the viral vector at a force of or of about 1600 g. In some embodiments, the force is the force at the internal surface of the side wall of the internal cavity and/or at a surface layer of the cells.

In certain embodiments, the cells are spinoculated, e.g., the cell composition containing cells and viral vector is rotated, for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes; or between or between about 5 minutes and 120 minutes, 30 minutes and 90 minutes, 15 minutes and 60 minutes, 15 minutes and 45 minutes, 30 minutes and 60 minutes or 45 minutes and 60 minutes, each inclusive. In some embodiments, the cells are spinoculated with the viral vector for or for about 30 minutes. In certain embodiments, the cells are spinoculated with the viral vector for or for about 60 minutes.

In some embodiments, the method of transduction includes a spinoculation, e.g., a rotation or centrifugation of the transduction composition, and optionally air, in the centrifugal chamber for greater than or about 5 minutes, such as greater than or about 10 minutes, greater than or about 15 minutes, greater than or about 20 minutes, greater than or about 30 minutes, greater than or about 45 minutes, greater than or about 60 minutes, greater than or about 90 minutes or greater than or about 120 minutes. In some embodiments, the transduction composition, and optionally air, is rotated or centrifuged in the centrifugal chamber for greater than 5 minutes, but for no more than 60 minutes, no more than 45 minutes, no more than 30 minutes or no more than 15 minutes. In particular embodiments, the transduction includes rotation or centrifugation for or for about 60 minutes.

In some embodiments, the method of transduction includes rotation or centrifugation of the transduction composition, and optionally air, in the centrifugal chamber for between or between about 10 minutes and 60 minutes, 15 minutes and 60 minutes, 15 minutes and 45 minutes, 30 minutes and 60 minutes or 45 minutes and 60 minutes, each inclusive, and at a force at the internal surface of the side wall of the internal cavity and/or at a surface layer of the cells of, of about, or at 1000 g, 1100 g, 1200 g, 1400 g, 1500 g, 1600 g, 1800 g, 2000 g, 2200 g, 2400 g, 2800 g, 3200 g or 3600 g. In particular embodiments, the method of transduction includes rotation or centrifugation of the transduction composition, e.g., the cells and the viral vector particles, at or at about 1600 g for or for about 60 minutes.

2. Viral Vector Particles

In some embodiments, recombinant nucleic acids are transferred into cells using recombinant infectious virus particles, such as, e.g., vectors derived from simian virus 40 (SV40), adenoviruses, adeno-associated virus (AAV). In some embodiments, recombinant nucleic acids are transferred into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), or spleen focus forming virus (SFFV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

The viral vector genome is typically constructed in a plasmid form that can be transfected into a packaging or producer cell line. In any of such examples, the nucleic acid encoding a recombinant protein, such as a recombinant receptor, is inserted or located in a region of the viral vector, such as generally in a non-essential region of the viral genome. In some embodiments, the nucleic acid is inserted into the viral genome in the place of certain viral sequences to produce a virus that is replication defective.

Any of a variety of known methods can be used to produce retroviral particles whose genome contains an RNA copy of the viral vector genome. In some embodiments, at least two components are involved in making a virus-based gene delivery system: first, packaging plasmids, encompassing the structural proteins as well as the enzymes necessary to generate a viral vector particle, and second, the viral vector itself, i.e., the genetic material to be transferred. Biosafety safeguards can be introduced in the design of one or both of these components.

In some embodiments, the packaging plasmid can contain all retroviral, such as HIV-1, proteins other than envelope proteins (Naldini et al., 1998). In other embodiments, viral vectors can lack additional viral genes, such as those that are associated with virulence, e.g. vpr, vif, vpu and nef, and/or Tat, a primary transactivator of HIV. In some embodiments, lentiviral vectors, such as HIV-based lentiviral vectors, comprise only three genes of the parental virus: gag, pol and rev, which reduces or eliminates the possibility of reconstitution of a wild-type virus through recombination.

In some embodiments, the viral vector genome is introduced into a packaging cell line that contains all the components necessary to package viral genomic RNA, transcribed from the viral vector genome, into viral particles. Alternatively, the viral vector genome may comprise one or more genes encoding viral components in addition to the one or more sequences, e.g., recombinant nucleic acids, of interest. In some aspects, in order to prevent replication of the genome in the target cell, however, endogenous viral genes required for replication are removed and provided separately in the packaging cell line.

In some embodiments, a packaging cell line is transfected with one or more plasmid vectors containing the components necessary to generate the particles. In some embodiments, a packaging cell line is transfected with a plasmid containing the viral vector genome, including the LTRs, the cis-acting packaging sequence and the sequence of interest, i.e. a nucleic acid encoding an antigen receptor, such as a CAR; and one or more helper plasmids encoding the virus enzymatic and/or structural components, such as Gag, pol and/or rev. In some embodiments, multiple vectors are utilized to separate the various genetic components that generate the retroviral vector particles. In some such embodiments, providing separate vectors to the packaging cell reduces the chance of recombination events that might otherwise generate replication competent viruses. In some embodiments, a single plasmid vector having all of the retroviral components can be used.

In some embodiments, the retroviral vector particle, such as lentiviral vector particle, is pseudotyped to increase the transduction efficiency of host cells. For example, a retroviral vector particle, such as a lentiviral vector particle, in some embodiments is pseudotyped with a VSV-G glycoprotein, which provides a broad cell host range extending the cell types that can be transduced. In some embodiments, a packaging cell line is transfected with a plasmid or polynucleotide encoding a non-native envelope glycoprotein, such as to include xenotropic, polytropic or amphotropic envelopes, such as Sindbis virus envelope, GALV or VSV-G.

In some embodiments, the packaging cell line provides the components, including viral regulatory and structural proteins, that are required in trans for the packaging of the viral genomic RNA into lentiviral vector particles. In some embodiments, the packaging cell line may be any cell line that is capable of expressing lentiviral proteins and producing functional lentiviral vector particles. In some aspects, suitable packaging cell lines include 293 (ATCC CCL X), 293T, HeLA (ATCC CCL 2), D17 (ATCC CCL 183), MDCK (ATCC CCL 34), BHK (ATCC CCL-10) and Cf2Th (ATCC CRL 1430) cells.

In some embodiments, the packaging cell line stably expresses the viral protein(s). For example, in some aspects, a packaging cell line containing the gag, pol, rev and/or other structural genes but without the LTR and packaging components can be constructed. In some embodiments, a packaging cell line can be transiently transfected with nucleic acid molecules encoding one or more viral proteins along with the viral vector genome containing a nucleic acid molecule encoding a heterologous protein, and/or a nucleic acid encoding an envelope glycoprotein.

In some embodiments, the viral vectors and the packaging and/or helper plasmids are introduced via transfection or infection into the packaging cell line. The packaging cell line produces viral vector particles that contain the viral vector genome. Methods for transfection or infection are well known. Non-limiting examples include calcium phosphate, DEAE-dextran and lipofection methods, electroporation and microinjection.

When a recombinant plasmid and the retroviral LTR and packaging sequences are introduced into a special cell line (e.g., by calcium phosphate precipitation for example), the packaging sequences may permit the RNA transcript of the recombinant plasmid to be packaged into viral particles, which then may be secreted into the culture media. The media containing the recombinant retroviruses in some embodiments is then collected, optionally concentrated, and used for gene transfer. For example, in some aspects, after cotransfection of the packaging plasmids and the transfer vector to the packaging cell line, the viral vector particles are recovered from the culture media and titered by standard methods used by those of skill in the art.

In some embodiments, a retroviral vector, such as a lentiviral vector, can be produced in a packaging cell line, such as an exemplary HEK 293T cell line, by introduction of plasmids to allow generation of lentiviral particles. In some embodiments, a packaging cell is transfected and/or contains a polynucleotide encoding gag and pol, and a polynucleotide encoding a recombinant receptor, such as an antigen receptor, for example, a CAR. In some embodiments, the packaging cell line is optionally and/or additionally transfected with and/or contains a polynucleotide encoding a rev protein. In some embodiments, the packaging cell line is optionally and/or additionally transfected with and/or contains a polynucleotide encoding a non-native envelope glycoprotein, such as VSV-G. In some such embodiments, approximately two days after transfection of cells, e.g. HEK 293T cells, the cell supernatant contains recombinant lentiviral vectors, which can be recovered and titered.

Recovered and/or produced retroviral vector particles can be used to transduce target cells using the methods as described. Once in the target cells, the viral RNA is reverse-transcribed, imported into the nucleus and stably integrated into the host genome. One or two days after the integration of the viral RNA, the expression of the recombinant protein, e.g. antigen receptor, such as CAR, can be detected.

3. Incubating the Cells

In particular embodiments, genetic engineering, such as by transforming (e.g. transducing) the cells with a viral vector, further includes one or more steps of incubating the cells after the introducing or contacting of the cells with the viral vector. In some embodiments, cells, e.g., cells of the transformed cell population (also called "transformed cells"), are incubated subsequent to processes for genetically engineering, transforming, transducing, or transfecting the cells to introduce the viral vector into the cells. In particular embodiments, the incubation results in a population of incubated cells (also referred to herein as an incubated cell population).

In some embodiments, the cells, e.g. transformed cells, are incubated after the introducing of the heterologous or recombinant polynucleotide, e.g., viral vector particles is carried out without further processing of the cells. In particular embodiments, prior to the incubating, the cells are washed, such as to remove or substantially remove exogenous or remaining polynucleotides encoding the heterologous or recombinant polynucleotide, e.g. viral vector particles, such as those remaining in the media after the genetic engineering process following the spinoculation.

In some such embodiments, the further incubation is effected under conditions to result in integration of the viral vector into a host genome of one or more of the cells. For example, the further incubation provides time for the viral vector that may be bound to the T cells following transduction, e.g. via spinoculation, to integrate within the genome of the cell to delivery the gene of interest. In some aspects, the further incubation is carried out under conditions to allow the cells, e.g. transformed cells, to rest or recover in which the culture of the cells during the incubation supports or maintains the health of the cells. In particular embodiments, the cells are incubated under static conditions, such as conditions that do not involve centrifugation, shaking, rotating, rocking, or perfusion, e.g., continuous or semi-continuous perfusion of the media.

It is within the level of a skilled artisan to assess or determine if the incubation has resulted in integration of viral vector particles into a host genome, and hence to empirically determine the conditions for a further incubation. In some embodiments, integration of a viral vector into a host genome can be assessed by measuring the level of expression of a recombinant protein, such as a heterologous protein, encoded by a nucleic acid contained in the genome of the viral vector particle following incubation. A number of well-known methods for assessing expression level of recombinant molecules may be used, such as detection by affinity-based methods, e.g., immunoaffinity-based methods, e.g., in the context of cell surface proteins, such as by flow cytometry. In some examples, the expression is measured by detection of a transduction marker and/or reporter construct. In some embodiments, nucleic acid encoding a truncated surface protein is included within the vector and used as a marker of expression and/or enhancement thereof.

In certain embodiments, the incubation is performed under static conditions, such as conditions that do not involve centrifugation, shaking, rotating, rocking, or perfusion, e.g., continuous or semi-continuous perfusion of the media. In some embodiments, either prior to or shortly after, e.g., within 5, 15, or 30 minutes, the initiation of the incubation, the cells are transferred (e.g., transferred under sterile conditions) to a container such as a bag or vial, and placed in an incubator.

In some embodiments, at least a portion of the incubation is carried out in the internal cavity of a centrifugal chamber, such as described in International Publication Number WO2016/073602.

In some embodiments, the cells that have been introduced with a polynucleotide encoding the heterologous or recombinant polypeptide, e.g., the viral vectors, are transferred into a container for the incubation. In some embodiments, the container is a vial. In particular embodiments, the container is a bag. In some embodiments, the cells, and optionally the heterologous or recombinant polypeptide, are transferred into the container under closed or sterile conditions. In some embodiments, the container, e.g., the vial or bag, is then placed into an incubator for all or a portion of the incubation. In particular embodiments, incubator is set at, at about, or at least 16° C., 24° C., or 35° C. In some embodiments, the incubator is set at 37° C., at about at 37° C., or at 37° C.±2° C., ±1° C., ±0.5° C., or ±0.1° C.

In some aspects, the conditions for the incubation can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some embodiments, the incubation is performed in serum free media. In some embodiments, the serum free media is a defined and/or well-defined cell culture media. In certain embodiments, the serum free media is a controlled culture media that has been processed, e.g., filtered to remove inhibitors and/or growth factors. In some embodiments, the serum free media contains proteins. In certain embodiments, the serum-free media may contain serum albumin, hydrolysates, growth factors, hormones, carrier proteins, and/or attachment factors.

In particular embodiments, the cells are incubated in the presence of one or more cytokines. In certain embodiments, the one or more cytokines are recombinant cytokines. In particular embodiments, the one or more cytokines are human recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the one or more cytokines is or includes IL-15. In particular embodiments, the one or more cytokines is or includes IL-7. In particular embodiments, the one or more cytokines is or includes recombinant IL-2.

In particular embodiments, the cells are incubated in the presence of IL-2, IL-7, and/or IL-15. In certain embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are incubated in the presence of recombinant IL-2, IL-7, and IL-15.

In some embodiments, the cells, e.g., the transformed cells, are incubated with a cytokine, e.g., a recombinant human cytokine, at a concentration of between 1 IU/mL and 1,000 IU/mL, between 10 IU/mL and 50 IU/mL, between 50 IU/mL and 100 IU/mL, between 100 IU/mL and 200 IU/mL, between 100 IU/mL and 500 IU/mL, between 250 IU/mL and 500 IU/mL, or between 500 IU/mL and 1,000 IU/mL.

In some embodiments, the cells, e.g., the transformed cells, are incubated with IL-2, e.g., human recombinant IL-2, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., transformed cells, are incubated with recombinant IL-2 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 100 IU/mL. In some embodiments, the cells, e.g., the transformed cells, are incubated in the presence of or of about 100 IU/mL of recombinant IL-2, e.g., human recombinant IL-2.

In some embodiments, the cells, e.g., the transformed cells, are incubated with recombinant IL-7, e.g., human recombinant IL-7, at a concentration between 100 IU/mL and 2,000 IU/mL, between 500 IU/mL and 1,000 IU/mL, between 100 IU/mL and 500 IU/mL, between 500 IU/mL and 750 IU/mL, between 750 IU/mL and 1,000 IU/mL, or between 550 IU/mL and 650 IU/mL. In particular embodiments, the cells, e.g., the transformed cells, are incubated with IL-7 at a concentration at or at about 50 IU/mL, 100 IU/mL, 150 IU/mL, 200 IU/mL, 250 IU/mL, 300 IU/mL, 350 IU/mL, 400 IU/mL, 450 IU/mL, 500 IU/mL, 550 IU/mL, 600 IU/mL, 650 IU/mL, 700 IU/mL, 750 IU/mL, 800 IU/mL, 750 IU/mL, 750 IU/mL, 750 IU/mL, or 1,000 IU/mL. In particular embodiments, the cells, e.g., the transformed cells, are incubated in the presence of or of about 600 IU/mL of IL-7.

In some embodiments, the cells, e.g., the transformed cells, are incubated with recombinant IL-15, e.g., human recombinant IL-15, at a concentration between 1 IU/mL and 500 IU/mL, between 10 IU/mL and 250 IU/mL, between 50 IU/mL and 200 IU/mL, between 50 IU/mL and 150 IU/mL, between 75 IU/mL and 125 IU/mL, between 100 IU/mL and 200 IU/mL, or between 10 IU/mL and 100 IU/mL. In particular embodiments, cells, e.g., transformed cells, are incubated with recombinant IL-15 at a concentration at or at about 50 IU/mL, 60 IU/mL, 70 IU/mL, 80 IU/mL, 90 IU/mL, 100 IU/mL, 110 IU/mL, 120 IU/mL, 130 IU/mL, 140 IU/mL, 150 IU/mL, 160 IU/mL, 170 IU/mL, 180 IU/mL, 190 IU/mL, or 200 IU/mL. In some embodiments, the cells, e.g., the transformed cells, are incubated in the presence of or of about 100 IU/mL of recombinant IL-15, e.g., human recombinant IL-2.

In particular embodiments, the cells, e.g., transformed cells, are incubated in the presence of IL-2, IL-7, and/or IL-15. In some embodiments, the IL-2, IL-7, and/or IL-15 are recombinant. In certain embodiments, the IL-2, IL-7, and/or IL-15 are human. In particular embodiments, the one or more cytokines are or include human recombinant IL-2, IL-7, and/or IL-15. In certain embodiments, the cells are incubated in the presence of recombinant IL-2, IL-7, and IL-15.

In some embodiments, all or a portion of the incubation, e.g., of the non-expanded process, is performed in a media comprising a basal medium (e.g., a CTS OpTmizer basal media (Thermofisher)), glutamine, and one or more recombinant cytokines, such as recombinant IL-2, IL-7, and/or IL-15. In some embodiments, the media can contain one or more additional components, such as set froth in Section II. B. In some embodiments, the one or more additional components may include a dipeptide form of L-glutamine (e.g., L-alanyl-L-glutamine). In some embodiments, the one or more additional components are provided by an additional supplement, e.g. OpTmizer® supplement (Thermofisher). In some embodiments, the media is a serum-free media and does not contain any serum component. In some aspects, the media can contain one or more serum-substituting proteins, such as as one or more of albumin, insulin or transferrin (e.g. CTS™ Immune Cell Serum Replacement). Exemplary serum-free media or components thereof are described in Section II.

In some embodiments, the cells are incubated in the presence of the same or similar media as was present during the stimulation of the cells, such as carried out in connection with methods or processes of stimulation described above. In some embodiments, the cells are incubated in media having the same cytokines as the media present during stimulation of the cells, such as carried out in connection with methods or processes of stimulation described above. In certain embodiments, the cells are incubated in media having the same cytokines at the same concentrations as the media present during stimulation of the cells, such as carried out in connection with methods or processes of stimulation described above. In some embodiments, the cells are incubated in the absence of recombinant cytokines. In some embodiments, the cells are incubated in the absence of one or more cytokines as described herein. In some embodiments, the cells are incubated in the absence of all the cytokines described herein.

In some aspects, the further incubation is carried out under conditions to allow the cells to rest or recover that does not include the presence of a stimulating condition, e.g. in the form of recombinant cytokines or other stimulating agents. For example, the incubating is carried out in the presence of a lean media sufficient to support or maintain the culture of health of the cells during the incubation.

In some embodiments, all or a portion of the incubation is performed in basal media, such as a basal media without one or more recombinant cytokines or without any recombinant cytokine. In some embodiments, the medium does not comprise one or more recombinant cytokines, such as recombinant human IL-2, recombinant human IL-7, and/or recombinant human IL-15. In some aspects, the incubation is carried out without any recombinant cytokines. In certain embodiments, the basal media is supplemented with additional additives. In some embodiments, the basal media is not supplemented with any additional additives. Additives to cell culture media may include, but is not limited to nutrients, sugars, e.g., glucose, amino acids, vitamins, or additives such as ATP and NADH. Other additives also can be added but in general the specific additives and amounts are such that the incubation of the media with the cells facilitates maintenance of the cells but minimizes, limits and/or does not induce the metabolic activity of the cells during the incubation.

In particular embodiments, the media is a basal media that does not contain one or more recombinant cytokines and that does not contain a serum component, i.e. is a serum-free media, but may contain one or more additional components such as described in Section II. B. In particular embodiments, use of such a serum-free media in all or a portion of the incubation, e.g., of the non-expanded process, provides for a lean media that provides for maintenance of the cells but does not include certain factors that may activate or render the cells metabolically active thereby fostering the cells in a state that is or is likely to be a resting or a quiescent state. In some aspects, incubation in the presence of such a serum-free media allows the cells to recover or rest after the stimulation and genetic engineering (e.g. transduction). In some aspects, incubation in the presence of such a serum-free media results in an output composition containing cells that are less susceptible to damage or loss of viability, e.g., during or following the manufacturing process and when the harvested/formulated cells are cryopreserved and then thawed immediately prior to use. In some embodiments, cells in the output composition when thawed have lower levels of caspase or other marker of apoptosis than cells that have been incubated in a similar media but containing one or more recombinant cytokines, serum, or other factors that may make the cells more metabolically active at cryopreservation of the output composition.

In some embodiments, the basal medium contains a mixture of inorganic salts, sugars, amino acids, and, optionally, vitamins, organic acids and/or buffers or other well known cell culture nutrients. In addition to nutrients, the medium also helps maintain pH and osmolality. In some aspects, the reagents of the basal media support cell growth, proliferation and/or expansion. A wide variety of commercially available basal media are well known to those skilled in the art, and include Dulbeccos' Modified Eagles Medium (DMEM), Roswell Park Memorial Institute Medium (RPMI), Iscove modified Dulbeccos' medium and Hams medium. In some embodiments, the basal medium is Iscove's Modified Dulbecco's Medium, RPMI-1640, or α-MEM.

In some embodiments, the basal media is a balanced salt solution (e.g., PBS, DPBS, HBSS, EBSS). In some embodiments, the basal media is selected from Dulbecco's Modified Eagle's Medium (DMEM), Minimal Essential Medium (MEM), Basal Medium Eagle (BME), F-10, F-12, RPMI 1640, Glasgow's Minimal Essential Medium (GMEM), alpha Minimal Essential Medium (alpha MEM), Iscove's Modified Dulbecco's Medium, and M199. In some embodiments, the basal media is a complex medium (e.g., RPMI-1640, IMDM). In some embodiments, the basal medium is OpTmizer™ CTS™ T-Cell Expansion Basal Medium (ThermoFisher).

In some embodiments, the basal medium is free of a protein. In some embodiments, the basal medium is free of a human protein (e.g., a human serum protein). In some embodiments, the basal medium is serum-free. In some embodiments, the basal medium is free of serum derived from human. In some embodiments, the basal medium is free of a recombinant protein. In some embodiments, the basal medium is free of a human protein and a recombinant protein. In some embodiments, the basal medium is free of one or more or all cytokines as described herein. In some embodiments, all or a portion of the incubation, e.g., of the non-expanded process, is performed in basal medium without any additional additives or recombinant cytokines. In some embodiments, the basal media is a CTS OpTmizer basal media (Thermofisher) without any additional additives or recombinant cytokines.

In some embodiments, all or a portion of the incubation, e.g., of the non-expanded process, is performed in a media comprising a basal medium and glutamine, e.g., a CTS OpTmizer basal media (Thermofisher) with glutamine.

In some embodiments, all or a portion of the incubation, e.g., of the non-expanded process, is performed in a media comprising a basal medium (e.g., a CTS OpTmizer basal media (Thermofisher)) without one or more recombinant cytokines, such as recombinant human IL-2, recombinant human IL-7, and/or recombinant human IL-15. In some embodiments, the medium is supplemented with one or more additional non-serum component, such as set forth in Section II.B. In some embodiments, the one or more supplement is serum-free. In some embodiments, the serum-free medium further comprises a free form of an amino acid such as L-glutamine. In some embodiments, the serum-free medium does not comprise a serum replacement supplement. In some embodiments, the serum-free medium does not comprise a dipeptide form of L-glutamine (e.g., L-alanyl-L-glutamine). In some embodiments, the serum-free medium does not comprise any recombinant cytokine. In some embodiments, the serum-free medium comprises a basal medium supplemented with a T cell supplement and a free form of L-glutamine, and does not contain any immune cell serum replacement, any dipeptide form of L-glutamine, or any recombinant cytokine. In some embodiments, the serum-free medium comprises a basal medium (e.g. OpTmizer™ T-Cell Expansion Basal Medium), L-glutamine and one or more additional components such as provided by a supplement (e.g. OpTmizer™ T-Cell Expansion Supplement).

In particular embodiments, the cells are incubated in the serum free medium at a concentration of or of about $0.25\times10^6$ cells/mL, $0.5\times10^6$ cells/mL, $0.75\times10^6$ cells/mL, $1.0\times10^6$ cells/mL, $1.25\times10^6$ cells/mL, $1.5\times10^6$ cells/mL, $1.75\times10^6$ cells/mL, or $2.0\times10^6$ cells/mL. In particular embodiments, the cells are incubated in the serum free medium at a concentration of or of about $0.75\times10^6$ cells/mL. In some embodiments, the incubating is for or for about between 18 hours and 30 hours. In particular embodiments, the incubating is for or for about 24 hours or for for for about one day. In some embodiments, the incubating is for or for about 48 hours or 72 hours, or for or for about 2 days or 3 days, respectively. In particular embodiments, the incubating is for or for about 24 hours±6 hours, 48 hours±6 hours, or 72 hours±6 hours. In particular embodiments, the incubating is for or for about 72 hours, 72±4 hours, or for or for about 3 days, e.g., during which time the cells are incubated in the serum free medium at a concentration of or of about $0.75\times10^6$ cells/mL. In some embodiments, all or a portion of the incubation is performed in a serum free media comprising a basal medium (e.g., a CTS OpTmizer basal media (Thermofisher)) without one or more recombinant cytokines, such as recombinant human IL-2, recombinant human IL-7, and/or recombinant human IL-15. In some embodiments, the serum-free media is supplemented with L-glutamine and/or one or more cell supplement, e.g. OpTmizer™ T-Cell Expansion Supplement, but does not contain any immune cell serum replacement, any dipeptide form of L-glutamine, or any recombinant cytokine.

In particular embodiments, the cells are incubated in the absence of cytokines. In particular embodiments, the cells are incubated in the absence of any recombinant cytokine. In particular embodiments, the cells are incubated in the absence of one or more recombinant cytokine, such as recombinant IL-2, IL-7, and/or IL-15.

In some embodiments, the basal medium further comprises glutamine, such as L-glutamine. In some aspects, the glutamine is a free form of glutamine, such as L-glutamine. In some embodiments, the concentration of the glutamine, such as L-glutamine, in the basal medium is about or less than about about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of glutamin, such as L-glutamine, in the basal medium is at least about 0.5 mM, 1 mM, 1.5 mM, 2 mM, 2.5 mM, 3 mM, 3.5 mM, 4 mM, 4.5 mM, or 5 mM. In some embodiments, the concentration of glutamine, such as L-glutamine, in the basal medium is at most about 2 mM, 2.5 mM, 3 mM, 3.5 mM, 4 mM, 4.5 mM, 5 mM. In some embodiments, the concentration of glutamine, such as L-glutamine, in the basal medium is about 2 mM. In some embodiments, the basal medium further may comprises a protein or a peptide. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II. In some embodiments, the protein or peptide comprises a transferrin. In some embodiments, the protein or peptide comprises a fibronectin. In some embodiments, the protein or peptide comprises aprotinin. In some embodiments, the protein comprises fetuin.

In some embodiments, the one or more additional protein is part of a serum replacement supplement that is added to the basal medium. Examples of serum replacement supplements include, for example, Immune Cell Serum Replacement (ThermoFisher, #A2598101) or those described in Smith et al. *Clin Transl Immunology.* 2015 January; 4 (1): e31.

In certain embodiments, the cells are incubated after the introducing of the polynucleotide encoding the heterologous or recombinant protein, e.g., viral vector, for, for about, or for at least 18 hours, 24 hours, 30 hours, 36 hours, 40 hours, 48 hours, 54 hours, 60 hours, 72 hours, 84 hours, 96 hours, or more than 96 hours. In certain embodiments, the cells are incubated after the introducing of the polynucleotide encoding the heterologous or recombinant protein, e.g., viral vector, for, for about, or for at least one day, 2 days, 3 days, 4 days, or more than 4 days. In some embodiments, the incubating is performed for an amount of time between 30 minutes and 2 hours, between 1 hour and 8 hours, between 6 hours and 12 hours, between 12 hours and 18 hours, between 16 hours and 24 hours, between 18 hours and 30 hours, between 24 hours and 48 hours, between 24 hours and 72 hours, between 42 hours and 54 hours, between 60 hours and 120 hours between 96 hours and 120 hours, between 90 hours and between 1 days and 7 days, between 3 days and 8 days, between 1 day and 3 days, between 4 days and 6 days, or between 4 days and 5 days prior to the genetic engineering. In some embodiments, the incubating is for or for about between 18 hours and 30 hours. In particular embodiments, the incubating is for or for about 24 hours or for for for about one day.

In certain embodiments, the total duration of the incubation is, is about, or is at least 12 hours, 18 hours, 24 hours, 30 hours, 36 hours, 42 hours, 48 hours, 54 hours, 60 hours, 72 hours, 84 hours, 96 hours, 108 hours, or 120 hours. In certain embodiments, the total duration of the incubation is, is about, or is at least one day, 2 days, 3 days, 4 days, or 5 days. In particular embodiments, the incubation is completed at, at about, or within 120 hours, 108 hours, 96 hours, 84 hours, 72 hours, 60 hours, 54 hours, 48 hours, 42 hours, 36 hours, 30 hours, 24 hours, 18 hours, or 12 hours. In particular embodiments, the incubation is completed at, at about, or within one day, 2 days, 3 days, 4 days, or 5 days. In some embodiments, the total duration of the incubation is between or between about 12 hour and 120 hours, 18 hour and 96 hours, 24 hours and 72 hours, or 24 hours and 48 hours, inclusive. In some embodiments, the total duration of the incubation is between or about between 1 hour and 48 hours, 4 hours and 36 hours, 8 hours and 30 hours or 12 hours and 24 hours, inclusive. In particular embodiments, the incubation is performed for or for about 24 hours, 48 hours, or 72 hours, or for or for about 1 day, 2 days, or 3 days, respectively. In particular embodiments, the incubation is performed for 24 hours±6 hours, 48 hours±6 hours, or 72 hours±6 hours. In particular embodiments, the incubation is performed for or for about 72 hours or for or for about 3 days.

In particular embodiments, the incubation is initiated at, at about, or is at least 12 hours, 18 hours, 24 hours, 30 hours, 36 hours, 42 hours, 48 hours after the initiation of the stimulation. In particular embodiments, the incubation is initiated at, at about, or is at least 0.5 days, one day, 1.5 days, or 2 days after the initiation of the stimulation. In particular embodiments, the incubation is initiated at, at about, or within 120 hours, 108 hours, 96 hours, 84 hours, 72 hours, 60 hours, 54 hours, 48 hours, 42 hours, 36 hours, 30 hours, 24 hours, 18 hours, or 12 hours of the initiation of the stimulation. In particular embodiments, the incubation is initiated at, at about, or within 5 days, 4 days, 3 days, 2 days, one day, or 0.5 days of the initiation of the stimulation.

In some embodiments, the incubation is completed between or between about 24 hour and 120 hours, 36 hour and 108 hours, 48 hours and 96 hours, or 48 hours and 72 hours, inclusive, after the initiation of the stimulation. In some embodiments, the incubation is completed at, about, or within 120 hours, 108 hours, 96 hours, 72 hours, 48 hours, or 36 hours from the initiation of the stimulation. In some embodiments, the incubation is completed at, about, or within 5 days, 4.5 days, 4 days, 3 days, 2 days, or 1.5 days from the initiation of the stimulation. In particular embodiments, the incubation is completed after hours 24 hours±6 hours, 48 hours±6 hours, or 72 hours±6 hours after the initiation of the stimulation. In some embodiments, the incubation is completed after or after about 72 hours or after or after about 3 days.

In some embodiments, the incubation is carried out for an amount of time sufficient for the heterologous or recombinant polynucleotide to be integrated into the genome. In particular embodiments, the incubation is performed for an amount of time sufficient for at least an integrated viral copy number (iVCN) of, of about, or of at least 0.1, 0.5, 1, 2, 3, 4, 5, or greater than 5 per diploid genome. In particular embodiments, the incubation is performed for an amount of time sufficient for at least an iVCN of, of about, or of at least 0.5 or 1. In particular embodiments, the incubation is carried out for an amount of time sufficient for the heterologous or recombinant polynucleotide to be stably integrated into the genome. In particular embodiments, the heterologous or recombinant polynucleotide is considered to be stably integrated when the iVCN per diploid genome does not change by more than 20%, 15%, 10%, 5%, 1%, or 0.1% over a period of time, e.g. at least 12, 24, or 48 hours. In particular embodiments, the incubation is completed prior to the stable integration.

In certain embodiments, the incubation is performed or carried out at least until the integrated vector is detected in the genome. In some embodiments, the incubation is completed prior to achieving stable integrated vector copy number (iVCN) per diploid genome. In particular embodiments, the incubation is performed or carried out at least until the integrated vector is detected in the genome but prior to achieving a stable iVCN per diploid genome. In certain embodiments, a stable iVCN per diploid genome is achieved when the iVCN peaks and/or remains unchanged, or unchanged within a tolerated error, for a period of time. In some embodiments, the tolerated error is, is within, or is about ±40%, ±35%, ±30%, ±25%, ±20%, ±15%, ±10%, ±5%, ±2%, ±1%, or less than ±1%. In certain embodiments, the period of time is, is about, or is at least 2 hours, 4 hours, 6 hours, 8 hours, 12 hours, 16 hours, 18 hours, 24 hours, 36 hours, 48 hours, 60 hours, or 72 hours. In certain embodiments, the period of time is, is about, or is at least one day, 2 days, or 3 days. In certain embodiments, the stable iVCN per diploid genome is achieved when the iVCN peaks and remains unchanged, or unchanged within a tolerated error, e.g., ±25%, for a period of time that is, is about, or is at least 24 hours or one day. In some embodiments, a stable iVCN per diploid genome is achieved when the fraction of iVCN to total vector copy number (VCN) in the diploid genome of the population of transformed cells, on average, is, is at least or is about 0.6. 0.7. 0.8, 0.9, 1.0, 1.1, 1.2, 1.3, 1.4, or 1.5, or is within a tolerated error thereof, e.g., ±25%, ±20%, ±15%, ±10%, ±5%, or ±1%. In certain embodiments, a stable iVCN per diploid genome is achieved when the fraction of iVCN to total vector copy number (VCN) in the diploid genome of the population of transformed cells, on average, is or is about 0.8, or is within a tolerated error thereof. In some embodiments, a stable iVCN per diploid genome is achieved when the fraction of iVCN to total vector copy number (VCN) in the diploid genome of the population of transformed cells, on average, is or is about 1.0 or is within a tolerated error thereof.

In some embodiments, the incubation is completed before the iVCN of reaches, reaches about, or reaches at least 5.0, 4.0, 3.0, 2.5, 2.0, 1.75, 1.5, 1.25, 1.2, 1.1, 1.0, 0.9, 0.8, 0.75, 0.7, 0.6, 0.5, 0.4, 0.3, or 0.25 copies per diploid genome. In certain embodiments, the incubation is completed before the iVCN reaches or about 1.0 copy per diploid genome. In particular embodiments, the incubation is completed before the iVCN reaches or about 0.5 copies per diploid genome.

In certain embodiments, the cells are harvested prior to, prior to about, or prior to at least one, two, three, four, five, six, eight, ten, twenty, or more cell doublings of the cell population, e.g., doublings that occur during the incubating. In particular embodiments, the amount of cell doublings may be calculated by measuring the number of viable cells in a population at different time points, such as at different times or stages of an engineering process. In particular embodiment, the cell doubling can be calculated by comparing the total amount of viable cells at one time point to the total number of viable cells present at an earlier time point. In certain embodiments, the incubation is completed prior to, to about, or to at least one, two, three, four, five, six, eight, ten, twenty, or more cell doublings of the cell population, e.g., doublings that occur during the incubating. In certain aspects, the cell doubling is calculated by determining the total nucleated cell number (TNC) when the incubation is initiated and when the incubation completed, and then determining the natural log of the product of the TNC at the completion divided by the TNC at the initiation, and then dividing said natural log of the product by the natural log of 2.

In some aspects, the number of doublings of that occurs in a population, e.g., during an engineering process, is determined using the following formula:

$$\text{Cell doublings} = \frac{\ln\left(\frac{TNC \text{ at harvest}}{TNC \text{ 3 days post-activation}}\right)}{\ln 2} \quad 1)$$

In some aspects, the number of doublings of that occurs in a population, e.g., during an engineering process, using the following formula:

$$\text{Cell doublings} = \frac{\ln\left(\frac{TNC \text{ at harvest}}{TNC \text{ at initiation of the simulating}}\right)}{\ln 2} \quad 2)$$

In certain embodiments, the number of doublings that occurs in a population, e.g., during the engineering process, is determined suing the following formula:

$$\text{Cell doublings} = \frac{\ln\left(\frac{TNC \text{ at harvest}}{TNC \text{ following stimulation}}\right)}{\ln 2} \quad 3)$$

In various embodiments, the number of doublings that occurs in a population, e.g., during the engineering process, is determined suing the following formula:

$$\text{Cell doublings} = \frac{\ln\left(\frac{TNC \text{ at harvest}}{TNC \text{ at transduction}}\right)}{\ln 2} \quad 4)$$

In particular embodiments, the number of doublings that occurs in a population, e.g., during the engineering process, is determined suing the following formula:

$$\text{Cell doublings} = \frac{\ln\left(\frac{TNC \text{ at harvest}}{TNC \text{ at the begining of the incubation}}\right)}{\ln 2} \quad 5)$$

In certain embodiments, the incubation is completed before the total number cells, e.g., total number of incubated cells or cells undergoing the incubation, is greater than or than about one, two, three, four, five, six, eight, ten, twenty, or more than twenty times the number of cells of the input population, e.g., the total number of cells that were contacted with the stimulatory reagent. In various embodiments, the incubation is completed before the total number of incubated cells is greater than or than about one, two, three, four, five, six, eight, ten, twenty, or more than twenty times the total number of cells that were transformed, transduced, or spinoculated, e.g., the total number of cells that were contacted with a viral vector. In certain embodiments, the cells are T cells, viable T cells, CD3+ T cells, CD4+ T cells, CD8+ T cells, CAR expressing T cells, or a combination of any of the foregoing. In some embodiments, the incubation is completed before the total number of cells is greater than the total number of cells of the input population. In some embodiments, the incubation is completed before the total number of viable CD3+ T cells is greater than the total number of viable CD3+ cells of the input population. In certain embodiments, the incubation is completed before the total number of cells is greater than the total number of cells of the transformed, transduced, or spinoculated cells. In some embodiments, the incubation is completed before the total number of viable CD3+ T cells is greater than the total number of viable CD3+ of the transformed, transduced, or spinoculated cells.

In some embodiments, the total cell number or total viable cell number of the cell population remains similar, the same, or essentially the same during the incubation. In particular embodiments, the total cell number or total viable cell number of the cell population does not change during the incubation. In some aspects, the total cell number or total viable cell number decreases during the incubation. In particular aspects, the total viable cell number is, is about, or is less than 95%, 90%, 85%, 80%, 75%, 70%, 65%, 60%, 55%, of 50% of the total cell number or total viable cell number of the input population prior to, e.g., immediately prior to, or at the initiation of the stimulation.

D. Small Molecules in Process

In some embodiments, provided herein are methods comprising manufacturing or producing engineered cells (e.g., CAR-T cells) in the presence of a modulating agent, thereby improving the persistence, lack of exhaustion, and/or efficacy of the engineered cells manufactured or produced by the methods. In some aspects, the provided methods produce compositions of cells that include primary T cells engineered to express a recombinant receptor, such as for use in cell therapy, that (i) contain fewer exhausted cells and/or fewer cells that display markers or phenotypes associated with exhaustion; (ii) contain an increased percentage of memory-like T cells, such as long-lived memory T cells; (iii) are less differentiated; (iv) exhibit improved or enhanced survival, expansion, persistence, and/or anti-tumor activity; (v) exhibit improved therapeutic efficacy; and/or (vi) exhibit improved clinical durability of response, as compared to compositions of engineered cells that are produced by alternative methods, such as alternative methods that are not carried out in the presence of the modulating agent. In some embodiments, the comparison to an alternative process is made to the same process that differs only in that the alternative process is not carried out in the presence of the modulating agent.

In some embodiments, the modulating agent is in contact with the cells or cell populations (e.g., the modulating agent is in a cell or interacts with one or more cell surface molecule) prior to collecting, harvesting, or formulating the cells. In some embodiments, the modulating agent is present prior to, during, or after the cells are subjected to stimulation, e.g., T cell activation. In some embodiments, the modulating agent is in contact with the cells or cell populations (e.g., the modulating agent is in a cell or interacts with one or more cell surface molecule) prior to or during the stimulation, e.g., a stimulation described herein such as in Section I-B. In some embodiments, the modulating agent is present prior to, during, or after the cells are subjected to engineering, e.g., transduction. In some embodiments, the modulating agent is in contact with the cells or cell populations (e.g., the modulating agent is in a cell or interacts with one or more cell surface molecule) prior to or during the engineering, e.g., an engineering described herein such as in Section I-C. In some embodiments, the modulating agent is in contact with the cells or cell populations (e.g., the modulating agent is in a cell or interacts with one or more cell surface molecule) during or after the incubation, e.g., an incubation described herein such as in Section I-C-3. In some embodiments, the modulating agent is in contact with the cells or cell populations (e.g., the modulating agent is in a cell or interacts with one or more cell surface molecule) during the stimulation (e.g., a stimulation described herein such as in Section I-B), during the engineering (an engineering described herein such as in Section I-C), and/or during the incubation (e.g., an incubation described herein such as in Section I-C-3). In certain embodiments, the cells or cell population undergoes a process, procedure, step, or technique in the presence of the modulating agent after the incubation but prior to steps for collecting, harvesting, or formulating the cells. In particular embodiments, the cells or cell population undergoes a process, procedure, step, or technique in the presence of the modulating agent after the incubation.

In some embodiments, cells to be engineered (e.g. transduced) are contacted (e.g., incubated) with the modulating agent, e.g. in a culture media, prior to the engineering. In some embodiments, the cells are engineered in the presence of the modulating agent. In some embodiments, one or more engineered cells are contacted (e.g., incubated) with the modulating agent, e.g. in a culture media such as a basal medium without one or more recombinant cytokines or without any recombinant cytokine. Also provided in some embodiments are compositions during the manufacture or production of engineered cells, e.g., for cell-based therapies, that comprise (i) the modulating agent and (ii) cells to be engineered and/or cells that have been subjected to engineering (including engineered cells), such as primary immune cells (e.g., T cells).

In some embodiments, the modulating agent is selected from the group consisting of a PI3K inhibitor, an Akt pathway, an mTOR inhibitor, a Ras/ERK inhibitor, an NF-κB inhibitor, a BET inhibitor, a CDK inhibitor, a CRAC channel inhibitor, a Cox inhibitor, a dopamine antagonist, an ERK5 inhibitor, a glucocorticoid, an IGF-1R inhibitor, an IKK inhibitor, a JAK inhibitor, Lck inhibitor, a PDKI inhibitor, a Raf inhibitor, and a Syk inhibitor. In some embodiments, the Src inhibitors include, but are not limited to dasatinib, saracatinib, bosutinib, KX01, and rebastinib (DCC-2036). In some embodiments, the Src inhibitor comprises rebastinib (DCC-2036). Certain agents useful as the modulating agent of the present disclosure are disclosed in WO2019018603, WO2018106595, and PCT/US2018/058812, all of which are incorporated herein by reference in the entirety.

In some embodiments, the modulating agent is or comprises a compound, a small molecule, e.g., small organic molecule, a polynucleotide, an oligonucleotide, an siRNA, or a polypeptide, or a fragment, isoform, variant, analog, or derivative thereof that inhibits, reduces, prevents, and/or is capable of inhibiting, reducing, or preventing, one or more activities of the target such as mTOR. In particular embodiments, the agent is a small molecule with a molecular weight of less than 10 kD, less than 9 kD, less than 8 kD, less than 7 kD, less than 6 kD, less than 5 kD, less than 4 kD, less than 3 kD, less than 2 kD, less than 1 kD, less than 0.5 kD, or less than 0.1 kD.

In some embodiments, the modulating agent is or comprises an agent that inhibits mTOR activity. In some embodiments, cells to be engineered (e.g. transduced) are contacted (e.g., incubated) with an mTOR inhibitor prior to the engineering. In some embodiments, the cells are engineered in the presence of an mTOR inhibitor. In some embodiments, one or more engineered cells are contacted (e.g., incubated) with an mTOR inhibitor, e.g. in a culture media such as a basal medium without one or more recombinant cytokines or without any recombinant cytokine. Also provided in some embodiments are compositions during the manufacture or production of engineered cells that comprise (i) an mTOR inhibitor and (ii) cells to be engineered and/or cells that have been subjected to engineering (including engineered cells).

In some embodiments, an agent that inhibits mTOR activity inhibits, reduces, and/or decreases, and/or is capable of inhibiting, reducing, and/or decreasing at least one activity of mTOR. In particular embodiments, an agent that inhibits mTOR activity inhibits, reduces, and/or decreases, and/or is capable of inhibiting, reducing, and/or decreasing an mTOR kinase activity. In some embodiments, an agent that inhibits mTOR activity inhibits, reduces, and/or decreases, and/or is capable of inhibiting, reducing, and/or decreasing an mTORC1 activity, e.g., an mTORC1 kinase activity, and/or an mTORC2 activity. In some embodiments, the agent that inhibits mTOR activity prevents the formation of and/or destabilizes the mTORC1 complex. In particular embodiments, the agent that inhibits activity prevents the formation of and/or destabilizes the mTORC2 complex.

In particular embodiments, the agent that inhibits mTOR activity inhibits the activity of at least one additional kinase. In certain embodiments, the at least one additional kinase is PI3K. In particular embodiments, the agent that inhibits mTOR activity: (i) does not inhibit PI3K activity; (ii) does not detectably inhibit PI3K activity at the $IC_{50}$ for mTOR activity; and/or (iii) does not detectably inhibit PI3K at all concentrations that detectably inhibit mTOR activity. In some embodiments, the agent that inhibits mTOR activity inhibits, e.g., selectively inhibits, mTORC1 and mTORC2 kinase activity relative to PI3K activity. In certain embodiments, the agent that inhibits mTOR activity inhibits mTORC1 and mTORC2 kinase activity. In particular embodiments, the agent that inhibits mTOR activity selectively inhibits mTORC1 activity, such as the mTORC1 kinase activity.

In certain embodiments, the agent that inhibits mTOR activity: (i) does not inhibit mTORC2 activity; (ii) does not detectably inhibit mTORC2 activity at the $IC_{50}$ for mTORC1 activity; and/or (iii) does not detectably inhibit mTORC2 at all concentrations that detectably inhibit mTORC1 activity.

In some embodiments, the agents that inhibit mTOR activity include, but are not limited to, CC214-1 (Celgene), CC214-2 (Celgene), CC0470324, GDC0980, SAR245409, VS5584, PI-103, SF1126, BGT226, XL765, PF-04691502, Dactolisib (codenamed NVP-BEZ235 and BEZ-235), a pyrazolopyrimidine, Torin 1, Torkinib (PP242), PP30, Ku-0063794, WAY-600 (Wyeth), WAY-687 (Wyeth), WAY-354 (Wyeth), DS3078a, rapamycin (sirolimus), temsirolimus (CC1779), everolimus (RAD001), deforolimus (AP23573), AZD8055 (AstraZeneca), and OSI-027 (OSI). In some embodiments, the agent that inhibits mTOR activity has or includes a formula that is provided in Formula (I), Formula (II), or Formula (III). In some embodiments, the agent is Compound 155, Compound 246, or Compound 63.

In particular embodiments, the agent comprises a formula set forth in Formula (I), Formula (I)

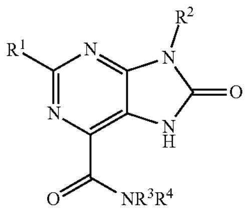

wherein $R^1$ is substituted or unsubstituted $C_{1-8}$ alkyl, substituted or unsubstituted aryl, substituted or unsubstituted heteroaryl, substituted or unsubstituted cycloalkyl, or substituted or unsubstituted heterocycloalkyl, $R^2$ is substituted or unsubstituted $C_{1-8}$alkyl, substituted or unsubstituted aryl, substituted or unsubstituted heteroaryl, substituted or unsubstituted cycloalkyl, or substituted or unsubstituted heterocycloalkyl, and $R^3$ and $R^4$ are independently H or $C_{1-8}$ alkyl. In some embodiments, the agent that inhibits mTOR activity is or comprises a compound of Formula (I), or a pharmaceutically acceptable salt or solvate thereof. In some embodiments, the agent that inhibits mTOR activity is or comprises a compound of Formula (I), or a pharmaceutically acceptable salt thereof. In some embodiments, the agent that inhibits mTOR activity is or comprises 2-(3-hydroxyphenyl)-9-(2-isopropylphenyl)-8-oxo-8,9-dihydro-7H-purine-6-carboxamide, or a pharmaceutically acceptable salt or solvate thereof. In some embodiments, the agent that inhibits mTOR activity is or comprises

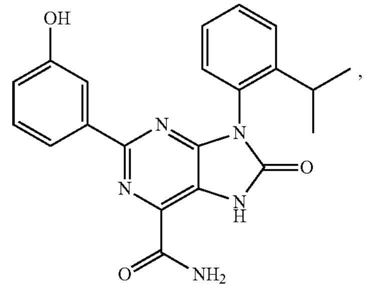 [SMILES: CC(C)c1ccccc1-n1c(=O)[nH]c2c(C(N)=O)nc(-c3cccc(O)c3)nc21]

or a pharmaceutically acceptable salt thereof.

In some embodiments, the agent comprises a formula set forth in Formula (II),

Formula (II)

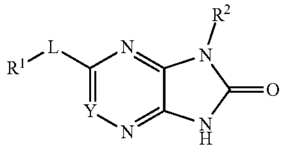

wherein L is a direct bond, NH or O, Y is N or $CR^3$, wherein $R^1$ is H, substituted or unsubstituted $C_{1-8}$ alkyl, substituted or unsubstituted $C_{2-8}$ alkenyl, substituted or unsubstituted aryl, substituted or unsubstituted heteroaryl, substituted or unsubstituted cycloalkyl or substituted or unsubstituted heterocycloalkyl, $R^2$ is H, substituted or unsubstituted $C_{1-8}$ alkyl, substituted or unsubstituted aryl, substituted or unsubstituted heteroaryl, substituted or unsubstituted cycloalkyl, or substituted or unsubstituted heterocycloalkyl, $R^3$ is H, substituted or unsubstituted $C_{1-8}$ alkyl, substituted or unsubstituted aryl, substituted or unsubstituted heteroaryl, substituted or unsubstituted cycloalkyl, substituted or unsubstituted heterocycloalkyl, $—NHR^4$ or $—N(R^4)_2$, and $R^4$ is at each occurrence independently substituted or unsubstituted $C_{1-8}$ alkyl, substituted or unsubstituted aryl, substituted or unsubstituted heteroaryl, substituted or unsubstituted cycloalkyl, or substituted or unsubstituted heterocycloalkyl. In some embodiments, the agent that inhibits mTOR activity is or comprises a compound of Formula (II), or a pharmaceutically acceptable salt or solvate thereof. In some embodiments, the agent that inhibits mTOR activity is or comprises 6-(4-(2H-1,2,4-triazol-3-yl)phenyl)-1-(2-(tetrahydro-2H-pyran-4-yl)ethyl)-1H-imidazo[4,5-b]pyrazine-2(3H)-one, or a pharmaceutically acceptable salt or solvate thereof. In some embodiments, the agent that inhibits mTOR activity is or comprises

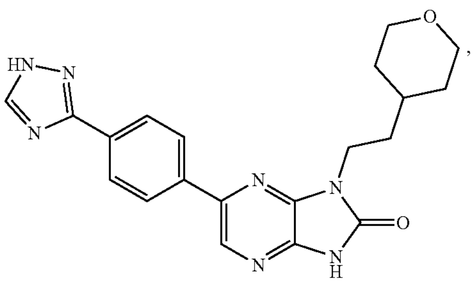 [SMILES: O=c1[nH]c2ncc(-c3ccc(-c4nc[nH]n4)cc3)nc2n1CCC1CCOCC1]

or a pharmaceutically acceptable salt thereof.

In particular embodiments, the agent comprises a formula set forth in Formula (III), Formula (III)

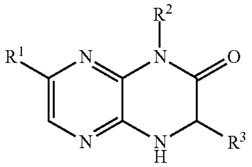

wherein $R^1$ is substituted or unsubstituted $C_{1-8}$ alkyl, substituted or unsubstituted aryl, substituted or unsubstituted cycloalkyl, substituted or unsubstituted heterocyclyl, or substituted or unsubstituted heterocyclylalkyl, $R^2$ is H, substituted or unsubstituted $C_{1-8}$ alkyl, substituted or unsubstituted cycloalkyl, substituted or unsubstituted heterocyclyl, substituted or unsubstituted heterocyclylalkyl, substituted or unsubstituted aralkyl, or substituted or unsubstituted cycloalkylalkyl, and $R^3$ is H, or a substituted or unsubstituted $C_{1-8}$ alkyl. In certain embodiments, $R^1$ is substituted or unsubstituted aryl or substituted or unsubstituted heteroaryl. In some embodiments, $R^1$ is pyridyl that is substituted. In some embodiments, the agent that inhibits mTOR activity is or comprises a compound of Formula (III), or a pharmaceutically acceptable salt or solvate thereof. In some embodiments, the agent that inhibits mTOR activity is or comprises a compound of Formula (III), or a pharmaceutically acceptable salt thereof. In some embodiments, the agent that inhibits mTOR activity is or comprises 7-(6-(2-hydroxypropan-2-yl) pyridin-3-yl)-1-((1r,4r)-4-methoxycyclohexyl)-3,4-dihydropyrazino[2,3-b]pyrazin-2 (1H)-one, or a pharmaceutically acceptable salt or solvate thereof. In some embodiments, the agent that inhibits mTOR activity is or comprises

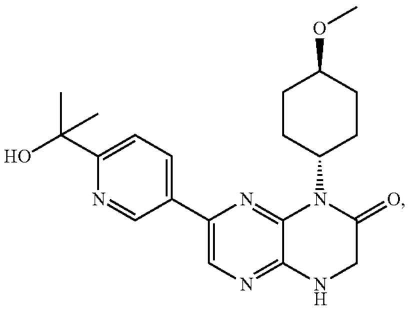 [SMILES: CO[C@H]1CC[C@H](N2C(=O)CNc3ncc(-c4ccc(C(C)(C)O)nc4)nc32)CC1]

or a pharmaceutically acceptable salt thereof.

As understood by those skilled in the art, the scope of the present invention also includes analogues or derivatives of all other agents functionally categorized under their respective class based on their targets, which analogues or derivatives include, but are not limited to, salt, ester, ether, solvate, hydrate, stereoisomer or prodrug.

E. Removal of Stimulatory Reagents

In some embodiments, the stimulatory reagent is removed or separated from the cells or cell populations prior to collecting, harvesting, or formulating the cells. In some embodiments, the stimulatory reagents are removed or separated from the cells or cell populations after or during the incubation, e.g., an incubation described herein such as in Section I-C. In certain embodiments, the cells or cell population undergoes a process, procedure, step, or technique to remove the stimulatory reagent after the incubation but prior to steps for collecting, harvesting, or formulating the cells. In particular embodiments, the cells or cell population undergoes a process, procedure, step, or technique to remove the stimulatory reagent after the incubation. In some aspects, when stimulatory reagent is separated or removed from the cells during the incubation, the cells are returned to the same incubation conditions as prior to the separation or removal for the remaining duration of the incubation.

In certain embodiments, the stimulatory reagent is removed and/or separated from the cells. Without wishing to be bound by theory, particular embodiments contemplate that the binding and/or association between a stimulatory reagent and cells may, in some circumstances, be reduced over time during the incubation. In certain embodiments, one or more agents may be added to reduce the binding and/or association between the stimulatory reagent and the cells. In particular embodiments, a change in cell culture conditions, e.g., the addition of an agent, may reduce the binding and/or association between the stimulatory reagent and the cells. Thus, in some embodiments, the stimulatory reagent may be removed from an incubation, cell culture system, and/or a solution separately from the cells, e.g., without removing the cells from the incubation, cell culture system, and/or a solution as well.

In certain embodiments, the stimulatory reagent is separated and/or removed from the cells after an amount of time. In particular embodiments, the amount of time is an amount of time from the initiation of the stimulation. In particular embodiments the start of the incubation is considered at or at about the time the cells are contacted with the stimulatory reagent and/or a media or solution containing the stimulatory reagent. In particular embodiments, the stimulatory reagent is removed or separated from the cells within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the stimulatory reagent is removed or separated from the cells within or within about 5 days, 4 days, 3 days, 2 days, one day, or 0.5 days, inclusive, of the initiation of the stimulation. In particular embodiments, the stimulatory reagent is removed or separated from the cells at or at about 48 hours or at or at about 2 days after the stimulation is initiated. In certain embodiments, the stimulatory reagent is removed or separated from the cells at or at about 72 hours or at or at about 3 days after the stimulation is initiated. In some embodiments, the stimulatory reagent is removed or separated from the cells at or at about 96 hours or at or at about 4 days after the stimulation is initiated.

1. Removal of Bead Reagents

In certain embodiments, the bead stimulatory reagent, e.g., an anti-CD3/anti-CD28 antibody conjugated paramagnetic bead, is separated or removed from the cells or the cell population. Methods for removing stimulatory reagents (e.g. stimulatory reagents that are or contain particles such as bead particles or magnetizable particles) from cells are known. In some embodiments, the use of competing antibodies, such as non-labeled antibodies, can be used, which, for example, bind to a primary antibody of the stimulatory reagent and alter its affinity for its antigen on the cell, thereby permitting for gentle detachment. In some cases, after detachment, the competing antibodies may remain associated with the particle (e.g. bead particle) while the unreacted antibody is or may be washed away and the cell is free of isolating, selecting, enriching and/or activating antibody. Exemplary of such a reagent is DETACaBEAD (Friedl et al. 1995; Entschladen et al. 1997). In some embodiments, particles (e.g. bead particles) can be removed in the presence of a cleavable linker (e.g. DNA linker), whereby the particle-bound antibodies are conjugated to the linker (e.g. CELLection, Dynal). In some cases, the linker region provides a cleavable site to remove the particles (e.g. bead particles) from the cells after isolation, for example, by the addition of DNase or other releasing buffer. In some embodiments, other enzymatic methods can also be employed for release of a particle (e.g. bead particle) from cells. In some embodiments, the particles (e.g. bead particles or magnetizable particles) are biodegradable.

In some embodiments, the stimulatory reagent is magnetic, paramagnetic, and/or superparamagnetic, and/or contains a bead that is magnetic, paramagnetic, or superparamagnetic, and the stimulatory reagent may be removed from the cells by exposing the cells to a magnetic field. Examples of suitable equipment containing magnets for generating the magnetic field include DynaMag CTS (Thermo Fisher), Magnetic Separator (Takara) and EasySep Magnet (Stem Cell Technologies).

In particular embodiments, the stimulatory reagent is removed or separated from the cells prior to the completion of the provided methods, e.g., prior to harvesting, collecting, and/or formulating engineered cells produced by the methods provided herein. In some embodiments, the stimulatory reagent is removed and/or separated from the cells after engineering, e.g., transducing or transfecting, the cells.

In some embodiments, the stimulatory bead reagent, e.g., the stimulatory magnetic bead reagent, is removed or separated from the cells or cell populations prior to collecting, harvesting, or formulating the cells. In some embodiments, the stimulatory bead reagent, e.g., the stimulatory magnetic bead reagent, are removed or separated from the cells or cell populations by exposure to a magnetic field during or after the incubation, e.g., an incubation described herein such as in Section I-C. In certain embodiments, the cells or cell population are exposed to the magnetic field to remove the stimulatory bead reagent, e.g., the stimulatory magnetic bead reagent, after the incubation but prior to steps for collecting, harvesting, or formulating the cells. In particular embodiments, the cells or cell population undergoes is exposed to the magnetic field to remove the stimulatory bead reagent, e.g., the stimulatory magnetic bead reagent, after the incubation. In some aspects, when the stimulatory bead reagent is separated or removed from the cells or cell population during the incubation, the cells or cell population are returned to the same incubation conditions as prior to the exposure to the magnetic field for the remaining duration of the incubation.

In particular embodiments, the stimulatory bead reagent, e.g., the stimulatory magnetic bead reagent, is removed or separated from the cells, e.g., by exposure to a magnetic field, within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the stimulatory bead reagent, e.g., the stimulatory magnetic bead reagent, is removed or separated from the cells, e.g., by exposure to a magnetic field, within or within about 5 days, 4 days, 3 days, 2 days, one day, or 0.5 days, inclusive, of the initiation of the stimulation. In certain embodiments, the stimulatory bead reagent, e.g., the stimulatory magnetic bead reagent, is removed or separated from the cells, e.g., by exposure to a magnetic field, at or at about 72 hours or at or at about 3 days after the stimulation is initiated. In certain embodiments, the stimulatory bead reagent, e.g., the stimulatory magnetic bead reagent, is removed or separated from the cells, e.g., by exposure to a magnetic field, at or at about 48 hours or at or at about 2 days after the stimulation is initiated. In some embodiments, the stimulatory bead reagent, e.g., the stimulatory magnetic bead reagent, is removed or separated from the cells, e.g., by exposure to a magnetic field, at or at about 96 hours or at or at about 4 days after the stimulation is initiated.

2. Removal of Oligomeric Reagents

In some embodiments, the population of incubated T cells was produced or generated in accord with any of the methods provided herein in which a substance, such as a competition agent, was added to T cells to disrupt, such as to lessen and/or terminate, the signaling of the stimulatory agent or agents. In some embodiments, the population of the incubated T cells contains the presence of a substance, such as a competition agent, e.g. biotin or a biotin analog, e.g. D-Biotin. In some embodiments, the substance, such as a competition agent, e.g. biotin or a biotin analog, e.g. D-Biotin, is present in an amount that is at least 1.5-fold greater, at least 2-fold, at least 3-fold, at least 4-fold, at least 5-fold, at least 10-fold, at least 100-fold, at least 1000-fold or more greater than the amount of the substance in a reference population or preparation of cultured T cells in which the substance was not added exogenously during the incubation. In some embodiments, the amount of the substance, such as a competition agent, e.g. biotin or a biotin analog, e.g. D-Biotin, in the population of cultured T cells is from or from about 10 μM to 100 μM, 100 μM to 1 mM, 100 μM to 500 μM or 10 μM to 100 μM. In some embodiments, 10 μM or about 10 μM of biotin or a biotin analog, e.g., D-biotin, is added to the cells or the cell population to separate or remove the oligomeric stimulatory reagent from the cells or cell population.

In certain embodiments, the one or more agents (e.g., agents that stimulate or activate a TCR and/or a coreceptor) associate with, such as are reversibly bound to, the oligomeric reagent, such as via the plurality of the particular binding sites (e.g., binding sites Z) present on the oligomeric reagent. In some cases, this results in the agents being closely arranged to each other such that an avidity effect can take place if a target cell having (at least two copies of) a cell surface molecule that is bound by or recognized by the agent is brought into contact with the agent. In some aspects, the receptor binding reagent has a low affinity towards the receptor molecule of the cell at binding site B, such that the receptor binding reagent dissociates from the cell in the presence of the competition reagent. Thus, in some embodiments, the agents are removed from the cells in the presence of the competition reagent.

In some embodiments, the oligomeric stimulatory reagent is a streptavidin mutein oligomer with reversibly attached anti-CD3 and anti-CD28 Fabs. In some embodiments, the Fabs are attached contain streptavidin binding domains, e.g., that allow for the reversible attachment to the streptavidin mutein oligomer. In some cases, anti-CD3 and anti-CD28 Fabs are closely arranged to each other such that an avidity effect can take place if a T cell expressing CD3 and/or CD28 is brought into contact with the oligomeric stimulatory reagent with the reversibly attached Fabs. In some aspects, the Fabs have a low affinity towards CD3 and CD28, such that the Fabs dissociate from the cell in the presence of the competition reagent, e.g., biotin or a biotin variant or analogue. Thus, in some embodiments, the Fabs are removed or dissociated from the cells in the presence of the competition reagent, e.g., D-biotin.

In some embodiments, the oligomeric stimulatory stimulatory reagent, e.g., the oligomeric stimulatory streptavidin mutein reagent, is removed or separated from the cells or cell populations prior to collecting, harvesting, or formulating the cells. In some embodiments, oligomeric stimulatory reagent, e.g., the oligomeric stimulatory streptavidin mutein reagent, is removed or separated from the cells or cell populations by contact or exposure to a competition reagent, e.g., biotin or a biotin analog such as D-biotin, after or during the incubation, e.g., an incubation described herein such as in Section I-C-3. In certain embodiments, the cells or cell population are contacted or exposed to a competition reagent, e.g., biotin or a biotin analog such as D-biotin, to remove oligomeric stimulatory reagent, e.g., the oligomeric stimulatory streptavidin mutein reagent, after the incubation but prior to steps for collecting, harvesting, or formulating the cells. In particular embodiments, the cells or cell population are contacted or exposed to a competition reagent, e.g., biotin or a biotin analog such as D-biotin, to remove the oligomeric stimulatory reagent, e.g., the oligomeric stimulatory streptavidin mutein reagent, after the incubation. In some aspects, when oligomeric stimulatory reagent, e.g., the oligomeric stimulatory streptavidin mutein reagent, is separated or removed from the cells during the incubation, e.g., by contact or exposure to a competition reagent, e.g., biotin or a biotin analog such as D-biotin, the cells are returned to the same incubation conditions as prior to the separation or removal for the remaining duration of the incubation.

In some embodiments, the cells are contacted with, with about, or with at least 0.01 μM, 0.05 μM, 0.1 μM, 0.5 μM, 1 μM, 2 μM, 3 μM, 4 μM, 5 μM, 10 μM, 100 μM, 500 μM, 0.01 μM, 1 mM, or 10 mM of the competition reagent to remove or separate the oligomeric stimulatory reagent from the cells. In various embodiments, the cells are contacted with, with about, or with at least 0.01 μM, 0.05 μM, 0.1 μM, 0.5 μM, 1 μM, 2 μM, 3 μM, 4 μM, 5 UM, 10 μM, 100 μM, 500 μM, 0.01 μM, 1 mM, or 10 mM of biotin or a biotin analog such as D-biotin, to remove or separate the stimulatory streptavidin mutein oligomers with reversibly attached anti-CD3 and anti-CD28 Fabs from the cells. In various embodiments, the cells are contacted with between or between about 100 μM and 10 mM, e.g., 1 mM, of biotin or a biotin analog such as D-biotin, to remove or separate the oligomeric stimulatory reagent, such as streptavidin mutein oligomers with reversibly attached anti-CD3 and anti-CD28 Fabs from the cells. In various embodiments, the cells are contacted with between or between about 100 μM and 10 mM, e.g., 1 mM, of biotin or a biotin analog such as D-biotin for or for about 2 hours, 6 hours, 12 hours, 18 hours, 24 hours, 30 hours, 36 hours, 42 hours, or 48 hours post contact or exposure to D-biotin.

In particular embodiments, the oligomeric stimulatory reagent, e.g., the oligomeric stimulatory streptavidin mutein reagent, is removed or separated from the cells within or within about 120 hours, 108 hours, 96 hours, 84 hours, 72 hours, 60 hours, 48 hours, 36 hours, 24 hours, or 12 hours, inclusive, of the initiation of the stimulation. In particular embodiments, the oligomeric stimulatory reagent, e.g., the oligomeric stimulatory streptavidin mutein reagent, is removed or separated from the cells within or within about 5 days, 4 days, 3 days, 2 days, one day or 0.5 days, inclusive, of the initiation of the stimulation. In particular embodiments, the oligomeric stimulatory reagent, e.g., the oligomeric stimulatory streptavidin mutein reagent, is removed or separated from the cells at or at about 48 hours or at or at about 2 days after the stimulation is initiated. In certain embodiments, the oligomeric stimulatory reagent, e.g., the oligomeric stimulatory streptavidin mutein reagent, is removed or separated from the cells at or at about 72 hours or at or at about 3 days after the stimulation is initiated. In some embodiments, the oligomeric stimulatory reagent, e.g., the oligomeric stimulatory streptavidin mutein reagent is removed or separated from the cells at or at about 96 hours or at or at about 4 days after the stimulation is initiated.

In certain embodiments, the cells or cell population are contacted or exposed to a competition reagent, e.g., biotin or a biotin analog such as D-biotin, to remove oligomeric stimulatory reagent, e.g., the oligomeric stimulatory streptavidin mutein reagent, at or at about 48 hours or at or at about 2 days after the stimulation is initiated, e.g., during or after the incubation described herein such as in Section I-C-3. In some aspects, when oligomeric stimulatory reagent, e.g., the oligomeric stimulatory streptavidin mutein reagent, is separated or removed from the cells during the incubation, e.g., by contact or exposure to a competition reagent, e.g., biotin or a biotin analog such as D-biotin, the cells are returned to the same incubation conditions as prior to the separation or removal for the remaining duration of the incubation. In other aspects, when oligomeric stimulatory reagent, e.g., the oligomeric stimulatory streptavidin mutein reagent, is separated or removed from the cells after the incubation, e.g., by contact or exposure to a competition reagent, e.g., biotin or a biotin analog such as D-biotin, the cells are further incubated for or for about 2 hours, 6 hours, 12 hours, 18 hours, 24 hours, 30 hours, 36 hours, 42 hours, or 48 hours post contact or exposure to the competition reagent. In some embodiments, the transduced cells with D-Biotin treatment are further incubated for or for about 48 hours post D-Biotin addition.

F. Harvesting, Collecting, or Formulating the Cells

In some embodiments, the cells are harvested or collected. In particular embodiments, the cells are collected of harvested after the completion of the incubation. In certain embodiments, the collected or harvested cells are the cells of an output population. In some embodiments, the output population includes cells that are viable, CD3+, CD4+, CD8+, and/or positive for a recombinant receptor, e.g., CAR+. In particular embodiments, the harvested CD4+ T cells and formulated CD8+ T cells are the output CD4+ and CD8+ T cells. In particular embodiments, a formulated cell population, e.g., a formulated population of enriched CD4+ and CD8+ cells, is an output cell population, e.g., an output population of enriched CD4+ and CD8+ cells.

In some embodiments, the cells or cell population that is harvested, collected, or formulated have not undergone any expansion, e.g., any conditions where the cells were incubated or cultivated under conditions that increase the amount of viable cells during the incubation or cultivation. For example, in some aspects, the cells that are harvested have not undergone any incubation or cultivation where the amount of total viable cells is increased at the end of the incubation or cultivation as compared to the number of total viable cells at the beginning of the incubation or cultivation. In some embodiments, the cells that are harvested have not undergone any incubation or cultivation step explicitly for the purpose of increasing (e.g., expanding) the total number of viable cells at the end of the incubation or cultivation process compared to the beginning of said incubation or cultivation process. In some embodiments, the cells are incubated or cultivated under conditions that may result in expansion, but the incubating or cultivating conditions are not carried out for purposes of expanding the cell population. In some embodiments, the cells that are harvested may have undergone expansion despite having been manufactured in a process that does not include an expansion step. In some embodiments, a manufacturing process that does not include an expansion step is referred to as a non-expanded or minimally expanded process. A "non-expanded" process may also be referred to as a "minimally expanded" process. In some embodiments, a non-expanded or minimally expanded process may result in cells having undergone expansion despite the process not including a step for expansion. In some embodiments, the the cells that are harvested may have undergone an incubation or cultivating step that includes a media composition designed to reduce, suppress, minimize, or eliminate expansion of a cell population as a whole. In some embodiments, the collected, harvested, or formulated cells have not previously undergone an incubation or cultivation that was performed in a bioreactor, or under conditions where the cells were rocked, rotated, shaken, or perfused for all or a portion of the incubation or cultivation.

In some embodiments, a cell selection, isolation, separation, enrichment, and/or purification step is performed before the cells or cell population is harvested, collected, or formulated. In some embodiments, the cell selection, isolation, separation, enrichment, and/or purification step is carried out using chromatography as disclosed herein. In some embodiments, a T cell selection step by chromatography is performed after T cell transduction, but prior to harvesting, prior to collecting, and/or prior to formulating the cells. In some embodiments, a T cell selection step by chromatography is performed immediately prior to harvesting the cells.

In certain embodiments, the amount of time from the initiation of the stimulation to collecting, harvesting, or formulating the cells is, is about, or is less than 36 hours, 42 hours, 48 hours, 54 hours, 60 hours, 72 hours, 84 hours, 96 hours, 108 hours, or 120 hours. In certain embodiments, the amount of time from the initiation of the stimulation to collecting, harvesting, or formulating the cells is, is about, or is less than 1.5 days, 2 days, 3 days, 4 days, or 5 days. In some embodiments, the amount of time from the initiation of the stimulation to collecting, harvesting, or formulating the cells for generating engineered cells, from the initiation of the stimulation to collecting, harvesting, or formulating the cells is between or between about 36 hours and 120 hours, 48 hours and 96 hours, or 48 hours and 72 hours, inclusive, or between or between about 1.5 days and 5 days, 2 days and 4 days, or 2 day and 3 days, inclusive. In particular embodiments, the amount of time from the initiation of incubation to harvesting, collecting, or formulating the cells is, is about, or is less than 48 hours, 72 hours, or 96 hours. In particular embodiments, the amount of time from the initiation of incubation to harvesting, collecting, or formulating the cells is, is about, or is less than 2 days, 3 days, or 4 days. In particular embodiments, the amount of time from the initiation of incubation to harvesting, collecting, or formulating the cells is 48 hours±6 hours, 72 hours±6 hours, or 96 hours±6 hours. In particular embodiments, the amount of time from the initiation of incubation to harvesting, collecting, or formulating the cells is or is about 96 hours or four days.

In particular embodiments, the cells are harvested, collected, or formulated in a serum-free medium, such as one described herein in Section II or in PCT/US2018/064627, which is incorporated herein by reference. In some embodiments, the cells are harvested, collected, or formulated into the same serum-free medium as used during the incubation, e.g., as described herein in Section I-C-3.

In particular embodiments, the cells are harvested, collected or formulated in a basal media that does not contain one or more recombinant cytokines and that does not contain a serum component, i.e. is a serum-free media, but may contain one or more additional components such as described in Section II. B. In particular embodiments, use of such a serum-free media provides for a lean media that provides for maintenance of cells but does not include certain factors that may activate or render the cells metabolically active thereby fostering the cells in a state that is or is likely to be a resting or a quiescent state. In some aspects, incubation in the presence of such a serum-free media allows the cells to recover or rest after the stimulation and genetic engineering (e.g. transduction). In some aspects, harvesting, collecting or formulating cells in the presence of such a serum-free media results in a formulation of the output composition containing cells that are less susceptible to damage or loss of viability, e.g., when the harvested/formulated cells are cryopreserved and then thawed immediately prior to use. In some embodiments, cells in the output composition when thawed have lower levels of caspase or other marker of apoptosis than cells that have been incubated in a similar media but containing one or more recombinant cytokines, serum, or other factors that may make the cells more metabolically active at cryopreservation of the output composition.

In certain embodiments, one or more populations of enriched T cells are formulated. In particular embodiments, one or more populations of enriched T cells are formulated after the one or more populations have been engineered and/or cultivated. In particular embodiments, the one or more populations are input populations. In some embodiments, the one or more input populations have been previously cryoprotected and stored, and are thawed prior to the incubation.

In certain embodiments, the cells are harvested or collected at least when the integrated vector is detected in the genome. In some embodiments, the cells are harvested or collected prior to stable integrated vector copy number (iVCN) per diploid genome. In particular embodiments, the cells are harvested or collected after the integrated vector is detected in the genome but prior to when a stable iVCN per diploid genome is achieved.

In some embodiments, the cells are harvested or collected before the iVCN of reaches, reaches about, or reaches at least 5.0, 4.0, 3.0, 2.5, 2.0, 1.75, 1.5, 1.25, 1.2, 1.1, 1.0, 0.9, 0.8, 0.75, 0.7, 0.6, 0.5, 0.4, 0.3, or 0.25 copies per diploid genome. In particular embodiments, the cells are harvested or collected before the iVCN reaches or about 1.0 copy per diploid genome. In some embodiments, the cells are collected or harvested before the iVCN reaches or about 0.5 copies per diploid genome.

In certain embodiments, the cells are harvested prior to, prior to about, or prior to at least one, two, three, four, five, six, eight, ten, twenty, or more cell doublings of the cell population, e.g., doublings that occur during the incubating.

In particular embodiments, the cells are harvested or collected at a time before the total number cells, e.g., total number of incubated cells or cells undergoing the incubation, is greater than or than about one, two, three, four, five, six, eight, ten, twenty, or more than twenty times the number of cells of the input population, e.g., the total number of cells that were contacted with the stimulatory reagent. In some embodiments, the cells are harvested or collected at a time before the total number of incubated cells is greater than or than about one, two, three, four, five, six, eight, ten, twenty, or more than twenty times the total number of cells that were transformed, transduced, or spinoculated, e.g., the total number of cells that were contacted with a viral vector. In certain embodiments, the cells are T cells, viable T cells, CD3+ T cells, CD4+ T cells, CD8+ T cells, CAR expressing T cells, or a combination of any of the foregoing. In particular embodiments, the cells are harvested or collected at a time before the total number of cells is greater than the total number of cells of the input population. In various embodiments, the cells are harvested or collected at a time before the total number of viable CD3+ T cells is greater than the total number of viable CD3+ cells of the input population. In particular embodiments, the cells are harvested or collected at a time before the total number of cells is greater than the total number of cells of the transformed, transduced, or spinoculated cells. In various embodiments, the cells are harvested or collected at a time before the total number of viable CD3+ T cells is greater than the total number of viable CD3+ cells of the transformed, transduced, or spinoculated cells. In various embodiments, the cells are harvested or collected at a time before the total number of viable CD4+ cells and CD8+ cells is greater than the total number of viable CD4+ cells and CD8+ cells of the input population. In particular embodiments, the cells are harvested or collected at a time before the total number of cells is greater than the total number of cells of the transformed, transduced, or spinoculated cells. In various embodiments, the cells are harvested or collected at a time before the total number of viable CD4+ cells and CD8+ cells is greater than the total number of viable CD4+ cells and CD8+ cells of the transformed, transduced, or spinoculated cells.

In certain embodiments, the process comprises a step of filtering the cell composition during or after the harvesting or collecting, e.g., using a filter (e.g., a 40 μm filter), for example, to remove large particulates. In certain embodiments, the filtering step is performed while the cells are being harvested or collected. For example, a filter may be in-line with between the cells being incubated after transduction and a harvesting/collection device such as the Sepax® or Sepax 2® cell processing systems. In certain embodiments, the cells are harvested or collected and then filtered before the filtered composition is optionally washed. In certain embodiments, the cells are harvested or collected, washed, and the washed cell composition is filtered.

In certain embodiments, the formulated cells are output cells. In some embodiments, a formulated population of enriched T cells is an output population of enriched T cells. In particular embodiments, the formulated CD4+ T cells and formulated CD8+ T cells are the output CD4+ and CD8+ T cells. In particular embodiments, a formulated cell population, e.g., a formulated population of enriched CD4+ and CD8+ cells, is an output cell population, e.g., an output population of enriched CD4+ and CD8+ cells.

In some embodiments, cells can be formulated into a container, such as a bag or vial.

In some embodiments, the cells are formulated in a pharmaceutically acceptable buffer, which may, in some aspects, include a pharmaceutically acceptable carrier or excipient. In some embodiments, the processing includes exchange of a medium into a medium or formulation buffer that is pharmaceutically acceptable or desired for administration to a subject. In some embodiments, the processing steps can involve washing the transduced and/or expanded cells to replace the cells in a pharmaceutically acceptable buffer that can include one or more optional pharmaceutically acceptable carriers or excipients. Exemplary of such pharmaceutical forms, including pharmaceutically acceptable carriers or excipients, can be any described below in conjunction with forms acceptable for administering the cells and compositions to a subject. The pharmaceutical composition in some embodiments contains the cells in amounts effective to treat or prevent the disease or condition, such as a therapeutically effective or prophylactically effective amount.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulations can include aqueous solutions. The formulation or composition may also contain more than one active ingredient useful for the particular indication, disease, or condition being treated with the cells, preferably those with activities complementary to the cells, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, and/or vincristine.

Compositions in some embodiments are provided as sterile liquid preparations, e.g., isotonic aqueous solutions, suspensions, emulsions, dispersions, or viscous compositions, which may in some aspects be buffered to a selected pH. Liquid compositions can comprise carriers, which can be a solvent or dispersing medium containing, for example, water, saline, phosphate buffered saline, polyol (for example, glycerol, propylene glycol, liquid polyethylene glycol) and suitable mixtures thereof. Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

In some embodiments, the formulation buffer contains a cryopreservative. In some embodiments, the cell are formulated with a cryopreservative solution that contains 1.0% to 30% DMSO solution, such as a 5% to 20% DMSO solution or a 5% to 10% DMSO solution. In some embodiments, the cryopreservation solution is or contains, for example, PBS containing 20% DMSO and 8% human serum albumin (HSA), or other suitable cell freezing media. In some embodiments, the cryopreservative solution is or contains, for example, at least or about 7.5% DMSO. In some embodiments, the processing steps can involve washing the transduced and/or expanded cells to replace the cells in a cryopreservative solution. In some embodiments, the cells are frozen, e.g., cryoprotected or cryopreserved, in media and/or solution with a final concentration of or of about 12.5%, 12.0%, 11.5%, 11.0%, 10.5%, 10.0%, 9.5%, 9.0%, 8.5%, 8.0%, 7.5%, 7.0%, 6.5%, 6.0%, 5.5%, or 5.0% DMSO, or between 1% and 15%, between 6% and 12%, between 5% and 10%, or between 6% and 8% DMSO. In particular embodiments, the cells are frozen, e.g., cryoprotected or cryopreserved, in media and/or solution with a final concentration of or of about 5.0%, 4.5%, 4.0%, 3.5%, 3.0%, 2.5%, 2.0%, 1.5%, 1.25%, 1.0%, 0.75%, 0.5%, or 0.25% HSA, or between 0.1% and −5%, between 0.25% and 4%, between 0.5% and 2%, or between 1% and 2% HSA.

In particular embodiments, the composition of enriched T cells, e.g., T cells that have been stimulated, engineered, and/or cultivated, are formulated, cryoprotected, and then stored for an amount of time. In certain embodiments, the formulated, cryoprotected cells are stored until the cells are released for infusion. In particular embodiments, the formulated cryoprotected cells are stored for between 1 day and 6 months, between 1 month and 3 months, between 1 day and 14 days, between 1 day and 7 days, between 3 days and 6 days, between 6 months and 12 months, or longer than 12 months. In some embodiments, the cells are cryoprotected and stored for, for about, or for less than 1 days, 2 days, 3 days, 4 days, 5 days, 6 days, or 7 days. In certain embodiments, the cells are thawed and administered to a subject after the storage. In certain embodiments, the cells are stored for or for about 5 days. In some embodiments, the formulated cells are not cryopreserved.

In some embodiments, the formulation is carried out using one or more processing step including washing, diluting or concentrating the cells, such as the cultured or expanded cells. In some embodiments, the processing can include dilution or concentration of the cells to a desired concentration or number, such as unit dose form compositions including the number of cells for administration in a given dose or fraction thereof. In some embodiments, the processing steps can include a volume-reduction to thereby increase the concentration of cells as desired. In some embodiments, the processing steps can include a volume-addition to thereby decrease the concentration of cells as desired. In some embodiments, the processing includes adding a volume of a formulation buffer to transduced and/or expanded cells. In some embodiments, the volume of formulation buffer is from or from about 10 mL to 1000 mL, such as at least or about at least or about or 50 mL, 100 mL, 200 mL, 300 mL, 400 mL, 500 mL, 600 mL, 700 mL, 800 mL, 900 mL or 1000 mL.

In some embodiments, such processing steps for formulating a cell composition are carried out in a closed system. Exemplary of such processing steps can be performed using a centrifugal chamber in conjunction with one or more systems or kits associated with a cell processing system, such as a centrifugal chamber produced and sold by Biosafe SA, including those for use with the Sepax® or Sepax 2® cell processing systems. An exemplary system and process is described in International Publication Number WO2016/073602. In some embodiments, the method includes effecting expression from the internal cavity of the centrifugal chamber a formulated composition, which is the resulting composition of cells formulated in a formulation buffer, such as pharmaceutically acceptable buffer, in any of the above embodiments as described. In some embodiments, the expression of the formulated composition is to a container, such as a bag that is operably linked as part of a closed system with the centrifugal chamber. In some embodiments, the container, such as bag, is connected to a system at an output line or output position.

In some embodiments, the closed system, such as associated with a centrifugal chamber or cell processing system, includes a multi-port output kit containing a multi-way tubing manifold associated at each end of a tubing line with a port to which one or a plurality of containers can be connected for expression of the formulated composition. In some aspects, a desired number or plurality of output containers, e.g., bags, can be sterilely connected to one or more, generally two or more, such as at least 3, 4, 5, 6, 7, 8 or more of the ports of the multi-port output. For example, in some embodiments, one or more containers, e.g., bags can be attached to the ports, or to fewer than all of the ports. Thus, in some embodiments, the system can effect expression of the output composition into a plurality of output bags.

In some aspects, cells can be expressed to the one or more of the plurality of output bags in an amount for dosage administration, such as for a single unit dosage administration or multiple dosage administration. For example, in some embodiments, the output bags may each contain the number of cells for administration in a given dose or fraction thereof. Thus, each bag, in some aspects, may contain a single unit dose for administration or may contain a fraction of a desired dose such that more than one of the plurality of output bags, such as two of the output bags, or 3 of the output bags, together constitute a dose for administration.

Thus, the containers, e.g., output bags, generally contain the cells to be administered, e.g., one or more unit doses thereof. The unit dose may be an amount or number of the cells to be administered to the subject or twice the number (or more) of the cells to be administered. It may be the lowest dose or lowest possible dose of the cells that would be administered to the subject.

In some embodiments, each of the containers, e.g., bags, individually comprises a unit dose of the cells. Thus in some embodiments, each of the containers comprises the same or approximately or substantially the same number of cells. In some embodiments, each unit dose contains at least or about at least $1\times10^6$, $2\times10^6$, $5\times10^6$, $1\times10^7$, $5\times10^7$, or $1\times10^8$ engineered cells, total cells, T cells, or PBMCs. In some embodiments, the volume of the formulated cell composition in each bag is 10 mL to 100 mL, such as at least or about at least 20 mL, 30 mL, 40 mL, 50 mL, 60 mL, 70 mL, 80 mL, 90 mL or 100 mL.

In some embodiments, such cells produced by the method, or a composition comprising such cells, are administered to a subject for treating a disease or condition.

G. Sequential Selection, Parallel Selection, and Polishing

The methods provided herein allow for multiple selection steps, for example by column chromatography, to isolate and/or enrich a target cell population (e.g., T cells, CD3+, CD4+, CD8+ T cells). In some embodiments, one or more selection steps are carried out at one or more time points or following certain steps of the process for creating an output therapeutic cell composition, for example a process as described by Sections IA-F above. In some embodiments, selection steps that occur following initial cell selection, for example as described in Section I-A, are referred to as polishing steps. Polishing steps may be performed for a variety of purposes, including, but not limited to, further purification of the cell composition, selection of specific cell subtypes (e.g., CD28+, CD62L+, CCR7+, CD27+, CD127+, CD4+, CD8+, CD45RA+, and/or CD45RO+ T cells), removal of dead cells (e.g., selection of viable cells), selection of successfully engineered cells (e.g., cells expressing a transgene (e.g., chimeric antigen receptor (CAR), T cell receptor (TCR), etc.), or for adjusting the ratio, total number, or concentration of specific cell types (e.g., CD4+ to CD8+ cells, CAR+ or TCR+ cells to CAR- or TCR-cells, or total number or concentration of CD4+, CD8+, CAR+, TCR+, and/or viable cells). In some embodiments, a selection step (e.g., polishing step) is useful for increasing product control and/or decreasing between patient variance.

In some embodiments, a selection step (e.g., an initial selection step and/or a polishing step) includes multiple selection steps for, for example, further purifying the cell composition, selection of specific cell subtypes, selection of viable cells, selection of engineered cells, and/or adjusting the ratio, total number, or concentration of cells. In some embodiments, a selection step (e.g., polishing step) is performed prior to incubation, for example incubation as described in Section I-C-3. In some embodiments, a selection step (e.g., polishing step) is performed prior to harvesting and collection, for example harvesting and collection as described in Section I-H.

In some aspects, such methods (e.g., selection steps (e.g., initial selection and/or polishing steps)) are achieved by a single process stream, such as in a closed system, by employing sequential selections in which a plurality of different cell populations from a sample (e.g., output composition of stimulated and/or engineered cells), as provided herein, are enriched and/or isolated. In some aspects, carrying out the separation or isolation in the same vessel or set of vessels, e.g., tubing set, is achieved by carrying out sequential positive and negative selection steps, the subsequent step subjecting the negative and/or positive fraction from the previous step to further selection, where the entire process is carried out in the same tube or tubing set. In one embodiment, a sample (e.g., output composition of stimulated and/or engineered cells) containing target cells is subjected to a sequential selection in which a first selection is effected to enrich for one of the CD4+ or CD8+ populations, and the non-selected cells from the first selection are used as the source of cells for a second selection to enrich for the other of the CD4+ or CD8+ populations. In some embodiments, a further selection or selections can be effected to enrich for sub-populations of one or both of the CD4+ or CD8+ population, for example, central memory T ($T_{CM}$) cells or naïve T cells. In some embodiments, specific subpopulations of T cells (e.g., CD3+, CD4+, CD8+ cells), such as cells positive or expressing high levels of one or more surface markers, e.g., CD28+, CD62L+, CCR7+, CD27+, CD127+, CD4+, CD8+, CD45RA+, and/or CD45RO+ T cells, are selected by positive or negative selection techniques during a selection step (e.g., an initial selection step and/or a polishing step). In some embodiments, a cell population (e.g., output composition of stimulated and/or engineered cells) containing target cells is subjected to a sequential selection in which the polishing step selects for viable cells. In some embodiments, the polishing step allows for controlling or adjusting the ratio or total number of cells in the cell composition.

In one embodiment, a sample (e.g., output composition of stimulated and/or engineered cells) containing target cells is subjected to a sequential selection in which a first selection is effected to enrich for a CD3+ population. In some embodiments, a further selection or selections can be effected to enrich for sub-populations of the CD3+ population, for example, CD4+ cells. In some embodiments, a further selection or selections can be effected to enrich for sub-populations of the CD3+ population, for example, CD8+ cells. In some embodiments, the further selection or selections can be effected to enrich for viable cells. In some embodiments, the further selection or selections can be effected to enrich subpopulations of CD3+ cells, for example CD3+CD4+ and/or CD3+CD8+ cells that are viable. In some embodiments, selecting viable cells includes or consists of removing dead cells from the cell population (e.g., output composition of stimulated and/or engineered cells or subpopulations thereof).

In some embodiments, the methods (e.g., selection steps (e.g., an initial selection step and/or a polishing steps) disclosed in this Section do not need to be carried out using sequential selection techniques. In some embodiments, the methods (e.g., selection steps (e.g., initial selection and/or polishing steps)) disclosed in this Section can be carried out using sequential selection techniques in combination with parallel selection techniques. In some embodiments, the selection step (e.g., initial selection and/or polishing step)

does not employ sequential selection or may employ sequential selection that does not occur in a closed system or in a set of vessels using the same tubing. In some embodiments, the selection step (e.g., initial selection and/or polishing step) is accomplished in a single step, for example using a single chromatography column. In some embodiments, the selection step (e.g., initial selection and/or polishing step) is accomplished using a parallel selection technique. For example, the selection step (e.g., initial selection and/or polishing step) is achieved by carrying out positive and/or negative selection steps simultaneously, for example in a closed system where the entire process is carried out in the same tube or tubing set. In some embodiments, a sample (e.g., output composition of stimulated and/or engineered cells) containing target cells is subjected to a parallel selection in which the sample (e.g., output composition of stimulated and/or engineered cells) is load onto two or more chromatography columns, where each column effects selection of a cell population. In some embodiments, the two or more chromatography columns effect selection of CD3+, CD4+, or CD8+ populations individually. In some embodiments, the two or more chromatography columns effect selection of the same cell population. For example, the two or more chromatography columns may effect selection of CD3+ cells. In some embodiments, the two or more chromatography columns, including affinity chromatography or gel permeation chromatography, independently effect selection of the same cell population. In some embodiments, the two or more chromatography columns, including affinity chromatography or gel permeation chromatography, independently effect selection of different cell populations. In some embodiments, a further selection or selections can be effected to enrich for subpopulations of one or all cell populations selected via parallel selection. For example, selected cells may be further selected for central memory T ($T_{CM}$) cells or naïve T cells. In some embodiments, a sample (e.g., output composition of stimulated and/or engineered cells) containing target cells (e.g., CD3+ cells) is subjected to a parallel selection in which parallel selection is effected to enrich for a CD4+ population and a CD8+ population. In some embodiments, a further selection or selections can be effected to enrich for sub-populations of the CD4+ and CD8+ populations, for example, central memory T ($T_{CM}$) cells or naïve T cells. It is contemplated that in some aspects, specific subpopulations of T cells (e.g., CD3+, CD4+, CD8+ T cells), such as cells positive or expressing high levels of one or more surface markers, e.g., CD28+, CD62L+, CCR7+, CD27+, CD127+, CD4+, CD8+, CD45RA+, and/or CD45RO+ T cells, are selected by positive or negative selection techniques. In some embodiments, a sample (e.g., output composition of stimulated and/or engineered cells) containing target cells (e.g., CD3+ cells) is subjected to a parallel selection in which parallel selection is effected to enrich for central memory T ($T_{CM}$) cells or naïve T cells. In some embodiments, a further selection or selections can be effected to enrich for subpopulations of the central memory T ($T_{CM}$) cells or naïve T cells, for example, CD4+, CD3+, or CD8+ cells. In some embodiments, the further selections carried out after the parallel selection are accomplished via sequential selection techniques.

In some embodiments, a selection step (e.g., initial selection and/or polishing step) can be carried out using beads labeled with selection agents as described herein, and the positive and negative fractions from the first selection step can be retained, followed by further positive selection of the positive fraction to enrich for a second selection marker, such as by using beads labeled with a second selection agent or by subjecting the positive fraction to column chromatography as described above. In some embodiments, one or more polishing steps are carried out using column chromatography as described herein, for example chromatography as described in Section I-A and/or chromatography including agent and reagent systems as described above. In some embodiments, selection steps (e.g., initial selection and/or polishing steps) are accomplished using one or more methods including bead separation and column chromatography. In some embodiments, the selection steps (e.g., initial selection and/or polishing steps) are accomplished using column chromatography.

In some aspects, isolating the plurality of populations in a single or in the same isolation or separation vessel or set of vessels, such as a single column or set of columns, and/or same tube, or tubing set or using the same separation matrix or media or reagents, such as the same magnetic matrix, affinity-labeled solid support, or antibodies or other binding partners, include features that streamline the isolation, for example, resulting in reduced cost, time, complexity, need for handling of samples, use of . . . resources, reagents, or equipment. In some aspects, such features are advantageous in that they minimize cost, efficiency, time, and/or complexity associated with the methods, and/or avoid potential harm to the cell product, such as harm caused by infection, contamination, and/or changes in temperature. The methods provided herein allow for multiple selection steps to enrich target populations both prior to or following cell selection combined with on-column stimulation.

The methods provided herein further allow for the selection and enrichment of successfully stimulated and engineered cells. For example, in some embodiments, the sequential selection, parallel selection, or single selection procedures described above may be used to identify stimulated cells expressing recombinant receptors (e.g., CARs, TCRs). In some embodiments, cells expressing the recombinant receptor (e.g., CAR) can be further enriched (e.g., polished) for sub-population cells, e.g., CD4+ CAR+ T cells, CD8+ CAR+ T cells, CD28+, CD62L+, CCR7+, CD27+, CD127+, CD45RA+, CD45RO+ T cells, and/or viable cells. In some embodiments, the selection step (e.g., initial selection and/or polishing step) allows control or adjustment of the ratio, concentration, or total number of cells expressing a recombinant receptor (e.g., CAR, TCR) and/or subpopulations thereof. In some embodiments, enriched (e.g., polished) populations can be formulated for use (e.g., administration) for cell therapy.

H. Exemplary Features of the Process and/or Output Populations

In particular embodiments, the provided methods are used in connection with a process that produces or generates an output population of engineered T cells from one or more input populations, such as input populations obtained, selected, or enriched from a single biological sample. In certain embodiments, the output population contains cells that express a recombinant receptor, e.g., a TCR or a CAR. In particular embodiments, the cells of the output populations are suitable for administration to a subject as a therapy, e.g., an autologous cell therapy.

In particular embodiments, the provided methods are used in connection with an entire process for generating or producing output cells and/or an output populations of engineered T cells, such as a process including some or all of the steps of: stimulating cells from an input population; engineering, transforming, transducing, or transfecting the stimulated cells to express or contain a heterologous or recombinant polynucleotide, e.g., a polynucleotide encoding a recombinant receptor such as a CAR; incubating the cells, removing or separating a stimulatory reagent from the cells, and harvesting and collecting the cells, in some aspects thereby generating an output population of engineered T cells.

In some embodiments, the provided methods are used in connection with an entire process for generating or producing output cells and/or output compositions of enriched T cells, such as a process including some or all of the steps of: collecting or obtaining a biological sample; isolating, selecting, or enriching input cells from the biological sample; cryofreezing and storing the and then thawing the input cells; stimulating the cells; genetically engineering the stimulated cells to express or contain a recombinant polynucleotide, e.g., a polynucleotide encoding a recombinant receptor such as a CAR; formulating the cultivated cells in an output composition; and cryofreezing and storing the formulated output cells until the cells are released for infusion and or administration to a subject. In some embodiments, the provided methods do not include a step to expand or increase the number of cells during the process, such as by cultivating the cells in a bioreactor under conditions where the cells expand, such as to a threshold amount that is at least 3, 4, 5, or more times the amount, level, or concentration of the cells as compared to the input population. In some embodiments, genetically engineering the cells is or includes steps for transducing the cells with a viral vector, such as by spinoculating the cells in the presence of viral particles and then incubating the cells under static conditions in the presence of the viral particles.

In certain embodiments, the total duration of the provided process for generating engineered cells, from the initiation of the stimulation to collecting, harvesting, or formulating the cells is, is about, or is less than 36 hours, 42 hours, 48 hours, 54 hours, 60 hours, 72 hours, 84 hours, 96 hours, 108 hours, or 120 hours. In certain embodiments, the total duration of the provided process for generating engineered cells, from the initiation of the stimulation to collecting, harvesting, or formulating the cells is, is about, or is less than 1.5 days, 2 days, 3 days, 4 days, or 5 days. In some embodiments, the total duration of the provided process for generating engineered cells, from the initiation of the stimulation to collecting, harvesting, or formulating the cells is between or between about 36 hours and 120 hours, 48 hours and 96 hours, or 48 hours and 72 hours, inclusive, or between or between about 1.5 days and 5 days, 2 days and 4 days, or 2 days and 3 days, inclusive. In particular embodiments, the amount of time to complete the provided process as measured from the initiation of incubation to harvesting, collecting, or formulating the cells is, is about, or is less than 48 hours, 72 hours, or 96 hours, or is, is about, or is less than 2 days, 3 days, or 4 days. In particular embodiments, the amount of time to complete the provided process as measured from the initiation of incubation to harvesting, collecting, or formulating the cells is 48 hours±6 hours, 72 hours±6 hours, or 96 hours±6 hours.

In some embodiments, the incubation, e.g., as disclosed in Section I-C-3, is completed between or between about 24 hour and 120 hours, 36 hour and 108 hours, 48 hours and 96 hours, or 48 hours and 72 hours, inclusive, after the initiation of the stimulation. In some embodiments, the incubation is completed at, about, or within 120 hours, 108 hours, 96 hours, 72 hours, 48 hours, or 36 hours from the initiation of the stimulation. In particular embodiments, the incubation are completed after 24 hours±6 hours, 48 hours #6 hours, or 72 hours±6 hours. In some embodiments, the incubation is completed between or between about one day and 5 days, 1.5 days and 4.5 days, 2 days and 4 days, or 2 day and 3 days, inclusive, after the initiation of the stimulation. In some embodiments, the incubation is completed at, about, or within 5 days, 4 days, 3 days, 2 days, or 1.5 days from the initiation of the stimulation.

In some embodiments, the entire process is performed with a single population of enriched T cells, e.g., CD4+ and CD8+ T cells. In certain embodiments, the process is performed with two or more input populations of enriched T cells (e.g., CD4 and CD8 cells) that are combined prior to and/or during the process to generate or produce a single output population of enriched T cells. In some embodiments, the enriched T cells are or include engineered T cells, e.g., T cells transduced to express a recombinant receptor.

In some embodiments, an output population, e.g., a population of engineered T cells, is generated by (i) incubating an input population of or containing T cells under stimulating conditions for between or between about 18 and 30 hours, inclusive, (ii) introducing a heterologous or recombinant polynucleotide encoding a recombinant receptor into T cells of the stimulated population, (iii) incubating the cells, and then (iv) collecting or harvesting the incubated cells.

In some embodiments, the cells are collected or harvested within between 36 and 108 hours or between 1.5 days and 4.5 days after the incubation under stimulatory conditions is initiated. In particular embodiments, the cells are collected or harvested within 48 hours or two days after the transformed (e.g., genetically engineered, transduced, or transfected) T cells achieve a stable integrated vector copy number (iVCN) per genome that does not increase or decrease by more than 20% within a span of 24-48 hours or one to two days. In some embodiments, the integration is considered stable when the measured iVCN of a cell population is within or within about 20%, 15%, 10%, or 5% of the total vector copy number (VCN) measured in the population. Particular embodiments contemplate that to achieve a stable integration, the cells must be incubated for, for about, or for at least 48 hours, 60 hours, or 72 hours, or one day, 2 days, or 3 days, after the viral vector is contacted or introduced to the cells. In some embodiments, the stable integration occurs within or with about 72 hours of the incubation. In some embodiments, the cells are collected or harvested at a time when the total number of transformed T cells is at or less than the total number of cells of the input population. In various embodiments, the cells are collected or harvested at a time before the cells of the input population have doubled more than three, two, or one time(s).

In certain embodiments, an output population, e.g., a population of engineered T cells, is generated by (i) incubating an input population comprising T cells under stimulating conditions for between 18 and 30 hours, inclusive, in the presence of a stimulatory reagent, e.g., a stimulatory reagent described herein, such as in Section I-B-1, (ii) transducing the stimulated T cells with a viral vector encoding a recombinant receptor, such as by spinoculating the stimulated T cells in the presence of the viral vector, (iii) incubating the transduced T cells under static conditions for between or between 18 hours and 96 hours, inclusive, and (iv) harvesting T cells of the transformed population within between or between about 36 and 108 hours after the incubation under stimulatory conditions is initiated.

In some embodiments, the process associated with the provided methods is compared to an alternative process. For example, in some embodiments, the provided methods herein are compared an alternative process that contains a step for expanding the cells. In particular embodiments, the alternative process may differ in one or more specific aspects, but otherwise contains similar or the same features, aspects, steps, stages, reagents, and/or conditions of the process associated with the provided methods. In some embodiments, the alternative process is similar as the process associated with the provided methods, e.g., lacks or does not include expansion, but differs in a manner that includes, but is not limited to, one or more of; different reagents and/or media formulations; presence of serum during the incubation, transduction, transfection, and/or cultivation; different cellular makeup of the input population, e.g., ratio of CD4+ to CD8+ T cells; different stimulating conditions and/or a different stimulatory reagent; different ratio of stimulatory reagent to cells; different vector and/or method of transduction; different timing or order for incubating, transducing, and/or transfecting the cells; absence or difference of one or more recombinant cytokines present during the incubation or transduction (e.g., different cytokines or different concentrations), or different timing for harvesting or collecting the cells.

In some embodiments, the duration or amount of time required to complete the provided process, as measured from the isolation, enrichment, and/or selection input cells (e.g., CD4+ or CD8+ T cells) from a biological sample to the time at which a the output cells are collected, formulated, and/or cryoprotected is, is about, or is less than 48 hours, 72 hours, 96 hours, 120 hours, 2 days, 3 days, 4 days, 5 days, 7 days, or 10 days. In some embodiments, isolated, selected, or enriched cells are not cryoprotected prior to the stimulation, and the duration or amount of time required to complete the provided process, as measured from the isolation, enrichment, and/or selection input cells (to the time at which a the output cells are collected, formulated, and/or cryoprotected is, is about, or is less than 48 hours, 72 hours, 96 hours, or 120 hours, or 2 days, 3 days, 4 days, or 5 days.

In certain embodiments, the provided processes are performed on a population of cells, e.g., CD4+ and CD8+ T cells, that were isolated, enriched, or selected from a biological sample. In some aspects, the provided methods can produce or generate a composition of engineered T cells from when a biological sample is collected from a subject within a shortened amount of time as compared to other methods or processes. In some embodiments, the provided methods can produce or generate engineered T cells, including any or all times where biological samples, or enriched, isolated, or selected cells are cryopreserved and stored prior to steps for stimulation or transduction, within or within about 10 days, 9 days, 8 days, 7 days, 6 days, 5 days, 4 days, 3 days, 2 days, or within or within about 120 hours, 96 hours, 72 hours, or 48 hours, from when a biological sample is collected from a subject to when the engineered T cells are collected, harvested, or formulated (e.g., for cryopreservation or administration). In particular embodiments, the provided methods can produce or generate engineered T cells, including any or all times where biological samples, or enriched, isolated, or selected cells are cryopreserved and stored prior to steps for stimulation or transduction, within between or between about 6 days and 8 days, inclusive, from when the biological sample is collected from a subject to when the engineered T cells are collected, harvested, or formulated.

In certain embodiments, the provided methods are used in connection with a process for generating or producing output cells and/or output populations of enriched T cells. In particular embodiments, the output cells and/or output populations of enriched T cells are or include cells that were collected, obtained, isolated, selected, and/or enriched from the biological sample, such as a blood sample or leukapheresis sample; incubated under stimulating conditions; engineered, e.g., transduced, to express or contain a recombinant polynucleotide, e.g., a polynucleotide encoding a recombinant receptor such as a CAR; cultivated to a threshold amount, density, or expansion; and/or formulated. In some embodiments, the of the output population have been previously cryoprotected and thawed, e.g., during, prior to, and/or after one or more steps of the process. In some embodiments, the output population contains T cells, e.g., CD4+ T cells and CD8+ T cells, that express a recombinant receptor, e.g., a CAR.

In some embodiments, at least 30%, at least 40%, at least 45%, at least 50%, at least 55%, at least 60%, at least 65%, at least 70%, at least 75%, at least 80%, at least 85%, or at least 90%, at least 95%, of the cells of the output population express the recombinant receptor. In certain embodiments, at least 50% of the cells of the output composition express the recombinant receptor. In certain embodiments, at least 30%, at least 40%, at least 45%, at least 50%, at least 55%, at least 60%, at least 65%, at least 70%, at least 75%, at least 80%, at least 85%, at least 90%, or at least 95%, of the CD3+ T cells of the output composition express the recombinant receptor. In some embodiments, at least 50% of the CD3+ T cells of the output composition express the recombinant receptor. In particular embodiments, at least at least 30%, at least 40%, at least 45%, at least 50%, at least 55%, at least 60%, at least 65%, at least 70%, at least 75%, at least 80%, at least 85%, at least 90%, at least 95%, at least 97%, at least 99%, or more than 99% of the CD4+ T cells of the output composition express the recombinant receptor. In particular embodiments, at least 50% of the CD4+ T cells of the output composition express the recombinant receptor. In some embodiments, at least at least 30%, at least 40%, at least 45%, at least 50%, at least 55%, at least 60%, at least 65%, at least 70%, at least 75%, at least 80%, at least 85%, at least 90%, at least 95%, at least 97%, at least 99%, or more than 99% of the CD8+ T cells of the output composition express the recombinant receptor. In certain embodiments, at least 50% of the CD8+ T cells of the output composition express the recombinant receptor.

In particular embodiments, the cells of the output composition have improved cytolytic activity towards cells expressing an antigen bound by and/or recognized by the recombinant receptor (e.g., target cells) as compared output cells produced by an alternative process, e.g., a process that includes one or more steps of expanding the cells. In some embodiments, when the cells of the output composition are exposed to the cells that express the antigen, e.g., the target cells, the cells of the output composition kill, kill about, or kill at least 25%, 30%, 35%, 40%, 45%, 50%, 55%, 60%, 70%, 75%, 80%, 85%, 90%, 95%, or 100% of cells that express the antigen. In certain embodiments, the cells of the output composition kill at least 25%, 50%, 75%, 100%, 150%, or 1-fold, 2-fold, 3-fold, 4-fold, or 5-fold greater amount of cells that express the antigen, e.g., target cells, than output cells produced by the alternative process under similar or the same conditions.

In particular embodiments, the cells of the output population have improved anti-tumor activity in vivo as compared to output cells produced by an alternative process, e.g., a process that includes one or more steps of expanding the cells. In some embodiments, when the cells of the output composition are administered to a subject, e.g., a subject having a tumor or cancer, the cells of the output population kill, kill about, or kill at least 25%, 30%, 35%, 40%, 45%, 50%, 55%, 60%, 70%, 75%, 80%, 85%, 90%, 95%, or 100% of the tumor cells, e.g., cancer or tumor cells expressing the antigen, in the subject. In certain embodiments, the cells of the output composition kill at least 25%, 50%, 75%, 100%, 150%, or 1-fold, 2-fold, 3-fold, 4-fold, or 5-fold greater amount of tumor cells in vivo than output cells produced by the alternative process under similar or the same conditions.

In particular embodiments, a majority of the cells of the output population are naïve-like, central memory, and/or effector memory cells. In particular embodiments, a majority of the cells of the output population are naïve-like or central memory cells. In some embodiments, a majority of the cells of the output population are positive for one or more of CCR7 or CD27 expression. In certain embodiments, the cells of the output population have a greater portion of naïve-like or central memory cells that output populations generated from alternative processes, such as processes that involve expansion.

In certain embodiments, the cells of the output population have a low portion and/or frequency of cells that are exhausted and/or senescent. In particular embodiments, the cells of the output population have a low portion and/or frequency of cells that are exhausted and/or senescent. In some embodiments, less than 40%, less than 35%, less than 30%, less than 25%, less than 20%, less than 15%, less than 10%, less than 5%, or less than 1% of the cells of the output population are exhausted and/or senescent. In certain embodiments, less than 25% of the cells of the output population are exhausted and/or senescent. In certain embodiments, less than less than 10% of the cells of the output population are exhausted and/or senescent. In particular embodiments, the cells have a low portion In some embodiments, the cells of the output population have a low portion and/or frequency of cells that are negative for CD27 and CCR7 expression, e.g., surface expression. In particular embodiments, the cells of the output population have a low portion and/or frequency of CD27-CCR7-cells. In some embodiments, less than 40%, less than 35%, less than 30%, less than 25%, less than 20%, less than 15%, less than 10%, less than 5%, or less than 1% of the cells of the output population are CD27-CCR7-cells. In certain embodiments, less than 25% of the cells of the output population are CD27-CCR7-cells. In certain embodiments, less than less than 10% of the cells of the output population are CD27-CCR7-cells. In embodiments, less than 5% of the cells of the output population are CD27-CCR7-cells.

In some embodiments, the cells of the output population have a high portion and/or frequency of cells that are positive for one or both of CD27 and CCR7 expression, e.g., surface expression. In some embodiments, the cells of the output population have a high portion and/or frequency of cells that are positive for one or both of CD27 and CCR7. In some embodiments, at least 50%, at least 60%, at least 70%, at least 75%, at least 80%, at least 85%, at least 90%, at least 95%, or greater than 95% of the cells of the output population are positive for one or both of CD27 and CCR7. In various embodiments, at least 50%, at least 60%, at least 70%, at least 75%, at least 80%, at least 85%, at least 90%, at least 95% or greater than 95% of the CD4+CAR+ cells of the output population are positive for one or both of CD27 and CCR7. In some embodiments, at least 50%, at least 60%, at least 70%, at least 75%, at least 80%, at least 85%, at least 90%, at least 95% or greater than 95% of the CD8+CAR+ cells of the output population are positive for one or both of CD27 and CCR7.

In certain embodiments, the cells of the output population have a high portion and/or frequency of cells that are positive for CD27 and CCR7 expression, e.g., surface expression. In some embodiments, the cells of the output population have a high portion and/or frequency of CD27+ CCR7+ cells. In some embodiments, at least 50%, at least 60%, at least 70%, at least 75%, at least 80%, at least 85%, at least 90%, at least 95%, or greater than 95% of the cells of the output population are CD27+CCR7+ cells. In various embodiments, at least 50%, at least 60%, at least 70%, at least 75%, at least 80%, at least 85%, at least 90%, at least 95% or greater than 95% of the CD4+CAR+ cells of the output population are CD27+CCR7+ cells. In some embodiments, at least 50%, at least 60%, at least 70%, at least 75%, at least 80%, at least 85%, at least 90%, at least 95% or greater than 95% of the CD8+ CAR+ cells of the output population are CD27+CCR7+ cells.

In certain embodiments, the cells of the output population have a low portion and/or frequency of cells that are negative for CCR7 and positive for CD45RA expression, e.g., surface expression. In some embodiments, the cells of the output population have a low portion and/or frequency of CCR7−CD45RA+ cells. In particular embodiments, less than 40%, less than 35%, less than 30%, less than 25%, less than 20%, less than 15%, less than 10%, less than 5%, or less than 1% of the cells of the output population are CCR7−CD45RA+ cells. In some embodiments, less than 25% of the cells of the output population are CCR7−CD45RA+ cells. In particular embodiments, less than less than 10% of the cells of the output population are CCR7−CD45RA+ cells. In certain embodiments, less than 5% of the cells of the output population are CCR7−CD45RA+ cells.

In particular embodiments, the cells are harvested prior to, prior to about, or prior to at least one, two, three, four, five, six, eight, ten, twenty, or more cell doublings of the cell population, e.g., doublings that occur during the incubating. In certain embodiments, the cells are harvested prior to any doubling of the population, e.g., doubling that occurs during the incubation. In some aspects, reducing the doubling that may occur during an engineering process will, in some embodiments, increase the portion of engineered T cells that are naïve-like. In some embodiments, increasing the doubling during an engineering process increases T cell differentiation that may occur during the engineering process.

In some aspects, it is contemplated that, for a process for generating or producing engineered cell compositions, reducing the expansion or cell doublings that occur during the process, e.g., during the incubation, increases the amount or portion of naïve-like T cells of the resulting engineered cell composition. In particular aspects, increasing the expansion or cell doublings that occur during the process increases the amount or portion of differentiated T cells of the resulting engineered cell composition. In some aspects, it is contemplated that process, such as the processes provided herein, that increase or enlarge the portion of naïve-like cells in the resulting engineered cell composition may increase the potency, efficacy, and persistence, e.g., in vivo after administration, of the engineered cell composition.

1. Processes Using Stimulatory Bead Reagents

In some embodiments, an output population, e.g., a population of engineered T cells, is generated by steps that include: (i) incubating an input population of or containing T cells under with a stimulatory reagent continuing a bead, e.g., a bead-based stimulatory reagent described herein such as in Section I-B-1-a, for between or between about 18 and 30 hours, inclusive, (ii) introducing a heterologous or recombinant polynucleotide encoding a recombinant receptor into T cells of the stimulated population, (iii) incubating the cells under static conditions, (iv) removing or separating the paramagnetic bead reagents from the cells, and (v) collecting or harvesting the incubated cells.

In certain embodiments, an output population, e.g., a population of engineered T cells, is generated by (i) incubating an input population comprising T cells under stimulating conditions for between 18 and 30 hours, inclusive, in the presence of an anti-CD3/anti-CD28 antibody conjugated paramagnetic bead, (ii) transducing the stimulated T cells with a viral vector encoding a recombinant receptor, such as by spinoculating the stimulated T cells in the presence of the viral vector, (iii) incubating the transduced T cells under static conditions for between or between about 42 hours and 84 hours, inclusive, and (iv) harvesting or collecting the T cells.

In some embodiments, the provided methods for producing a population of engineered cells include one or more of stimulating an input population of T cells in the presence of anti-CD3 and anti-CD28 antibody conjugated paramagnetic beads at a ratio of 1:1 beads:cells in media containing recombinant IL-2, Il-7, and IL-15 for between 18 and 30 hours, inclusive; transducing the cells with a viral vector encoding a recombinant receptor by first spinoculating the cells in the presence of the viral vector 30 minutes at a force of 693 g and then incubating the spinoculated cells with the viral vector for between 48 hours and 96 hours, inclusive; exposing the cells to a magnet to remove or separate the anti-CD3 and anti-CD28 antibody conjugated paramagnetic beads from the cells; and collecting or harvesting the cells.

In some embodiments, the cells are harvested or collected from between or between about 54 hours and 120 hours, inclusive, from the initiation of the stimulation. In various embodiments, the cells are harvested or collected between 60 hours and 108 hours or 72 hours and 96 hours, inclusive, after the initiation of the stimulation. In particular embodiments, the anti-CD3 and anti-CD28 antibody conjugated paramagnetic beads removed or separated from the cells between 60 hours and 108 hours or 72 hours and 96 hours, inclusive, after the initiation of the stimulation.

In some embodiments, the anti-CD3 and anti-CD28 antibody conjugated paramagnetic beads are removed or separated from the cells after or after about 48 hours e.g., 48 hours±6 hours from the initiation of the stimulation. In some embodiments, the anti-CD3 and anti-CD28 antibody conjugated paramagnetic beads are removed or separated from the cells after or after about 72 hours e.g., 72 hours±6 hours from the initiation of the stimulation. In particular embodiments, the anti-CD3 and anti-CD28 antibody conjugated paramagnetic beads are removed or separated from the cells after or after about 96 hours, e.g., 96 hours±6 hours, from the initiation of the stimulation. In some embodiments, the anti-CD3 and anti-CD28 antibody conjugated paramagnetic beads are removed or separated from the cells during the incubation, and cells are returned to the incubation after exposure to the magnetic field. In particular embodiments, the anti-CD3 and anti-CD28 antibody conjugated paramagnetic beads are removed or separated from the cells after the incubation, and cells are collected or harvested after exposure to the magnetic field.

2. Oligomeric Stimulatory Reagent Based Protocols

In some embodiments, an output population, e.g., a population of engineered T cells, is generated by steps that include: incubating an input population of or containing T cells with a oligomeric stimulatory particle reagent, e.g., an oligomer-based stimulatory reagent described herein such as in Section I-B-1-b, for between or between about 18 and 30 hours, inclusive; introducing a heterologous or recombinant polynucleotide encoding a recombinant receptor into T cells of the stimulated population, (iii) incubating the cells under static conditions, (iv) removing or separating the stimulatory reagents from the cells by adding a competition reagent, and (v) collecting or harvesting the incubated cells.

In certain embodiments, an output population, e.g., a population of engineered T cells, is generated by steps that include: incubating an input population comprising T cells under stimulating conditions for between 18 and 30 hours, inclusive, in the presence of a streptavidin mutein oligomer with reversibly attached anti-CD3/anti-CD28 Fabs; transducing the stimulated T cells with a viral vector encoding a recombinant receptor, such as by spinoculating the stimulated T cells in the presence of the viral vector, and then incubating the transduced T cells under static conditions for between or between about 42 hours and 84 hours, inclusive; and harvesting or collecting the T cells.

In some embodiments, the provided methods for producing a population of engineered cells include one or more of stimulating an input population of T cells in the presence of oligomeric streptavidin mutein with reversibly attached anti-CD3/anti-CD28 Fabs in an amount of between or between about 0.4 μg and 8 μg per $10^6$ cells, inclusive, e.g., 1.2 μg per $10^6$ cells, in serum free media containing recombinant IL-2, IL-7, and IL-15 for between 18 and 30 hours, inclusive; transducing the cells with a viral vector encoding a recombinant receptor by first spinoculating the cells in the presence of the viral vector 30 minutes at a force of 693 g and then incubating the spinoculated cells with the viral vector for between 24 hours and 96 hours, inclusive; adding biotin (e.g., D-biotin) to the cells to remove or separate the oligomeric streptavidin mutein with reversibly attached anti-CD3/anti-CD28 Fabs from the cells; and collecting or harvesting the cells.

In some embodiments, the cells are harvested or collected from between or between about 36 hours and 96 hours, inclusive, from the initiation of the stimulation. In various embodiments, the cells are harvested or collected between 36 hours and 108 hours or 48 hours and 96 hours, inclusive, after the initiation of the stimulation. In particular embodiments, the oligomeric streptavidin mutein with reversibly attached anti-CD3/anti-CD28 Fabs are removed or separated from the cells between 36 hours and 96 hours or 48 hours and 72 hours, inclusive, after the initiation of the stimulation.

In some embodiments, the oligomeric streptavidin mutein with reversibly attached anti-CD3/anti-CD28 Fab are removed or separated from the cells after or after about 48 hours e.g., 48 hours±6 hours from the initiation of the stimulation. In particular embodiments, the oligomeric streptavidin mutein with reversibly attached anti-CD3/anti-CD28 Fabs are removed or separated from the cells after or after about 72 hours, e.g., 72 hours±6 hours, from the initiation of the stimulation. In particular embodiments, the oligomeric streptavidin mutein with reversibly attached anti-CD3/anti-CD28 Fabs are removed or separated from the cells after or after about 96 hours, e.g., 96 hours±6 hours, from the initiation of the stimulation. In particular embodiments, the oligomeric streptavidin mutein with reversibly attached anti-CD3/anti-CD28 Fabs are removed or separated from the cells after the incubation, and cells are collected or harvested after the addition of biotin or a biotin analogue. In certain embodiments, the oligomeric streptavidin mutein with reversibly attached anti-CD3/anti-CD28 Fabs are removed or separated from the cells during the incubation, such that the cells are returned to the incubation after the addition of the biotin or biotin analog.

In some embodiments, the incubation is performed in the presence of recombinant cytokines (e.g. IL-2, IL-7, and IL-15) in serum free media. In certain embodiments, the incubation is performed in the absence of recombinant cytokines. In particular embodiments, the incubation is performed in the presence of basal media. In certain embodiments, incubation in basal media increases the integration, e.g., stable integration of the heterologous or recombinant nucleotide, increases the percentage of cells expressing the recombinant receptor, improves potency, or reduces differentiation of the cells as compared to processes where cells stimulated with oligomeric stimulatory reagents are incubated in the presence of serum free media containing recombinant cytokines.

In particular embodiments, the removal of the oligomeric stimulatory reagent, e.g., the oligomeric streptavidin mutein with reversibly attached anti-CD3/anti-CD28 Fabs, such as by the addition of biotin or a biotin analogue, reduces the amount cell loss that can occur when stimulatory reagents are separated or removed from cells. In some embodiments, less than or less than about 30%, 25%, 20%, 15%, 10%, or 5% of the cells are lost, killed, or separated from the cell population when the oligomeric stimulatory reagent is separated or removed from the cells. In certain embodiments, output populations generated from processes that use oligomeric stimulatory reagents for stimulation have, have about, or have at least 15%, 20%, 25%, 30%, 35%, 40%, 45%, or 50% more total cells than output populations generated from processes that utilize alternative stimulatory reagents, such as antibody conjugated paramagnetic beads.

3. Vector Copy Number

In some embodiments, genomic integration of transgene sequences, such as transgene sequences encoding a recombinant receptor, e.g. a CAR, can be assessed in cells produced in connection with any of the provided processes for engineering cells. In some embodiments, the integrated copy number is assessed, which is the copy number of the transgene sequence integrated into the chromosomal DNA or genomic DNA of cells.

In some embodiments, methods for assessing genomic integration of a transgene sequence involve separating a high molecular weight fraction of deoxyribonucleic acid (DNA), such as DNA species that are greater than or greater than about 10 kilobases (kb), from DNA isolated from one or more cell. In some aspects, such separation can be carried out by methods such as pulse field gel electrophoresis (PFGE). In some aspects, the one or more cell contains, or is suspected to contain, at least one engineered cell comprising a transgene sequence encoding a recombinant protein. In some aspects, the methods involve determining the presence, absence or amount of the transgene sequence integrated into the genome of the one or more cell, for example, by quantitative methods such as quantitative polymerase chain reaction (qPCR), digital PCR (dPCR) or droplet digital PCR (ddPCR).

In some embodiments, the high molecular weight fraction primarily contain large DNA molecules such as chromosomal or genomic DNA, and contain low or almost no molecules that are smaller than the threshold value for size, such as plasmids, non-integrated DNA fragments, linear complementary DNA (cDNA), autointegrants, long terminal repeat (LTR) circles or other residual species or molecules that have not been integrated into the genome. In some embodiments, by determining the presence, absence or amount of the transgene sequences in the high molecular weight fraction, the detected transgene sequences represent those that have been integrated into the genome of the engineered cell, and minimizes the detection of non-integrated transgene sequences.

In some embodiments, the high molecular weight fraction comprises DNA molecules that are greater than or greater than about 10 kilobases (kb) in size. In some embodiments, the high molecular weight fraction comprises DNA molecules that are greater than or greater than about 10, 11, 12, 12.5, 13, 14, 15, 16, 17, 17.5, 18, 19, 20, 25 or 30 kilobases (kb) or more in size. In some embodiments, the high molecular weight fraction comprises DNA molecules that are greater than or greater than about 10, 12.5, 15, 17.5 or 20 kilobases (kb) or more in size. In some aspects, the high molecular weight fraction contains genomic DNA or genomic DNA fragments, and excludes or separates non-integrated or residual nucleic acid species that can be present in the DNA sample. In some aspects, the high molecular weight fraction, e.g., DNA samples that are above a threshold value such as about 10, 11, 12, 12.5, 13, 14, 15, 16, 17, 17.5, 18, 19, 20, 25 or 30 kilobases (kb) or more. In some embodiments, the threshold value is greater than or greater than about 10, 12.5, 15, 17.5 or 20 kilobases (kb) or more.

In some embodiments, the high molecular weight fraction is separated or isolated using an electrophoresis-based method. In some aspects, electrophoresis separates biomolecules by charge and/or size via mobility through a separating matrix in the presence of an electric field. In some embodiments, electrophoresis systems can be used to fractionate, analyze, and collect particular analytes, including nucleic acid molecules, based on size or molecular weight. In some aspects, a fraction is or includes a subset of the plurality of molecules. In some aspects, a fraction can be defined or determined by size or molecular weight, or in some aspects, by any physical property that causes it to migrate at a faster or slower rate than other molecules or fractions of a plurality when driven to migrate through a buffer composition of the disclosure by the force of an electric field (i.e., electrophoretic mobility).

In some embodiments, the high molecular weight fraction is separated or isolated using pulse field gel electrophoresis (PFGE). In some aspects, PFGE involves introducing an alternating voltage gradient in an electrophoresis system to improve the resolution of larger nucleic acid molecules, such as chromosomal or genomic DNA. In some aspects, the voltage of the electrophoresis system is periodically switched among three directions: one that runs through the central axis of the gel and two that run at an angle of 60 degrees either side. In some aspects, exemplary systems and methods for separating or isolating nucleic acid molecules by PFGE include those described in, e.g., U.S. Pat. No. 9,599,590; US 2017/0240882; or US 2017/0254774.

In some aspects, the electrophoresis, such as PFGE, can be performed using an apparatus or system. In some aspects, the apparatus or system is an automated system or high-throughput system. Exemplary systems for performing PFGE, include, those described in, e.g., U.S. Pat. No. 9,599,590; US 2017/0240882; or US 2017/0254774, or commercially available apparatus or system, such as Pippin Prep, Blue Pippin or Pippin HT (Sage Science); CHEF Mapper® XA System, CHEF-DR® III Variable Angle System, CHEF-DR II System (Bio-Rad); and Biometra Rotaphor 8 System (Analytik Jena AG).

In some aspects, exemplary samples for assessment include a nucleic acid, an oligonucleotide, a DNA molecule, a RNA molecule, or any combination thereof. In some aspects, the sample can include, an amino acid, a peptide, a protein, or any combination thereof. In some aspects, the sample can be a whole cell lysate, or the DNA or protein fraction of a cell lysate, such as lysate of cells engineered for adoptive cell therapy.

In some embodiments, nucleic acids from the samples can include genomic DNA, double-stranded DNA (dsDNA), single-stranded DNA (ssDNA), coding DNA (or cDNA), messenger RNA (mRNA), short interfering RNA (siRNA), short-hairpin RNA (shRNA), microRNA (miRNA), single-stranded RNA, double-stranded RNA (dsRNA), a morpholino, RNA interference (RNAi) molecule, mitochondrial nucleic acid, chloroplast nucleic acid, viral DNA, viral RNA, and other organelles with separate genetic material. In some aspects, the nucleic acids from the sample can also include nucleic acid analogs that contain modified, synthetic, or non-naturally occurring nucleotides or structural elements or other alternative/modified nucleic acid chemistries, such as base analogs such as inosine, intercalators (U.S. Pat. No. 4,835,263) and minor groove binders (U.S. Pat. No. 5,801,115).

In some embodiments, prior to isolating or separating a high- or low-molecular weight fraction, the samples can be combined with a reagent that imparts a net negative charge, denatures a peptide or protein, or digests a DNA or RNA molecule prior to assessment in an electrophoresis system. In some aspects, samples can be combined with agents that impart fluorescent, magnetic, or radioactive properties to the sample or fractions thereof for the purpose of detection. In some examples, a dsDNA sample is mixed with ethidium bromide, applied to the electrophoresis cassette, and fractions of the sample are detected using an ultrabright green LED.

In some aspects, a system for separating or isolating the nucleic acid samples, such as an electrophoresis system, can be automated and/or high-throughput. In some aspects, the electrophoresis system can utilize disposable consumables or reagents, such as an electrophoresis cassette.

In some aspects, determining the presence, absence or amount of the transgene sequence can be performed using methods for determining the presence, absence or amount of a nucleic acid sequence. In particular, methods used to quantitate nucleic acid sequences, such quantitative polymerase chain reaction (qPCR) or related methods, can be employed in determining the copy number of the transgene sequence in a sample containing DNA, or in a particular fraction, such as the high molecular weight fraction, that is separated or isolated from samples containing DNA. In some embodiments, the determining the presence, absence or amount of the transgene sequence comprises determining the copy number, for example, using any one of the exemplary assays below to quantitate nucleic acid molecules.

In some aspects, the presence, absence and/or amount of a particular sequence can be detected using a probe or a primer, that can specifically bind or recognize all or a portion of the transgene sequence. In some embodiments, copy number can be determined using probes that can specifically detect a portion of the transgene sequence, or primer sequences that can specifically amplify a portion of the transgene sequence. In some aspects, the probe or primer sequences can specifically detect, bind or recognize a portion of the transgene sequence, such as a portion of the transgene sequence that is heterologous, exogenous or transgenic to the cell. In some embodiments, the primers or probe used for qPCR or other nucleic acid-based methods are specific for binding, recognizing and/or amplifying nucleic acids encoding the recombinant protein, and/or other components or elements of the plasmid and/or vector, including regulatory elements, e.g., promoters, transcriptional and/or post-transcriptional regulatory elements or response elements, or markers, e.g., surrogate markers. In some aspects, the probes or primers can be used for exemplary methods to determine the presence, absence and/or amount of transgene sequences, such as quantitative PCR (qPCR), digital PCR (dPCR) or droplet digital PCR (ddPCR).

In some aspects, the determining of the presence, absence or amount comprises determining the amount of the transgene sequence, such as determining the mass, weight, concentration or copy number of the transgene sequences, in one or more cells or in a biological sample containing one or more cells. In some aspects, the determining of the presence, absence or amount of a nucleic acid sequence, or assessing the mass, weight, concentration or copy number of the transgene sequences can be performed in a portion of a population of cells or a portion of a biological sample, and can be normalized, averaged, and/or extrapolated to determine the presence, absence or amount in the entire sample or entire population of cells.

In some embodiments, the determining the presence, absence or amount of the transgene sequence comprises determining the mass, weight, concentration or copy number of the transgene sequence per diploid genome or per cell in the one or more cells. In some embodiments, the one or more cell comprises a population of cells in which a plurality of cells of the population comprise the transgene sequence encoding the recombinant protein. In some embodiments, the copy number is an average or mean copy number per diploid genome or per cell among the population of cells.

In some aspects, determining the copy number comprises determining the number of copies of the transgene sequences present in one or more cells, or in a biological sample. In some aspects, the copy number can be expressed as an average or mean copy number. In some aspects, the copy number of a particular integrated transgene includes the number of integrants (containing transgene sequences) per cell. In some aspects, the copy number of a particular integrated transgene includes the number of integrants (containing transgene sequences) per diploid genome. In some aspects, the copy number of transgene sequence is expressed as the number of integrated transgene sequences per cell. In some aspects, the copy number of transgene sequence is expressed as the number of integrated transgene sequences per diploid genome. In some aspects, the one or more cell comprises a population of cells in which a plurality of cells of the population comprise the transgene sequence encoding the recombinant protein. In some embodiments, the copy number is an average or mean copy number per diploid genome or per cell among the population of cells.

In some embodiments, the determining the amount of the transgene sequence comprises assessing the mass, weight, concentration or copy number of the transgene sequence per the one or more cells, optionally per CD3+, CD4+ and/or CD8+ cell, and/or per cell expressing the recombinant protein. In some aspects, surface markers or phenotypes expressed on the cell can be determined using cell-based methods, such as by flow cytometry or immunostaining. In some aspects, the cells expressing the recombinant protein can be determined using cell-based methods, such as by flow cytometry or immunostaining, for example with an anti-idiotypic antibody or staining for a surrogate marker. In some aspects, the amount of transgene sequences can be normalized to the number of particular cells, such as CD3+, CD4+ and/or CD8+ cell, and/or per cell expressing the recombinant protein, or per total number of cells, such as per total number of cells in the sample or per total number of cells undergoing an engineering process.

In some embodiments, the determined copy number is expressed as a normalized value. In some embodiments, the determined copy number is quantified as a number of copy of the transgene sequence per genome or per cell. In some aspects, the per genome value is expressed as copy of the transgene sequence per diploid genome, as a typical somatic cell, such as a T cell, contains a diploid genome. In some aspects, the determined copy number can be normalized against the copy number of a known reference gene in the genome of the cell. In some aspects, the reference gene is RRP30 (encoding ribonuclease P protein subunit p30), or 18S rRNA (18S ribosomal RNA), 28S rRNA (28S ribosomal RNA), TUBA (α-tubulin), ACTB (β-actin), β2M (β2-microglobulin), ALB (albumin), RPL32 (ribosomal protein L32), TBP (TATA sequence binding protein), CYCC (cyclophilin C), EF1A (elongation factor 1α), GAPDH (glyceraldehyde-3-phosphate dehydrogenase), HPRT (hypoxanthine phosphoribosyl transferase) or RPII (RNA polymerase II). In some embodiments, the determined copy number is quantified as copy of the transgene sequence per microgram of DNA.

In some aspects, the copy number is an average, mean, or median copy number from a plurality or population of cells, such as a plurality or population of engineered cells. In some aspects, the copy number is an average or mean copy number from a plurality or population of cells, such as a plurality or population of engineered cells. In some aspects, the average or mean copy number is determined from a plurality or population of cells, such as a plurality or population of cells undergoing one or more steps of the engineering or manufacturing process, or in a cell composition, such as a cell composition for administration to a subject. In some aspects, a normalized average copy number is determined, for example, as an average or mean copy number of the transgene sequences normalized to a reference gene, such as a known gene that is present in two copies in a diploid genome. In some aspects, normalization to a reference gene that is typically present in two copies per diploid genome, can correspond to the copy number in a cell, such as a diploid cell. Thus, in some aspects, the normalized average or mean copy number can correspond to the average or mean copy number of the detected transgene sequences among a plurality or a population of cells, for example, T cells that typically have a diploid genome.

In some embodiments, the determining the presence, absence or amount of the transgene sequence is carried out by polymerase chain reaction (PCR). In some embodiments, the PCR is quantitative polymerase chain reaction (qPCR), digital PCR or droplet digital PCR, such as any described below. In some embodiments, the presence, absence or amount of the transgene sequence is determined by droplet digital PCR. In some embodiments, the PCR is carried out using one or more primers that is complementary to or is capable of specifically amplifying at least a portion of the transgene sequence, and in some cases, one or more primers that is complementary to or is capable of specifically amplifying at least a portion of a reference gene.

In some aspects, qPCR can be used to detect the accumulation of amplification product measured as the reaction progresses, in real time, with product quantification after each cycle. Thus, in some aspects, qPCR can be used to determine the copy number of a particular nucleic acid sequence, such as the transgene sequence, in a sample. In some aspects, qPCR employs fluorescent reporter molecule in each reaction well that yields increased fluorescence with an increasing amount of product DNA. In some aspects, fluorescence chemistries employed include DNA-binding dyes and fluorescently labeled sequence-specific primers or probes. In some aspects, qPCR employs a specialized thermal cycler with the capacity to illuminate each sample at a specified wavelength and detect the fluorescence emitted by the excited fluorophore. In some aspects, the measured fluorescence is proportional to the total amount of amplicon; the change in fluorescence over time is used to calculate the amount of amplicon produced in each cycle.

In some embodiments, dPCR is a method for detecting and quantifying nucleic acids, and permits accurate quantitative analysis and the highly sensitive detection of a target nucleic acid molecule. In some aspects, dPCR involves a limiting dilution of DNA into a succession of individual PCR reactions (or partitions). In some aspects, limiting dilution can employ the principles of partitioning with nanofluidics and emulsion chemistries, based on random distribution of the template nucleic acid to be assessed, e.g., transgene sequences, and Poisson statistics to measure the quantities of DNA present for a given proportion of positive partitions. In some aspects, dPCR is generally linear and are sensitive, capable of detecting or quantifying very small amounts of DNA. In some aspects, dPCR permits absolute quantification of a DNA sample using a single molecule counting method without a standard curve, and absolute quantification can be obtained from PCR for a single partition per well (see Pohl et al., (2004) Expert Rev. Mol. Diagn. 4 (1), 41-47).

Exemplary commercially available apparatuses or systems for dPCR include Raindrop™ Digital PCR System (Raindance™ Technologies); QX200™ Droplet Digital™ PCR System (Bio-Rad); BioMark™ HD System and qdPCR 37K™ IFC (Fluidigm Corporation) and QuantStudio™ 3D Digital PCR System (Life Technologies™) (see, e.g., Huggett et al. (2013) Clinical Chemistry 59:1691-1693; Shuga, et al. (2013) Nucleic Acids Research 41 (16): e159; Whale et al. (2013) PLOS One 3: e58177).

In some embodiments, the presence, absence or amount of the transgene sequences, such as transgene sequences encoding a recombinant protein, for integration into the genome of the engineered cell, is determined using droplet digital polymerase chain reaction (ddPCR). ddPCR is a type of digital PCR, in which the PCR solution is divided or partitioned into smaller reactions through a water-oil emulsion chemistry, to generate numerous droplets. In some aspects, particular surfactants can be used to generate the water-in-oil droplets. (see, e.g., Hindson et al., (2011) Anal Chem 83 (22): 8604-8610; Pinheiro et al., (2012) Anal Chem 84, 1003-1011). In some aspects, each individual droplet is subsequently run as individual reaction. In some aspects, the PCR sample is partitioned into nanoliter-size samples and encapsulated into oil droplets. In some aspects, the oil droplets are made using a droplet generator that applies a vacuum to each of the wells. In an exemplary case, approximately 20,000 oil droplets for individual reactions can be made from a 20 μL sample volume.

In some aspects, methods assessing integrated copy number can be performed at various time points to determine and compare the timing, extent or progress of genetic engineering, such as integration of the introduced transgene sequences into the genome of the cell into which the transgene sequences are introduced. In some aspects, the methods can be carried out at various stages of an engineering or manufacturing process for engineered cell compositions, such as any of the processes described. For example, the provided methods can be performed at various stages of an expanded engineering process or a non-expanded engineering process.

In some aspects, cells engineered by the provided methods are assessed for genomic integration of a transgene sequence, such as encoding a recombinant receptor, e.g. CAR, using the assays for vector copy number described above. In some embodiments, the methods involve separating a high molecular weight fraction of greater than or greater than about 10 kilobases (kb) from deoxyribonucleic acid (DNA) isolated from a cell, wherein prior to the separating, the cell has been introduced with a polynucleotide comprising the transgene sequence under conditions for integration of the transgene sequence into a genome of the cell, such as by viral transduction; and determining the presence, absence or amount of the transgene sequence in the high molecular weight fraction.

4. Exemplary Features of the Output Compositions.

In certain embodiments, the provided methods are used in connection with a process for generating or producing output cells and/or output compositions of enriched T cells, e.g., a therapeutic T cell composition. In particular embodiments, the output composition is a composition of cells enriched for CD3+ T cells. In some embodiments, at least or about 60%, at least or about 65%, at least or about 70%, at least or about 75%, at least or about 80%, at least or about 85%, at least or about 90%, at least or about 95%, at least or about 98%, at least or about 98.5%, at least or about 99%, at least or about 99.5%, at least or about 99.9%, 100%, or about 100% of the total cells in the output composition are CD3+ T cells. In some embodiments, at least or about 86%, at least or about 86.5%, at least or about 87%, at least or about 87.5%, at least or about 88%, at least or about 88.5%, at least or about 89%, at least or about 89.5%, at least or about 90%, at least or about 90.5%, at least or about 91%, at least or about 91.5%, at least or about 92%, at least or about 92.5%, at least or about 93%, at least or about 93.5%, at least or about 94%, at least or about 94.5%, at least or about 95%, at least or about 95.5%, at least or about 96%, at least or about 96.5%, at least or about 97%, at least or about 97.5%, at least or about 98%, or at least or about 98.5% of the total cells in the output composition are CD3+ T cells. In some embodiments, between about 80% and about 100%, between about 85% and about 98%, between about 88% and about 96%, or between about 90% and about 94% of the total cells in the output composition are CD3+ T cells. In some embodiments, the output composition consists essentially of CD3+ T cells. In some embodiments, at least or about 90% of the total cells in the output composition are CD3+ T cells and at least or about 40% of the total cells in the output composition express the recombinant receptor (e.g., the CAR).

In certain embodiments, the output composition is a composition of cells enriched for CD4+ T cells and CD8+ T cells. In particular embodiments, CD4+ T cells and CD8+ T cells account for at least or about 60%, at least or about 65%, at least or about 70%, at least or about 75%, at least or about 80%, at least or about 85%, at least or about 90%, at least or about 95%, at least or about 98%, at least or about 98.5%, at least or about 99%, at least or about 99.5%, at least or about 99.9%, 100%, or about 100% of the total cells in the output composition. In some embodiments, CD4+ T cells and CD8+ T cells account for at least or about 86%, at least or about 86.5%, at least or about 87%, at least or about 87.5%, at least or about 88%, at least or about 88.5%, at least or about 89%, at least or about 89.5%, at least or about 90%, at least or about 90.5%, at least or about 91%, at least or about 91.5%, at least or about 92%, at least or about 92.5%, at least or about 93%, at least or about 93.5%, at least or about 94%, at least or about 94.5%, at least or about 95%, at least or about 95.5%, at least or about 96%, at least or about 96.5%, at least or about 97%, at least or about 97.5%, at least or about 98%, or at least or about 98.5% of the total cells in the output composition. In some embodiments, CD4+ T cells and CD8+ T cells account for between about 80% and about 100%, between about 85% and about 98%, between about 88% and about 96%, or between about 90% and about 94% of the total cells in the output composition. In some embodiments, the output composition consists essentially of CD4+ T cells and CD8+ T cells.

In particular embodiments, the output composition contains between at or about 10% and at or about 90%, between at or about 20% and at or about 80%, between at or about 25% and at or about 75%, between at or about 30% and at or about 70%, between at or about 35% and at or about 65%, between at or about 40% and at or about 60%, between at or about 55% and at or about 45%, or about 50% or 50% CD4+ T cells and at or about between at or about 10% and at or about 90%, between at or about 20% and at or about 80%, between at or about 25% and at or about 75%, between at or about 30% and at or about 70%, between at or about 35% and at or about 65%, between at or about 40% and at or about 60%, between at or about 55% and at or about 45%, or about 50% or 50% CD8+ T cells. In certain embodiments, the output composition contains between at or about 35% and at or about 65%, between at or about 40% and at or about 60%, between at or about 55% and at or about 45%, or about 50% or 50% CD4+ T cells and at or about between at or about 35% and at or about 65%, between at or about 40% and at or about 60%, between at or about 55% and at or about 45%, or about 50% or 50% CD8+ T cells. In particular embodiments, the output contains between at or about 35% and at or about 65% CD4+ T cells and at or about between at or about 35% and at or about 65% CD8+ T cells. In particular embodiments, the output composition contains a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells to CD8+ T cells. In some embodiments, the composition of cells has a ratio of or of about 3:1, of or of about 2.8:1, of or of about 2.5:1, of or of about 2.25:1, of or of about 2:1, of or of about 1.8:1, of or of about 1.7:1, of or of about 1.6:1, of or of about 1.5:1, of or of about 1.4:1, of or of about 1.3:1, of or of about 1.2:1, of or of about 1.1:1, of or of about 1:1, of or of about 1:1.1, of or of about 1:1.2, of or of about 1:1.3, of or of about 1:1.4, of or of about 1:1.5, of or of about 1:1.6, of or of about 1:1.7, of or of about 1:1.8, of or of about 1:2, of or of about 1:2.25, of or of about 1:2.5, of or of about 1:2.8, or of or of about 1:3 CD4+ T cells to CD8+ T cells.

In some embodiments, at least at or about 75%, at least at or about 80%, at least at or about 85%, at least at or about 90%, at least at or about 95%, at least at or about 97%, at least at or about 98%, or at least at or about 99% of the output compositions produced by the methods provided herein have a ratio of CD4+ T cells to CD8+ T cells of between 10:90 and 90:10, between 20:80 and 80:20, between 75:25 and 25:75, between 70:30 and 30:70, between 35:65 and 65:35, between 40:60 and 60:40, between 45:55 and 55:45, or about 50:50 or 50:50. In particular embodiments, at least 80%, at least 85%, or at least 90% of the output compositions produced by the methods provided herein have a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells to CD8+ T cells. In certain embodiments, at least 90% of the output compositions produced by the methods provided herein have a ratio of CD4+ T cells to CD8+ T cells of between 1:2 and 2:1. In particular embodiments, at least 90% of the output compositions produced by the methods provided herein have a ratio of CD4+ T cells to CD8+ T cells of between 1.5:1 and 1:1.5, between 1.25:1 and 1:1.25, or between 1.1:1 and 1:1.1.

In some embodiments, the output composition contains a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells that express the recombinant receptor, e.g., the CAR, to CD8+ T cells that express the recombinant receptor, e.g., the CAR. In some embodiments, the ratio of CD4+ T cells that express the recombinant receptor (e.g., the CAR) to CD8+ T cells that express the recombinant receptor (e.g., the CAR) in the output composition is of or of about 3:1, of or of about 2.8:1, of or of about 2.5:1, of or of about 2.25:1, of or of about 2:1, of or of about 1.8:1, of or of about 1.7:1, of or of about 1.6:1, of or of about 1.5:1, of or of about 1.4:1, of or of about 1.3:1, of or of about 1.2:1, of or of about 1.1:1, of or of about 1:1, of or of about 1:1.1, of or of about 1:1.2, of or of about 1:1.3, of or of about 1:1.4, of or of about 1:1.5, of or of about 1:1.6, of or of about 1:1.7, of or of about 1:1.8, of or of about 1:2, of or of about 1:2.25, of or of about 1:2.5, of or of about 1:2.8, or of or of about 1:3.

In particular embodiments, at least 80%, at least 85%, or at least 90% of the output compositions produced by the methods provided herein have a ratio of between 3:1 and 1:3, between 2.5:1 and 1:2.5, between 2:1 and 1:2, between 1.5:1 and 1:1.5, between 1.4:1 and 1:1.4, between 1.3:1 and 1:1.3, between 1.2:1 and 1:1.2, or between 1.1:1 and 1:1.1 CD4+ T cells that express the recombinant receptor, e.g., the CAR, to CD8+ T cells that express the recombinant receptor, e.g., the CAR. In certain embodiments, at least 90% of the output compositions produced by the methods provided herein have a ratio of CD4+ T cells to CD8+ T cells of between 1:2 and 2:1. In particular embodiments, at least 90% of the output compositions produced by the methods provided herein have a ratio of CD4+ T cells to CD8+ T cells of between 1.5:1 and 1:1.5, between 1.25:1 and 1:1.25, between 1.1:1 and 1:1.1.

In some embodiments, an output composition generated or produced in connection with the provided methods contains cells expressing a recombinant receptor, e.g., a TCR or a CAR. In some embodiments, expressing a recombinant receptor may include, but is not limited to, having one or more recombinant receptor proteins localized at the cell membrane and/or cell surface, having a detectable amount of recombinant receptor protein, having a detectable amount of mRNA encoding the recombinant receptor, having or containing a recombinant polynucleotide that encodes the recombinant receptor, and/or having or containing an mRNA or protein that is a surrogate marker for recombinant receptor expression.

In some embodiments, at least or about 5%, at least or about 10%, at least or about 20%, at least or about 30%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 97%, at least or about 99%, or more than 99% of the cells of the output composition express the recombinant receptor. In certain embodiments, at least or about 50% of the cells of the output composition express the recombinant receptor. In certain embodiments, at least or about 5%, at least or about 10%, at least or about 20%, at least or about 30%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 97%, at least or about 99%, or more than 99% of the CD3+ T cells of the output composition express the recombinant receptor. In some embodiments, at least or about 50% of the CD3+ T cells of the output composition express the recombinant receptor. In certain embodiments, at least or about 5%, at least or about 10%, at least or about 20%, at least or about 30%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 97%, at least or about 99%, or more than 99% of the cells of the output composition are CD3+ T cells that express the recombinant receptor. In some embodiments, at least or about 50% of the cells of the output composition are CD3+ T cells that express the recombinant receptor.

In particular embodiments, at least or about 30%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 97%, at least or about 99%, or more than 99% of the CD4+ T cells of the output composition express the recombinant receptor. In particular embodiments, at least or about 50% of the CD4+ T cells of the output composition express the recombinant receptor. In some embodiments, at least or about 30%, at least or about 40%, at least or about 45%, at least or about 50%, at least or about 55%, at least or about 60%, at least or about 65%, at least or about 70%, at least or about 75%, at least or about 80%, at least or about 85%, at least or about 90%, at least or about 95%, at least or about 97%, at least or about 99%, or more than 99% of the CD8+ T cells of the output composition express the recombinant receptor. In certain embodiments, at least or about 50% of the CD8+ T cells of the output composition express the recombinant receptor.

In particular embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable cells. In some embodiments, the output composition contains at least at or about 75% viable cells. In certain embodiments, the output composition contains at least at or about 85%, at least at or about 90%, or at least at or about 95% viable cells. In some embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD3+ T cells. In particular embodiments, the output composition contains at least at or about 75% viable CD3+ T cells. In certain embodiments, the output composition contains at least at or about 85%, at least at or about 90%, or at least at or about 95% viable CD3+ T cells. In some embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD4+ T cells. In certain embodiments, the output composition contains at least at or about 75% viable CD4+ T cells. In particular embodiments, the output composition contains at least at or about 85%, at least at or about 90%, or at least at or about 95% viable CD4+ T cells. In particular embodiments, the output composition contains at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% viable CD8+ T cells. In some embodiments, the output composition contains at least at or about 75% viable CD8+ T cells. In certain embodiments, the output composition contains at least at or about 85%, at least at or about 90%, or at least at or about 95% viable CD8+ T cells.

In particular embodiments, the output cells have a low portion and/or frequency of cells that are undergoing and/or are prepared, primed, and/or entering apoptosis. In particular embodiments, the output cells have a low portion and/or frequency of cells that are positive for an apoptotic marker. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition express, contain, and/or are positive for an apoptotic marker. In certain embodiments, less than at or about 25% of the cells of the output composition express, contain, and/or are positive for a marker of apoptosis. In certain embodiments, less than at or about less than at or about 10% cells of the output composition express, contain, and/or are positive for an apoptotic marker.

In particular embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) cells of the output composition are viable cells, e.g., cells negative for an apoptotic marker, such as a caspase (e.g., an activated caspase-3). In certain embodiments, at least at or about 85%, at least at or about 90%, or at least at or about 95% of recombinant receptor-expressing (e.g., CAR+) cells of the output composition are viable cells, e.g., cells negative for an apoptotic marker, such as a caspase (e.g., an activated caspase-3). In some embodiments, at least at or about 90% of recombinant receptor-expressing (e.g., CAR+) cells of the output composition are viable cells, e.g., cells negative for an apoptotic marker, such as a caspase (e.g., an activated caspase-3). In some embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of CD3+ T cells of the output composition are viable cells, e.g., cells negative for an apoptotic marker, such as a caspase (e.g., an activated caspase-3). In certain embodiments, at least at or about 85%, at least at or about 90%, or at least at or about 95% of CD3+ T cells of the output composition are viable cells, e.g., cells negative for an apoptotic marker, such as a caspase (e.g., an activated caspase-3). In particular embodiments, at least at or about 90% of CD3+ T cells of the output composition are viable cells, e.g., cells negative for an apoptotic marker, such as a caspase (e.g., an activated caspase-3). In some embodiments, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) CD3+ T cells of the output composition are viable cells, e.g., cells negative for an apoptotic marker, such as a caspase (e.g., an activated caspase-3). In particular embodiments, at least at or about 85%, at least at or about 90%, or at least at or about 95% of recombinant receptor-expressing (e.g., CAR+) CD3+ T cells of the output composition are viable cells, e.g., cells negative for an apoptotic marker, such as a caspase (e.g., an activated caspase-3). In certain embodiments, at least at or about 90% of recombinant receptor-expressing (e.g., CAR+) CD3+ T cells of the output composition are viable cells, e.g., cells negative for an apoptotic marker, such as a caspase (e.g., an activated caspase-3).

In particular embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In certain embodiments, on average, at least at or about 85%, at least at or about 90%, or at least at or about 95% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In some embodiments, on average, at least at or about 90% of recombinant receptor-expressing (e.g., CAR+) cells of a plurality of output compositions produced by the method disclosed herein are viable cells, e.g., cells negative for an apoptotic marker, such as a caspase (e.g., an activated caspase-3). In some embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of CD3+ T cells of a plurality of output compositions produced by the method disclosed herein are viable cells, e.g., cells negative for an apoptotic marker, such as a caspase (e.g., an activated caspase-3). In certain embodiments, on average, at least at or about 85%, at least at or about 90%, or at least at or about 95% of CD3+ T cells of a plurality of output compositions produced by the method disclosed herein are viable cells, e.g., cells negative for an apoptotic marker, such as a caspase (e.g., an activated caspase-3). In particular embodiments, on average, at least at or about 90% of CD3+ T cells of a plurality of output compositions produced by the method disclosed herein are viable cells, e.g., cells negative for an apoptotic marker, such as a caspase (e.g., an activated caspase-3). In some embodiments, on average, at least at or about 50%, at least at or about 60%, at least at or about 70%, at least at or about 75%, at least at or about 80%, at least at or about 85%, at least at or about 90%, at least at or about 95%, at least at or about 99%, or at least at or about 99.9% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3). In particular embodiments, on average, at least 85%, at least 90%, or at least 95% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3). In certain embodiments, on average, at least 90% of recombinant receptor-expressing (e.g., CAR+) CD3+ T cells of a plurality of output compositions produced by the method disclosed herein are viable cells, e.g., cells negative for an apoptotic marker, such as a caspase (e.g., an activated caspase-3).

In any of the proceeding embodiments, the plurality of output compositions produced by the method disclosed herein may be originated from the same or different donors. In some aspects, at least two of the plurality of output compositions are originated from different donors. In some aspects, each of the plurality of output compositions is originated from one of a number of different donors, e.g., from about 2, about 5, about 10, about 15, about 20, about 25, about 30, about 35, about 40, about 45, about 50, about 55, about 60, or more than about 60 different donors, e.g., patients in need of a cell therapy such as a CAR-T cell therapy.

In any of the proceeding embodiments, the output composition can comprise about or at least about $10\times10^6$, about or at least about $20\times10^6$, about or at least about $25\times10^6$, about or at least about $50\times10^6$, about or at least about $100\times10^6$, about or at least about $200\times10^6$, about or at least about $400\times10^6$, about or at least about $600\times10^6$, about or at least about $800\times10^6$, about or at least about $1000\times10^6$, about or at least about $1200\times10^6$, about or at least about $1400\times10^6$, about or at least about $1600\times10^6$, about or at least about $1800\times10^6$, about or at least about $2000\times10^6$, about or at least about $2500\times10^6$, about or at least about $3000\times10^6$, or about or at least about $4000\times10^6$ total cells, e.g., total viable cells, in one or more containers such as vials. In any of the proceeding embodiments, the volume of the output composition can be between 1.0 mL and 10 mL, inclusive, optionally at or about 2 mL, at or about 3 mL, at or about 4 mL, at or about 5 mL, at or about 6 mL, at or about 7 mL, at or about 8 mL, at or about 9 mL, or at or about 10 mL, or any value between any of the foregoing. In some embodiments, the output composition is contained in a plurality of containers, such as 2, 3, 4, 5, 6, 7, 8, 9, 10 or more vials. In any of the proceeding embodiments, the output composition can comprise about or at least about $5\times10^6$, about or at least about $10\times10^6$, about or at least about $20\times10^6$, about or at least about $25\times10^6$, about or at least about $50\times10^6$, about or at least about $100\times10^6$, about or at least about $150\times10^6$, about or at least about $200\times10^6$, about or at least about $250\times10^6$, about or at least about $300\times10^6$, about or at least about $350\times10^6$, about or at least about $400\times10^6$, about or at least about $450\times10^6$, about or at least about $500\times10^6$, about or at least about $550\times10^6$, or about or at least about $600\times10^6$ total cells, e.g., total viable cells, per unit container such as per vial. In some embodiments, cells of the output composition in the one or more containers are at a density of, of about, or at least $5\times10^6$ cells/mL, $10\times10^6$ cells/mL, $20\times10^6$ cells/mL, $30\times10^6$ cells/mL, $40\times10^6$ cells/mL, $50\times10^6$ cells/mL, $60\times10^6$ cells/mL, $70\times10^6$ cells/mL, $80\times10^6$ cells/mL, $90\times10^6$ cells/mL, $100\times10^6$ cells/mL, $110\times10^6$ cells/mL, $120\times10^6$ cells/mL, $130\times10^6$ cells/mL, $140\times10^6$ cells/mL, or $150\times10^6$ cells/mL in a solution or buffer, e.g., in a cryopreservation solution or buffer. In some embodiments, about or up to about $900\times10^6$ cells (e.g., viable CD4+ T cells and viable CD8+ T cells, or viable CD3+ T cells) are subjected to stimulation, where about or up to about $600\times10^6$ cells (e.g., viable CD4+ T cells and viable CD8+ T cells, or viable CD3+ T cells) of the stimulated composition are subjected to genetic engineering such as with a viral vector, e.g. by transduction, or a non-viral method of genetic engineering followed by incubation in a serum-free basal media (e.g., supplemented with one or more supplements) without any recombinant cytokine for about 72 hours or about three days. In some embodiments, the output composition produced comprises between about $100\times10^6$ and about $1400\times10^6$ total cells, e.g., total viable cells, in one or more containers such as vials.

In particular embodiments, a majority of the cells of the output composition are naïve or naïve-like cells, central memory cells, and/or effector memory cells. In particular embodiments, a majority of the cells of the output composition are naïve-like or central memory cells. In some embodiments, a majority of the cells of the output composition are central memory cells. In some aspects, less differentiated cells, e.g., central memory cells, are longer lived and exhaust less rapidly, thereby increasing persistence and durability. In some aspects, a responder to a cell therapy, such as a CAR-T cell therapy, has increased expression of central memory genes. See, e.g., Fraietta et al. (2018) Nat Med. 24 (5): 563-571.

In certain embodiments, the cells of the output composition have a high portion and/or frequency of naïve-like T cells or T cells that are surface positive for a marker expressed on naïve-like T cells. In certain embodiments, the cells of the output compositions have a greater portion and/or frequency of naïve-like cells than output compositions generated from alternative processes, such as processes that involve expansion (e.g. processes that include an expansion unit operation and/or include steps intended to cause expansion of cells). In certain embodiments, naïve-like T cells may include cells in various differentiation states and may be characterized by positive or high expression (e.g., surface expression or intracellular expression) of certain cell markers and/or negative or low expression (e.g., surface expression or intracellular expression) of other cell markers. In some aspects, naïve-like T cells are characterized by positive or high expression of CCR7, CD45RA, CD28, and/or CD27. In some aspects, naïve-like T cells are characterized by negative expression of CD25, CD45RO, CD56, CD62L, and/or KLRG1. In some aspects, naïve-like T cells are characterized by low expression of CD95. In certain embodiments, naïve-like T cells or the T cells that are surface positive for a marker expressed on naïve-like T cells are CCR7+CD45RA+, where the cells are CD27+ or CD27−. In certain embodiments, naïve-like T cells or the T cells that are surface positive for a marker expressed on naïve-like T cells are CD27+CCR7+, where the cells are CD45RA+ or CD45RA−. In certain embodiments, naïve-like T cells or the T cells that are surface positive for a marker expressed on naïve-like T cells are CD62L−CCR7+.

In particular embodiments, the cells of the output composition are enriched in CCR7+ cells. CCR7 is a chemokine receptor that is involved in T cell entry into lymph nodes. In particular aspects, CCR7 is expressed by naïve or naïve-like T cells (e.g. CCR7+CD45RA+ or CCR7+CD27+) and central memory T cells (CCR7+CD45RA−). In some embodiments, provided compositions of engineered T cells produced by the provided methods include a population of T cells in which greater than at or about 50%, greater than at or about 55%, greater than or greater than at or about 60%, greater than or greater than at or about 65%, greater than or greater than at or about 70%, greater than or greater than at or about 75%, greater than or greater than at or about 80%, greater than or greater than at or about 85%, or greater than or greater than at or about 90%, of the T cells of the population are central memory and naïve-like T cells. In some embodiments, provided compositions of engineered T cells produced by the provided methods include a population of T cells in which greater than at or about 50%, greater than at or about 55%, greater than or greater than at or about 60%, greater than or greater than at or about 65%, greater than or greater than at or about 70%, greater than or greater than at or about 75%, greater than or greater than at or about 80%, greater than or greater than at or about 85%, or greater than or greater than at or about 90%, of the T cells of the population are CCR7+ T cells. In some embodiments, provided compositions of engineered T cells produced by the provided methods include a population of T cells in which greater than at or about 50%, greater than at or about 55%, greater than or greater than at or about 60%, greater than or greater than at or about 65%, greater than or greater than at or about 70%, greater than or greater than at or about 75%, greater than or greater than at or about 80%, greater than or greater than at or about 85%, or greater than or greater than at or about 90%, of the T cells of the population are CCR7+CD27+. In some embodiments, provided compositions of engineered T cells produced by the provided methods include a population of T cells in which greater than at or about 50%, greater than at or about 55%, greater than or greater than at or about 60%, greater than or greater than at or about 65%, greater than or greater than at or about 70%, greater than or greater than at or about 75%, greater than or greater than at or about 80%, greater than or greater than at or about 85%, or greater than or greater than at or about 90%, of the T cells of the population are CCR7+CD45RA−.

In certain embodiments, the cells of the output composition have a high portion and/or frequency of central memory T cells or T cells that are surface positive for a marker expressed on central memory T cells. In certain embodiments, the cells of the output compositions have a greater portion and/or frequency of central memory cells than output compositions generated from alternative processes, such as processes that involve expansion (e.g. processes that include an expansion unit operation and/or include steps intended to cause expansion of cells). In certain embodiments, central memory T cells may include cells in various differentiation states and may be characterized by positive or high expression (e.g., surface expression) of certain cell markers and/or negative or low expression (e.g., surface expression) of other cell markers. In some aspects, central memory T cells are characterized by positive or high expression of CD45RO, CD62L, CCR7, CD28, CD3, and/or CD127. In some aspects, central memory T cells are characterized by negative or low expression of CD45RA and/or granzyme B. In certain embodiments, central memory T cells or the T cells that are surface positive for a marker expressed on central memory T cells are CCR7+CD45RA−.

In certain embodiments, the cells of the output compositions have a greater portion and/or frequency of naïve-like cells and central memory cells than output compositions generated from alternative processes, such as processes that involve expansion (e.g. processes that include an expansion unit operation and/or include steps intended to cause expansion of cells).

In certain embodiments, the cells of the output composition have a low portion and/or frequency of effector memory and/or effector memory RA T cells or T cells that are surface positive for a marker expressed on effector memory and/or effector memory RA T cells. In certain embodiments, the cells of the output compositions have a lower portion and/or frequency of effector memory and/or effector memory RA T cells than output compositions generated from alternative processes, such as processes that involve expansion (e.g. processes that include an expansion unit operation and/or include steps intended to cause expansion of cells). In certain embodiments, effector memory and/or effector memory RA T cells may include cells in various differentiation states and may be characterized by positive or high expression (e.g., surface expression or intracellular expression) of certain cell markers and/or negative or low expression (e.g., surface expression or intracellular expression) of other cell markers. In certain embodiments, effector memory T cells or the T cells that are surface positive for a marker expressed on effector memory T cells are CCR7−CD45RA−. In certain embodiments, effector memory RA T cells or the T cells that are surface positive for a marker expressed on effector memory RA T cells are CCR7−CD45RA+.

In certain embodiments, the cells of the output compositions have a lower portion and/or frequency of effector memory T cells than output compositions generated from alternative processes, such as processes that involve expansion (e.g. processes that include an expansion unit operation and/or include steps intended to cause expansion of cells). In certain embodiments, the cells of the output compositions have a lower portion and/or frequency of effector memory RA T cells than output compositions generated from alternative processes, such as processes that involve expansion (e.g. processes that include an expansion unit operation and/or include steps intended to cause expansion of cells). In certain embodiments, the cells of the output compositions have a greater portion and/or frequency of naïve-like cells and central memory cells and a lower portion and/or frequency of effector memory and effector memory RA T cells, than output compositions generated from alternative processes, such as processes that involve expansion (e.g. processes that include an expansion unit operation and/or include steps intended to cause expansion of cells).

In certain embodiments, the cells of the output composition have a high portion and/or frequency of naïve-like and/or central memory cells. In certain embodiments, the cells of the output composition have a high portion and/or frequency of central memory cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the cells of the output composition are of a memory phenotype, are of a naïve-like or central memory phenotype, or are naïve-like or central memory T cells, or are central memory T cells. In certain embodiments, at least or at or about 50%, at least or at or about 55%, at least or at or about 60%, or at least or at or about 65% of the CD4+ T cells and CD8+ T cells of the output composition are naïve-like or central memory T cells, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ T cells of the output composition are naïve-like or central memory CD4+ T cells, or are central memory CD4+ T cells. In certain embodiments, at least or at or about 50%, at least or at or about 55%, at least or at or about 60%, or at least or at or about 65% of the CD4+ T cells of the output composition are naïve-like or central memory CD4+ T cells, or are central memory CD4+

T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ T cells of the output composition are naïve-like or central memory CD4+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+CAR+ T cells of the output composition are naïve-like or central memory CD4+CAR+ T cells, or are central memory CD4+CAR+ T cells. In certain embodiments, at least or at or about 50%, at least or at or about 55%, at least or at or about 60%, or at least or at or about 65% of the CD4+CAR+ T cells of the output composition are naïve-like or central memory CD4+CAR+ T cells, or are central memory CD4+CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+CAR+ T cells of the output composition are naïve-like or central memory CD4+CAR+ T cells, or are central memory CD4+CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+ T cells of the output composition are naïve-like or central memory CD8+ T cells, or are central memory CD8+ T cells. In certain embodiments, at least or at or about 50%, at least or at or about 55%, at least or at or about 60%, or at least or at or about 65% of the CD8+ T cells of the output composition are naïve-like or central memory CD8+ T cells, or are central memory CD8+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ T cells of the output composition are naïve-like or central memory CD8+ T cells, or are central memory CD8+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+CAR+ T cells of the output composition are naïve-like or central memory CD8+CAR+ T cells, or are central memory CD8+CAR+ T cells. In certain embodiments, at least or at or about 50%, at least or at or about 55%, at least or at or about 60%, or at least or at or about 65% of the CD8+CAR+ T cells of the output composition are naïve-like or central memory CD8+CAR+ T cells, or are central memory CD8+CAR+ T cells. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+CAR+ T cells of the output composition are naïve-like or central memory CD8+CAR+ T cells, or are central memory CD8+CAR+ T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CAR+ T cells (e.g., the CD4+CAR+ T cells and the CD8+CAR+ T cells) of the output composition are naïve-like or central memory T cells, or are central memory T cells. In certain embodiments, at least or at or about 50%, at least or at or about 55%, at least or at or about 60%, or at least or at or about 65% of the CAR+ T cells (e.g., the CD4+CAR+ T cells and the CD8+CAR+ T cells) of the output composition are naïve-like or central memory T cells, or are central memory T cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CAR+ T cells in the composition are CD27+, CD28+, CCR7+, CD45RA−, CD45RO+, CD62L+, CD3+, CD95+, granzyme B−, and/or CD127+. In some embodiments, at least or at or about 50%, at least or at or about 55%, at least or at or about 60%, or at least or at or about 65% of the CAR+ T cells in the composition are CD27+, CD28+, CCR7+, CD45RA−, CD45RO+, CD62L+, CD3+, CD95+, granzyme B−, and/or CD127+.

In certain embodiments, at least or at or about 85% of the cells of the output composition are of a naïve-like or central memory phenotype, or are naïve-like or central memory T cells. In certain embodiments, less than or at or about 15% of the cells of the output composition are of an effector or effector RA phenotype, or are effector or effector RA T cells. In certain embodiments, the cells of the output composition have a low portion and/or frequency of cells that are exhausted and/or senescent. In particular embodiments, the cells of the output composition have a low portion and/or frequency of cells that are exhausted and/or senescent. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are exhausted and/or senescent. In certain embodiments, less than at or about 25% of the cells of the output composition are exhausted and/or senescent. In certain embodiments, less than at or about less than at or about 10% of the cells of the output composition are exhausted and/or senescent.

In some embodiments, the cells of the output composition have a low portion and/or frequency of cells that are negative for CD27 and CD28 expression, e.g., surface expression. In particular embodiments, the cells of the output composition have a low portion and/or frequency of CD27-CD28-cells. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are CD27-CD28-cells. In certain embodiments, less than at or about 25% of the cells of the output composition are CD27-CD28-cells. In certain embodiments, less than at or about less than at or about 10% of the cells of the output composition are CD27-CD28-cells. In embodiments, less than at or about 5% of the cells of the output composition are CD27-CD28-cells.

In certain embodiments, the cells of the output composition have a high portion and/or frequency of cells that are positive for CD27 and CD28 expression, e.g., surface expression. In some embodiments, the cells of the output composition have a high portion and/or frequency of CD27+ CD28+ cells. In some embodiments, at least at or about 50%, at least at or about 60%, at least at or about 70%, at least at or about 75%, at least at or about 80%, at least at or about 85%, at least at or about 90%, at least at or about 95%, or greater than at or about 95% of the cells of the output composition are CD27+CD28+ cells. In certain embodiments, less than at or about 25% of the cells of the output composition are CD27-CD28-cells. In certain embodiments, at least at or about 50% of the cells of the output composition are CD27+CD28+ cells. In embodiments, at least at or about 75% of the cells of the output composition are CD27+ CD28+ cells.

In particular embodiments, the cells of the output composition have a low portion and/or frequency of cells that are $T_{EMRA}$ cells. In particular embodiments, the cells of the output composition have a low portion and/or frequency of $T_{EMRA}$ cells. In some embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are $T_{EMRA}$ cells. In some embodiments, less than at or about 25% of the cells of the output composition are $T_{EMRA}$ cells. In some embodiments, less than at or about 10% of the cells of the output composition are $T_{EMRA}$ cells. In some embodiments, less than at or about 5% of the cells of the output composition are $T_{EMRA}$ cells.

In certain embodiments, the cells of the output composition have a low portion and/or frequency of cells that are negative for CCR7 and positive for CD45RA expression, e.g., surface expression. In some embodiments, the cells of the output composition have a low portion and/or frequency of CCR7−CD45RA+ cells. In particular embodiments, less than at or about 40%, less than at or about 35%, less than at or about 30%, less than at or about 25%, less than at or about 20%, less than at or about 15%, less than at or about 10%, less than at or about 5%, or less than at or about 1% of the cells of the output composition are CCR7−CD45RA+ cells. In some embodiments, less than at or about 25% of the cells of the output composition are CCR7−CD45RA+ cells. In particular embodiments, less than at or about less than at or about 10% of the cells of the output composition are CCR7−CD45RA+ cells. In certain embodiments, less than at or about 5% of the cells of the output composition are CCR7-CD45RA+ cells.

In certain embodiments, the cells of the output composition have a high portion and/or frequency of T cells in an early stage of differentiation, or T cells that are surface positive for a marker expressed on T cells in an early stage of differentiation. In certain embodiments, the cells of the output compositions have a greater portion and/or frequency of T cells in an early stage of differentiation than output compositions generated from alternative processes, such as processes that involve expansion (e.g. processes that include an expansion unit operation and/or include steps intended to cause expansion of cells). In certain embodiments, T cells in an early stage of differentiation may be characterized by positive or high expression (e.g., surface expression or intracellular expression) of certain cell markers and/or negative or low expression (e.g., surface expression or intracellular expression) of other cell markers. In some aspects, T cells in an early stage of differentiation are characterized by positive or high expression of CCR7 and/or CD27. In certain embodiments, T cells in an early stage of differentiation or the T cells that are surface positive for a marker expressed on T cells in an early stage of differentiation are CCR7+ CD27+.

In certain embodiments, the cells of the output composition have a low portion and/or frequency of T cells in an intermediate stage of differentiation, or T cells that are surface positive for a marker expressed on T cells in an intermediate stage of differentiation. In certain embodiments, the cells of the output compositions have a lower portion and/or frequency of T cells in an intermediate stage of differentiation than output compositions generated from alternative processes, such as processes that involve expansion. In certain embodiments, T cells in an intermediate stage of differentiation may be characterized by positive or high expression (e.g., surface expression or intracellular expression) of certain cell markers and/or negative or low expression (e.g., surface expression or intracellular expression) of other cell markers. In certain embodiments, T cells in an intermediate stage of differentiation or the T cells that are surface positive for a marker expressed on T cells in an intermediate stage of differentiation are CCR7+CD27−. In certain embodiments, T cells in an intermediate stage of differentiation or the T cells that are surface positive for a marker expressed on T cells in an intermediate stage of differentiation are CCR7−CD27+. In certain embodiments, T cells in an intermediate stage of differentiation or the T cells that are surface positive for a marker expressed on T cells in an intermediate stage of differentiation include cells that are CCR7+CD27− and cells that are CCR7−CD27+.

In certain embodiments, the cells of the output composition have a low portion and/or frequency of highly differentiated T cells, or T cells that are surface positive for a marker expressed on highly differentiated T cells. In certain embodiments, the cells of the output compositions have a lower portion and/or frequency of highly differentiated T cells than output compositions generated from alternative processes, such as processes that involve expansion. In certain embodiments, highly differentiated T cells may be characterized by positive or high expression (e.g., surface expression or intracellular expression) of certain cell markers and/or negative or low expression (e.g., surface expression or intracellular expression) of other cell markers. In some aspects, highly differentiated T cells are characterized by negative or low expression of CCR7 and/or CD27. In certain embodiments, highly differentiated T cells or the T cells that are surface positive for a marker expressed on highly differentiated T cells are CCR7−CD27−.

In certain embodiments, the cells of the output compositions have a greater portion and/or frequency of T cells in an early stage of differentiation (e.g., cells that are CCR7+ CD27+), a lower portion and/or frequency of T cells in an intermediate stage of differentiation (e.g., cells that are CCR7+CD27− and/or cells that are CCR7−CD27+), and a lower portion and/or frequency of highly differentiated T cells (e.g., cells that are CCR7−CD27−), than output compositions generated from alternative processes, such as processes that involve expansion.

In certain embodiments, the cells of the output compositions have a greater portion and/or frequency of naïve-like cells and central memory cells than output compositions generated from alternative processes, such as processes that involve expansion. In certain embodiments, the naïve-like cells and central memory cells include cells in various differentiation states, including T cells in an early stage of differentiation, e.g., cells that are CCR7+CD27+.

In certain embodiments, the cells of the output composition have a high portion and/or frequency of cells that are positive for CCR7 and CD27 expression, e.g., surface expression. In some embodiments, the cells of the output composition have a high portion and/or frequency of CCR7+ CD27+ cells. In certain embodiments, less than or less than about 5%, less than or less than about 10%, less than or less than about 15%, less than or less than about 20%, less than or less than about 25%, or less than or less than about 30% of the cells the output composition are CCR7- or CD27- cells. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, at least or at or about 98%, or greater than 98% of the cells of the output composition are CCR7+CD27+. In certain embodiments, at least or at or about 50%, at least or at or about 55%, at least or at or about 60%, or at least or at or about 65% of the CD4+ T cells and CD8+ T cells of the output composition are CCR7+CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+ T cells of the output composition are CCR7+CD27+. In certain embodiments, at least or at or about 50%, at least or at or about 55%, at least or at or about 60%, or at least or at or about 65% of the CD4+ T cells of the output composition are CCR7+CD27+. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+ T cells of the output composition are CCR7+ CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD4+CAR+ T cells of the output composition are CCR7+CD27+. In certain embodiments, at least or at or about 50%, at least or at or about 55%, at least or at or about 60%, or at least or at or about 65% of the CD4+CAR+ T cells of the output composition are CCR7+CD27+. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD4+CAR+ T cells of the output composition are CCR7+ CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+ T cells of the output composition are CCR7+CD27+. In certain embodiments, at least or at or about 50%, at least or at or about 55%, at least or at or about 60%, or at least or at or about 65% of the CD8+ T cells of the output composition are CCR7+ CD27+. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+ T cells of the output composition are CCR7+CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CD8+CAR+ T cells of the output composition are CCR7+ CD27+. In certain embodiments, at least or at or about 50%, at least or at or about 55%, at least or at or about 60%, or at least or at or about 65% of the CD8+CAR+ T cells of the output composition are CCR7+CD27+. In certain embodiments, between at or about 40% and at or about 65%, between at or about 40% and at or about 45%, between at or about 45% and at or about 50%, between at or about 50% and at or about 55%, between at or about 55% and at or about 60%, or between at or about 60% and at or about 65% of the CD8+CAR+ T cells of the output composition are CCR7+CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CAR+ T cells (e.g., the CD4+CAR+ T cells and the CD8+CAR+ T cells) of the output composition are CCR7+CD27+. In certain embodiments, at least or at or about 50%, at least or at or about 55%, at least or at or about 60%, or at least or at or about 65% of the CAR+ T cells (e.g., the CD4+CAR+ T cells and the CD8+CAR+ T cells) of the output composition are CCR7+ CD27+. In some embodiments, at least or at or about 30%, at least or at or about 40%, at least or at or about 50%, at least or at or about 60%, at least or at or about 70%, at least or at or about 75%, at least or at or about 80%, at least or at or about 85%, at least or at or about 90%, at least or at or about 95%, or greater than 95% of the CAR+ T cells in the composition are CD27+, CD28+, CCR7+, CD45RA−, CD45RO+, CD62L+, CD3+, CD95+, granzyme B−, and/or CD127+. In some embodiments, at least or at or about 50%, at least or at or about 55%, at least or at or about 60%, or at least or at or about 65% of the CAR+ T cells in the composition are CD27+, CD28+, CCR7+, CD45RA−, CD45RO+, CD62L+, CD3+, CD95+, granzyme B−, and/or CD127+.

In some embodiments, provided herein is a therapeutic T cell composition comprising and/or enriched in CD3+ T cells expressing a recombinant receptor, wherein at least 50%, 60%, 70%, 80% or 90% of the total receptor$^+$/CD3+ cells in the composition are CD27+CCR7+. In some embodiments, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD3+ T cells. In some embodiments, at least or at least about 90% of the cells in the composition are CD3+ T cells, and at least or at least about 40%, 50%, 60%, 70%, 80% or 90% of the total receptor$^+$/CD3$^+$ cells in the composition are CD27+CCR7+. In some embodiments, at least or at least about 95% of the cells in the composition are CD3+ T cells, and at least or at least about 50%, 60%, 70%, 80% or 90% of the total receptor$^+$/CD3$^+$ cells in the composition are CD27+CCR7+. In some embodiments, at least or at least about 98% of the cells in the composition are CD3+ T cells, and at least or at least about 50%, 60%, 70%, 80% or 90% of the total receptor$^+$/CD3$^+$ cells in the composition are CD27+CCR7+. In some embodiments, at least 50%, 60%, 70%, 80% or 90% of the cells in the composition are CD3+ T cells, at least 50% of the total receptor$^+$/CD8$^+$ cells in the composition are CD27+CCR7+ and at least 50% of the total receptor$^+$/CD4$^+$ cells in the composition are CD27+CCR7+. In some embodiments, at least 90% of the cells in the composition are CD3+ T cells, at least 50%, 60%, 70%, 80% or 90% of the total receptor$^+$/CD8$^+$ cells in the composition are CD27+CCR7+, and at least 50%, 60%, 70%, 80% or 90% of the total receptor$^+$/CD4$^+$ cells in the composition are CD27+CCR7+.

In some embodiments, provided herein is a therapeutic T cell composition comprising and/or enriched in CD3+ T cells expressing a recombinant receptor, wherein at least 50%, 60%, 70%, 80% or 90% of the total receptor$^+$/CD3+ cells in the composition are naïve-like T cells or central memory T cells or are surface positive for a marker expressed on naïve-like T cells or central memory T cells. In some embodiments, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD3+ T cells. In some embodiments, at least or at least about 90% of the cells in the composition are CD3+ T cells, and at least or at least about 40%, 50%, 60%, 70%, 80% or 90% of the total receptor$^+$/CD3+ cells in the composition are naïve-like T cells or central memory T cells or are surface positive for a marker expressed on naïve-like T cells or central memory T cells. In some embodiments, at least or at least about 95% of the cells in the composition are CD3+ T cells, and at least or at least about 50%, 60%, 70%, 80% or 90% of the total receptor$^+$/CD3$^+$ cells in the composition are naïve-like T cells or central memory T cells or are surface positive for a marker expressed on naïve-like T cells or central memory T cells. In some embodiments, at least or at least about 98% of the cells in the composition are CD3+ T cells, and at least or at least about 50%, 60%, 70%, 80% or 90% of the total receptor$^+$/CD3+ cells in the composition are naïve-like T cells or central memory T cells or are surface positive for a marker expressed on naïve-like T cells or central memory T cells. In some embodiments, at least 50%, 60%, 70%, 80% or 90% of the cells in the composition are CD3+ T cells, at least 50% of the total receptor$^+$/CD8$^+$ cells in the composition are naïve-like T cells or central memory T cells or are surface positive for a marker expressed on naïve-like T cells or central memory T cells and at least 50% of the total receptor$^+$/CD4$^+$ cells in the composition are naïve-like T cells or central memory T cells or are surface positive for a marker expressed on naïve-like T cells or central memory T cells. In some embodiments, at least 90% of the cells in the composition are CD3+ T cells, at least 50%, 60%, 70%, 80% or 90% of the total receptor$^+$/CD8$^+$ cells in the composition are naïve-like T cells or central memory T cells or are surface positive for a marker expressed on naïve-like T cells or central memory T cells, and at least 50%, 60%, 70%, 80% or 90% of the total receptor$^+$/CD4$^+$ cells in the composition are naïve-like T cells or central memory T cells or are surface positive for a marker expressed on naïve-like T cells or central memory T cells.

In some embodiments, provided herein is a therapeutic T cell composition comprising and/or enriched in CD4+ T cells and CD8+ T cells expressing a recombinant receptor, wherein at least 50%, 60%, 70%, 80% or 90% of the total receptor$^+$/CD4$^+$ and receptor$^+$/CD8$^+$ cells in the composition are CD27+CCR7+. In some embodiments, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells.

In some embodiments, provided herein is a therapeutic T cell composition comprising and/or enriched in CD4+ T cells and CD8+ T cells expressing a recombinant receptor, wherein at least 50%, 60%, 70%, 80% or 90% of the total receptor+/CD4+ and receptor+/CD8+ cells in the composition are naïve-like T cells or central memory T cells or are surface positive for a marker expressed on naïve-like T cells or central memory T cells. In some embodiments, at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells. In some embodiments, at least or at least about 90% of the cells in the composition are CD4+ T cells and CD8+ T cells, and at least or at least about 40%, 50%, 60%, 70%, 80% or 90% of the total receptor+/CD4+ and receptor+/CD8+ cells in the composition are naïve-like T cells or central memory T cells or are surface positive for a marker expressed on naïve-like T cells or central memory T cells. In some embodiments, at least or at least about 95% of the cells in the composition are CD4+ T cells and CD8+ T cells, and at least or at least about 50%, 60%, 70%, 80% or 90% of the total receptor+/CD4+ and receptor+/CD8+ cells in the composition are naïve-like T cells or central memory T cells or are surface positive for a marker expressed on naïve-like T cells or central memory T cells. In some embodiments, at least or at least about 98% of the cells in the composition are CD4+ T cells and CD8+ T cells, and at least or at least about 50%, 60%, 70%, 80% or 90% of the total receptor$^+$/CD4$^+$ and receptor$^+$/CD8$^+$ cells in the composition are naïve-like T cells or central memory T cells or are surface positive for a marker expressed on naïve-like T cells or central memory T cells. In some embodiments, at least 50%, 60%, 70%, 80% or 90% of the cells in the composition are CD4+ T cells and CD8+ T cells, at least 50% of the total receptor$^+$/CD8$^+$ cells in the composition are naïve-like T cells or central memory T cells or are surface positive for a marker expressed on naïve-like T cells or central memory T cells and at least 50% of the total receptor$^+$/CD4$^+$ cells in the composition are naïve-like T cells or central memory T cells or are surface positive for a marker expressed on naïve-like T cells or central memory T cells. In some embodiments, at least 90% of the cells in the composition are CD4+ T cells and CD8+ T cells, at least 50%, 60%, 70%, 80% or 90% of the total receptor$^+$/CD8$^+$ cells in the composition are naïve-like T cells or central memory T cells or are surface positive for a marker expressed on naïve-like T cells or central memory T cells, and at least 50%, 60%, 70%, 80% or 90% of the total receptor$^+$/CD4$^+$ cells in the composition are naïve-like T cells or central memory T cells or are surface positive for a marker expressed on naïve-like T cells or central memory T cells.

In certain embodiments, disclosed herein is a therapeutic T cell composition comprising CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are CD27+CCR7+ and at least 30%, 40%, 50%, 60%, 70%, 80% or 90% of the total receptor$^+$/CD4$^+$ cells in the composition are CD27+CCR7+, wherein at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD3+ T cells. In certain embodiments, disclosed herein is a therapeutic T cell composition comprising CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are CD27+CCR7+ and at least 30%, 40%, 50%, 60%, 70%, 80% or 90% of the total receptor$^+$/CD4$^+$ cells in the composition are CD27+CCR7+, wherein at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells. In some aspects, at least or at least about 90% of the cells in the composition are CD4+ T cells and CD8+ T cells, at least or at least about 60% of the total receptor$^+$/CD8$^+$ cells in the composition are CD27+CCR7+, and at least or at least about 40% of the total receptor$^+$/CD4$^+$ cells in the therapeutic T cell composition are CD27+CCR7+. In some aspects, at least or at least about 95% of the cells in the composition are CD4+ T cells and CD8+ T cells, at least or at least about 65% of the total receptor$^+$/CD8$^+$ cells in the composition are CD27+CCR7+, and at least or at least about 45% of the total receptor$^+$/CD4$^+$ cells in the therapeutic T cell composition are CD27+CCR7+. In some aspects, at least or at least about 98% of the cells in the composition are CD4+ T cells and CD8+ T cells, at least or at least about 70%, at least or at least about 75%, at least or at least about 80%, or at least or at least about 85% of the total receptor$^+$/CD8$^+$ cells in the composition are CD27+CCR7+, and at least or at least about 50%, at least or at least about 55%, at least or at least about 60%, or at least or at least about 65% of the total receptor$^+$/CD4$^+$ cells in the therapeutic T cell composition are CD27+CCR7+. In some aspects, at least or at least about 98% of the cells in the composition are CD4+ T cells and CD8+ T cells, at least or at least about 75% of the total receptor$^+$/CD8$^+$ cells in the composition are CD27+CCR7+, and at least or at least about 55% of the total receptor$^+$/CD4$^+$ cells in the therapeutic T cell composition are CD27+CCR7+. In some aspects, at least or at least about 98% of the cells in the composition are CD4+ T cells and CD8+ T cells, at least or at least about 80% of the total receptor$^+$/CD8$^+$ cells in the composition are CD27+CCR7+, and at least or at least about 60% of the total receptor$^+$/CD4$^+$ cells in the composition are CD27+CCR7+. In some aspects, at least or at least about 98% of the cells in the composition are CD4+ T cells and CD8+ T cells, at least or at least about 85% of the total receptor$^+$/CD8$^+$ cells in the composition are CD27+CCR7+, and at least or at least about 65% of the total receptor$^+$/CD4$^+$ cells in the composition are CD27+CCR7+. In some aspects, at least or at least about 98% of the cells in the composition are CD4+ T cells and CD8+ T cells, at least or at least about 90% of the total receptor$^+$/CD8$^+$ cells in the composition are CD27+CCR7+, and at least or at least about 70% of the total receptor$^+$/CD4$^+$ cells in the composition are CD27+CCR7+. In some aspects, at least 90% of the cells in the composition are CD4+ T cells and CD8+ T cells, at least 60% of the total receptor$^+$/CD8$^+$ cells in the composition are CD27+CCR7+ and at least 40% of the total receptor$^+$/CD4$^+$ cells in the composition are CD27+CCR7+. In some aspects, at least 90% of the cells in the composition are CD4+ T cells and CD8+ T cells, at least 70% of the total receptor$^+$/CD8$^+$ cells in the composition are CD27+CCR7+ and at least 50% of the total receptor$^+$/CD4$^+$ cells in the composition are CD27+CCR7+. In some aspects, at least 90% of the cells in the composition are CD4+ T cells and CD8+ T cells, at least 70% of the total receptor$^+$/CD8$^+$ cells in the composition are CD27+CCR7+ and at least 60% of the total receptor$^+$/CD4$^+$ cells in the composition are CD27+CCR7+. In some aspects, at least 95% of the cells in the composition are CD4+ T cells and CD8+ T cells, at least 70% of the total receptor$^+$/CD8$^+$ cells in the composition are CD27+CCR7+ and at least 70% of the total receptor$^+$/CD4$^+$ cells in the composition are CD27+CCR7+. In some aspects, at least 95% of the cells in the composition are CD4+ T cells and CD8+ T cells, at least 80% of the total receptor$^+$/CD8$^+$ cells in the composition are CD27+CCR7+ and at least 80% of the total receptor$^+$/CD4$^+$ cells in the composition are CD27+CCR7+.

In any of the preceding embodiments, a percentage of cells positive/negative for one or more markers (e.g., CD3, CD4, CD8, CD27, CD28, CCR7, or CD45RA, etc.) within a cell population or composition can be an average, mean, or median percentage from a plurality of output compositions produced by the method disclosed herein. In some embodiments, a percentage of cells positive for a marker within a cell population or composition is an average of such percentages from a plurality of output compositions produced by the method disclosed herein. In some embodiments, the plurality of output compositions are produced by the method disclosed herein from a plurality of input compositions, which may be originated from the same biological sample or different biological samples (e.g., PBMCs or an apheresis or leukapheresis sample), e.g., from the same donor or different donors. In some aspects, the average is based on the plurality of about or at least about 5, about or at least about 10, about or at least about 15, about or at least about 20, about or at least about 25, about or at least about 30, about or at least about 35, about or at least about 40, about or at least about 45, about or at least about 50, about or at least about 55, about or at least about 60, about or at least about 100, or more than about 100 output compositions produced by the method disclosed herein.

In some embodiments, wherein on average in a plurality of output compositions (e.g., about or at least about 5) produced by the method, at least at or about, or at or about, 80%, 85%, 90%, 95%, 96%, 97%, 98%, or 99% of the total number of T cells in the composition or of the total number of T cells in the composition expressing the recombinant protein, are CD4+ T cells and CD8+ T cells. In some embodiments, on average in a plurality of output compositions (e.g., about or at least about 5) produced by the method, at least 50%, 60%, 70%, 80% or 90% of the total receptor$^+$/CD4$^+$ and receptor$^+$/CD8$^+$ cells in the composition are naïve-like T cells or are surface positive for a marker expressed on naïve-like T cells (e.g., CD27+CCR7+ cells). In some embodiments, a plurality of (e.g., about or at least about 5) output compositions produced by the method disclosed herein, on average, comprise at least 50%, 60%, 70%, 80% or 90% naïve-like T cells or central memory T cells or are surface positive for a marker expressed on naïve-like T cells or central memory T cells, of the total receptor$^+$/CD4$^+$ and receptor$^+$/CD8$^+$ cells in the composition. In some embodiments, a plurality of (e.g., about or at least about 5) output compositions produced by the method disclosed herein, on average, comprise at least 50%, 60%, 70%, 80% or 90% CD27+CCR7+ cells of the total receptor$^+$/CD4$^+$ and receptor$^+$/CD8$^+$ cells in the composition. In some embodiments, a plurality of (e.g., about or at least about 5) output compositions produced by the method disclosed herein, on average, comprise at least or at least about 80%, 85%, 90%, 95%, 96%, 97%, 98%, or 99% CD3+ T cells. In some embodiments, a plurality of (e.g., about or at least about 5) output compositions produced by the method disclosed herein, on average, comprise at least 50%, 60%, 70%, 80% or 90% naïve-like T cells or are surface positive for a marker expressed on naïve-like T cells (e.g., CD27+CCR7+ cells), of the total receptor$^+$/CD3+ cells in the composition. In some embodiments, a plurality of (e.g., about or at least about 5) output compositions produced by the method disclosed herein, on average, comprise at least 50%, 60%, 70%, 80% or 90% naïve-like T cells or central memory T cells or are surface positive for a marker expressed on naïve-like T cells or central memory T cells, of the total receptor$^+$/CD3+ cells in the composition. In some embodiments, a plurality of (e.g., about or at least about 5) output compositions produced by the method disclosed herein, on average, comprise at least 50%, 60%, 70%, 80% or 90% CD27+CCR7+ cells of the total receptor$^+$/CD3+ cells in the composition.

II. Serum-Free Medium Formulations and Related Components

One or more steps of the provided methods can be carried out in the presence of a serum-free media containing a free form of glutamine (i.e., L-glutamine) in a basal medium. One or more further supplements can be added, including one or more supplements containing at least one protein, such as a serum-substituting protein, or one or more other components supporting maintenance, growth and/or expansion of cells. In some embodiments, the serum-free media contains a synthetic amino acid (e.g., a dipeptide form of L-glutamine, e.g., L-alanyl-L-glutamine), In some embodiments, the concentration of the synthetic amino acid (e.g., a dipeptide form of L-glutamine, e.g., L-alanyl-L-glutamine) is at or about 0.5 mM to at or about 5 mM (such as 2 mM). In some embodiments, the concentration of L-glutamine is at or about 0.5 mM to at or about 5 mM (such as 2 mM). In some embodiments, the at least one protein is a human protein or a recombinant protein, such as a serum-substituting protein, e.g. albumin. In some embodiments, the serum free media further comprises one or more recombinant cytokine (such as IL-2, IL-7, or IL-15). In some embodiments, the serum free media does not further comprise one or more recombinant cytokine (such as IL-2, IL-7, or IL-15). In some embodiments, the serum-free media does not comprise phenol red.

In some embodiments, the provided serum-free media is produced or prepared from a liquid basal medium and one or more supplements.

In some embodiments, the serum-free media can contain a synthetic amino acid that is capable of being converted into L-glutamine in a cell culture, such as a synthetic amino acid that is a dipeptide form of L-glutamine, e.g., L-alanyl-L-glutamine. In some cases, the synthetic amino acid is provided in a basal medium in which is contained a free of L-glutamine and a protein. In some embodiments, the concentration of the synthetic amino acid (e.g., a dipeptide form of L-glutamine, e.g., L-alanyl-L-glutamine) is at or about 0.5 mM to at or about 5 mM (such as 2 mM). In some embodiments, the at least one protein is a human-derived protein, a recombinant protein, or both. In some embodiments, the basal medium does not comprise phenol red.

In some embodiments, among supplements for preparing a serum-free media is a supplement comprising at least one protein and a free form of glutamine, e.g. L-glutamine, wherein the supplement is frozen or has been frozen after L-glutamine becomes a component thereof. In some embodiments, the concentration of L-glutamine in the supplement is less than 200 mM, such as less than 150 mM, 100 mM or less, such as 20 mM to 120 mM, or 40 mM to 100 mM, such as or about 80 mM. In some embodiments, the concentration of L-glutamine after the supplement has been combined with basal medium is about 0.5 mM to about 5 mM (such as 2 mM). In some embodiments, the at least one protein is not of a non-mammalian origin. In some embodiments, the at least one protein is a human protein or a human-derived protein or is recombinant. In some embodiments, the at least one protein includes albumin, e.g. human or recombinant human albumin.

A. Basal Medium

In some embodiments, the basal medium comprises a carbon source such as glucose, water, one or more salts, and a source of amino acids and nitrogen.

In some embodiments, the basal medium comprises an amino acid. In some embodiments, the amino acid comprises aspartic acid, glutamic acid, asparagine, serine, glutamine, histidine, glycine, threonine, arginine, alanine, tyrosine, cysteine, valine, methionine, norvaline, tryptophan, phenylalanine, isoleucine, leucine, lysine, hydroxyproline, sarcosine, and/or proline.

In some embodiments, the basal medium comprises at least one synthetic amino acid. In some embodiments, the synthetic amino acid is capable of being converted into a free form of glutamine (i.e., L-glutamine) in a cell culture comprising a cell. In some embodiments, the cell comprises a human cell. In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the synthetic amino acid is a stabilized form of glutamine (i.e., L-glutamine). In some embodiments, the synthetic amino acid is more stable than glutamine (i.e., L-glutamine) in an aqueous solution (e.g., a basal medium). In some embodiments, the synthetic amino acid does not produce a significant amount of glutamine in the basal medium. In some embodiments, the synthetic amino acid does not produce a significant amount of pyrrolidone carboxylic acid or ammonia in the basal medium. In some embodiments, the synthetic amino acid does not produce a significant amount of glutamine (i.e., L-glutamine) for at least about 1, 3, 5, 7, 9, 11 13, or 14 days in the basal medium. In some embodiments, the synthetic amino acid does not produce a significant amount of glutamine (i.e., L-glutamine) for at least about 1, 2, 3, 4, 5, 6, 7, or 8 weeks in the basal medium. In some embodiments, the synthetic amino acid does not produce a significant amount of glutamine (i.e., L-glutamine) for at least about 1, 2, 3, 4, 5, 6, 7, 8, 9, 10, 11, or 12 months in the basal medium. In some embodiments, the synthetic amino acid does not produce a significant amount of glutamine (i.e., L-glutamine) for at least 1, 2, 3, 4, or 5 years in the basal medium. In some embodiments, the synthetic amino acid does not produce a significant amount of pyrrolidone carboxylic acid or ammonia for at least about 1, 3, 5, 7, 9, 11 13, or 14 days in the basal medium. In some embodiments, the synthetic amino acid does not produce a significant amount of pyrrolidone carboxylic acid or ammonia for at least about 1, 2, 3, 4, 5, 6, 7, or 8 weeks in the basal medium. In some embodiments, the synthetic amino acid does not produce a significant amount of pyrrolidone carboxylic acid or ammonia for at least about 1, 2, 3, 4, 5, 6, 7, 8, 9, 10, 11, or 12 months in the basal medium. In some embodiments, the synthetic amino acid does not produce a significant amount of pyrrolidone carboxylic acid or ammonia for at least 1, 2, 3, 4, or 5 years in the basal medium.

In some embodiments, the synthetic amino acid is soluble in an aqueous solution (e.g., a basal medium). In some embodiments, the solubility of the synthetic amino acid in the aqueous solution is higher than a free form of glutamine (i.e., L-glutamine).

In some embodiments, the synthetic amino acid is capable of being transported into a cell, wherein it can be converted into a free form of glutamine (i.e., L-glutamine). In some embodiments, the cell comprises an immune cell. In some embodiments, the cell is a genetically engineered cell. In some embodiments, the cell is a T cell. In some embodiments, the cell is a genetically engineered T cell. In some embodiments, the cell is genetically engineered to express a recombinant receptor (e.g., a chimeric antigen receptor). In some embodiments, the cell is a chimeric antigen receptor (CAR) expressing T cells.

In some embodiments, the synthetic amino acid is a dipeptide. In some embodiments, the synthetic amino acid is a tripeptide. In some embodiments, the synthetic amino acid is a dipeptide form of L-glutamine (e.g., L-alanyl-L-glutamine), such as the dipeptide in Glutamax™ that does not spontaneously degrade in the basal medium.

In some embodiments, the concentration of the dipeptide form of L-glutamine (e.g., L-alanyl-L-glutamine) in the basal medium is about 0.5 mM-5 mM. In some embodiments, the concentration of the dipeptide form of L-glutamine (e.g., L-alanyl-L-glutamine) in the basal medium is at or about 2 mM. In some embodiments, the concentration of the dipeptide form of L-glutamine (e.g., L-alanyl-L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the dipeptide form of L-glutamine (e.g., L-alanyl-L-glutamine) in the basal medium is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of dipeptide form of L-glutamine (e.g., L-alanyl-L-glutamine) in the basal medium is at least about at or 0.5 mM, 1 mM, 1.5 mM, 2 mM, 2.5 mM, 3 mM, 3.5 mM, 4 mM, 4.5 mM, or 5 mM. In some embodiments, the concentration of the dipeptide form of L-glutamine (e.g., L-alanyl-L-glutamine) in the basal medium is or is about 2 mM. In some embodiments, the concentration of the dipeptide form of L-glutamine (e.g., L-alanyl-L-glutamine) in the basal medium is at most at or about 2 mM, 2.5 mM, 3 mM, 3.5 mM, 4 mM, 4.5 mM, 5 mM, 5.5 mM, 6 mM, 6.5 mM, 7 mM, 7.5 mM, 8 mM, 8.5 mM, 9 mM, 9.5 mM, 10 mM, 12.5 mM, 15 mM, 17.5 mM, or 20 mM.

In some embodiments, the basal medium does not comprise L-glutamine or does not comprise a significant amount of L-glutamine.

In some embodiments, the basal medium comprises L-glutamine. In some embodiments, the concentration of the L-glutamine in the basal medium is at or about or less than at or about 0.1 mM, 0.2 mM, 0.3 mM, 0.4 mM, or 0.5 mM. In some embodiments, the concentration of the L-glutamine in the basal medium is at or about or less than at or about 1 mM, 2 mM, 3 mM, 4 mM, or 5 mM. In some embodiments, the concentration of the L-glutamine in the basal medium is at or about 2 mM.

In some embodiments, the one or more amino acids, including at least one synthetic amino acid that is capable of being converted into a free form of glutamine (i.e., L-glutamine), e.g. dipeptide form of L-glutamine, such as L-alanyl-L-glutamine, is provided in a basal medium. In some embodiments, the basal media is an artificial or synthetic medium. In some embodiments, the basal media is or comprises a balanced salt solution (e.g., PBS, DPBS, HBSS, EBSS). In some embodiments, the basal media is selected from Dulbecco's Modified Eagle's Medium (DMEM), Minimal Essential Medium (MEM), Basal Medium Eagle (BME), F-10, F-12, RPMI 1640, Glasgow's Minimal Essential Medium (GMEM), alpha Minimal Essential Medium (alpha MEM), Iscove's Modified Dulbecco's Medium, and M199. In some embodiments, the basal media is a complex medium (e.g., RPMI-1640, IMDM). In some embodiments, the basal medium is OpTmizer™ CTS™ T-Cell Expansion Basal Medium (ThermoFisher).

In some embodiments, the basal media comprises a nutrient mixture of inorganic salts, sugars, amino acids, optionally also containing vitamins, organic acids, antioxidants, and/or buffers.

In some embodiments, the basal medium comprises $CO_3^{2-}$ and $HCO_3^-$. In some embodiments, the $CO_3^{2-}/HCO_3^-$ content of the basal medium is balanced with gaseous $CO_2$ (e.g., 5-10%), thereby maintaining an optimal pH in the medium. In some embodiments, the basal medium comprises a zwitterion, e.g. HEPES. In some embodiments, the basal medium comprises phenol red. In some embodiments, the basal medium does not comprise phenol red.

In some embodiments, the basal medium comprises an inorganic salt. In some embodiments, the inorganic salt promotes the osmotic balance. In some embodiments, the inorganic salt regulates membrane potential by providing sodium, potassium, and calcium ions.

In some embodiments, the basal medium comprises one or more carbohydrates. In some embodiments, the carbohydrate comprises glucose. In some embodiments, the carbohydrate comprises galactose. In some embodiments, the carbohydrate comprises maltose. In some embodiments, the carbohydrate comprises fructose.

In some embodiments, the basal medium comprises fatty acid. In some embodiments, the basal medium comprises lipid. In some embodiments, the basal medium comprises vitamin (e.g., Vitamin A, Vitamin B7, Vitamin B9, Vitamin B12, Vitamin C, Vitamin E). In some embodiments, the basal medium comprises a trace element. In some embodiments, the trace element comprises copper. In some embodiments, the trace element comprises zinc. In some embodiments, the trace element comprises selenium. In some embodiments, the trace element comprises tricarboxylic acid intermediate.

In some embodiments, the basal medium contains a mixture of inorganic salts, sugars, amino acids, and, optionally, vitamins, organic acids and/or buffers or other well known cell culture nutrients. In addition to nutrients, the medium also helps maintain pH and osmolality. In some aspects, the reagents of the basal media support cell growth, proliferation and/or expansion. A wide variety of basal media are available and include Dulbeccos' Modified Eagles Medium (DMEM), Roswell Park Memorial Institute Medium (RPMI), Iscove modified Dulbeccos' medium and Hams medium. In some embodiments, the basal medium is Iscove's Modified Dulbecco's Medium, RPMI-1640, or α-MEM.

In some embodiments, the basal medium is free of a protein. In some embodiments, the basal medium is free of a human protein (e.g., a human serum protein). In some embodiments, the basal medium is serum-free. In some embodiments, the basal medium is free of serum derived from human. In some embodiments, the basal medium is free of a recombinant protein. In some embodiments, the basal medium is free of a human protein and a recombinant protein.

In some embodiments, the basal medium comprises a protein or a peptide. In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II. In some embodiments, the protein or peptide comprises a transferrin. In some embodiments, the protein or peptide comprises a fibronectin. In some embodiments, the protein or peptide comprises aprotinin. In some embodiments, the protein comprises fetuin.

In some embodiments, the basal medium (e.g. OpTmizer™ CTS™ T-Cell Expansion Basal Medium) is a liquid formulation. In some embodiments, the basal medium has not been frozen or is instructed not to be frozen (e.g., according to its protocol) prior to an intended use. In some embodiments, the basal medium is stored at at or about 2° C. to 8° C. In some embodiments, the basal medium is stored at room temperature. In some embodiments, the basal medium is stable for at least at or about 1, 2, 3, 4, 5, or 6 weeks when stored at 2° C. to 8° C. In some embodiments, the basal medium is stable for at least at or about 1, 2, 3, 4, 5, or 6 months when stored at 2° C. to 8° C.

B. Additional Components and Supplement

In some embodiments, the serum-free media includes the basal medium and one or more additional components, which can be provided by one or more supplements. In some embodiments, the one or more supplement includes at least a first supplement, comprising a free form of glutamine (i.e., L-glutamine). In some embodiments, such a supplement is frozen prior to use and/or incorporation into a basal medium. In some embodiments, the supplement such as these described herein is intended to be used as a media supplement (e.g., a media supplement for a basal medium). In some embodiments, the first supplement and/or further supplement provides for the maintenance of a cell. In some embodiments, the cell is a primary cell. In some embodiments, the cell is an immune cell. In some embodiments, the cell is a T cell. In some embodiments, the cell is a CD4 T cell or CD8 T cell. In some embodiments, the cell is a cell from human. In some embodiments, the cell is an immune cell from human. In some embodiments, the cell is a T cell from human. In some embodiments, the cell is a primary immune cell from human. In some embodiments, the cell is a genetically engineered cell. In some embodiments, the cell is a genetically engineered cell derived from human. In some embodiments, the cell is a genetically engineered T cell (e.g., a chimeric antigen receptor (CAR) expressing T cell) from human.

In some embodiments, the first supplement is stored or is recommended to be stored at or about −20° C. to at or about 0° C. before its intended use. In some embodiments, the supplement is stored or is recommended to be stored at less than about 0° C. In some embodiments, the supplement is frozen immediately or quickly after the free form of glutamine (i.e., L-glutamine) becomes a component thereof until the time when the supplement is used for its intended use. In some embodiments, the supplement is frozen for the majority of the time after the free form of glutamine (i.e., L-glutamine) becomes a component thereof until the time when the supplement is used for its intended use. In some embodiments, the supplement is not kept as a liquid for more than 1, 2, 3, 4, 5, 6, or 7 days after the free form of glutamine (i.e., L-glutamine) becomes a component thereof until the time when the supplement is used for its intended use. In some embodiments, the supplement is not kept as a liquid for more than or more than about 4, 8, 12, 16, 20, or 24 hours after the free form of glutamine (i.e., L-glutamine) becomes a component thereof until the time when the supplement is used for its intended use. In some embodiments, the supplement is frozen for the majority of the time both before and after the free form of glutamine (i.e., L-glutamine) becomes a component thereof until the time when the supplement is used for its intended use. In some embodiments, the supplement is at or below room temperature (e.g., the temperature of the supplement is under or under about 20° C., 15° C., 10° C., 5° C., or 0° C.) when the free form of glutamine (i.e., L-glutamine) becomes a component of the supplement. In one aspect, the presence of the L-glutamine in the frozen supplement ensured its stability prior to addition to the basal media to minimize variable glutamine concentration and/or increasing ammonia concentration in the serum-free media formulation that can occur due to instability of L-glutamine.

In some embodiments, the free form L-glutamine in the supplement does not precipitate when the supplement is thawed. In some embodiments, the free form L-glutamine in the supplement does not precipitate when the supplement is a liquid. In some embodiments, the free form L-glutamine in the supplement does not precipitate when the supplement is thawed under room temperature. In some embodiments, the concentration of free form L-glutamine in the supplement is at or about or less than or less than about 400 mM, 300 mM, 200 mM, 180 mM, 160 mM, 140 mM, 120 mM, 100 mM or 80 mM. In some embodiments, the concentration of L-glutamine in the supplement is about 200 mM.

In some embodiments, the concentration of the free form of glutamine (i.e., L-glutamine) in the supplement is such that after the supplement is combined with a basal medium (such as these described herein), the concentration of the free form of glutamine (i.e., L-glutamine) in the media is at or about 0.5 mM-5 mM. In some embodiments, the concentration of the free form of glutamine (i.e., L-glutamine) in the basal medium is at or about 2 mM. In some embodiments, the concentration of the free form of glutamine (i.e., L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, 0.5 mM-5 mM, 1 mM-1.5 mM, 1 mM-2 mM, 1 mM-2.5 mM, 1 mM-3 mM, 1 mM-3.5 mM, 1 mM-4 mM, 1 mM-4.5 mM, 1 mM-5 mM, 1.5 mM-2 mM, 1.5 mM-2.5 mM, 1.5 mM-3 mM, 1.5 mM-3.5 mM, 1.5 mM-4 mM, 1.5 mM-4.5 mM, 1.5 mM-5 mM, 2 mM-2.5 mM, 2 mM-3 mM, 2 mM-3.5 mM, 2 mM-4 mM, 2 mM-4.5 mM, 2 mM-5 mM, 2.5 mM-3 mM, 2.5 mM-3.5 mM, 2.5 mM-4 mM, 2.5 mM-4.5 mM, 2.5 mM-5 mM, 3 mM-3.5 mM, 3 mM-4 mM, 3 mM-4.5 mM, 3 mM-5 mM, 3.5 mM-4 mM, 3.5 mM-4.5 mM, 3.5 mM-5 mM, 4 mM-4.5 mM, 4 mM-5 mM, or 4.5 mM-5 mM, each inclusive. In some embodiments, the concentration of the free form of glutamine (i.e., L-glutamine) in the basal medium is at or about 5 mM-7.5 mM, 5 mM-10 mM, 5 mM-12.5 mM, 5 mM-15 mM, 5 mM-17.5 mM, 5 mM-20 mM, 7.5 mM-10 mM, 7.5 mM-12.5 mM, 7.5 mM-15 mM, 7.5 mM-17.5 mM, 7.5 mM-20 mM, 10 mM-12.5 mM, 10 mM-15 mM, 10 mM-17.5 mM, 10 mM-20 mM, 12.5 mM-15 mM, 12.5 mM-17.5 mM, 12.5 mM-20 mM, 15 mM-17.5 mM, 15 mM-20 mM, or 17.5 mM-20 mM, each inclusive. In some embodiments, the concentration of the free form of glutamine (i.e., L-glutamine) in the basal medium is at least at or about 0.5 mM, 1 mM, 1.5 mM, 2 mM, 2.5 mM, 3 mM, 3.5 mM, 4 mM, 4.5 mM, or 5 mM. In some embodiments, the concentration of the free form of glutamine (i.e., L-glutamine) in the basal medium is at most at or about 2 mM.

In some embodiments, the first supplement contains one or more additional components. In some embodiments, a further supplement, such as a second supplement, is provided to provide one or more additional components. In some embodiments, the supplements, the first supplement and optionally one or more further supplements, e.g. second supplement, are combined with the basal media to provide the one or more additional components to the basal media.

In some embodiments, the one or more additional components include at least one protein. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the protein is an albumin or albumin substitute. In some embodiments, the albumin is a human derived albumin. In some embodiments, the albumin is a recombinant albumin. In some embodiments, the albumin is a natural human serum albumin. In some embodiments, the albumin is a recombinant human serum albumin. In some embodiments, the albumin is a recombinant albumin from a non-human source. Albumin substitutes may be any protein or polypeptide source. Examples of such protein or polypeptide samples include but are not limited to bovine pituitary extract, plant hydrolysate (e.g., rice hydrolysate), fetal calf albumin (fetuin), egg albumin, human serum albumin (HSA), or another animal-derived albumins, chick extract, bovine embryo extract, AlbuMAX® I, and AlbuMAX® II.

In some embodiments, the one or more additional components include an albumin. In some embodiments, the albumin is human albumin or derived from human albumin. In some embodiments, the albumin is derived from human serum or human plasma. In some embodiments, the albumin is a recombinant albumin. In some embodiments, the recombinant albumin is derived from human. In some embodiments, the recombinant albumin is not derived from human. In some embodiments, the supplement comprises a natural albumin. In some embodiments, the natural albumin is derived from human. In some embodiments, the natural albumin is not derived from human. In some embodiments, the concentration of the albumin in the supplement is such that after the supplement is combined with a basal medium (such as these described herein), at or about the concentration of the albumin in the media is at or about 0 mg/mL to at or about 2 mg/mL, at or about 0 mg/mL to at or about 4 mg/mL, at or about 0 mg/mL to at or about 6 mg/mL, at or about 0 mg/mL to at or about 8 mg/mL, at or about 0 mg/mL to at or about 10 mg/mL, at or about 0 mg/mL to at or about 12 mg/mL, at or about 2 mg/mL to at or about 4 mg/mL, at or about 2 mg/mL to at or about 6 mg/mL, at or about 2 mg/mL to at or about 8 mg/mL, at or about 2 mg/mL to at or about 10 mg/mL, at or about 2 mg/mL to at or about 12 mg/mL, at or about 4 mg/mL to at or about 6 mg/mL, at or about 4 mg/mL to at or about 8 mg/mL, at or about 4 mg/mL to at or about 10 mg/mL, at or about 4 mg/mL to at or about 12 mg/mL, at or about 6 mg/mL to at or about 8 mg/mL, at or about 6 mg/mL to at or about 10 mg/mL, at or about 6 mg/mL to at or about 12 mg/mL, at or about 8 mg/mL to at or about 10 mg/mL, at or about 8 mg/mL to at or about 12 mg/mL, at or about 10 mg/mL to at or about 12 mg/mL, or at or about 10 mg/mL to at or about 15 mg/mL each inclusive. In some embodiments, the albumin in the media is at or about 5 mg/mL.

In some embodiments, the one or more additional components include a transferrin or transferrin substitute. In some embodiments, a transferrin substitute is a compound which may replace transferrin in the supplement to give substantially similar results as transferrin. Examples of transferrin substitutes include but are not limited to any iron chelate compound. Iron chelate compounds which may be used include but are not limited to iron chelates of ethylenediaminetetraacetic acid (EDTA), ethylene glycol-bis(β-aminoethyl ether)-N,N,N',N'-tetraacetic acid (EGTA), deferoxamine mesylate, dimercaptopropanol, diethylenetriamine-pentaacetic acid (DPT A), and trans-1,2-diaminocyclohexane-N,N,N',N'-tetraacetic acid (CDTA), as well as a ferric citrate chelate and a ferrous sulfate chelate. In some embodiments, the transferrin is iron saturated transferrin. In some embodiments, the transferrin is iron saturated human transferrin.

In some embodiments, the transferrin or transferrin substitute is human transferrin or is derived from human transferrin. In some embodiments, the transferrin or transferrin substitute is derived from human serum or plasma. In some embodiments, the transferrin or transferrin substitute is recombinant transferrin. In some embodiments, the concentration of the transferrin is such that after the supplement is combined with a basal medium (such as these described herein), the concentration of the transferrin in the media is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, at or about 10 mg/L to at or about 750 mg/L. In some embodiments, the concentration of the transferrin is such that after the supplement is combined with a basal medium (such as these described herein), the concentration of the transferrin in the media is at or about 100 mg/L. In some embodiments, the concentration of the transferrin is such that after the supplement is combined with a basal medium (such as these described herein), the concentration of the transferrin in the media is at or about 50 mg/L to at or about 150 mg/L.

In some embodiments, the one or more additional components include insulin or insulin substitute. In some embodiments, an insulin substitute is a zinc containing compound which may be used in place of insulin to give substantially similar results as insulin. Examples of insulin substitutes include but are not limited to zinc chloride, zinc nitrate, zinc bromide, and zinc sulfate. A number of insulins are known to those of ordinary skill in the art. See Gilman, A. G. et al, Eds., The Pharmacological Basis of Therapeutics, Pergamon Press, New York, 1990, pp. 1463-1495. In some embodiments, insulin, rather than an insulin substitute, is used in the supplement and the medium. In some embodiments, the insulin is zinc insulin. In some embodiments, the insulin is human zinc insulin.

In some embodiments, the insulin is a human insulin or derived from human insulin. In some embodiments, the insulin is a recombinant insulin. In some embodiment, the insulin is a recombinant human insulin. In some embodiment, the concentration of the insulin (or insulin substitute) is such that after the supplement is combined with a basal medium (such as these described herein), at or about the concentration of the insulin (or insulin substitute) in the media is about 1 mg/L to at or about 2.5 mg/L, at or about 1 mg/L to at or about 5 mg/L, at or about 1 mg/L to at or about 7.5 mg/L, at or about 1 mg/L to at or about 10 mg/L, at or about 1 mg/L to at or about 12.5 mg/L, at or about 1 mg/L to at or about 15 mg/L, at or about 1 mg/L to at or about 17.5 mg/L, at or about 1 mg/L to at or about 20 mg/L, at or about 1 mg/L to at or about 22.5 mg/L, at or about 1 mg/L to at or about 25 mg/L, at or about 1 mg/L to at or about 27.5 mg/L, at or about 1 mg/L to at or about 30 mg/L. In some embodiments, the concentration of insulin or insulin substitute in the media is at or about 10 mg/L. In some embodiments, the concentration of insulin or insulin substitute in the media is at or about 7.5 mg/L to at or about 12.5 mg/L.

In some embodiments, the one or more additional components include a growth factor. In some embodiments, the growth factor comprises epidermal growth factor (EGF). In some embodiments, the growth factor comprises fibroblast growth factor (FGF). In some embodiments, the growth factor comprises insulin-like growth factor (IGF). In some embodiments, the growth factor comprises nerve growth factor (NGF). In some embodiments, the growth factor comprises platelet-derived growth factor (PDGF). In some embodiments, the growth factor comprises transforming growth factor (TGF).

In some embodiments, the one or more additional components include a hormone (e.g., growth hormone, insulin, hydrocortisone, triiodothyronine, estrogen, androgen, progesterone, prolactin, follicle-stimulating hormone, gastrin-releasing peptide). In some embodiment, the one or more additional components include alpha-globulin or beta-globulin. In some embodiment, the one or more additional components include a peptide or peptide fraction (e.g., protein hydrolysate derived from animal, microorganism or plant).

In some embodiments, the one or more additional components include a lipid. In some embodiments, the lipid comprises cholesterol. In some embodiments, the lipid comprises steroid. In some embodiments, the lipid comprises fatty acid (e.g., palmitate, stearate, oleate, linoleate). In some embodiments, the lipid comprises ethanolamine. In some embodiments, the lipid comprises choline. In some embodiments, the lipid comprises inositol.

In some embodiments, the one or more additional components comprises a transition metal. In some embodiments, the transition metal comprises iron. In some embodiments, the transition metal comprises zinc. In some embodiments, the transition metal comprises copper. In some embodiments, the transition metal comprises chromium. In some embodiments, the transition metal comprises iodine. In some embodiments, the transition metal comprises cobalt. In some embodiments, the transition metal comprises selenium. In some embodiments, the transition metal comprises magnesium. In some embodiments, the transition metal comprises molybdenum.

In some embodiments, the one or more additional components include a vitamin. In some embodiments, the vitamin comprises a fat-soluble vitamin (e.g., Vitamin A, Vitamin D, Vitamin E, Vitamin K). In some embodiments, the vitamin comprises a water-soluble vitamin (e.g., B1, B2, B6, B12, C, folate).

In some embodiments, the one or more additional components include a polyamine. In some embodiments, the polyamine comprises putrescine. In some embodiments the polyamine comprises spermidine. In some embodiments, the polyamine comprises spermine.

In some embodiments, the one or more additional components include a reductant. In some embodiments, the reductant comprises a 2-mercaptoethanol. In some embodiments, the reductant includes an alpha-thioglycerol. In some embodiments, the reductant comprises reduced glutathione.

In some embodiments, the one or more additional components include a protective additive. In some embodiments, the protective additive comprises carboxymethyl cellulose. In some embodiments, the protective additive comprises polyvinyl pyrrolidone. In some embodiments, the protective additive comprises pluronic F-68. In some embodiments, the protective additive comprises Tween 80.

In some embodiments, the one or more additional components include an adhesion factor. In some embodiments the adhesion factor comprises fibronectin. In some embodiments, the adhesion factor comprises laminin.

In some embodiments, the one or more additional components is one or more of one or more antioxidants, one or more albumins or albumin substitutes, one or more lipid agents, one or more insulins or insulin substitutes, one or more transferrins or transferrin substitutes, one or more trace elements, and one or more glucocorticoids. In some embodiments, the antioxidants include N-acetyl-L-cysteine, 2-mercaptoethanol, or D,L-tocopherol acetate, or derivatives or mixtures thereof. In some embodiments, the albumin is human serum albumin. In some embodiments, the lipid agents include Human Ex-Cite® or ethanolamine or derivatives and mixtures thereof. In some embodiments, the insulin is human zinc insulin. In some embodiments, transferrin is human iron-saturated transferrin. In some embodiments, the trace element is Se4+. In some embodiments, glucocorticoid is hydrocortisone. In some embodiments, the supplement is concentrated.

In some embodiments, the one or more additional components comprises one or more antioxidants, and one or more ingredients selected from the group consisting of one or more albumins or albumin substitutes, one or more lipid agents, one or more insulins or insulin substitutes, one or more transferrins or transferrin substitutes, one or more trace elements, and one or more glucocorticoids.

In some embodiments, the one or more additional components comprises one or more of N-acetyl-L cysteine, human serum albumin, Human Ex-Cyte®, ethanolamine, human zinc insulin, human iron saturated transferrin, Se4+, hydrocortisone, D,L-tocopherol acetate, and/or 2-mercaptoethanol.

In some embodiments, the one or more additional components include N-acetyl-L-cysteine (NAC). In some embodiments, the concentration of NAC is such that after the supplement is combined with a basal medium (such as these described herein), the concentration of NAC of in the basal medium is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, at or about 10 mg/L to at or about 700 mg/L.

In some embodiments, the concentration of NAC in the basal medium is at or about 0 mM to at or about 1 mM, at or about 0 mM to at or about 2 mM, at or about 0 mM to at or about 3 mM, at or about 0 mM to at or about 4 mM, at or about 0 mM to at or about 5 mM, at or about 0 mM to at or about 6 mM, at or about 0 mM to at or about 7 mM, at or about 0 mM to at or about 8 mM, at or about 0 mM to at or about 9 mM, at or about 0 mM to at or about 10 mM, at or about 0 mM to at or about 12 mM, at or about 0 mM to at or about 14 mM, at or about 0 mM to at or about 16 mM, at or about 0 mM to at or about 18 mM, at or about 0 mM to at or about 20 mM.

In some embodiments, the one or more additional components include ethanolamine. In some embodiments, the concentration of ethanolamine is such that after the supplement is combined with a basal medium (such as these described herein), the concentration of ethanolamine in the basal medium is at or about 0 mg/L to at or about 2 mg/L, at or about 0 mg/L to at or about 4 mg/L, at or about 0 mg/L to at or about 6 mg/L, at or about 0 mg/L to at or about 8 mg/L, at or about 0 mg/L to at or about 10 mg/L, at or about 0 mg/L to at or about 12 mg/L, at or about 0 mg/L to at or about 14 mg/L, at or about 0 mg/L to at or about 16 mg/L, at or about 0 mg/L to at or about 18 mg/L, at or about 0 mg/L to at or about 20 mg/L, at or about 0 mg/L to at or about 22 mg/L, at or about 0 mg/L to at or about 24 mg/L, at or about 0 mg/L to at or about 26 mg/L, at or about 0 mg/L to at or about 28 mg/L, at or about 0 mg/L to at or about 30 mg/L.

In some embodiments, the one or more additional components can be provided by adding one or more supplements, such as a first supplement and one or more further or additional supplement to the basal medium.

In some embodiments, the first supplement is prepared by adding or mixing L-glutamine with existing supplements containing one or more desired components. In some embodiments, L-glutamine is added or mixed with a serum replacement supplement, for example, an immune cell serum replacement, e.g., ThermoFisher, #A2598101 or the CTS™ Immune Cell Serum Replacement. In some embodiments, the L-glutamine is added to or mixed with a supplement that includes an immune cell serum replacement described in Smith et al. *Clin Transl Immunology.* 2015 January; 4 (1): e31.

In some embodiments, the serum-free medium formulation comprises at or about 90% to 98.75% (v/v) of the basal medium and at or about 1.25% to 10% (v/v) of the first supplement. In some embodiments, the serum-free medium formulation comprises at or about 90% to 97.5% (v/v) of the basal medium and at or about 1.25% to 5% (v/v) of the first supplement. In some embodiments, the serum-free medium formulation comprises at or about 95% (v/v) of the basal medium and at or about 2.5%+0.2% (v/v) of the first supplement, such as at or about 2.5% (v/v). In some embodiments, a liter of the basal medium is supplemented with at or about 25 milliliter of the first supplement.

In some embodiments, a further supplement, e.g. second supplement, is combined with the basal media to provide the one or more additional components. In some embodiments, the second supplement comprises one or more additional components, such as any described above, including one or more antioxidants, one or more albumins or albumin substitutes, one or more lipid agents, one or more insulins or insulin substitutes, one or more transferrins or transferrin substitutes, one or more trace elements, and one or more glucocorticoids. Exemplary components of a second supplement are described above. In some embodiments, the second supplement comprises an albumin, N-acetylcysteine (NAC) and ethanolamine. In some embodiments, the second supplement comprises an albumin, N-acetylcysteine (NAC) and ethanolamine, wherein the concentration of albumin, NAC and/or ethanolamine is such that after the second supplement is combined with a basal medium (such as these described herein), the concentration of albumin, NAC and/or ethanolamine is substantially the same as described herein. In some embodiments, the albumin is a human derived albumin. In some embodiments, the albumin is a human derived albumin from human plasma or serum. In some embodiments, the second supplement is a liquid and does not include, or does not include a significant amount of a free form of glutamine (i.e., L-glutamine). In some embodiments, the second supplement comprises OpTmizer® supplement (Thermofisher, part of A1048503).

In some embodiments, the second supplement is liquid. In some embodiments, the second supplement is not frozen, or not recommended to be frozen for the storage. In some embodiments, the serum-free medium formulation comprises about 1.25% to 5% (v/v) of the second supplement, such as or about 2.5%±0.2%, such as or about 2.5% or 2.6%. In some embodiments, a liter of the basal medium is supplemented with about 26 milliliter of the second supplement. In some embodiments, the serum-free medium formulation comprises at or about 90% to 97.5% (v/v) of the basal medium and at or about 1.25% to 5% (v/v) of the second supplement. In some embodiments, the serum-free medium formulation comprises at or about 95% (v/v) of the basal medium and at or about 2.5%±0.2% (v/v) of the second supplement, such as at or about 2.5% (v/v) or 2.6%

(v/v). In some embodiments, a liter of the basal medium is supplemented with at or about 25 milliliter or 26 milliliters of the second supplement.

In some embodiments, both the first supplement (e.g. serum replacement supplement, e.g. CTS™ Immune Cell Serum Replacement) and a further supplement (e.g. OpTmizer® Cell Supplement) are added to the basal medium. In some embodiments, the serum-free medium formulation comprises about 90% to 97.5% (v/v) of the basal medium, about 1.25% to 5% (v/v) of the first supplement, and about 1.25% to 5% (v/v) of the second supplement. In some embodiments, the serum-free medium formulation comprises about 95% (v/v) of the basal medium, about 2.5%±0.2% (v/v) of the first supplement, and about 2.5%±0.2% (v/v) of the second supplement.

In some embodiments, the one or more supplement is concentrated at or about 2 to at or about 100 fold. In some embodiments, the supplement is at or about a 40× formulation. In some embodiments, a liter of the basal medium is supplemented with at or about 20 to 30 milliliters, such as 25±2 milliliter, of at least one supplement, including the first supplement and, in some cases, one or more further supplement.

C. Serum-Free Media

In some embodiments, the serum-free media comprises a basal medium and a synthetic amino acid (e.g., a dipeptide form of L-glutamine, e.g., L-alanyl-L-glutamine) a free form of glutamine (i.e., L-glutamine). In some embodiments, the serum-free media comprises a basal medium and a synthetic amino acid (e.g., a dipeptide form of L-glutamine, e.g., L-alanyl-L-glutamine) a free form of glutamine (i.e., L-glutamine). In some embodiments, the serum-free media further comprises at least one protein or additional component such as to support maintenance of T cell during the proved process for generating engineered T cells.

In some embodiments, the serum-free media is a form that contains a synthetic amino acid (e.g., a dipeptide form of L-glutamine, e.g., L-alanyl-L-glutamine) that is capable of being converted into a free form of glutamine (i.e., L-glutamine) in a cell culture comprising a cell, wherein the media is serum-free. In some embodiments, the synthetic amino acid is soluble in an aqueous solution (e.g., a serum-free media). In some embodiments, the solubility of the synthetic amino acid in the aqueous solution is higher than a free form of glutamine (i.e., L-glutamine). In some embodiments, the concentration of the dipeptide form of L-glutamine (e.g., L-alanyl-L-glutamine) in the serum-free media is at or about 0.5 mM-5 mM. In some embodiments, the concentration of the dipeptide form of L-glutamine (e.g., L-alanyl-L-glutamine) in the serum-free media is at or about 2 mM. In some embodiments, the concentration of the dipeptide form of L-glutamine (e.g., L-alanyl-L-glutamine) is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, or 0.5 mM-5 mM, each inclusive. In some embodiments, the concentration of dipeptide form of L-glutamine (e.g., L-alanyl-L-glutamine) in the serum-free media is at least at or about 0.5 mM, 1 mM, 1.5 mM, 2 mM, 2.5 mM, 3 mM, 3.5 mM, 4 mM, 4.5 mM, or 5 mM. In some embodiments, the concentration of the dipeptide form of L-glutamine, such as L-alanyl-L-glutamine, in the serum-free media is at or about 2 mM, and the concentration of the free form of L-glutamine in the serum-free media is at or about 2 mM.

In some embodiments, the concentration of the free form of glutamine (i.e., L-glutamine) in the serum-free media is about 0.5 mM-5 mM. In some embodiments, the concentration of the free form of glutamine (i.e., L-glutamine) in the serum-free media is at or about 2 mM. In some embodiments, the concentration of the free form of glutamine (i.e., L-glutamine) in the serum-free media is at or about 0.5 mM-1 mM, 0.5 mM-1.5 mM, 0.5 mM-2 mM, 0.5 mM-2.5 mM, 0.5 mM-3 mM, 0.5 mM-3.5 mM, 0.5 mM-4 mM, 0.5 mM-4.5 mM, or 0.5 mM-5 mM, each inclusive. In some embodiments, the concentration of the free form of glutamine (i.e., L-glutamine) in the media is at least at or about 0.5 mM, 1 mM, 1.5 mM, 2 mM, 2.5 mM, 3 mM, 3.5 mM, 4 mM, 4.5 mM, or 5 mM.

In some embodiments, the serum-free media comprises at least one protein. In some embodiments, the at least one protein is not of non-mammalian origin. In some embodiments, the at least one protein is human or derived from human. In some embodiments, the at least one protein is recombinant. In some embodiments, the one or more additional components include at least one protein. In some embodiments, the at least one protein is not of non-mammalian origin. In some embodiments, the at least one protein is human or derived from human. In some embodiments, the at least one protein is recombinant. In some embodiments, the at least one protein includes albumin, transferrin, insulin, fibronectin, aprotinin or fetuin. In some embodiments, the protein comprises one or more of albumin, insulin or transferrin, optionally one or more of a human or recombinant albumin, insulin or transferrin.

In some embodiments, the serum-free media comprises an albumin. In some embodiments, the albumin is derived from human. In some embodiments, the albumin is derived from human serum or human plasma. In some embodiments, the albumin is a recombinant albumin. In some embodiments, the recombinant albumin is derived from human. In some embodiment, the recombinant albumin is not derived from human. In some embodiments, the supplement comprises a natural albumin. In some embodiments, the natural albumin is derived from human. In some embodiments, the natural albumin is not derived from human. In some embodiments, the concentration of the albumin in the serum-free media is at or about 0 mg/mL to at or about 2 mg/mL, at or about 0 mg/mL to at or about 4 mg/mL, at or about 0 mg/mL to at or about 6 mg/mL, at or about 0 mg/mL to at or about 8 mg/mL, at or about 0 mg/mL to at or about 10 mg/mL, at or about 0 mg/mL to at or about 12 mg/mL, at or about 2 mg/mL to at or about 4 mg/mL, at or about 2 mg/mL to at or about 6 mg/mL, at or about 2 mg/mL to at or about 8 mg/mL, at or about 2 mg/mL to at or about 10 mg/mL, at or about 2 mg/mL to at or about 12 mg/mL, at or about 4 mg/mL to at or about 6 mg/mL, at or about 4 mg/mL to at or about 8 mg/mL, at or about 4 mg/mL to at or about 10 mg/mL, at or about 4 mg/mL to at or about 12 mg/mL, at or about 6 mg/mL to at or about 8 mg/mL, at or about 6 mg/mL to at or about 10 mg/mL, at or about 6 mg/mL to at or about 12 mg/mL, at or about 8 mg/mL to at or about 10 mg/mL, at or about 8 mg/mL to at or about 12 mg/mL, at or about 10 mg/mL to at or about 12 mg/mL, or at or about 10 mg/mL to at or about 15 mg/mL each inclusive. In some embodiments, the albumin in the media is at or about 5 mg/mL.

In some embodiments, the serum-free media comprises a transferrin or transferrin substitute (such as these described herein). In some embodiments, the transferrin or transferrin substitute is derived from human. In some embodiments, the transferrin or transferrin substitute is derived from human serum or plasma. In some embodiments, the concentration of the transferrin in the serum-free media is at or about 10 mg/L to at or about 50 mg/L, at or about 10 mg/L to at or about 100 mg/L, at or about 10 mg/L to at or about 150 mg/L, at or about 10 mg/L to at or about 200 mg/L, at or about 10 mg/L to at or about 250 mg/L, at or about 10 mg/L to at or about 300 mg/L, at or about 10 mg/L to at or about 350 mg/L, at or about 10 mg/L to at or about 400 mg/L, at or about 10 mg/L to at or about 450 mg/L, at or about 10 mg/L to at or about 500 mg/L, at or about 10 mg/L to at or about 550 mg/L, at or about 10 mg/L to at or about 600 mg/L, at or about 10 mg/L to at or about 650 mg/L, or at or about 10 mg/L to at or about 750 mg/L. In some embodiments, the concentration of the transferrin in the serum-free media is at or about 100 mg/L. In some embodiments, the concentration of the transferrin in the serum-free media is at or about 50 mg/L to 150 mg/L.

In some embodiments, the supplement comprises insulin or insulin substitute (such as these described herein). In some embodiments, the insulin is derived from human. In some embodiments, the insulin is a recombinant insulin. In some embodiment, the insulin is a recombinant human insulin. In some embodiment, the concentration of the insulin (or insulin substitute) in the serum-free media is at or about 1 mg/L to at or about 2.5 mg/L, at or about 1 mg/L to at or about 5 mg/L, at or about 1 mg/L to at or about 7.5 mg/L, at or about 1 mg/L to at or about 10 mg/L, at or about 1 mg/L to at or about 12.5 mg/L, at or about 1 mg/L to at or about 15 mg/L, at or about 1 mg/L to at or about 17.5 mg/L, at or about 1 mg/L to at or about 20 mg/L, at or about 1 mg/L to at or about 22.5 mg/L, at or about 1 mg/L to at or about 25 mg/L, at or about 1 mg/L to at or about 27.5 mg/L, or at or about 1 mg/L to at or about 30 mg/L. In some embodiments, the concentration of insulin or insulin substitute in the serum-free media is at or about 10 mg/L. In some embodiments, the concentration of insulin or insulin substitute in the serum-free media is at or about 7.5 mg/L to at or about 12.5 mg/L.

In some embodiments, the serum-free media does not comprise phenol red. In some embodiments, the serum-free media comprises phenol red.

In some embodiments, the serum-free media comprises a nutrient mixture of inorganic salts, sugars, amino acids, optionally also containing vitamins, organic acids, antioxidants, lipids, growth factors, N-acetylcysteine, ethanolamine and/or buffers. Examples include those described herein, such as in the section above, including inorganic salts, sugars, amino acids, vitamins, organic acids, antioxidants, lipids, growth factors, N-acetylcysteine, ethanolamine and/or buffers.

In some embodiments, the serum free media comprises one or more ingredients selected from one or more of one or more antioxidants, one or more albumins or albumin substitutes, one or more lipid agents, one or more insulins or insulin substitutes, one or more transferrins or transferrin substitutes, one or more trace elements, one or more glucocorticoids, one or more inorganic salts, one or more energy sources, one or more buffering agents, one or more pyruvate salts, one or more pH indicators, one or more amino acids, and one or more vitamins. In some embodiments, the antioxidants are selecting from the group consisting of N-acetyl-L-cysteine, 2-mercaptoethanol, and D,L-tocopherol acetate, or derivatives or mixtures thereof. In some embodiments, the albumin is human serum albumin. In some embodiments, the lipid agents are Human Ex-Cyte® and ethanolamine. In some embodiments, the insulin is human zinc insulin. In some embodiments, the transferrin is human iron-saturated transferrin. In some embodiments, the glucocorticoid is hydrocortisone. In some embodiments, inorganic salt ingredient comprises one or more inorganic salts selected from the group consisting of one or more calcium salts, one or more potassium salts, one or more magnesium salts, one or more sodium salts, one or more carbonate salts, and one or more phosphate salts. In some embodiments, the energy source is D-glucose. In some embodiments, the buffering agent is HEPES. In some embodiments, the pyruvate salt is sodium pyruvate. In some embodiments, the pH indicator is phenol red. In some embodiments, amino acid ingredient comprises one or more amino acids selected from the group consisting of glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, and salts and derivatives thereof. In some embodiments, the vitamin ingredient comprises one or more vitamins selected from the group consisting of biotin, D-calcium pantothenate, choline chloride, folic acid, i-inositol, niacinamide, pyridoxal HCl, riboflavin, thiamine HCl, and vitamin B12 and derivatives thereof. In some embodiments, ingredients comprise N-acetyl-L-cysteine, 2-mercaptoethanol, human serum albumin, D,L-tocopherol acetate, Human Ex-Cyte®, ethanolamine, human zinc insulin, iron-saturated transferrin, Se4+, hydrocortisone, $Ca^{2+}$, $K^+$, $Mg^{2+}$, $Na^+$, $CO_3^{2-}$, $PO_4^{3-}$, D-glucose, HEPES, sodium pyruvate, phenol red, glycine, L-alanine, L-asparagine, L-cysteine, L-aspartic acid, L-glutamic acid, L-phenylalanine, L-histidine, L-isoleucine, L-lysine, L-leucine, L-glutamine, L-arginine HCL, L-methionine, L-proline, L-hydroxyproline, L-serine, L-threonine, L-tryptophan, L-tyrosine, and L-valine, biotin, D-calcium pantothenate, choline chloride, folic acid, i-inositol, niacinamide, pyridoxal HCl, riboflavin, thiamine HCl, and vitamin B12.

In some embodiments, there is provided a serum-free media comprising a basal medium and at least one supplement. Various examples of basal medium and supplements are described herein, such as in the section above.

In some embodiments, the serum-free medium formulation comprises at or about 90% to at or about 97:5% (v/v) of the basal medium, at or about 2.5% to at or about 10% (v/v) of a supplement, e.g. a first supplement and/or a second supplement. In some embodiments, the serum-free medium formulation comprises at or about 90% to at or about 97.5% (v/v) of the basal medium, at or about 1.25% to at or about 5% (v/v) of a first supplement, and at or about 1.25% to at or about 5% (v/v) of a second supplement.

In some embodiments, the serum-free medium comprises a basal medium, such as the OpTmizer™ T-Cell Expansion Basal Medium (ThermoFisher)), supplemented with one or more supplement. In some embodiments, the one or more supplement is serum-free. In some embodiments, the serum-free medium comprises a basal medium supplemented with a supplement for the maintenance of a cell (e.g., a T cell), such as the OpTmizer™ T-Cell Expansion Supplement (ThermoFisher). In some embodiments, the serum-free medium further comprises a free form of an amino acid such as L-glutamine. In some embodiments, the serum free media does not contain a recombinant cytokine, such as one or more of recombinant human IL-2, recombinant human IL-7, and/or recombinant human IL-15. In particular embodiments, the serum-free media can be used in any one or more steps of the process described herein, such as one or more steps described in Section I. In some embodiments, such as serum-free medium is used during the incubation and/or harvesting, collecting or formulation of cells.

In some embodiments, the serum-free medium comprises a basal medium supplemented with a T cell supplement and a free form of L-glutamine. In some embodiments, the serum-free medium comprises the OpTmizer™ T-Cell Expansion Basal Medium supplemented with the OpTmizer™ T-Cell Expansion Supplement and L-glutamine. In some embodiments, the serum-free medium comprises the OpTmizer™ T-Cell Expansion Basal Medium supplemented with about 2.6% OpTmizer™ T-Cell Expansion Supplement, and about 1.0% L-glutamine (about 2 mM in final concentration). In some embodiments, such a serum-free media does not contain a recombinant cytokine, such as one or more of recombinant human IL-2, recombinant human IL-7, and/or recombinant human IL-15. In particular embodiments, the serum-free media can be used in any one or more steps of the process described herein, such as one or more steps described in Section I. In some embodiments, such as serum-free medium is used during the incubation and/or harvesting, collecting or formulation of cells.

In some embodiments, the serum-free medium comprises a basal medium supplemented with a supplement for the maintenance of a cell (e.g., a T cell), such as the OpTmizer™ T-Cell Expansion Supplement (ThermoFisher) and further comprises a serum replacement supplement, for example, an immune cell serum replacement, e.g., ThermoFisher, #A2596101, the CTS™ Immune Cell Serum Replacement, or the immune cell serum replacement described in Smith et al. *Clin Transl Immunology.* 2015 January; 4 (1): e31. In some embodiments, the serum-free medium further comprises a free form of an amino acid such as L-glutamine. In some embodiments, the serum-free medium further comprises a dipeptide form of L-glutamine (e.g., L-alanyl-L-glutamine), such as the dipeptide in Glutamax™ (ThermoFisher). In some embodiments, the serum-free media comprises one or more cytokine. In certain embodiments, the one or more cytokines are recombinant cytokines. In certain embodiments, the one or more cytokines bind to and/or are capable of binding to receptors that are expressed by and/or are endogenous to T cells. In particular embodiments, the one or more cytokines is or includes a member of the 4-alpha-helix bundle family of cytokines. In some embodiments, members of the 4-alpha-helix bundle family of cytokines include, but are not limited to, interleukin-2 (IL-2), interleukin-4 (IL-4), interleukin-7 (IL-7), interleukin-9 (IL-9), interleukin 12 (IL-12), interleukin 15 (IL-15), granulocyte colony-stimulating factor (G-CSF), and granulocyte-macrophage colony-stimulating factor (GM-CSF). In some embodiments, the serum-free medium further comprises one or more of recombinant human IL-2, recombinant human IL-7, and/or recombinant human IL-15. In particular embodiments, the serum-free media can be used in any one or more steps of the process described herein, such as one or more steps described in Section I. In particular embodiments, the serum-free media can be used in any one or more steps involving sample preparation, selection, stimulation and/or engineering.

In some embodiments, the serum-free medium comprises a basal medium supplemented with a T cell supplement, an immune cell serum replacement, a free form of L-glutamine, a dipeptide form of L-glutamine, a recombinant IL-2, a recombinant IL-7, and/or a recombinant IL-15. In some embodiments, the serum-free medium comprises the OpTmizer™ T-Cell Expansion Basal Medium supplemented with the OpTmizer™ T-Cell Expansion Supplement, the CTS™ Immune Cell Serum Replacement, L-glutamine, L-alanyl-L-glutamine, a recombinant human IL-2, a recombinant human IL-7, and a recombinant human IL-15. In some embodiments, the serum-free medium comprises the OpTmizer™ T-Cell Expansion Basal Medium supplemented with about 2.6% OpTmizer™ T-Cell Expansion Supplement, about 2.5% CTS™ Immune Cell Serum Replacement, about 1.0% L-glutamine (about 2 mM in final concentration), about 1.0% L-alanyl-L-glutamine (about 2 mM in final concentration), about 100 IU/mL recombinant human IL-2, about 600 IU/mL recombinant human IL-7, and about 100 IU/mL recombinant human IL-15. In particular embodiments, the serum-free media can be used in any one or more steps of the process described herein, such as one or more steps described in Section I. In particular embodiments, the serum-free media can be used in any one or more steps involving sample preparation, selection, stimulation and/or engineering.

In some embodiments, the serum-free media is a concentrated media formulation. In some embodiments, the serum-free media is not a concentrated media formulation. In some embodiments, the serum-free media is from at or about 2× to at or about 100× concentrated. In some embodiments, the serum-free media is at or about 10× formulation. In some embodiments, the serum-free media can be stored at at or about 2° C. to 8° C.

III. Recombinant Proteins

In various embodiments, provided are engineered, transformed, transduced, or transfected cells, such as immune cells, such as T cells, that express one or more recombinant proteins(s). In particular embodiments, at least one of the one or more recombinant proteins is a recombinant receptor, e.g., antigen receptors and receptors containing one or more component thereof.

A. Recombinant Receptors

In some embodiments, provided are engineered cells, such as immune cells, such as T cells, that express one or more recombinant receptor(s). Among the receptors are antigen receptors and receptors containing one or more component thereof. The recombinant receptors may include chimeric receptors, such as those containing ligand-binding domains or binding fragments thereof and intracellular signaling domains or regions, functional non-TCR antigen receptors, chimeric antigen receptors (CARs), T cell receptors (TCRs), such as recombinant or transgenic TCRs, chimeric autoantibody receptor (CAAR) and components of any of the foregoing. The recombinant receptor, such as a CAR, generally includes the extracellular antigen (or ligand) binding domain linked to one or more intracellular signaling components, in some aspects via linkers and/or transmembrane domain(s). In some embodiments, the engineered cells express two or more receptors that contain different components, domains or regions. In some aspects, two or more receptors allows spatial or temporal regulation or control of specificity, activity, antigen (or ligand) binding, function and/or expression of the recombinant receptors.

1. Chimeric Antigen Receptors (CARs)

In some embodiments, the engineered cells, such as T cells, express a recombinant receptor such as a chimeric antigen receptor (CAR) with specificity for a particular antigen (or marker or ligand), such as an antigen expressed on the surface of a particular cell type. In some embodiments, the antigen is a polypeptide. In some embodiments, the antigen is a carbohydrate or other molecule. In some embodiments, the antigen is selectively expressed or overexpressed on cells of the disease or condition, e.g., the tumor or pathogenic cells, as compared to normal or non-targeted cells or tissues, e.g., in healthy cells or tissues. In other embodiments, the antigen is expressed on normal cells and/or is expressed on the engineered cells. In some aspects, the recombinant receptor, e.g., a CAR, includes one or more regions or domains selected from an extracellular ligand- (e.g., antigen-) binding or regions or domains, e.g., any of the antibody or fragment described here, and in an intracellular signaling region. In some embodiments, the ligand- (e.g., antigen-) binding region or domain is or includes an scFv or a single-domain $V_H$ antibody and the intracellular signaling region or domain is or contains an ITAM. In some aspects, the intracellular signaling region or domain includes a signaling domain of a CD3-zeta (CD3ζ) chain or a portion thereof. In some aspects, the extracellular ligand- (e.g., antigen-) binding region or domain(s) and the intracellular signaling region or domain(s) are linked or connected via one or more linkers and/or transmembrane domain(s). In some embodiments, the chimeric antigen receptor includes a transmembrane domain disposed between the extracellular domain and the intracellular signaling region.

Exemplary antigen receptors, including CARs, and methods for engineering and introducing such receptors into cells, include those described, for example, in International Pat. App. Pub. International Pat. App. Pub. Nos. WO2000/14257, WO2013/126726, WO2012/129514, WO2014/031687, WO2013/166321, WO2013/071154, WO2013/123061, U.S. Pat. App. Pub. Nos. US2002131960, US2013287748, US20130149337, U.S. Pat. Nos. 6,451,995, 7,446,190, 8,252,592, 8,339,645, 8,398,282, 7,446,179, 6,410,319, 7,070,995, 7,265,209, 7,354,762, 7,446,191, 8,324,353, and 8,479,118, and European Pat. App. No. EP2537416, and/or those described by Sadelain et al., Cancer Discov. 2013 April; 3 (4): 388-398; Davila et al. (2013) PLOS ONE 8 (4): e61338; Turtle et al., Curr. Opin. Immunol., 2012 October; 24 (5): 633-39; and Wu et al., Cancer, 2012 Mar. 18 (2): 160-75. In some aspects, the antigen receptors include a CAR as described in U.S. Pat. No. 7,446,190, and those described in International Pat. App. Pub. No. WO 2014/055668. Examples of the CARs include CARs as disclosed in any of the aforementioned references, such as WO2014/031687, U.S. Pat. Nos. 8,339,645, 7,446,179, US 2013/0149337, U.S. Pat. Nos. 7,446,190, 8,389,282, Kochenderfer et al., 2013, Nature Reviews Clinical Oncology, 10, 267-276 (2013); Wang et al. (2012) J. Immunother. 35 (9): 689-701; and Brentjens et al., Sci Transl Med. 2013 5 (177).

In some embodiments, the recombinant receptor, e.g., antigen receptor contains an extracellular antigen- or ligand-binding domain that binds, e.g., specifically binds, to an antigen, a ligand and/or a marker. Among the antigen receptors are functional non-TCR antigen receptors, such as chimeric antigen receptors (CARs). In some embodiments, the antigen receptor is a CAR that contains an extracellular antigen-recognition domain that specifically binds to an antigen. In some embodiments, the CAR is constructed with a specificity for a particular antigen, marker or ligand, such as an antigen expressed in a particular cell type to be targeted by adoptive therapy, e.g., a cancer marker, and/or an antigen intended to induce a dampening response, such as an antigen expressed on a normal or non-diseased cell type. Thus, the CAR typically includes in its extracellular portion one or more ligand- (e.g., antigen-) binding molecules, such as one or more antigen-binding fragment, domain, or portion, or one or more antibody variable domains, and/or antibody molecules. In some embodiments, the CAR includes an antigen-binding portion or portions of an antibody molecule, such as a single-chain antibody fragment (scFv) derived from the variable heavy ($V_H$) and variable light ($V_L$) chains of a monoclonal antibody (mAb), or a single domain antibody (sdAb), such as sdFv, nanobody, $V_H$H and $V_{NAR}$. In some embodiments, an antigen-binding fragment comprises antibody variable regions joined by a flexible linker.

In some embodiments, the CAR contains an antibody or an antigen-binding fragment (e.g. scFv) that specifically recognizes an antigen or ligand, such as an intact antigen, expressed on the surface of a cell. In some embodiments, the antigen or ligand, is a protein expressed on the surface of cells. In some embodiments, the antigen or ligand is a polypeptide. In some embodiments, it is a carbohydrate or other molecule. In some embodiments, the antigen or ligand is selectively expressed or overexpressed on cells of the disease or condition, e.g., the tumor or pathogenic cells, as compared to normal or non-targeted cells or tissues. In other embodiments, the antigen is expressed on normal cells and/or is expressed on the engineered cells.

In some embodiments, among the antigens targeted by the chimeric receptors are those expressed in the context of a disease, condition, or cell type to be targeted via the adoptive cell therapy. Among the diseases and conditions are proliferative, neoplastic, and malignant diseases and disorders, including cancers and tumors, including hematologic cancers, cancers of the immune system, such as lymphomas, leukemias, and/or myelomas, such as B, T, and myeloid leukemias, lymphomas, and multiple myelomas.

In some embodiments, the antigen or ligand is a tumor antigen or cancer marker. In some embodiments, the antigen or ligand the antigen is or includes αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Rα), IL-13 receptor alpha 2 (IL-13Rα2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30. In some embodiments, the antigen is or includes a pathogen-specific or pathogen-expressed antigen, such as a viral antigen (e.g., a viral antigen from HIV, HCV, HBV), bacterial antigens, and/or parasitic antigens.

In some embodiments, the antibody is an antigen-binding fragment, such as a scFv, that includes one or more linkers joining two antibody domains or regions, such as a heavy chain variable ($V_H$) region and a light chain variable ($V_L$) region. The linker typically is a peptide linker, e.g., a flexible and/or soluble peptide linker. Among the linkers are those rich in glycine and serine and/or in some cases threonine. In some embodiments, the linkers further include charged residues such as lysine and/or glutamate, which can improve solubility. In some embodiments, the linkers further include one or more proline. In some aspects, the linkers rich in glycine and serine (and/or threonine) include at least 80%, 85%, 90%, 91%, 92%, 93%, 94%, 95%, 96%, 97%, 98%, or 99% such amino acid(s). In some embodiments, they include at least at or about 50%, 55%, 60%, 70%, or 75%, glycine, serine, and/or threonine. In some embodiments, the linker is comprised substantially entirely of glycine, serine, and/or threonine. The linkers generally are between about 5 and about 50 amino acids in length, typically between at or about 10 and at or about 30, e.g., 10, 11, 12, 13, 14, 15, 16, 17, 18, 19, 20, 21, 22, 23, 24, 25, 26, 27, 28, 29, or 30, and in some examples between 10 and 25 amino acids in length. Exemplary linkers include linkers having various numbers of repeats of the sequence GGGGS (4GS; SEQ ID NO: 115) or GGGS (3GS; SEQ ID NO: 116), such as between 2, 3, 4, and 5 repeats of such a sequence. Exemplary linkers include those having or consisting of a sequence set forth in SEQ ID NO: 52 (GGGGSGGGGSGGGGS), SEQ ID NO: 58 (GSTSGSGKPGSGEGSTKG) or SEQ ID NO: 117 (SRGGGGSGGGGSGGGGSLEMA).

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19.

In some embodiments the scFv and/or $V_H$ domains is derived from FMC63. FMC63 generally refers to a mouse monoclonal IgG1 antibody raised against Nalm-1 and -16 cells expressing CD19 of human origin (Ling, N. R., et al. (1987). *Leucocyte typing III.* 302). The FMC63 antibody comprises CDR H1 set forth in SEQ ID NO: 38; CDR H2 set forth in SEQ ID NO:39; CDR H3 set forth in SEQ ID NOS: 40 or 54; and CDR L1 set forth in SEQ ID NO: 35; CDR L2 set forth in SEQ ID NO:36 or 55; and CDR L3 set forth in SEQ ID NO:37 or 56. The FMC63 antibody comprises the heavy chain variable region ($V_H$) comprising the amino acid sequence of SEQ ID NO: 41 and the light chain variable region ($V_L$) comprising the amino acid sequence of SEQ ID NO: 42. In some embodiments, the scFv comprises a variable light chain containing a CDR L1 sequence of SEQ ID NO:35, a CDR L2 sequence of SEQ ID NO:36, and a CDR L3 sequence of SEQ ID NO:37 and/or a variable heavy chain containing a CDR H1 sequence of SEQ ID NO:38, a CDR H2 sequence of SEQ ID NO:39, and a CDR H3 sequence of SEQ ID NO:40, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of FMC63 set forth in SEQ ID NO:41 and a variable light chain region of FMC63 set forth in SEQ ID NO:42, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:58. In some embodiments, the scFv comprises, in order, a $V_H$, a linker, and a $V_L$. In some embodiments, the scFv comprises, in order, a $V_L$, a linker, and a $V_H$. In some embodiments, the scFv is encoded by a sequence of nucleotides set forth in SEQ ID NO:57 or a sequence that exhibits at least 85%, 86%, 87%, 88%, 89%, 90%, 91%, 92%, 93%, 94%, 95%, 96%, 97%, 98%, or 99% sequence identity to SEQ ID NO: 57. In some embodiments, the scFv comprises the sequence of amino acids set forth in SEQ ID NO: 43 or a sequence that exhibits at least 85%, 86%, 87%, 88%, 89%, 90%, 91%, 92%, 93%, 94%, 95%, 96%, 97%, 98%, or 99% sequence identity to SEQ ID NO:43.

In some embodiments, the scFv and/or $V_H$ domain is derived from SJ25C1. SJ25C1 is a mouse monoclonal IgG1 antibody raised against Nalm-1 and -16 cells expressing CD19 of human origin (Ling, N. R., et al. (1987). *Leucocyte typing III.* 302). The SJ25C1 antibody comprises CDR H1, H2 and H3 set forth in SEQ ID NOS: 47-49, respectively, and CDR L1, L2 and L3 sequences set forth in SEQ ID NOS: 44-46, respectively. The SJ25C1 antibody comprises the heavy chain variable region ($V_H$) comprising the amino acid sequence of SEQ ID NO: 50 and the light chain variable region ($V_L$) comprising the amino acid sequence of SEQ ID NO: 51. In some embodiments, the svFv comprises a variable light chain containing a CDR L1 sequence set forth in SEQ ID NO:44; a CDR L2 set forth in SEQ ID NO: 45; and a CDR L3 set forth in SEQ ID NO:46; and/or a variable heavy chain containing a CDR H1 set forth in SEQ ID NO:47, a CDR H2 set forth in SEQ ID NO:48, and a CDR H3 set forth in SEQ ID NO:49, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the scFv comprises a variable heavy chain region of SJ25C1 set forth in SEQ ID NO:50 and a variable light chain region of SJ25C1 set forth in SEQ ID NO:51, or a variant of any of the foregoing having at least 85%, 86%, 87%, 88%, 89%, 90%, 91%, 92%, 93%, 94%, 95%, 96%, 97%, 98%, 99% or more sequence identity thereto. In some embodiments, the variable heavy and variable light chains are connected by a linker. In some embodiments, the linker is set forth in SEQ ID NO:52. In some embodiments, the scFv comprises, in order, a $V_H$, a linker, and a $V_L$. In some embodiments, the scFv comprises, in order, a $V_L$, a linker, and a $V_H$. In some embodiments, the scFv comprises the sequence of amino acids set forth in SEQ ID NO:53 or a sequence that exhibits at least 85%, 86%, 87%, 88%, 89%, 90%, 91%, 92%, 93%, 94%, 95%, 96%, 97%, 98%, or 99% sequence identity to SEQ ID NO: 53.

In some embodiments, the antibody or an antigen-binding fragment (e.g. scFv or $V_H$ domain) specifically recognizes an antigen, such as BCMA. In some embodiments, the antibody or antigen-binding fragment is derived from, or is a variant of, antibodies or antigen-binding fragment that specifically binds to BCMA.

In some embodiments, the CAR is an anti-BCMA CAR that is specific for BCMA, e.g. human BCMA. Chimeric antigen receptors containing anti-BCMA antibodies, including mouse anti-human BCMA antibodies and human anti-human antibodies, and cells expressing such chimeric receptors have been previously described. See Carpenter et al., Clin Cancer Res., 2013, 19 (8): 2048-2060, WO 2016/090320, WO2016090327, WO2010104949A2 and WO2017173256. In some embodiments, the antigen or antigen binding domain is BCMA. In some embodiments, the scFv contains a VH and a VL derived from an antibody or an antibody fragment specific to BCMA. In some embodiments, the antibody or antibody fragment that binds BCMA is or contains a VH and a VL from an antibody or antibody fragment set forth in International Patent Applications, Publication Number WO 2016/090327 and WO 2016/090320.

In some embodiments, the anti-BCMA CAR contains an antigen-binding domain, such as an scFv, containing a variable heavy ($V_H$) and/or a variable light ($V_L$) region derived from an antibody described in WO 2016/090320 or WO2016090327. In some embodiments, the antigen-binding domain, such as an scFv, contains a $V_H$ set forth in SEQ ID NO: 109 and a $V_L$ set forth in SEQ ID NO: 110. In some embodiments, the antigen-binding domain, such as an scFv, contains a $V_H$ set forth in SEQ ID NO: 111 and a $V_L$ set forth in SEQ ID NO: 112. In some embodiments, the antigen-binding domain, such as an scFv, contains a $V_H$ set forth in SEQ ID NO: 113 and a $V_L$ set forth in SEQ ID NO: 114. In some embodiments, the antigen-binding domain, such as an scFv, contains a $V_H$ set forth in SEQ ID NO: 106 and a $V_L$ set forth in SEQ ID NO: 107. In some embodiment the antigen-binding domain, such as an scFv, contains a $V_H$ set forth in SEQ ID NO: 118 and a $V_L$ set forth in SEQ ID NO: 119. In some embodiments, the antigen-binding domain, such as an scFv, contains a $V_H$ set forth in SEQ ID NO: 120 and a $V_L$ set forth in SEQ ID NO: 121. In some embodiments, the antigen-binding domain, such as an scFv, contains a $V_H$ set forth in SEQ ID NO: 122 and a $V_L$ set forth in SEQ ID NO: 123. In some embodiments, the $V_H$ or $V_L$ has a sequence of amino acids that exhibits at least 85%, 86%, 87%, 88%, 89%, 90%, 91%, 92%, 93%, 94%, 95%, 96%, 97%, 98%, 99% or more sequence identity to any of the foregoing $V_H$ or $V_L$ sequences, and retains binding to BCMA. In some embodiments, the $V_H$ region is amino-terminal to the $V_L$ region. In some embodiments, the $V_H$ region is carboxy-terminal to the $V_L$ region.

In some embodiments, the antigen or antigen binding domain is GPRC5D. In some embodiments, the scFv contains a VH and a VL derived from an antibody or an antibody fragment specific to GPRC5D. In some embodiments, the antibody or antibody fragment that binds GPRC5D is or contains a VH and a VL from an antibody or antibody fragment set forth in International Patent Applications, Publication Number WO 2016/090329 and WO 2016/090312

In some aspects, the CAR contains a ligand- (e.g., antigen-) binding domain that binds or recognizes, e.g., specifically binds, a universal tag or a universal epitope. In some aspects, the binding domain can bind a molecule, a tag, a polypeptide and/or an epitope that can be linked to a different binding molecule (e.g., antibody or antigen-binding fragment) that recognizes an antigen associated with a disease or disorder. Exemplary tag or epitope includes a dye (e.g., fluorescein isothiocyanate) or a biotin. In some aspects, a binding molecule (e.g., antibody or antigen-binding fragment) linked to a tag, that recognizes the antigen associated with a disease or disorder, e.g., tumor antigen, with an engineered cell expressing a CAR specific for the tag, to effect cytotoxicity or other effector function of the engineered cell. In some aspects, the specificity of the CAR to the antigen associated with a disease or disorder is provided by the tagged binding molecule (e.g., antibody), and different tagged binding molecule can be used to target different antigens. Exemplary CARs specific for a universal tag or a universal epitope include those described, e.g., in U.S. Pat. No. 9,233,125, WO 2016/030414, Urbanska et al., (2012) Cancer Res 72:1844-1852, and Tamada et al., (2012). Clin Cancer Res 18:6436-6445.

In some embodiments, the antigen is or includes a pathogen-specific or pathogen-expressed antigen. In some embodiments, the antigen is a viral antigen (such as a viral antigen from HIV, HCV, HBV, etc.), bacterial antigens, and/or parasitic antigens. In some embodiments, the CAR contains a TCR-like antibody, such as an antibody or an antigen-binding fragment (e.g. scFv) that specifically recognizes an intracellular antigen, such as a tumor-associated antigen, presented on the cell surface as a major histocompatibility complex (MHC)-peptide complex. In some embodiments, an antibody or antigen-binding portion thereof that recognizes an MHC-peptide complex can be expressed on cells as part of a recombinant receptor, such as an antigen receptor. Among the antigen receptors are functional non-T cell receptor (TCR) antigen receptors, such as chimeric antigen receptors (CARs). In some embodiments, a CAR containing an antibody or antigen-binding fragment that exhibits TCR-like specificity directed against peptide-MHC complexes also may be referred to as a TCR-like CAR. In some embodiments, the CAR is a TCR-like CAR and the antigen is a processed peptide antigen, such as a peptide antigen of an intracellular protein, which, like a TCR, is recognized on the cell surface in the context of an MHC molecule. In some embodiments, the extracellular antigen-binding domain specific for an MHC-peptide complex of a TCR-like CAR is linked to one or more intracellular signaling components, in some aspects via linkers and/or transmembrane domain(s). In some embodiments, such molecules can typically mimic or approximate a signal through a natural antigen receptor, such as a TCR, and, optionally, a signal through such a receptor in combination with a costimulatory receptor.

Reference to "Major histocompatibility complex" (MHC) refers to a protein, generally a glycoprotein, that contains a polymorphic peptide binding site or binding groove that can, in some cases, complex with peptide antigens of polypeptides, including peptide antigens processed by the cell machinery. In some cases, MHC molecules can be displayed or expressed on the cell surface, including as a complex with peptide, i.e. MHC-peptide complex, for presentation of an antigen in a conformation recognizable by an antigen receptor on T cells, such as a TCRs or TCR-like antibody. Generally, MHC class I molecules are heterodimers having a membrane spanning $\alpha$ chain, in some cases with three a domains, and a non-covalently associated β2 microglobulin. Generally, MHC class II molecules are composed of two transmembrane glycoproteins, α and β, both of which typically span the membrane. An MHC molecule can include an effective portion of an MHC that contains an antigen binding site or sites for binding a peptide and the sequences necessary for recognition by the appropriate antigen receptor. In some embodiments, MHC class I molecules deliver peptides originating in the cytosol to the cell surface, where a MHC-peptide complex is recognized by T cells, such as generally $CD8^+$ T cells, but in some cases $CD4^+$ T cells. In some embodiments, MHC class II molecules deliver peptides originating in the vesicular system to the cell surface, where they are typically recognized by $CD4^+$ T cells. Generally, MHC molecules are encoded by a group of linked loci, which are collectively termed H-2 in the mouse and human leukocyte antigen (HLA) in humans. Hence, typically human MHC can also be referred to as human leukocyte antigen (HLA).

The term "MHC-peptide complex" or "peptide-MHC complex" or variations thereof, refers to a complex or association of a peptide antigen and an MHC molecule, such as, generally, by non-covalent interactions of the peptide in the binding groove or cleft of the MHC molecule. In some embodiments, the MHC-peptide complex is present or displayed on the surface of cells. In some embodiments, the MHC-peptide complex can be specifically recognized by an antigen receptor, such as a TCR, TCR-like CAR or antigen-binding portions thereof.

In some embodiments, a peptide, such as a peptide antigen or epitope, of a polypeptide can associate with an MHC molecule, such as for recognition by an antigen receptor. Generally, the peptide is derived from or based on a fragment of a longer biological molecule, such as a polypeptide or protein. In some embodiments, the peptide typically is about 8 to about 24 amino acids in length. In some embodiments, a peptide has a length of from or from about 9 to 22 amino acids for recognition in the MHC Class II complex. In some embodiments, a peptide has a length of from or from about 8 to 13 amino acids for recognition in the MHC Class I complex. In some embodiments, upon recognition of the peptide in the context of an MHC molecule, such as MHC-peptide complex, the antigen receptor, such as TCR or TCR-like CAR, produces or triggers an activation signal to the T cell that induces a T cell response, such as T cell proliferation, cytokine production, a cytotoxic T cell response or other response.

In some embodiments, a TCR-like antibody or antigen-binding portion, are known or can be produced by known methods (see e.g. US Published Application Nos. US 2002/0150914; US 2003/0223994; US 2004/0191260; US 2006/0034850; US 2007/00992530; US20090226474; US20090304679; and International App. Pub. No. WO 03/068201).

In some embodiments, an antibody or antigen-binding portion thereof that specifically binds to a MHC-peptide complex, can be produced by immunizing a host with an effective amount of an immunogen containing a specific MHC-peptide complex. In some cases, the peptide of the MHC-peptide complex is an epitope of antigen capable of binding to the MHC, such as a tumor antigen, for example a universal tumor antigen, myeloma antigen or other antigen as described below. In some embodiments, an effective amount of the immunogen is then administered to a host for eliciting an immune response, wherein the immunogen retains a three-dimensional form thereof for a period of time sufficient to elicit an immune response against the three-dimensional presentation of the peptide in the binding groove of the MHC molecule. Serum collected from the host is then assayed to determine if desired antibodies that recognize a three-dimensional presentation of the peptide in the binding groove of the MHC molecule is being produced. In some embodiments, the produced antibodies can be assessed to confirm that the antibody can differentiate the MHC-peptide complex from the MHC molecule alone, the peptide of interest alone, and a complex of MHC and irrelevant peptide. The desired antibodies can then be isolated.

In some embodiments, an antibody or antigen-binding portion thereof that specifically binds to an MHC-peptide complex can be produced by employing antibody library display methods, such as phage antibody libraries. In some embodiments, phage display libraries of mutant Fab, scFv or other antibody forms can be generated, for example, in which members of the library are mutated at one or more residues of a CDR or CDRs. See e.g. US Pat. App. Pub. No. US20020150914, US20140294841; and Cohen C J. et al. (2003) *J Mol. Recogn.* 16:324-332.

The term "antibody" herein is used in the broadest sense and includes polyclonal and monoclonal antibodies, including intact antibodies and functional (antigen-binding) antibody fragments, including fragment antigen binding (Fab) fragments, $F(ab')_2$ fragments, Fab' fragments, Fv fragments, recombinant IgG (rIgG) fragments, variable heavy chain ($V_H$) regions capable of specifically binding the antigen, single chain antibody fragments, including single chain variable fragments (scFv), and single domain antibodies (e.g., sdAb, sdFv, nanobody, $V_H$H or $V_{NAR}$) or fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD. In some aspects, the CAR is a bispecific CAR, e.g., containing two antigen-binding domains with different specificities.

In some embodiments, the antigen-binding proteins, antibodies and antigen binding fragments thereof specifically recognize an antigen of a full-length antibody. In some embodiments, the heavy and light chains of an antibody can be full-length or can be an antigen-binding portion (a Fab, F(ab')2, Fv or a single chain Fv fragment (scFv)). In other embodiments, the antibody heavy chain constant region is chosen from, e.g., IgG1, IgG2, IgG3, IgG4, IgM, IgA1, IgA2, IgD, and IgE, particularly chosen from, e.g., IgG1, IgG2, IgG3, and IgG4, more particularly, IgG1 (e.g., human IgG1). In another embodiment, the antibody light chain constant region is chosen from, e.g., kappa or lambda, particularly kappa.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, $F(ab')_2$; diabodies; linear antibodies; variable heavy chain ($V_H$) regions, single-chain antibody molecules such as scFvs and single-domain $V_H$ single antibodies; and multispecific antibodies formed from antibody fragments. In particular embodiments, the antibodies are single-chain antibody fragments comprising a variable heavy chain region and/or a variable light chain region, such as scFvs.

The term "variable region" or "variable domain" refers to the domain of an antibody heavy or light chain that is involved in binding the antibody to antigen. The variable domains of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150: 880-887 (1993); Clarkson et al., Nature 352:624-628 (1991).

Single-domain antibodies (sdAb) are antibody fragments comprising all or a portion of the heavy chain variable domain or all or a portion of the light chain variable domain of an antibody. In certain embodiments, a single-domain antibody is a human single-domain antibody. In some embodiments, the CAR comprises an antibody heavy chain domain that specifically binds the antigen, such as a cancer marker or cell surface antigen of a cell or disease to be targeted, such as a tumor cell or a cancer cell, such as any of the target antigens described herein or known. Exemplary single-domain antibodies include sdFv, nanobody, $V_H$H or $V_{NAR}$.

Antibody fragments can be made by various techniques, including but not limited to proteolytic digestion of an intact antibody as well as production by recombinant host cells. In some embodiments, the antibodies are recombinantly produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody. In some embodiments, the antibody fragments are scFvs.

A "humanized" antibody is an antibody in which all or substantially all CDR amino acid residues are derived from non-human CDRs and all or substantially all FR amino acid residues are derived from human FRs. A humanized antibody optionally may include at least a portion of an antibody constant region derived from a human antibody. A "humanized form" of a non-human antibody, refers to a variant of the non-human antibody that has undergone humanization, typically to reduce immunogenicity to humans, while retaining the specificity and affinity of the parental non-human antibody. In some embodiments, some FR residues in a humanized antibody are substituted with corresponding residues from a non-human antibody (e.g., the antibody from which the CDR residues are derived), e.g., to restore or improve antibody specificity or affinity.

Thus, in some embodiments, the chimeric antigen receptor, including TCR-like CARs, includes an extracellular portion containing an antibody or antibody fragment. In some embodiments, the antibody or fragment includes an scFv. In some aspects, the antibody or antigen-binding fragment can be obtained by screening a plurality, such as a library, of antigen-binding fragments or molecules, such as by screening an scFv library for binding to a specific antigen or ligand.

In some aspects, the recombinant receptor, e.g., a chimeric antigen receptor, includes an extracellular portion containing one or more ligand- (e.g., antigen-) binding domains, such as an antibody or fragment thereof, and one or more intracellular signaling region or domain (also interchangeably called a cytoplasmic signaling domain or region). In some aspects, the recombinant receptor, e.g., CAR, further includes a spacer and/or a transmembrane domain or portion. In some aspects, the spacer and/or transmembrane domain can link the extracellular portion containing the ligand- (e.g., antigen-) binding domain and the intracellular signaling region(s) or domain(s).

In some embodiments, the recombinant receptor such as the CAR further includes a spacer, which may be or include at least a portion of an immunoglobulin constant region or variant or modified version thereof, such as a hinge region, e.g., an IgG4 hinge region, and/or a $C_H1/C_L$ and/or Fc region. In some embodiments, the recombinant receptor further comprises a spacer and/or a hinge region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. In some embodiments, the spacer is less than 250 amino acids in length, less than 200 amino acids in length, less than 150 amino acids in length, less than 100 amino acids in length, less than 75 amino acids in length, less than 50 amino acids in length, less than 25 amino acids in length, less than 20 amino acids in length, less than 15 amino acids in length, less than 12 amino acids in length, or less than 10 amino acids in length. In some embodiments, the spacer is from or from about 10 to 250 amino acids in length, 10 to 150 amino acids in length, 10 to 100 amino acids in length, 10 to 50 amino acids in length, 10 to 25 amino acids in length, 10 to 15 amino acids in length, 15 to 250 amino acids in length, 15 to 150 amino acids in length, 15 to 100 amino acids in length, 15 to 50 amino acids in length, 15 to 25 amino acids in length, 25 to 250 amino acids in length, 25 to 100 amino acids in length, 25 to 50 amino acids in length, 50 to 250 amino acids in length, 50 to 150 amino acids in length, 50 to 100 amino acids in length, 100 to 250 amino acids in length, 100 to 150 amino acids in length, or 150 to 250 amino acids in length. Exemplary spacers include IgG4 hinge alone, IgG4 hinge linked to $C_H2$ and $C_H3$ domains, or IgG4 hinge linked to the $C_H3$ domain. Exemplary spacers include, but are not limited to, those described in Hudecek et al. (2013) *Clin. Cancer Res.*, 19:3153, Hudecek et al. (2015) Cancer Immunol Res. 3 (2): 125-135 or International Pat. App. Pub. No. WO2014031687.

In some aspects, the spacer contains only a hinge region of an IgG, such as only a hinge of IgG4 or IgG1, such as the hinge only spacer set forth in SEQ ID NO:1, and is encoded by the sequence set forth in SEQ ID NO: 2. In other embodiments, the spacer is an Ig hinge, e.g., and IgG4 hinge, linked to a $C_H2$ and/or $C_H3$ domains. In some embodiments, the spacer is an Ig hinge, e.g., an IgG4 hinge, linked to $C_H2$ and $C_H3$ domains, such as set forth in SEQ ID NO: 3. In some embodiments, the spacer is an Ig hinge, e.g., an IgG4 hinge, linked to a $C_H3$ domain only, such as set forth in SEQ ID NO: 4. In some embodiments, the encoded spacer is or contains the sequence set forth in SEQ ID NO: 108. In some embodiments, the spacer is or comprises a glycine-serine rich sequence or other flexible linker such as known flexible linkers. In some embodiments, the constant region or portion is of IgD. In some embodiments, the spacer has the sequence set forth in SEQ ID NO: 5. In some embodiments, the spacer has a sequence of amino acids that exhibits at least or at least about 85%, 86%, 87%, 88%, 89%, 90%, 91%, 92%, 93%, 94%, 95%, 96%, 97%, 98%, 99% or more sequence identity to any of SEQ ID NOS: 1, 3, 4 and 5.

In some embodiments, the spacer can be derived all or in part from IgG4 and/or IgG2. In some embodiments, the spacer can be a chimeric polypeptide containing one or more of a hinge, $C_H2$ and/or $C_H3$ sequence(s) derived from IgG4, IgG2, and/or IgG2 and IgG4. In some embodiments, the spacer can contain mutations, such as one or more single amino acid mutations in one or more domains. In some examples, the amino acid modification is a substitution of a proline (P) for a serine(S) in the hinge region of an IgG4. In some embodiments, the amino acid modification is a substitution of a glutamine (Q) for an asparagine (N) to reduce glycosylation heterogeneity, such as an N to Q substitution at a position corresponding to position 177 in the $C_H2$ region of the IgG4 heavy chain constant region sequence set forth in SEQ ID NO: 60 (Uniprot Accession No. P01861; position corresponding to position 297 by EU numbering and position 79 of the hinge-$C_H2$-$C_H3$ spacer sequence set forth in SEQ ID NO:4) or an N to Q substitution at a position corresponding to position 176 in the $C_H2$ region of the IgG2 heavy chain constant region sequence set forth in SEQ ID NO: 59 (Uniprot Accession No. P01859; position corresponding to position 297 by EU numbering).

In some aspects, the spacer is a polypeptide spacer such as one or more selected from: (a) comprises or consists of all or a portion of an immunoglobulin hinge or a modified version thereof or comprises about 15 amino acids or less, and does not comprise a CD28 extracellular region or a CD8 extracellular region, (b) comprises or consists of all or a portion of an immunoglobulin hinge, optionally an IgG4 hinge, or a modified version thereof and/or comprises about 15 amino acids or less, and does not comprise a CD28 extracellular region or a CD8 extracellular region, or (c) is at or about 12 amino acids in length and/or comprises or consists of all or a portion of an immunoglobulin hinge, optionally an IgG4, or a modified version thereof; or (d) consists or comprises the sequence of amino acids set forth in SEQ ID NOS: 1, 3-5 or 27-34, or a variant of any of the foregoing having at least 85%, 86%, 87%, 88%, 89%, 90%, 91%, 92%, 93%, 94%, 95%, 96%, 97%, 98%, 99% or more sequence identity thereto, or (e) comprises or consists of the formula $X_1PPX_2P$ (SEQ ID NO: 31), where $X_1$ is glycine, cysteine or arginine and $X_2$ is cysteine or threonine.

In some embodiments, the ligand- (e.g., antigen-) binding or recognition domain of the CAR is linked to one or more intracellular signaling components, such as an intracellular signaling region or domain, and/or signaling components that mimic activation through an antigen receptor complex, such as a TCR complex, and/or signal via another cell surface receptor. Thus, in some embodiments, the antigen binding component (e.g., antibody) is linked to one or more transmembrane and intracellular signaling region(s) or domain(s). In some embodiments, the transmembrane domain is fused to the extracellular domain. In some embodiments, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

The transmembrane domain in some embodiments is derived either from a natural or from a synthetic source. Where the source is natural, the domain in some aspects is derived from any membrane-bound or transmembrane protein. Transmembrane regions include those derived from (i.e., comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 (4-1BB), or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s). In some aspects, the transmembrane domain contains a transmembrane portion of CD28 or a variant thereof. The extracellular domain and transmembrane can be linked directly or indirectly. In some embodiments, the extracellular domain and transmembrane are linked by a spacer, such as any described herein.

In some embodiments, the transmembrane domain of the receptor, e.g., the CAR is a transmembrane domain of human CD28 or variant thereof, e.g., a 27-amino acid transmembrane domain of a human CD28 (Accession No.: P10747.1), or is a transmembrane domain that comprises the sequence of amino acids set forth in SEQ ID NO: 8 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO:8; in some embodiments, the transmembrane-domain containing portion of the recombinant receptor comprises the sequence of amino acids set forth in SEQ ID NO: 9 or a sequence of amino acids having at least or at least about 85%, 86%, 87%, 88%, 89%, 90%, 91%, 92%, 93%, 94%, 95%, 96%, 97%, 98%, 99% or more sequence identity thereto.

In some aspects, the recombinant receptor, e.g., CAR, includes an intracellular signaling region or domain (also interchangeably called a cytoplasmic signaling domain or region). In some embodiments, the intracellular signaling region comprises an intracellular signaling domain. In some embodiments, the intracellular signaling region or domain is or comprises a primary signaling domain, a signaling domain that is capable of stimulating and/or inducing a primary activation signal in a T cell, a signaling domain of a T cell receptor (TCR) component (e.g. an intracellular signaling domain or region of a CD3-zeta (CD3ζ) chain or a functional variant or signaling portion thereof), and/or a signaling domain comprising an immunoreceptor tyrosine-based activation motif (ITAM). In some embodiments, the recombinant receptor, e.g., CAR, includes an extracellular portion containing the antibody or fragment and an intracellular signaling region or domain.

In some embodiments, the recombinant receptor, e.g., CAR, includes at least one intracellular signaling component or components, such as an intracellular signaling region or domain. Among the intracellular signaling region are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the CAR.

In some embodiments, upon ligation of the CAR, the cytoplasmic domain or intracellular signaling region of the CAR stimulates and/or activates at least one of the normal effector functions or responses of the immune cell, e.g., T cell engineered to express the CAR. For example, in some contexts, the CAR induces a function of a T cell such as cytolytic activity or T-helper activity, such as secretion of cytokines or other factors. In some embodiments, a truncated portion of an intracellular signaling region or domain of an antigen receptor component or costimulatory molecule is used in place of an intact immunostimulatory chain, for example, if it transduces the effector function signal. In some embodiments, the intracellular signaling regions, e.g., comprising intracellular domain or domains, include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability. In some embodiments, the intracellular signaling regions, e.g., comprising intracellular domain or domains, include the cytoplasmic sequences of a region or domain that is involved in providing costimulatory signal.

In some embodiments, the receptor includes an intracellular component of a TCR complex, such as a TCR CD3 chain that mediates T-cell activation and cytotoxicity, e.g., CD3 zeta chain. Thus, in some aspects, the antigen-binding or antigen-recognition domain is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor gamma (FcR γ), CD8 alpha, CD8 beta, CD4, CD25, or CD16. For example, in some aspects, the CAR includes a chimeric molecule between CD3 zeta (CD35) or FcR γ and one or more of CD8 alpha, CD8 beta, CD4, CD25 or CD16.

In the context of a natural TCR, full activation generally requires not only signaling through the TCR, but also a costimulatory signal. T cell activation is in some aspects described as being mediated by two classes of cytoplasmic signaling sequences: those that initiate antigen-dependent primary activation through the TCR (primary cytoplasmic signaling region(s) or domain(s)), and those that act in an antigen-independent manner to provide a secondary or co-stimulatory signal (secondary cytoplasmic signaling region (s) or domain(s)). In some aspects, the CAR includes one or both of such signaling components.

In some aspects, the CAR includes a primary cytoplasmic signaling region that regulates primary stimulation and/or activation of the TCR complex. Primary cytoplasmic signaling region(s) that act in a stimulatory manner may contain signaling motifs which are known as immunoreceptor tyrosine-based activation motifs or ITAMs. Examples of ITAM containing primary cytoplasmic signaling region(s) include those derived from TCR or CD3 zeta (CD35), Fc receptor (FcR) gamma or FcR beta. In some embodiments, cytoplasmic signaling regions or domains in the CAR contain(s) a cytoplasmic signaling domain, portion thereof, or sequence derived from CD3 zeta. In some embodiments, the intracellular (or cytoplasmic) signaling region comprises a human CD3 chain, optionally a CD3 zeta stimulatory signaling domain or functional variant thereof, such as an 112 AA cytoplasmic domain of isoform 3 of human CD35 (Accession No.: P20963.2) or a CD3 zeta signaling domain as described in U.S. Pat. No. 7,446,190 or U.S. Pat. No. 8,911,993. In some embodiments, the intracellular signaling region comprises the sequence of amino acids set forth in SEQ ID NO: 13, 14 or 15 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 13, 14 or 15.

Thus, in some embodiments, to promote full stimulation and/or activation, one or more components for generating secondary or costimulatory signal is also included in the CAR. In other embodiments, the CAR does not include a component for generating a costimulatory signal. In some aspects, an additional CAR is expressed in the same cell and provides the component for generating the secondary or costimulatory signal.

In some embodiments, the CAR includes a signaling region and/or transmembrane portion of a costimulatory receptor, such as CD28, 4-1BB, OX40 (CD134), CD27, DAP10, DAP12, ICOS and/or other costimulatory receptors. In some aspects, the same CAR includes both the primary cytoplasmic signaling region and costimulatory signaling components.

In some embodiments, one or more different recombinant receptors can contain one or more different intracellular signaling region(s) or domain(s). In some embodiments, the primary cytoplasmic signaling region is included within one CAR, whereas the costimulatory component is provided by another receptor, e.g., another CAR recognizing another antigen. In some embodiments, the CARs include activating or stimulatory CARs, and costimulatory CARs, both expressed on the same cell (see WO2014/055668).

In certain embodiments, the intracellular signaling region comprises a CD28 transmembrane and signaling domain linked to a CD3 (e.g., CD3 zeta) intracellular domain. In some embodiments, the intracellular signaling region comprises a chimeric CD28 and CD137 (4-1BB, TNFRSF9) co-stimulatory domains, linked to a CD3 zeta intracellular domain.

In some embodiments, the CAR encompasses one or more, e.g., two or more, costimulatory domains and primary cytoplasmic signaling region, in the cytoplasmic portion. Exemplary CARs include intracellular components, such as intracellular signaling region(s) or domain(s), of CD3-zeta, CD28, CD137 (4-1BB), OX40 (CD134), CD27, DAP10, DAP12, NKG2D and/or ICOS. In some embodiments, the chimeric antigen receptor contains an intracellular signaling region or domain of a T cell costimulatory molecule, e.g., from CD28, CD137 (4-1BB), OX40 (CD134), CD27, DAP10, DAP12, NKG2D and/or ICOS, in some cases, between the transmembrane domain and intracellular signaling region or domain. In some aspects, the T cell costimulatory molecule is one or more of CD28, CD137 (4-1BB), OX40 (CD134), CD27, DAP10, DAP12, NKG2D and/or ICOS.

In some embodiments, the intracellular signaling region or domain comprises an intracellular costimulatory signaling domain of human CD28 or functional variant or portion thereof, such as a 41 amino acid domain thereof and/or such a domain with an LL to GG substitution at positions 186-187 of a native CD28 protein. In some embodiments, the intracellular signaling domain can comprise the sequence of amino acids set forth in SEQ ID NO: 10 or 11 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 10 or 11. In some embodiments, the intracellular region comprises an intracellular costimulatory signaling region or domain of CD137 (4-1BB) or functional variant or portion thereof, such as a 42-amino acid cytoplasmic domain of a human 4-1BB (Accession No. Q07011.1) or functional variant or portion thereof, such as the sequence of amino acids set forth in SEQ ID NO: 12 or a sequence of amino acids that exhibits at least or at least about 85%, 86%, 87%, 88%, 89%, 90%, 91%, 92%, 93%, 94%, 95%, 96%, 97%, 98%, 99% or more sequence identity to SEQ ID NO: 12.

In some cases, CARs are referred to as first, second, third or fourth generation CARs. In some aspects, a first generation CAR is one that solely provides a primary stimulation or activation signal, e.g., via CD3-chain induced signal upon antigen binding; in some aspects, a second-generation CAR is one that provides such a signal and costimulatory signal, such as one including an intracellular signaling region(s) or domain(s) from one or more costimulatory receptor such as CD28, CD137 (4-1BB), OX40 (CD134), CD27, DAP10, DAP12, NKG2D, ICOS and/or other costimulatory receptors; in some aspects, a third generation CAR is one that includes multiple costimulatory domains of different costimulatory receptors, e.g., selected from CD28, CD137 (4-1BB), OX40 (CD134), CD27, DAP10, DAP12, NKG2D, ICOS and/or other costimulatory receptors; in some aspects, a fourth generation CAR is one that includes three or more costimulatory domains of different costimulatory receptors, e.g., selected from CD28, CD137 (4-1BB), OX40 (CD134), CD27, DAP10, DAP12, NKG2D, ICOS and/or other costimulatory receptors.

In some embodiments, the cell is engineered to express one or more additional molecules and/or polypeptides and/or combinatorial and/or multiple-targeting approaches are used to regulate, control, or modulate function and/or activity of the CAR. Exemplary approaches employed for CARS and combinatorial approaches are described, e.g., in the combinatorial approaches and multi-targeting section described below.

In some embodiments, the CAR contains an antibody, e.g., an antibody fragment, a transmembrane domain that is or contains a transmembrane portion of CD28 or a functional variant thereof, and an intracellular signaling region containing a signaling portion of CD28 or functional variant thereof and a signaling portion of CD3 zeta or functional variant thereof. In some embodiments, the CAR contains an antibody, e.g., antibody fragment, a transmembrane domain that is or contains a transmembrane portion of CD28 or a functional variant thereof, and an intracellular signaling domain containing a signaling portion of a 4-1BB or functional variant thereof and a signaling portion of CD3 zeta or functional variant thereof. In some such embodiments, the receptor further includes a spacer containing a portion of an Ig molecule, such as a human Ig molecule, such as an Ig hinge, e.g. an IgG4 hinge, such as a hinge-only spacer.

2. Modified Approaches

In some embodiments, the engineered cells include cells that employ modified approaches, e.g., multi-targeting strategies or regulatable receptors. In some embodiments, the modified strategies or approaches include employing multiple polypeptides, such as two or more polypeptides. In some embodiments, exemplary modified approaches or strategies include expression of two or more genetically engineered receptors on the cell, each recognizing the same of a different antigen and typically each including different regions or domains, such as a different intracellular signaling component. In some embodiments, exemplary modified approaches or strategies include expression of one or more polypeptide chains encode one or more domains or regions of a CAR. In some aspects, the various polypeptide chains in combination can perform functions or activities of a CAR, and/or regulate, control, or modulate function and/or activity of the CAR. In some aspects, multi-targeting strategies include a CAR that is a bispecific CAR, e.g., targeting two antigens, such as by containing two antigen-binding domains with different specificities.

In some embodiments, the modified strategies or approaches include combinations of activating and costimulatory CARs, e.g., targeting two different antigens present individually on off-target, e.g., normal cells, but present together only on cells of the disease or condition to be treated. In some embodiments, the multi-targeting strategies include cells expressing an activating and an inhibitory CAR, such as those in which the activating CAR binds to one antigen expressed on both normal or non-diseased cells and cells of the disease or condition to be treated, and the inhibitory CAR binds to another antigen expressed only on the normal cells or cells which it is not desired to treat. In some aspects, the modified strategies or approaches include recombinant receptors, e.g., CARs, that are capable of being regulated, modulated or controlled.

In some embodiments, modified approaches or strategies include engineering the cells to express one or more polypeptide chains encode one or more domains or regions of a CAR. In some aspects, various polypeptide chains in combination can comprise a CAR. In some embodiments, one or more additional domains or regions are present in the CAR. In some embodiments, various domains or regions present in one or more polypeptide chains combinatorial and/or multiple-targeting approaches are used to regulate, control, or modulate function and/or activity of the CAR. In some embodiments, the engineered cells express two or more receptors that contain different components, domains or regions. In some aspects, two or more receptors allows spatial or temporal regulation or control of specificity, activity, antigen (or ligand) binding, function and/or expression of the recombinant receptors.

In some aspects, one or more polypeptide chain encoding domains or regions of a CAR can target one or more antigens or molecules. Exemplary multi-targeting strategies are described, for example, in International Pat. App. Pub. No. WO 2014055668 or Fedorov et al., Sci. Transl. Medicine, Sci Transl Med. (2013) 5 (215): 215ra172; Sadelain, Curr Opin Immunol. (2016) 41:68-76; Wang et al. (2017) Front. Immunol. 8:1934; Mirzaei et al. (2017) Front. Immunol. 8:1850; Marin-Acevedo et al. (2018) Journal of Hematology & Oncology 11:8; Fesnak et al. (2016) Nat Rev Cancer. 16 (9): 566-581; and Abate-Daga and Davila, (2016) Molecular Therapy-Oncolytics 3, 16014.

For example, in some embodiments, the engineered cells can express a first recombinant receptor (e.g., CAR or TCR) which is capable of inducing an activating or stimulating signal to the cell, generally upon specific binding to the antigen recognized by the first receptor, e.g., the first antigen. In some embodiments, the cell can further express a second recombinant receptor (e.g., CAR or TCR), e.g., a chimeric costimulatory receptor, which is capable of inducing a costimulatory signal to the immune cell, generally upon specific binding to a second antigen recognized by the second receptor. In some embodiments, the first antigen and second antigen are the same. In some embodiments, the first antigen and second antigen are different.

In some embodiments, the first and/or second recombinant receptor (e.g. CAR or TCR) is capable of inducing an activating or stimulating signal to the cell. In some embodiments, the receptor includes an intracellular signaling component containing ITAM or ITAM-like motifs. In some embodiments, the activation induced by the first receptor involves a signal transduction or change in protein expression in the cell resulting in initiation of an immune response, such as ITAM phosphorylation and/or initiation of ITAM-mediated signal transduction cascade, formation of an immunological synapse and/or clustering of molecules near the bound receptor (e.g., CD4 or CD8, etc.), activation of one or more transcription factors, such as NF-κB and/or AP-1, and/or induction of gene expression of factors such as cytokines, proliferation, and/or survival.

In some embodiments, the first and/or second receptor includes intracellular signaling regions or domains of costimulatory receptors such as CD28, CD137 (4-1BB), OX40 (CD134), CD27, DAP10, DAP12, NKG2D, ICOS and/or other costimulatory receptors. In some embodiments, the first and second receptors can contain intracellular signaling domain(s) of a costimulatory receptor that are different. In one embodiment, the first receptor contains a CD28 costimulatory signaling region and the second receptor contain a 4-1BB co-stimulatory signaling region or vice versa.

In some embodiments, the first and/or second receptor includes both an intracellular signaling domain containing ITAM or ITAM-like motifs and an intracellular signaling domain of a costimulatory receptor.

In some embodiments, the first receptor contains an intracellular signaling domain containing ITAM or ITAM-like motifs and the second receptor contains an intracellular signaling domain of a costimulatory receptor. The costimulatory signal in combination with the activating or stimulating signal induced in the same cell is one that results in an immune response, such as a robust and sustained immune response, such as increased gene expression, secretion of cytokines and other factors, and T cell mediated effector functions such as cell killing.

In some embodiments, neither ligation of the first receptor alone nor ligation of the second receptor alone induces a robust immune response. In some aspects, if only one receptor is ligated, the cell becomes tolerized or unresponsive to antigen, or inhibited, and/or is not induced to proliferate or secrete factors or carry out effector functions. In some such embodiments, however, when the plurality of receptors are ligated, such as upon encounter of a cell expressing the first and second antigens, a desired response is achieved, such as full immune activation or stimulation, e.g., as indicated by secretion of one or more cytokine, proliferation, persistence, and/or carrying out an immune effector function such as cytotoxic killing of a target cell.

In some embodiments, the activating domain is included within one CAR, whereas the costimulatory component is provided by another CAR recognizing another antigen. In some embodiments, the CARs include activating or stimulatory CARs, costimulatory CARs, both expressed on the same cell (see WO2014/055668). In some aspects, the cells include one or more stimulatory or activating CAR and/or a costimulatory CAR.

In some embodiments, the cells expressing the recombinant receptor further include inhibitory CARs (iCARs, see Fedorov et al., *Sci. Transl. Medicine,* 5 (215) (2013), such as a CAR recognizing an antigen other than the one associated with and/or specific for the disease or condition whereby an activating signal delivered through the disease-targeting CAR is diminished or inhibited by binding of the inhibitory CAR to its ligand, e.g., to reduce off-target effects.

In some embodiments, the two receptors induce, respectively, an activating and an inhibitory signal to the cell, such that ligation of one of the receptor to its antigen activates the cell or induces a response, but ligation of the second inhibitory receptor to its antigen induces a signal that suppresses or dampens that response. Examples are combinations of activating CARs and inhibitory CARs (iCARs). Such a strategy may be used, for example, to reduce the likelihood of off-target effects in the context in which the activating CAR binds an antigen expressed in a disease or condition but which is also expressed on normal cells, and the inhibitory receptor binds to a separate antigen which is expressed on the normal cells but not cells of the disease or condition.

In some aspects, the chimeric receptor is or includes an inhibitory CAR (e.g. iCAR) and includes intracellular components that dampen or suppress an immune response, such as an ITAM- and/or co stimulatory-promoted response in the cell. Exemplary of such intracellular signaling components are those found on immune checkpoint molecules, including PD-1, CTLA4, LAG3, BTLA, OX2R, TIM-3, TIGIT, LAIR-1, PGE2 receptors, EP2/4 Adenosine receptors including A2AR. In some aspects, the engineered cell includes an inhibitory CAR including a signaling domain of or derived from such an inhibitory molecule, such that it serves to dampen the response of the cell, for example, that induced by an activating and/or costimulatory CAR.

In some embodiments, a multi-targeting strategy is employed in a case where an antigen associated with a particular disease or condition is expressed on a non-diseased cell and/or is expressed on the engineered cell itself, either transiently (e.g., upon stimulation in association with genetic engineering) or permanently. In such cases, by requiring ligation of two separate and individually specific antigen receptors, specificity, selectivity, and/or efficacy may be improved.

In some embodiments, the plurality of antigens, e.g., the first and second antigens, are expressed on the cell, tissue, or disease or condition being targeted, such as on the cancer cell. In some aspects, the cell, tissue, disease or condition is multiple myeloma or a multiple myeloma cell. In some embodiments, one or more of the plurality of antigens generally also is expressed on a cell which it is not desired to target with the cell therapy, such as a normal or non-diseased cell or tissue, and/or the engineered cells themselves. In such embodiments, by requiring ligation of multiple receptors to achieve a response of the cell, specificity and/or efficacy is achieved.

In some embodiments, one of the first and/or second recombinant receptor is a recombinant receptor that can regulate the expression, antigen binding and/or activity of the other recombinant receptor.

In some aspects, a two receptor system can be used to regulate the expression of the recombinant receptors. In some embodiments, the first recombinant receptor contains a first ligand- (e.g., antigen-) binding domain linked to a regulatory molecule, such as a transcription factor, linked via a regulatable cleavage element. In some aspects, the regulatable cleavage element is derived from a modified Notch receptor (e.g., synNotch), which is capable of cleaving and releasing an intracellular domain upon engagement of the first ligand- (e.g., antigen-) biding domain. In some aspects, the second recombinant receptor contains a second ligand- (e.g., antigen-) binding domain linked to an intracellular signaling component capable of inducing an activating or stimulating signal to the cell, such as an ITAM-containing intracellular signaling domain. In some aspects, the nucleic acid sequence encoding the second recombinant receptor is operably linked to transcriptional regulatory elements, e.g., promoter, that is capable of being regulated by a particular transcription factor, e.g., transcription factor encoded by the first recombinant receptor. In some aspects, engagement of a ligand or an antigen to the first ligand- (e.g., antigen-) binding domain leads to proteolytic release of the transcription factor, which in turn can induce the expression of the second recombinant receptor (see Roybal et al. (2016) Cell 164: 770-779; Morsut et al. (2016) Cell 164:780-791). In some embodiments, the first antigen and second antigen are different.

In some cases, the cell is engineered to express one or more additional molecules, e.g., an additional effector molecule and/or an accessory molecule. In some cases, the engineered cells are called "armored CARs" or T cells redirected for universal cytokine killing (TRUCKs). In some embodiments, the additional effector molecule is a soluble molecule. In some embodiments, the additional effector molecule is a membrane-bound molecule. In some aspects, the additional effector molecule can be used to overcome or counteract the effect of an immunosuppressive environment, such as a tumor microenvironment (TME). In some aspects, exemplary additional molecule includes a cytokine, a cytokine receptor, a chimeric co-stimulatory receptor, a co-stimulatory ligand and other modulators of T cell function or activity. In some embodiments, the additional molecules expressed by the engineered cell include IL-7, IL-12, IL-15, CD40 ligand (CD40L), and 4-1BB ligand (4-1BBL). In some aspects, the additional molecule is an additional receptor, e.g., a membrane-bound receptor, that binds a different molecule. For example, in some embodiments, the additional molecule is a cytokine receptor or a chemokine receptor, e.g., IL-4 receptor or CCL2 receptor.

In some embodiments, the CAR is a multi-specific CAR, e.g., contains a plurality of ligand- (e.g., antigen-) binding domains that can bind and/or recognize, e.g., specifically bind, a plurality of different antigens. In some aspects, the CAR is a bispecific CAR. In some embodiments, the CAR contains a bispecific binding domain, e.g., a bispecific antibody or fragment thereof, containing at least one antigen-binding domain binding to different surface antigens on a target cell, e.g., selected from any of the listed antigens as described herein, e.g. CD19 and CD22 or CD19 and CD20. In some embodiments, binding of the bispecific binding domain to each of its epitope or antigen can result in stimulation of function, activity and/or responses of the T cell, e.g., cytotoxic activity and subsequent lysis of the target cell. Among such exemplary bispecific binding domain can include tandem scFv molecules, in some cases fused to each other via, e.g. a flexible linker; diabodies and derivatives thereof, including tandem diabodies (Holliger et al, Prot Eng 9, 299-305 (1996); Kipriyanov et al, J Mol Biol 293, 41-66 (1999)); dual affinity retargeting (DART) molecules that can include the diabody format with a C-terminal disulfide bridge; bispecific T cell engager (BiTE) molecules, which contain tandem scFv molecules fused by a flexible linker (see e.g. Nagorsen and Bauerle, Exp Cell Res 317, 1255-1260 (2011); or triomabs that include whole hybrid mouse/rat IgG molecules (Seimetz et al, Cancer Treat Rev 36, 458-467 (2010). Any of such binding domains can be contained in any of the recombinant receptors described herein.

In some instances, the recombinant receptor, e.g., CAR, is capable of being regulated, is desirable to optimize the safety and efficacy of a therapy with the recombinant receptor. In some aspects, provided herein is an engineered cell comprising a recombinant receptor that is capable of being regulated. A recombinant receptor that is capable of being regulated, also referred to herein as a "regulatable recombinant receptor," refers to a set of polypeptides, such as a set of at least two polypeptides, which when expressed in an engineered cell (e.g., engineered T cell), provides the engineered cell with the ability to generate an intracellular signal under the control of an inducer.

In some embodiments, the polypeptides of the regulatable recombinant receptor provided herein contain multimerization domains that are capable of multimerization with another multimerization domain. In some embodiments, the multimerization domain is capable of multimerization upon binding to an inducer. For example, the multimerization domain can bind an inducer, such as a chemical inducer, which results in multimerization of the polypeptides of the regulatable recombinant receptor by virtue of multimerization of the multimerization domain, thereby producing the regulatable recombinant receptor. In some embodiments, one polypeptide of the regulatable recombinant receptor comprises a ligand- (e.g., antigen-) binding domain and a different polypeptide of the regulatable recombinant receptor comprises an intracellular signaling region, wherein multimerization of the two polypeptides by virtue of multimerization of the multimerization domain produces a regulatable recombinant receptor comprising a ligand-binding domain and an intracellular signaling region. In some embodiments, multimerization can induce, modulate, activate, mediate and/or promote signals in the engineered cell containing the regulatable recombinant receptor. In some embodiments, an inducer binds to a multimerization domain at least one polypeptide of a regulatable recombinant receptor and induces a conformational change of the regulatable recombinant receptor, wherein the conformational change activates signaling. In some embodiments, binding of a ligand to such recombinant receptors induces conformational changes in the recombinant receptor, including, in some cases, recombinant receptor oligomerization, which can render the receptors competent for intracellular signaling.

In some embodiments, an inducer functions to couple or multimerize (e.g., dimerize) a set of at least two polypeptides of a regulatable recombinant receptor expressed in an engineered cell in order for the regulatable recombinant receptor to produce a desired intracellular signal such as during interaction of the regulatable recombinant receptor with a target antigen. Coupling or multimerization of at least two polypeptides of a regulatable recombinant receptor by an inducer is achieved upon binding of an inducer to a multimerization domain. For example, in some embodiments, a first polypeptide and a second polypeptide in an engineered cell may each comprise a multimerization domain capable of binding an inducer. Upon binding of the multimerization domain by the inducer, the first polypeptide and the second polypeptide are coupled together to produce the desired intracellular signal. In some embodiments, a multimerization domain is located on an intracellular portion of a polypeptide. In some embodiments, a multimerization domain is located on an extracellular portion of a polypeptide.

In some embodiments, a set of at least two polypeptides of a regulatable recombinant receptor comprises two, three, four, or five or more polypeptides. In some embodiments, the set of at least two polypeptides are the same polypeptides, for example, two, three, or more of the same polypeptides comprising an intracellular signaling region, and a multimerization domain. In some embodiments, the set of at least two polypeptides are different polypeptides, for example, a first polypeptide comprising an ligand- (e.g., antigen-) binding domain and a multimerization domain and a second polypeptide comprising an intracellular signaling region and a multimerization domain. In some embodiments, the intercellular signal is generated in the presence of an inducer. In some embodiments, the intracellular signal is generated in the absence of an inducer, e.g., an inducer interferes with multimerization of at least two polypeptides of a regulatable recombinant receptor thereby preventing intracellular signaling by the regulatable recombinant receptor.

In some embodiments, the provided multimerization domain can multimerize (e.g., dimerize), upon binding of an inducer. An inducer contemplated herein includes, but is not limited to, a chemical inducer or a protein (e.g., a caspase). In some embodiments, the inducer is selected from an estrogen, a glucocorticoid, a vitamin D, a steroid, a tetracycline, a cyclosporine, Rapamycin, Coumermycin, Gibberellin, FK1012, FK506, FKCsA, rimiducid or HaXS, or analogs or derivatives thereof. In some embodiments, the inducer is AP20187 or an AP20187 analog, such as, AP1510.

In some embodiments, the provided multimerization domain can multimerize (e.g., dimerize), upon binding of an inducer such as an inducer provided herein. In some embodiments, the multimerization domain can be from an FKBP, a cyclophilin receptor, a steroid receptor, a tetracycline receptor, an estrogen receptor, a glucocorticoid receptor, a vitamin D receptor, Calcineurin A, CyP-Fas, FRB domain of mTOR, GyrB, GAI, GID1, Snap-tag and/or HaloTag, or portions or derivatives thereof. In some embodiments, the multimerization domain is an FK506 binding protein (FKBP) or derivative thereof, or fragment and/or multimer thereof, such as FKBP12v36. In some embodiments, FKBP comprises the amino acid sequence (SEQ ID NO: 85)
GVQVETISPGDGRTFPKRGQTCVVHYTGMLEDGKKMDSSRDRNKPFKFML
GKQEVIRGWEEGVAQMSVGQRAKLTISPDYAYGATGHPGIIPPHATLVFD
VELLKLE.

In some embodiments, FKBP12v36 comprises the amino acid sequence (SEQ ID NO: 85)
GVQVETISPGDGRTFPKRGQTCVVHYTGMLEDGKKVDSSRDRNKPFKFML
GKQEVIRGWEEGVAQMSVGQRAKLTISPDYAYGATGHPGIIPPHATLVFD
VELLKLE.

Exemplary inducers and corresponding multimerization domains are known, e.g., as described in U.S. Pat. App. Pub. No. 2016/0046700, Clackson et al. (1998) Proc Natl Acad Sci USA. 95 (18): 10437-42; Spencer et al. (1993) Science 262 (5136): 1019-24; Farrar et al. (1996) Nature 383 (6596): 178-81; Miyamoto et al. (2012) Nature Chemical Biology 8 (5): 465-70; Erhart et al. (2013) Chemistry and Biology 20 (4): 549-57). In some embodiments, the inducer is rimiducid (also known as AP1903; CAS Index Name: 2-Piperidinecarboxylic acid, 1-[(2S)-1-oxo-2-(3,4,5-trimethoxyphenyl) butyl]-, 1,2-ethanediylbis [imino (2-oxo-2, 1-ethanediyl) oxy-3,1-phenylene[(1R)-3-(3,4-Dimethoxyphenyl) propylidene]]ester, [2S-[1 (R*),2R*[S*[S*[1 (R*),2R]]]]]-(9Cl); CAS Registry Number: 195514-63-7; Molecular Formula: C78H98N4020; Molecular Weight: 1411.65), and the multimerization domain is an FK506 binding protein (FKBP).

In some embodiments, the cell membrane of the engineered cell is impermeable to the inducer. In some embodiments, the cell membrane of the engineered cell is permeable to the inducer.

In some embodiments, the provided polypeptides of the regulatable recombinant receptor are not part of a multimer or a dimer in the absence of the inducer. Upon the binding of the inducer, the multimerization domains can multimerize, e.g., dimerize. In some aspects, multimerization of the multimerization domain results in multimerization of a polypeptide of the regulatable recombinant receptor with another polypeptide of the regulatable recombinant receptor, e.g. multimeric complex of at least two polypeptides of the regulatable recombinant receptors. In some embodiments, multimerization of the multimerization domain can induce, modulate, activate, mediate and/or promote signal transduction by virtue of inducing physical proximity of signaling components or formation of the multimer or dimer. In some embodiments, upon the binding of an inducer, multimerization of the multimerization domain also induces multimerization of signaling domains linked, directly or indirectly, to the multimerization domain. In some embodiments, the multimerization induces, modulates, activates, mediates and/or promotes signaling through the signaling domain or region. In some embodiments, the signaling domain or region linked to the multimerization domain is an intracellular signaling region.

In some embodiments, the multimerization domain is intracellular or is associated with the cell membrane on the intracellular or cytoplasmic side of the engineered cell (e.g., engineered T cell). In some aspects, the intracellular multimerization domain is linked, directly or indirectly, to a membrane association domain (e.g., a lipid linking domain), such as a myristoylation domain, palmitoylation domain, prenylation domain, or a transmembrane domain. In some embodiments, the multimerization domain is intracellular, and is linked to the extracellular ligand- (e.g., antigen-) binding domain via a transmembrane domain. In some embodiments, the intracellular multimerization domain is linked, directly or indirectly, to the intracellular signaling region. In some aspects, induced multimerization of the multimerization domain also brings the intracellular signaling regions in proximity with one another, to allow multimerization, e.g., dimerization, and stimulate intracellular signaling. In some embodiments, a polypeptide of the regulatable recombinant receptor comprises a transmembrane domain, one or more intracellular signaling region(s), and one or more multimerization domain(s), each of which are linked directly or indirectly.

In some embodiments, the multimerization domain is extracellular or is associated with the cell membrane on the extracellular side of the engineered cell (e.g., engineered T cell). In some aspects, the extracellular multimerization domain is linked, directly or indirectly, to a membrane association domain (e.g., a lipid linking domain), such as a myristoylation domain, palmitoylation domain, prenylation domain, or a transmembrane domain. In some embodiments, the extracellular multimerization domain is linked, directly or indirectly, to a ligand-binding domain, e.g., an antigen-binding domain such as for binding to an antigen associated with a disease. In some embodiments, the multimerization domain is extracellular, and is linked to an intracellular signaling region via a transmembrane domain.

In some aspects, the membrane association domain is a transmembrane domain of an existing transmembrane protein. In some examples, the membrane association domain is any of the transmembrane domains described above. In some aspects, the membrane association domain contains protein-protein interaction motifs or transmembrane sequences.

In some aspects, the membrane association domain is an acylation domain, such as a myristoylation domain, palmitoylation domain, prenylation domain (i.e., farnesylation, geranyl-geranylation, CAAX Box). For example, the membrane association domain can be an acylation sequence motif present in N-terminus or C-terminus of a protein. Such domains contain particular sequence motifs that can be recognized by acyltransferases that transfer acyl moieties to the polypeptide that contains the domain. For example, the acylation motifs can be modified with a single acyl moiety (in some cases, followed by several positively charged residues (e.g. human c-Src: MGSNKSKPKDASQRRR (SEQ ID NO: 86) to improve association with anionic lipid head groups). In other aspects, the acetylation motif is capable of being modified with multiple acyl moieties. For example, dual acylation regions are located within the N-terminal regions of certain protein kinases, such as a subset of Src family members (e.g., Yes, Fyn, Lck) and G-protein alpha subunits. Exemplary dual acylation regions contain the sequence motif Met-Gly-Cys-Xaa-Cys, (SEQ ID NO:87) where the Met is cleaved, the Gly is N-acylated and one of the Cys residues is S-acylated. The Gly often is myristoylated and a Cys can be palmitoylated.

Other exemplary acylation regions include sequence motif Cys-Ala-Ala-Xaa (so called "CAAX boxes"; SEQ ID NO:88) that can modified with C15 or O10 isoprenyl moieties, and are known in the art (see, e.g., Gauthier-Campbell et al. (2004) Molecular Biology of the Cell 15:2205-2217; Glabati et al. (1994) Biochem. J. 303:697-700 and Zlakine et al. (1997) J. Cell Science 110:673-679; ten Klooster et al. (2007) Biology of the Cell 99:1-12; Vincent et al. (2003) Nature Biotechnology 21:936-40). In some embodiments, the acyl moiety is a C1-C20 alkyl, C2-C20 alkenyl, C2-C20 alkynyl, $C_3$-$C_6$ cycloalkyl, C1-C4 haloalkyl, C4-C12 cycloalkylalkyl, aryl, substituted aryl, or aryl (C1-C4) alkyl. In some embodiments, the acyl-containing moiety is a fatty acid, and examples of fatty acid moieties are propyl (C3), butyl (C4), pentyl (C5), hexyl (C6), heptyl (C7), octyl (C8), nonyl (C9), decyl (C10), undecyl (C11), lauryl (C12), myristyl (C14), palmityl (C16), stearyl (C18), arachidyl (C20), behenyl (C22) and lignoceryl moieties (C24), and each moiety can contain 0, 1, 2, 3, 4, 5, 6, 7 or 8 unsaturated bonds (i.e., double bonds). In some examples, the acyl moiety is a lipid molecule, such as a phosphatidyl lipid (e.g., phosphatidyl serine, phosphatidyl inositol, phosphatidyl ethanolamine, phosphatidyl choline), sphingolipid (e.g., shingomyelin, sphingosine, ceramide, ganglioside, cerebroside), or modified versions thereof. In certain embodiments, one, two, three, four or five or more acyl moieties are linked to a membrane association domain.

In some aspects, the membrane association domain is a domain that promotes an addition of a glycolipid (also known as glycosyl phosphatidylinositols or GPIs). In some aspects, a GPI molecule is post-translationally attached to a protein target by a transamidation reaction, which results in the cleavage of a carboxy-terminal GPI signal sequence (see, e.g., White et al. (2000) J. Cell Sci. 113:721) and the simultaneous transfer of the already synthesized GPI anchor molecule to the newly formed carboxy-terminal amino acid (See, e.g., Varki A, et al., editors. Essentials of Glycobiology. Cold Spring Harbor (NY): Cold Spring Harbor Laboratory Press; 1999. Chapter 10, Glycophospholipid Anchors. Available from: https://www.ncbi.nlm.nih.gov/books/NBK20711/see www.ncbi.nlm.nih.gov/books/NBK20711). In certain embodiments, the membrane association domain is a GPI signal sequence.

In some embodiments, a multimerization domain as provided herein is linked to an intracellular signaling regions, e.g., a primary signaling domain and/or costimulatory signaling domains. In some embodiments, the multimerization domain is extracellular, and is linked to the intracellular signaling region via a transmembrane domain. In some embodiments, the multimerization domain is intracellular, and is linked to the ligand- (e.g., antigen-) binding domain via a transmembrane domain. The ligand-binding domain and transmembrane domain can be linked directly or indirectly. In some embodiments, the ligand-binding domain and transmembrane are linked by a spacer, such as any described herein. In some embodiments, the multimerization domain is an FK506 binding protein (FKBP) or derivative or fragment thereof, such as FKBP12v36. In some examples, upon the introduction of an inducer, such as a rimiducid, the polypeptides of the regulatable recombinant receptor multimerize, e.g., dimerize, thereby stimulating the signaling domains associated with the multimerization domain and forming a multimeric complex. Formation of the multimeric complex results in inducing, modulating, stimulating, activating, mediating and/or promoting signals through intracellular signaling region.

In some embodiments, signaling through the regulatable recombinant receptor can be modulated in a conditional manner through conditional multimerization. For example, the multimerization domain of the polypeptides of the regulatable recombinant receptor can bind an inducer to multimerize, and the inducer can be provided exogenously. In some aspects, upon binding of the inducer, the multimerization domain multimerizes and induces, modulates, activates, mediates and/or promotes signaling through the signaling domain. For example, the inducer can be exogenously administered, thereby controlling the location and duration of the signal provided to the engineered cell containing the regulatable recombinant receptor. In some embodiments, the multimerization domain of the polypeptides of the regulatable recombinant receptor can bind an inducer to multimerize, and the inducer can be provided endogenously. For example, the inducer can be produced endogenously by the engineered cell (e.g., engineered T cell) from a recombinant expression vector or from the genome of the engineered cell under the control of an inducible or conditional promoter, thereby controlling the location and duration of the signal provided to the engineered cell containing the regulatable recombinant receptor.

In some embodiments, the regulatable recombinant receptor is controlled using a suicide switch. Exemplary recombinant receptors utilize an inducible caspase-9 (iCasp9) system, comprising a fusion of human caspase-9 and a modified FKBP dimerization domain, allowing conditional dimerization upon binding with an inducer, e.g., AP1903. Upon dimerization by binding of the inducer, caspase-9 becomes activated and results in apoptosis and cell death of the cells expressing the chimeric receptor (see, e.g., Di Stasi et al. (2011) N. Engl. J. Med. 365:1673-1683).

In some embodiments, exemplary regulatable recombinant receptor includes: (1) a first polypeptide of a regulatable recombinant receptor comprising: (i) intracellular signaling region; and (ii) at least one multimerization domain capable of binding an inducer; and (2) a second polypeptide of a regulatable recombinant receptor comprising: (i) a ligand- (e.g., antigen-) binding domain; (ii) a transmembrane domain; and (iii) at least one multimerization domain capable of binding an inducer. In some embodiments, exemplary regulatable recombinant receptor includes: (1) a first polypeptide of a regulatable recombinant receptor comprising: (i) a transmembrane domain or an acylation domain; (ii) intracellular signaling region; and (iii) at least one multimerization domain capable of binding an inducer; and (2) a second polypeptide of a regulatable recombinant receptor comprising: (i) a ligand- (e.g., antigen-) binding domain; (ii) a transmembrane domain; and (iii) at least one multimerization domain capable of binding an inducer. In some embodiments, the intracellular signaling region further comprises a costimulatory signaling domain. In some embodiments, the second polypeptide further comprises a costimulatory signaling domain. In some embodiments, the at least one multimerization domain(s) on both polypeptides is intracellular. In some embodiments, the at least one multimerization domain(s) on both polypeptides is extracellular.

In some embodiments, exemplary regulatable recombinant receptor includes: (1) a first polypeptide of a regulatable recombinant receptor comprising: (i) at least one extracellular multimerization domain capable of binding an inducer; (ii) a transmembrane domain; and (iii) intracellular signaling region; and (2) a second polypeptide of a regulatable recombinant receptor comprising: (i) a ligand- (e.g., antigen-) binding domain; (ii) at least one extracellular multimerization domain capable of binding an inducer and (iii) a transmembrane domain, an acylation domain or a GPI signal sequence. In some embodiments, the intracellular signaling region further comprises a costimulatory signaling domain. In some embodiments, the second polypeptide further comprises a costimulatory signaling domain.

In some embodiments, exemplary regulatable recombinant receptor includes: (1) a first polypeptide of a regulatable recombinant receptor comprising: (i) a transmembrane domain or an acylation domain; (ii) at least one costimulatory domain; (iii) a multimerization domain capable of binding an inducer and (iv) intracellular signaling region; and (iii) at least one costimulatory domain; and (2) a second polypeptide of a regulatable recombinant receptor comprising: (i) a ligand- (e.g., antigen-) binding domain; (ii) a transmembrane domain; (iii) at least one costimulatory domain; and (iv) at least one extracellular multimerization domain capable of binding an inducer.

In some aspects, any of the regions and/or domains described in the exemplary regulatable recombinant receptors can be ordered in various different orders. In some aspects, the various polypeptides of the regulatable recombinant receptor(s) contain the multimerization domain on the same side of the cell membrane, e.g., the multimerization domain in the two or more polypeptides are all intracellular or all extracellular.

Variations of regulatable recombinant receptors are known, for example, described in U.S. Pat. App. Pub. No. 2014/0286987, U.S. Pat. App. Pub. No. 2015/0266973, International Pat. App. Pub. No. WO2014/127261, and International Pat. App. Pub. No. WO2015/142675.

3. Chimeric Auto-Antibody Receptor (CAAR)

In some embodiments, the recombinant receptor is a chimeric autoantibody receptor (CAAR). In some embodiments, the CAAR binds, e.g., specifically binds, or recognizes, an autoantibody. In some embodiments, a cell expressing the CAAR, such as a T cell engineered to express a CAAR, can be used to bind to and kill autoantibody-expressing cells, but not normal antibody expressing cells. In some embodiments, CAAR-expressing cells can be used to treat an autoimmune disease associated with expression of self-antigens, such as autoimmune diseases. In some embodiments, CAAR-expressing cells can target B cells that ultimately produce the autoantibodies and display the autoantibodies on their cell surfaces, mark these B cells as disease-specific targets for therapeutic intervention. In some embodiments, CAAR-expressing cells can be used to efficiently target and kill the pathogenic B cells in autoimmune diseases by targeting the disease-causing B cells using an antigen-specific chimeric autoantibody receptor. In some embodiments, the recombinant receptor is a CAAR, such as any described in U.S. Patent Application Pub. No. US 2017/0051035, which is incorporated herein by reference in its entirety.

In some embodiments, the CAAR comprises an autoantibody binding domain, a transmembrane domain, and one or more intracellular signaling region or domain (also interchangeably called a cytoplasmic signaling domain or region). In some embodiments, the intracellular signaling region comprises an intracellular signaling domain. In some embodiments, the intracellular signaling domain is or comprises a primary signaling domain, a signaling domain that is capable of stimulating and/or inducing a primary activation signal in a T cell, a signaling domain of a T cell receptor (TCR) component (e.g. an intracellular signaling domain or region of a CD3-zeta (CD3ζ) chain or a functional variant or signaling portion thereof), and/or a signaling domain comprising an immunoreceptor tyrosine-based activation motif (ITAM).

In some embodiments, the autoantibody binding domain comprises an autoantigen or a fragment thereof. The choice of autoantigen can depend upon the type of autoantibody being targeted. For example, the autoantigen may be chosen because it recognizes an autoantibody on a target cell, such as a B cell, associated with a particular disease state, e.g. an autoimmune disease, such as an autoantibody-mediated autoimmune disease. In some embodiments, the autoimmune disease includes pemphigus vulgaris (PV). Exemplary autoantigens include desmoglein 1 (Dsg1) and Dsg3.

4. T Cell Receptors (TCRs)

In some embodiments, engineered cells, such as T cells, express a T cell receptor (TCR) or antigen-binding portion thereof that recognizes an intracellular and/or a peptide epitope or T cell epitope of a target polypeptide, such as an antigen of a tumor, viral or autoimmune protein. In some aspects, the recombinant receptor is or includes a recombinant TCR.

In some embodiments, a "T cell receptor" or "TCR" is a molecule that contains a variable $\alpha$ and $\beta$ chains (also known as TCR$\alpha$ and TCR$\beta$, respectively) or a variable $\gamma$ and $\delta$ chains (also known as TCR$\alpha$ and TCR$\beta$, respectively), or antigen-binding portions thereof, and which is capable of specifically binding to a peptide bound to an MHC molecule. In some embodiments, the TCR is in the $\alpha\beta$ form. Typically, TCRs that exist in $\alpha\beta$ and $\gamma\delta$ forms are generally structurally similar, but T cells expressing them may have distinct anatomical locations or functions. A TCR can be found on the surface of a cell or in soluble form. Generally, a TCR is found on the surface of T cells (or T lymphocytes) where it is generally responsible for recognizing antigens bound to major histocompatibility complex (MHC) molecules.

Unless otherwise stated, the term "TCR" should be understood to encompass full TCRs as well as antigen-binding portions or antigen-binding fragments thereof. In some embodiments, the TCR is an intact or full-length TCR, including TCRs in the αβ form or γδ form. In some embodiments, the TCR is an antigen-binding portion that is less than a full-length TCR but that binds to a specific peptide bound in an MHC molecule, such as binds to an MHC-peptide complex. In some cases, an antigen-binding portion or fragment of a TCR can contain only a portion of the structural domains of a full-length or intact TCR, but yet is able to bind the peptide epitope, such as MHC-peptide complex, to which the full TCR binds. In some cases, an antigen-binding portion contains the variable domains of a TCR, such as variable α ($V_\alpha$) chain and variable β ($V_\beta$) chain of a TCR, or antigen-binding fragments thereof sufficient to form a binding site for binding to a specific MHC-peptide complex.

In some embodiments, the variable domains of the TCR contain hypervariable loops, or complementarity determining regions (CDRs), which generally are the primary contributors to antigen recognition and binding capabilities and specificity. In some embodiments, a CDR of a TCR or combination thereof forms all or substantially all of the antigen-binding site of a given TCR molecule. The various CDRs within a variable region of a TCR chain generally are separated by framework regions (FRs), which generally display less variability among TCR molecules as compared to the CDRs (see, e.g., Jores et al., Proc. Nat'l Acad. Sci. U.S.A. 87:9138, 1990; Chothia et al., EMBO J. 7:3745, 1988; see also Lefranc et al., Dev. Comp. Immunol. 27:55, 2003). In some embodiments, CDR3 is the main CDR responsible for antigen binding or specificity, or is the most important among the three CDRs on a given TCR variable region for antigen recognition, and/or for interaction with the processed peptide portion of the peptide-MHC complex. In some contexts, the CDR1 of the alpha chain can interact with the N-terminal part of certain antigenic peptides. In some contexts, CDR1 of the beta chain can interact with the C-terminal part of the peptide. In some contexts, CDR2 contributes most strongly to or is the primary CDR responsible for the interaction with or recognition of the MHC portion of the MHC-peptide complex. In some embodiments, the variable region of the β-chain can contain a further hypervariable region (CDR4 or HVR4), which generally is involved in superantigen binding and not antigen recognition (Kotb (1995) Clinical Microbiology Reviews, 8:411-426).

In some embodiments, a TCR also can contain a constant domain, a transmembrane domain and/or a short cytoplasmic tail (see, e.g., Janeway et al., Immunobiology: The Immune System in Health and Disease, 3rd Ed., Current Biology Publications, p. 4:33, 1997). In some aspects, each chain of the TCR can possess one N-terminal immunoglobulin variable domain, one immunoglobulin constant domain, a transmembrane region, and a short cytoplasmic tail at the C-terminal end. In some embodiments, a TCR is associated with invariant proteins of the CD3 complex involved in mediating signal transduction.

In some embodiments, a TCR chain contains one or more constant domain. For example, the extracellular portion of a given TCR chain (e.g., α-chain or β-chain) can contain two immunoglobulin-like domains, such as a variable domain (e.g., Va or VB; typically amino acids 1 to 116 based on Kabat numbering Kabat et al., "Sequences of Proteins of Immunological Interest, US Dept. Health and Human Services, Public Health Service National Institutes of Health, 1991, 5th ed.) and a constant domain (e.g., α-chain constant domain or Ca, typically positions 117 to 259 of the chain based on Kabat numbering or β chain constant domain or $C_\beta$, typically positions 117 to 295 of the chain based on Kabat) adjacent to the cell membrane. For example, in some cases, the extracellular portion of the TCR formed by the two chains contains two membrane-proximal constant domains, and two membrane-distal variable domains, which variable domains each contain CDRs. The constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains.

In some embodiments, the TCR chains contain a transmembrane domain. In some embodiments, the transmembrane domain is positively charged. In some cases, the TCR chain contains a cytoplasmic tail. In some cases, the structure allows the TCR to associate with other molecules like CD3 and subunits thereof. For example, a TCR containing constant domains with a transmembrane region may anchor the protein in the cell membrane and associate with invariant subunits of the CD3 signaling apparatus or complex. The intracellular tails of CD3 signaling subunits (e.g. CD3γ, CD3δ, CD3ε and CD3ζ chains) contain one or more immunoreceptor tyrosine-based activation motif or ITAM that are involved in the signaling capacity of the TCR complex.

In some embodiments, the TCR contains various domains or regions. In some cases, the exact domain or region can vary depending on the particular structural or homology modeling or other features used to describe a particular domain. It is understood that reference to amino acids, including to a specific sequence set forth as a SEQ ID NO used to describe domain organization of a recombinant receptor, e.g., TCR, are for illustrative purposes and are not meant to limit the scope of the embodiments provided. In some cases, the specific domain (e.g. variable or constant) can be several amino acids (such as one, two, three or four) longer or shorter. In some aspects, residues of a TCR are known or can be identified according to the International Immunogenetics Information System (IMGT) numbering system (see e.g. www.imgt.org; see also, Lefranc et al. (2003) Developmental and Comparative Immunology, 2&; 55-77; and The T Cell Factsbook 2nd Edition, Lefranc and LeFranc Academic Press 2001). Using this system, the CDR1 sequences within a TCR Va chains and/or VB chain correspond to the amino acids present between residue numbers 27-38, inclusive, the CDR2 sequences within a TCR Va chain and/or VB chain correspond to the amino acids present between residue numbers 56-65, inclusive, and the CDR3 sequences within a TCR Va chain and/or VB chain correspond to the amino acids present between residue numbers 105-117, inclusive.

In some embodiments, the α chain and β chain of a TCR each further contain a constant domain. In some embodiments, the α chain constant domain (Cα) and β chain constant domain (CB) individually are mammalian, such as is a human or murine constant domain. In some embodiments, the constant domain is adjacent to the cell membrane. For example, in some cases, the extracellular portion of the TCR formed by the two chains contains two membrane-proximal constant domains, and two membrane-distal variable domains, which variable domains each contain CDRs.

In some embodiments, each of the Cα and Cβ domains is human. In some embodiments, the Cα is encoded by the TRAC gene (IMGT nomenclature) or is a variant thereof. In some embodiments, the Cβ is encoded by TRBC1 or TRBC2 genes (IMGT nomenclature) or is a variant thereof. In some embodiments, any of the provided TCRs or antigen-binding fragments thereof can be a human/mouse chimeric TCR. In some cases, the TCR or antigen-binding fragment thereof have a chain and/or a β chain comprising a mouse constant region. In some aspects, the Ca and/or CB regions are mouse constant regions. In some of any such embodiments, the TCR or antigen-binding fragment thereof is encoded by a nucleotide sequence that has been codon-optimized.

In some of any such embodiments, the binding molecule or TCR or antigen-binding fragment thereof is isolated or purified or is recombinant. In some of any such embodiments, the binding molecule or TCR or antigen-binding fragment thereof is human.

In some embodiments, the TCR may be a heterodimer of two chains α and β that are linked, such as by a disulfide bond or disulfide bonds. In some embodiments, the constant domain of the TCR may contain short connecting sequences in which a cysteine residue forms a disulfide bond, thereby linking the two chains of the TCR. In some embodiments, a TCR may have an additional cysteine residue in each of the α and β chains, such that the TCR contains two disulfide bonds in the constant domains. In some embodiments, each of the constant and variable domains contains disulfide bonds formed by cysteine residues.

In some embodiments, the TCR may be a heterodimer of two chains α and β (or optionally γ and δ) or it may be a single chain TCR construct. In some embodiments, the TCR is a heterodimer containing two separate chains (α and β chains or γ and δ chains) that are linked, such as by a disulfide bond or disulfide bonds.

In some embodiments, the TCR can be generated from a known TCR sequence(s), such as sequences of Vα,β chains, for which a substantially full-length coding sequence is readily available. Methods for obtaining full-length TCR sequences, including V chain sequences, from cell sources are well known. In some embodiments, nucleic acids encoding the TCR can be obtained from a variety of sources, such as by polymerase chain reaction (PCR) amplification of TCR-encoding nucleic acids within or isolated from a given cell or cells, or synthesis of publicly available TCR DNA sequences.

In some embodiments, the recombinant receptors include recombinant TCRs and/or TCRs cloned from naturally occurring T cells. In some embodiments, a high-affinity T cell clone for a target antigen (e.g., a cancer antigen) is identified, isolated from a patient, and introduced into the cells. In some embodiments, the TCR clone for a target antigen has been generated in transgenic mice engineered with human immune system genes (e.g., the human leukocyte antigen system, or HLA). See, e.g., tumor antigens (see, e.g., Parkhurst et al. (2009) Clin Cancer Res. 15:169-180 and Cohen et al. (2005) J Immunol. 175:5799-5808. In some embodiments, phage display is used to isolate TCRs against a target antigen (see, e.g., Varela-Rohena et al. (2008) Nat Med. 14:1390-1395 and Li (2005) Nat Biotechnol. 23:349-354.

In some embodiments, the TCR is obtained from a biological source, such as from cells such as from a T cell (e.g. cytotoxic T cell), T-cell hybridomas or other publicly available source. In some embodiments, the T-cells can be obtained from in vivo isolated cells. In some embodiments, the TCR is a thymically selected TCR. In some embodiments, the TCR is a neoepitope-restricted TCR. In some embodiments, the T-cells can be a cultured T-cell hybridoma or clone. In some embodiments, the TCR or antigen-binding portion thereof or antigen-binding fragment thereof can be synthetically generated from knowledge of the sequence of the TCR.

In some embodiments, the TCR is generated from a TCR identified or selected from screening a library of candidate TCRs against a target polypeptide antigen, or target T cell epitope thereof. TCR libraries can be generated by amplification of the repertoire of Va and VB from T cells isolated from a subject, including cells present in PBMCs, spleen or other lymphoid organ. In some cases, T cells can be amplified from tumor-infiltrating lymphocytes (TILs). In some embodiments, TCR libraries can be generated from CD4+ or CD8+ cells. In some embodiments, the TCRs can be amplified from a T cell source of a normal of healthy subject, i.e. normal TCR libraries. In some embodiments, the TCRs can be amplified from a T cell source of a diseased subject, i.e., diseased TCR libraries. In some embodiments, degenerate primers are used to amplify the gene repertoire of Vα and Vβ, such as by RT-PCR in samples, such as T cells, obtained from humans. In some embodiments, libraries, such as single-chain TCR (scTv) libraries, can be assembled from naïve Vα and Vβ libraries in which the amplified products are cloned or assembled to be separated by a linker. Depending on the source of the subject and cells, the libraries can be HLA allele-specific. Alternatively, in some embodiments, TCR libraries can be generated by mutagenesis or diversification of a parent or scaffold TCR molecule.

In some aspects, the TCRs are subjected to directed evolution, such as by mutagenesis, e.g., of the α or β chain. In some aspects, particular residues within CDRs of the TCR are altered. In some embodiments, selected TCRs can be modified by affinity maturation. In some embodiments, antigen-specific T cells may be selected, such as by screening to assess CTL activity against the peptide. In some aspects, TCRs, e.g. present on the antigen-specific T cells, may be selected, such as by binding activity, e.g., particular affinity or avidity for the antigen.

In some embodiments, the TCR or antigen-binding portion thereof is one that has been modified or engineered. In some embodiments, directed evolution methods are used to generate TCRs with altered properties, such as with higher affinity for a specific MHC-peptide complex. In some embodiments, directed evolution is achieved by display methods including, but not limited to, yeast display (Holler et al. (2003) Nat Immunol, 4, 55-62; Holler et al. (2000) Proc Natl Acad Sci USA, 97, 5387-92), phage display (Li et al. (2005) Nat Biotechnol, 23, 349-54), or T cell display (Chervin et al. (2008) J Immunol Methods, 339, 175-84). In some embodiments, display approaches involve engineering, or modifying, a known, parent or reference TCR. For example, in some cases, a wild-type TCR can be used as a template for producing mutagenized TCRs in which in one or more residues of the CDRs are mutated, and mutants with an desired altered property, such as higher affinity for a desired target antigen, are selected.

In some embodiments, the antigen is a tumor antigen that can be a glioma-associated antigen, β-human chorionic gonadotropin, alphafetoprotein (AFP), B-cell maturation antigen (BCMA, BCM), B-cell activating factor receptor (BAFFR, BR3), and/or transmembrane activator and CAML interactor (TACI), Fc Receptor-like 5 (FCRL5, FcRH5), lectin-reactive AFP, thyroglobulin, RAGE-1, MN-CA IX, human telomerase reverse transcriptase, RU1, RU2 (AS), intestinal carboxyl esterase, mut hsp70-2, M-CSF, Melanin- A/MART-1, WT-1, S-100, MBP, CD63, MUC1 (e.g. MUC1-8), p53, Ras, cyclin B1, HER-2/neu, carcinoembryonic antigen (CEA), gp100, MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A11, MAGE-B1, MAGE-B2, MAGE-B3, MAGE-B4, MAGE-C1, BAGE, GAGE-1, GAGE-2, p15, tyrosinase, tyrosinase-related protein 1 (TRP-1), tyrosinase-related protein 2 (TRP-2), β-catenin, NY-ESO-1, LAGE-1a, PP1, MDM2, MDM4, EGVFvIII, Tax, SSX2, telomerase, TARP, pp65, CDK4, vimentin, S100, eIF-4A1, IFN-inducible p78, and melanotransferrin (p97), Uroplakin II, prostate specific antigen (PSA), human kallikrein (huK2), prostate specific membrane antigen (PSM), and prostatic acid phosphatase (PAP), neutrophil elastase, ephrin B2, BA-46, beta-catenin, Bcr-abl, E2A-PRL, H4-RET, IGH-IGK, MYL-RAR, Caspase 8 or a B-Raf antigen. Other tumor antigens can include any derived from FRa, CD24, CD44, CD133, CD 166, epCAM, CA-125, HE4, Oval, estrogen receptor, progesterone receptor, uPA, PAI-1, CD19, CD20, CD22, ROR1, mesothelin, CD33/IL3Ra, c-Met, PSMA, Glycolipid F77, GD-2, insulin growth factor (IGF)-I, IGF-II and IGF-I receptor. Specific tumor-associated antigens or T cell epitopes are known (see e.g. van der Bruggen et al. (2013) Cancer Immun, available at www.cancerimmunity.org/peptide/; Cheever et al. (2009) Clin Cancer Res, 15, 5323-37).

In some embodiments, the antigen is a viral antigen. Many viral antigen targets have been identified and are known, including peptides derived from viral genomes in HIV, HTLV and other viruses (see e.g., Addo et al. (2007) PLOS ONE, 2, e321; Tsomides et al. (1994) J Exp Med, 180, 1283-93; Utz et al. (1996) J Virol, 70, 843-51). Exemplary viral antigens include, but are not limited to, an antigen from hepatitis A, hepatitis B (e.g., HBV core and surface antigens (HBVc, HBVs)), hepatitis C (HCV), Epstein-Barr virus (e.g. EBVA), human papillomavirus (HPV; e.g. E6 and E7), human immunodeficiency type-1 virus (HIV1), Kaposi's sarcoma herpes virus (KSHV), human papilloma virus (HPV), influenza virus, Lassa virus, HTLN-1, HIN-1, HIN-II, CMN, EBN or HPN. In some embodiments, the target protein is a bacterial antigen or other pathogenic antigen, such as *Mycobacterium tuberculosis* (MT) antigens, trypanosome, e.g., Tiypansoma *cruzi* (*T. cruzi*), antigens such as surface antigen (TSA), or malaria antigens. Specific viral antigen or epitopes or other pathogenic antigens or T cell epitopes are known (see e.g., Addo et al. (2007) PLOS ONE, 2: e321; Anikeeva et al. (2009) Clin Immunol, 130:98-109).

In some embodiments, the antigen is an antigen derived from a virus associated with cancer, such as an oncogenic virus. For example, an oncogenic virus is one in which infection from certain viruses are known to lead to the development of different types of cancers, for example, hepatitis A, hepatitis B (e.g., HBV core and surface antigens (HBVc, HBVs)), hepatitis C (HCV), human papilloma virus (HPV), hepatitis viral infections, Epstein-Barr virus (EBV), human herpes virus 8 (HHV-8), human T-cell leukemia virus-1 (HTLV-1), human T-cell leukemia virus-2 (HTLV-2), or a cytomegalovirus (CMV) antigen.

In some embodiments, the viral antigen is an HPV antigen, which, in some cases, can lead to a greater risk of developing cervical cancer. In some embodiments, the antigen can be a HPV-16 antigen, and HPV-18 antigen, and HPV-31 antigen, an HPV-33 antigen or an HPV-35 antigen. In some embodiments, the viral antigen is an HPV-16 antigen (e.g., seroreactive regions of the E1, E2, E6 and/or E7 proteins of HPV-16, see e.g., U.S. Pat. No. 6,531,127) or an HPV-18 antigen (e.g., seroreactive regions of the L1 and/or L2 proteins of HPV-18, such as described in U.S. Pat. No. 5,840,306). In some embodiments, the viral antigen is an HPV-16 antigen that is from the E6 and/or E7 proteins of HPV-16. In some embodiments, the TCR is a TCR directed against an HPV-16 E6 or HPV-16 E7. In some embodiments, the TCR is a TCR described in, e.g., WO 2015/184228, WO 2015/009604 and WO 2015/009606.

In some embodiments, the viral antigen is a HBV or HCV antigen, which, in some cases, can lead to a greater risk of developing liver cancer than HBV or HCV negative subjects. For example, in some embodiments, the heterologous antigen is an HBV antigen, such as a hepatitis B core antigen or a hepatitis B envelope antigen (US2012/0308580).

In some embodiments, the viral antigen is an EBV antigen, which, in some cases, can lead to a greater risk for developing Burkitt's lymphoma, nasopharyngeal carcinoma and Hodgkin's disease than EBV negative subjects. For example, EBV is a human herpes virus that, in some cases, is found associated with numerous human tumors of diverse tissue origin. While primarily found as an asymptomatic infection, EBV-positive tumors can be characterized by active expression of viral gene products, such as EBNA-1, LMP-1 and LMP-2A. In some embodiments, the heterologous antigen is an EBV antigen that can include Epstein-Barr nuclear antigen (EBNA)-1, EBNA-2, EBNA-3A, EBNA-3B, EBNA-3C, EBNA-leader protein (EBNA-LP), latent membrane proteins LMP-1, LMP-2A and LMP-2B, EBV-EA, EBV-MA or EBV-VCA.

In some embodiments, the viral antigen is an HTLV-1 or HTLV-2 antigen, which, in some cases, can lead to a greater risk for developing T-cell leukemia than HTLV-1 or HTLV-2 negative subjects. For example, in some embodiments, the heterologous antigen is an HTLV-antigen, such as TAX.

In some embodiments, the viral antigen is a HHV-8 antigen, which, in some cases, can lead to a greater risk for developing Kaposi's sarcoma than HHV-8 negative subjects. In some embodiments, the heterologous antigen is a CMV antigen, such as pp65 or pp64 (see U.S. Pat. No. 8,361,473).

In some embodiments, the antigen is an autoantigen, such as an antigen of a polypeptide associated with an autoimmune disease or disorder. In some embodiments, the autoimmune disease or disorder can be multiple sclerosis (MS), rheumatoid arthritis (RA), Sjogren syndrome, scleroderma, polymyositis, dermatomyositis, systemic lupus erythematosus, juvenile rheumatoid arthritis, ankylosing spondylitis, myasthenia gravis (MG), bullous pemphigoid (antibodies to basement membrane at dermal-epidermal junction), pemphigus (antibodies to mucopolysaccharide protein complex or intracellular cement substance), glomerulonephritis (antibodies to glomerular basement membrane), Goodpasture's syndrome, autoimmune hemolytic anemia (antibodies to erythrocytes), Hashimoto's disease (antibodies to thyroid), pernicious anemia (antibodies to intrinsic factor), idiopathic thrombocytopenia purpura (antibodies to platelets), Grave's disease, or Addison's disease (antibodies to thyroglobulin). In some embodiments, the autoantigen, such as an autoantigen associated with one of the foregoing autoimmune disease, can be collagen, such as type II collagen, mycobacterial heat shock protein, thyroglobulin, acetyl choline receptor (AcHR), myelin basic protein (MBP) or proteolipid protein (PLP). Specific autoimmune associated epitopes or antigens are known (see e.g., Bulek et al. (2012) Nat Immunol, 13:283-9; Harkiolaki et al. (2009) Immunity, 30:348-57; Skowera et al. (2008) J Clin Invest, 1 (18): 3390-402).

In some embodiments, peptides of a target polypeptide for use in producing or generating a TCR of interest are known or can be readily identified. In some embodiments, peptides suitable for use in generating TCRs or antigen-binding portions can be determined based on the presence of an HLA-restricted motif in a target polypeptide of interest, such as a target polypeptide described below. In some embodiments, peptides are identified using available computer prediction models. In some examples, HLA-A0201-binding motifs and the cleavage sites for proteasomes and immune-proteasomes using computer prediction models are known. In some embodiments, for predicting MHC class I binding sites, such models include, but are not limited to, ProPred1 (Singh and Raghava (2001) Bioinformatics 17 (12): 1236-1237, and SYFPEITHI (see Schuler et al. (2007) Immunoinformatics Methods in Molecular Biology, 409 (1): 75-93 2007). In some embodiments, the MHC-restricted epitope is HLA-A0201, which is expressed in approximately 39-46% of all Caucasians and therefore, represents a suitable choice of MHC antigen for use preparing a TCR or other MHC-peptide binding molecule.

In some embodiments, the TCR or antigen binding portion thereof may be a recombinantly produced natural protein or mutated form thereof in which one or more property, such as binding characteristic, has been altered. In some embodiments, a TCR may be derived from one of various animal species, such as human, mouse, rat, or other mammal. A TCR may be cell-bound or in soluble form. In some embodiments, for purposes of the provided methods, the TCR is in cell-bound form expressed on the surface of a cell.

In some embodiments, the recombinant TCR is a full-length TCR. In some embodiments, the recombinant TCR is an antigen-binding portion. In some embodiments, the TCR is a dimeric TCR (dTCR). In some embodiments, the TCR is a single-chain TCR (scTCR). In some embodiments, a dTCR or scTCR have the structures as described in, e.g., International Pat. App. Pub. No. WO 03/020763, WO 04/033685 and WO 2011/044186.

In some embodiments, the recombinant TCR contains a sequence corresponding to the transmembrane sequence. In some embodiments, the TCR does contain a sequence corresponding to cytoplasmic sequences. In some embodiments, the TCR is capable of forming a TCR complex with CD3. In some embodiments, any of the recombinant TCRs, including a dTCR or scTCR, can be linked to signaling domains that yield an active TCR on the surface of a T cell. In some embodiments, the recombinant TCR is expressed on the surface of cells. In some embodiments of the dTCR or scTCR containing introduced or engineered inter-chain disulfide bonds, the native disulfide bonds are not present. In some embodiments, the one or more of the native cysteines forming a native inter-chain disulfide bonds are substituted to another residue, such as to a serine or alanine. In some embodiments, an introduced or engineered disulfide bond can be formed by mutating non-cysteine residues on the first and second segments to cysteine. Exemplary non-native disulfide bonds of a TCR are described in published International PCT No. WO2006/000830.

In certain embodiments, the TCR contains one or more modifications(s) to introduce one or more cysteine residues that are capable of forming one or more non-native disulfide bridges between the TCRα chain and TCRβ chain. In some embodiments, the TCR contains a TCRα chain or a portion thereof containing a TCRα constant domain containing one or more cysteine residues capable of forming a non-native disulfide bond with a TCRβ chain. In some embodiments, the transgene encodes a TCRβ chain or a portion thereof containing a TCRβ constant domain containing one or more cysteine residues capable of forming a non-native disulfide bond with a TCRα chain. In some embodiments, the TCR comprises a TCRα and/or TCRβ chain and/or a TCRα and/or TCRβ chain constant domains containing one or more modifications to introduce one or more disulfide bonds. In some embodiments, the transgene encodes a TCRα and/or TCRβ chain and/or a TCRα and/or TCRβ with one or more modifications to remove or prevent a native disulfide bond, e.g., between the TCRα by the transgene and the endogenous TCRβ chain, or between the TCRβ by the transgene and the endogenous TCR α chain. In some embodiments, one or more native cysteines that form and/or are capable of forming a native inter-chain disulfide bond are substituted to another residue, e.g., serine or alanine. In some embodiments, the cysteine is introduced at one or more of residue Thr48, Thr45, Tyr10, Thr45, and Ser15 with reference to numbering of a TCRα constant domain. In certain embodiments, cysteines can be introduced at residue Ser57, Ser77, Ser17, Asp59, of Glu15 of the TCRβ chain constant domain. Exemplary non-native disulfide bonds of a TCR are described in published International PCT No. WO2006/000830, WO 2006/037960 and Kuball et al. (2007) Blood, 109:2331-2338.

In some embodiments, the recombinant TCR is a dimeric TCR (dTCR). In some embodiments, the dTCR contains a first polypeptide wherein a sequence corresponding to a TCR α chain variable region sequence is fused to the N terminus of a sequence corresponding to a TCR α chain constant region extracellular sequence, and a second polypeptide wherein a sequence corresponding to a TCR β chain variable region sequence is fused to the N terminus a sequence corresponding to a TCR β chain constant region extracellular sequence, the first and second polypeptides being linked by a disulfide bond. In some embodiments, the bond can correspond to the native inter-chain disulfide bond present in native dimeric αβ TCRs. In some embodiments, the inter-chain disulfide bonds are not present in a native TCR. For example, in some embodiments, one or more cysteines can be incorporated into the constant region extracellular sequences of dTCR polypeptide pair. In some cases, both a native and a non-native disulfide bond may be desirable. In some embodiments, the TCR contains a transmembrane sequence to anchor to the membrane.

In some embodiments, the dTCR contains a TCR α chain containing a variable α domain, a constant α domain and a first dimerization motif attached to the C-terminus of the constant α domain, and a TCR β chain comprising a variable β domain, a constant β domain and a first dimerization motif attached to the C-terminus of the constant β domain, wherein the first and second dimerization motifs interact to form a covalent bond between an amino acid in the first dimerization motif and an amino acid in the second dimerization motif linking the TCR α chain and TCR β chain together.

In some embodiments, the recombinant TCR is a single-chain TCR (scTCR or scTv). Typically, a scTCR can be generated using known methods, See e.g., See Hoo, W. F. et al. PNAS (USA) 89, 4759 (1992); Wülfing, C. and Plückthun, A., J. Mol. Biol. 242, 655 (1994); Kurucz, I. et al. PNAS (USA) 90 3830 (1993); International Pat. App. Pub. Nos. WO 96/13593, WO 96/18105, WO 99/60120, WO 99/18129, WO 03/020763, WO 2011/044186; and Schlueter, C. J. et al. J. Mol. Biol. 256, 859 (1996). In some embodiments, the scTCR contains an introduced non-native disulfide inter-chain bond to facilitate the association of the TCR chains (see e.g. International Pat. App. Pub. No. WO 03/020763). In some embodiments, the scTCR is a non-disulfide linked truncated TCR in which heterologous leucine zippers fused to the C-termini thereof facilitate chain association (see e.g. International Pat. App. Pub. No. WO 99/60120). In some embodiments, the scTCR contains a TCRα variable domain covalently linked to a TCRβ variable domain via a peptide linker (see e.g., International Pat. App. Pub. No. WO 99/18129).

In some embodiments, the scTCR contains a first segment constituted by an amino acid sequence corresponding to a TCR α chain variable region, a second segment constituted by an amino acid sequence corresponding to a TCR β chain variable region sequence fused to the N terminus of an amino acid sequence corresponding to a TCR β chain constant domain extracellular sequence, and a linker sequence linking the C terminus of the first segment to the N terminus of the second segment. In some embodiments, the scTCR contains a first segment constituted by an a chain variable region sequence fused to the N terminus of an a chain extracellular constant domain sequence, and a second segment constituted by a β chain variable region sequence fused to the N terminus of a sequence β chain extracellular constant and transmembrane sequence, and, optionally, a linker sequence linking the C terminus of the first segment to the N terminus of the second segment. In some embodiments, the scTCR contains a first segment constituted by a TCR β chain variable region sequence fused to the N terminus of a β chain extracellular constant domain sequence, and a second segment constituted by an a chain variable region sequence fused to the N terminus of a sequence α chain extracellular constant and transmembrane sequence, and, optionally, a linker sequence linking the C terminus of the first segment to the N terminus of the second segment.

In some embodiments, the linker of the scTCRs that links the first and second TCR segments can be any linker capable of forming a single polypeptide strand, while retaining TCR binding specificity. In some embodiments, the linker sequence may, for example, have the formula -P-AA-P- wherein P is proline and AA represents an amino acid sequence wherein the amino acids are glycine and serine. In some embodiments, the first and second segments are paired so that the variable region sequences thereof are orientated for such binding. Hence, in some cases, the linker has a sufficient length to span the distance between the C terminus of the first segment and the N terminus of the second segment, or vice versa, but is not too long to block or reduces bonding of the scTCR to the target ligand. In some embodiments, the linker can contain from or from about 10 to 45 amino acids, such as 10 to 30 amino acids or 26 to 41 amino acids residues, for example 29, 30, 31 or 32 amino acids. In some embodiments, the linker has the formula -PGGG-$(SGGGG)_5$-P- wherein P is proline, G is glycine and S is serine (SEQ ID NO:22). In some embodiments, the linker has the sequence GSADDAKKDAAKKDGKS (SEQ ID NO:23)

In some embodiments, the scTCR contains a covalent disulfide bond linking a residue of the immunoglobulin region of the constant domain of the α chain to a residue of the immunoglobulin region of the constant domain of the β chain. In some embodiments, the interchain disulfide bond in a native TCR is not present. For example, in some embodiments, one or more cysteines can be incorporated into the constant region extracellular sequences of the first and second segments of the scTCR polypeptide. In some cases, both a native and a non-native disulfide bond may be desirable.

In some embodiments, the TCR or antigen-binding fragment thereof exhibits an affinity with an equilibrium dissociation constant ($K_D$) for a target antigen of between or between about $10^{-5}$ and $10^{-12}$ M and all individual values and ranges therein. In some embodiments, the target antigen is an MHC-peptide complex or ligand.

B. Nucleic Acids, Vectors and Methods for Genetic Engineering

In some embodiments, the cells, e.g., T cells, are genetically engineered to express a recombinant receptor. In some embodiments, the engineering is carried out by introducing one or more polynucleotide(s) that encode the recombinant receptor or portions or components thereof. Also provided are polynucleotides encoding a recombinant receptor, and vectors or constructs containing such nucleic acids and/or polynucleotides.

In some embodiments, the polynucleotide encoding the recombinant receptor contains at least one promoter that is operatively linked to control expression of the recombinant receptor. In some examples, the polynucleotide contains two, three, or more promoters operatively linked to control expression of the recombinant receptor. In some embodiments, polynucleotide can contain regulatory sequences, such as transcription and translation initiation and termination codons, which are specific to the type of host (e.g., bacterium, fungus, plant, or animal) into which the polynucleotide is to be introduced, as appropriate and taking into consideration whether the polynucleotide is DNA- or RNA-based. In some embodiments, the polynucleotide can contain regulatory/control elements, such as a promoter, an enhancer, an intron, a polyadenylation signal, a Kozak consensus sequence, internal ribosome entry sites (IRES), a 2A sequence, and splice acceptor or donor. In some embodiments, the polynucleotide can contain a nonnative promoter operably linked to the nucleotide sequence encoding the recombinant receptor and/or one or more additional polypeptide(s). In some embodiments, the promoter is selected from among an RNA pol I, pol II or pol III promoter. In some embodiments, the promoter is recognized by RNA polymerase II (e.g., a CMV, SV40 early region or adenovirus major late promoter). In another embodiment, the promoter is recognized by RNA polymerase III (e.g., a U6 or H1 promoter). In some embodiments, the promoter can be a non-viral promoter or a viral promoter, such as a cytomegalovirus (CMV) promoter, an SV40 promoter, an RSV promoter, and a promoter found in the long-terminal repeat of the murine stem cell virus. Other known promoters also are contemplated.

In some embodiments, the promoter is or comprises a constitutive promoter. Exemplary constitutive promoters include, e.g., simian virus 40 early promoter (SV40), cytomegalovirus immediate-early promoter (CMV), human Ubiquitin C promoter (UBC), human elongation factor 1α promoter (EF1α), mouse phosphoglycerate kinase 1 promoter (PGK), and chicken β-Actin promoter coupled with CMV early enhancer (CAGG). In some embodiments, the constitutive promoter is a synthetic or modified promoter. In some embodiments, the promoter is or comprises an MND promoter, a synthetic promoter that contains the U3 region of a modified MoMuLV LTR with myeloproliferative sarcoma virus enhancer (see Challita et al. (1995) J. Virol. 69 (2): 748-755). In some embodiments, the promoter is a tissue-specific promoter. In another embodiment, the promoter is a viral promoter. In another embodiment, the promoter is a non-viral promoter. In some embodiments, exemplary promoters can include, but are not limited to, human elongation factor 1 alpha (EF1α) promoter or a modified form thereof or the MND promoter.

In another embodiment, the promoter is a regulated promoter (e.g., inducible promoter). In some embodiments, the promoter is an inducible promoter or a repressible promoter. In some embodiments, the promoter comprises a Lac operator sequence, a tetracycline operator sequence, a galactose operator sequence or a doxycycline operator sequence, or is an analog thereof or is capable of being bound by or recognized by a Lac repressor or a tetracycline repressor, or an analog thereof. In some embodiments, the polynucleotide does not include a regulatory element, e.g. promoter.

In some cases, the nucleic acid sequence encoding the recombinant receptor contains a signal sequence that encodes a signal peptide. In some aspects, the signal sequence may encode a signal peptide derived from a native polypeptide. In other aspects, the signal sequence may encode a heterologous or non-native signal peptide, such as the exemplary signal peptide of the GMCSFR alpha chain set forth in SEQ ID NO:25 and encoded by the nucleotide sequence set forth in SEQ ID NO:24. In some cases, the nucleic acid sequence encoding the recombinant receptor, e.g., chimeric antigen receptor (CAR) contains a signal sequence that encodes a signal peptide. Non-limiting exemplary signal peptides include, for example, the GMCSFR alpha chain signal peptide set forth in SEQ ID NO: 25 and encoded by the nucleotide sequence set forth in SEQ ID NO:24, or the CD8 alpha signal peptide set forth in SEQ ID NO: 26.

In some embodiments, the polynucleotide contains a nucleic acid sequence encoding one or more additional polypeptides, e.g., one or more marker(s) and/or one or more effector molecules. In some embodiments, the one or more marker(s) includes a transduction marker, a surrogate marker and/or a selection marker. Among additional nucleic acid sequences introduced, e.g., encoding for one or more additional polypeptide(s), include nucleic acid sequences that can improve the efficacy of therapy, such as by promoting viability and/or function of transferred cells; nucleic acid sequences to provide a genetic marker for selection and/or evaluation of the cells, such as to assess in vivo survival or localization; nucleic acid sequences to improve safety, for example, by making the cell susceptible to negative selection in vivo as described by Lupton S. D. et al., *Mol. and Cell Biol.,* 11:6 (1991); and Riddell et al., *Human Gene Therapy* 3:319-338 (1992); see also WO 1992008796 and WO 1994028143 describing the use of bifunctional selectable fusion genes derived from fusing a dominant positive selectable marker with a negative selectable marker, and U.S. Pat. No. 6,040,177.

In some embodiments, the marker is a transduction marker or a surrogate marker. A transduction marker or a surrogate marker can be used to detect cells that have been introduced with the polynucleotide, e.g., a polynucleotide encoding a recombinant receptor. In some embodiments, the transduction marker can indicate or confirm modification of a cell. In some embodiments, the surrogate marker is a protein that is made to be co-expressed on the cell surface with the recombinant receptor, e.g. CAR. In particular embodiments, such a surrogate marker is a surface protein that has been modified to have little or no activity. In certain embodiments, the surrogate marker is encoded on the same polynucleotide that encodes the recombinant receptor. In some embodiments, the nucleic acid sequence encoding the recombinant receptor is operably linked to a nucleic acid sequence encoding a marker, optionally separated by an internal ribosome entry site (IRES), or a nucleic acid encoding a self-cleaving peptide or a peptide that causes ribosome skipping, such as a 2A sequence. Extrinsic marker genes may in some cases be utilized in connection with engineered cell to permit detection or selection of cells and, in some cases, also to promote cell elimination and/or cell suicide.

Exemplary surrogate markers can include truncated forms of cell surface polypeptides, such as truncated forms that are non-functional and to not transduce or are not capable of transducing a signal or a signal ordinarily transduced by the full-length form of the cell surface polypeptide, and/or do not or are not capable of internalizing. Exemplary truncated cell surface polypeptides including truncated forms of growth factors or other receptors such as a truncated human epidermal growth factor receptor 2 (HER2), a truncated epidermal growth factor receptor (tEGFR, exemplary tEGFR sequence set forth in SEQ ID NO: 7 or 16) or a prostate-specific membrane antigen (PSMA) or modified form thereof, such as a truncated PSMA (tPSMA). In some aspects, tEGFR may contain an epitope recognized by the antibody cetuximab (Erbitux®) or other therapeutic anti-EGFR antibody or binding molecule, which can be used to identify or select cells that have been engineered with the tEGFR construct and an encoded exogenous protein, and/or to eliminate or separate cells expressing the encoded exogenous protein. See U.S. Pat. No. 8,802,374 and Liu et al., Nature Biotech. 2016 April; 34 (4): 430-434). In some aspects, the marker, e.g. surrogate marker, includes all or part (e.g., truncated form) of CD34, a NGFR, a CD19 or a truncated CD19, e.g., a truncated non-human CD19. An exemplary polypeptide for a truncated EGFR (e.g. tEGFR) comprises the sequence of amino acids set forth in SEQ ID NO: 7 or 16 or a sequence of amino acids that exhibits at least 85%, 86%, 87%, 88%, 89%, 90%, 91%, 92%, 93%, 94%, 95%, 96%, 97%, 98%, 99% or more sequence identity to SEQ ID NO: 7 or 16.

In some embodiments, the marker is or comprises a detectable protein, such as a fluorescent protein, such as green fluorescent protein (GFP), enhanced green fluorescent protein (EGFP), such as super-fold GFP (sfGFP), red fluorescent protein (RFP), such as tdTomato, mCherry, mStrawberry, AsRed2, DsRed or DsRed2, cyan fluorescent protein (CFP), blue green fluorescent protein (BFP), enhanced blue fluorescent protein (EBFP), and yellow fluorescent protein (YFP), and variants thereof, including species variants, monomeric variants, codon-optimized, stabilized and/or enhanced variants of the fluorescent proteins. In some embodiments, the marker is or comprises an enzyme, such as a luciferase, the lacZ gene from *E. coli*, alkaline phosphatase, secreted embryonic alkaline phosphatase (SEAP), chloramphenicol acetyl transferase (CAT). Exemplary light-emitting reporter genes include luciferase (luc), β-galactosidase, chloramphenicol acetyltransferase (CAT), β-glucuronidase (GUS) or variants thereof. In some aspects, expression of the enzyme can be detected by addition of a substrate that can be detected upon the expression and functional activity of the enzyme.

In some embodiments, the marker is a selection marker. In some embodiments, the selection marker is or comprises a polypeptide that confers resistance to exogenous agents or drugs. In some embodiments, the selection marker is an antibiotic resistance gene. In some embodiments, the selection marker is an antibiotic resistance gene confers antibiotic resistance to a mammalian cell. In some embodiments, the selection marker is or comprises a Puromycin resistance gene, a Hygromycin resistance gene, a Blasticidin resistance gene, a Neomycin resistance gene, a Geneticin resistance gene or a Zeocin resistance gene or a modified form thereof.

Any of the recombinant receptors and/or the additional polypeptide(s) described herein can be encoded by one or more polynucleotides containing one or more nucleic acid sequences encoding recombinant receptors, in any combinations, orientation or arrangements. For example, one, two, three or more polynucleotides can encode one, two, three or more different polypeptides, e.g., recombinant receptors or portions or components thereof, and/or one or more additional polypeptide(s), e.g., a marker and/or an effector molecule. In some embodiments, one polynucleotide contains a nucleic acid sequence encoding a recombinant receptor, e.g., CAR, or portion or components thereof, and a nucleic acid sequence encoding one or more additional polypeptide(s). In some embodiments, one vector or construct contains a nucleic acid sequence encoding a recombinant receptor, e.g., CAR, or portion or components thereof, and a separate vector or construct contains a nucleic acid sequence encoding one or more additional polypeptide (s). In some embodiments, the nucleic acid sequence encoding the recombinant receptor and the nucleic acid sequence encoding the one or more additional polypeptide(s) are operably linked to two different promoters. In some embodiments, the nucleic acid encoding the recombinant receptor is present upstream of the nucleic acid encoding the one or more additional polypeptide(s). In some embodiments, the nucleic acid encoding the recombinant receptor is present downstream of the nucleic acid encoding one or more additional polypeptide(s).

In certain cases, one polynucleotide contains nucleic acid sequences encode two or more different polypeptide chains, e.g., a recombinant receptor and one or more additional polypeptide(s), e.g., a marker and/or an effector molecule. In some embodiments, the nucleic acid sequences encoding two or more different polypeptide chains, e.g., a recombinant receptor and one or more additional polypeptide(s), are present in two separate polynucleotides. For example, two separate polynucleotides are provided, and each can be individually transferred or introduced into the cell for expression in the cell. In some embodiments, the nucleic acid sequences encoding the marker and the nucleic acid sequences encoding the recombinant receptor are present or inserted at different locations within the genome of the cell. In some embodiments, the nucleic acid sequences encoding the marker and the nucleic acid sequences encoding the recombinant receptor are operably linked to two different promoters.

In some embodiments, such as those where the polynucleotide contains a first and second nucleic acid sequence, the coding sequences encoding each of the different polypeptide chains can be operatively linked to a promoter, which can be the same or different. In some embodiments, the nucleic acid molecule can contain a promoter that drives the expression of two or more different polypeptide chains. In some embodiments, such nucleic acid molecules can be multicistronic (bicistronic or tricistronic, see e.g., U.S. Pat. No. 6,060,273). In some embodiments, the nucleic acid sequences encoding the recombinant receptor and the nucleic acid sequences encoding the one or more additional polypeptide(s) are operably linked to the same promoter and are optionally separated by an internal ribosome entry site (IRES), or a nucleic acid encoding a self-cleaving peptide or a peptide that causes ribosome skipping, such as a 2A element. For example, an exemplary marker, and optionally a ribosome skipping sequence sequence, can be any as disclosed in PCT Pub. No. WO2014031687.

In some embodiments, transcription units can be engineered as a bicistronic unit containing an IRES, which allows coexpression of gene products (e.g. encoding the recombinant receptor and the additional polypeptide) by a message from a single promoter. Alternatively, in some cases, a single promoter may direct expression of an RNA that contains, in a single open reading frame (ORF), two or three genes (e.g. encoding the marker and encoding the recombinant receptor) separated from one another by sequences encoding a self-cleavage peptide (e.g., 2A sequences) or a protease recognition site (e.g., furin). The ORF thus encodes a single polypeptide, which, either during (in the case of 2A) or after translation, is processed into the individual proteins. In some cases, the peptide, such as a T2A, can cause the ribosome to skip (ribosome skipping) synthesis of a peptide bond at the C-terminus of a 2A element, leading to separation between the end of the 2A sequence and the next peptide downstream (see, e.g., de Felipe, Genetic Vaccines and Ther. 2:13 (2004) and de Felipe et al. Traffic 5:616-626 (2004)). Various 2A elements are known. Examples of 2A sequences that can be used in the methods and system disclosed herein, without limitation, 2A sequences from the foot-and-mouth disease virus (F2A, e.g., SEQ ID NO: 21), equine rhinitis A virus (E2A, e.g., SEQ ID NO: 20), Thosea asigna virus (T2A, e.g., SEQ ID NO: 6 or 17), and porcine teschovirus-1 (P2A, e.g., SEQ ID NO: 18 or 19) as described in U.S. Patent Pub. No. 20070116690.

In some embodiments, the polynucleotide encoding the recombinant receptor and/or additional polypeptide is contained in a vector or can be cloned into one or more vector(s). In some embodiments, the one or more vector(s) can be used to transform or transfect a host cell, e.g., a cell for engineering. Exemplary vectors include vectors designed for introduction, propagation and expansion or for expression or both, such as plasmids and viral vectors. In some aspects, the vector is an expression vector, e.g., a recombinant expression vector. In some embodiments, the recombinant expression vectors can be prepared using standard recombinant DNA techniques.

In some embodiments, the vector can be a vector of the pUC series (Fermentas Life Sciences), the pBluescript series (Stratagene, LaJolla, Calif.), the pET series (Novagen, Madison, Wis.), the pGEX series (Pharmacia Biotech, Uppsala, Sweden), or the pEX series (Clontech, Palo Alto, Calif.). In some cases, bacteriophage vectors, such as λG10, λGT11, λZapII (Stratagene), λEMBL4, and λNM1149, also can be used. In some embodiments, plant expression vectors can be used and include pBI01, pBI101.2, pBI101.3, pBI121 and pBIN19 (Clontech). In some embodiments, animal expression vectors include pEUK-Cl, pMAM and pMAMneo (Clontech).

In some embodiments, the vector is a viral vector, such as a retroviral vector. In some embodiments, the polynucleotide encoding the recombinant receptor and/or additional polypeptide(s) are introduced into the cell via retroviral or lentiviral vectors, or via transposons (see, e.g., Baum et al. (2006) Molecular Therapy: The Journal of the American Society of Gene Therapy. 13:1050-1063; Frecha et al. (2010) Molecular Therapy 18:1748-1757; and Hackett et al. (2010) Molecular Therapy 18:674-683).

In some embodiments, one or more polynucleotide(s) are introduced into cells using recombinant infectious virus particles, such as, e.g., vectors derived from simian virus 40 (SV40), adenoviruses, adeno-associated virus (AAV). In some embodiments, one or more polynucleotide(s) are introduced into T cells using recombinant lentiviral vectors or retroviral vectors, such as gamma-retroviral vectors (see, e.g., Koste et al. (2014) Gene Therapy 2014 Apr. 3. doi: 10.1038/gt.2014.25; Carlens et al. (2000) Exp Hematol 28 (10): 1137-46; Alonso-Camino et al. (2013) Mol Ther Nucl Acids 2, e93; Park et al., Trends Biotechnol. 2011 Nov. 29 (11): 550-557.

In some embodiments, the vector is a retroviral vector. In some aspects, a retroviral vector has a long terminal repeat sequence (LTR), e.g., a retroviral vector derived from the Moloney murine leukemia virus (MoMLV), myeloproliferative sarcoma virus (MPSV), murine embryonic stem cell virus (MESV), murine stem cell virus (MSCV), spleen focus forming virus (SFFV), or adeno-associated virus (AAV). Most retroviral vectors are derived from murine retroviruses. In some embodiments, the retroviruses include those derived from any avian or mammalian cell source. The retroviruses typically are amphotropic, meaning that they are capable of infecting host cells of several species, including humans. In one embodiment, the gene to be expressed replaces the retroviral gag, pol and/or env sequences. A number of illustrative retroviral systems have been described (e.g., U.S. Pat. Nos. 5,219,740; 6,207,453; 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; and Boris-Lawrie and Temin (1993) Cur. Opin. Genet. Develop. 3:102-109.

Methods of lentiviral transduction are known. Exemplary methods are described in, e.g., Wang et al. (2012) J. Immunother. 35 (9): 689-701; Cooper et al. (2003) Blood. 101: 1637-1644; Verhoeyen et al. (2009) Methods Mol Biol. 506:97-114; and Cavalieri et al. (2003) Blood. 102 (2): 497-505. In some embodiments, the polynucleotide encoding the recombinant receptor and/or one or more additional polypeptide(s), is introduced into a composition containing cultured cells, such as by retroviral transduction, transfection, or transformation.

In some embodiments, one or more polynucleotide(s) are introduced into a T cell using electroporation (see, e.g., Chicaybam et al, (2013) PLOS ONE 8 (3): e60298 and Van Tedeloo et al. (2000) Gene Therapy 7 (16): 1431-1437). In some embodiments, recombinant nucleic acids are transferred into T cells via transposition (see, e.g., Manuri et al. (2010) Hum Gene Ther 21 (4): 427-437; Sharma et al. (2013) Molec Ther Nucl Acids 2, e74; and Huang et al. (2009) Methods Mol Biol 506:115-126). In some aspects, transposon-based systems can be used to introduce a polynucleotide including a recombinant protein, such as PiggyBac or Sleeping Beauty-based gene transfer systems. Other methods of introducing and expressing genetic material, e.g., polynucleotides and/or vectors, into immune cells include calcium phosphate transfection (e.g., as described in Current Protocols in Molecular Biology, John Wiley & Sons, New York. N.Y.), protoplast fusion, cationic liposome-mediated transfection; tungsten particle-facilitated microparticle bombardment (Johnston, Nature, 346:776-777 (1990)); and strontium phosphate DNA co-precipitation (Brash et al., Mol. Cell Biol., 7:2031-2034 (1987) and other approaches described in, e.g., International Pat. App. Pub. No. WO 2014055668, and U.S. Pat. No. 7,446,190.

In some embodiments, the one or more polynucleotide(s) or vector(s) encoding a recombinant receptor and/or additional polypeptide(s) may be introduced into cells, e.g., T cells, either during or after expansion. This introduction of the polynucleotide(s) or vector(s) can be carried out with any suitable retroviral vector, for example. Resulting genetically engineered cells can then be liberated from the initial stimulus (e.g., anti-CD3/anti-CD28 stimulus) and subsequently be stimulated in the presence of a second type of stimulus (e.g., via a de novo introduced recombinant receptor). This second type of stimulus may include an antigenic stimulus in form of a peptide/MHC molecule, the cognate (cross-linking) ligand of the genetically introduced receptor (e.g. natural antigen and/or ligand of a CAR) or any ligand (such as an antibody) that directly binds within the framework of the new receptor (e.g. by recognizing constant regions within the receptor). See, for example, Cheadle et al, "Chimeric antigen receptors for T-cell based therapy" Methods Mol Biol. 2012; 907:645-66 or Barrett et al., Chimeric Antigen Receptor Therapy for Cancer Annual Review of Medicine Vol. 65:333-347 (2014).

In some cases, a vector may be used that does not require that the cells, e.g., T cells, are activated. In some such instances, the cells may be selected and/or transduced prior to activation. Thus, the cells may be engineered prior to, or subsequent to culturing of the cells, and in some cases at the same time as or during at least a portion of the culturing.

IV. Methods of Treatment

Provided herein are methods of treatment, e.g., including administering any of the engineered cells or compositions containing engineered cells described herein. In some aspects, also provided are methods of administering any of the engineered cells or compositions containing engineered cells described herein to a subject, such as a subject that has a disease or disorder. In some aspects, also provided are uses of any of the engineered cells or compositions containing engineered cells described herein for treatment of a disease or disorder. In some aspects, also provided are uses of any of the engineered cells or compositions containing engineered cells described herein for the manufacture of a medicament for the treatment of a disease or disorder. In some aspects, also provided are any of the engineered cells or compositions containing engineered cells described herein, for use in treatment of a disease or disorder, or for administration to a subject having a disease or disorder.

Methods for administration of cells for adoptive cell therapy are known and may be used in connection with the provided methods and compositions. For example, adoptive T cell therapy methods are described, e.g., in US Pat. App. Pub. No. 2003/0170238 to Gruenberg et al; U.S. Pat. No. 4,690,915 to Rosenberg; Rosenberg (2011) Nat Rev Clin Oncol. 8 (10): 577-85). See, e.g., Themeli et al. (2013) Nat Biotechnol. 31 (10): 928-933; Tsukahara et al. (2013) Biochem Biophys Res Commun 438 (1): 84-9; Davila et al. (2013) PLOS ONE 8 (4): e61338.

The disease or condition that is treated can be any in which expression of an antigen is associated with and/or involved in the etiology of a disease condition or disorder, e.g. causes, exacerbates or otherwise is involved in such disease, condition, or disorder. Exemplary diseases and conditions can include diseases or conditions associated with malignancy or transformation of cells (e.g. cancer), autoimmune or inflammatory disease, or an infectious disease, e.g. caused by a bacterial, viral or other pathogen. Exemplary antigens, which include antigens associated with various diseases and conditions that can be treated, are described above. In particular embodiments, the chimeric antigen receptor or transgenic TCR specifically binds to an antigen associated with the disease or condition.

Among the diseases, conditions, and disorders are tumors, including solid tumors, hematologic malignancies, and melanomas, and including localized and metastatic tumors, infectious diseases, such as infection with a virus or other pathogen, e.g., HIV, HCV, HBV, CMV, HPV, and parasitic disease, and autoimmune and inflammatory diseases. In some embodiments, the disease, disorder or condition is a tumor, cancer, malignancy, neoplasm, or other proliferative disease or disorder. Such diseases include but are not limited to leukemia, lymphoma, e.g., acute myeloid (or myelogenous) leukemia (AML), chronic myeloid (or myelogenous) leukemia (CML), acute lymphocytic (or lymphoblastic) leukemia (ALL), chronic lymphocytic leukemia (CLL), hairy cell leukemia (HCL), small lymphocytic lymphoma (SLL), Mantle cell lymphoma (MCL), Marginal zone lymphoma, Burkitt lymphoma, Hodgkin lymphoma (HL), non-Hodgkin lymphoma (NHL), Anaplastic large cell lymphoma (ALCL), follicular lymphoma, refractory follicular lymphoma, diffuse large B-cell lymphoma (DLBCL) and multiple myeloma (MM). In some embodiments, disease or condition is a B cell malignancy selected from among acute lymphoblastic leukemia (ALL), adult ALL, chronic lymphoblastic leukemia (CLL), non-Hodgkin lymphoma (NHL), and Diffuse Large B-Cell Lymphoma (DLBCL). In some embodiments, the disease or condition is NHL and the NHL is selected from the group consisting of aggressive NHL, diffuse large B cell lymphoma (DLBCL), NOS (de novo and transformed from indolent), primary mediastinal large B cell lymphoma (PMBCL), T cell/histocyte-rich large B cell lymphoma (TCHRBCL), Burkitt's lymphoma, mantle cell lymphoma (MCL), and/or follicular lymphoma (FL), optionally, follicular lymphoma Grade 3B (FL3B).

In some embodiments, the disease or condition is an infectious disease or condition, such as, but not limited to, viral, retroviral, bacterial, and protozoal infections, immunodeficiency, Cytomegalovirus (CMV), Epstein-Barr virus (EBV), adenovirus, BK polyomavirus. In some embodiments, the disease or condition is an autoimmune or inflammatory disease or condition, such as arthritis, e.g., rheumatoid arthritis (RA), Type I diabetes, systemic lupus erythematosus (SLE), inflammatory bowel disease, psoriasis, scleroderma, autoimmune thyroid disease, Grave's disease, Crohn's disease, multiple sclerosis, asthma, and/or a disease or condition associated with transplant.

In some embodiments, the antigen associated with the disease or disorder is or includes $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen$_{1B}$ (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, epidermal growth factor protein (EGFR), truncated epidermal growth factor protein (tEGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22R$\alpha$), IL-13 receptor alpha 2 (IL-13R$\alpha$2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT) vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens. Antigens targeted by the receptors in some embodiments include antigens associated with a B cell malignancy, such as any of a number of known B cell marker. In some embodiments, the antigen is or includes CD20, CD19, CD22, ROR1, CD45, CD21, CD5, CD33, Igkappa, Iglambda, CD79a, CD79b or CD30. In some embodiments, the antigen is or includes a pathogen-specific or pathogen-expressed antigen, such as a viral antigen (e.g., a viral antigen from HIV, HCV, HBV), bacterial antigens, and/or parasitic antigens.

In some embodiments, the antibody or an antigen-binding fragment (e.g. scFv or $V_H$ domain) specifically recognizes an antigen, such as CD19. In some embodiments, the antibody or antigen-binding fragment is derived from, or is a variant of, antibodies or antigen-binding fragment that specifically binds to CD19. In some embodiments, the cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject.

The cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells. In some embodiments, it is administered by multiple bolus administrations of the cells, for example, over a period of no more than 3 days, or by continuous infusion administration of the cells. In some embodiments, administration of the cell dose or any additional therapies, e.g., the lymphodepleting therapy, intervention therapy and/or combination therapy, is carried out via outpatient delivery.

For the prevention or treatment of disease, the appropriate dosage may depend on the type of disease to be treated, the type of cells or recombinant receptors, the severity and course of the disease, whether the cells are administered for preventive or therapeutic purposes, previous therapy, the subject's clinical history and response to the cells, and the discretion of the attending physician. The compositions and cells are in some embodiments suitably administered to the subject at one time or over a series of treatments.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agents include a cytokine, such as IL-2, for example, to enhance persistence. In some embodiments, the methods comprise administration of a chemotherapeutic agent.

In some embodiments, the methods comprise administration of a chemotherapeutic agent, e.g., a conditioning chemotherapeutic agent, for example, to reduce tumor burden prior to the administration.

Preconditioning subjects with immunodepleting (e.g., lymphodepleting) therapies in some aspects can improve the effects of adoptive cell therapy (ACT).

Thus, in some embodiments, the methods include administering a preconditioning agent, such as a lymphodepleting or chemotherapeutic agent, such as cyclophosphamide, fludarabine, or combinations thereof, to a subject prior to the initiation of the cell therapy. For example, the subject may be administered a preconditioning agent at least 2 days prior, such as at least 3, 4, 5, 6, or 7 days prior, to the initiation of the cell therapy. In some embodiments, the subject is administered a preconditioning agent no more than 7 days prior, such as no more than 6, 5, 4, 3, or 2 days prior, to the initiation of the cell therapy.

In some embodiments, the subject is preconditioned with cyclophosphamide at a dose between or between about 20 mg/kg and 100 mg/kg, such as between or between about 40 mg/kg and 80 mg/kg. In some aspects, the subject is preconditioned with or with about 60 mg/kg of cyclophosphamide. In some embodiments, the cyclophosphamide can be administered in a single dose or can be administered in a plurality of doses, such as given daily, every other day or every three days. In some embodiments, the cyclophosphamide is administered once daily for one or two days. In some embodiments, where the lymphodepleting agent comprises cyclophosphamide, the subject is administered cyclophosphamide at a dose between or between about 100 mg/m2 and 500 mg/m2, such as between or between about 200 mg/m2 and 400 mg/m2, or 250 mg/m2 and 350 mg/m2, inclusive. In some instances, the subject is administered about 300 $mg/m^2$ of cyclophosphamide. In some embodiments, the cyclophosphamide can be administered in a single dose or can be administered in a plurality of doses, such as given daily, every other day or every three days. In some embodiments, cyclophosphamide is administered daily, such as for 1-5 days, for example, for 3 to 5 days. In some instances, the subject is administered about 300 $mg/m^2$ of cyclophosphamide, daily for 3 days, prior to initiation of the cell therapy.

In some embodiments, where the lymphodepleting agent comprises fludarabine, the subject is administered fludarabine at a dose between or between about 1 $mg/m^2$ and 100 $mg/m^2$, such as between or between about 10 $mg/m^2$ and 75 $mg/m^2$, 15 $mg/m^2$ and 50 $mg/m^2$, 20 $mg/m^2$ and 40 $mg/m^2$, or 24 $mg/m^2$ and 35 $mg/m^2$, inclusive. In some instances, the subject is administered about 30 $mg/m^2$ of fludarabine. In some embodiments, the fludarabine can be administered in a single dose or can be administered in a plurality of doses, such as given daily, every other day or every three days. In some embodiments, fludarabine is administered daily, such as for 1-5 days, for example, for 3 to 5 days. In some instances, the subject is administered about 30 $mg/m^2$ of fludarabine, daily for 3 days, prior to initiation of the cell therapy.

In some embodiments, the lymphodepleting agent comprises a combination of agents, such as a combination of cyclophosphamide and fludarabine. Thus, the combination of agents may include cyclophosphamide at any dose or administration schedule, such as those described above, and fludarabine at any dose or administration schedule, such as those described above. For example, in some aspects, the subject is administered 60 mg/kg (~2 $g/m^2$) of cyclophosphamide and 3 to 5 doses of 25 $mg/m^2$ fludarabine prior to the first or subsequent dose.

Following administration of the cells, the biological activity of the engineered cell populations in some embodiments is measured, e.g., by any of a number of known methods. Parameters to assess include specific binding of an engineered or natural T cell or other immune cell to antigen, in vivo, e.g., by imaging, or ex vivo, e.g., by ELISA or flow cytometry. In certain embodiments, the ability of the engineered cells to destroy target cells can be measured using any suitable known methods, such as cytotoxicity assays described in, for example, Kochenderfer et al., J. Immunotherapy, 32 (7): 689-702 (2009), and Herman et al. J. Immunological Methods, 285 (1): 25-40 (2004). In certain embodiments, the biological activity of the cells is measured by assaying expression and/or secretion of one or more cytokines, such as CD107a, IFNγ, IL-2, and TNF. In some aspects the biological activity is measured by assessing clinical outcome, such as reduction in tumor burden or load.

In certain embodiments, the engineered cells are further modified in any number of ways, such that their therapeutic or prophylactic efficacy is increased. For example, the engineered CAR or TCR expressed by the population can be conjugated either directly or indirectly through a linker to a targeting moiety. The practice of conjugating compounds, e.g., the CAR or TCR, to targeting moieties is known. See, for instance, Wadwa et al., J. Drug Targeting 3:111 (1995), and U.S. Pat. No. 5,087,616.

In some embodiments, the cells are administered as part of a combination treatment, such as simultaneously with or sequentially with, in any order, another therapeutic intervention, such as an antibody or engineered cell or receptor or agent, such as a cytotoxic or therapeutic agent. The cells in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells are administered prior to the one or more additional therapeutic agents. In some embodiments, the cells are administered after the one or more additional therapeutic agents. In some embodiments, the one or more additional agent includes a cytokine, such as IL-2, for example, to enhance persistence.

A. Dosing

In some embodiments, a dose of cells is administered to subjects in accord with the provided methods, and/or with the provided articles of manufacture or compositions. In some embodiments, the size or timing of the doses is determined as a function of the particular disease or condition in the subject. In some cases, the size or timing of the doses for a particular disease in view of the provided description may be empirically determined.

In some embodiments, the dose of cells comprises between at or about $2\times10^5$ of the cells/kg and at or about $2\times10^6$ of the cells/kg, such as between at or about $4\times10^5$ of the cells/kg and at or about $1\times10^6$ of the cells/kg or between at or about $6\times10^5$ of the cells/kg and at or about $8\times10^5$ of the cells/kg. In some embodiments, the dose of cells comprises no more than $2\times10^5$ of the cells (e.g. antigen-expressing, such as CAR-expressing cells) per kilogram body weight of the subject (cells/kg), such as no more than at or about $3\times10^5$ cells/kg, no more than at or about $4\times10^5$ cells/kg, no more than at or about $5\times10^5$ cells/kg, no more than at or about $6\times10^5$ cells/kg, no more than at or about $7\times10^5$ cells/kg, no more than at or about $8\times10^5$ cells/kg, no more than at or about $9\times10^5$ cells/kg, no more than at or about $1\times10^6$ cells/kg, or no more than at or about $2\times10^6$ cells/kg. In some embodiments, the dose of cells comprises at least or at least about or at or about $2\times10^5$ of the cells (e.g. antigen-expressing, such as CAR-expressing cells) per kilogram body weight of the subject (cells/kg), such as at least or at least about or at or about $3\times10^5$ cells/kg, at least or at least about or at or about $4\times10^5$ cells/kg, at least or at least about or at or about $5\times10^5$ cells/kg, at least or at least about or at or about $6\times10^5$ cells/kg, at least or at least about or at or about $7\times10^5$ cells/kg, at least or at least about or at or about $8\times10^5$ cells/kg, at least or at least about or at or about $9\times10^5$ cells/kg, at least or at least about or at or about $1\times10^6$ cells/kg, or at least or at least about or at or about $2\times10^6$ cells/kg.

In certain embodiments, the cells, or individual populations of sub-types of cells, are administered to the subject at a range of about one million to about 100 billion cells and/or that amount of cells per kilogram of body weight, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges and/or per kilogram of body weight. Dosages may vary depending on attributes particular to the disease or disorder and/or patient and/or other treatments.

In some embodiments, the dose of cells is a flat dose of cells or fixed dose of cells such that the dose of cells is not tied to or based on the body surface area or weight of a subject.

In some embodiments, for example, where the subject is a human, the dose includes fewer than about $5\times10^8$ total recombinant receptor (e.g., CAR)-expressing cells, T cells, or peripheral blood mononuclear cells (PBMCs), e.g., in the range of about $1\times10^6$ to $5\times10^8$ such cells, such as $2\times10^6$, $5\times10^6$, $1\times10^7$, $5\times10^7$, $1\times10^8$, or $5\times10^8$ total such cells, or the range between any two of the foregoing values.

In some embodiments, the dose of genetically engineered cells comprises from or from about $1\times10^5$ to $5\times10^8$ total CAR-expressing T cells, $1\times10^5$ to $2.5\times10^8$ total CAR-expressing T cells, $1\times10^5$ to $1\times10^8$ total CAR-expressing T cells, $1\times10^5$ to $5\times10^7$ total CAR-expressing T cells, $1\times10^5$ to $2.5\times10^7$ total CAR-expressing T cells, $1\times10^5$ to $1\times10^7$ total CAR-expressing T cells, $1\times10^5$ to $5\times10^6$ total CAR-expressing T cells, $1\times10^5$ to $2.5\times10^6$ total CAR-expressing T cells, $1\times10^5$ to $1\times10^6$ total CAR-expressing T cells, $1\times10^6$ to $5\times10^8$ total CAR-expressing T cells, $1\times10^6$ to $2.5\times10^8$ total CAR-expressing T cells, $1\times10^6$ to $1\times10^8$ total CAR-expressing T cells, $1\times10^6$ to $5\times10^7$ total CAR-expressing T cells, $1\times10^6$ to $2.5\times10^7$ total CAR-expressing T cells, $1\times10^6$ to $1\times10^7$ total CAR-expressing T cells, $1\times10^6$ to $5\times10^6$ total CAR-expressing T cells, $1\times10^6$ to $2.5\times10^6$ total CAR-expressing T cells, $2.5\times10^6$ to $5\times10^8$ total CAR-expressing T cells, $2.5\times10^6$ to $2.5\times10^8$ total CAR-expressing T cells, $2.5\times10^6$ to $1\times10^8$ total CAR-expressing T cells, $2.5\times10^6$ to $5\times10^7$ total CAR-expressing T cells, $2.5\times10^6$ to $2.5\times10^7$ total CAR-expressing T cells, $2.5\times10^6$ to $1\times10^7$ total CAR-expressing T cells, $2.5\times10^6$ to $5\times10^6$ total CAR-expressing T cells, $5\times10^6$ to $5\times10^8$ total CAR-expressing T cells, $5\times10^6$ to $2.5\times10^8$ total CAR-expressing T cells, $5\times10^6$ to $1\times10^8$ total CAR-expressing T cells, $5\times10^6$ to $5\times10^7$ total CAR-expressing T cells, $5\times10^6$ to $2.5\times10^7$ total CAR-expressing T cells, $5\times10^6$ to $1\times10^7$ total CAR-expressing T cells, $1\times10^7$ to $5\times10^8$ total CAR-expressing T cells, $1\times10^7$ to $2.5\times10^8$ total CAR-expressing T cells, $1\times10^7$ to $1\times10^8$ total CAR-expressing T cells, $1\times10^7$ to $5\times10^7$ total CAR-expressing T cells, $1\times10^7$ to $2.5\times10^7$ total CAR-expressing T cells, $2.5\times10^7$ to $5\times10^8$ total CAR-expressing T cells, $2.5\times10^7$ to $2.5\times10^8$ total CAR-expressing T cells, $2.5\times10^7$ to $1\times10^8$ total CAR-expressing T cells, $2.5\times10^7$ to $5\times10^7$ total CAR-expressing T cells, $5\times10^7$ to $5\times10^8$ total CAR-expressing T cells, $5\times10^7$ to $2.5\times10^8$ total CAR-expressing T cells, $5\times10^7$ to $1\times10^8$ total CAR-expressing T cells, $1\times10^8$ to $5\times10^8$ total CAR-expressing T cells, $1\times10^8$ to $2.5\times10^8$ total CAR-expressing T cells, or $2.5\times10^8$ to $5\times10^8$ total CAR-expressing T cells. In some embodiments, the dose of genetically engineered T cells is or contains less than $50\times10^6$ total CAR-expressing T cells. In certain embodiments, the dose is or contains less than $25\times10^6$ total CD4+ CAR-expressing T cells. In various embodiments, the dose is or contains less than $25\times10^6$ total CD8+ CAR-expressing T cells.

In some embodiments, the dose of genetically engineered cells comprises at least or at least about $1\times10^5$ CAR-expressing cells, at least or at least about $2.5\times10^5$ CAR-expressing cells, at least or at least about $5\times10^5$ CAR-expressing cells, at least or at least about $1\times10^6$ CAR-expressing cells, at least or at least about $2.5\times10^6$ CAR-expressing cells, at least or at least about $5\times10^6$ CAR-expressing cells, at least or at least about $1\times10^7$ CAR-expressing cells, at least or at least about $2.5\times10^7$ CAR-expressing cells, at least or at least about $5\times10^7$ CAR-expressing cells, at least or at least about $1\times10^8$ CAR-expressing cells, at least or at least about $2.5\times10^8$ CAR-expressing cells, or at least or at least about $5\times10^8$ CAR-expressing cells.

In some embodiments, the cell therapy comprises administration of a dose comprising a number of cell from or from about $1\times10^5$ to $5\times10^8$ total recombinant receptor-expressing cells, total T cells, or total peripheral blood mononuclear cells (PBMCs), from or from about $5\times10^5$ to $1\times10^7$ total recombinant receptor-expressing cells, total T cells, or total peripheral blood mononuclear cells (PBMCs) or from or from about $1\times10^6$ to $1\times10^7$ total recombinant receptor-expressing cells, total T cells, or total peripheral blood mononuclear cells (PBMCs), each inclusive. In some embodiments, the cell therapy comprises administration of a dose of cells comprising a number of cells at least or at least about $1\times10^5$ total recombinant receptor-expressing cells, total T cells, or total peripheral blood mononuclear cells (PBMCs), such at least or at least $1\times10^6$, at least or at least about $1\times10^7$, at least or at least about $1\times10^8$ of such cells. In some embodiments, the number is with reference to the total number of CD3+, CD4+, or CD8+, in some cases also recombinant receptor-expressing (e.g. CAR+) cells. In some embodiments, the cell therapy comprises administration of a dose comprising a number of cell from or from about $1\times10^5$ to $5\times10^8$ CD3+ or CD8+ total T cells or CD3+ or CD8+ recombinant receptor-expressing cells, from or from about $5\times10^5$ to $1\times10^7$ CD3+ or CD8+ total T cells or CD3+ or CD8+ recombinant receptor-expressing cells, or from or from about $1\times10^6$ to $1\times10^7$ CD3+ or CD8+ total T cells or CD3+ or CD8+recombinant receptor-expressing cells, each inclusive. In some embodiments, the cell therapy comprises administration of a dose comprising a number of cell from or from about $1\times10^5$ to $5\times10^8$ total CD3+/CAR+ or CD8+/CAR+ cells, from or from about $5\times10^5$ to $1\times10^7$ total CD3+/CAR+ or CD8+/CAR+ cells, or from or from about $1\times10^6$ to $1\times10^7$ total CD3+/CAR+ or CD8+/CAR+ cells, each inclusive.

In some embodiments, the T cells of the dose include CD4+ T cells, CD8+ T cells or CD4+ and CD8+ T cells.

In some embodiments, for example, where the subject is human, the CD8+ T cells of the dose, including in a dose including CD4+ and CD8+ T cells, includes between about $1\times10^6$ and $5\times10^8$ total recombinant receptor (e.g., CAR)-expressing CD8+ cells, e.g., in the range of about $5\times10^6$ to $1\times10^8$ such cells, such cells $1\times10^7$, $2.5\times10^7$, $5\times10^7$, $7.5\times10^7$, $1\times10^8$, or $5\times10^8$ total such cells, or the range between any two of the foregoing values. In some embodiments, the patient is administered multiple doses, and each of the doses or the total dose can be within any of the foregoing values. In some embodiments, the dose of cells comprises the administration of from or from about $1\times10^7$ to $0.75\times10^8$ total recombinant receptor-expressing CD8+ T cells, $1\times10^7$ to $2.5\times10^7$ total recombinant receptor-expressing CD8+ T cells, from or from about $1\times10^7$ to $0.75\times10^8$ total recombinant receptor-expressing CD8+ T cells, each inclusive. In some embodiments, the dose of cells comprises the administration of or about $1\times10^7$, $2.5\times10^7$, $5\times10^7$ $7.5\times10^7$, $1\times10^8$, or $5\times10^8$ total recombinant receptor-expressing CD8+ T cells.

In some embodiments, the dose of cells, e.g., recombinant receptor-expressing T cells, is administered to the subject as a single dose or is administered only one time within a period of two weeks, one month, three months, six months, 1 year or more.

In the context of adoptive cell therapy, administration of a given "dose" encompasses administration of the given amount or number of cells as a single composition and/or single uninterrupted administration, e.g., as a single injection or continuous infusion, and also encompasses administration of the given amount or number of cells as a split dose or as a plurality of compositions, provided in multiple individual compositions or infusions, over a specified period of time, such as over no more than 3 days. Thus, in some contexts, the dose is a single or continuous administration of the specified number of cells, given or initiated at a single point in time. In some contexts, however, the dose is administered in multiple injections or infusions over a period of no more than three days, such as once a day for three days or for two days or by multiple infusions over a single day period.

Thus, in some aspects, the cells of the dose are administered in a single pharmaceutical composition. In some embodiments, the cells of the dose are administered in a plurality of compositions, collectively containing the cells of the dose.

In some embodiments, the term "split dose" refers to a dose that is split so that it is administered over more than one day. This type of dosing is encompassed by the present methods and is considered to be a single dose.

Thus, the dose of cells may be administered as a split dose, e.g., a split dose administered over time. For example, in some embodiments, the dose may be administered to the subject over 2 days or over 3 days. Exemplary methods for split dosing include administering 25% of the dose on the first day and administering the remaining 75% of the dose on the second day. In other embodiments, 33% of the dose may be administered on the first day and the remaining 67% administered on the second day. In some aspects, 10% of the dose is administered on the first day, 30% of the dose is administered on the second day, and 60% of the dose is administered on the third day. In some embodiments, the split dose is not spread over more than 3 days.

In some embodiments, cells of the dose may be administered by administration of a plurality of compositions or solutions, such as a first and a second, optionally more, each containing some cells of the dose. In some aspects, the plurality of compositions, each containing a different population and/or sub-types of cells, are administered separately or independently, optionally within a certain period of time. For example, the populations or sub-types of cells can include CD8+ and CD4+ T cells, respectively, and/or CD8+- and CD4+-enriched populations, respectively, e.g., CD4+ and/or CD8+ T cells each individually including cells genetically engineered to express the recombinant receptor. In some embodiments, the administration of the dose comprises administration of a first composition comprising a dose of CD8+ T cells or a dose of CD4+ T cells and administration of a second composition comprising the other of the dose of CD4+ T cells and the CD8+ T cells.

In some embodiments, the administration of the composition or dose, e.g., administration of the plurality of cell compositions, involves administration of the cell compositions separately. In some aspects, the separate administrations are carried out simultaneously, or sequentially, in any order. In some embodiments, the dose comprises a first composition and a second composition, and the first composition and second composition are administered 0 to 12 hours apart, 0 to 6 hours apart or 0 to 2 hours apart. In some embodiments, the initiation of administration of the first composition and the initiation of administration of the second composition are carried out no more than 2 hours, no more than 1 hour, or no more than 30 minutes apart, no more than 15 minutes, no more than 10 minutes or no more than 5 minutes apart. In some embodiments, the initiation and/or completion of administration of the first composition and the completion and/or initiation of administration of the second composition are carried out no more than 2 hours, no more than 1 hour, or no more than 30 minutes apart, no more than 15 minutes, no more than 10 minutes or no more than 5 minutes apart.

In some composition, the first composition, e.g., first composition of the dose, comprises CD4+ T cells. In some composition, the first composition, e.g., first composition of the dose, comprises CD8+ T cells. In some embodiments, the first composition is administered prior to the second composition.

In some embodiments, the dose or composition of cells includes a defined or target ratio of CD4+ cells expressing a recombinant receptor to CD8+ cells expressing a recombinant receptor and/or of CD4+ cells to CD8+ cells, which ratio optionally is approximately 1:1 or is between approximately 1:3 and approximately 3:1, such as approximately 1:1. In some aspects, the administration of a composition or dose with the target or desired ratio of different cell populations (such as CD4+:CD8+ ratio or CAR+CD4+:CAR+ CD8+ ratio, e.g., 1:1) involves the administration of a cell composition containing one of the populations and then administration of a separate cell composition comprising the other of the populations, where the administration is at or approximately at the target or desired ratio. In some aspects, administration of a dose or composition of cells at a defined ratio leads to improved expansion, persistence and/or antitumor activity of the T cell therapy.

In some embodiments, the subject receives multiple doses, e.g., two or more doses or multiple consecutive doses, of the cells. In some embodiments, two doses are administered to a subject. In some embodiments, the subject receives the consecutive dose, e.g., second dose, is administered approximately 4, 5, 6, 7, 8, 9, 10, 11, 12, 13, 14, 15, 16, 17, 18, 19, 20 or 21 days after the first dose. In some embodiments, multiple consecutive doses are administered following the first dose, such that an additional dose or doses are administered following administration of the consecutive dose. In some aspects, the number of cells administered to the subject in the additional dose is the same as or similar to the first dose and/or consecutive dose. In some embodiments, the additional dose or doses are larger than prior doses.

In some aspects, the size of the first and/or consecutive dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some aspects, the time between the administration of the first dose and the administration of the consecutive dose is about 9 to about 35 days, about 14 to about 28 days, or 15 to 27 days. In some embodiments, the administration of the consecutive dose is at a time point more than about 14 days after and less than about 28 days after the administration of the first dose. In some aspects, the time between the first and consecutive dose is about 21 days. In some embodiments, an additional dose or doses, e.g. consecutive doses, are administered following administration of the consecutive dose. In some aspects, the additional consecutive dose or doses are administered at least about 14 and less than about 28 days following administration of a prior dose. In some embodiments, the additional dose is administered less than about 14 days following the prior dose, for example, 4, 5, 6, 7, 8, 9, 10, 11, 12, or 13 days after the prior dose. In some embodiments, no dose is administered less than about 14 days following the prior dose and/or no dose is administered more than about 28 days after the prior dose.

In some embodiments, the dose of cells, e.g., recombinant receptor-expressing cells, comprises two doses (e.g., a double dose), comprising a first dose of the T cells and a consecutive dose of the T cells, wherein one or both of the first dose and the second dose comprises administration of the split dose of T cells.

In some embodiments, the dose of cells is generally large enough to be effective in reducing disease burden.

In some embodiments, the cells are administered at a desired dosage, which in some aspects includes a desired dose or number of cells or cell type(s) and/or a desired ratio of cell types. Thus, the dosage of cells in some embodiments is based on a total number of cells (or number per kg body weight) and a desired ratio of the individual populations or sub-types, such as the CD4+ to CD8+ ratio. In some embodiments, the dosage of cells is based on a desired total number (or number per kg of body weight) of cells in the individual populations or of individual cell types. In some embodiments, the dosage is based on a combination of such features, such as a desired number of total cells, desired ratio, and desired total number of cells in the individual populations.

In some embodiments, the populations or sub-types of cells, such as CD8+ and CD4+ T cells, are administered at or within a tolerated difference of a desired dose of total cells, such as a desired dose of T cells. In some aspects, the desired dose is a desired number of cells or a desired number of cells per unit of body weight of the subject to whom the cells are administered, e.g., cells/kg. In some aspects, the desired dose is at or above a minimum number of cells or minimum number of cells per unit of body weight. In some aspects, among the total cells, administered at the desired dose, the individual populations or sub-types are present at or near a desired output ratio (such as CD4+ to CD8+ ratio), e.g., within a certain tolerated difference or error of such a ratio.

In some embodiments, the cells are administered at or within a tolerated difference of a desired dose of one or more of the individual populations or sub-types of cells, such as a desired dose of CD4+ cells and/or a desired dose of CD8+ cells. In some aspects, the desired dose is a desired number of cells of the sub-type or population, or a desired number of such cells per unit of body weight of the subject to whom the cells are administered, e.g., cells/kg. In some aspects, the desired dose is at or above a minimum number of cells of the population or sub-type, or minimum number of cells of the population or sub-type per unit of body weight.

Thus, in some embodiments, the dosage is based on a desired fixed dose of total cells and a desired ratio, and/or based on a desired fixed dose of one or more, e.g., each, of the individual sub-types or sub-populations. Thus, in some embodiments, the dosage is based on a desired fixed or minimum dose of T cells and a desired ratio of $CD4^+$ to $CD8^+$ cells, and/or is based on a desired fixed or minimum dose of $CD4^+$ and/or $CD8^+$ cells.

In some embodiments, the cells are administered at or within a tolerated range of a desired output ratio of multiple cell populations or sub-types, such as CD4+ and CD8+ cells or sub-types. In some aspects, the desired ratio can be a specific ratio or can be a range of ratios. for example, in some embodiments, the desired ratio (e.g., ratio of CD4+ to CD8+ cells) is between at or about 5:1 and at or about 5:1 (or greater than about 1:5 and less than about 5:1), or between at or about 1:3 and at or about 3:1 (or greater than about 1:3 and less than about 3:1), such as between at or about 2:1 and at or about 1:5 (or greater than about 1:5 and less than about 2:1, such as at or about 5:1, 4.5:1, 4:1, 3.5:1, 3:1, 2.5:1, 2:1, 1.9:1, 1.8:1, 1.7:1, 1.6:1, 1.5:1, 1.4:1, 1.3:1, 1.2:1, 1.1:1, 1:1, 1:1.1, 1:1.2, 1:1.3, 1:1.4, 1:1.5, 1:1.6, 1:1.7, 1:1.8, 1:1.9:1:2, 1:2.5, 1:3, 1:3.5, 1:4, 1:4.5, or 1:5. In some aspects, the tolerated difference is within about 1%, about 2%, about 3%, about 4% about 5%, about 10%, about 15%, about 20%, about 25%, about 30%, about 35%, about 40%, about 45%, about 50% of the desired ratio, including any value in between these ranges.

In particular embodiments, the numbers and/or concentrations of cells refer to the number of recombinant receptor (e.g., CAR)-expressing cells. In other embodiments, the numbers and/or concentrations of cells refer to the number or concentration of all cells, T cells, or peripheral blood mononuclear cells (PBMCs) administered.

In some aspects, the size of the dose is determined based on one or more criteria such as response of the subject to prior treatment, e.g. chemotherapy, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

In some embodiments, the methods also include administering one or more additional doses of cells expressing a chimeric antigen receptor (CAR) and/or lymphodepleting therapy, and/or one or more steps of the methods are repeated. In some embodiments, the one or more additional dose is the same as the initial dose. In some embodiments, the one or more additional dose is different from the initial dose, e.g., higher, such as 2-fold, 3-fold, 4-fold, 5-fold, 6-fold, 7-fold, 8-fold, 9-fold or 10-fold or more higher than the initial dose, or lower, such as e.g., higher, such as 2-fold, 3-fold, 4-fold, 5-fold, 6-fold, 7-fold, 8-fold, 9-fold or 10-fold or more lower than the initial dose. In some embodiments, administration of one or more additional doses is determined based on response of the subject to the initial treatment or any prior treatment, disease burden in the subject, such as tumor load, bulk, size, or degree, extent, or type of metastasis, stage, and/or likelihood or incidence of the subject developing toxic outcomes, e.g., CRS, macrophage activation syndrome, tumor lysis syndrome, neurotoxicity, and/or a host immune response against the cells and/or recombinant receptors being administered.

V. Compositions and Formulations

In some embodiments, provided herein are therapeutic compositions (e.g., therapeutic T cell compositions) generated by any of the manufacturing processes disclosed herein, e.g., an output composition such as those disclosed in Section I-H-4. In some embodiments, provided herein are therapeutic compositions (e.g., therapeutic T cell compositions) having any one or more of the features disclosed herein, e.g., in Section I-H-4. In some embodiments, the dose of cells comprising cells engineered with a recombinant antigen receptor, e.g. CAR or TCR, is provided as a composition or formulation, such as a pharmaceutical composition or formulation. Such compositions can be used in accord with the provided methods, and/or with the provided articles of manufacture or compositions, such as in the prevention or treatment of diseases, conditions, and disorders, or in detection, diagnostic, and prognostic methods.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In some aspects, the choice of carrier is determined in part by the particular cell or agent and/or by the method of administration. Accordingly, there are a variety of suitable formulations. For example, the pharmaceutical composition can contain preservatives. Suitable preservatives may include, for example, methylparaben, propylparaben, sodium benzoate, and benzalkonium chloride. In some aspects, a mixture of two or more preservatives is used. The preservative or mixtures thereof are typically present in an amount of about 0.0001% to about 2% by weight of the total composition. Carriers are described, e.g., by Remington's Pharmaceutical Sciences 16th edition, Osol, A. Ed. (1980). Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. The buffering agent or mixtures thereof are typically present in an amount of about 0.001% to about 4% by weight of the total composition. Methods for preparing administrable pharmaceutical compositions are known. Exemplary methods are described in more detail in, for example, Remington: The Science and Practice of Pharmacy, Lippincott Williams & Wilkins; 21st ed. (May 1, 2005).

The formulation or composition may also contain more than one active ingredient useful for the particular indication, disease, or condition being prevented or treated with the cells or agents, where the respective activities do not adversely affect one another. Such active ingredients are suitably present in combination in amounts that are effective for the purpose intended. Thus, in some embodiments, the pharmaceutical composition further includes other pharmaceutically active agents or drugs, such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc. In some embodiments, the agents or cells are administered in the form of a salt, e.g., a pharmaceutically acceptable salt. Suitable pharmaceutically acceptable acid addition salts include those derived from mineral acids, such as hydrochloric, hydrobromic, phosphoric, metaphosphoric, nitric, and sulphuric acids, and organic acids, such as tartaric, acetic, citric, malic, lactic, fumaric, benzoic, glycolic, gluconic, succinic, and arylsulphonic acids, for example, p-toluenesulphonic acid.

The pharmaceutical composition in some embodiments contains agents or cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition.

The agents or cells can be administered by any suitable means, for example, by bolus infusion, by injection, e.g., intravenous or subcutaneous injections, intraocular injection, periocular injection, subretinal injection, intravitreal injection, trans-septal injection, subscleral injection, intrachoroidal injection, intracameral injection, subconjectval injection, subconjuntival injection, sub-Tenon's injection, retrobulbar injection, peribulbar injection, or posterior juxtascleral delivery. In some embodiments, they are administered by parenteral, intrapulmonary, and intranasal, and, if desired for local treatment, intralesional administration. Parenteral infusions include intramuscular, intravenous, intraarterial, intraperitoneal, or subcutaneous administration. In some embodiments, a given dose is administered by a single bolus administration of the cells or agent. In some embodiments, it is administered by multiple bolus administrations of the cells or agent, for example, over a period of no more than 3 days, or by continuous infusion administration of the cells or agent.

For the prevention or treatment of disease, the appropriate dosage may depend on the type of disease to be treated, the type of agent or agents, the type of cells or recombinant receptors, the severity and course of the disease, whether the agent or cells are administered for preventive or therapeutic purposes, previous therapy, the subject's clinical history and response to the agent or the cells, and the discretion of the attending physician. The compositions are in some embodiments suitably administered to the subject at one time or over a series of treatments.

The cells or agents may be administered using standard administration techniques, formulations, and/or devices. Provided are formulations and devices, such as syringes and vials, for storage and administration of the compositions. With respect to cells, administration can be autologous or heterologous. For example, immunoresponsive cells or progenitors can be obtained from one subject, and administered to the same subject or a different, compatible subject. Peripheral blood derived immunoresponsive cells or their progeny (e.g., in vivo, ex vivo or in vitro derived) can be administered via localized injection, including catheter administration, systemic injection, localized injection, intravenous injection, or parenteral administration. When administering a therapeutic composition (e.g., a pharmaceutical composition containing a genetically modified immunoresponsive cell or an agent that treats or ameliorates symptoms of neurotoxicity), it will generally be formulated in a unit dosage injectable form (solution, suspension, emulsion).

Formulations include those for oral, intravenous, intraperitoneal, subcutaneous, pulmonary, transdermal, intramuscular, intranasal, buccal, sublingual, or suppository administration. In some embodiments, the agent or cell populations are administered parenterally. The term "parenteral," as used herein, includes intravenous, intramuscular, subcutaneous, rectal, vaginal, and intraperitoneal administration. In some embodiments, the agent or cell populations are administered to a subject using peripheral systemic delivery by intravenous, intraperitoneal, or subcutaneous injection.

Compositions in some embodiments are provided as sterile liquid preparations, e.g., isotonic aqueous solutions, suspensions, emulsions, dispersions, or viscous compositions, which may in some aspects be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues. Liquid or viscous compositions can comprise carriers, which can be a solvent or dispersing medium containing, for example, water, saline, phosphate buffered saline, polyol (for example, glycerol, propylene glycol, liquid polyethylene glycol) and suitable mixtures thereof.

Sterile injectable solutions can be prepared by incorporating the agent or cells in a solvent, such as in admixture with a suitable carrier, diluent, or excipient such as sterile water, physiological saline, glucose, dextrose, or the like.

The formulations to be used for in vivo administration are generally sterile. Sterility may be readily accomplished, e.g., by filtration through sterile filtration membranes.

VI. Definitions

Unless defined otherwise, all terms of art, notations and other technical and scientific terms or terminology used herein are intended to have the same meaning as is commonly understood by one of ordinary skill in the art to which the claimed subject matter pertains. In some cases, terms with commonly understood meanings are defined herein for clarity and/or for ready reference, and the inclusion of such definitions herein should not necessarily be construed to represent a substantial difference over what is generally understood in the art.

As used herein, the singular forms “a,” “an,” and “the” include plural referents unless the context clearly dictates otherwise. For example, “a” or “an” means “at least one” or “one or more.” It is understood that aspects and variations described herein include “consisting” and/or “consisting essentially of” aspects and variations.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

The term “about” as used herein refers to the usual error range for the respective value readily known. Reference to “about” a value or parameter herein includes (and describes) embodiments that are directed to that value or parameter per se. For example, description referring to “about X” includes description of “X”.

As used herein, recitation that nucleotides or amino acid positions “correspond to” nucleotides or amino acid positions in a disclosed sequence, such as set forth in the Sequence listing, refers to nucleotides or amino acid positions identified upon alignment with the disclosed sequence to maximize identity using a standard alignment algorithm, such as the GAP algorithm. By aligning the sequences, corresponding residues can be identified, for example, using conserved and identical amino acid residues as guides. In general, to identify corresponding positions, the sequences of amino acids are aligned so that the highest order match is obtained (see, e.g.: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; Carrillo et al. (1988) SIAM J Applied Math 48:1073).

The term “vector,” as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as “expression vectors.” Among the vectors are viral vectors, such as retroviral, e.g., gammaretroviral and lentiviral vectors.

The terms “host cell,” “host cell line,” and “host cell culture” are used interchangeably and refer to cells into which exogenous nucleic acid has been introduced, including the progeny of such cells. Host cells include “transformants” and “transformed cells,” which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As used herein, a statement that a cell or population of cells is “positive” for a particular marker refers to the detectable presence on or in the cell of a particular marker, typically a surface marker. When referring to a surface marker, the term refers to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

As used herein, a statement that a cell or population of cells is “negative” for a particular marker refers to the absence of substantial detectable presence on or in the cell of a particular marker, typically a surface marker. When referring to a surface marker, the term refers to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

As used herein, “percent (%) amino acid sequence identity” and “percent identity” when used with respect to an amino acid sequence (reference polypeptide sequence) is defined as the percentage of amino acid residues in a candidate sequence (e.g., the subject antibody or fragment) that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various known ways, for instance, using publicly available computer software such as BLAST, BLAST-2, ALIGN or Megalign (DNASTAR) software. Appropriate parameters for aligning sequences can be determined, including any algorithms needed to achieve maximal alignment over the full length of the sequences being compared.

An amino acid substitution may include replacement of one amino acid in a polypeptide with another amino acid. The substitution may be a conservative amino acid substitution or a non-conservative amino acid substitution. Amino acid substitutions may be introduced into a binding molecule, e.g., antibody, of interest and the products screened for a desired activity, e.g., retained/improved antigen binding, decreased immunogenicity, or improved ADCC or CDC.

Amino acids generally can be grouped according to the following common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

In some embodiments, conservative substitutions can involve the exchange of a member of one of these classes for another member of the same class. In some embodiments, non-conservative amino acid substitutions can involve exchanging a member of one of these classes for another class.

As used herein, a composition refers to any mixture of two or more products, substances, or compounds, including cells. It may be a solution, a suspension, liquid, powder, a paste, aqueous, non-aqueous or any combination thereof.

As used herein, a "subject" is a mammal, such as a human or other animal, and typically is human.

VII. Exemplary Embodiments

Among the provided embodiments are:

1. A method for producing a composition of engineered T cells, the method comprising: (a) exposing an input composition comprising primary T cells with a stimulatory reagent under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out: (i) at a time between 24 and 120 hours, inclusive, after the exposing to the stimulatory reagent is initiated; (ii) at a time when integrated vector is detected in the genome but prior to achieving a stable integrated vector copy number (iVCN) per diploid genome; (iii) at a time before the total number of viable cells at the harvesting is more than or more than about three times, two times, or the same or about the same as the number of total viable cells of the stimulated population; and/or (iv) at a time when the percentage of CD27+CCR7+ is greater than or greater than about 60% among total T cells in the population, total CD3+ T cells in the population, total CD4+ T cells in the population, or total CD8+ T cells, or of recombinant protein-expressing cells thereof, in the population; thereby producing a composition of engineered cells.
2. The method of embodiment 1, wherein the input composition comprises at least $300\times10^6$ viable primary T cells.
3. The method of embodiment 1 or embodiment 2, wherein the stimulatory reagent is capable of activating one or more intracellular signaling domains of one or more components of a TCR complex and one or more intracellular signaling domains of one or more costimulatory molecules.
4. A method for producing a composition of engineered T cells, the method comprising: (a) exposing an input composition comprising at least $300\times10^6$ viable primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out: (i) at a time between 48 and 120 hours, inclusive, after the exposing to the stimulatory reagent is initiated; (ii) at a time when integrated vector is detected in the genome but prior to achieving a stable integrated vector copy number (iVCN) per diploid genome; (iii) at a time before the total number of viable cells at the harvesting is more than or more than about three times, two times, or the same or about the same as the number of total viable cells of the stimulated population; and/or (iv) at a time when the percentage of naïve-like T cells is greater than or greater than about 60% among total T cells in the population, total CD3+ cells in the population, total CD4+ T cells in the population, or total CD8+ T cells, or of recombinant protein-expressing cells thereof, in the population; thereby producing a composition of engineered cells.
5. The method of any of embodiments 1-4, wherein the harvesting is carried out at a time when integrated vector is detected in the genome but prior to achieving stable iVCN per diploid genome.
6. The method of embodiment 5, wherein stable iVCN per diploid genome is achieved when the iVCN peaks and remains unchanged, or unchanged within a tolerated error, for a period of time greater than 24 hours.
7. The method of embodiment 5, wherein stable iVCN per diploid genome is achieved when the fraction of iVCN to total vector copy number (VCN) in the diploid genome of the population of transformed cells, on average, is or is about 1.0 or is within a tolerated error thereof.
8. The method of any of embodiments 1-7, wherein the harvesting is carried out at a time when the fraction of integrated vector copy number (iVCN) to total VCN in the population of transformed cells, on average, is less than 0.8.
9. The method of any of embodiments 1-8, wherein the naïve-like T cells comprise CD27+CCR7+ T cells.
10. A method for producing a composition of engineered T cells, the method comprising: (a) exposing an input composition comprising primary T cells to a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, after the exposing to the stimulatory reagent is initiated, wherein at the time of harvesting the integrated vector copy number (iVCN) of the population of transformed cells, on average, is between or between about 0.4 copies per diploid genome and 2.0 copies per diploid genome; thereby producing a composition of engineered cells.

11. The method of any of embodiments 1-10, wherein the harvesting is carried out at a time when the iVCN of the population of transformed cells, on average, is less than or less than about 2.0 copies per diploid genome.
12. The method of any of embodiments 1-10, wherein the harvesting is carried out at a time when the iVCN of the population of transformed cells, on average, is less than or less than about 1.5 copies per diploid genome.
13. The method of any of embodiments 1-10, wherein the harvesting is carried out at a time when the iVCN of the population of transformed cells, on average, is less than or less than about 1.0 copy per diploid genome.
14. The method of any of embodiments 1-10, wherein the harvesting is carried out at a time when the iVCN of the population of transformed cells, on average, is less than or less than about 0.75 copies per diploid genome.
15. The method of any of embodiments 1-10, wherein the harvesting is carried out at a time when the iVCN of the population of transformed cells, on average, is less than or less than about 0.5 copies per diploid genome.
16. A method for producing a composition of engineered T cells, the method comprising: (a) exposing an input composition comprising primary T cells with a stimulatory reagent under conditions to stimulate T cells, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, after the exposing to the stimulatory reagent is initiated, wherein at the time of harvesting the percentage of naïve-like cells is greater than or greater than about 60% among total T cells in the population, total CD4+ T cells in the population or total CD8+ T cells, or of recombinant protein-expressing cells thereof, in the population; thereby producing a composition of engineered cells.
17. The method of any of embodiments 1-16, wherein at the time of harvesting: the percentage of naïve-like T cells is greater than or greater than about 60% among total recombinant protein-expressing cells in the population, optionally greater than or greater than about 65%, 70%, 80%, 90% or 95% total recombinant protein-expressing T cells in the population; the percentage of naïve-like T cells is greater than or greater than about 40% among total recombinant protein-expressing CD4+ T cells in the population, optionally greater than or greater than about 50%, 60%, 70%, 80%, 90% or 95% total recombinant protein-expressing CD4+ cells in the population; or the percentage of naïve-like T cells is greater than or greater than about 40% among total recombinant protein-expressing CD8+ T cells in the population, optionally greater than or greater than about 50%, 60%, 70%, 80%, 90% or 95% total recombinant protein-expressing CD8+ cells in the population.
18. The method of any of embodiments 1-17, wherein subsequent to the introducing and prior to the harvesting the method further comprises incubating the population of transformed cells for up to 96 hours, optionally wherein the incubation is carried out at a temperature of about 37° C.
19. The method of embodiment 18, wherein the incubating is carried out for up to 72 hours subsequent to the introducing.
20. The method of embodiment 18, wherein the incubating is carried out for up to 48 hours subsequent to the introducing.
21. The method of embodiment 18, wherein the incubating is carried out for up to 24 hours subsequent to the introducing.
22. The method of any of embodiments 18-21, wherein the incubation is carried out for at least 18 hours.
23. The method of any of embodiments 1-22, wherein the harvesting is carried out within 96 hours after the exposing to the stimulatory agent is initiated.
24. The method of any of embodiments 1-22, wherein the harvesting is carried out within 72 hours after the exposing to the stimulatory agent is initiated.
25. The method of any of embodiments 1-22, wherein the harvesting is carried out within 48 hours after the exposing to the stimulatory agent is initiated.
26. The method of any of embodiments 1-25, wherein one or both of the exposing and the introducing is carried out in the presence of one or more recombinant cytokines.
27. The method of any of embodiments 18-26, wherein the incubating is carried out in the presence of one or more recombinant cytokines.
28. The method of any of embodiments 18-26, wherein the incubating is carried out in basal media lacking one or more recombinant cytokines.
29. The method of any of embodiments 16-28, wherein the naïve-like T cells comprise CD27+CCR7+ cells.
30. A method for producing a composition of engineered T cells, the method comprising: (a) exposing an input composition comprising primary T cells with a stimulatory reagent under conditions to stimulate T cells comprising the presence of one or more recombinant cytokines, thereby generating a stimulated population, wherein the stimulatory reagent is capable of activating one or more intracellular signaling domains of one or more components of a TCR complex and one or more intracellular signaling domains of one or more costimulatory molecules; (b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours, optionally wherein the incubation is carried out at a temperature of about 37° C., wherein the incubating is carried out in basal media lacking one or more recombinant cytokines; and (c) subsequent to the incubating, harvesting T cells of the transformed population, thereby producing a composition of engineered cells, wherein the harvesting is carried out at a time between 48 and 120 hours, inclusive, after the exposing to the stimulatory reagent is initiated; thereby producing a composition of engineered cells.
31. The method of any of embodiments 26-30, wherein the one or more recombinant cytokines are human.
32. The method of any of embodiments 26-31, wherein the one or more recombinant cytokines are selected from recombinant IL-2, recombinant IL-7 and recombinant IL-15, optionally between 10 and 200 IU/mL recombinant IL-2; between 100 IU/mL and 1,000 IU/mL recombinant IL-7; and/or between 10 and 200 IU/mL recombinant IL-15.

33. The method of any of embodiments 26-32, wherein the one or more recombinant cytokines are or comprise recombinant IL-2, recombinant IL-7 and recombinant IL-15, optionally between 10 and 200 IU/mL recombinant IL-2; between 100 IU/mL and 1,000 IU/mL recombinant IL-7; and between 10 and 200 IU/mL recombinant IL-15.
34. The method of any of embodiments 1-33, wherein one or both of the exposing and the introducing is carried out in serum free media.
35. The method of any of embodiments 1-34, wherein the stimulatory reagent comprises (i) a primary agent that specifically binds to a member of a TCR complex, optionally that specifically binds to CD3 and (ii) a secondary agent that specifically binds to a T cell costimulatory molecule, optionally wherein the costimulatory molecule is selected from CD28, CD137 (4-1-BB), OX40, or ICOS.
36. The method of embodiment 35, wherein the one or both of the primary and secondary agents comprise an antibody or an antigen-binding fragment thereof.
37. The method of embodiment 35 or 36, wherein the primary and secondary agents comprise an antibody, optionally wherein the stimulatory reagent comprises incubation with an anti-CD3 antibody and an anti-CD28 antibody, or an antigen-binding fragment thereof.
38. The method of any one of embodiments 35-37, wherein the primary agent and secondary agent are present or attached on the surface of a solid support.
39. The method of embodiment 38, wherein the solid support is or comprises a bead.
40. The method of embodiment 39, wherein the ratio of beads to cells is less than 3:1.
41. A method for producing a composition of engineered T cells, the method comprising: (a) exposing an input composition comprising primary T cells with a stimulatory reagent comprising a bead having attached thereto (i) a primary agent that specifically binds to a member of a TCR complex, optionally that specifically binds to CD3 and (ii) a secondary agent that specifically binds to a T cell costimulatory molecule, wherein the ratio of beads to cells is less than 3:1 and the exposing is carried out under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, after the exposing to the stimulatory reagent is initiated; thereby producing a composition of engineered cells.
42. The method of embodiments 39-41, wherein the ratio of beads to cells is or is about 1:1.
43. The method any of embodiments 39-42, wherein the bead has attached thereto an anti-CD3 antibody and an anti-CD28 antibody, or an antigen-binding fragment thereof.
44. The method of embodiment 35 or embodiment 36, wherein the primary agent and secondary agent are reversibly bound on the surface of an oligomeric particle reagent comprising a plurality of streptavidin or streptavidin mutein molecules.
45. A method for producing a composition of engineered T cells, the method comprising: (a) exposing an input composition comprising primary T cells with a stimulatory reagent comprising an oligomeric particle reagent comprising a plurality of streptavidin or streptavidin mutein molecules, the oligomeric particle reagent having reversibly bound thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells, thereby generating a stimulated population; (b) introducing into T cells of the stimulated population, a viral vector comprising a heterologous polynucleotide encoding a recombinant protein, thereby generating a population of transformed cells; and (c) harvesting T cells of the transformed population, wherein the harvesting is carried out at a time between 48 and 120 hours, inclusive, after the exposing to the stimulatory reagent is initiated, thereby producing a composition of engineered cells.
46. The method of embodiment 44 or embodiment 45, wherein the exposing is carried out with an amount of the stimulatory reagent that is between or between about 0.1 μg and 20 μg, inclusive, per $10^6$ cells in the input composition.
47. A method for stimulating T cells, the method comprising exposing an input composition comprising T cells with a stimulatory reagent in an amount between or between about 0.1 μg and 20 μg, inclusive, per $10^6$ cells in the input composition, said stimulatory reagent comprising an oligomeric particle reagent comprising a plurality of streptavidin or streptavidin mutein molecules, wherein the exposing is carried out under conditions to stimulate T cells, thereby generating a stimulated population.
48. A method for stimulating T cells, the method comprising exposing an input composition comprising T cells with a stimulatory reagent in an amount between or between about 0.1 μg and 20 μg, inclusive, per $10^6$ cells in the input composition, said stimulatory reagent comprising an oligomeric particle reagent comprising a plurality of streptavidin or streptavidin mutein molecules having attached thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells, thereby generating a stimulated population.
49. The method of embodiment 48, wherein the input composition comprises primary T cells.
50. The method of any of embodiments 41-47, wherein subsequent to the introducing and prior to the harvesting the method further comprises incubating the population of transformed cells for up to 96 hours, optionally wherein the incubation is carried out at a temperature of about 37° C.
51. The method of embodiment 50, wherein the incubating is carried out for up to 72 hours subsequent to the introducing.
52. The method of embodiment 50, wherein the incubating is carried out for up to 48 hours subsequent to the introducing.

53. The method of embodiment 50, wherein the incubating is carried out for up to 24 hours subsequent to the introducing.
54. The method of any of embodiments 41-46 and 50-53, wherein the harvesting is carried out within 96 hours after the exposing the input composition with the stimulatory agent is initiated.
55. The method of any of embodiments 41-46 and 50-54, wherein the harvesting is carried out within 72 hours after the exposing the input composition with the stimulatory agent is initiated.
56. The method of any of embodiments 42-47 and 52-55, wherein the harvesting is carried out within 48 hours after the exposing the input composition with the stimulatory agent is initiated.
57. The method of any of embodiments 42-47 and 52-56, wherein one or both of the exposing and the introducing is carried out in the presence of one or more recombinant cytokines.
58. The method of any of embodiments 42-47 and 52-57, wherein the incubating is carried out in the presence of one or more recombinant cytokines.
59. The method of any of embodiments 42-47 and 52-58, wherein the incubating is carried out in basal media lacking one or more recombinant cytokines.
60. A method for producing a composition of engineered T cells, the method comprising:
(a) exposing an input composition comprising primary T cells with a stimulatory reagent comprising a bead having attached thereto (i) a primary agent that specifically binds to a member of a TCR complex, optionally that specifically binds to CD3 and (ii) a secondary agent that specifically binds to a T cell costimulatory molecule, wherein the ratio of beads to cells is less than 3:1 and the exposing is carried out under conditions to stimulate T cells comprising the presence of one or more recombinant cytokines, thereby generating a stimulated population;
(b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours, optionally wherein the incubation is carried out at a temperature of about 37° C., wherein the incubating is carried out in basal media lacking one or more recombinant cytokines; and (d) subsequent to the incubating, harvesting T cells of the transformed population, thereby producing a composition of engineered cells, wherein the harvesting is carried out at a time between 48 and 120 hours, inclusive, after the exposing to the stimulatory reagent is initiated; thereby producing a composition of engineered cells.
61. A method for producing a composition of engineered T cells, the method comprising:
(a) exposing an input composition comprising primary T cells with a stimulatory reagent comprising an oligomeric particle reagent comprising a plurality of streptavidin or streptavidin mutein molecules, the oligomeric particle reagent having attached thereto (i) a primary agent that specifically binds to a member of a TCR complex, optionally that specifically binds to CD3 and (ii) a secondary agent that specifically binds to a T cell costimulatory molecule, wherein the exposing is carried out under conditions to stimulate T cells comprising the presence of one or more recombinant cytokines, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of one or more recombinant cytokines; (c) incubating the population of transformed cells for up to 96 hours, optionally wherein the incubation is carried out at a temperature of about 37° C., wherein the incubating is carried out in basal media lacking one or more recombinant cytokines; and (d) subsequent to the incubating, harvesting T cells of the transformed population, thereby producing a composition of engineered cells, wherein the harvesting is carried out at a time between 48 and 120 hours, inclusive, after the exposing to the stimulatory reagent is initiated; thereby producing a composition of engineered cells.
62. The method of any of embodiments 46-59, or 61, wherein the exposing is carried out with an amount of the stimulatory reagent that is between or between about 0.4 μg and 8 μg, inclusive, per $10^6$ cells in the input composition.
63. The method of any of embodiments 46-59, 61, or 62 wherein the exposing is carried out with an amount of the stimulatory reagent that is between or between about 0.8 μg and 4 μg, inclusive, per $10^6$ cells in the input composition.
64. The method of any of embodiments 46-59, or 61-63, wherein the exposing is carried out with an amount of the stimulatory reagent that is or is about 0.8 μg per $10^6$ cells in the input composition.
65. The method of any of embodiments 57-64, wherein the one or more recombinant cytokines are human.
66. The method of any of embodiments 57-65, wherein the one or more recombinant cytokines are selected from recombinant IL-2, recombinant IL-7 and/or recombinant IL-15, optionally between 10 and 200 IU/mL recombinant IL-2; between 100 IU/mL and 1,000 IU/mL recombinant IL-7; and/or between 10 and 200 IU/mL recombinant IL-15.
67. The method of any of embodiments 57-66, wherein the one or more recombinant cytokines are or comprise recombinant IL-2, recombinant IL-7 and recombinant IL-15, optionally between 10 and 200 IU/mL recombinant IL-2; between 100 IU/mL and 1,000 IU/mL recombinant IL-7; and between 10 and 200 IU/mL recombinant IL-15.
68. The method of any of embodiments 1-67, wherein one or both of the exposing and the introducing is carried out in serum free media.
69. The method of any of embodiments 18-68, wherein the incubating is carried out in serum free media.
70. The method of any of embodiments 39-43, 50-60 or 65-69 wherein the ratio of beads to cells is from or from about 2:1 to 0.5:1.
71. The method of any of embodiments 39-43, 50-60 or 65-70, wherein the ratio of beads to cells is at or at about 1:1.
72. The method of any of embodiments 39-43, 50-60 or 65-71, wherein the bead comprises a diameter of greater than or greater than about 3.5 μm but no more than about 9 μm or no more than about 8 μm or no more than about 7 μm or no more than about 6 μm or no more than about 5 μm.

73. The method of any of embodiments 39-43, 50-60 or 65-72, wherein the bead comprises a diameter of or about 4.5 μm.
74. The method of any of embodiments 39-43, 50-60 or 65-73, wherein the bead is inert.
75. The method of any of embodiments 39-43, 50-60 or 65-74, wherein the bead is or comprises a polystyrene surface.
76. The method of any of embodiments 39-43, 50-60, or 65-75, wherein the bead is paramagnetic or superparamagnetic.
77. The method of 76, the method further comprising, prior to the harvesting, exposing the cells to a magnetic field either subsequent to or during the incubation, thereby removing the stimulatory reagent from the cells.
78. The method of any of embodiments 44-59 and 61-69, wherein the streptavidin or streptavidin mutein molecules bind to or are capable of binding to biotin, avidin, a biotin analog or mutein, an avidin analog or mutein, and/or a biologically active fragment thereof.
79. The method of any of embodiments 44-59 and 61-69, wherein each of the plurality of streptavidin mutein molecules comprise the amino acid sequence $Val^{44}$-$Thr^{45}$-$Ala^{46}$-$Arg^{47}$ or $Ile^{44}$-$Gly^{45}$-$Ala^{46}$-$Arg^{47}$ at sequence positions corresponding to positions 44 to 47 with reference to positions in streptavidin in the sequence of amino acids set forth in SEQ ID NO: 61.
80. The method of any of embodiments 44-59 and 61-69, wherein each of the plurality of the streptavidin mutein molecules comprises: a) the sequence of amino acids set forth in any of SEQ ID NOS: 62, 63, 68, 75-77, or 80-83; b) a sequence of amino acids that exhibit at least 85%, 86%, 87%, 88%, 89%, 89%, 90%, 91%, 92%, 93%, 94%, 95%, 96%, 97%, 98%, 99% or more sequence identity to any of SEQ ID NOS: 62, 63, 68, 75-77, or 80-83 and contain the amino acid sequence corresponding to $Val^{44}$-$Thr^{45}$-$Ala^{46}$-$Arg^{47}$ or $Ile^{44}$-$Gly^{45}$-$Ala^{46}$-$Arg^{47}$ and/or reversibly bind to biotin, a biotin analog or a streptavidin-binding peptide; or c) a functional fragment of a) or b) that reversibly binds to biotin, a biotin analog, or a streptavidin-binding peptide.
81. The method of any of embodiments 44-59, 61-69 or 80, wherein the plurality of streptavidin mutein molecules comprise the sequence of amino acids set forth in SEQ ID NO: 63 or 68.
82. The method of any of embodiments 44-59, 61-69, 80, or 81, wherein the primary agent and the secondary agent each comprise a streptavidin-binding peptide.
83. The method of embodiment 82, wherein the streptavidin-binding peptide selected from the group consisting of Trp-Ser-His-Pro-Gln-Phe-Glu-Lys (SEQ ID NO: 64), Ser-Ala-Trp-Ser-His-Pro-Gln-Phe-Glu-Lys-$(GlyGlyGlySer)_3$-Trp-Ser-His-Pro-Gln-Phe-Glu-Lys (SEQ ID NO:73), Trp-Ser-His-Pro-Gln-Phe-Glu-Lys-$(GlyGlyGlySer)_3$-Trp-Ser-His-Pro-Gln-Phe-Glu-Lys (SEQ ID NO: 65), Trp-Ser-His-Pro-Gln-Phe-Glu-Lys-$(GlyGlyGlySer)_2$-Trp-Ser-His-Pro-Gln-Phe-Glu-Lys (SEQ ID NO: 66) and Trp-Ser-His-Pro-Gln-Phe-Glu-Lys-$(GlyGlyGlySer)_2$Gly-Gly-Ser-Ala-Trp-Ser-His-Pro-Gln-Phe-Glu-Lys (SEQ ID NO: 67).
84. The method of any of embodiments 44-59, 61-69, or 81-83, wherein the one or both of the primary and secondary agents comprise an antibody or an antigen-binding fragment thereof.
85. The method of embodiment 84, wherein the one or more agents is or comprises a monovalent antibody fragment.
86. The method of embodiment 84 or embodiment 85, wherein one or both of the primary and secondary agent is or comprises a Fab.
87. The method of any of embodiments 44-59, 61-69, or 81-86, wherein the oligomeric particle reagent comprises a radius of greater than 60 nm, greater than 70 nm, greater than 80 nm, or greater than 90 nm.
88. The method of any of embodiments 44-59, 61-69, or 81-87, wherein the oligomeric particle reagent comprises: a radius of between 50 nm and 150 nm, between 75 nm and 125 nm, between 80 nm and 115 nm, or between 90 nm and 110 nm, inclusive; or a radius of 90 nm±15 nm, or 95 nm±20-25 nm.
89. The method of any of embodiments 44-59, 61-69, or 81-88, wherein the oligomeric particle reagent comprises a molecular weight of: at least $5\times10^7$ g/mol, or at least $1\times10^8$ g/mol; and/or between $5\times10^7$ g/mol and $5\times10^8$ g/mol, between $1\times10^8$ g/mol and $5\times10^8$ g/mol, or between $1\times10^8$ g/mol and $2\times10^8$ g/mol.
90. The method of any of embodiments 44-59, 61-69, or 81-89, wherein the oligomeric particle reagent comprises at least 500 streptavidin or streptavidin mutein tetramers, at least 1,000 streptavidin or streptavidin mutein tetramers, at least 1,500 streptavidin or streptavidin mutein tetramers, or at least 2,000 streptavidin or streptavidin mutein tetramers; and/or; between 1,000 and 20,000 streptavidin or streptavidin mutein tetramers, between 1,000 and 10,000 streptavidin or streptavidin mutein tetramers, or between 2,000 and 5,000 streptavidin or streptavidin mutein tetramers.
91. The method of any of embodiments 44-59, 61-69, or 81-90, the method further comprising adding a substance to the cells either subsequent to or during at least a portion of the incubating, wherein the substance is capable of reversing the bond between the primary and secondary agent and the oligomeric particle reagent.
92. The method of embodiment 91, wherein the substance is a free binding partner and/or is a competition agent.
93. The method of embodiment 91 or embodiment 92, wherein the presence of the substance terminates or lessens the signal induced or modulated by the primary and secondary agent in the T cells.
94. The method of any of embodiments 91-93, wherein the substance is or comprises a streptavidin-binding peptide, biotin or a biologically active fragment, or a biotin analog or biologically active fragment.
95. The method of embodiment 94, wherein the substance is or comprises a streptavidin-binding peptide and the streptavidin-binding peptide is selected from the group consisting of Trp-Ser-His-Pro-Gln-Phe-Glu-Lys (SEQ ID NO: 64), Ser-Ala-Trp-Ser-His-Pro-Gln-Phe-Glu-Lys-$(GlyGlyGlySer)_3$-Trp-Ser-His-Pro-Gln-Phe-Glu-Lys (SEQ ID NO:73), Trp-Ser-His-Pro-Gln-Phe-Glu-Lys-$(GlyGlyGlySer)_3$-Trp-Ser-His-Pro-Gln-Phe-Glu-Lys (SEQ ID NO: 65), Trp-Ser-His-Pro-Gln-Phe-Glu-Lys-$(GlyGlyGlySer)_2$-Trp-Ser-His-Pro-Gln-Phe-Glu-Lys (SEQ ID NO: 66) and Trp-Ser-His-Pro-Gin-Phe-Glu-Lys-$(GlyGlyGlySer)_2$Gly-Gly-Ser-Ala-Trp-Ser-His-Pro-Gln-Phe-Glu-Lys (SEQ ID NO: 67).
96. The method of embodiment 94, wherein the substance is or comprises biotin or a biologically active fragment, or a biotin analog or biologically active fragment.
97. The method of any of embodiments 91-96, wherein the substance is added between or between about 42 hours and 120 hours, inclusive, after the exposing to the stimulatory agent is initiated.

98. The method of any of embodiments 91-97, wherein the substance is added between or between about 72 hours and 96 hours after the exposing to the stimulatory agent is initiated.

99. The method of any of embodiments 91-98, wherein the substance is added or is added about 48 hours after the exposing to the stimulatory agent.

100. The method of any of embodiments 91-99, wherein the substance is added or is added about 72 hours after the exposing to the stimulatory agent.

101. The method of any of embodiments 91-100, wherein the substance is added or is added about 96 hours after the exposing to the stimulatory agent.

102. The method of any of embodiments 91-101, wherein the substance is added subsequent to the incubation and prior to the harvesting.

103. The method of any of embodiments 91-102, wherein the substance is added during at least a portion of the incubating, and wherein the incubating continues after the substance is added.

104. The method of embodiment 102, wherein, after the substance is added, the incubating is performed in the presence of basal media lacking recombinant cytokines.

105. A method for producing a composition of engineered T cells, the method comprising: (a) exposing an input composition comprising primary T cells with between or between about 0.02 μg and 8 μg per $10^6$ cells of a stimulatory reagent comprising an oligomeric particle reagent comprising a plurality of streptavidin or streptavidin mutein molecules, the oligomeric particle reagent having attached thereto (i) a primary agent that specifically binds to CD3 and (ii) a secondary agent that specifically binds CD28, wherein the exposing is carried out in the presence of serum free media with recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for, optionally wherein the incubation is carried out at a temperature of about 37° C., for between 24 hours and 96 hours, and adding a substance comprising biotin or a biologically active fragment thereof, optionally a D-biotin, or a biotin analog or biologically active fragment thereof during at least a portion of the incubating; and (d) subsequent to the incubating, harvesting T cells of the transformed population, thereby producing a composition of engineered cells, wherein the harvesting is carried out at a time between 72 and 96 hours, inclusive, after the exposing to the stimulatory reagent is initiated; thereby producing a composition of engineered cells.

106. The method of any of embodiments 10-105, wherein the input composition comprises at least $300\times10^6$ viable primary T cells.

107. The method of any of embodiments 10-106, wherein the input composition comprises or comprises about $600\times10^6$ viable primary T cells.

108. The method of any of embodiments 1-107 wherein the input composition comprises a ratio of between 1.5:1 and 2.0 to 1 CD4+ to CD8+ cells 109. The method of any of embodiments 1-108, wherein the input composition comprises a ratio of between 1.2:1 and 0.8:1 CD4+ to CD8+ cells, optionally at or about 1:1 CD4+ to CD8+ T cells.

110. A method for producing a composition of engineered T cells, the method comprising: (a) exposing an input composition comprising at least $300\times10^6$ primary T cells, said primary T cells comprising a ratio of or of about 1:1 CD4+ T cells to CD8+ T cells, with between or between about 0.4 μg and 8 μg per $10^6$ cells of a stimulatory reagent comprising an oligomeric particle reagent comprising a plurality of streptavidin or streptavidin mutein molecules, the oligomeric particle reagent having attached thereto (i) a primary agent that specifically binds to CD3 and (ii) a secondary agent that specifically binds CD28, wherein the input composition comprises a ratio of between 2:1 and 1:2 CD4+ to CD8+ T cells and comprises at least $300\times10^6$ CD4+ and CD8+ T cells, and wherein the exposing is carried out in the presence of serum free media comprising recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for between or between about 24 hour to 72 hours, optionally wherein the incubation is carried out at a temperature of about 37° C.; and adding a substance comprising biotin or a biologically active fragment thereof, optionally a D-biotin, or a biotin analog or biologically active fragment thereof during at least a portion of the incubation, wherein the adding is carried out at a time between 48 and 72 hours, inclusive, after the exposing to the stimulatory reagent is initiated; and (d) subsequent to the incubating, harvesting T cells of the transformed population, thereby producing a composition of engineered cells, wherein the harvesting is carried out at a time between 72 and 96 hours, inclusive, after the exposing to the stimulatory reagent is initiated; thereby producing a composition of engineered cells.

111. The method of any of embodiments 105-110, wherein the substance is added or is added about 48 hours after the exposing to the stimulatory agent.

112. The method of any of embodiments 105-110, wherein the substance is added or is added about 72 hours after the exposing to the stimulatory agent.

113. The method of any of embodiments 105-110, wherein the substance is added or is added about 96 hours after the exposing to the stimulatory agent.

114. A method for producing a composition of engineered T cells, the method comprising: (a) exposing an input composition comprising at least $300\times10^6$ primary T cells, said primary T cells comprising a ratio of or of about 1:1 CD4+ T cells to CD8+ T cells, a stimulatory reagent comprising a paramagnetic bead at a ratio of beads to cells is from or from about 2:1 to 0.5:1, wherein the bead is an inert paramagnetic bead comprising a polystyrene coating and a diameter of or of about 4.5 μm, the bead having attached thereto (i) an anti-CD3 antibody or antigen-binding fragment thereof and an anti-CD28 antibody or antigen-binding fragment thereof, wherein the input composition comprises a ratio of between 2:1 and 1:2 CD4+ to CD8+ T cells and comprises at least $300\times10^6$ CD4+ and CD8+ T cells, and wherein the exposing is carried out in the presence of serum free media comprising recombinant IL-2, IL-7, and IL-15, thereby generating a stimulated population; (b) introducing into T cells of the stimulated population, a viral vector comprising a heterologous polynucleotide encoding a recombinant protein, thereby generating a population of transformed cells, wherein the introducing is carried out in the presence of serum free media with recombinant IL-2, IL-7, and IL-15; (c) incubating the population of transformed cells under static conditions for between 48 hours and 72 hours, inclusive, optionally wherein the incubation is carried out at a temperature of about 37° C.; (d) subsequent to the incubating, exposing the cells to a magnetic field to remove the stimulatory reagent from the cells and then harvesting the T cells, thereby producing a composition of engineered cells, wherein the harvesting is carried out at a time between 72 and 96 hours, inclusive, after the exposing to the stimulatory reagent is initiated; thereby producing a composition of engineered cells.

115. The method of embodiment 113 or 114, wherein at least a portion of the incubating is performed in the presence of serum free media comprising recombinant IL-2, IL-7, and IL-15.

116. The method of any of embodiments 113-115, wherein the incubating is carried out in basal media lacking recombinant cytokines.

117. The method of any of embodiments 44-59, 61-69, 81-113, 115, or 116, wherein the incubating is carried out for or for about 24 hours subsequent to the introducing.

118. The method of any of embodiments 18-117, wherein the incubating is carried out for or for about 48 hours subsequent to the introducing.

119. The method of any of embodiments 18-117, wherein the incubating is carried out for or for about 72 hours subsequent to the introducing.

120 The method of any of embodiments 1-119, wherein prior to the exposing to the stimulatory reagent, enriching CD4+ or CD8+ T cells from a biological sample, wherein the enriching comprises: (a) performing a first selection in a closed system, said first selection comprising enriching for one of (i) CD4+ cells and (ii) CD8+ cells from a sample containing primary human T cells, the enrichment thereby generating a first selected population and a non-selected population; and (b) performing a second selection in the closed system, said second selection comprising enriching for the other of (i) CD4+ cells and (ii) CD8+ cells from the non-selected population, the enrichment thereby generating a second selected population, wherein the enriching produces separate enriched populations of CD4+ T cells and for CD8+ T cells, wherein the separate enriched populations each comprise cells from one of the of the first selected population or the second selected population, and wherein the input composition comprises cells from one or more of the enriched population of CD4+ T cells and the enriched population of CD8+ T cells.

121. The method of embodiment 120, wherein the separate enriched populations of CD4+ T cells and CD8+ T cells are combined, thereby producing the input composition.

122. The method of embodiment 121, wherein said combining is performed in the closed system, optionally wherein the closed system is automated 123. The method of any of embodiments 120-122, wherein enriching cells in the first and/or second selection comprises performing positive selection or negative selection based on expression of a cell surface marker.

124. The method of any of embodiments 120-123, wherein enriching cells in the first or second selection comprises performing a plurality of positive or negative selection steps based on expression of a cell surface marker or markers to enrich for CD4+ or CD8+ cells.

125. The method of any of embodiments 120-124, wherein the enriching cells in the first and/or second selection comprises immunoaffinity-based selection.

126. The method of embodiment 125, wherein the enriching cells in the first and second selections comprises immunoaffinity-based selection.

127. The method of any of embodiments 120-126, wherein the immunoaffinity-based selection is effected by contacting cells with an antibody immobilized on or attached to an affinity chromatography matrix, said antibody capable of specifically binding to a cell surface marker to effect positive or negative selection of CD4+ or CD8+ cells.

128. The method of embodiment 127, further comprising, after contacting cells in the sample to an affinity chromatography matrix in the first selection and/or second selection, applying the competition reagent to disrupt the bond between the binding partner and binding reagent, thereby recovering the selected cells from the matrix.

129. The method of any of embodiments 120-128, wherein: (a) the enriching for the CD4+ cells comprises positive selection based on surface expression of CD4; (b) enriching for the CD8+ cells comprises positive selection based on surface expression of CD8; or both (a) and (b).

130. The method of any of embodiments 1-119, wherein prior to the exposing to the stimulatory reagent, enriching CD4+ or CD8+ T cells from a biological sample, wherein the enriching comprises contacting cells of said sample with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample; and recovering cells bound to the first and/or the second immunoaffinity reagent, thereby generating an enriched composition comprising CD4+ cells and CD8+ cells, and wherein the input composition comprises cells of the enriched composition comprising CD4+ cells and CD8+ cells.

131. The method of embodiment 130, wherein each of the immunoaffinity reagents comprises an antibody or antigen-binding fragment thereof.

132. The method of embodiment 130 or 131, wherein the immunoaffinity reagents are immobilized on the outside surface of a bead.

133. The method of embodiment 132, wherein the bead is a magnetic bead.

134. The method of embodiment 133, wherein the recovering cells bound to the first or the second immunoaffinity reagent comprises exposing the cells to a magnetic field.

134a. The method of any of embodiments 1-119, wherein the method comprises prior to the exposing to the stimulatory reagent, enriching CD3+ T cells from a biological sample, wherein the enriching comprises:

performing a selection in a closed system, said selection comprising enriching for CD3+ cells from a sample containing primary human T cells, the enrichment thereby generating a selected population and a non-selected population, wherein the enriched population comprises cells from the selected population, and wherein the input composition comprises cells from the enriched population of CD3+ T cells.

134b. The method of any of embodiments 1-119, wherein the method comprises prior to the exposing to the stimulatory reagent, enriching CD3+ T cells from a biological sample, wherein the enriching comprises contacting cells of said sample with an immunoaffinity reagent that specifically binds to CD3 in an incubation composition, under conditions whereby the immunoaffinity reagent specifically binds to CD3 on the surface of cells in the sample; and recovering cells bound to the immunoaffinity reagent, thereby generating an enriched composition comprising CD3+ cells, and wherein the input composition comprises cells of the enriched composition comprising CD3+ cells.

134c. The method of embodiment 134b, wherein the immunoaffinity reagent comprises an antibody or antigen-binding fragment thereof that specifically binds to CD3.

134d. The method of embodiment 134b or 134c, wherein the immunoaffinity reagent is immobilized on the outside surface of a bead.

134e. The method of embodiment 134d, wherein the bead is a magnetic bead.

134f. The method of embodiment 134e, wherein the recovering cells bound to the immunoaffinity reagent comprises exposing the cells to a magnetic field.

134g. The method of any one of embodiments 134a-134c, wherein the enriching cells in the selection comprises immunoaffinity-based selection.

134h. The method of embodiment 134g, wherein the immunoaffinity-based selection is effected by contacting cells with an antibody or antigen-binding fragment thereof immobilized on or attached to an affinity chromatography matrix, said antibody or antigen-binding fragment thereof capable of specifically binding to a cell surface marker to effect positive or negative selection of CD3+ cells.

134i. The method of embodiment 134h, further comprising, after contacting cells in the sample to an affinity chromatography matrix in the selection, applying a competition reagent to disrupt the bond between a binding partner and a binding reagent, thereby recovering the selected cells from the matrix.

134j. The method of any one of embodiments 134a-134c, wherein the enriching for the CD3+ cells comprises positive selection based on surface expression of CD3.

134k. The method of embodiment 134j, wherein the enriching for the CD3+ T cells does not comprises positive selection and/or negative selection based on surface expression of another T cell marker.

134l. The method of embodiment 134j or 134k, wherein the enriching for the CD3+ T cells does not comprises positive selection based on surface expression of CD4 and/or CD8.

135. The method of any of embodiments 120-134l, wherein the biological sample comprises primary T cells obtained from a subject, optionally a human subject.

136. The method of any of embodiments 120-135, wherein the biological sample is or comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product.

137. The method of any of embodiments 44-59, 61-69, 81-113, 115-136, wherein the harvesting is carried out at or at about 48 hours after the exposing to the stimulatory agent is initiated.

138. The method of any of embodiments 44-59, 61-69, 81-113, 115-136, wherein the harvesting is carried out at or at about two days or at or at about three days after the exposing to the stimulatory agent is initiated.

139. The method of any of embodiments 18-138, wherein the harvesting is carried out at or at about 72 hours after the exposing to the stimulatory agent is initiated.

140. The method of any of embodiments 18-138, wherein the harvesting is carried out at or at about 48 hours after the exposing to the stimulatory agent is initiated.

141. The method of any of embodiments 16-140, wherein the harvesting is carried out at a time when integrated vector is detected in the genome but prior to achieving stable iVCN per diploid genome.

142. The method of any of embodiments 16-140, wherein the harvesting is carried out at a time when the fraction of integrated vector copy number (iVCN) to total VCN in the population of transformed cells, on average, is less than 0.8.

143. The method of any of embodiments 16-142, wherein the harvesting is carried out at a time when the iVCN of the population of transformed cells, on average, is less than or less than about 2.0 copies per diploid genome.

144. The method of any of embodiments 16-142, wherein the harvesting is carried out at a time when the iVCN of the population of transformed cells, on average, is less than or less than about 1.5 copies per diploid genome.

145. The method of any of embodiments 16-142, wherein the harvesting is carried out at a time when the iVCN of the population of transformed cells, on average, is less than or less than about 1.0 copy per diploid genome.

146. The method of any of embodiments 16-142, wherein the harvesting is carried out at a time when the iVCN of the population of transformed cells, on average, is less than or less than about 0.75 copies per diploid genome.

147. The method of any of embodiments 16-142, wherein the harvesting is carried out at a time when the iVCN of the population of transformed cells, on average, is less than or less than about 0.5 copies per diploid genome.

148 The method of embodiment, the method of any of embodiments 1-147, wherein harvesting the cells comprises removing cellular debris by rinsing or washing the cells.

149. The method of any of embodiments 30-148, wherein the cells are harvested at a time when the percentage of naïve-like cells is greater than or greater than about 60% among total T cells in the population, total CD4+ T cells in the population or total CD8+ T cells, or of recombinant protein-expressing cells thereof, in the population.
150. The method of any of embodiments 30-148, wherein the cells are harvested at a time when the percentage of naïve like T cells is greater than or greater than about 60% among total T cells in the population, total CD4+ T cells in the population or total CD8+ T cells, or of recombinant protein-expressing cells thereof, in the population.
151. The method of embodiment 150, wherein at the time of harvesting: the percentage of naïve-like T cells is greater than or greater than about 60% among total recombinant protein-expressing cells in the population, optionally greater than or greater than about 65%, 70%, 80%, 90% or 95% total recombinant protein-expressing T cells in the population; the percentage of naïve-like T cells is greater than or greater than about 60% among total recombinant protein-expressing CD4+ T cells in the population, optionally greater than or greater than about 65%, 70%, 80%, 90% or 95% total recombinant protein-expressing CD4+ cells in the population; or the percentage of naïve-like T cells is greater than or greater than about 60% among total recombinant protein-expressing CD8+ T cells in the population, optionally greater than or greater than about 65%, 70%, 80%, 90% or 95% total recombinant protein-expressing CD8+ cells in the population.
152. The method of embodiment 150 or 151, wherein the naïve-like T cells comprise CD27+CCR7+ T cells.
153. The method of any of embodiments 1-152, further comprising formulating cells of the output composition for cryopreservation and/or administration to a subject, optionally in the presence of a pharmaceutically acceptable excipient.
154. The method of embodiment 153, wherein the cells of the output composition are formulated in the presence of a cryoprotectant.
155. The method of embodiment 154, wherein the cryoprotectant comprises DMSO.
156. The method of any of embodiments 153-155, wherein the cells of the output composition are formulated in a container, optionally a vial or a bag.
157. The method of any of embodiments 1-156, wherein the recombinant protein is a recombinant receptor is capable of binding to a target antigen that is associated with, specific to, and/or expressed on a cell or tissue of a disease, disorder or condition.
158. The method of embodiment 157, wherein the disease, disorder or condition is an infectious disease or disorder, an autoimmune disease, an inflammatory disease, or a tumor or a cancer.
159. The method of embodiment 158 wherein the target antigen is a tumor antigen.
160. The method of any of embodiments 156-158, wherein the target antigen is selected from among $\alpha v\beta 6$ integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD133, CD138, CD171, chondroitin sulfate proteoglycan 4 (CSPG4), epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrin receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), glypican-3 (GPC3), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22R$\alpha$), IL-13 receptor alpha 2 (IL-13R$\alpha$2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, MAGE-A10, mesothelin (MSLN), c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), Tyrosinase related protein 1 (TRP1, also known as TYRP1 or gp75), Tyrosinase related protein 2 (TRP2, also known as dopachrome tautomerase, dopachrome delta-isomerase or DCT), vascular endothelial growth factor receptor (VEGFR), vascular endothelial growth factor receptor 2 (VEGFR2), Wilms Tumor 1 (WT-1), a pathogen-specific or pathogen-expressed antigen, or an antigen associated with a universal tag, and/or biotinylated molecules, and/or molecules expressed by HIV, HCV, HBV or other pathogens.
161. The method of any of embodiments 1-47 or 50-160, wherein the recombinant protein is or comprises a functional non-TCR antigen receptor or a TCR or antigen-binding fragment thereof.
162. The method of any of embodiments 1-47 or 50-161, wherein the recombinant protein is a chimeric antigen receptor (CAR).
163. The method of any of embodiments 1-47 or 50-162, wherein the recombinant protein is an anti-BCMA CAR.
164. The method of any of embodiments 1-47 or 50-162, wherein the recombinant protein is an anti-CD19 CAR.
165. The method of any of embodiments 94-96, wherein the chimeric antigen receptor comprises an extracellular domain comprising an antigen-binding domain, a spacer and/or a hinge region, a transmembrane domain, and an intracellular signaling domain comprising a costimulatory signaling region.
166. The method of embodiment 165, wherein the extracellular domain comprising an antigen-binding domain comprises an scFv.

167. The method of embodiment 165 or 166, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

168. The method of embodiment 167, wherein the intracellular signaling domain is or comprises an intracellular signaling domain of a CD3 chain, optionally a CD3-zeta (CD35) chain, or a signaling portion thereof.

169. The method of any of embodiments 166-168, wherein the costimulatory signaling region comprises an intracellular signaling domain of a CD28, a 4-1BB or an ICOS or a signaling portion thereof.

170. The method of any of embodiments 34-40 or 68-169, wherein the serum free media comprises:

0.5 mM to 5 mM of a dipeptide form of L-glutamine in a basal media;

0.5 mM to 5 mM L-glutamine; and at least one protein, wherein the media is free of serum.

171. The method of any of embodiments 28-169, wherein the basal media lacking one or more recombinant cytokines comprises L-glutamine, optionally at a concentration of from about 0.5 mM to about 5 mM, optionally at a concentration of about 2 mM.

172. The method of any of embodiments 28-169 and 171, wherein the basal media lacking one or more recombinant cytokines is free of serum.

173. The method of any of embodiments 30-172, wherein the basal media further comprises at least one protein selected from one or more of albumin, insulin or transferrin, optionally one or more of a human or recombinant albumin, insulin or transferrin.

174. A composition comprising engineered cells produced by a method of any of embodiments 1-173.

174. A therapeutic T cell composition produced by the method of any of embodiments 1-173.

175. The therapeutic T cell composition of embodiment 174, wherein at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant protein, are naïve-like T cells or are T cells that are surface positive for a marker expressed on naïve-like T cells.

176. The therapeutic T cell composition of embodiment 175, wherein the naïve-like T cells:

are surface positive for a T cell activation marker selected from the group consisting of CD45RA, CD27, CD28, and CCR7; and/or are surface negative for a marker selected from the group consisting of CD25, CD45RO, CD56, CD62L, KLRG1; and/or have low expression of CD95; and/or are negative for intracellular expression of a cytokine selected from the group consisting of IL-2, IFN-γ, IL-4, IL-10.

177. The therapeutic T cell composition of embodiment 175, wherein the marker expressed on naïve-like T cell is selected from the group consisting of CD45RA, CD27, CD28, and CCR7.

178. The therapeutic T cell composition of any of embodiments 174-177, wherein the naïve-like T cells or the T cells that are surface positive for a marker expressed on naïve-like T cells are CCR7+CD45RA+, CD27+ CCR7+ or CD62L−CCR7+.

179. The therapeutic composition of any of embodiments 174-178, wherein at least 50%, 60%, 70%, 80% or 90% of the total receptor$^+$/CD8$^+$ cells in the composition are naïve-like T cells or are surface positive for a marker expressed on naïve-like T cells and at least 15%, 20%, 30%, 40%, 50%, 60%, 70%, 80% or 90% of the total receptor$^+$/CD4$^+$ cells in the composition are naïve-like T cells or are surface positive for a marker expressed on naïve-like T cells 180. A therapeutic T cell composition comprising CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are naïve-like T cells or are surface positive for a marker expressed on naïve-like T cells and at least 30%, 40%, 50%, 60%, 70%, 80% or 90% of the total receptor$^+$/CD4$^+$ cells in the composition are naïve-like T cells or are surface positive for a marker expressed on naïve-like T cells.

181. The therapeutic T cell composition of embodiment 180, wherein at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are naïve-like T cells or are T cells that are surface positive for a marker expressed on naïve-like T cells.

182. The therapeutic T cell composition of any of embodiments 179-181, wherein at least 60% of the total receptor$^+$/CD8$^+$ cells in the composition are naïve-like T cells or are surface positive for a marker expressed on naïve-like T cells and 30% of the total receptor$^+$/CD4$^+$ cells in the composition are naïve-like T cells or are surface positive for a marker expressed on naïve-like T cells.

183. The therapeutic T cell composition of any of embodiments 179-181, wherein at least 70% of the total receptor$^+$/CD8$^+$ cells in the composition are naïve-like T cells or are surface positive for a marker expressed on naïve-like T cells and 40% of the total receptor$^+$/CD4$^+$ cells in the composition are naïve-like T cells or are surface positive for a marker expressed on naïve-like T cells.

184. The therapeutic T cell composition of any of embodiments 179-181, wherein at least 70% of the total receptor$^+$/CD8$^+$ cells in the composition are naïve-like T cells or are surface positive for a marker expressed on naïve-like T cells and 50% of the total receptor$^+$/CD4$^+$ cells in the composition are naïve-like T cells or are surface positive for a marker expressed on naïve-like T cells.

185. The therapeutic T cell composition of any of embodiments 179-181, wherein at least 70% of the total receptor$^+$/CD8$^+$ cells in the composition are naïve-like T cells or are surface positive for a marker expressed on naïve-like T cells and 60% of the total receptor$^+$/CD4$^+$ cells in the composition are naïve-like T cells or are surface positive for a marker expressed on naïve-like T cells.

186. The therapeutic T cell composition of any of embodiments 179-181, wherein at least 70% of the total receptor$^+$/CD8$^+$ cells in the composition are naïve-like T cells or are surface positive for a marker expressed on naïve-like T cells and 70% of the total receptor$^+$/CD4$^+$ cells in the composition are naïve-like T cells or are surface positive for a marker expressed on naïve-like T cells.

187. The therapeutic T cell composition of any of embodiments 179-186, wherein the naïve-like T cells:

are surface positive for a T cell activation marker selected from the group consisting of CD45RA, CD27, CD28, and CCR7; and/or are surface negative for a marker selected from the group consisting of CD25, CD45RO, CD56, CD62L, KLRG1; and/or have low expression of CD95; and/or are negative for intracellular expression of a cytokine selected from the group consisting of IL-2, IFN-γ, IL-4, IL-10.

188. The therapeutic T cell composition of any of embodiments 179-187, wherein the marker expressed on naïve-like T cell is selected from the group consisting of CD45RA, CD27, CD28, and CCR7.

189. The method of any of embodiments 179-188, wherein the receptor$^+$/CD4$^+$ T cells or the receptor$^+$/CD4$^+$ T cells that are naïve-like T cells or that are surface positive for a marker expressed on naïve-like T cells are CCR7+CD45RA+, CD27+CCR7+ or CD62L− CCR7+.

190. The method of any of embodiments 179-189, wherein the receptor$^+$/CD4$^+$ T cells or the receptor$^+$/CD4$^+$ T cells that are naïve-like T cells or that are surface positive for a marker expressed on naïve-like T cells are CD27+CCR7+.

191. The method of any of embodiments 179-190, wherein the receptor$^+$/CD8$^+$ T cells or the receptor$^+$/CD8$^+$ T cells that are naïve-like T cells or that are surface positive for a marker expressed on naïve-like T cells are CCR7+CD45RA+, CD27+CCR7+ or CD62L−CCR7+.

192. The method of any of embodiments 179-191, wherein the receptor$^+$/CD8$^+$ T cells or the receptor$^+$/CD8$^+$ T cells that are naïve-like T cells or that are surface positive for a marker expressed on naïve-like T cells are CD27+CCR7+.

193. A therapeutic T cell composition comprising CD4+ T cells expressing a recombinant receptor and CD8+ T cells expressing a recombinant receptor, wherein at least 50%, 60%, 70%, 80% or 90% of the total receptor$^+$/CD8$^+$ cells in the composition are CD27+CCR7+ and at least 30%, 40%, 50%, 60%, 70%, 80% or 90% of the total receptor$^+$/CD4$^+$ cells in the composition are CD27+CCR7+, optionally wherein at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD3+ T cells.

194. The therapeutic T cell composition of embodiment 193, wherein at least or at least about 80%, at least or at least about 85%, at least or at least about 90%, at least or at least about 95%, at least or at least about 96%, at least or at least about 97%, at least or at least about 98%, at least or at least about 99%, about 100%, or 100% of the cells in the composition are CD4+ T cells and CD8+ T cells.

195. The therapeutic T cell composition of embodiment 193 or 194, wherein at least or at least about 90% of the cells in the composition are CD4+ T cells and CD8+ T cells, at least or at least about 60% of the total receptor$^+$/CD8$^+$ cells in the composition are CD27+CCR7+, and at least or at least about 40% of the total receptor$^+$/CD4$^+$ cells in the composition are CD27+CCR7+.

196. The therapeutic T cell composition of any one of embodiments 193-195, wherein at least or at least about 95% of the cells in the composition are CD4+ T cells and CD8+ T cells, at least or at least about 65% of the total receptor$^+$/CD8$^+$ cells in the composition are CD27+CCR7+, and at least or at least about 45% of the total receptor$^+$/CD4$^+$ cells in the composition are CD27+CCR7+.

197. The therapeutic T cell composition of any one of embodiments 193-196, wherein at least or at least about 98% of the cells in the composition are CD4+ T cells and CD8+ T cells, at least or at least about 70%, at least or at least about 75%, at least or at least about 80%, or at least or at least about 85% of the total receptor$^+$/CD8$^+$ cells in the composition are CD27+CCR7+, and at least or at least about 50%, at least or at least about 55%, at least or at least about 60%, or at least or at least about 65% of the total receptor$^+$/CD4$^+$ cells in the composition are CD27+CCR7+.

198. The therapeutic T cell composition of any one of embodiments 193-197, wherein at least or at least about 98% of the cells in the composition are CD4+ T cells and CD8+ T cells, at least or at least about 75% of the total receptor$^+$/CD8$^+$ cells in the composition are CD27+CCR7+, and at least or at least about 55% of the total receptor$^+$/CD4$^+$ cells in the composition are CD27+CCR7+.

199. The therapeutic T cell composition of any one of embodiments 193-198, wherein at least or at least about 98% of the cells in the composition are CD4+ T cells and CD8+ T cells, at least or at least about 80% of the total receptor$^+$/CD8$^+$ cells in the composition are CD27+CCR7+, and at least or at least about 60% of the total receptor$^+$/CD4$^+$ cells in the composition are CD27+CCR7+.

200. The therapeutic T cell composition of any one of embodiments 193-199, wherein at least or at least about 98% of the cells in the composition are CD4+ T cells and CD8+ T cells, at least or at least about 85% of the total receptor$^+$/CD8$^+$ cells in the composition are CD27+CCR7+, and at least or at least about 65% of the total receptor$^+$/CD4$^+$ cells in the composition are CD27+CCR7+.

201. The therapeutic T cell composition of any one of embodiments 193-200, wherein at least or at least about 98% of the cells in the composition are CD4+ T cells and CD8+ T cells, at least or at least about 90% of the total receptor$^+$/CD8$^+$ cells in the composition are CD27+CCR7+, and at least or at least about 70% of the total receptor$^+$/CD4$^+$ cells in the composition are CD27+CCR7+.

202. The therapeutic T cell composition of embodiment 193, wherein at least 90% of the cells in the composition are CD4+ T cells and CD8+ T cells, at least 60% of the total receptor$^+$/CD8$^+$ cells in the composition are CD27+CCR7+ and at least 40% of the total receptor$^+$/CD4$^+$ cells in the composition are CD27+CCR7+.

203. The therapeutic T cell composition of embodiment 193, wherein at least 90% of the cells in the composition are CD4+ T cells and CD8+ T cells, at least 70% of the total receptor$^+$/CD8$^+$ cells in the composition are CD27+CCR7+ and at least 50% of the total receptor$^+$/CD4$^+$ cells in the composition are CD27+CCR7+.

204. The therapeutic T cell composition of embodiment 193, wherein at least 90% of the cells in the composition are CD4+ T cells and CD8+ T cells, at least 70% of the total receptor$^+$/CD8$^+$ cells in the composition are CD27+CCR7+ and at least 60% of the total receptor$^+$/CD4$^+$ cells in the composition are CD27+CCR7+.
205. The therapeutic T cell composition of embodiment 193, wherein at least 95% of the cells in the composition are CD4+ T cells and CD8+ T cells, at least 70% of the total receptor$^+$/CD8$^+$ cells in the composition are CD27+CCR7+ and at least 70% of the total receptor$^+$/CD4$^+$ cells in the composition are CD27+CCR7+.
206. The therapeutic T cell composition of embodiment 193, wherein at least 95% of the cells in the composition are CD4+ T cells and CD8+ T cells, at least 80% of the total receptor$^+$/CD8$^+$ cells in the composition are CD27+CCR7+ and at least 80% of the total receptor$^+$/CD4$^+$ cells in the composition are CD27+CCR7+.
207. The therapeutic T cell composition of any of embodiments 193-206, wherein at least at or about, or at or about, 40%, 50%, 60%, 70%, 80%, 85%, 90%, 91%, 92%, 93%, 94%, 95%, 96%, 97%, 98%, 99% or 100% of the total number of T cells in the composition or of the total number of T cells in the composition expressing the recombinant receptor, are CD27+CCR7+.
208. The therapeutic T cell composition of any of embodiments 174-207, wherein the ratio of receptor$^+$/CD4$^+$ T cells to receptor$^+$/CD8$^+$ T cells in the composition is between about 1:3 and about 3:1
209. The therapeutic T cell composition of any of embodiments 174-207, wherein the ratio of receptor$^+$/CD4$^+$ T cells to receptor$^+$/CD8$^+$ T cells in the composition is between about 1:2 and about 2:1.
210. The therapeutic T cell composition of any of embodiments 174-207, wherein the ratio of receptor$^+$/CD4$^+$ T cells to receptor$^+$/CD8$^+$ T cells in the composition is at or about 1:1.
211. The therapeutic T cell composition of any of embodiments 174-210, wherein the composition comprises one or more unit doses of cells.
212. The therapeutic T cell composition of embodiment 211, wherein the unit dose comprises between or between about $1\times10^4$ and $50\times10^6$ T cells.
213. The therapeutic T cell composition of any of embodiments 174-212, wherein the recombinant protein is or comprises a chimeric receptor and/or a recombinant antigen receptor.
214. The composition of any of embodiments 174-213, wherein the recombinant protein is capable of binding to a target antigen that is associated with, specific to, and/or expressed on a cell or tissue of a disease, disorder or condition.
215. The composition of embodiment 214, wherein the disease, disorder or condition is an infectious disease or disorder, an autoimmune disease, an inflammatory disease, or a tumor or a cancer.
216. The composition of embodiment 214 or embodiment 215, wherein the target antigen is a tumor antigen.
217. The composition of any of embodiments 214-216, wherein the target antigen is selected from among αvβ6 integrin (avb6 integrin), B cell maturation antigen (BCMA), B7-H3, B7-H6, carbonic anhydrase 9 (CA9, also known as CAIX or G250), a cancer-testis antigen, cancer/testis antigen 1B (CTAG, also known as NY-ESO-1 and LAGE-2), carcinoembryonic antigen (CEA), a cyclin, cyclin A2, C—C Motif Chemokine Ligand 1 (CCL-1), CD19, CD20, CD22, CD23, CD24, CD30, CD33, CD38, CD44, CD44v6, CD44v7/8, CD123, CD138, CD171, epidermal growth factor protein (EGFR), type III epidermal growth factor receptor mutation (EGFR vIII), epithelial glycoprotein 2 (EPG-2), epithelial glycoprotein 40 (EPG-40), ephrinB2, ephrine receptor A2 (EPHa2), estrogen receptor, Fc receptor like 5 (FCRL5; also known as Fc receptor homolog 5 or FCRH5), fetal acetylcholine receptor (fetal AchR), a folate binding protein (FBP), folate receptor alpha, ganglioside GD2, O-acetylated GD2 (OGD2), ganglioside GD3, glycoprotein 100 (gp100), G Protein Coupled Receptor 5D (GPRC5D), Her2/neu (receptor tyrosine kinase erb-B2), Her3 (erb-B3), Her4 (erb-B4), erbB dimers, Human high molecular weight-melanoma-associated antigen (HMW-MAA), hepatitis B surface antigen, Human leukocyte antigen A1 (HLA-A1), Human leukocyte antigen A2 (HLA-A2), IL-22 receptor alpha (IL-22Ra), IL-13 receptor alpha 2 (IL-13Ra2), kinase insert domain receptor (kdr), kappa light chain, L1 cell adhesion molecule (L1-CAM), CE7 epitope of L1-CAM, Leucine Rich Repeat Containing 8 Family Member A (LRRC8A), Lewis Y, Melanoma-associated antigen (MAGE)-A1, MAGE-A3, MAGE-A6, mesothelin, c-Met, murine cytomegalovirus (CMV), mucin 1 (MUC1), MUC16, natural killer group 2 member D (NKG2D) ligands, melan A (MART-1), neural cell adhesion molecule (NCAM), oncofetal antigen, Preferentially expressed antigen of melanoma (PRAME), progesterone receptor, a prostate specific antigen, prostate stem cell antigen (PSCA), prostate specific membrane antigen (PSMA), Receptor Tyrosine Kinase Like Orphan Receptor 1 (ROR1), survivin, Trophoblast glycoprotein (TPBG also known as 5T4), tumor-associated glycoprotein 72 (TAG72), vascular endothelial growth factor receptor (VEGFR), vascular endothelial growth factor receptor 2 (VEGFR2), Wilms Tumor 1 (WT-1), a pathogen-specific antigen, or an antigen associated with a universal tag, and/or biotinylated molecules, and/or molecules expressed by HIV, HCV, HBV or other pathogens.
218. The composition of any of embodiments 174-217, wherein the recombinant protein is or comprises a functional non-TCR antigen receptor or a TCR or antigen-binding fragment thereof.
219. The composition of any of embodiments 174-218, wherein the recombinant protein is a chimeric antigen receptor (CAR).
220. The composition of any of embodiments 174-219, wherein the recombinant protein comprises an extracellular domain comprising an antigen-binding domain.
221. The composition of embodiment 220, wherein the antigen-binding domain is or comprises an antibody or an antibody fragment thereof, which optionally is a single chain fragment.
222. The composition of embodiment 221, wherein the fragment comprises antibody variable regions joined by a flexible linker.
223. The composition of embodiment 221 or 222, wherein the fragment comprises an scFv.
224. The composition of any of embodiments 174-223, wherein the recombinant protein comprises an intracellular signaling region.
225. The composition of embodiment 224, wherein the intracellular signaling region comprises an intracellular signaling domain.

226. The composition of embodiment 225, wherein the intracellular signaling domain is or comprises a primary signaling domain, a signaling domain that is capable of inducing a primary activation signal in a T cell, a signaling domain of a T cell receptor (TCR) component, and/or a signaling domain comprising an immunoreceptor tyrosine-based activation motif (ITAM).

227. The composition of embodiment 226, wherein the intracellular signaling domain is or comprises an intracellular signaling domain of a CD3 chain, optionally a CD3-zeta (CD3ζ) chain, or a signaling portion thereof.

228. The composition of any of embodiments 224-227, wherein the recombinant protein further comprises a transmembrane domain disposed between the extracellular domain and the intracellular signaling region.

229. The composition of any of embodiments 224-228, wherein the intracellular signaling region further comprises a costimulatory signaling domain.

230. The composition of embodiment 229, wherein the costimulatory signaling domain comprises an intracellular signaling domain of a T cell costimulatory molecule or a signaling portion thereof.

231. The composition of embodiment 229 or embodiment 230, wherein the costimulatory signaling domain comprises an intracellular signaling domain of a CD28, a 4-1BB or an ICOS or a signaling portion thereof.

232. The composition of any of embodiments 229-231, wherein the costimulatory signaling domain is between the transmembrane domain and the intracellular signaling domain.

233. The composition of any of embodiments 174-232, wherein the T cells are primary T cells obtained from a subject.

234. The composition of embodiment 233, wherein the T cells are autologous to the subject.

235. The composition of embodiment 234, wherein the T cells are allogeneic to the subject.

236. The composition of any of embodiments 174-235, comprising a pharmaceutically acceptable excipient.

237. The composition of embodiment 236, wherein the at least 60% of total T cells, total CD4+ T cells, or total CD8+ T cells of the composition, of recombinant protein-expressing cells thereof are CD27+CCR7+.

238. An article of manufacture, comprising the composition of any of embodiments 174-229 and instructions for administering the output composition to a subject.

239. The article of manufacture of embodiment 238, wherein the subject has a disease or condition, optionally wherein the recombinant receptor specifically recognizes or specifically bind to an antigen associated with, or expressed or present on cells of, the disease or condition.

240. A method of treating a subject having or suspected of having a disease or condition, the method comprising administering to the subject a dose of T cells from a composition of any of embodiments 174-237.

241. The method of embodiment 240, wherein the dose of T cells is administered to the subject as a single dose or is administered only one time within a period of two weeks, one month, three months, six months, 1 year or more.

242. The method of embodiment 240 or 241, wherein the dose of T cells comprises between at or about $1\times10^4$ and $50\times10^6$ T cells, inclusive.

243. The method of any of embodiments 240-242, wherein the dose of T cells comprises less than $50\times10^6$ T cells, $10\times10^6$ T cells, $5\times10^6$ T cells, $1\times10^6$ T cells, $0.5\times10^6$ T cells, or $1\times10^5$ T cells.

244. The method of any of embodiments 240-243, wherein the dose of T cells comprises or comprises about $20\times10^6$ T cells.

245. The method of any of embodiments 240-243, wherein the dose of T cells comprises or comprises about $10\times10^6$ T cells.

246. The method of any of embodiments 240-243, wherein the dose of T cells comprises or comprises about $2\times10^6$ T cells.

247. The method of any of embodiments 240-243, wherein the dose of T cells comprises or comprises about $1\times10^6$ T cells.

248. The method of any of embodiments 240-247, wherein the T cells of the dose are total T cells, total viable T cells, total viable recombinant receptor expressing T cells, total viable recombinant receptor expressing CD4+ T cells, or total viable recombinant receptor expressing CD8+ T cells.

249. The method of any of embodiments 240-248, wherein the disease or condition is a cancer.

250. The method of any of embodiments 240-249, wherein the disease or condition is a myeloma, leukemia or lymphoma.

251. The method of any of embodiments 240-250, wherein the disease or condition is a B cell malignancy and/or is acute lymphoblastic leukemia (ALL), adult ALL, chronic lymphoblastic leukemia (CLL), non-Hodgkin lymphoma (NHL), and Diffuse Large B-Cell Lymphoma (DLBCL).

VIII. Examples

The following examples are included for illustrative purposes only and are not intended to limit the scope of the invention.

Example 1: Non-Expanded Processes for Manufacture of T Cell Compositions Containing CAR+ T Cells Engineered compositions of primary T cells containing T cells expressing chimeric antigen receptors (CARs) were produced by a process that utilized a stimulatory reagent composed of paramagnetic polystyrene-coated beads with attached anti-CD3 and anti-CD28 antibodies or an anti-CD3/anti-CD28 Fab conjugated oligomeric reagent to activate T cells prior to transduction with a viral vector but that did not involve a subsequent expansion of the cells. For comparison, T cells from the same donor were engineered by a process that included an expansion step. Features of the exemplary non-expanded process and expanded process were compared as described in Example 4.

a. Non-Expanded Process-Anti-CD3/Anti-CD28 Beads

Separate compositions of CD4+ and CD8+ cells were selected from isolated PBMCs from a leukapheresis sample from a human donor, and the selected cell compositions were cryofrozen. The separate compositions of CD4+ and CD8+ T cells were subsequently thawed and mixed at a ratio of 1:1 of viable CD4+ T cells to viable CD8+ T cells. Approximately $300\times10^6$ T cells ($150\times10^6$ CD4+ and $150\times10^6$ CD8+ T cells) of the mixed input cell composition were stimulated by incubating the cells for 18-30 hours in the presence of anti-CD3/anti-CD28 antibody conjugated beads at a 1:1 bead to cell ratio in serum free media. The media also contained recombinant IL-2, IL-7, and IL-15.

Following the stimulation, the cells were washed and resuspended in the serum free media containing additives as well as recombinant IL-2, IL-7 and IL-15. The cells were then transduced with a lentiviral vector encoding an anti-BCMA CAR by spinoculation at approximately 693 g for 30 minutes. The CAR contained an scFv antigen-binding domain specific for BCMA, a CD28 transmembrane region, a 4-1BB costimulatory signaling region, and a CD3-zeta derived intracellular signaling domain. The vector also encoded a truncated receptor molecule that served as a surrogate marker for CAR expression that was separated from the CAR construct by a T2A sequence.

After the spinoculation, the cells were washed and resuspended either in the serum free media containing recombinant IL-2, IL-7 and IL-15 (complete media) or in basal media without any additional additives or recombinant cytokines (basal media). The cells of each of the resuspended compositions were incubated at about 37.0° C. in an incubator. At 96 hours after initiation of the stimulation, cells were rinsed twice in the presence of a magnetic field to remove the anti-CD3/anti-CD28 antibody conjugated paramagnetic beads, formulated in a solution containing 10% DMSO. The formulated cell composition was transferred to a bag or vial and was stored at approximately −80° C.

b. Non-Expanded Process-Anti-CD3/Anti-CD28 Oligomeric Reagent

Separate compositions of CD4+ and CD8+ cells were selected from isolated PBMCs from a leukapheresis sample from the same human donor as described in Example 1a, and the selected cell compositions were cryofrozen. The separate compositions of CD4+ and CD8+ T cells were subsequently thawed and mixed at a ratio of 1:1 of viable CD4+ T cells to viable CD8+ T cells. Approximately 300×10$^6$ T cells (150×10$^6$ CD4+ and 150×10$^6$ CD8+ T cells) of the mixed input composition were stimulated by incubation with 4 μg anti-CD3/anti-CD28 Fab conjugated oligomeric streptavidin mutein reagents, generated as described in Example 2, per 10$^6$ cells (where 4 μg of the oligomeric stimulatory reagent includes 3 μg of oligomeric particles and 0.5 μg of anti-CD3 Fabs and 0.5 μg of anti-CD28 Fabs). The incubation was carried out in serum free media containing recombinant IL-2, IL-7, and IL-15 for between 18-30 hours.

Following the stimulation, the cells were washed and resuspended in the serum free media containing recombinant IL-2, IL-7 and IL-15. The cells were then transduced with a lentiviral vector encoding the anti-BCMA CAR described in Example 1a by spinoculation at 693 g for 30 minutes. After the spinoculation, the cells were washed and resuspended in the serum free media containing recombinant IL-2, IL-7 and IL-15. The cells were incubated at about 37.0° C. in an incubator. After 24 hours, 48 hours or 96 hours after initiation of the stimulation, 0.1 mM or 1 mM D-biotin was added to dissociate anti-CD3 and anti-CD28 Fab reagents from oligomeric streptavidin reagents, and then the cells were washed and formulated in the presence of a cryoprotectant as described in Example 1a.

c. Expanded Process

Separate compositions of CD4+ and CD8+ cells were selected from isolated PBMCs from a leukapheresis sample from the same human donor as described above, and the selected cell compositions were cryofrozen. The separate compositions of CD4+ and CD8+ T cells were subsequently thawed and mixed at a ratio of 1:1 of viable CD4+ T cells to viable CD8+ T cells. Approximately 300×10$^6$ T cells (150×10$^6$ CD4+ and 150×10$^6$ CD8+ T cells) of the mixed composition were stimulated in the presence of paramagnetic polystyrene-coated beads with attached anti-CD3 and anti-CD28 antibodies at a 1:1 bead to cell ratio in serum free media containing recombinant IL-2, IL-7, and IL-15 for between 18 to 30 hours.

Following the incubation, approximately 100×10$^6$ viable cells from the stimulated cell composition were concentrated in the serum free media containing recombinant IL-2, IL-7 and IL-15. The cells were transduced with a lentiviral vector encoding the same anti-BCMA CAR as described above by spinoculation at approximately 1600 g for 60 minutes. After spinoculation, the cells were resuspended in the serum free media containing recombinant IL-2, IL-7, and IL-15, and incubated for about 18 to 30 hours at about 37° C.

The cells were then cultivated for expansion by transfer to a bioreactor (e.g. a rocking motion bioreactor) in about 500 mL of the exemplary serum free media containing twice the concentration of IL-2, IL-7, and IL-15 as used during the incubation and transduction steps. When a set viable cell density was achieved, perfusion was initiated, where media was replaced by semi-continuous perfusion with continual mixing. The cells were cultivated the next day in the bioreactor until a threshold cell density of about 3×10$^6$ cells/ml was achieved, which typically occurred in a process involving 6-7 days of expansion. The anti-CD3 and anti-CD28 antibody conjugated paramagnetic beads were removed from the cell composition by exposure to a magnetic field. The cells were then collected, formulated and cryoprotected as described above.

d. Summary of Processes

Table E1 summarizes the processes generated using methods as described above.

TABLE E1

| Arm | Stimulatory Reagent | Cell Number | Transduction | Expansion | Removal of stimulatory reagent | Harvest |
|---|---|---|---|---|---|---|
| 1 | Beads | 1.5 × 10$^6$ CD4 and 1.5 × 10$^6$ CD8 | Spinoculation & static incubation for 18-30 hours | Until TNC of ~3 × 10$^9$ cells, about 6-7 days | Wash and debead | Following debead |
| | | | | | Day following threshold number | |
| 2 | Beads | 1.5 × 10$^6$ CD4 and 1.5 × 10$^6$ CD8 | Spinoculation & static incubation for 96 hours in complete media | None | Wash and debead | Following debead |
| | | | | | 96 hours after initiation of stimulation | |

TABLE E1-continued

| Arm | Stimulatory Reagent | Cell Number | Transduction | Expansion | Removal of stimulatory reagent | Harvest |
|---|---|---|---|---|---|---|
| 3 | Beads | $1.5 \times 10^6$ CD4 and $1.5 \times 10^6$ CD8 | Spinoculation & static incubation for 96 hours in basal media | None | Wash and debead | Following debead |
| | | | | | 96 hours after initiation of stimulation | |
| 4 | Oligomeric reagent | $1.5 \times 10^6$ CD4 and $1.5 \times 10^6$ CD8 | Spinoculation & static incubation for 24 hours in complete media | None | Biotin added and wash | Following dissociation |
| | | | | | 24 hours after initiation of stimulation | |
| 5 | Mock | $1.5 \times 10^6$ CD4 and $1.5 \times 10^6$ CD8 | Mock transduction & static incubation for 24 hours in complete media | None | 24 hours after initiation of stimulation | |

Example 2: Methods for Preparing an Anti-CD3/Anti-CD28 Fab Conjugated Oligomeric Reagent Comprising a Streptavidin Mutein An oligomeric reagent was prepared by polymerizing an exemplary streptavidin mutein designated STREP-TACTIN® M2 (a streptavidin homo-tetramer containing the mutein sequence of amino acids set forth in SEQ ID NO:68, see e.g. U.S. Pat. No. 6,103,493 and Voss and Skerra (1997) Protein Eng., 1:975-982, and Argarana et al. (1986) Nucleic Acids Research, 1871-1882). To prepare streptavidin muteins for oligomerization, streptavidin muteins containing one or more reactive thiol groups were incubated with maleimide activated streptavidin muteins. To prepare the thiolated streptavidin mutein, about 100 mg of streptavidin mutein was thiolated by incubation with 2-iminothiolane hydrochloride at a molar ratio of 1:100 at a pH of about 8.5 at 24° C. for 1 hour in 100 mM Borate buffer in a total volume of 2.6 mL. For the activation reaction, about 400 mg of streptavidin mutein was incubated with Succinimidyl-6-[(β-maleimidopropionamido) hexanoate (SMPH) at a molar ratio of 1:2 at a pH of about 7.2 at 24° C. for 1 hour in a total volume of about 10.4 mL in a sodium phosphate buffer. The thiolation and activation reactions were coordinated to start at about the same time, and the duration of the reactions was controlled.

After the reactions, the 2-Iminothiolane hydrochloride and SMPH were removed from the samples by individually carrying out gel filtration of the samples with PD-10 desalting columns (GE Healthcare). For each 2.5 mL volume of sample, a 1 mL PD-10 column was equilibrated and loaded with either thiolated mutein streptavidin or maelimdie mutein streptavidin and elution was carried out by adding 3.5 mL of coupling buffer (100 mM $NaH2PO_4$, 150 mM NaCl, 5 mM EDTA, pH 7.2). Gel filtration of the maleimide mutein streptavidin was carried out on 4 columns to account for the >10 ml volume and eluates were pooled. The timing of the activation and thiolation reactions and the timing between the end of the activation and thiolation reactions and the start of the oligomerization reactions were carefully controlled. Generally, no more than ten minutes was allowed to pass from the start of gel filtrations, i.e. the end of the activation and thiolation reactions, to when oligomerization reaction was initiated.

For oligomerization, the maleimide streptavidin mutein and thiolated streptavidin mutein samples were then combined into an overall volume of about 17.5 mL and incubated for 1 hour at a pH of 7.2 at 24° C. under stirring conditions at about 600 rpm. Because four times more streptavidin mutein was incubated with SMPH than with 2-iminothiolane hydrochloride, the molar ratio of thiolated streptavidin mutein and maleimide streptavidin mutein was 1:4 during the oligomerization reaction. After the reaction, remaining SH groups of the oligomerized streptavidin mutein reagent were saturated by incubation with N-Ethylmaleimide (NEM) for 15 min at 24° C. with stirring (about 600 rpm) followed by incubation for a further 16-20 hours at 4° C.

After incubation with NEM, the sample containing oligomerized streptavidin mutein was centrifuged and the supernatant was filtered through a 0.45 μm membrane (Millex-HP 0.45 μm from Merck Millopore). The filtered solution was then loaded into a column (Sephacryl S-300 HR HiPrep 26/60, GE Healthcare) for size exclusion chromatography (SEC) with an AKTA Explorer chromatography system (GE Healthcare). Fractions with a milli absorbance unit (mAU) greater than or equal to 1500 mAU were pooled.

The pooled sample containing oligomeric streptavidin mutein was treated with 100 mM hydroxylamine at a pH of 6.35 for 15 minutes at room temperature. To remove the hydroxylamine after treatment, sample was loaded onto a PD10 column (2.5 mL per column) and eluted with 3.5 mL of buffer containing 100 mM NaH2PO4, 140 mM NaCl, 1 mM EDTA, pH 7.2. The PD10 elutes were pooled and sterile filtered with a 0.45 μm filter followed by a 0.22 μm filter and then samples were frozen and stored at −80° C. Prior to freezing, the final concentration of the oligomeric streptavidin mutein reagent was measured and the size of the oligomeric streptavidin mutein reagent was determined by dynamic light scattering (DLS).

To evaluate the consistency of the oligomerization process, 10 oligomeric streptavidin mutein reagents were prepared using the methods described above from five different lots of streptavidin mutein (SAM). The average size, percent yield (determined by measuring absorbance at 280 nm without baseline correction), and activity (biotin binding) of the oligomers were assessed and the results are shown in Table E2. The results indicated that the resulting oligomeric streptavidin mutein reagents were consistent in these parameters with an average radius of 97 nm±10 nm and biotin binding of 40 nmol/mg±3 nmol/mg.

TABLE E2

| Comparison of oligomerized STREP-TACTIN from different batches. | | | | |
|---|---|---|---|---|
| | SAM lot | Radius (nm) | Yield(%) | Biotin Binding (nmol/mg) |
| Batch 1 | 1 | 92 | 74 | 41 |
| Batch 2 | 2 | 100 | 68 | 40 |
| Batch 3 | 2 | 106 | 82 | 37 |
| Batch 4 | 2 | 94 | 73 | 39 |
| Batch 5 | 3 | 87 | 79 | 41 |
| Batch 6 | 3 | 90 | 81 | 39 |
| Batch 7 | 4 | 97 | 84 | 43 |
| Batch 8 | 4 | 97 | 76 | 43 |
| Batch 9 | 5 | 102 | 85 | 42 |
| Batch 10 | 5 | 87 | 63 | 42 |

The average molecular weight (MW) of three oligomeric streptavidin mutein reagents generated as described above was measured by asymmetrical flow field-flow fractionation (AF4) performed with an HPLC system (AGILENT 1100 and Wyatt ECLIPSE DUALTEC) with UV detection (Agilent UV detector coupled with MALLS DAWN HELEOS (Wyatt)). The measurements by AF4 allowed for the calculation of the average number of streptavidin mutein tetramers in each oligomeric reagent assuming the average molecular weight of a streptavidin mutein tetramer of 52,500 g/mol (52.5 kDa) (Table E3).

TABLE E3

| Size and Molecular Weight of oligomeric streptavidin mutein reagents | | |
|---|---|---|
| Radius (nm) | MW (g/mol) | Number of Tetramers |
| 102 | $1.65 \times 10^8$ | 3150 |
| 82 | $1.08 \times 10^8$ | 2050 |
| 92 | $1.26 \times 10^8$ | 2280 |

Stimulatory agents (anti-CD3 and anti-CD28 Fab fragments) were multimerized by reversible binding to oligomeric streptavidin mutein reagent generated as described above. Anti-CD3 and anti-CD28 Fab fragments were reversibly bound to the streptavidin mutein oligomer via a streptavidin peptide-binding partner fused to each Fab fragment. The anti-CD3 Fab fragment was derived from the CD3 binding monoclonal antibody produced by the hybridoma cell line OKT3 (ATCC® CRL-8001™; see also U.S. Pat. No. 4,361,549), and contained the heavy chain variable domain and light chain variable domain of the anti-CD3 antibody OKT3 described in Arakawa et al J. Biochem. 120, 657-662 (1996). These sequences are set forth in SEQ ID NOs: 89 and 90, respectively. The anti-CD28 Fab fragment was derived from antibody CD28.3 (deposited as a synthetic single chain Fv construct under GenBank Accession No. AF451974.1; see also Vanhove et al., BLOOD, 15 Jul. 2003, Vol. 102, No. 2, pages 564-570) and contained the heavy and light chain variable domains of the anti-CD28 antibody CD28.3 set forth in SEQ ID NOS: 91 and 92, respectively. The Fab fragments were individually fused at the carboxy-terminus of their heavy chain to a streptavidin peptide-binding sequence containing a sequential arrangement of two streptavidin binding modules having the sequence of amino acids SAWSHPQFEK(GGGS)2GGSAWSHPQFEK (SEQ ID NO: 74). The peptide-tagged Fab fragments were recombinantly produced (see International Patent App. Pub. Nos. WO 2013/011011 and WO 2013/124474).

To effect reversible binding, peptide-tagged anti-CD3 and anti-CD28 Fab fragments were mixed with the oligomeric streptavidin mutein reagent at approximately room temperature, thereby reversibly binding them to the reagent via interaction between twin-strep-tags on the Fab fragments, which were binding partners capable of reversibly binding to binding sites on the reagent. In some cases, the peptide-tagged Fab fragments were pre-mixed prior to immobilization onto the oligomeric streptavidin mutein reagent, which, in some instances, can result in a more uniform distribution of the different Fab molecules. Binding of the peptide-tagged anti-CD3 and anti-CD28 to the oligomeric strepaviding mutein reagent can be disrupted, or reversed, by addition of D-biotin. D-biotin competes with the strep-tag on the agents for binding to the binding partner on the streptavidin mutein, thereby disrupting binding.

Example 3: Activity Assessment of Oligomerized Anti-CD3 and Anti-CD28 Fab Fragments Reversibly Bound to Strepatividin Mutein Oligomers Anti-CD3 and anti-CD28 Fab fragments, reversibly bound to various oligomeric streptavidin reagents from each of the batches described in Table E2 by the process described in Example 2, were assessed for the ability to stimulate T cells. These oligomeric streptavidin reagents had an average radius of about 95 nm. Metabolic activity of cells as an indicator of cell proliferation was assessed by colorimetric monitoring of cleavage of the stable tetrazolium salt WST-1 to a soluble formazan dye complex.

T cells, from three different donors, were incubated with the anti-CD3/anti-CD28 multimerized Fab fragments reversibly bound on an oligomeric streptavidin reagent. Cells were also incubated with control oligomeric reagents that had either an average radius of 101 (internal reference) or 36 nm, which also were reversibly bound to anti-CD3/anti-CD28 Fab fragments. After the incubation, WST-1 reagent was applied to the cells and the levels of metabolic activity were assessed by measuring the absorbance at 450 nm as a readout. The results were normalized to the number of cells in the culture being assayed and depicted as the ratio of WST-1 per cell number.

Figure 1B:
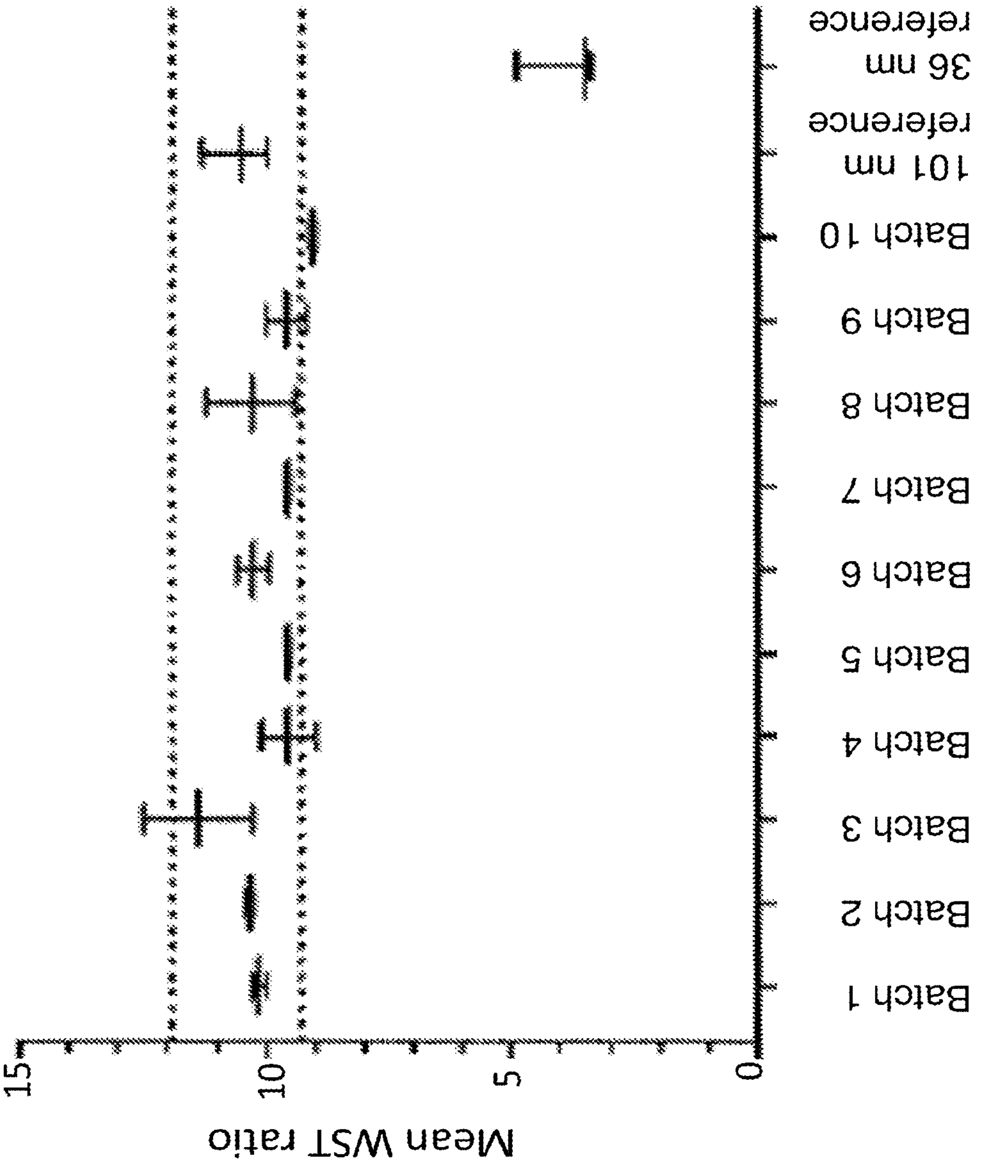

As shown in FIG. 1B, mean WST-1 activity of T cells stimulated with each of the tested reagents were comparable. Moreover, the degree of stimulation was similar for all tested reagents and was comparable to a similarly sized internal reference reagent (varying generally within +2 standard deviations). FIG. 1A shows the WST-1 activity depicted as a separate data point for each reagent. FIG. 1A and FIG. 1B indicate that stimulation of T cells, as observed by WST-1 activity, was lower using anti-CD3/anti-CD28 Fabs multimerized on a smaller 36 nm oligomeric streptavidin mutein reagent backbone.

Example 4: Characteristics of T Cell Compositions Across Different Manufacturing Processes T cell compositions generated as described in Example 1 were assessed for various phenotypic and functional features.

a) Viability and Cell Number

Figure 2B:
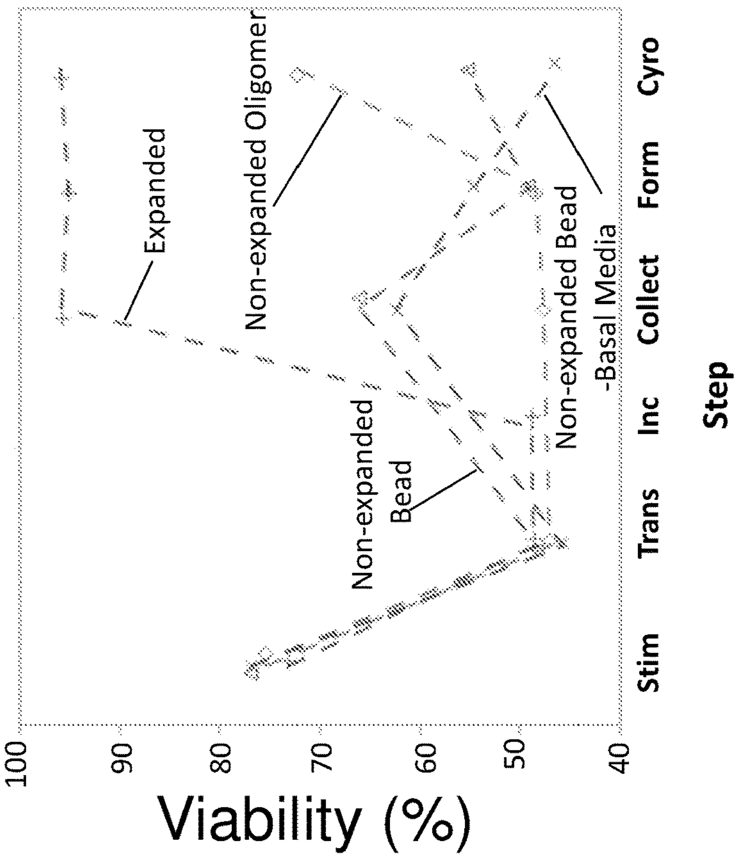
FIGS. 2A and 2B depict the total number of cells (TNC) (FIG. 2A) and the percentage of viable cells (Viability) (FIG. 2B), assessed from cell compositions generated from an expanded process (Expanded) and non-expanded processes involving a bead-based stimulatory reagent (Bead), a bead based stimulatory reagent and incubation in basal media (Bead-Basal Media) or an oligomeric stimulatory reagent (Oligomer) for generating T cell compositions that contain CAR+T cells. Results from samples collected at stimulation (Stim) transduction (Trans), incubation (Inc), harvest (Collect), cell formulation (Form), and cryopreservation (Cryo) steps are shown.
Figure 2A:
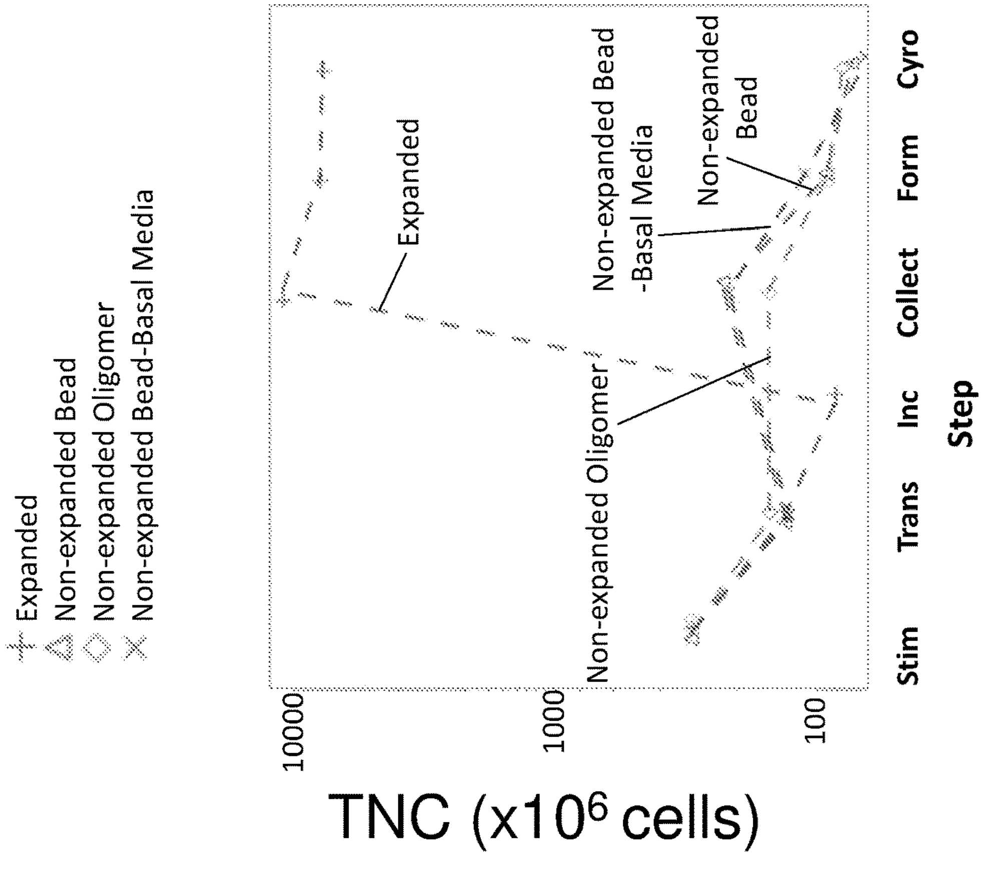

T cell compositions were assessed for total number of cells and the percentage of viable cells during different stages of the engineering processes for generating T cell compositions that contain CAR+ T cells. For each process, a sample from the T cell composition was collected at the initiation of the stimulation (stim), transduction (trans), incubation (inc), harvest (collect), cell formulation (form), and cryopreservation (Cyro) steps and analyzed to determine the total number of cells and the percentage of viable cells in the compositions. The results are set forth in FIGS. 2A and 2B. The cell compositions undergoing the expanded engineering process displayed a greater number of total cells with a greater percentage of viable cells than cell compositions generated in each non-expanded process. This result is consistent with the cultivation step, which is not included in the other processes, serving to increase the total number of cells and improve viability.

b) Cytolytic Activity

BCMA-expressing target cell line (RPMI-8226) were incubated with exemplary anti-BCMA CAR T cells from compositions generated by an expanded or non-expanded process as described in Example 1 at an effector to target cell (E:T) ratio of 27:1, 9:1, 3:1 or 1:1. The number of total live cells loaded per arm was identical. Cells from each condition were plated in triplicate. The target RPMI-8226 cells were labeled with NucLight Red (NLR) to permit their tracking by microscopy. Cytolytic activity was assessed by measuring the loss of viable target cells over a period of six days, as determined by red fluorescent signal (using the IncuCyte® Live Cell Analysis System, Essen Bioscience). Normalized target cell numbers were generated by dividing target cell counts to cell counts at the start of each culture. The percentage of target killing was assessed by measuring the area under the curve (AUC) for normalized target cell count over time and normalizing the inverse AUC (1/AUC) values by defining a 0% value (target cells alone) and a 100% value (CAR+ T cells co-cultured with target cells in vehicle control).

Figure 3:
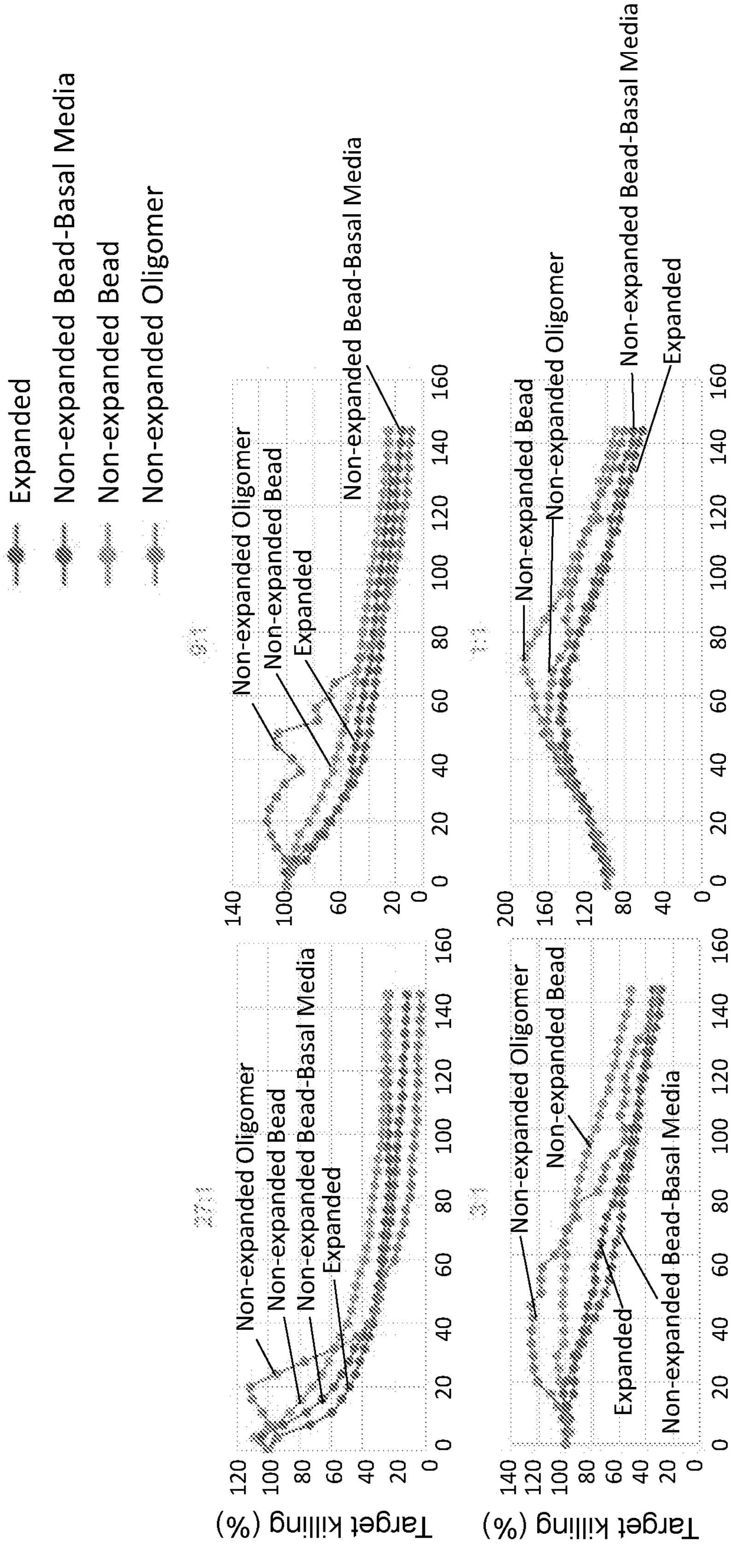
FIG. 3 displays the cytolytic activity of exemplary anti BCMA CAR T cells assessed from cell compositions generated from an expanded process (Expanded), and non-expanded processes involving (a) a bead-based stimulatory reagent (Bead), (b) a bead based stimulatory reagent and incubation in basal media (Bead-Basal Media) or (c) an oligomeric stimulatory reagent (Oligomer), each when incubated with a BCMA-expressing target cell line (RPMI-8226) at effector to target ratios of 27:1, 9:1, 3:1 or 1:1.

As shown in FIG. 3, CAR-T cells generated from a non-expanded process with anti-CD3/anti-CD28 conjugated beads exhibited a trend towards greater cytolytic activity when cells were incubated in basal media post-transduction compared to incubation in media with recombinant cytokines. The cytolytic activity was similar to CAR-T cells generated from an expanded process. CAR-T cells generated from a non-expanded process with an anti-CD3/anti-CD28 oligomeric reagent exhibited an initial delay in cytolytic activity, followed by a more potent long-term activity.

c) Phenotype and Differentiation Markers

Figure 4A:
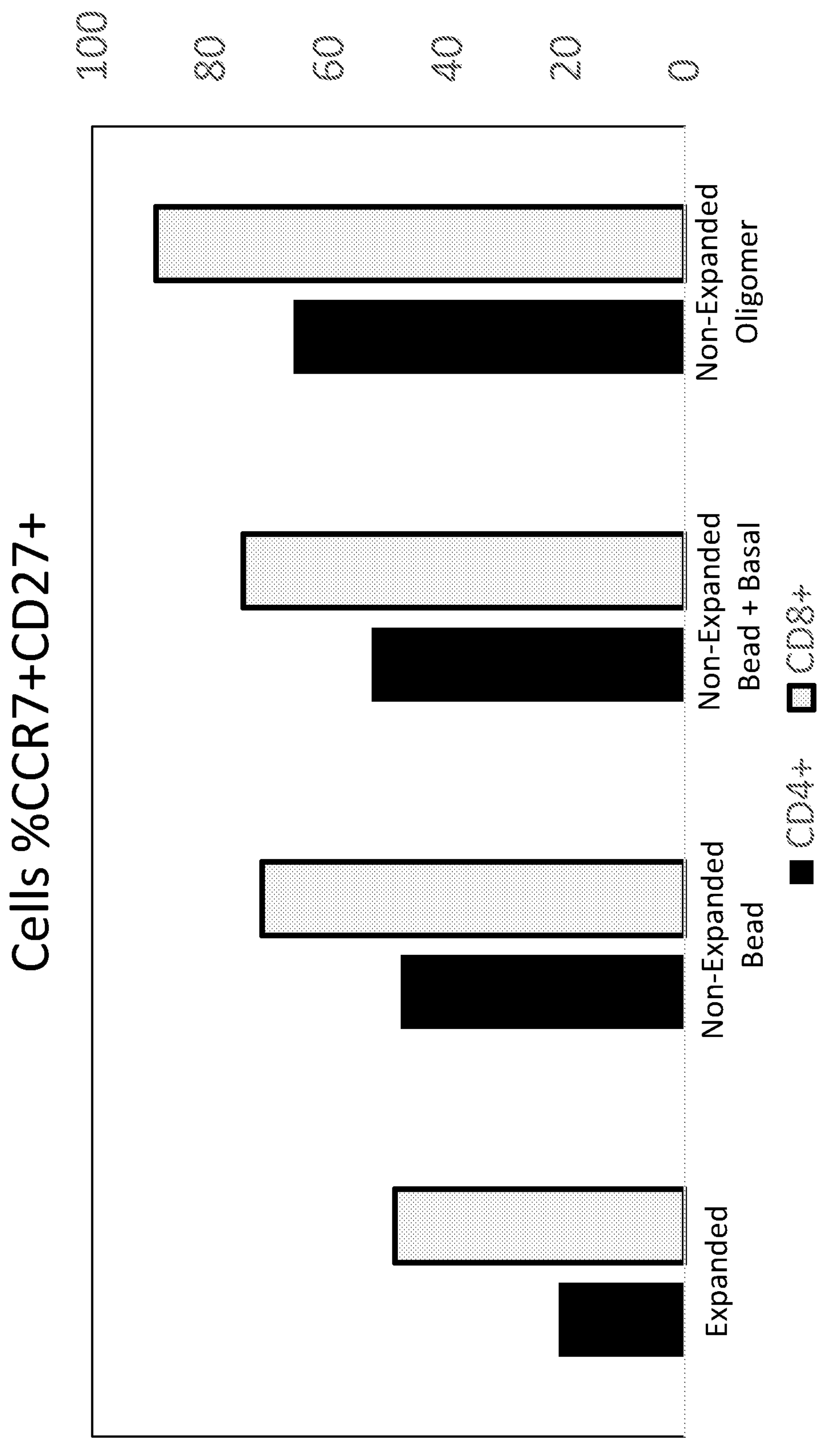
FIGS. 4A-4D depict results from CAR+ T cell compositions generated from an expanded process, and non-expanded processes involving (a) a bead-based stimulatory reagent (Bead), (b) a bead based stimulatory reagent and incubation in basal media (Bead-Basal Media), or (c) an oligomeric stimulatory reagent (Oligomer).
Figure 4B:
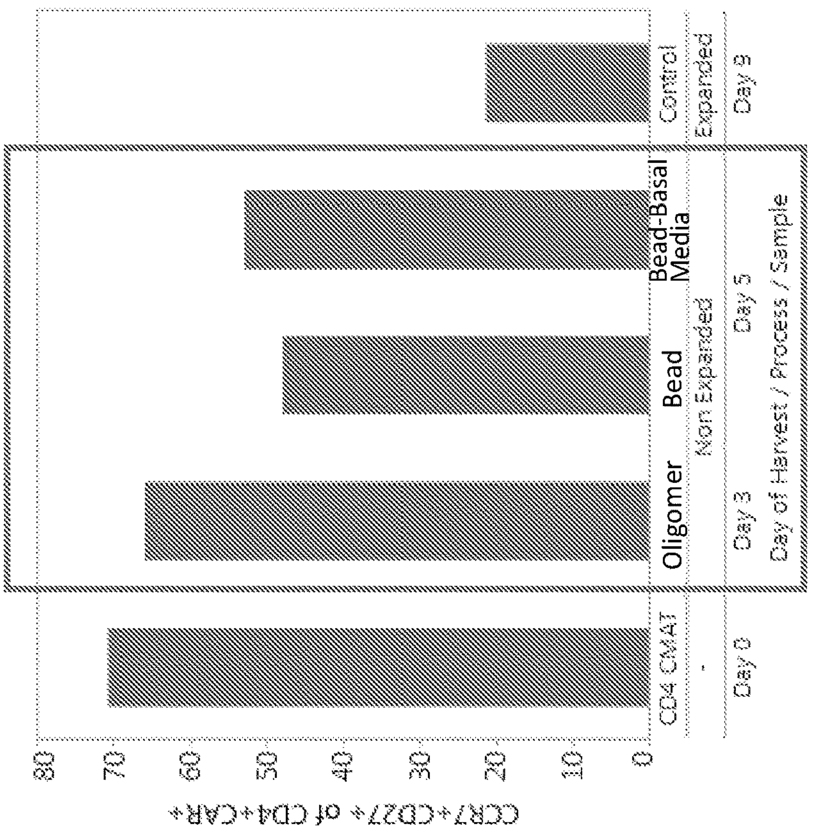
Figure 4C:
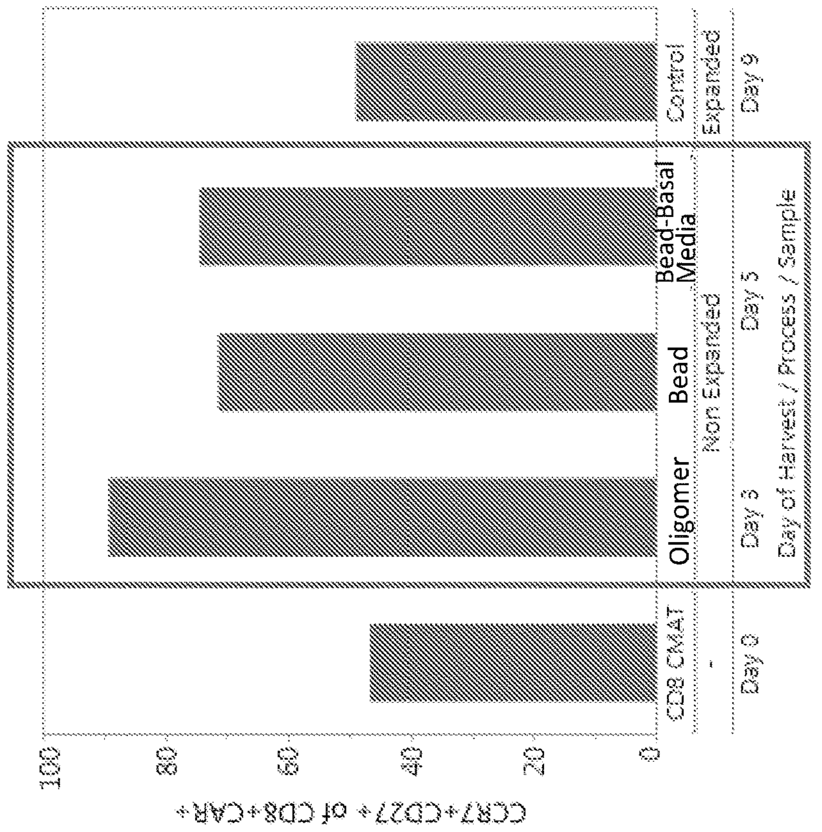

T cell compositions produced from expanded and non-expanded engineering processes were stained with antibodies recognizing surface markers including CD4, CD8, CCR7 and CD27 and quantified by flow cytometry. The percentage of CD4+CAR+ and CD8+CAR+ T cells positive for both CCR7 and CD27 staining are shown in FIG. 4A. FIG. 4B and FIG. 4C depict the percentage of CCR7+CD27+ cells for CD4+CAR+ T cells or CD8+CAR+, respectively, in the produced T cell compositions, compared to the percentage of CCR7+CD27+ cells in input composition prior to the incubation with the anti-CD3/anti-CD28 antibody conjugated bead stimulatory reagent (CMAT). As shown, a greater percentage of CCR7+CD27+ were observed in the T cell compositions produced from each non-expanded engineering process as compared to the expanded engineering process. These results are consistent with engineered cell compositions generated from non-expanded engineering processes having a greater portion of cells with a naïve-like, less differentiated phenotype than cell compositions generated by the expanded process.

Figure 4D:
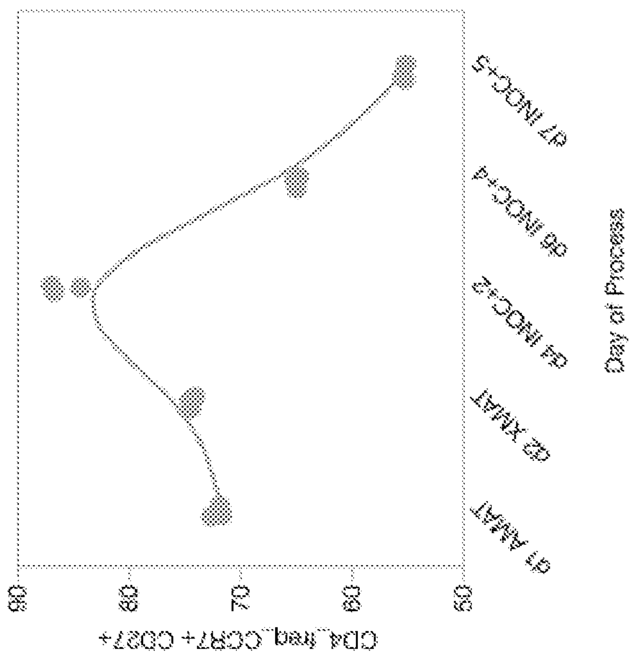

Further analysis of cells generated by the expanded process from a representative donor at various days during the process of manufacture, including at activation (AMAT), transduction (XMAT) or at various times after initiation of cultivation (inoc+2, inoc+4 or inoc+5), demonstrate expansion of cells is associated with a more differentiated phenotype as determined by a decreased percentage of CCR7+CD27+ cells (FIG. 4D).

Example 5: Assessment of Anti-Tumor Activity of Anti-BCMA CAR-T Cell Compositions Generated by Non-Expanded Manufacturing Processes CAR-T cell compositions generated from the non-expanded and expanded engineering processes described in Example 1 were evaluated in an in vivo mouse xenograft tumor model. Immunocompromised NOD-Scid-IL-2 Gamma receptor deficient (NSG) mice were engrafted with $2\times10^6$ OPM2 cells engineered to express Firefly luciferase to facilitate detection by bioluminescence imaging. Approximately $2\times10^6$ CAR+ T cells from engineered T cell compositions containing anti-BCMA CAR-T cells were administered into mice 12 days after tumor engraftment. Controls included mice that were injected with tumor cells only and mice injected with tumor cells and mock transduced T cell compositions. Mice from all groups were assessed for tumor burden by in-life luminescence imaging, body weight, and survival. The experimental groups are summarized in Table E4.

TABLE E4

| Experimental groups | | | | | | |
|---|---|---|---|---|---|---|
| Group No. | Group Description | Day cells collected | Mice per group | Percent CAR+ | CAR+ T cells admin. | Total T cells admin. |
| 1 | Tumor only | | 5 | | | |
| 2 | Mock transduction - Fab conjugated Oligomer | 3 | 8 | 60 | $2.00 \times 10^6$ | $3.33 \times 10^6$ |
| 3 | Expanded process - Beads | 10 | 8 | 72 | $2.00 \times 10^6$ | $2.78 \times 10^6$ |
| 4 | Non-expanded process-Oligomer reagent | 3 | 8 | 60 | $2.00 \times 10^6$ | $3.33 \times 10^6$ |
| 5 | Non-expanded process Beads | 5 | 8 | 60 | $2.00 \times 10^6$ | $3.33 \times 10^6$ |
| 6 | Non-expanded process beads and basal media | 5 | 8 | 68 | $2.00 \times 10^6$ | $2.94 \times 10^6$ |

Figure 5A:
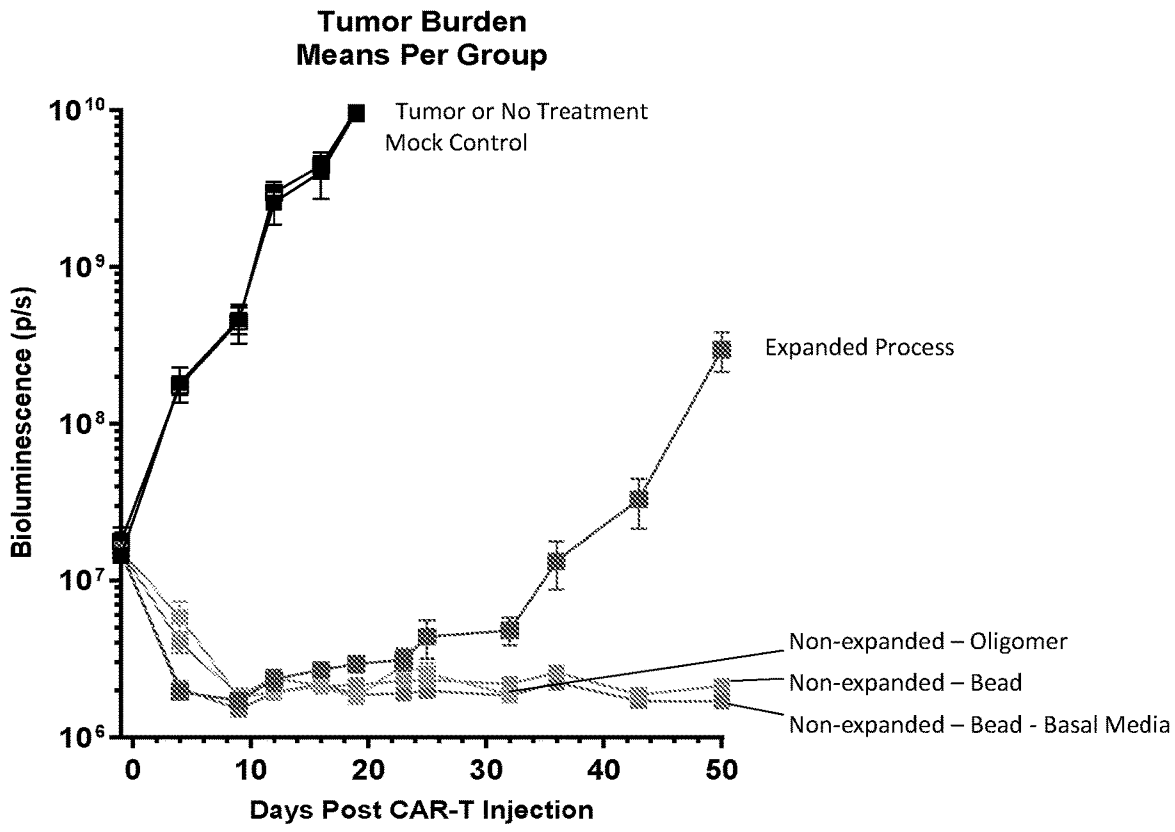
FIGS. 5A-5F depict tumor burden in an in vivo mouse xenograft tumor model after treatment with engineered CAR-T cell compositions generated by an expanded process, and non-expanded processes involving (a) a bead-based stimulatory reagent (Bead), (c) an oligomeric stimulatory reagent (Oligomer), or (d) a bead based stimulatory reagent incubated in basal media (Bead-Basal Media), each as compared to tumor only or mock transduction controls over a period of 50 days.
Figure 5B:
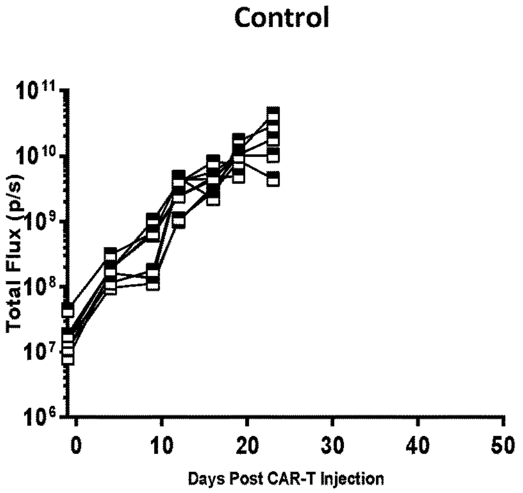
Figure 5C:
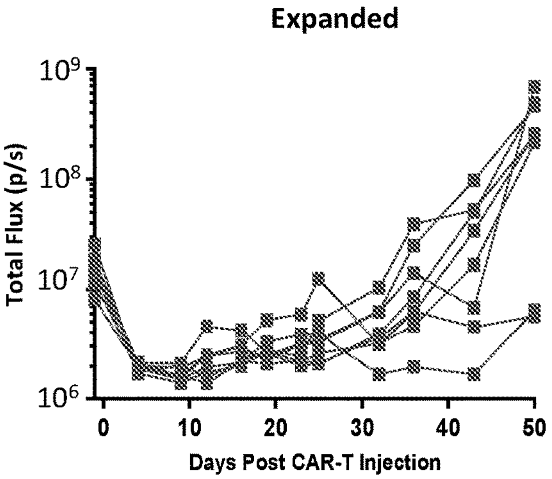
Figure 5D:
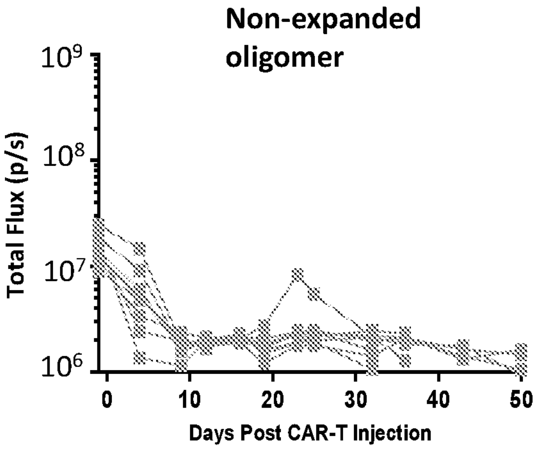
Figure 5E:
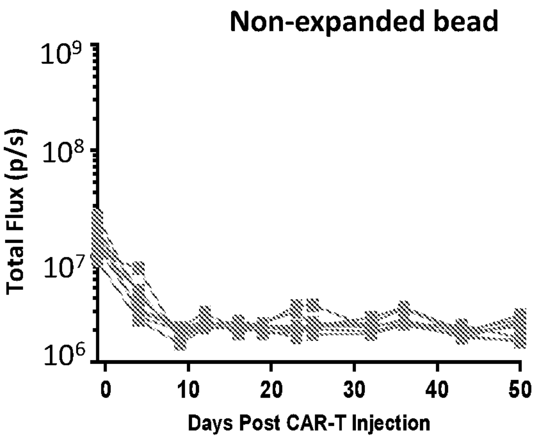
Figure 5F:
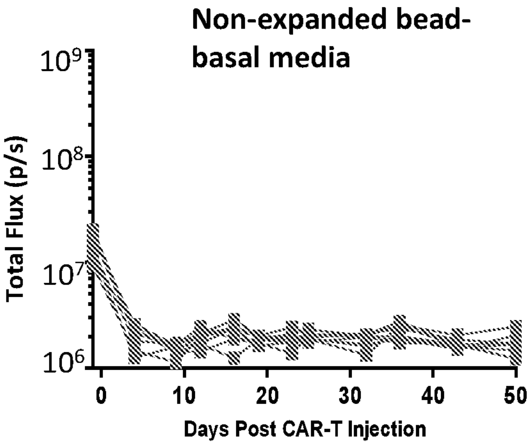
Figures 6A, 6B:
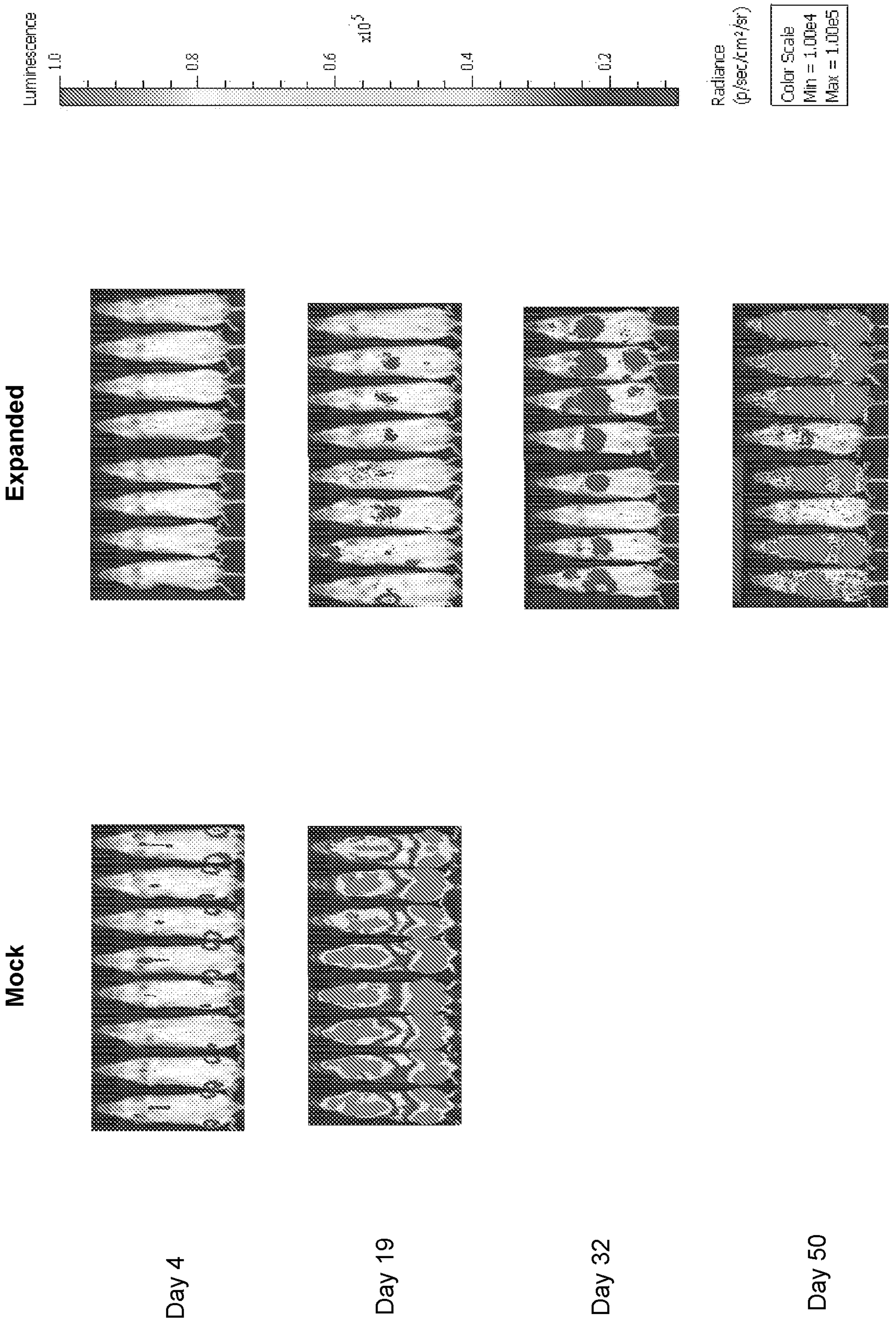
FIGS. 6A-6E depict representative bioluminescent images of tumor burden in an in vivo mouse xenograft tumor model at select days after mock transduction control (FIG. 6A) or treatment with engineered CAR-T cell compositions generated by an expanded process (Expanded) (FIG. 6B), and non-expanded processes involving an oligomeric stimulatory reagent (Oligomer) (FIG. 6C), a bead-based stimulatory reagent (Bead) (FIG. 6D), or a bead based stimulatory reagent incubated in basal media (Bead-Basal Media) (FIG. 6E), each over a period of 50 days.
Figures 6C, 6D, 6E:
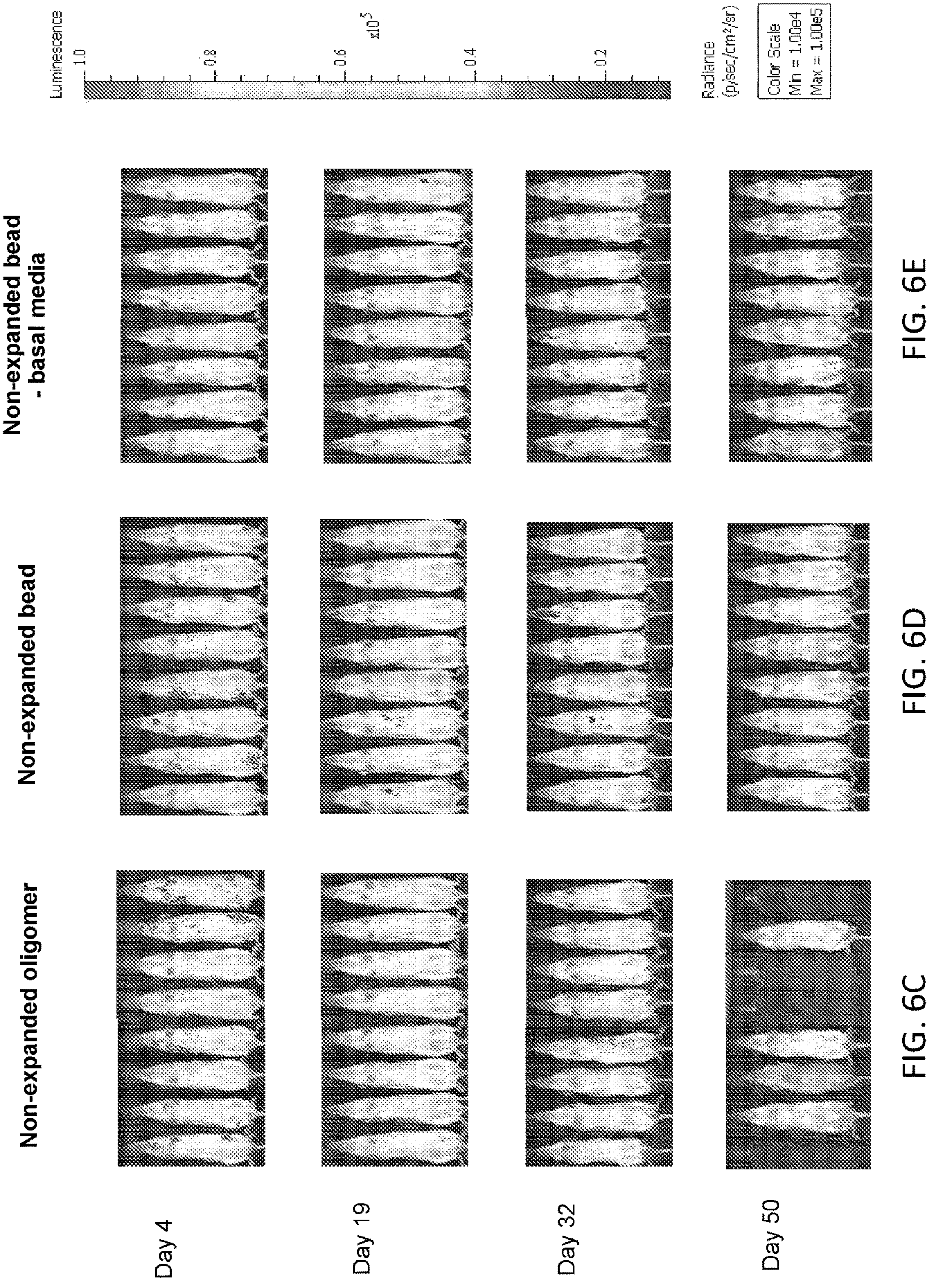

As shown in FIGS. 5A-5F, treatment with engineered cell compositions containing CAR-T cells reduced tumor burden associated with the tumor engraftment as compared to controls. In mice treated with the engineered CAR-T cells generated from the expanded engineering process, tumor burden was initially reduced as compared to the time of CAR-T cell administration (day 0), but detectably increased by 50 days (FIG. 5A). In contrast, the reduction of tumor burden persisted to at least day 50 in mice treated with CAR-T cells produced from the each of the non-expanded engineering processes. Results for individual mice in each assessed treatment group are shown in FIG. 5B (control), FIG. 5C (expanded process), FIG. 5D (non-expanded oligomer process), FIG. 5E (non-expanded bead process) and FIG. 5F (non-expanded bead process, basal media). Bioluminescence images at select days post-CAR T cell treatment are shown in FIGS. 6A-E, which show no to little detectable tumor burden in mice treated with CAR-T cells from non-expanded engineering process up until the day 50 time-point while tumor burden was increased in mice treated with CAR-T cells from an expanded process after an initial decline. These observations indicate that CAR-T cells generated from a non-expanded process have robust anti-tumor activity.

Figure 7:
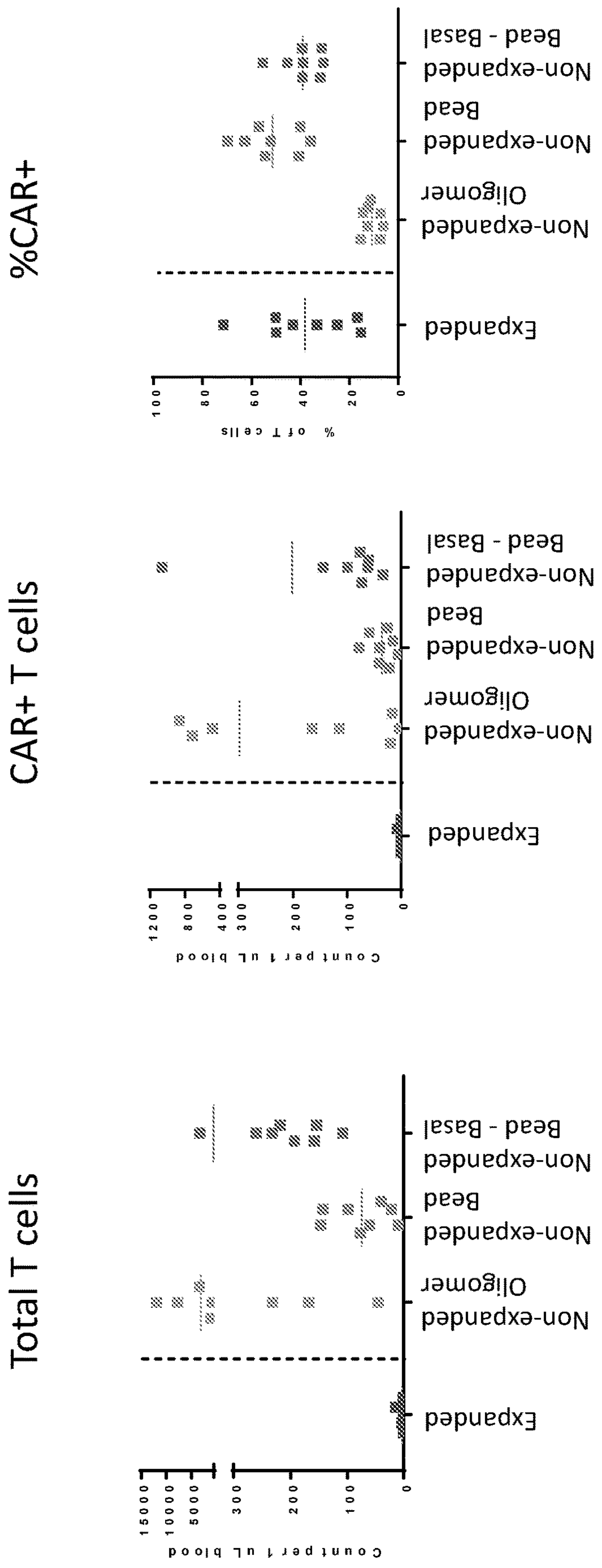
FIG. 7 depicts the total number of T cells and CAR+ T cells per μL of blood collected from mice subject to a xenograft tumor 33 days after treatment with engineered CAR-T cell compositions generated by an expanded process (Expanded), and non-expanded processes involving (a) an oligomeric stimulatory reagent (Oligomer), (b) a bead-based stimulatory reagent (Bead), or (c) a bead based stimulatory reagent incubated in basal media (Bead-Basal Media), as well as the percentage of CAR+ T cells within the total T cell population. Cells were stained with a reagent specific to the truncated receptor surrogate marker and analyzed by flow cytometry.

In vivo expansion and persistence were evaluated in CAR-T cell treated mice. Blood samples were collected from mice 33 days after administration of the CAR-T cells, and cells were stained with a reagent specific to the truncated receptor surrogate marker and analyzed by flow cytometry. As shown in FIG. 7, the total number of T cells and CAR+ T cells per μL of blood was increased in the samples obtained from mice administered CAR-T cells generated from non-expanded processes as compared to the expanded process. The greater degree of T cell expansion in mice treated with CAR-T cells generated by a non-expanded process is consistent with the generated cells having improved proliferative capacity.

Example 6: Assessment of Non-Expanded Manufacturing Process Using an Anti-CD3 and Anti-CD28 Fab Oligomeric Reagent for Engineering CAR+ T Cells T cell compositions containing anti-CD19 CAR+ T cells were generated by a non-expanded process using an anti-CD3/anti-CD28 Fab conjugated streptavidin mutein oligomers generated as described in Example 2. The non-expanded process was similar to the process described in Example 1, with the incubation carried out for 48 hours prior to addition of D-biotin. This shorter process was compared to a longer process (expanded process) in which the cells were incubated for 8 days after initiation of stimulation.

To generate T cell compositions in a non-expanded process, separate compositions of CD4+ and CD8+ cells were selected from isolated PBMCs from human leukapheresis samples of a human donor and were subsequently mixed at a ratio of 1:1 of viable CD4+ T cells to viable CD8+ T cells without any intermittent cryopreservation. In some cases, selected CD4+ and CD8+ T cells were separately cryofrozen prior to mixing, and then were thawed immediately before activation and mixed at a 1:1 ratio of viable CD4+ T cells to viable CD8+ T cells. Approximately $3\times10^7$ viable T cells from the mixed CD4+ and CD8+ T cells were stimulated by incubation with 4 μg anti-CD3/anti-CD28 Fab conjugated oligomeric streptavidin mutein reagents, generated as described in Example 2, per $10^6$ cells (where 4 μg of the oligomeric stimulatory reagent includes 3 μg of oligomeric particles and 0.5 μg of anti-CD3 Fabs and 0.5 μg of anti-CD28 Fabs). The incubation was carried out in serum free media containing recombinant IL-2, IL-7, and IL-15 for approximately 22 hours.

Following the incubation, the cells were washed and then transduced with a lentiviral vector encoding an anti-CD19 CAR. The CAR contained an anti-CD19 scFv derived from a murine antibody, an immunoglobulin spacer, a transmembrane domain derived from CD28, a costimulatory region derived from 4-1BB, and a CD3-zeta intracellular signaling domain. The vector also encoded a truncated receptor molecule that served as a surrogate marker for CAR expression that was separated from the CAR construct by a T2A sequence. The stimulated T cells were transduced with lentivirus by spinoculation at 1600 g for 60 minutes. After the spinoculation, the T cells were washed and resuspended in serum free media containing recombinant IL-2, IL-7 and IL-15, and incubated at about 37° C. in an incubator for approximately 48 hours. After the incubation, 1.0 mM D-biotin and mixed with the cells to dissociate anti-CD3 and anti-CD28 Fabs from oligomeric streptavidin reagents. After about 2 hours, the cells were washed to remove D-biotin and the oligomeric reagent and then were formulated in the presence of a cryoprotectant similar to as described in Example 1.

For comparison, anti-CD19 CAR-T cells were generated using an expanded process that utilized the anti-CD3 and anti-CD28 Fab conjugated streptavidin oligomers described in Example 2 as a stimulatory reagent. The process was smaller-scale in which approximately $3\times10^6$ T cells of the 1:1 mixed CD4+ and CD8+ T cells were activated with the anti-CD3/anti-CD28 Fab conjugated streptavidin oligomer, prior to transduction and cultivation in serum free media containing recombinant IL-2, IL-7 and IL-15 at about 37° C. Approximately 48 hours after initiation of the stimulation, 1.0 mM D-biotin was added and the cells were incubated for a further six days. Then, the cells were washed to remove D-biotin and the oligomeric reagent and then were formulated in the presence of a cryoprotectant.

Both the non-expanded and expanded engineering processes involved transduction with lentivirus encoding the same anti-CD19 CAR as described above.

Figure 8A:
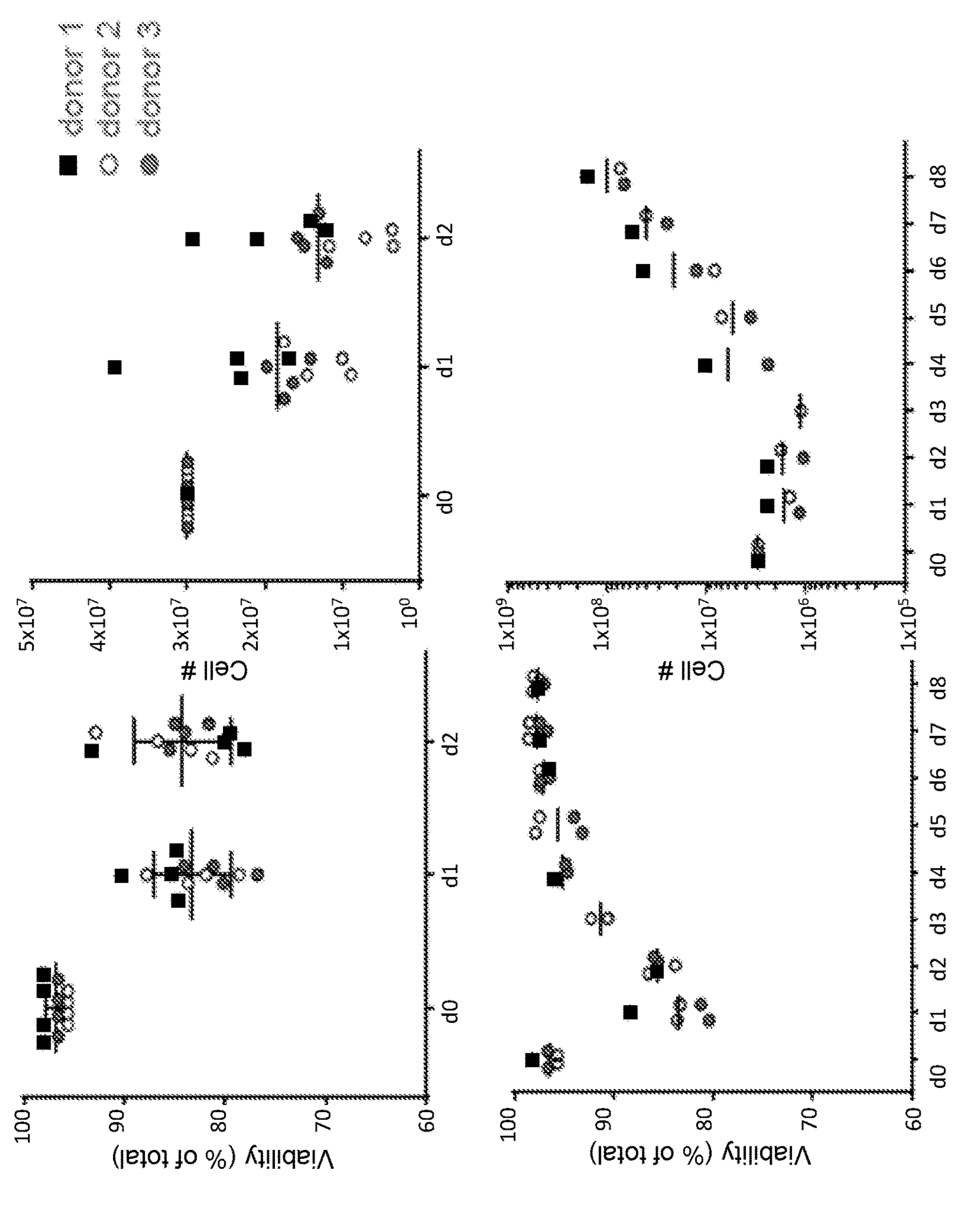
FIG. 8A and FIG. 8B depict the percentage of viable total cells and the total number of cells quantified from anti-CD19 CAR-T cell compositions transduced with lentivirus encoding anti-CD19 CAR and generated using either an expanded process (Expanded) or a non-expanded (Non-expanded) process using anti-CD3/anti-CD28 Fab conjugated streptavidin mutein oligomers as a stimulatory agent.
Figure 8B:
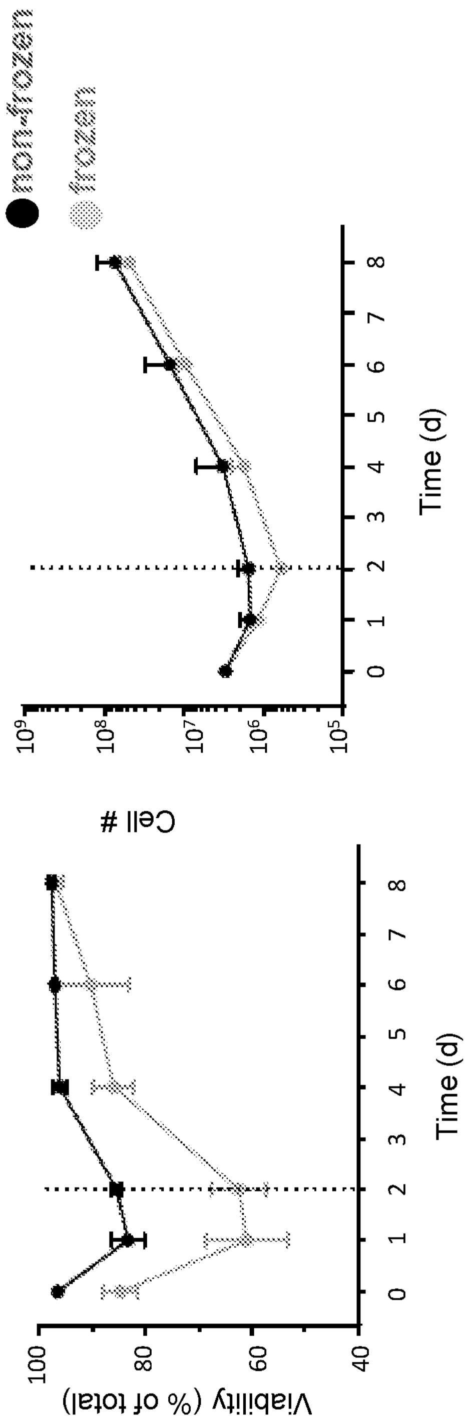

Samples from cell compositions undergoing each process were collected daily and analyzed to determine the total cell number and percentage of viable cells. As shown in FIG. 8A, the total number of cells and the percentage of viable cells decreased during the non-expanded engineering process from day 0 (d0) to day 2 (d2). In the expanded engineering process, cells displayed an initial decrease in cell viability that recovered towards the end of the process. As shown in FIG. 8B, the engineered T cells compositions generated from fresh or previously cryoprotected cells showed similar viability and CAR+ T cell number, with a trend of increased viability and total CAR-T cell numbers observed in T cell compositions generated from the fresh selected T cells.

Figure 9A:
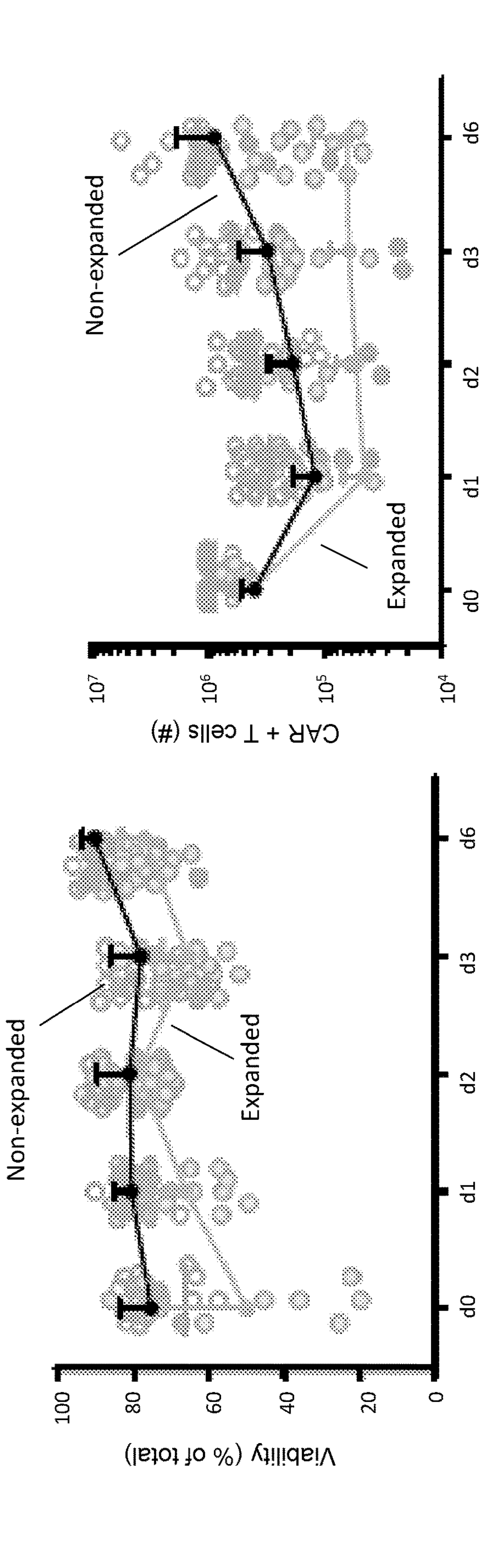
FIGS. 9A and 9B depict the viability of total cell number of anti-CD19 CAR-T cells during co-culture with CD19 expressing cells.
Figure 9B:
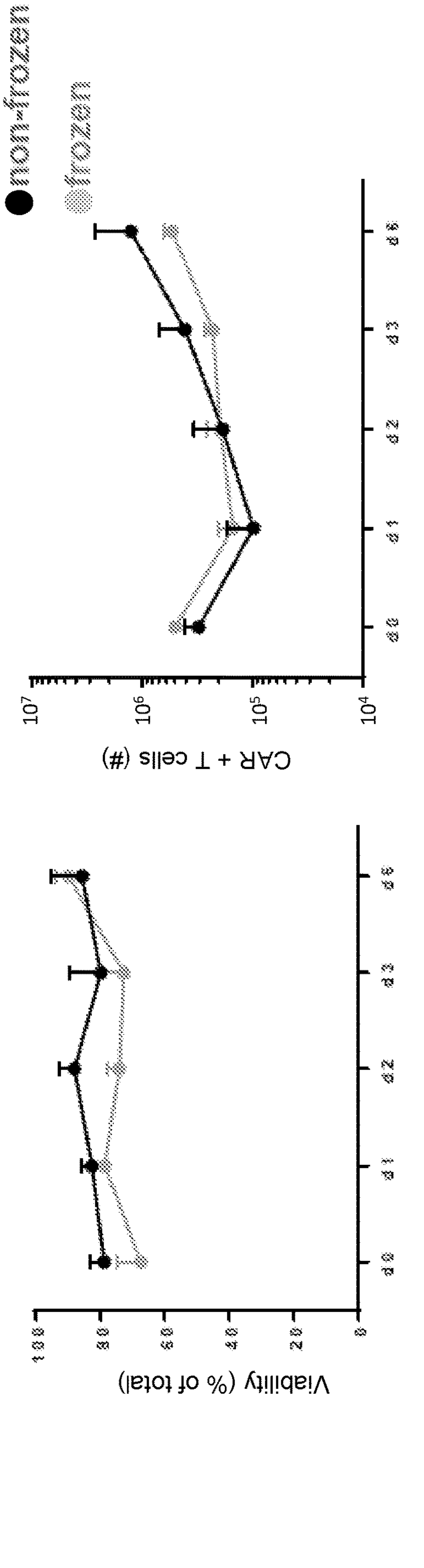

Antigen-specific activity of anti-CD19 CAR-T cells produced by the non-expanded process and the expanded control process was assessed by co-culture with HEK cells engineered to express CD19. The T cell compositions were assessed for viability and total CAR+ T cell number at various time points during the incubation with the antigen-expressing cells. As shown in FIG. 9A, the viability and number CAR-T cell at various days after antigen-stimulation produced from the accelerated process displayed a trend toward greater viability and percentage of total CAR+ T cells after stimulation with antigen. No difference in viability in this assay was observed in T cell compositions that had been cryopreserved prior to stimulation (frozen) compared to fresh T cells that were stimulated directly after selection (non-frozen) (FIG. 9B).

Figure 10:
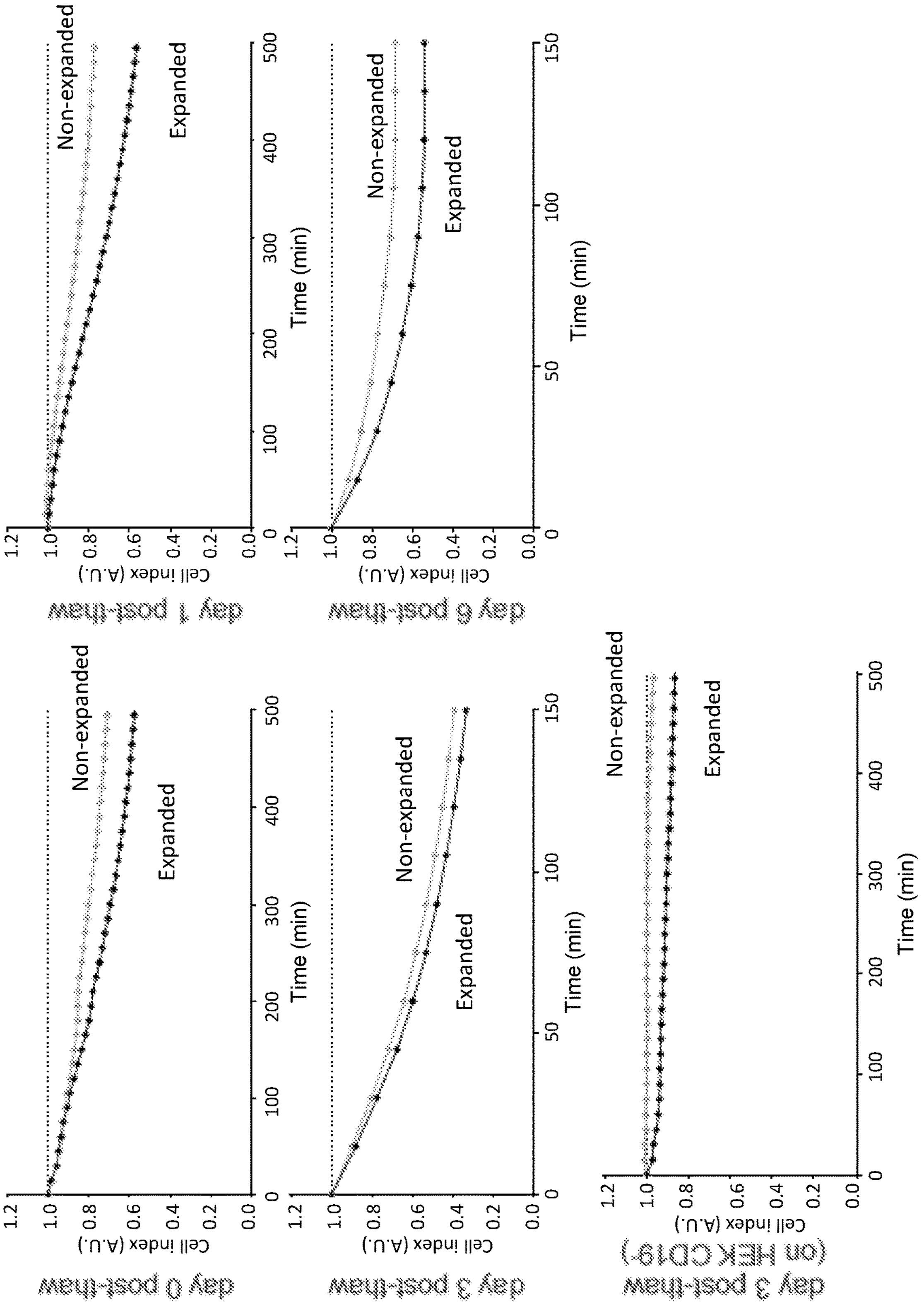
FIG. 10 shows the cytolytic activity of anti-CD19 CAR+T cell compositions containing cells generated using an expanded process or a non-expanded process and cryopreserved prior to stimulation. Cells were cocultured with CD19 expressing cells on day 0, 1, 3, or 6 post-thaw at a 10:1 effector to target cell ratio.

Cytolytic activity of T cell compositions containing the anti-CD19 CAR+ T cells produced by the non-expanded process and the expanded control process was also assessed. Cryopreserved T cell compositions were thawed, and either on the same day or 1, 3, or 6 days post thaw the T cells were co-cultured with HEK cell engineered to express CD19 at a 10:1 effector:target cell ratio. At times post-thaw, cells from T cell compositions generated by the non-expanded engineering process displayed a trend of improved cytolytic activity over T cell compositions generated by the expanded engineering process (FIG. 10).

Figure 11A:
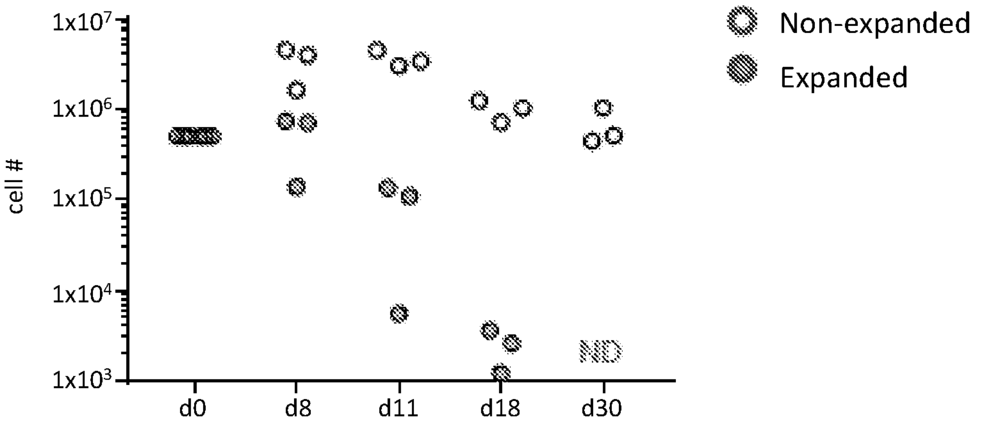
FIGS. 11A and 11B depict anti-CD19 CAR-T cells generated using an expanded process (Expanded), or a non-expanded process (Non-expanded) and cultured under long-term stimulation involving a co-culture with HEK cells engineered to express CD19 at a 5:1 effector to target cell ratio in media lacking additional recombinant cytokines.

The activity of cells from T cell compositions containing anti-CD19 CAR-T cells were assessed in a long-term stimulation assay involving a 30-day co-culture with antigen expressing cells, which mimics the fitness and ability of cells to survive upon long-term exposure to antigen as may occur in vivo up administration. T cell compositions generated from the non-expanded and the expanded control processes were co-cultured with HEK cells engineered to express CD19 at a 5:1 ratio of effector to target cells in media lacking additional recombinant cytokines. T cell samples were collected at various time points during the incubation and analyzed to determine cell number. As shown in FIG. 11A, viable T cells generated by the non-expanded engineering process were detectable in culture for the duration of the 30 day incubation, while the number of T cells generated from the expanded engineering process decreased with increasing time of antigen stimulation.

Figure 11B:
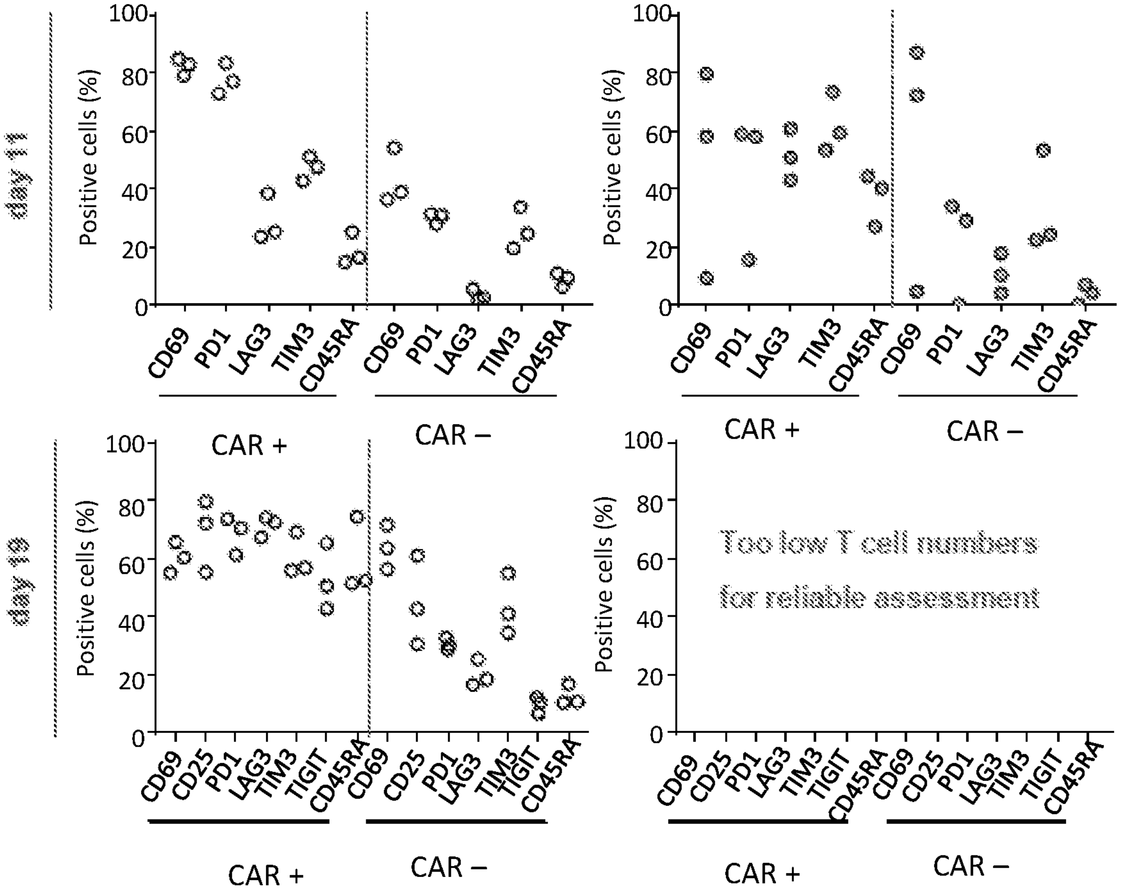

T cells from the long-term stimulation cultures were collected at days 11 and 19, and stained with antibodies against surface proteins including CD25, CD69, PD-1, LAG-3, TIM-3, CD45RA, and TIGIT, as well as for a surrogate marker of CAR expression. As shown by FIG. 11B, at day 11, CAR+ T cells from T cell compositions produced by the non-expanded engineering process displayed generally lower levels and/or more variable levels of exhaustion markers than CAR+ T cells from T cell compositions generated by the expanded engineering process. At day 19, there were too few T cells produced from the expanded engineering process to compare staining.

Example 7: Assessment of Anti-Tumor Activity of Anti-CD19 CAR-T Cell Compositions Generated by Non-Expanded Manufacturing Processes The in vivo efficacy of T cell compositions containing anti-CD19 CAR-T cells generated from the expanded or non-expanded engineering process described in Example 6 were compared. Immunocompromised NSG mice were injected with $5\times10^5$ B cell lymphoma cell line (Raji) at day −7. On day 0, mice were injected with $1\times10^6$, $0.5\times10^6$, or $0.25\times10^6$ CAR+ T cells from compositions produced by either a non-expanded or an expanded process. These doses are below the previously determined curative dose of anti-CD19 CAR-T cells ($1.5\times10^6$ CAR+ cells) in this xenograft tumor model.

Tumor burden was measured in vivo by in-life luminescence imaging at different time points up to 49 days following administration of CAR-T cells. In addition, blood samples were collected at different time points and assessed for the presence of tumor cells, total T cells, and CAR+ T cells. During this study, two mice were euthanized for humane reasons; both mice had been treated with CAR-T cell compositions generated from the expanded process (one received the dose of $1\times10^6$ CAR+ T cells and the other received the dose of $0.25\times10^6$ CAR+ T cells).

Figures 12A, 12B:
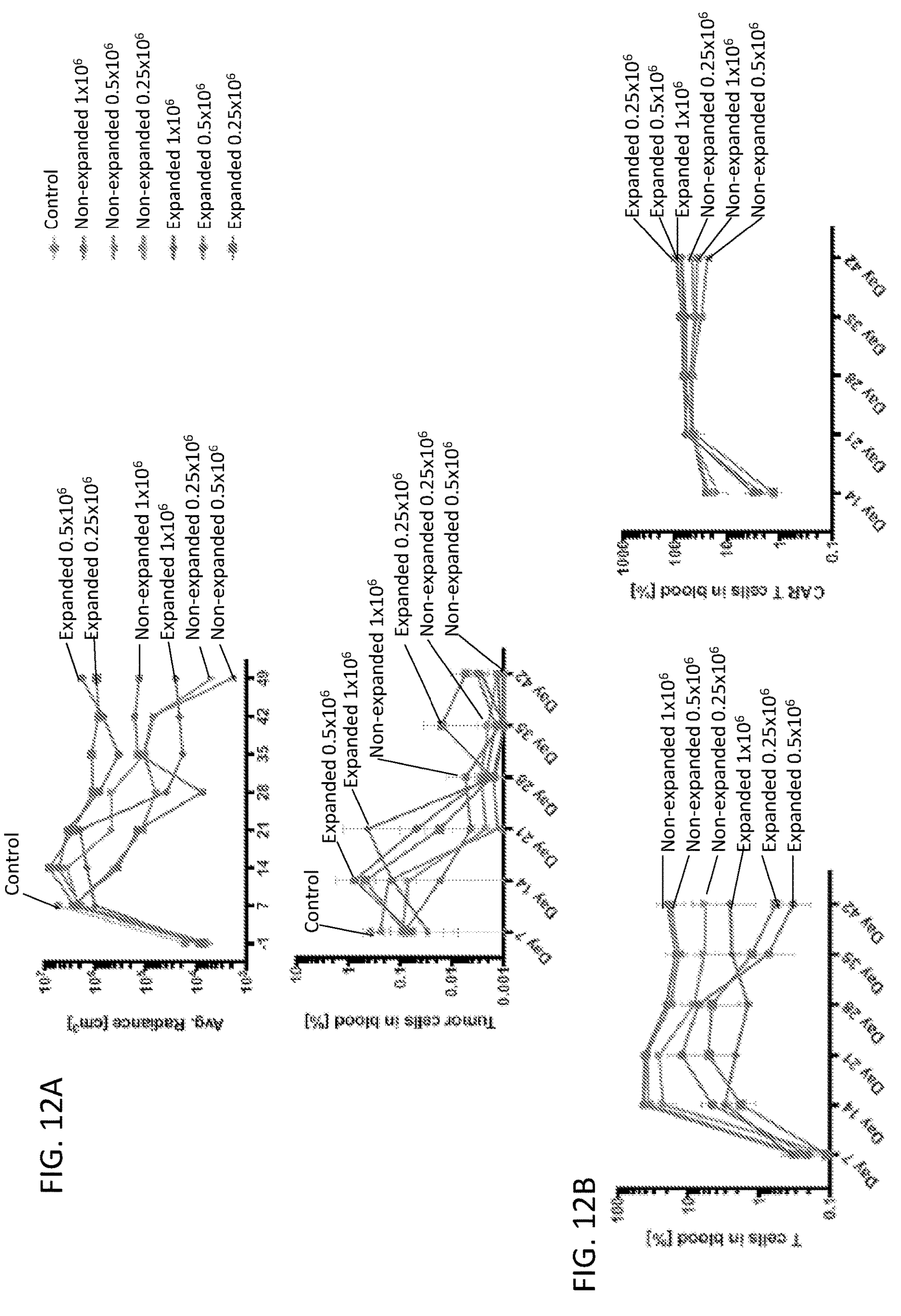
FIGS. 12A-12C show results from an in vivo tumor mouse model of mice injected on day 0 with $1\times10^6$, $0.5\times10^6$, or $0.25\times10^6$ anti-CD19 CAR-T cells generated using an expanded process (Expanded), or a non-expanded process (Non-expanded) or PBS control.
Figure 12C:
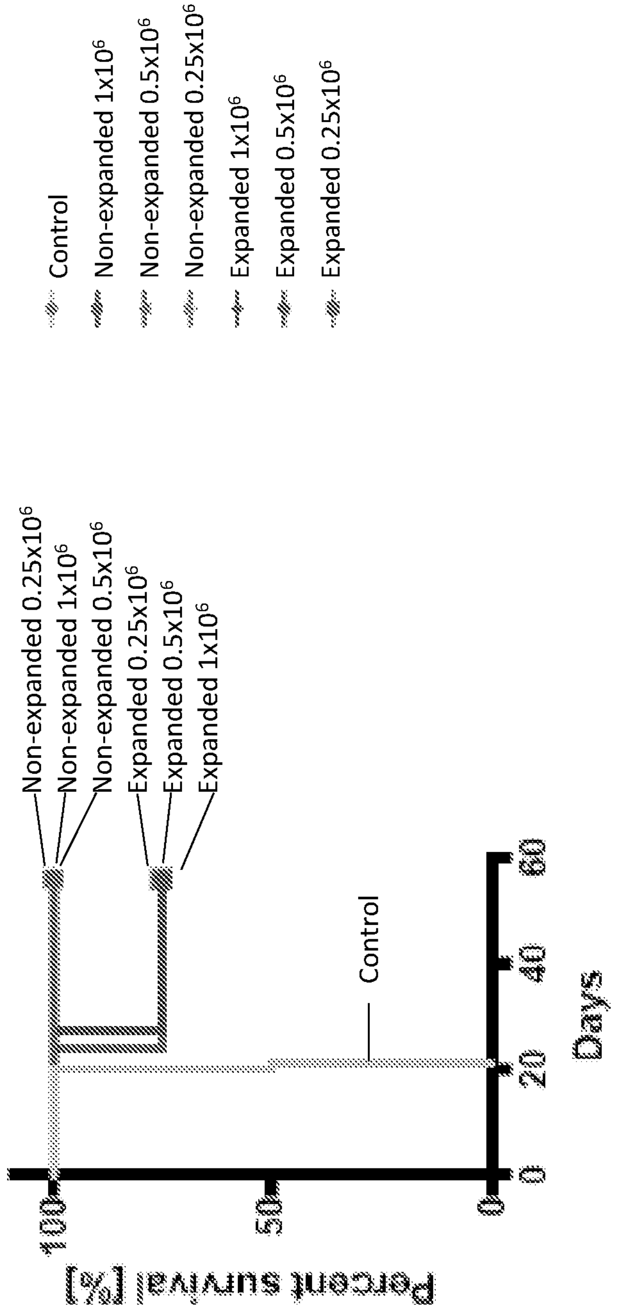

As shown in FIG. 12A, a reduced tumor burden and reduced circulating T cells were observed in mice administered CAR-T cell compositions generated from the non-expanded engineering process as compared to CAR-T cell compositions generated from the expanded process. Mice administered the lowest dose of cells generated from the non-expanded process exhibited reduced tumor burden, while tumor burden was not substantially changed in mice administered the same dose of CAR-T cells from an engineered composition produced with an expanded process. A greater number of circulating T cells in the blood also was observed in mice administered CAR-T cell compositions generated from the non-expanded engineering process as compared to the expanded engineering process, while similar numbers of circulating CAR+ T cells were observed between groups (FIG. 12B). The percent survival of mice was 100% up to day 60 after injection of $1\times10^6$ CAR-T cells in mice treated with engineered cells from a composition produced from the non-expanded process (FIG. 12C).

Example 8: Further Design of a Non-Expanded Process for Producing an Engineered T Cell Composition Engineered compositions of primary T cells containing T cells expressing CARs were produced using non-expanded processes described in Example 1, except that certain parameters in one or more steps were altered to assess suitability with the process. As a comparison, the CAR-engineered T cells were produced using the expanded process described in Example 1.

a. Non-Expanded Process-Anti-CD3/Anti-CD28 Beads

A non-expanded process using the process described in Example 1.a with anti-CD3/anti-CD28 antibody conjugated beads was carried out in which, after spinoculation, the cells were resuspended in serum free media without cytokines (basal media) and allowed to incubate at about 37.0° C. in an incubator for 96 hours after initiation of the stimulation with the anti-CD3/anti-CD28 beads.

In addition, a similar process was carried out except that, after spinoculation, the cells were resuspended in serum free media without cytokines (basal media) and allowed to incubate at about 37.0° C. in an incubator for 72 hours after initiation of the stimulation with the anti-CD3/anti-CD28 beads.

b. Non-Expanded Process-Anti-CD3/Anti-CD28 Fab Oligomeric Reagent

A non-expanded process using the process described in Example 1.b with anti-CD3/anti-CD28 Fab oligomeric reagent was carried out, except in which the amount of oligomeric reagent used during the stimulation was reduced 5-fold (0.2×; 0.8 μg per $10^6$ cells) compared to the process described in Example 1.

In one arm of the process, CD4+ and CD8+ T cells were selected and mixed at a 1:1 ratio to produce an input composition containing approximately $600\times10^6$ T cells ($300\times10^6$ CD4+ and $300\times10^6$ CD8+ T cells). Cells from the mixed input cell composition were stimulated by incubation with 480 μg (or 0.8 μg per $1\times10^6$ cells) anti-CD3/anti-CD28 Fab conjugated oligomeric streptavidin mutein reagents generated as described in Example 2, which was carried out in serum free media containing recombinant IL-2, IL-7 and IL-15 for between 18-30 hours. After stimulation, the cells were transduced with a lentiviral vector encoding the anti-BCMA CAR described in Example 1 by spinoculation at 693 g for 30 minutes. After the spinoculation, the cells were washed and resuspended in serum free media without recombinant cytokines (basal media), and incubated at about 37.0° C. in an incubator. After 24 hours after initiation of transduction (approximately 48 hours after initiation of stimulation), 1.0 mM D-biotin was added and mixed with the cells to dissociate anti-CD3 and anti-CD28 Fab reagents from oligomeric streptavidin reagents. The cells were further incubated for about 48 hours (96 hours after initiation of stimulation), and then were washed and formulated with a cryoprotectant as described in Example 1A.

In another arm of the process, CD4+ and CD8+ T cells were selected, mixed at a 1:1 ratio to produce an input composition containing approximately $600\times10^6$ T cells ($300\times10^6$ CD4+ and $300\times10^6$CD8+ T cells), and stimulated exactly as described above. In this arm, the cells were transduced with a lentiviral vector encoding the anti-BCMA CAR described in Example 1 by spinoculation at 693 g for 30 minutes. After the spinoculation, the cells were washed and resuspended in serum free media without recombinant cytokines (basal media) and incubated at about 37.0° C. in an incubator. After 24 hours after initiation of the transduction, 1.0 mM D-biotin was added and mixed with the cells to dissociate anti-CD3 and anti-CD28 Fab reagents from oligomeric streptavidin reagent. The cells were further incubated for an additional 24 hours (72 hours after initiation of stimulation), and then were washed and formulated with a cryoprotectant as described in Example 1A.

c. Summary of Processes

Table E5 summarizes the processes generated using methods as described above, in addition to a process using a mock empty vector . . .

TABLE E5

| Arm | Stim. Reagent | Cell Number | Transduction | Expansion | Removal of stimulatory reagent | Harvest |
|---|---|---|---|---|---|---|
| 1 | Beads | 1.5 × 106 CD4 and 1.5 × 106 CD8 | Spinoculation & incubation for 18-30 hours | Until TNC of ~3 × 109 cells, about 6-7 days | Wash and debead<br>Day following threshold number | Following debead |
| 2 | Beads | 3.0 × 106 CD4 and 3.0 × 106 CD8 | Spinoculation & incubation for about 72 hours in basal media | None | Wash and debead<br>About 96 hours after initiation of stimulation | Following debead |
| 3 | Beads | 3.0 × 106 CD4 and 3.0 × 106 CD8 | Spinoculation & incubation for about 48 hours in basal media | None | Wash and debead<br>About 72 hours after initiation of stimulation | Following debead |
| 4 | Oligo. 0.2X | 3.0 × 106 CD4 and 3.0 × 106 CD8 | Spinoculation & incubation for 72 hours in basal media | None | Biotin added during incubation about 24 hours after initiation of transduction | 96 hours after initiation of stimulation |
| 5 | Oligo. 0.2X | 3.0 × 106 CD4 and 3.0 × 106 CD8 | Spinoculation& incubation for 48 hours in basal media | None | Biotin added during incubation about 24 hours after initiation of transduction | 72 hours after initiation of stimulation |
| 6 | (Mock) Oligo. 0.2X | 1.5 × 106 CD4 and 1.5 × 106 CD8 | Mock transduction & static incubation for 72 hours in basal media | None | Biotin added about 24 hours after initiation of transduction | 96 hours after initiation of stimulation |

Example 9: Assessment of Phenotype and Function of Cells Generated from a Non-Expanded Process for Producing an Engineered T Cell Composition T cell compositions generated as described in Example 8 were assessed for various phenotypic and functional features.

a) Phenotype and Differentiation Markers

Figure 13A:
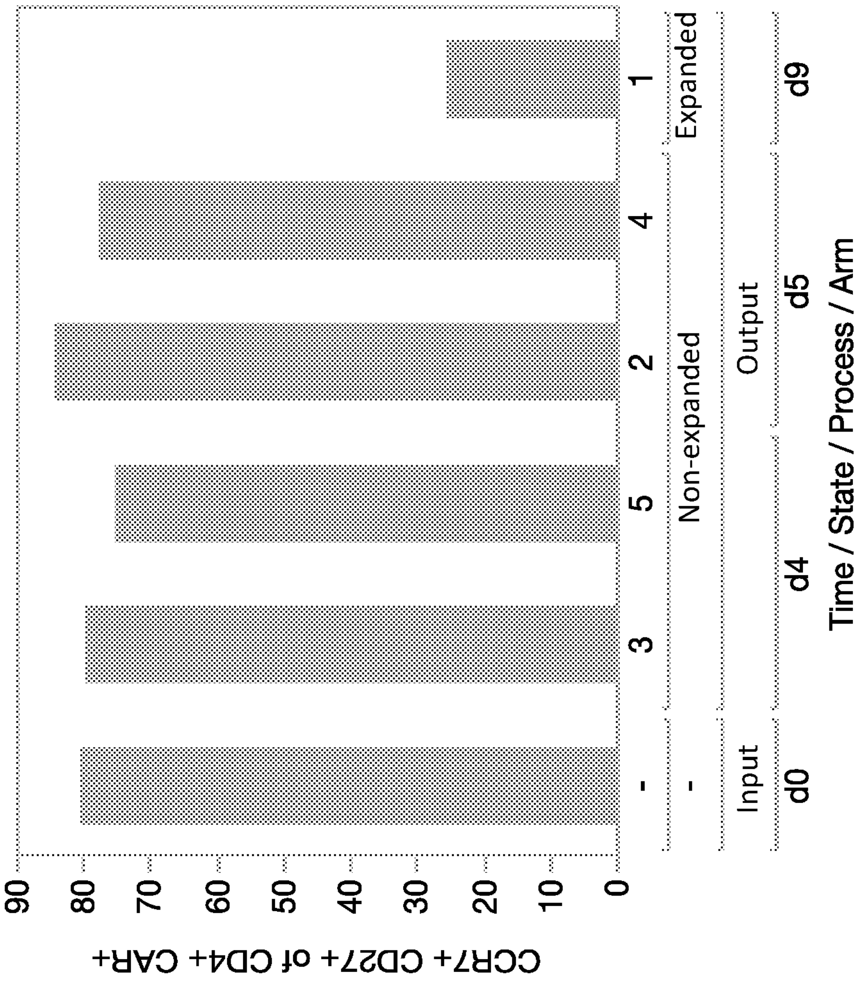
FIGS. 13A-13B depict engineered T cell (EC) compositions generated by an expanded processes involving a bead-based stimulatory reagent spinoculated and under static incubation for 18-30 hours (arm 1) and non-expanded processes involving spinoculation and an oligomeric stimulatory reagent incubated in basal media for 96 hours (arm 4), spinoculation and a bead-based stimulatory reagent incubated in basal media for 72 hours (arm 2), an oligomeric stimulatory reagent incubated in basal media for 72 hours (arm 5), bead-based stimulatory reagent incubated in basal media for 48 hours (arm 3) and non-stimulated cryopreserved T-cell compositions (CMAT).

T cell compositions produced from expanded and non-expanded engineering processes as described in Example 8 were stained with antibodies recognizing surface markers including CD4, CD8, CCR7 and CD27 and quantified by flow cytometry. The percentage of CCR7+CD27+ cells of CD4+CAR+ T cells are shown in FIG. 13A. As shown, a greater percentage of CCR7+CD27+ were observed in the T cell compositions produced from each non-expanded engineering process as compared to the expanded engineering process. The percentage of cells positive for CCR7 and CD27 was similar to the percentage of cells present in the input composition (CMAT) prior to stimulation and transduction.

Figure 13B:
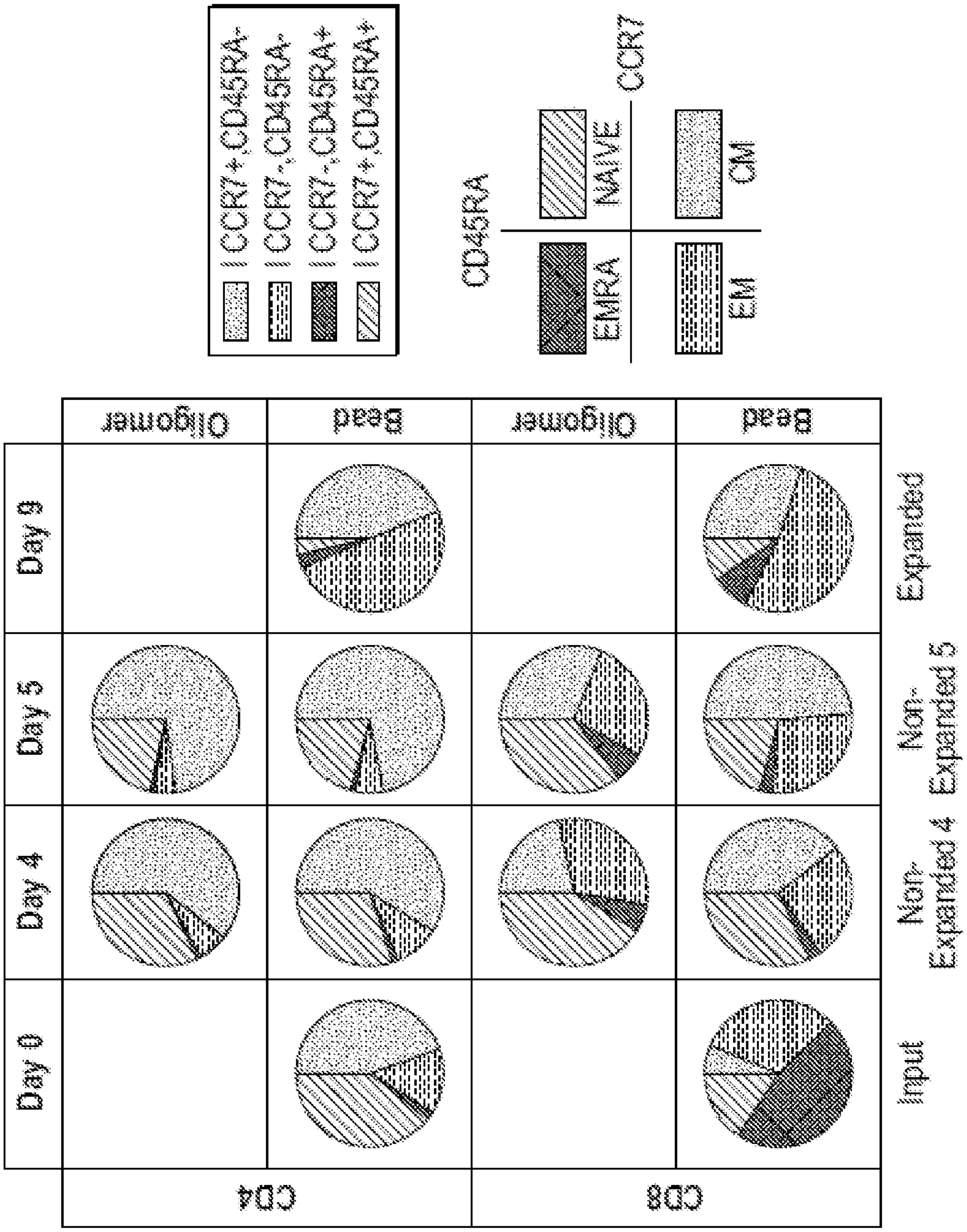

T cell compositions generated as described in Example 8 from expanded (day 9) and non-expanded engineering processes were stained with antibodies recognizing surface markers including CD4, CD8, CCR7, CD45RA and for the surrogate marker for CAR expression, and quantified by flow cytometry. The percentage of CD4+CAR+ T cells and CD8+CAR+ T cells that were indicative of effector memory CD45RA+ cells (CCR7−CD45RA+; EMRA), naïve-like T cells (CCR7+CD45RA+; NAIVE), effector memory (CCR7−CD45RA−; EM) or central memory (CCR7+CD45RA−; CM) are shown in FIG. 13B. Following the engineering process, the results show that T cells generated from non-expanded processes have a greater percentage of CD45RA+CCR7+naïve-like cells and CCR7+CD45RA− cells (central memory) compared to cells generated from an expanded process involving expansion of cells post-transduction. Similarly, effector memory CCR7−CD45RA− and effector memory CD45RA+ (CCR7−CD45RA+) cells were reduced among cells generated from non-expanded processes compared to cells generated from an expanded process involving expansion of cells post-transductions.

These results are consistent with engineered cell compositions generated from non-expanded engineering processes having a greater portion of cells with a naïve-like and central memory-like, less differentiated phenotype than cell compositions generated by the expanded process.

b. Cytolytic Activity

K562 cells were engineered to express BCMA (K562-BCMA) and were used as target cells. The K563-BCMA target cells were incubated with exemplary anti-BCMA CAR T cells from compositions generated by an expanded or non-expanded process as described in Example 8 at various effector to target cell (E:T) ratios for a duration of 0-96 hours. The effector cell numbers were adjusted to reflect total CAR+ cells based on expression of the surrogate marker. The target K562-BCMA target cells were labeled with NucLight Red (NLR) to permit their tracking by microscopy.

Cytolytic activity was assessed by measuring the loss of viable target cells every 4 hours over a period of 48 hours, 72 hours or 96 hours, as determined by red fluorescent signal (using the IncuCyte® Live Cell Analysis System, Essen Bioscience). Normalized target cell numbers were generated by dividing target cell counts to cell counts at the start of each culture. The percentage of target killing was assessed by measuring the area under the curve (AUC) for normalized target cell count over time and normalizing the inverse AUC (1/AUC) values by defining a 0% value (target cells alone) and a 100% value (CAR+ T cells co-cultured with target cells in vehicle control). The EC50 for killing is shown by the dotted line.

$$\text{Specific Lysis} = \frac{(T\text{ cell: Target}_{RedObjectCount} - \text{Target alone}_{RedObjectCount})}{(\text{Target: Permeabilization Buffer}_{RedObjectCount} - \text{Target alone}_{RedObjectCount})} \times 100$$

Figure 14:
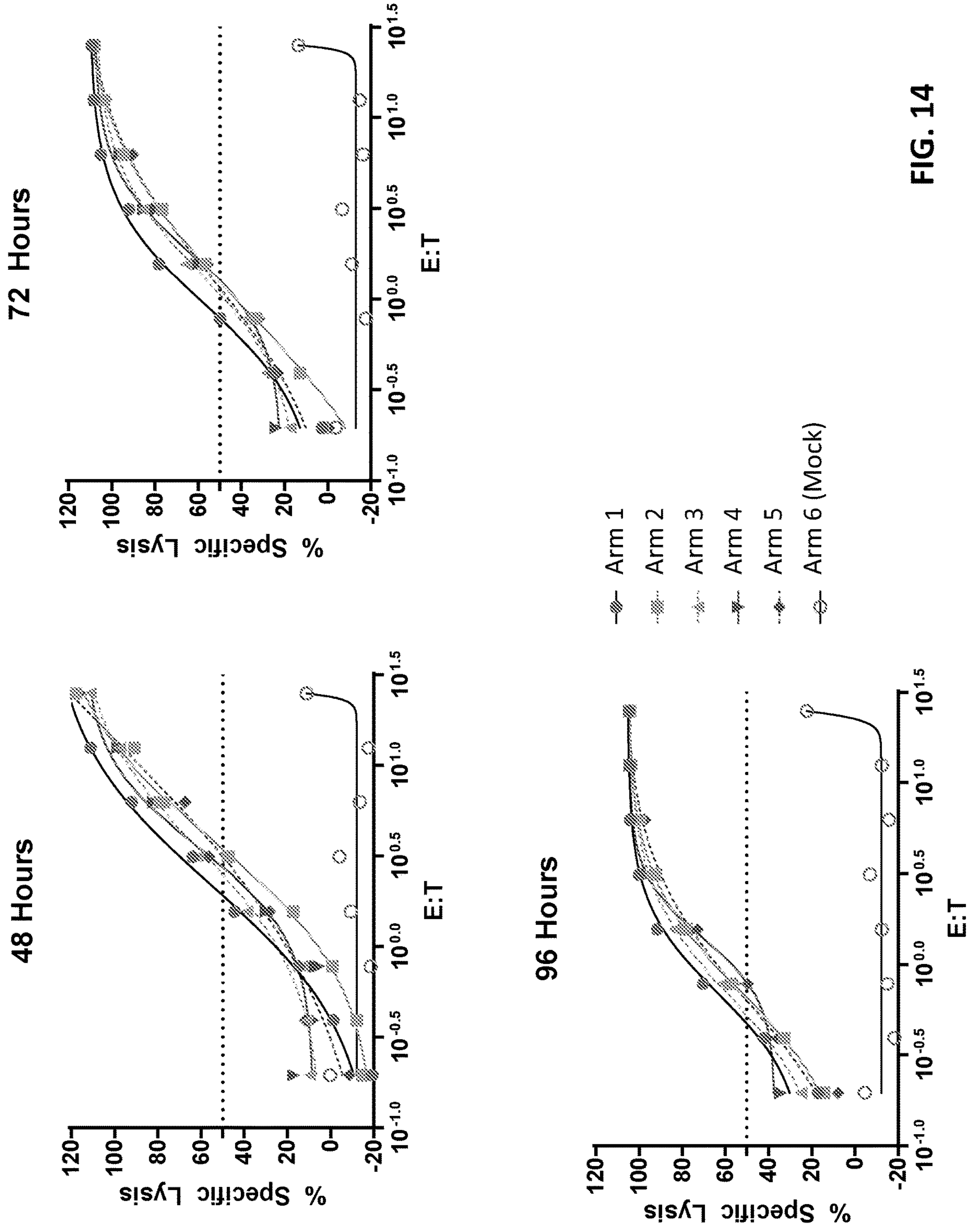
FIG. 14 shows the cytolytic activity (% specific lysis) of engineered T cell compositions generated by an expanded processes involving a bead-based stimulatory reagent spinoculated and under static incubation for 18-30 hours (arm 1) and non-expanded processes involving spinoculation and a bead-based stimulatory reagent incubated in basal media for 72 hours (arm 2), spinoculation and a bead-based stimulatory reagent incubated in basal media for 48 hours (arm 3) spinoculation and an oligomeric stimulatory reagent incubated in basal media for 96 hours (arm 4), spinoculation and an oligomeric stimulatory reagent and incubation in basal media for 72 hours (arm 5), in addition to a process using a mock empty vector (arm 6, mock), on K562-BCMA target cells at various effector to target ratios (E:T). Cytolytic activity was assessed by microscopy by loss of red fluorescent signal and normalized to cell counts at the start of each culture every 4 hours over a period of 48, 72 and 96 hours. Dotted line denotes EC50 for killing.

As shown in FIG. 14, all engineered T cell compositions generated in Example 8 exhibited equivalence in function as determined by similar cytolytic activity in this assay.

c. Chronic Stimulation

The activity of cells from T cell compositions generated as described in Example 8 were assessed in a long-term stimulation assay involving continuous incubation for 6 days in the presence of paramagnetic beads conjugated with recombinant BCMA Fc fusion proteins to provide a CAR-dependent stimulus, which mimics the fitness and ability of cells to survive upon long-term exposure to antigen as may occur in vivo up administration.

Figure 15A:
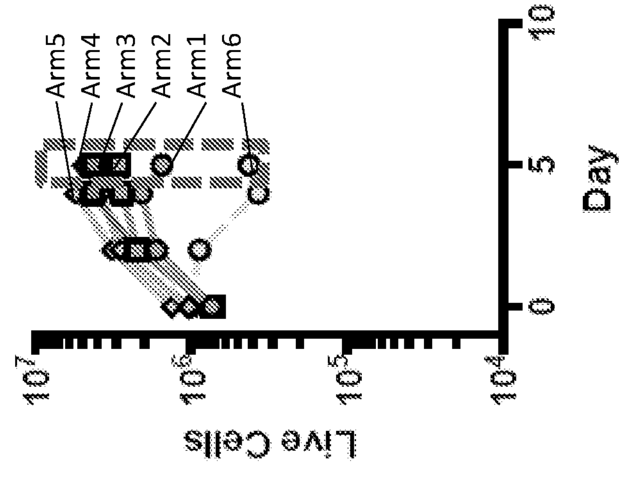
FIGS. 15A-15C depict the activity in a long-term stimulation assay involving continuous incubation with paramagnetic beads conjugated with recombinant BCMA Fc fusion proteins for 6 days of T cell compositions generated by an expanded processes involving a bead-based stimulatory reagent spinoculated and under static incubation for 18-30 hours (1), and non-expanded processes involving spinoculation and a bead-based stimulatory reagent incubated in basal media for 72 hours (2), spinoculation and a bead-based stimulatory reagent incubated in basal media for 48 hours (3), spinoculation and an oligomeric stimulatory reagent incubated in basal media for 96 hours (4), spinoculation and an oligomeric stimulatory reagent and incubation in basal media for 72 hours (5), in addition to a process using a mock empty vector (arm 6, mock).
Figure 15B:
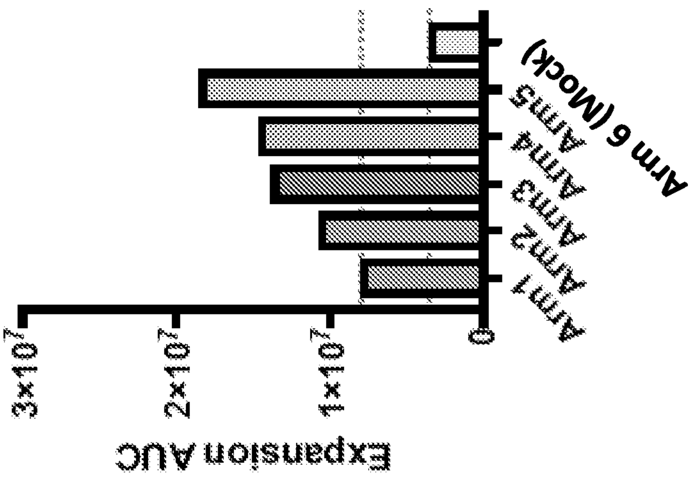
Figure 15C:
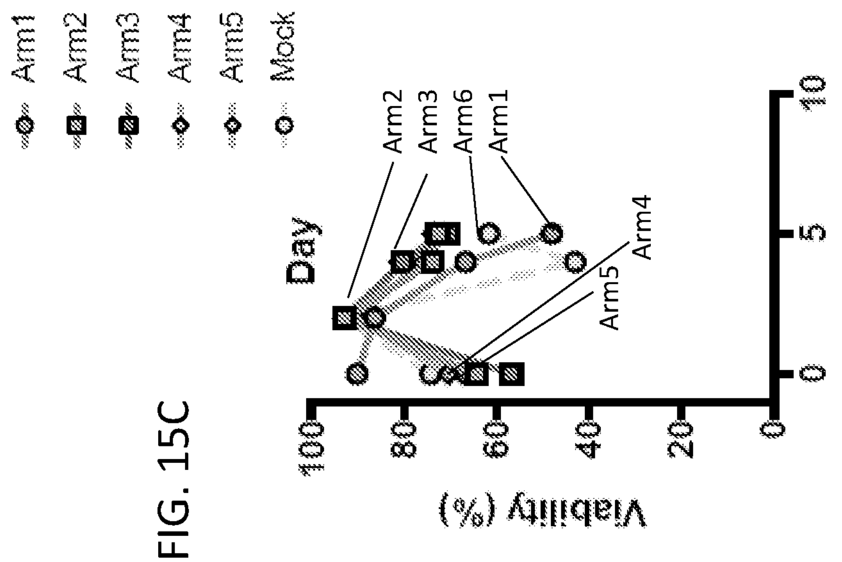

T cell compositions were assessed at various time points for total number of viable cells, expansion as quantified as the area under the curve for total viable cells measured from day 1 to day 6 of the incubation and percent viability, and results from an exemplary experiment are shown in FIGS. 15A-C, respectively. An increase in the total number of live cells T cell was observed during the course of the long-term stimulation (FIG. 15A). As shown in FIG. 15B, T cell compositions generated from non-expanded cell processes exhibited greater expansion of cells compared to cells that were generated by an expanded process, indicated an improved fitness of the cells generated from the non-expanded processes. In this assay, the percentage of viable cells was similar across among the T cells produced from the different engineering processes (FIG. 15C).

At the end of the stimulation at day 6, the cells were debeaded to remove the BCMA-Fc beads, and CAR frequency was determined to normalize CAR+ cells prior to assessing the ability of the cells to respond to second antigen stimulus in an intracellular cytokine staining endpoint assay. Cells that had not been stimulated with BCMA-Fc beads (D0) or cells from day 6 (D6) that had been stimulated with BCMA-Fc beads were cultured with RPMI-8226 cell line at an effector to target ratio of 1:1 normalized for CAR+ cells among groups. The cultures were incubated for 5 hours in the presence of Golgi inhibitor. The CAR+ T cells were then stained for intracellular accumulation of cytokines and analyzed by flow cytometry.

Figure 16A:
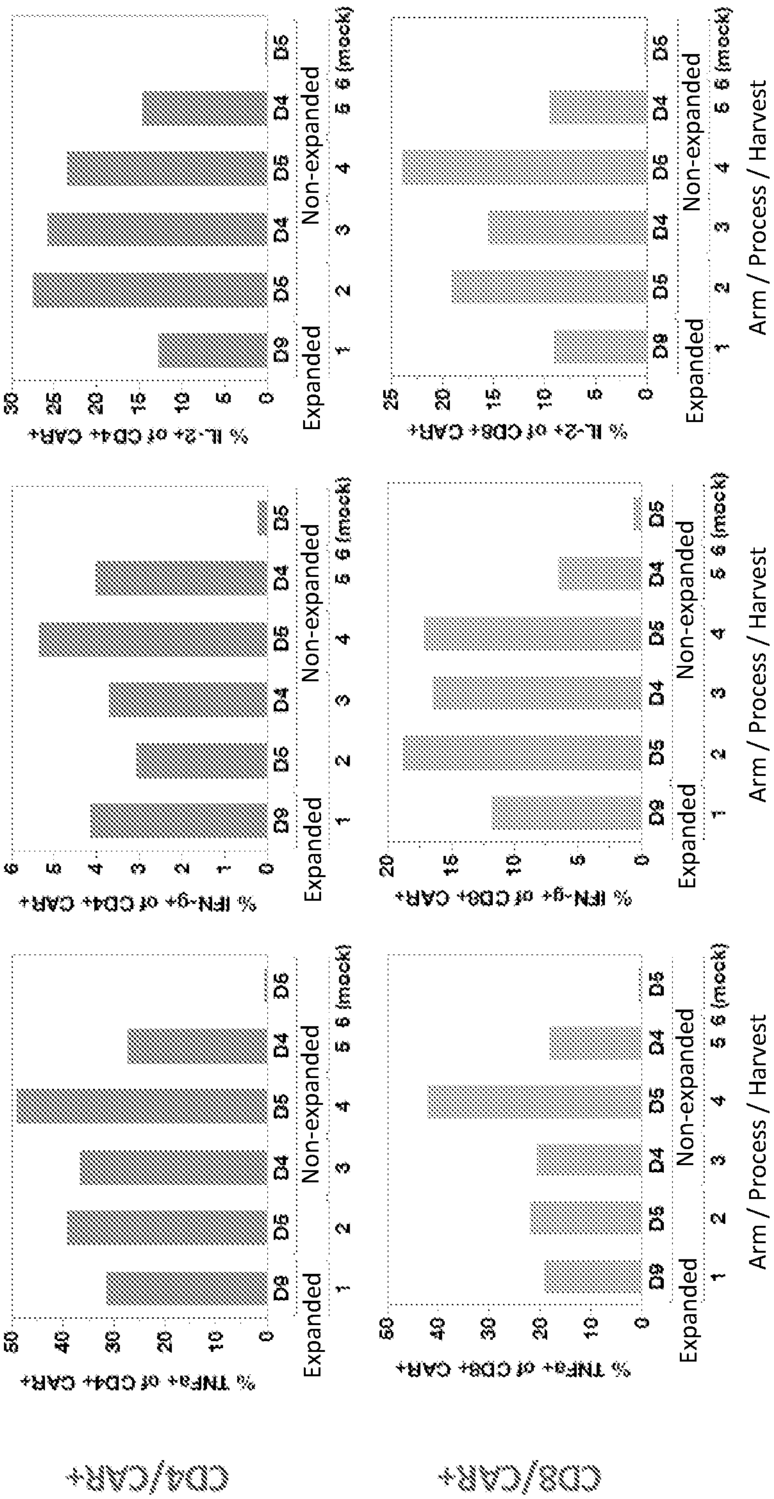
FIGS. 16A-16C depict cytokine profiles after long-term stimulation involving continuous incubation with paramagnetic beads conjugated with recombinant BCMA Fc fusion proteins for 6 days of the T cell compositions depicted in FIGS. 15A-15C.
Figure 16B:
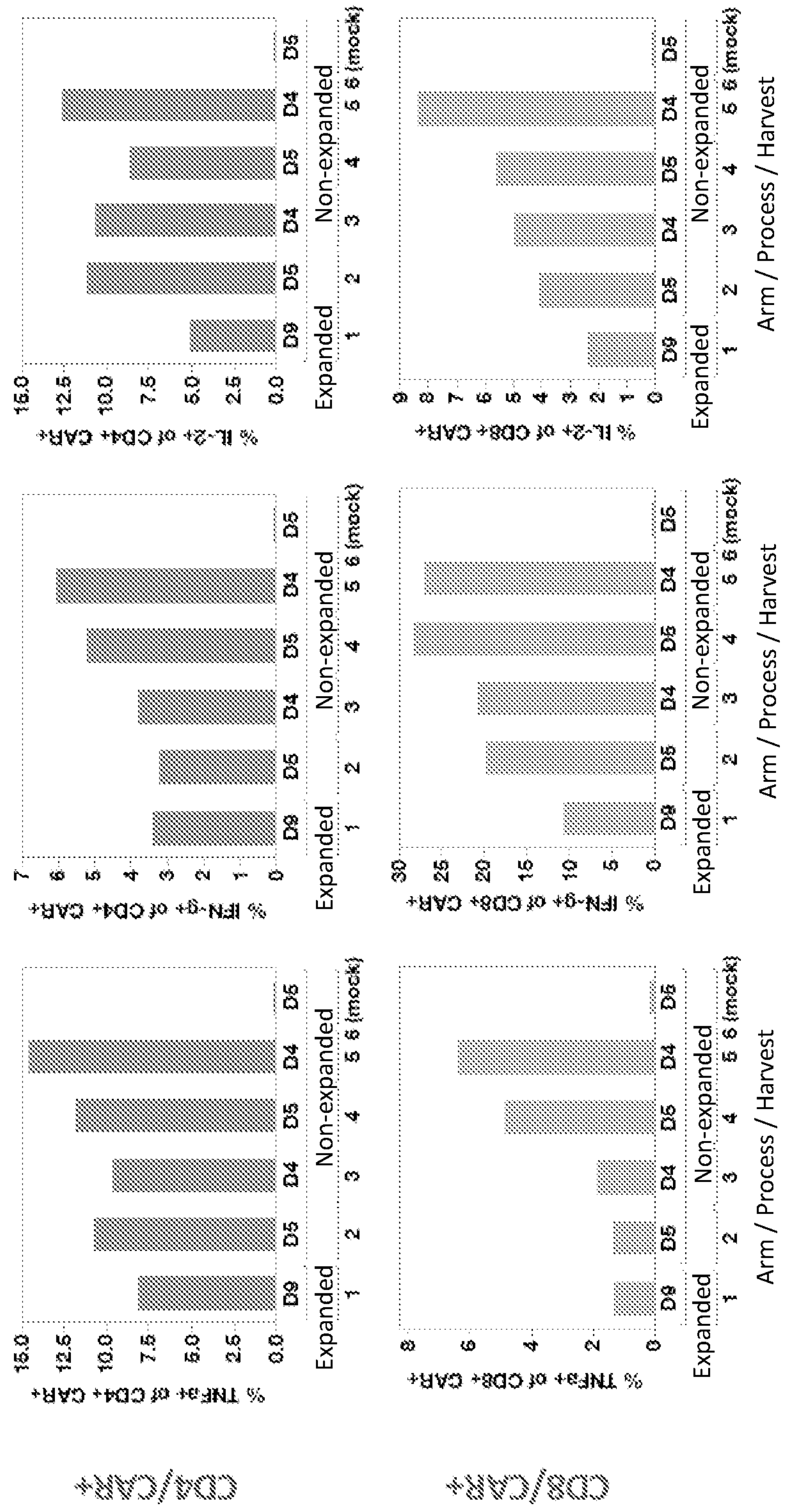
Figure 16C:
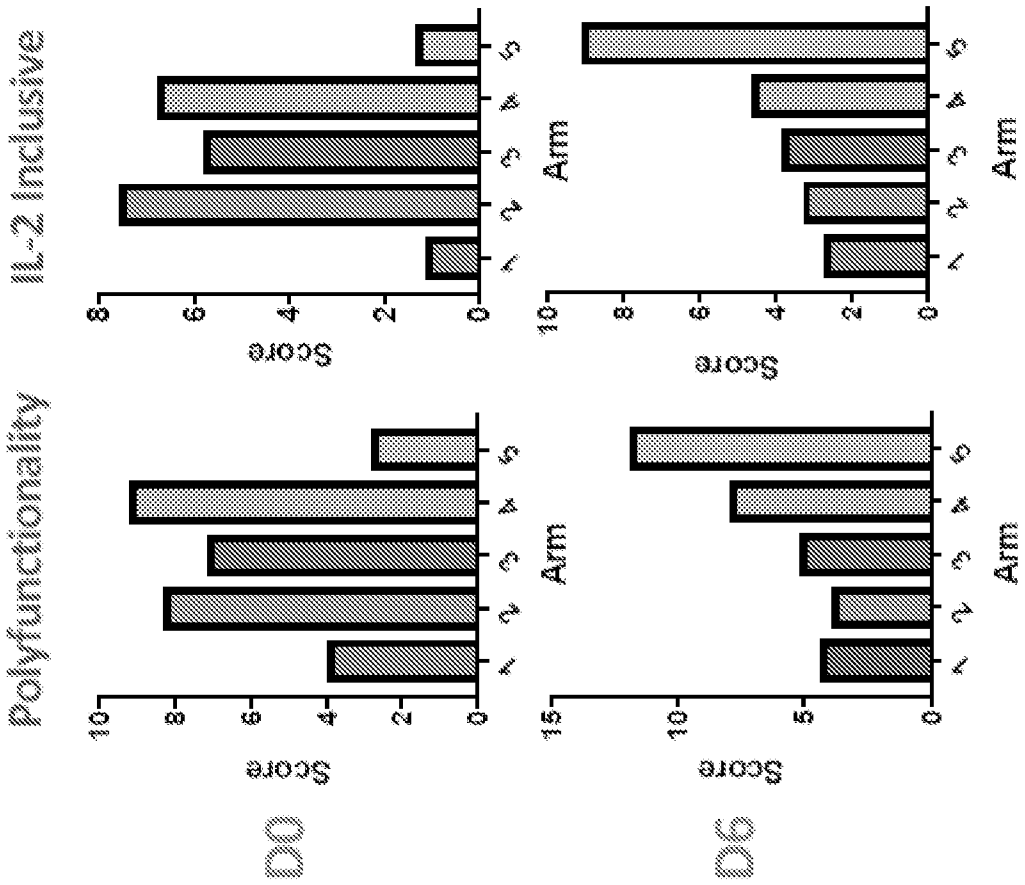

Cells generated from non-expanded processes exhibited similar or better cytokine profiles compared to cells generated from an expanded process at both day 0 (FIG. 16A) and day 6 after chronic stimulation (FIG. 16B). Polyfunctional cytokine production was assessed by flow cytometry following intracellular cytokine staining for IL-2, IFN-gamma, TNF-alpha and IL-13. A polyfunctional score from cumulative levels of cytokines as determined in CD4+CAR+ and CD8+CAR+ cells or an IL-2 inclusive score were determined, after the data were normalized by scaling within donor FIG. 16C. Cells generated from the non-expanded processes showed greater polyfunctionality than cells produced from an expanded process, including after a secondary antigen stimulus. These results are consistent with an observation that cells generated from a non-expanded process exhibit improved fitness.

Example 10: Relationship of Number of Doublings and Cell Differentiation or Patient Response Exemplary therapeutic T cell compositions containing autologous T cells expressing a chimeric antigen-receptor (CAR) specific for CD19 were generated. The anti-CD19 CAR contained an anti-CD19 scFv derived from a murine antibody (variable region derived from FMC63), an immunoglobulin-derived spacer, a transmembrane domain derived from CD28, a costimulatory region derived from 4-1BB, and a CD3-zeta intracellular signaling domain.

For generation of cell compositions for administration to subjects with Relapsed and Refractory Non-Hodgkin's Lymphoma (NHL), autologous cells were isolated from the subjects via leukapheresis. Leukapheresis samples were subjected to a process for generation of CAR-expressing cells. The process involved washing of cells using an automated wash and immunoaffinity based selection for purification of $CD4^+$ and $CD8^+$ T cells, resulting in two compositions, enriched for $CD8^+$ (in which a median of 99%, Inter Quartile Range (IQR) 98-100%, of cells were $CD8^+$) and CD4+ (in which a median of 99%, IQR 99-100%, cells were $CD4^+$) cells, respectively.

Cells of the enriched $CD4^+$ and $CD8^+$ compositions were activated with anti-CD3/anti-CD28 paramagnetic beads and then were separately subjected to lentiviral transduction with a vector encoding an anti-CD19 CAR with a 4-1BB costimulatory domain. Transduced populations then were separately incubated in the presence of stimulating reagents for cell expansion. Expanded $CD8^+$ and $CD4^+$ cells were formulated and cryopreserved separately and stored prior to administration. To minimize variations, between lots and/or cell compositions derived from different patients, such as those having different patient attributes, in parameters indicative of cell health, cells were held at constant volumes across lots. Cell products exhibited a tight range of viable cell concentrations (based on an assessment of cell compositions for one group of subjects, $CD8^+$: median $31\times10^6$ cells/mL, IQR 28-$40\times10^6$ cells/mL, N=38; $CD4^+$: median $35\times10^6$ cells/mL, IQR 31-$40\times10^6$, N=36).

The generated T cell compositions were used for administration in subjects with Relapsed and Refractory Non-Hodgkin's Lymphoma (NHL) as described below.

A. Exemplary Attributes of Therapeutic T Cell Compositions

The generated therapeutic T cell compositions, used for administration in subjects with Relapsed and Refractory Non-Hodgkin's Lymphoma (NHL) described below, were assessed for CCR7 and CD27 using flow cytometry. Surface expression levels of CD4 and truncated receptor used as a surrogate marker, also were assessed.

For each generated therapeutic composition, the number of doublings of the generated cell compositions also was determined based on total nuclear count (TNC) of cells, by dual-fluorescence staining with acridine orange (AO) and either propridum iodide (PI) or DAPI, using the following formula:

$$\text{Cell doublings} = \frac{\ln\left(\frac{TNC \text{ at harvest}}{TNC \text{ 3 days post-activation}}\right)}{\ln 2} \quad 1)$$

Figure 17A:
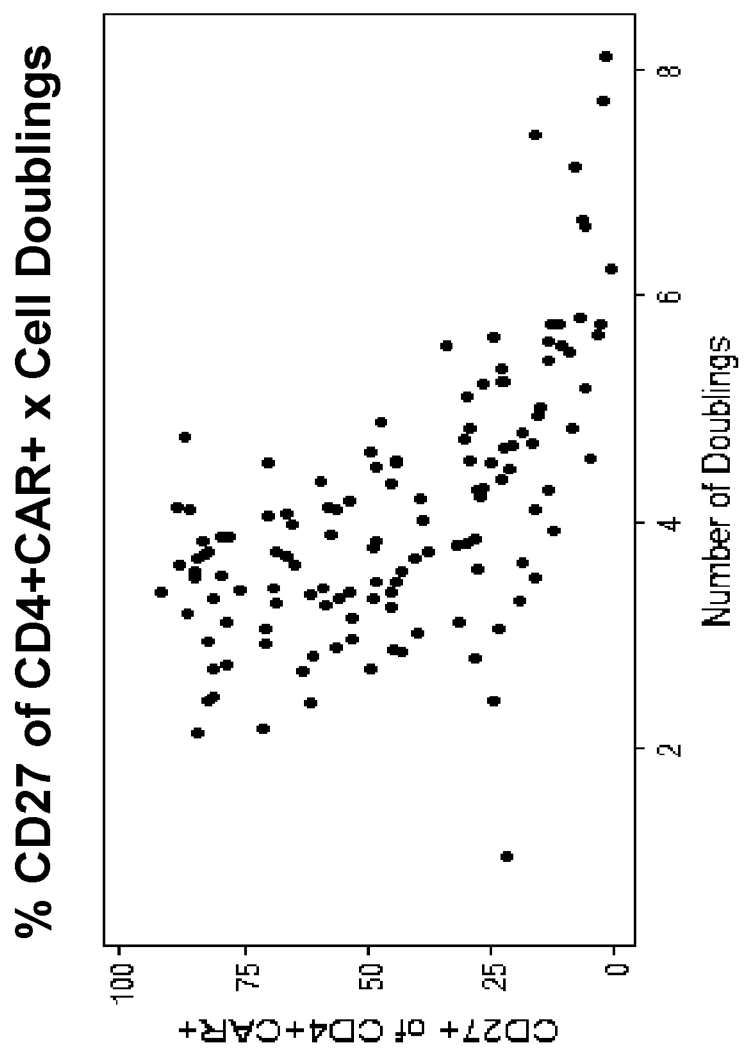
FIG. 17A shows the correlation between the number of doublings in the process for producing the therapeutic composition and the percentage of CD4+CAR+ cells that are positive for CD27+.
Figure 17B:
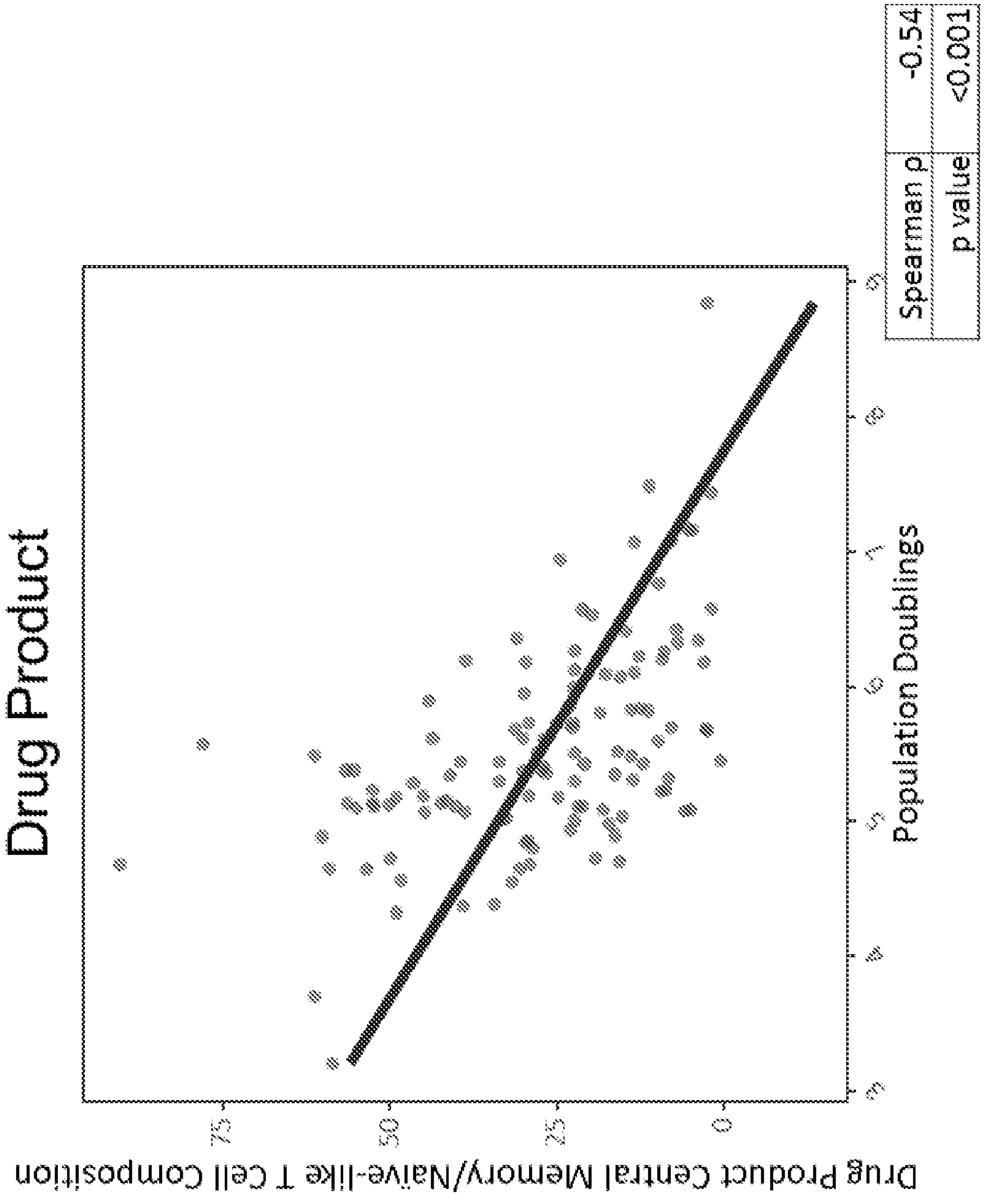
FIG. 17B shows the relationship between the percentage of central memory/naïve-like CD4+ T cells in the therapeutic output T cell composition (e.g., drug product) and the number of population doublings to achieve harvest criterion (Spearman ρ: −0.54; p-value: <0.001). A similar result was observed for CD8+ T cells in the therapeutic output T cell composition (e.g., drug product).

FIG. 17A shows the correlation between the number of doublings in the process for producing the therapeutic composition and the percentage of CD27+ cells of CD4+ CAR+ cells. Similar results were observed for CD8+ T cells. The results show that, in general, a lower number of doublings during the process to generate therapeutic T cell compositions is associated with increased levels of CD27+ cells. Without wishing to be bound by theory, the results described above are consistent with an observation that the increased percentage of CD27+ cells in the non-expanded processes generated as described in Examples above may be influenced by the limited doublings in these processes. In a another group of patients from the same study, similar results were shown (FIG. 17B)

Figure 17D:
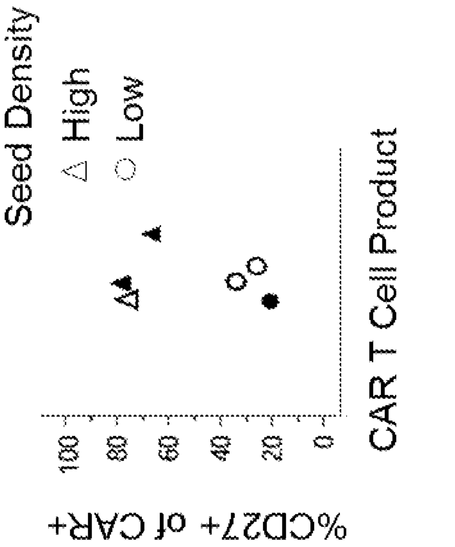
FIG. 17D shows the percentage of CD27+CAR+CD8+ T cells in the output therapeutic composition as a function of seed density during the expansion step of the production process.
Figure 17C:
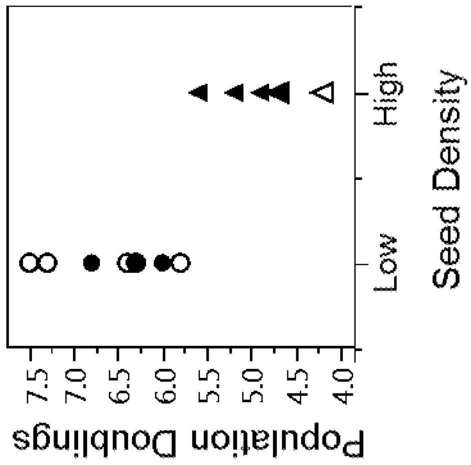
FIG. 17C shows the number of population doublings to reach harvest criterion for high (0.35×10^6 cells/mL) and low (0.05×10^6 cells/mL) seed density during the expansion step of the production process.
Figure 17E:
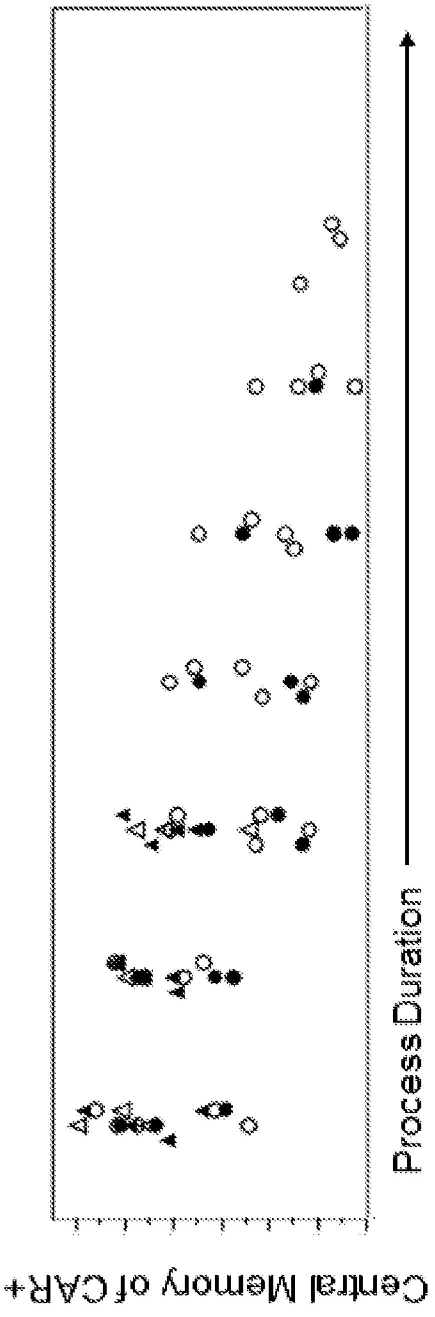
FIG. 17E shows the impact of processing duration on the amount of $T_{CM}$ cells in the output T cell composition.

Studies modeling in-process seed density during the expansion step in a process substantially the same as described above demonstrated that a relatively higher seed density (e.g. $0.35\times10^6$ cells/mL or greater) was expected to reduce the number of population doublings to achieve harvest criterion compared to a lower seed density (e.g. $0.05\times10^6$ cells/mL or lower) (FIG. 17C. Modeling also revealed that a relatively higher seed density (FIG. 17D) or a shorter process duration (FIG. 17E) also are expected to result in an increased percentage of CD8+CAR+ T cells positive for CD27 in the output therapeutic T cell composition (e.g., drug product) compared to a lower seed density or longer process duration, respectively. These data are consistent with a finding that a higher seed density of cells at the initiation of the expansion step or a shorter process duration can result in an increase in the proportion of central memory cells in the engineered therapeutic T cell composition.

B. Administration of Anti-CD19 CAR+ T Cell Composition

The therapeutic CAR+ T cell composition described above were administered to subjects with relapsed or refractory (R/R) aggressive non-Hodgkin's lymphoma (NHL) in a clinical study. Specifically, a cohort of adult human subjects with R/R NHL, including diffuse large B-cell lymphoma (DLBCL) de novo or transformed from indolent lymphoma (NOS), high-grade B-cell lymphoma (including double/triple hit), DLBCL transformed from chronic lymphocytic leukemia (CLL) or marginal zone lymphomas (MZL), primary mediastinal large b-cell lymphoma (PMBCL), and follicular lymphoma grade 3b (FLG3B), were administered with anti-CD19 CAR-expressing T cell compositions. Outcomes were separately assessed for a core subset of subjects within the full cohort (excluding those subjects with a poor performance status (ECOG 2), DLBCL transformed from marginal zone lymphomas (MZL) and/or chronic lymphocytic leukemia (CLL, Richter's), and excluding those subjects with primary mediastinal large b-cell lymphoma (PMBCL), and follicular lymphoma grade 3b (FLG3B) (core cohort)). The core cohort included subjects with DLBCL, NOS and transformed follicular lymphoma (tFL) or high grade B-cell lymphoma (double/triple hit) or high-grade B-cell lymphoma, with MYC and BCL2 and/or BCL6 rearrangements with DLBCL histology (double/triple hit) and with Eastern Cooperative Oncology Group performance status (ECOG PS) of 0 or 1 The analysis at this time point presented in this example is based on assessment of a total of 91 subjects in the full cohort (88 (65 from the CORE cohort) assessed for response and 91 (67 from the CORE cohort) assessed for safety) that had been administered the anti-CD19 CAR-expressing cells.

The cryopreserved cell compositions containing anti-CD19 CAR-expressing cells were thawed prior to intravenous administration. The therapeutic T cell dose was administered as a defined cell composition by administering the formulated $CD4^+$ $CAR^+$ cell population and the formulated $CD8^+$ $CAR^+$ population separately administered at a target ratio of approximately 1:1. Subjects were administered a single or double dose of CAR-expressing T cells (each single dose via separate infusions of $CD4^+$ CAR-expressing T cells and $CD8^+$ CAR-expressing T cells, respectively) as follows: a single dose of dose level 1 (DL1) containing $5\times10^7$ total CAR-expressing T cells, or a single dose of dose level 2 (DL2) containing $1\times10^8$ total CAR-expressing T cells. In some cases, the subjects were administered a double dose of DL1 in which each dose was administered approximately fourteen (14) days apart, administered on day 1 and day 14, including one subject that inadvertently received two DL2 doses via the two-dose schedule, due to a dosing error. The dose level and the target numbers of T cell subsets for the administered composition at DL1 and DL2 are set forth in Table E6. In the core cohort, 34 subjects were administered DL1, and 27 subjects were administered DL2.

TABLE E6

| Target dose level and number of T cell subsets for cell compositions containing anti-CD19 CAR T cells | | | |
|---|---|---|---|
| Dose level | Helper T cell ($T_H$) Dose ($CD4^+CAR^+$) | Cytotoxic T Cell ($T_C$) Dose ($CD8^+CAR^+$) | Total T Cell Dose ($CD3^+$ $CAR^+$) |
| 1 | $25 \times 10^6$ | $25 \times 10^6$ | $50 \times 10^6$ |
| 2 | $50 \times 10^6$ | $50 \times 10^6$ | $100 \times 10^6$ |

Table E7 shows the overall response and safety outcomes for the full cohort and the core cohort at the two dose levels. The objective response rate (ORR) was 74%, including 52% subjects who showed a complete response (CR). The incidence of any grade of cytokine release syndrome (CRS) was 35%, with 1% severe CRS; and the incidence of any grade of neurotoxicity (NT) was 19%, with 1% severe NT.

TABLE E7

| Response and Safety After $CAR^+$ Cell Administration | | | | |
|---|---|---|---|---|
| | FULL | CORE | | |
| | All Dose Levels | All Dose Levels[a] | DL1 | DL2 |
| Best Overall Response (BOR), n[b] | 88 | 65 | 34 | 27 |
| ORR, % (95% CI) | 74 (63, 83) | 80 (68, 89) | 77 (59, 89) | 82 (62, 94) |
| CR, % (95% CI) | 52 (41, 63) | 55 (43, 68) | 47 (30, 65) | 63 (42, 81) |
| Safety, n[c] | 91 | 67 | 34 | 29 |
| Any CRS, % (95% CI) | 35 (25, 46) | 36 (24, 48) | 41 (25, 59) | 24 (10, 44) |
| sCRS(grade 3-4), % (95% CI) | 1 (0, 6) | 1 (0, 8) | 38 (0, 15) | 0 |
| Any NT, % (95% CI) | 19 (11, 28) | 21 (12, 33) | 24 (11, 41) | 17 (6, 36) |
| sNT(grade 3-4), % (95% CI) | 12 (6, 21) | 15 (7, 26) | 21 (9, 38) | 7 (1, 23) |

[a]Four patients treated on DL1D (dose level 1, two-dose schedule) with similar outcomes.

[b]Includes patients with event of PD, death, or 28-day restaging scans. One patient did not have restaging scans available.

[c]Includes all subjects who have received at least one dose of conforming CAR-expressing cell product 28 days prior to data snapshot date or died.

C. Association Between Cell Attributes of Anti-CD19 CAR-Expressing T Cells and Response The relationship between certain phenotypic attributes of the CAR+ T cells in the therapeutic compositions and parameters associated with clinical response outcomes were assessed. The correlations between memory phenotype in the composition and function translated to a positive correlation between central memory subset composition and peak in vivo expansion of $CAR^+$ cells (ρ=0.42, P=0.002), and progression-free survival (PFS) (Kaplan-Meier survival estimate, P=0.0164) that were observed. FIGS. 18A-18D show the Kaplan-Meier survival curves for subjects who were administered CAR+ T cell compositions, divided into groups that were administered compositions containing a frequency of $CCR7^+CD27^+$ CAR+ T cells among $CD4^+$ $CAR^+$ T cells (FIG. 18A for progression free survival, FIG. 18C for duration of response) and among $CD8^+$ $CAR^+$ T cells (FIG. 18B for progression free survival, FIG. 18D for duration of response) that is above or below a certain threshold level. Higher $CCR7^+CD27^+$ memory cells in the composition was observed to be correlated with longer progression free survival.

Figure 18B:
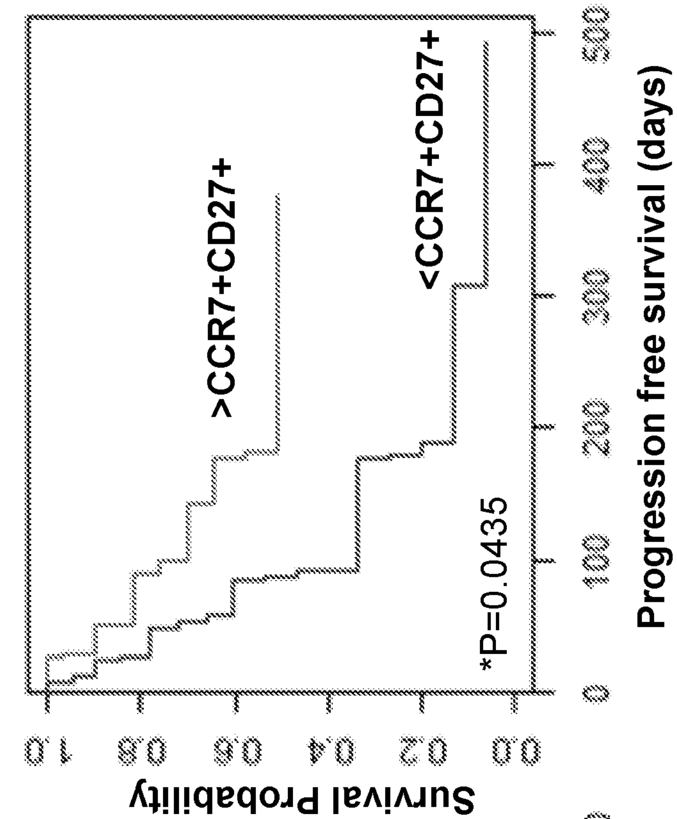
FIGS. 18A-18D show the Kaplan-Meier survival curves for subjects who were administered CAR+ T cell compositions, divided into groups that were administered compositions containing a percentage of $CCR7^+CD27^+$ $CAR^+$ T cells among $CD4^+$ $CAR^+$ T cells (FIG. 18A for progression free survival, FIG. 18C for duration of response) and among $CD8^+$ $CAR^+$ T cells (FIG. 18B for progression free survival, FIG. 18D for duration of response) that is above or below a certain threshold level.
Figure 18A:
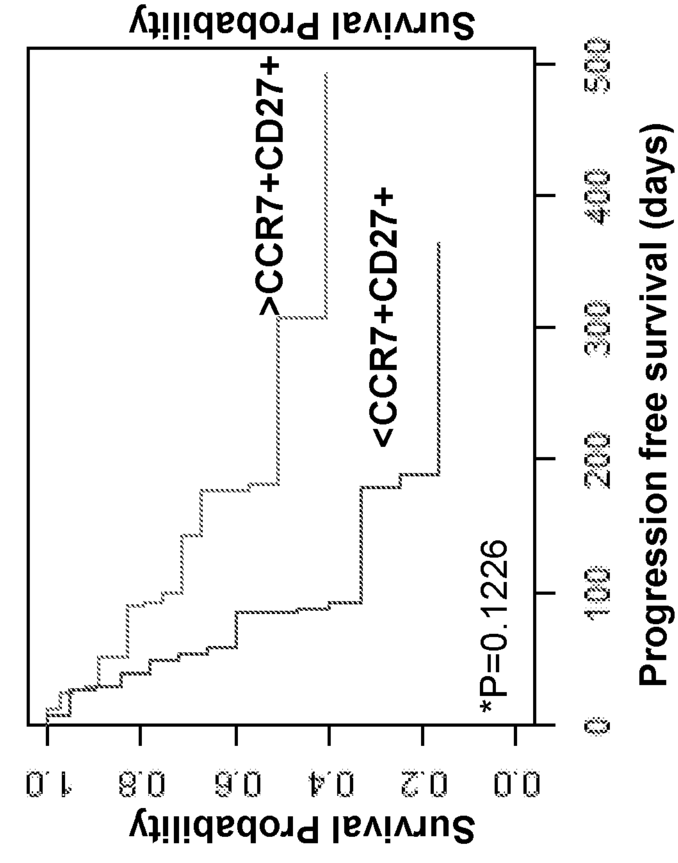
Figure 18D:
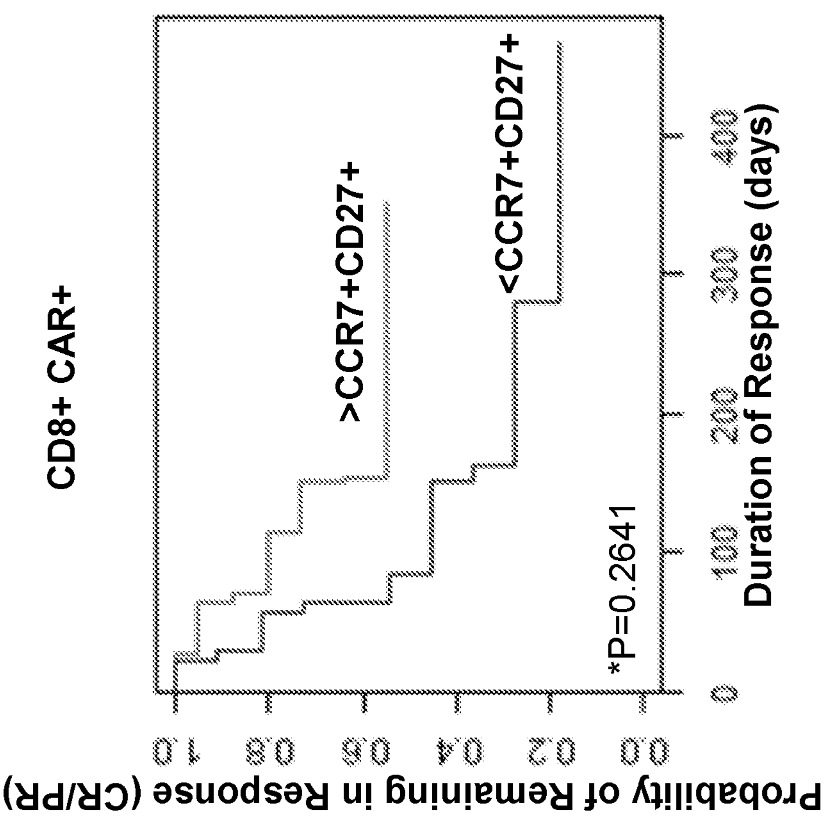
Figure 18C:
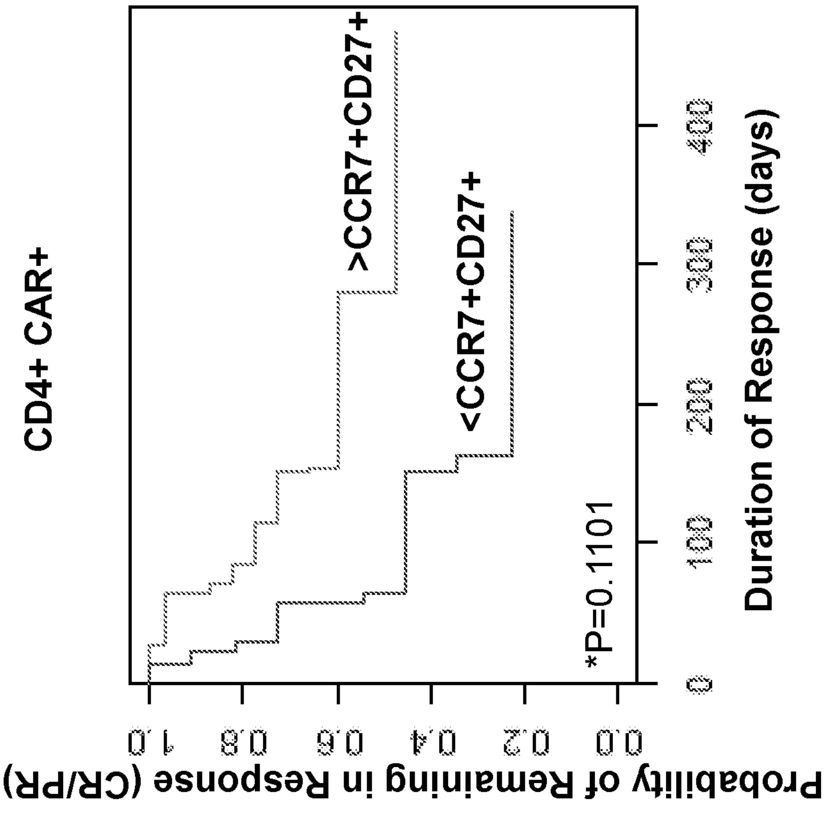
Figure 18E:
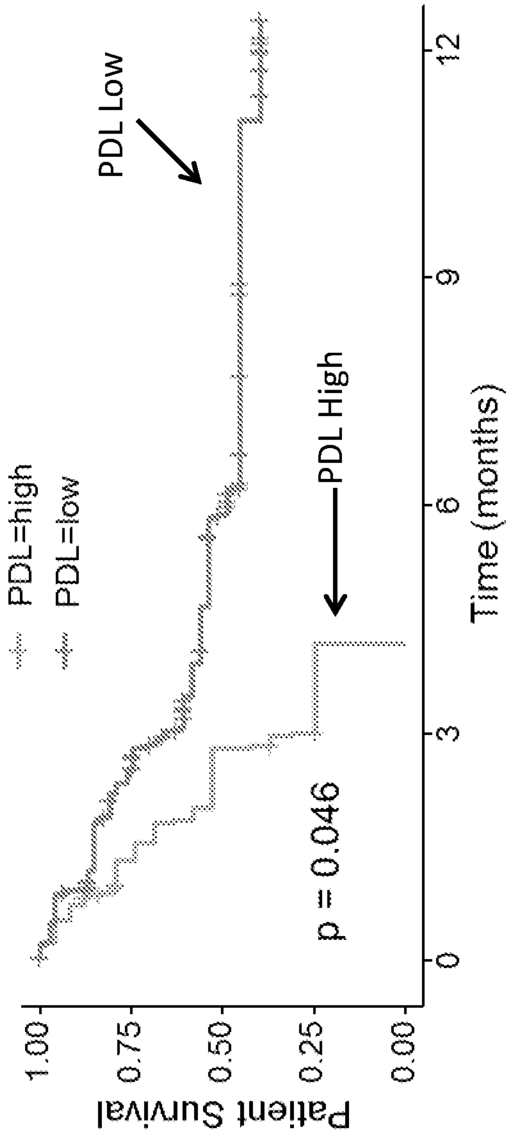
FIG. 18E shows a PFS curve based on an optimal-split log-rank test for patients with "high" or "low" numbers of population doublings (PDL) in CD8+/CAR+ T cells. Low PDL refers to <6 PDL and >6 PDL refers to high PDL.

Univariate analysis revealed an inverse correlation between T cell population doublings (PDL) during the process for producing the therapeutic T cell composition and the probability of progression free survival (PFS) in Non-Hodgkin Lymphoma (NHL) patients. FIG. 18E shows a PFS curve based on an optimal-split log-rank test for patients with “high” (>6 PDL) or “low” (<6 PDL) numbers of PDL in CD8+/CAR+ T cells. This result is consistent with a finding that factors that may limit the number of population doublings of T cells in a process for producing a therapeutic T cell composition may improve the likelihood of subjects exhibiting progression free survival that is durable.

Example 11: Assessment of Anti-Tumor Activity of Anti-BCMA CAR-T Cell Compositions Generated by Non-Expanded Manufacturing Processes CAR-T cell compositions generated from non-expanded and expanded engineering processes similar to as described in Example 8 were evaluated with an in vivo mouse xenograft tumor model as described in Example 5. Different doses of anti-BCMA CAR+ T cells from the engineered T cell compositions generated from the expanded and non-expanded processes were administered into mice 12 days after tumor engraftment. Controls included mice that were injected with tumor cells only and mice injected with tumor cells and mock transduced T cell compositions. The experimental groups are summarized in Table E8.

TABLE E8

| Summary of experimental groups | | | | | |
|---|---|---|---|---|---|
| Group No. | Group Description | Day cells collected | Percent CAR+ | CAR T cells admin. | Mice per group |
| 1 | Tumor only | | | | 5 |
| 2 | Expanded process - | 10 | 69 | $2 \times 10^6$ | 6 |
| 3 | Beads | | | $4 \times 10^5$ | 6 |
| 4 | | | | $8 \times 10^4$ | 6 |
| 5 | Non-expanded process- | 5 | 58 | $2 \times 10^6$ | 6 |
| 6 | Beads and basal media | | | $4 \times 10^5$ | 6 |
| 7 | | | | $8 \times 10^4$ | 6 |
| 8 | Non-expanded process | 4 | 55 | $2 \times 10^6$ | 6 |
| 9 | Beads and basal media | | | $4 \times 10^5$ | 6 |
| 10 | | | | $8 \times 10^4$ | 6 |
| 11 | | | | $2 \times 10^4$ | 6 |
| 12 | Non-expanded process | 5 | 46 | $2 \times 10^6$ | 6 |
| 13 | Oligomer reagent | | | $4 \times 10^5$ | 6 |
| 14 | | | | $8 \times 10^4$ | 6 |
| 15 | Non-expanded process | 4 | 36 | $2 \times 10^6$ | 6 |
| 16 | Oligomer reagent | | | $4 \times 10^5$ | 6 |
| 17 | | | | $8 \times 10^4$ | 6 |
| 18 | | | | $2 \times 10^4$ | 6 |
| 19 | Mock Transduction Non-expanded process Oligomer reagent | 5 | | | 6 |

Figure 19A:
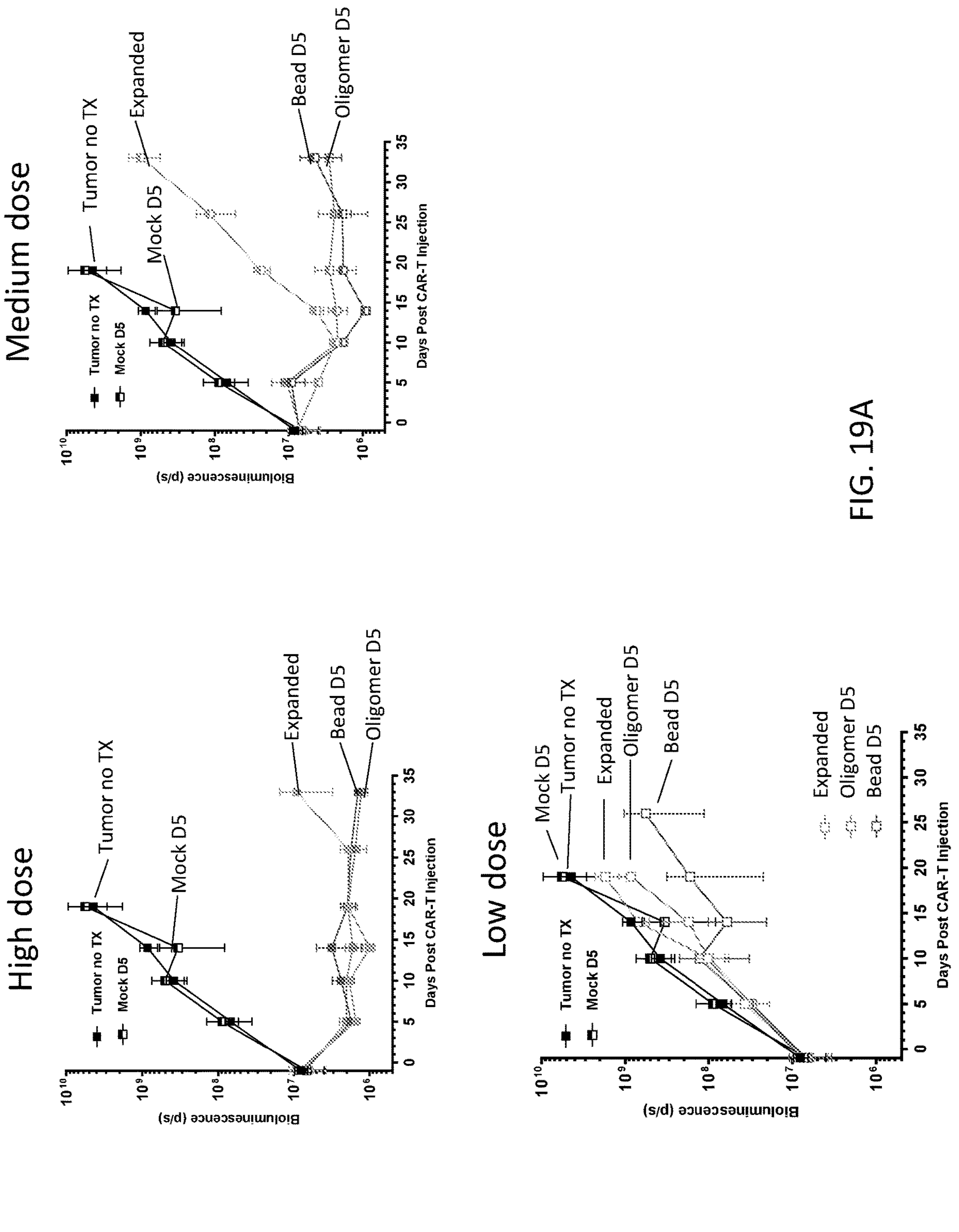
FIGS. 19A and 19B display tumor burden in mice treated with three different treatment doses: high ($2\times10^6$), medium ($4\times10^5$) and low ($8\times10^4$), of anti-BCMA CAR+ T cell compositions generated from an expanded and non-expanded process involving a bead-based (Bead) or an oligomeric (Oligomer) stimulatory reagent where cells were harvested on day 5 (D5.
Figure 19B:
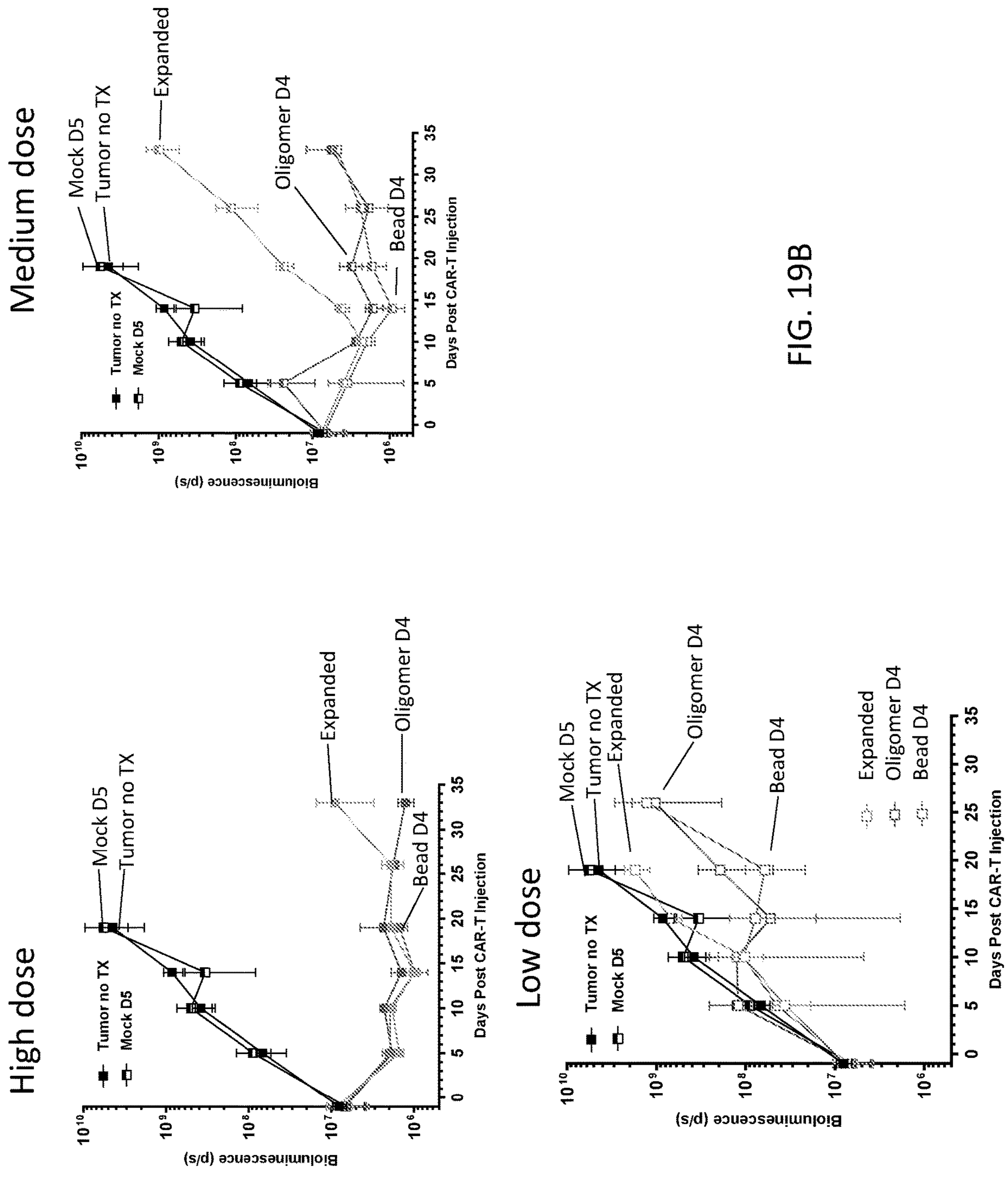

Mice from all groups were assessed for tumor burden by in-life luminescence imaging, body weight, and survival. As shown FIGS. 19A and 19B, mice treated with CAR T cells generated from the non-expanded processes where the cells were collected at day 5 (FIG. 19A) or day 4 (FIG. 19B) appeared to exhibit reduced tumor burden when administered the medium dose of approximately $4 \times 10^5$ anti-BCMA CAR+ T cells as compared to the mice administered CAR T cells from the expanded process.

Figure 20A:
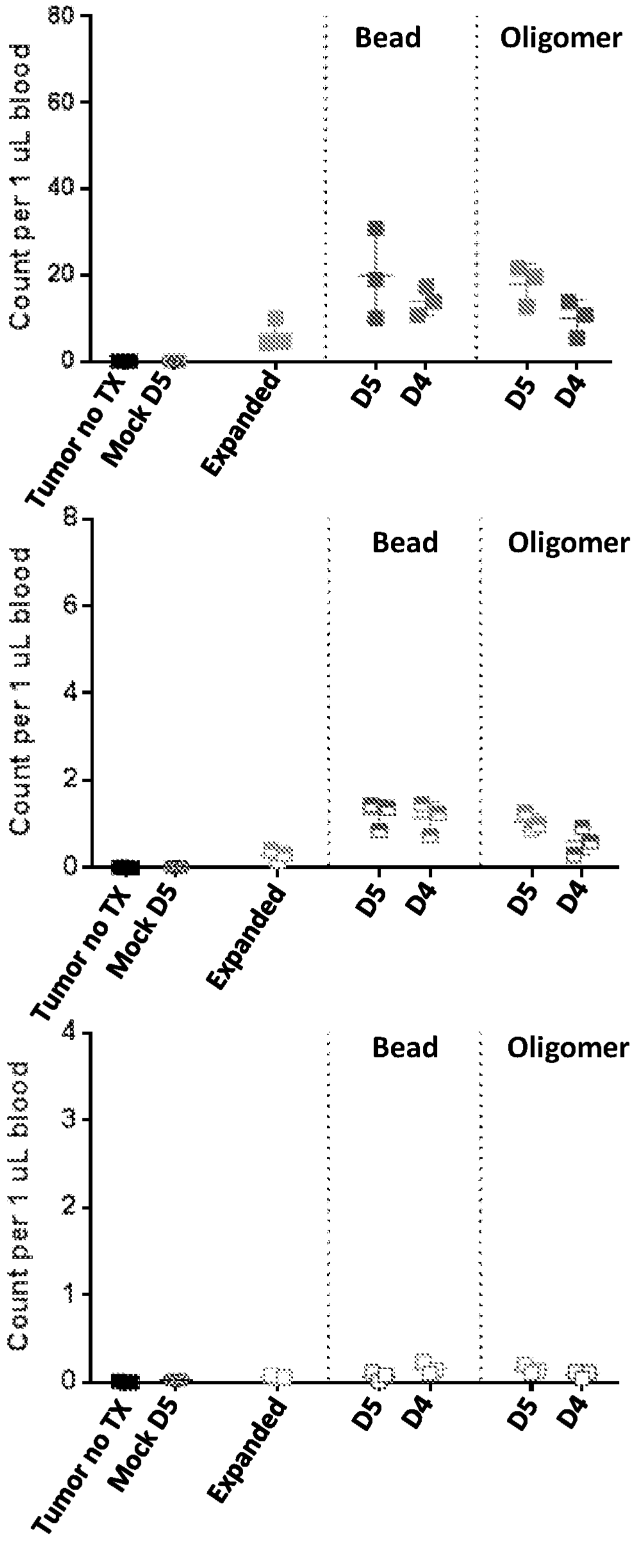
FIGS. 20A-20D show total number of T cells and CAR+ T cells per μL of blood collected from mice at 5 days (FIG. 20A), 13 days (FIG. 20B), 19 days (FIG. 20C), or 26 days (FIG. 20D), after administration of anti-BCMA CAR+ T cell compositions generated from an expanded (Expanded) and a non-expanded process involving a bead-based stimulatory reagent (Bead), or an oligomeric stimulatory reagent (Oligomer), and compared to controls including tumor cells only (Tumor no TX) and tumor cells with mock transduced T cell compositions (Mock).
Figure 20B:
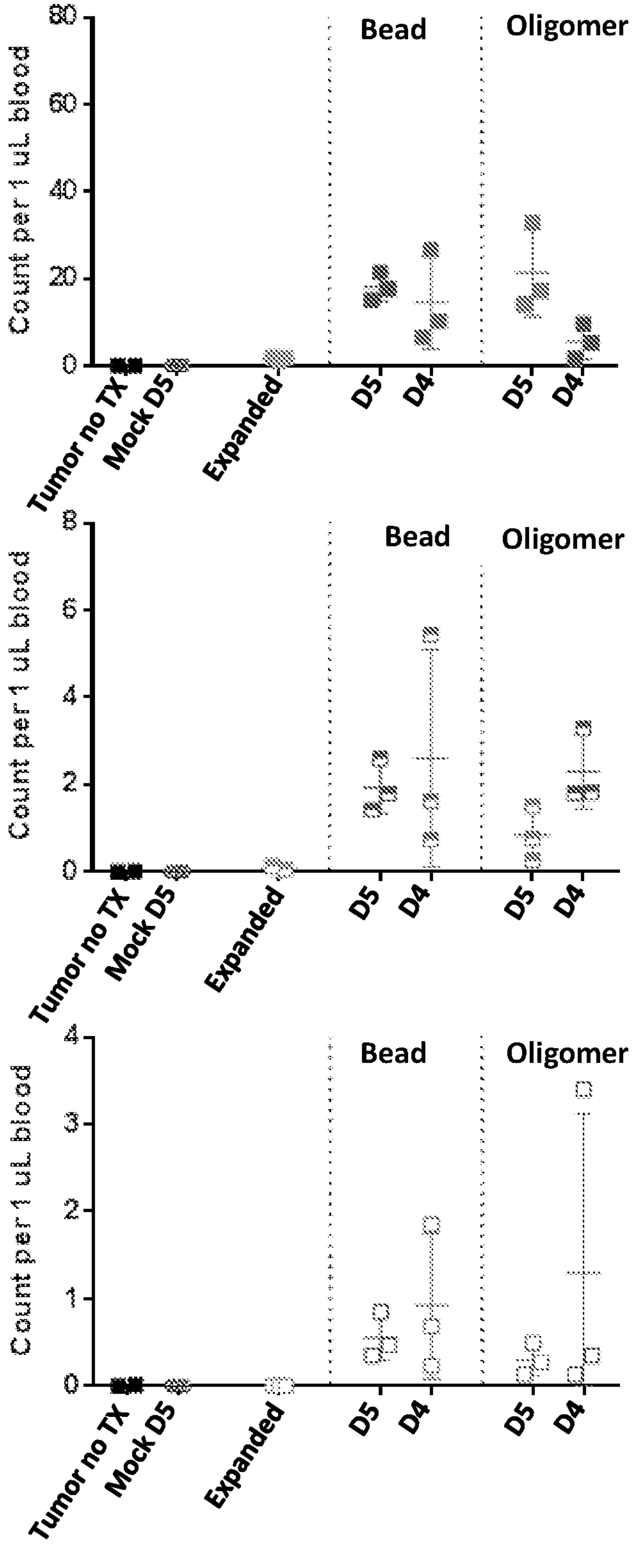
Figure 20C:
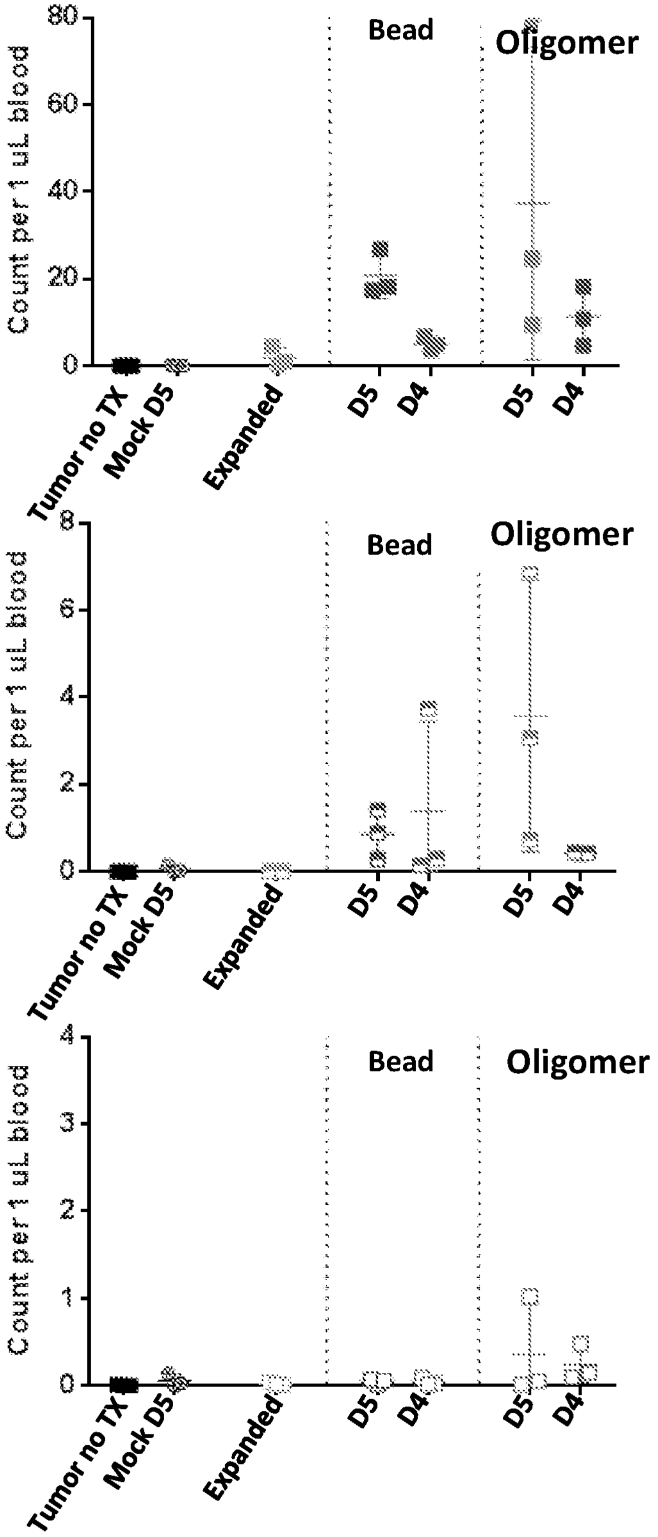
Figure 20D:
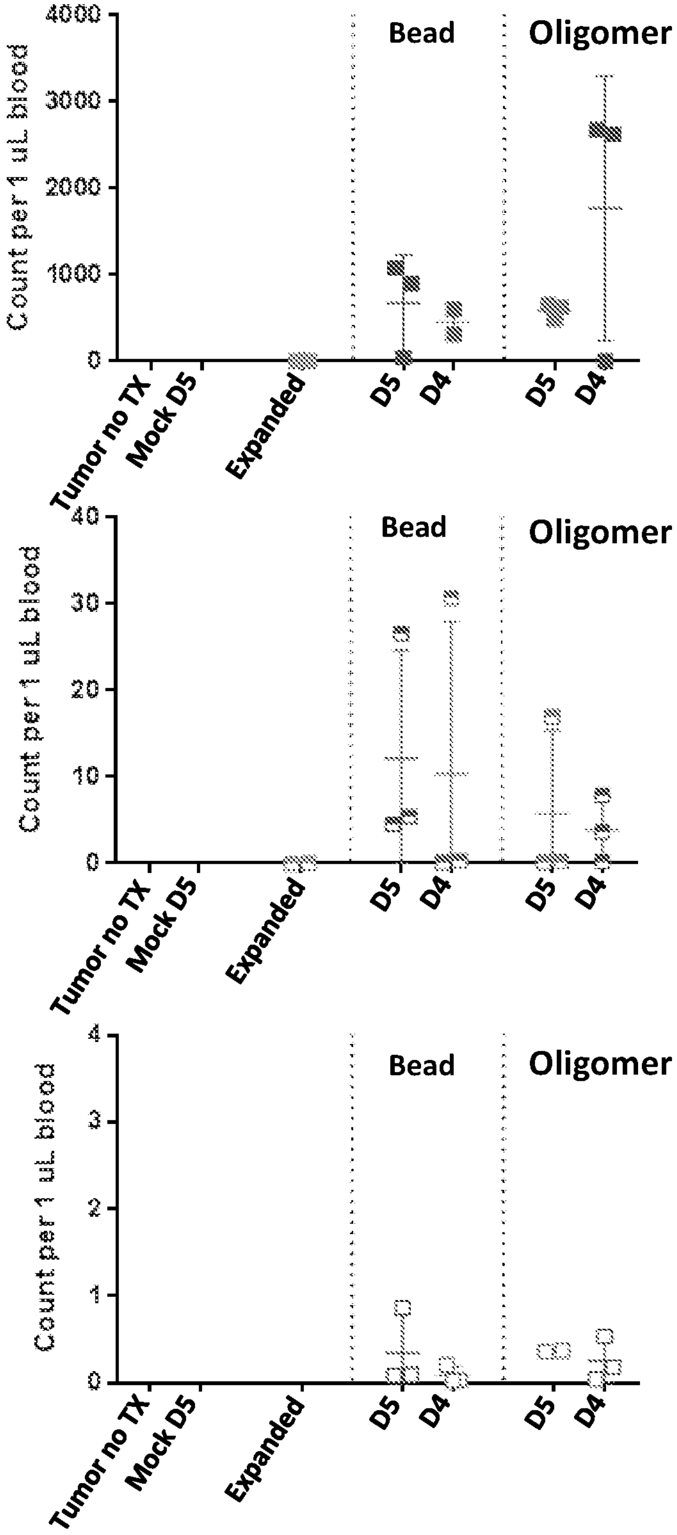

In vivo expansion and persistence were evaluated in CAR-T cell treated mice. Blood samples were collected from mice at 5 days (FIG. 20A), 13 days (FIG. 20B), 19 days (FIG. 20C), or 26 days (FIG. 20D), after administration of the CAR-T cells, and cells were analyzed by flow cytometry. For each of the different doses, the total number of T cells and CAR+ T cells per μL of blood were increased in the samples obtained from mice administered CAR+ T cells generated from non-expanded processes as compared to the expanded process.

Example 12: Method to Assess Integrated Transgene Copy Number in Cells Engineered to Express a Recombinant Protein with Pulse Field Gel Electrophoresis The use of pulse field gel electrophoresis (PFGE) was investigated as a strategy to separate high molecular weight DNA in methods for assessing vector copy number in cells transduced with a viral vector containing a transgene sequence encoding a recombinant protein.

A Jurkat T cell line was transduced with a lentiviral preparation containing a transgene sequence encoding a recombinant protein, in this case a chimeric antigen receptor (CAR). The cells were cultured for 3 days, and then genomic DNA was isolated from the cells. As a control, genomic DNA was isolated from cells that had not been transduced with a lentivirus encoding the transgene sequence, and the isolated genomic DNA was spiked with a known amount of a plasmid encoding the recombinant protein and a non-integrating viral packaging plasmid encoding Vesicular stomatitis Indiana virus G protein (VSVg).

The DNA samples were subjected to automated pulse field gel electrophoresis (PFGE) (e.g. BluePippin (Sage Science, Beverly, MA) device) to separate high molecular weight DNA species from low molecular weight, non-chromosomal DNA species below a threshold of 15 kb, 17.5 kb or 20 kb.

Exemplary quantitative polymerase chain reaction (qPCR) methods, such as droplet digital PCR (ddPCR), was carried out on the high molecular weight DNA sample using primers specific for a sequence unique to the transgene sequence (e.g., primers specific to a regulatory element of the recombinant protein). For comparison, ddPCR also was carried out with primers specific for VSVg-encoding sequences ("packaging plasmid") to detect the spiked DNA that is not expected to integrate into the chromosome of the cells or residual packaging plasmids in the transduced cells, and with primers specific for a housekeeping gene to detect genomic DNA in all samples (e.g., primers for a gene encoding ribonuclease P protein subunit p30 (RRP30; "genomic control"). Primers specific for the albumin (ALB) gene was used as as a reference for normalization. Reactions were also carried out on DNA samples that were not subject to PFGE (pre-gel). For ddPCR, samples were added to a mixture containing each primer set and probes, droplets were generated using a droplet generator, generated droplets were transferred to a PCR plate and amplification was carried out under the following PCR conditions: 95° C. 10 min; [94° C. 30 sec; 60° C. 1 min]×39 cycles at 2° C./sec ramp rate; 98° C. 10 min; and 4° C. indefinitely. Following amplification, signal from the droplets were measured on a droplet reader. Copy number of each gene was normalized to the number of diploid genomes (cp/diploid genome, using amplification with primers specific for the albumin (ALB) gene as a reference) or per 50 ng of genomic DNA.

Figure 21:
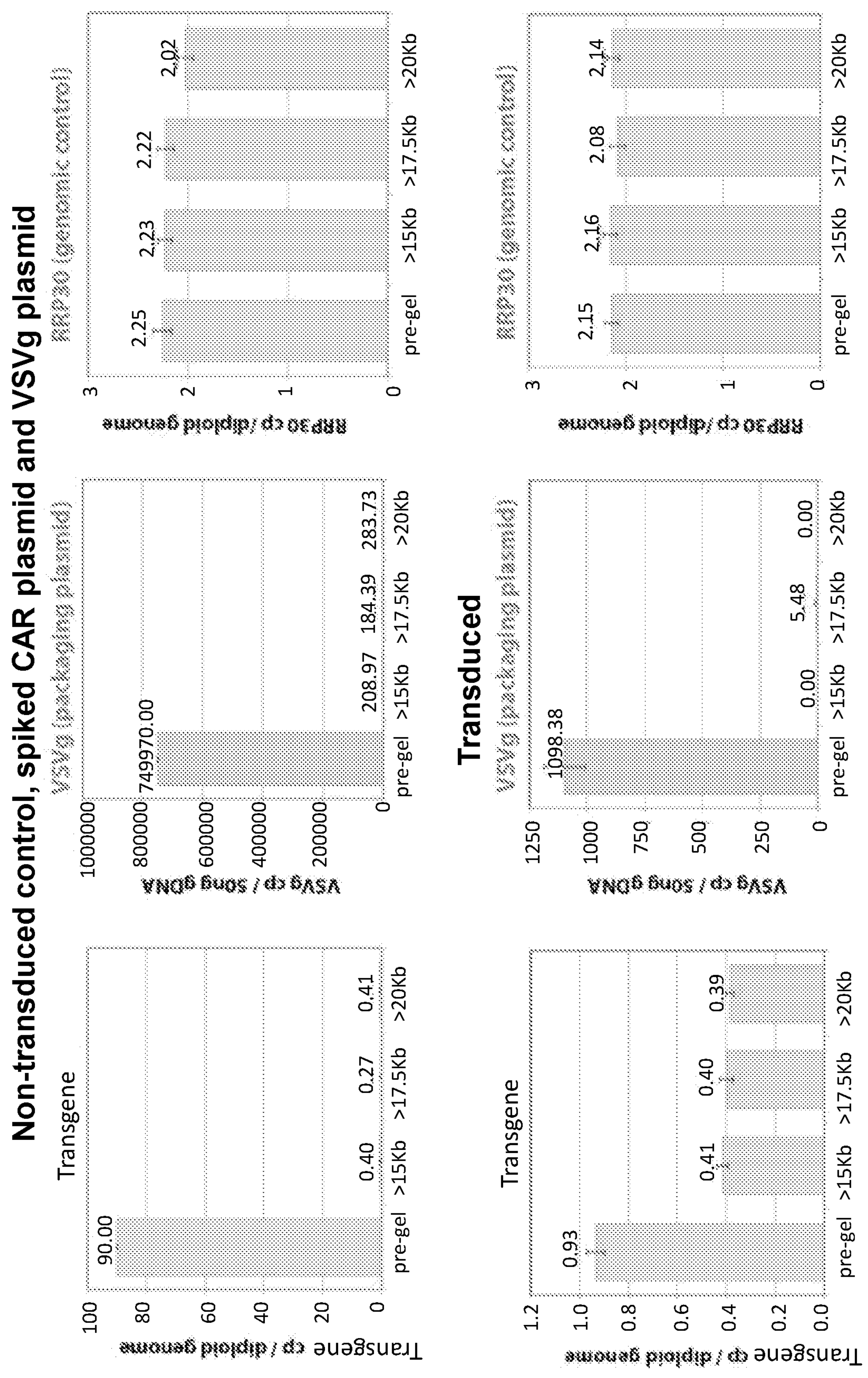
FIG. 21 shows the copy number as assessed by droplet digital PCR (ddPCR) before (pre-gel; standard vector copy number (VCN) assay) or after separating high molecular weight DNA fraction, above a threshold of 15 kb, 17.5 kb or 20 kb by pulse-field gel electrophoresis (PFGE) (integrated vector copy number (VCN) assay). The copy number was assessed using primers that specifically amplify a portion of the integrated transgene sequences; packaging plasmid (viral packaging plasmid encoding Vesicular stomatitis Indiana virus G protein (VSVg)), or a genomic control (gene encoding for ribonuclease P protein subunit p30 (RRP30)). The assessment was performed in a sample from transduced cells, or in a non-transduced control, spiked CAR plasmid and VSVg plasmid. Copy number of each gene was normalized to the number of diploid genomes (cp/diploid genome; using primers specific for the albumin gene as a reference) or per 50 ng of genomic DNA.

As shown in FIG. 21, top panel in non-transduced sample that contained spiked-in CAR-encoding plasmid and VSVg packaging plasmid, transgene sequences and VSVg sequences were only detected in samples that had not undergone PFGE (pre-gel). In contrast, genomic control sequences were detected in all samples subjected to PFGE for higher molecular weight DNA of 15 kb, 17.5 kb or 20 kb or higher. This result demonstrated that PFGE prior to PCR amplification of separated DNA, achieved separation of non-integrated lower molecular weight plasmids.

In transduced samples, the transgene sequences were detected in both the samples prior to PFGE (pre-gel) and in the samples subject to PFGE above 15 kb, 17.5 kb or 20 kb (bottom panel) VSVg packaging plasmid sequence was found in the pre-gel samples and were almost undetectable in the higher molecular weight DNA. These sequences, which possibly derive from residual plasmid sequences from viral production, were not expected to integrate into the genome of the cells. Genomic DNA, including chromosomal DNA, was also detected in all samples: the copy number of the RRP30 housekeeping gene was observed to be approximately 2 copies per diploid genome in all samples.

The assay including PFGE permitted detection of integrated or genomic sequences while removing non-integrated, low molecular weight nucleic acid species. Thus, the results show that the use of PFGE to separate high molecular weight DNA, prior to PCR amplification of transgene sequences from the isolated DNA, can be used as an integrated vector copy number (iVCN) assay to facilitate the specific determination of copy number of transgene sequences that has integrated into the genome.

Example 13: Comparison of Transgene Copy Number Assessed by Droplet Digital PCR (ddPCR) with or without Pulse Field Gel Electrophoresis (PFGE) at Various Time Points During Cell Manufacturing Process The iVCN method described in Example 12, involving separation of high-molecular weight species by PFGE prior to vector copy number analysis by qPCR, was used to assess integrated copy number of an exemplary transgene sequences encoding a chimeric antigen receptor (CAR) at various time points during cell engineering processes in both a Jurkat T cell line and primary T cells. The method was compared to a standard vector copy number (VCN) assay that did not include separation of the high- and low-molecular weight DNA species by pulse field gel electrophoresis (PFGE).

For the studies, genomic DNA was prepared from the cells and subjected to assessment of transgene sequence copy number by either (1) the iVCN method, generally as described in Example 12 above, using a threshold value for separation of >15 kb ("iVCN") and the PippinHT (Sage Science, Beverly, MA) device, or (2) a standard VCN method in which genomic DNA was not first separated by PFGE ("VCN"). In both assays, transgene copy number was determined by ddPCR using primers specific for a sequence unique to the transgene, and normalized to a diploid genome, as determined using primers specific for a reference gene (e.g., albumin (ALB) gene).

A) Jurkat Cell Line

Jurkat T cells were transduced with a lentiviral preparation containing transgene sequences encoding a CAR, generally as described in Example 12 above. Samples of cells were obtained prior to transduction ("pre"), at 5 minutes, 6 hours, 12 hours, 24 hours, 48 hours, 72 hours and 96 hours after transduction, and used for analysis of transgene copy number.

Figure 22B:
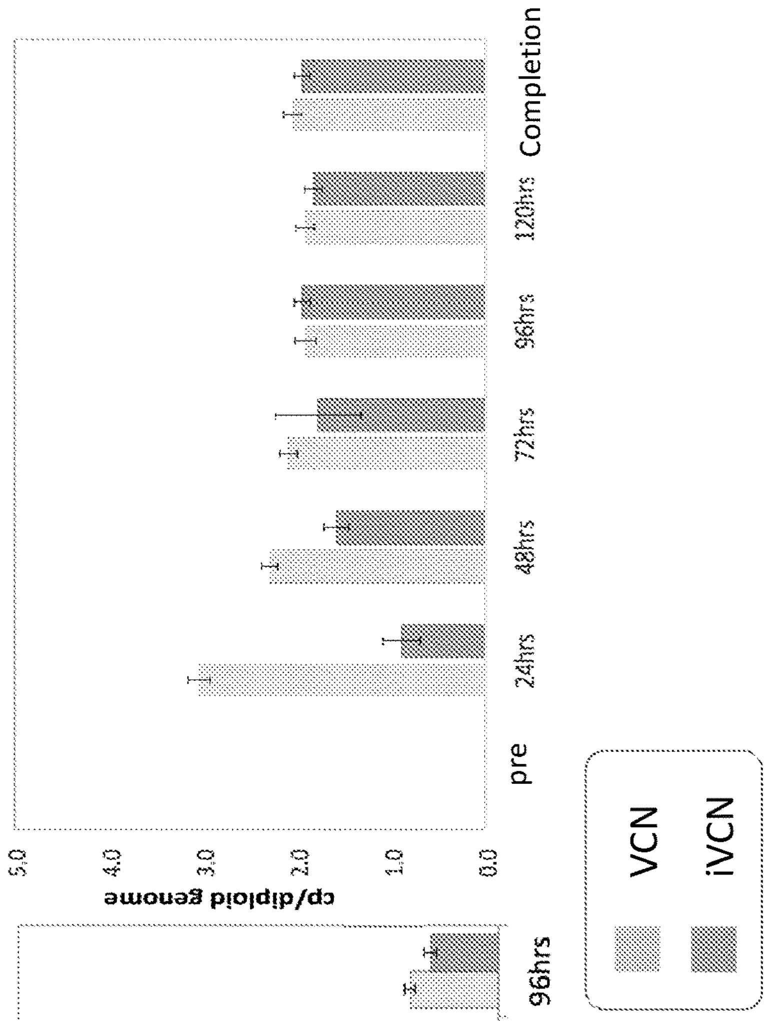
FIGS. 22A-22B depict the copy number as assessed by standard vector copy number (VCN) assay (genomic DNA samples that were not subject to PFGE, both high- and low-molecular weight DNA) and integrated copy number (in high-molecular weight DNA samples after PFGE) of transgene sequences at various time points (prior to transduction ("pre"), at 5 minutes, 6 hours, 12 hours, 24 hours, 48 hours, 72 hours and 96 hours after transduction, or at completion of the engineering process, "completion") for Jurkat T cells (FIG. 22A) or primary T cells isolated from human subjects (FIG. 22B), transduced with a lentiviral preparation containing transgene sequences encoding a CAR. Copy number of each gene was normalized to the number of diploid genomes (cp/diploid genome; using primers specific for the albumin gene as a reference).
Figure 22A:
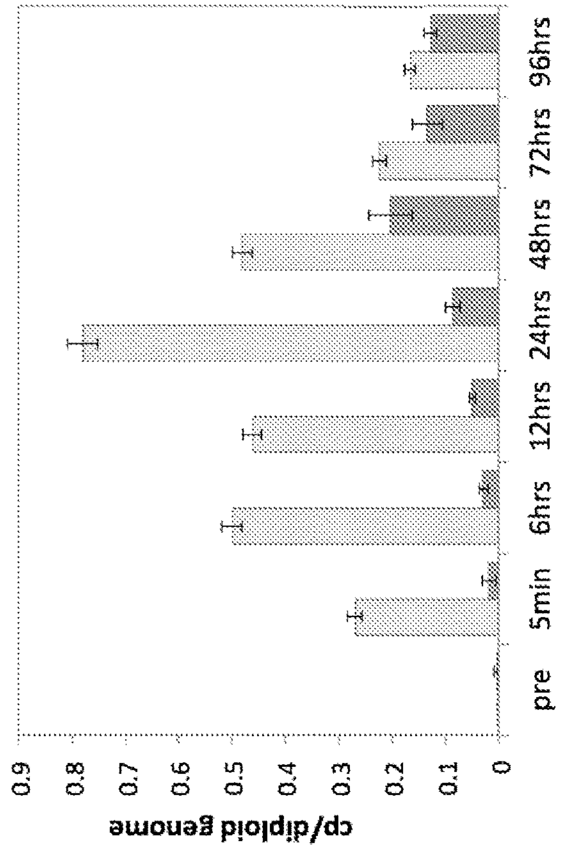

As shown in FIG. 22A, transgene copy number assessment with PFGE for detecting integrated copy number (iVCN) in the genome during various time points in the process of engineering Jurkat cells showed that transgene integration was not detectable until at around 6 hours in these cells, and increased until about 48 hours, at which time copy number detection generally plateaued. In contrast, transgene copy number assessment without PFGE, which detected the copy number of the transgene in the cells by the standard VCN method, demonstrated substantial detection of transgene sequence starting at much earlier time points. This observation is consistent with the ability of the standard VCN method to detect non-integrating transgene sequences, such as producer plasmids, linear or circular complementary DNA (cDNA) or autointegrants, at these early time points after cell engineering. The transgene copy number as determined without PFGE later decreased to levels similar to those detected by the iVCN integrated copy number assessment (with PFGE) around 96 hours, indicating that although transgene integration was complete by approximately 48 hours, standard VCN method without PFGE was not be accurate until around 96 hours or after transduction in these cells.

B) Primary Cell Engineering

Primary T cells from human subjects were engineered to express a CAR using an exemplary engineering process. Separate compositions of CD4+ and CD8+ cells were selected from isolated PBMCs from a leukapheresis sample, and the selected cell compositions were cryopreserved. The separate compositions of CD4+ and CD8+ T cells were subsequently thawed and mixed at a ratio of 1:1 of viable CD4+ T cells to viable CD8+ T cells. Approximately 300×$10^6$ T cells (150×$10^6$ CD4+ and 150×$10^6$ CD8+ T cells) of the mixed composition were stimulated in the presence of paramagnetic polystyrene-coated beads with attached anti-CD3 and anti-CD28 antibodies at a 1:1 bead to cell ratio in serum free media containing recombinant IL-2, IL-7 and IL-15 for between 18 to 30 hours.

Following the incubation, approximately 100×$10^6$ viable cells from the stimulated cell composition were washed and resuspended in the serum free media containing recombinant IL-2, IL-7 and IL-15. The cells were transduced with a lentiviral preparation encoding an anti-BCMA CAR by spinoculation at approximately 1600 g for 60 minutes. After spinoculation, the cells were washed and resuspended in the serum free media containing recombinant IL-2, IL-7 and IL-15, and incubated for about 18 to 30 hours at about 37° C. The anti-BCMA CAR contained an scFv antigen-binding domain specific for BCMA, a CD28 transmembrane region, a 4-1BB costimulatory signaling region, and a CD3-zeta derived intracellular signaling domain.

The cells were then cultivated for expansion by transfer to a bioreactor (e.g. a rocking motion bioreactor) in about 500 mL of media containing twice the concentration of cytokines as used during the incubation and transduction steps. When a set viable cell density was achieved, perfusion was initiated, where media was replaced by semi-continuous perfusion with continual mixing. The cells were cultivated in the bioreactor until a threshold number of cells (TNC) was achieved of about 3×$10^9$ cells, which typically occurred in a process involving 6-7 days of expansion. The anti-CD3 and anti-CD28 antibody conjugated paramagnetic beads were removed from the cell composition by exposure to a magnetic field. The cells were then collected and formulated with a cryoprotectant.

For analysis of DNA by iVCN and standard VCN methods as described above, samples of cells were obtained prior to transduction ("pre"), at 24 hours, 48 hours, 72 hours, 96 hours, 120 hours after transduction and at completion of the engineering process ("completion").

As shown in FIG. 22B, transgene copy number, as determined following PFGE (iVCN), was not detected until about 24 hours post-transduction and increased until about 48 to 72 hours. In the assay without PFGE (VCN), transgene copy number was much higher at the early time points (24 and 48 hours), but later decreased to levels similar to those detected by the integrated copy number assessment (iVCN) around 96 hours. In both assays, the assessed copy number was similar in samples obtained 96 hours or longer post-transduction.

The results confirm that assessment of vector copy number with PFGE (iVCN) reveal consistent timing of transgene integration at time points after transduction. The observations further show that assessment by standard VCN methods that do not involve PFGE can detect transgene sequences in cells at times before integration into the genome has occurred, and thus demonstrated that standard VCN methods may not be entirely appropriate to assess vector copy number on samples less than 4 days post-transduction.

Example 14: Assessment of Integrated Transgene Copy Number with Pulse Field Gel Electrophoresis (PFGE) During Various Non-Expanded Manufacturing Processes Copy number of transgenes encoding a chimeric antigen receptor (CAR) was assessed using the iVCN and VCN methods generally as described in Examples 12 and 13, at various time points during exemplary processes for producing a genetically engineering a T cell composition. The exemplary processes did not involve an expansion step after transduction, and differed in the stimulatory reagent, culture media, and harvesting times.

For each process, separate compositions of CD4+ and CD8+ primary human T cells were selected from two different human subjects (Donor A and Donor B) from isolated PBMCs from human leukapheresis samples. The selected cells were cryopreserved, subsequently thawed and mixed at a ratio of 1:1 of viable CD4+ T cells to viable CD8+ T cells. The mixed cell composition was stimulated by incubation with a stimulatory reagent as follows: (1) anti-CD3/anti-CD28 antibody conjugated paramagnetic beads ("beads"), (2) anti-CD3/anti-CD28 Fab conjugated oligomeric streptavidin mutein reagents at a concentration of 4.0 μg per $10^6$ cells, or (3) anti-CD3/anti-CD28 Fab conjugated oligomeric streptavidin mutein reagents at a concentration of 0.8 μg per $10^6$ cells. The incubation was carried out in serum free media with recombinant cytokines for approximately 18 to 30 hours.

The cells were then washed and transduced by spinoculation with a lentiviral preparation containing transgene sequences encoding a CAR. Cells were then incubated with basal media without serum, growth factors or recombinant cytokines ("basal") or serum free media containing recombinant IL-2, IL-5, and IL-15 cytokines ("complete"). After 96 hours after initiation of the incubation with the bead reagent, cells were exposed to a magnetic field to remove the paramagnetic beads. After 24 hours, 48 hours or 96 hours after initiation of the incubation with the oligomeric stimulatory reagent, cells were exposed to biotin for 10 minutes to dissociate and remove oligomeric streptavidin reagents. The cells were washed and formulated with a cryoprotectant.

The cells were thawed and genomic DNA was prepared from harvested cells. For assessment of transgene copy number, ddPCR using primers specific to the transgene sequence was carried out on DNA that had been subject to PFGE for high molecular weight fraction>15 kb, as described in Examples 12 and 13 above. The cell samples were also assessed by flow cytometry, staining for expression of the CAR, CD3 and activated caspase 3 (aCas3).

Figure 23A:
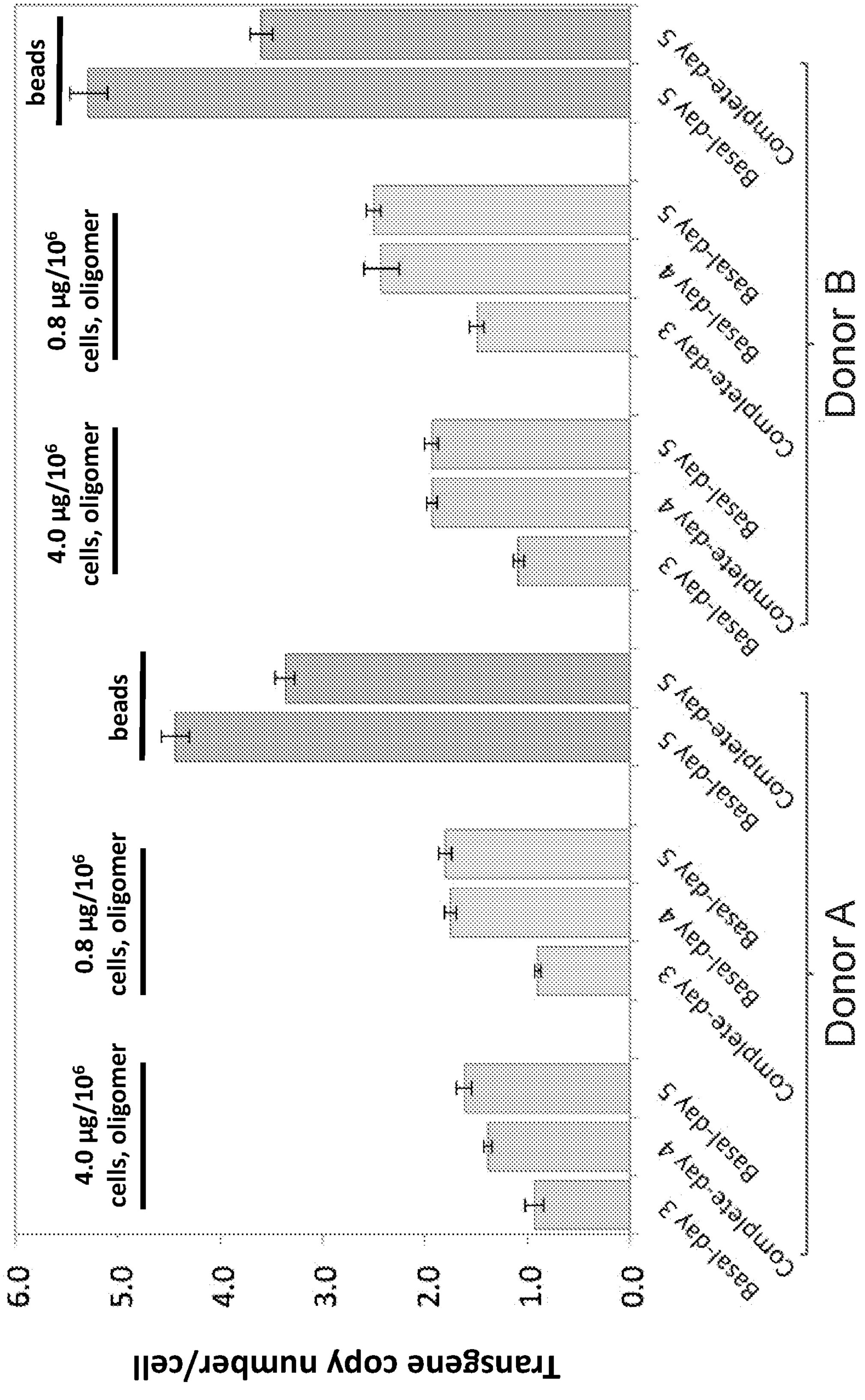
FIG. 23A shows the integrated copy number assessed on day 3, 4 or 5 of exemplary non-expanded T cell composition manufacturing processes, using primary T cells from two different human subjects (Donor A and Donor B) that were stimulated by incubation with (1) anti-CD3/anti-CD28 antibody conjugated paramagnetic beads ("beads"), (2) anti-CD3/anti-CD28 Fab conjugated oligomeric streptavidin mutein reagents at a concentration of 4.0 μg per $10^6$ cells, or (3) anti-CD3/anti-CD28 Fab conjugated oligomeric streptavidin mutein reagents at a concentration of 0.8 μg per $10^6$ cells, incubated in basal media without serum or growth factors ("basal") or serum free media containing IL-2, IL-5, and IL-15 ("complete") after transduction.
Figure 23B:
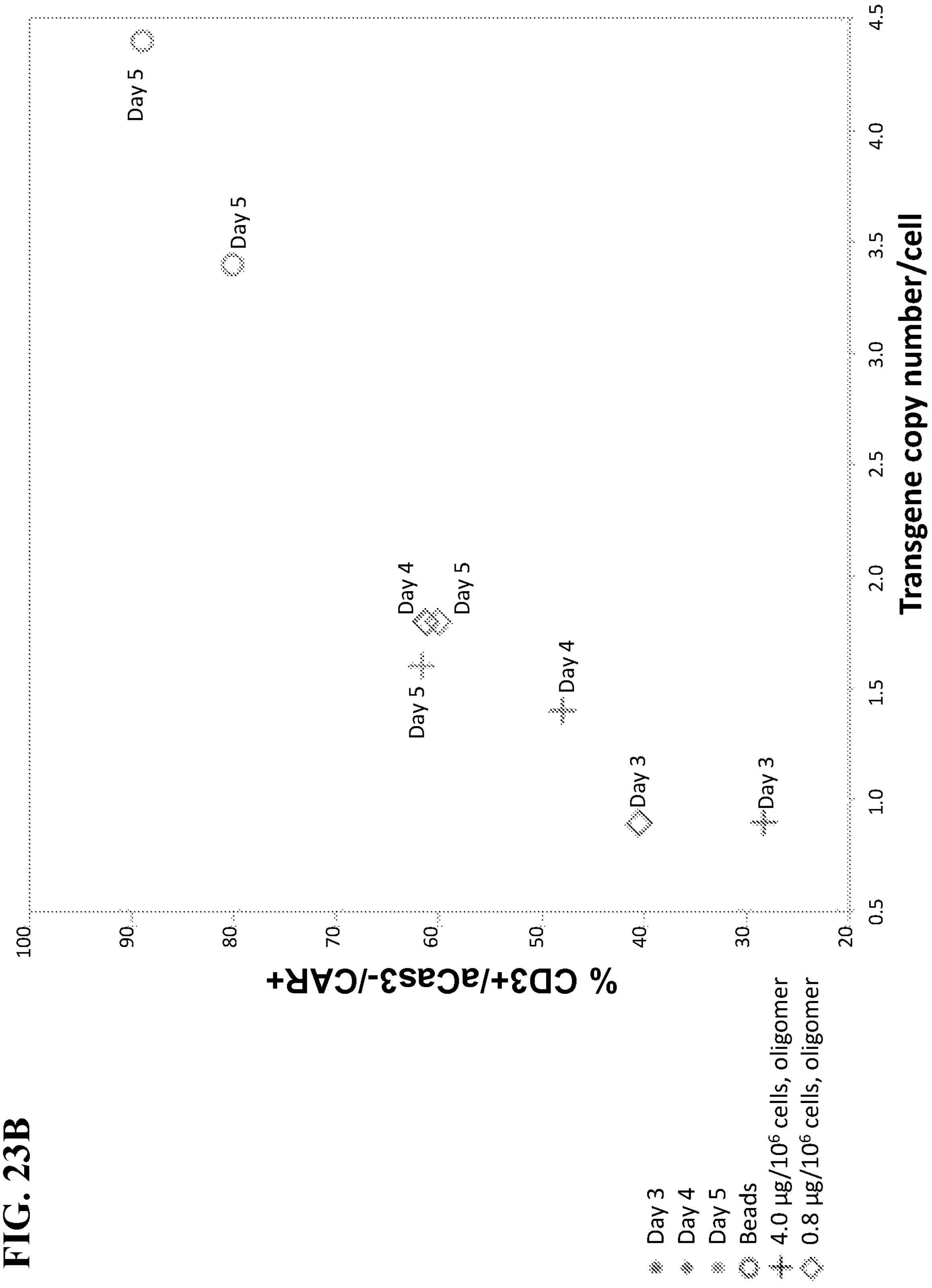
FIG. 23B depicts the correlation between the copy number as determined by iVCN and the percentage of CAR-expressing cell (as determined by the percentage of CD3+/activated Cas3−/CAR+ cells among CD3+ cells by flow cytometry).

The results are shown in FIGS. 23A-23B. As shown in FIG. 23A, for cells stimulated using the oligomeric reagent, integrated transgene copy number measured by iVCN increased in samples in which the incubation was carried out for 24 hours or 48 hours after initiation of the stimulation, but did not increase further. Transgene copy number as measured by standard VCN (without PFGE) remained substantially higher than the integrated transgene copy number as measured by iVCN, until about 96 hours after initiation of the stimulation. This result is consistent with an observation that a standard VCN method (without PFGE) was not accurate until the 96 hour time-point in this process. For cells stimulated using the bead reagent, at 96 hours, higher integrated copy number was observed for cells incubated with basal media compared to cells incubated with complete media. As shown in FIG. 23B, the integrated transgene copy number correlated with the percentage of CAR-expressing cell (as determined by the percentage of CD3+/activated Cas3−/CAR+ cells among CD3+ cells by flow cytometry). This result further supports the utility of the iVCN assay for assessing integrated copy number, particularly when assessing impact of different parameters, including time of incubation, media or reagents, in a process for engineering cells.

Example 15: Comparison of Integrated and Non-Integrated Transgene Copy Number Assessed by Droplet Digital Per (ddPCR) with or without Pulse Field Gel Electrophoresis (PFGE) During Various Cell Manufacturing Processes The number of integrated and non-integrated transgenes encoding a chimeric antigen receptor (CAR) was assessed by ddPCR on DNA samples, with or without pulse field gel electrophoresis (PFGE), obtained during various exemplary processes for producing a genetically engineering a T cell composition.

A) Exemplary Processes for Engineering T Cells

The exemplary processes included processes in which engineered cells were subjected to cell expansion (expanded process) and processes in which cells were not expanded (non-expanded process).

1) Expanded Process—Anti-CD3/Anti-CD28 Beads

An expanded process generally as described in Example 13.B was carried out.

2) Non-Expanded Process—Anti-CD3/Anti-CD28 Beads

A non-expanded process using anti-CD3/anti-CD28 antibody conjugated beads was carried, out similar to as described in Example 14. CD4+ and CD8+ T cells were selected and mixed at a 1:1 ratio to produce an input composition containing approximately $600\times10^6$ T cells ($300\times10^6$ CD4+ and $300\times10^6$ CD8+ T cells). The mixed input cell composition were stimulated by incubating the cells for 18-30 hours in the presence of anti-CD3/anti-CD28 antibody conjugated beads at a 1:1 bead to cell ratio in serum free media containing recombinant IL-2, IL-7 and IL-15. Following the stimulation, the cells were washed and resuspended in the serum free media containing recombinant IL-2, IL-7 and IL-15. The cells were then transduced with a lentiviral vector encoding the same anti-BCMA CAR used in the expanded process by spinoculation at approximately 693 g for 30 minutes.

In one arm, after spinoculation, the cells were resuspended in basal media without serum and without added growth factors or recombinant cytokines (basal media) and allowed to incubate at about 37.0° C. in an incubator for about 96 hours after initiation of the stimulation with the anti-CD3/anti-CD28 beads. In another arm, a similar process was carried out except that, after spinoculation, the cells were resuspended in basal media without added growth factors or recombinant cytokines (basal media) and allowed to incubate at about 37.0° C. in an incubator for about 72 hours after initiation of the stimulation with the anti-CD3/anti-CD28 beads.

3) Non-Expanded Process-Anti-CD3/Anti-CD28 Fab Oligomeric Reagent

A non-expanded process using anti-CD3/anti-CD28 Fab oligomeric reagent was carried out similar to as described in Example 14. CD4+ and CD8+ T cells were selected and mixed at a 1:1 ratio to produce an input composition containing approximately $600\times10^6$ T cells ($300\times10^6$ CD4+ and $300\times10^6$ CD8+ T cells). Cells from the mixed input cell composition were stimulated by incubation with 480 μg (or 0.8 μg per $1\times10^6$ cells) anti-CD3/anti-CD28 Fab conjugated oligomeric streptavidin mutein reagents generated as described in Example 2, which was carried out in serum free media containing recombinant IL-2, IL-7 and IL-15 for between 18-30 hours. After stimulation, the cells were transduced with a lentiviral vector encoding the same anti-BCMA CAR used in the expanded process, by spinoculation at 693 g for 30 minutes.

In one arm of the process, after the spinoculation, the cells were washed and resuspended in basal media without serum, added growth factors or recombinant cytokines (basal media), and incubated at about 37.0° C. in an incubator. About 24 hours after initiation of transduction (approximately 48 hours after initiation of stimulation), 1.0 mM D-biotin was added during the incubation and mixed with the cells to dissociate anti-CD3 and anti-CD28 Fab reagents from oligomeric streptavidin reagents. The cells were further incubated for about 48 hours (96 hours after initiation of stimulation), and then were washed and formulated with a cryoprotectant.

In another arm of the process, after the spinoculation, the cells were washed and resuspended in basal media without serum, added growth factors or recombinant cytokines (basal media) and incubated at about 37.0° C. in an incubator. About 24 hours after initiation of the transduction, 1.0 mM D-biotin was added during the incubation and mixed with the cells to dissociate anti-CD3 and anti-CD28 Fab reagents from oligomeric streptavidin reagent. The cells were further incubated for an additional 24 hours (72 hours after initiation of stimulation), and then were washed and formulated with a cryoprotectant.

4) Summary of Processes

Table E9 summarizes features of the processes as described above, in addition to a process using a mock empty vector.

TABLE E9

Summary of Processes

| Arm | Stim. Reagent | Cell Number | Transduction | Expansion | Removal of stimulatory reagent | Harvest |
|---|---|---|---|---|---|---|
| 1 | Beads | $1.5\times10^6$ CD4 and $1.5\times10^6$ CD8 | Spinoculation & incubation for 18-30 hours | Until TNC of ~$3\times10^9$ cells, about 6-7 days | Wash and debead | Following debead |
| | | | | | Day following threshold number | |
| 2 | Beads | $3.0\times10^6$ CD4 and $3.0\times10^6$ CD8 | Spinoculation & incubation for about 72 hours in basal media | None | Wash and debead | Following debead |
| | | | | | About 96 hours after initiation of stimulation | |
| 3 | Beads | $3.0\times10^6$ CD4 and $3.0\times10^6$ CD8 | Spinoculation & incubation for about 48 hours in basal media | None | Wash and debead | Following debead |
| | | | | | About 72 hours after initiation of stimulation | |
| 4 | Oligo. 0.2X | $3.0\times10^6$ CD4 and $3.0\times10^6$ CD8 | Spinoculation & incubation for 72 hours in basal media | None | Biotin added during incubation about 24 hours after stimulation | 96 hours after initiation of stimulation |
| 5 | Oligo. 0.2X | $3.0\times10^6$ CD4 and $3.0\times10^6$ CD8 | Spinoculation& incubation for 48 hours in basal media | None | Biotin added during incubation about 24 hours after initiation of stimulation | 72 hours after initiation of stimulation |
| 6 | (Mock) Oligo. 0.2X | $1.5\times10^6$ CD4 and $1.5\times10^6$ CD8 | Mock transduction & static incubation for 24 hours in complete media | None | Biotin added about 24 hours after initiation of stimulation | 96 hours after initiation of stimulation |

B) Assessment of Transgene Copy Number

The cells were thawed and genomic DNA was prepared from harvested cells. For assessment of integrated transgene copy number, ddPCR using primers specific to the transgene sequence was carried out on DNA that had been subject to PFGE for high molecular weight fraction>15 kb generally as described in Examples 12 and 13 ("iVCN"). For comparison, ddPCR using the primers specific to the transgene sequence also was carried out on DNA that had not been subject to PFGE ("VCN", both high- and low-molecular weight DNA). The cell samples were also assessed by flow cytometry, staining for expression of the CAR by staining for a surrogate marker or with an anti-idiotypic antibody that specifically binds to a portion of the CAR.

Figure 24B:
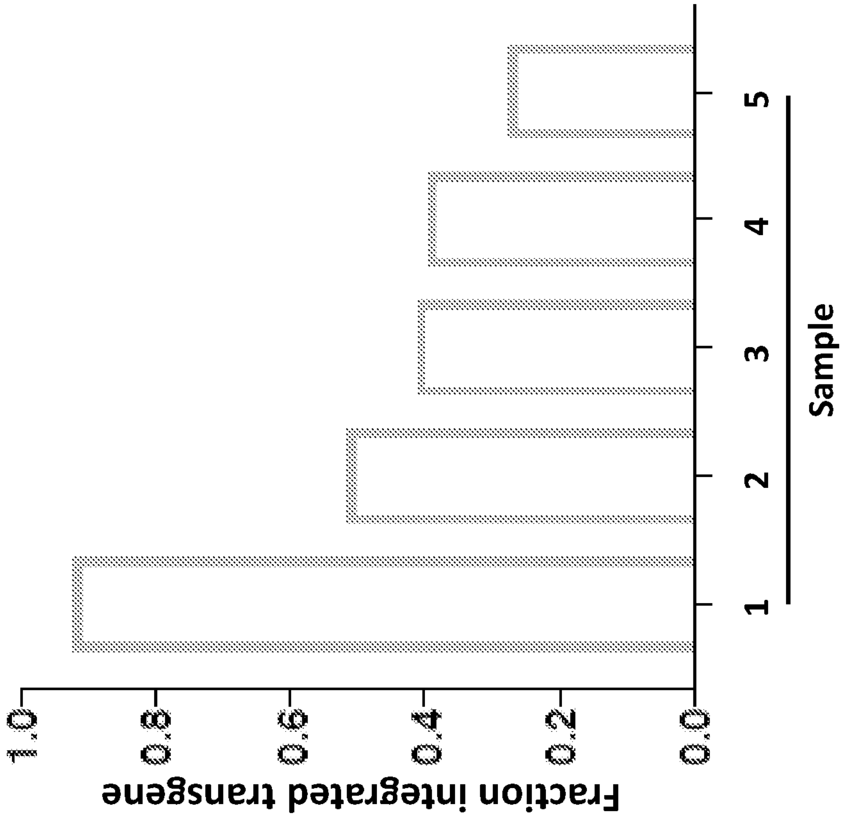
FIGS. 24A-24E depict the copy number per diploid genome as assessed by standard VCN (without PFGE) and iVCN (with PFGE) (FIG. 24A), fraction of integrated transgene (FIG. 4B), fraction of non-integrated transgene (FIG. 24C), non-integrated transgene copy number per diploid genome (FIG. 24D), and integrated copy number per CAR+ cell (FIG. 24E), during various exemplary expanded or non-expanded T cell composition manufacturing processes that employ different stimulating reagents and collection time, as set forth in Table E9.
Figure 24A:
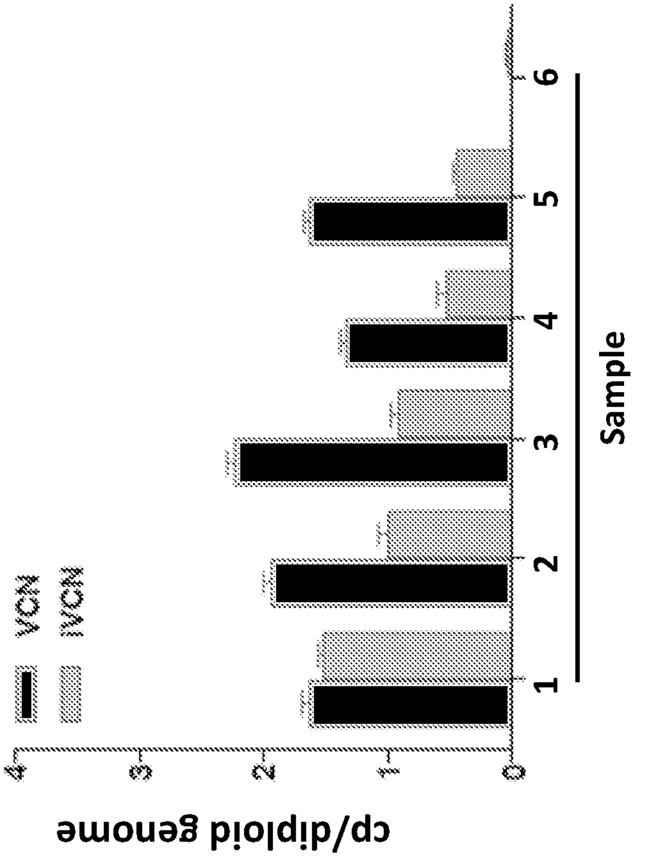
Figure 24D:
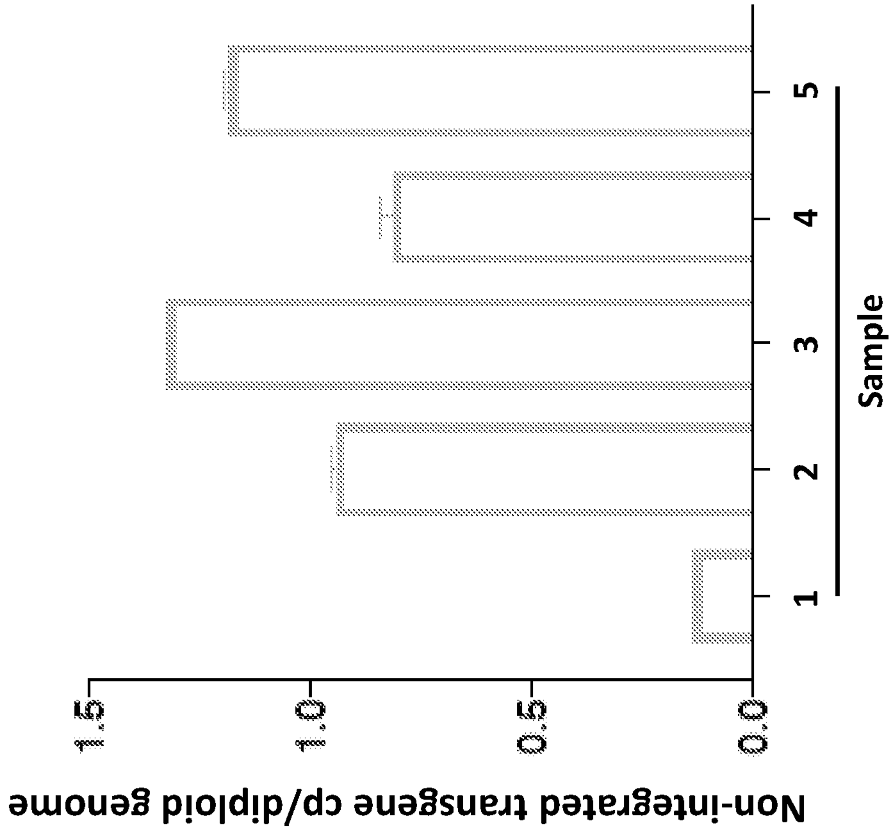
Figure 24C:
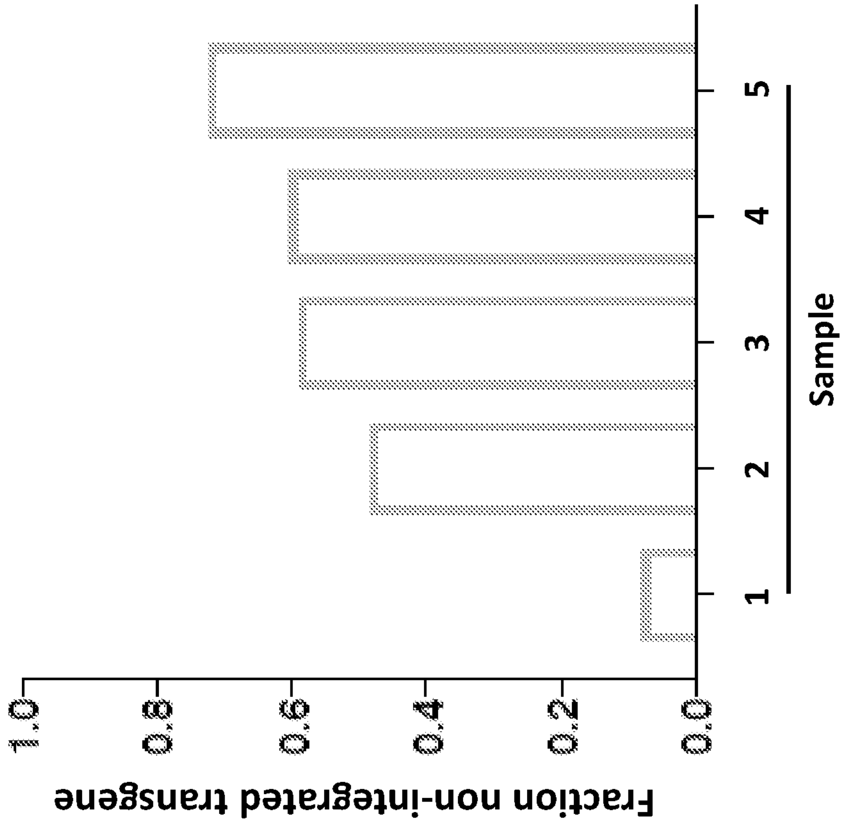
Figure 24E:
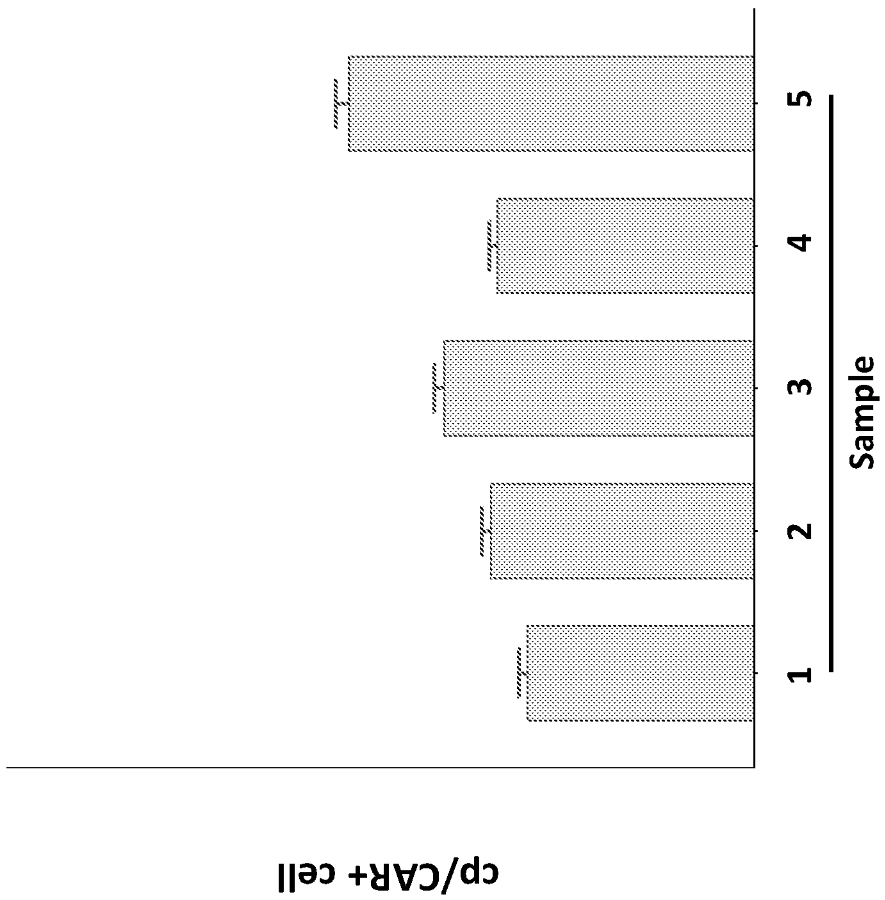

The results are shown in FIGS. 24A-24E. As shown in FIG. 24A, each of the shorter non-expanded processes produced cells that exhibited copy number as determined by VCN (without PFGE) that was higher than copy number as determined by iVCN (with PFGE), indicating that non-integrated transgene sequences were present in the samples that were engineered by these shorter processes. The fraction of integrated transgene, which was determined by dividing copy number using iVCN by VCN, was substantially lower in cells produced using the non-expanded processes (FIG. 24B). Similarly, the fraction of non-integrated transgene, which was determined as 1-fraction of integrated transgene, was substantially higher in cells produced using the non-expanded processes (FIG. 24C). As shown in FIG. 24D, the non-integrated transgene copy number, determined by subtracting the iVCN from VCN, was between about 0.8 and 1.3 on average, in cells produced using the shorter processes. Using a standard VCN without PFGE, the transgene copy number per CAR+ cell are shown in FIG. 24E. This results further supports the utility of the iVCN method for assessing integrated and non-integrated transgene copy number in a process for engineering cells.

Example 16: Comparison of Integrated and Non-Integrated Transgene Copy Number During Various Expanded Cell Manufacturing Processes Transgene copy number in DNA with or without pulse field gel electrophoresis (PFGE), was assessed by ddPCR at various time points in a process for genetically engineering T cells that included a step of expanding the cells after transduction.

Primary T cells from different human donors were engineered to express a CAR, as described in Example 13.B. Samples were obtained daily starting from day 0 to day 8 of the expanded process, including at thawed material (TMAT; day 0), at activation (AMAT; day 1), at transduction (XMAT; day 2) or at various times after initiation of cultivation to expand the cells (inoc+1 to inoc+6; representing days 3-8 of the process). Genomic DNA was prepared from the cell samples. For assessment of integrated transgene copy number, ddPCR using primers specific to the transgene sequence was carried out on DNA that had been subject to PFGE for high molecular weight fraction as described in Examples 12 and 13 ("iVCN"). For comparison, ddPCR using the primers specific to the transgene sequence also was carried out on DNA that was not subject to PFGE ("VCN", both high- and low-molecular weight DNA). The non-integrated transgene copy number, the fraction of integrated transgene and the fraction of non-integrated transgene were also determined, generally as described in Example 15 above.

Figure 25:
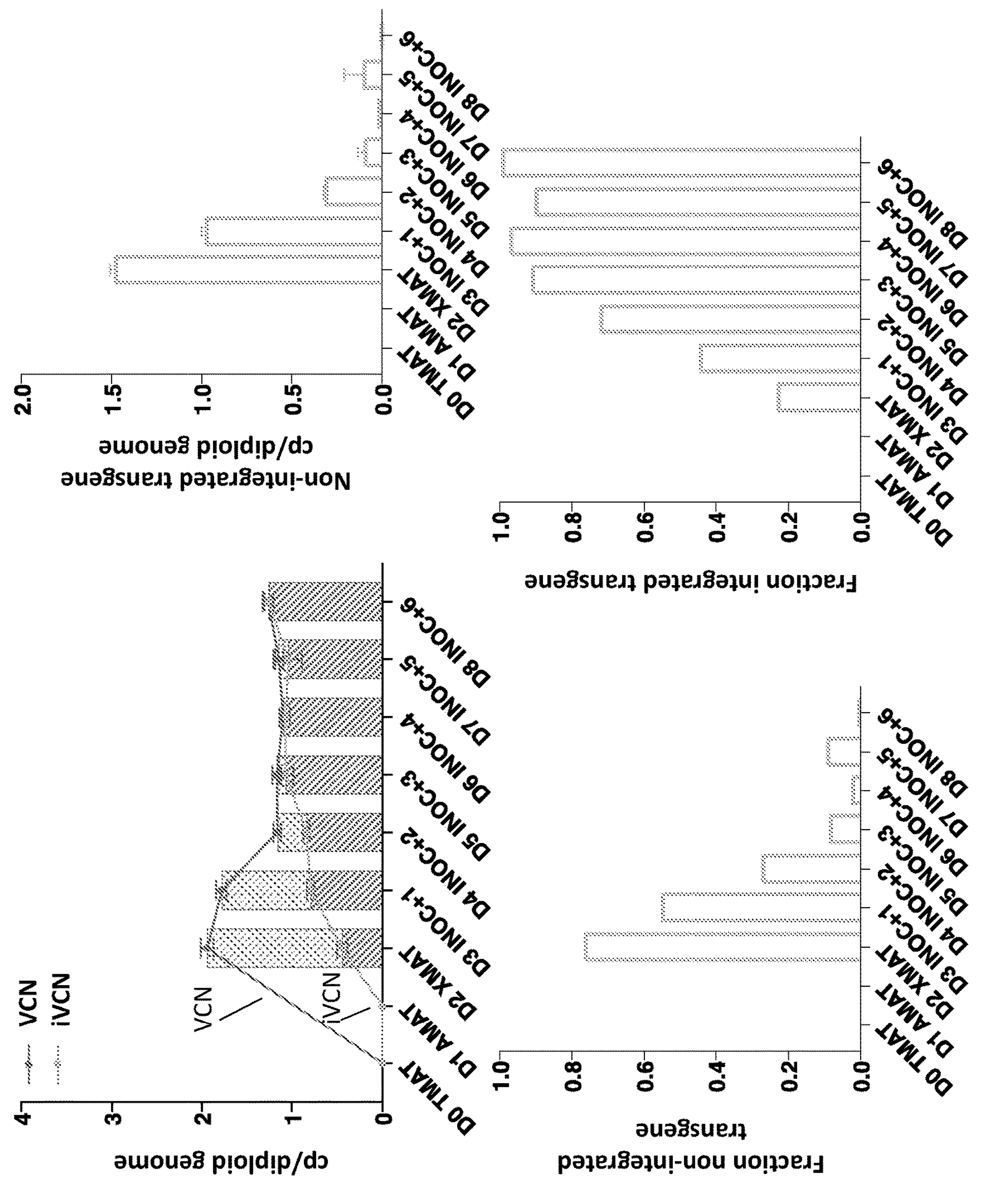
FIG. 25 depicts the copy number per diploid genome as assessed by standard VCN (without PFGE) and iVCN (with PFGE), non-integrated transgene copy number, fraction of non-integrated transgene and fraction of integrated transgene, during various time points in an exemplary engineering process to engineer primary T cells from various donors to express a chimeric antigen receptor (CAR). Assessed time points include from day 0 to day 8 of the expanded processes, including at thawed material (TMAT; day 0), at activation (AMAT; day 1), at transduction (XMAT; day 2) or at various times after initiation of cultivation (inoc+1 to inoc+6; representing days 3-8 of the process).

Representative results are shown in FIG. 25. As shown, on the day of transduction or at early time points after transduction (e.g., inoc+1, inoc+2), copy number as determined by the standard VCN method, determined from genomic DNA samples not subject to PFGE, included a substantial fraction of non-integrated transgenes. At later time points after transduction, copy number as determined by iVCN (with PFGE) and standard VCN (without PFGE) were about the same, indicating that non-integrated copies of the transgene were no longer present in the cells at these time points.

Example 17: Assessment of T Cell Clonality Using Sequencing and Analysis Methods Compositions of T cells were assessed for T cell clonal abundance, using single cell sequencing of T cell receptor (TCR) pairs, before and after genetic engineering to express a chimeric antigen receptor (CAR).

Autologous T cells were isolated from the subjects via leukapheresis by immunoaffinity based selection for purification of $CD4^+$ and $CD8^+$ T cells, resulting in two compositions, enriched for $CD8^+$ and CD4+ T cells, respectively. Cells of the enriched $CD4^+$ and $CD8^+$ compositions were activated with anti-CD3/anti-CD28 paramagnetic beads and then were separately subjected to lentiviral transduction with a vector encoding an anti-CD19 CAR. The anti-CD19 CAR contained an anti-CD19 scFv derived from a murine antibody (variable region derived from FMC63), an immunoglobulin-derived spacer, a transmembrane domain derived from CD28, a costimulatory region derived from 4-1BB, and a CD3-zeta intracellular signaling domain. Transduced populations then were separately incubated in the presence of stimulating reagents for cell expansion. Expanded $CD8^+$ and $CD4^+$ compositions containing CAR-expressing T cells were formulated and cryopreserved separately and stored.

T cell clonality of the isolated CD4+ and CD8+ T cell compositions before engineering (CMAT) and of the CD4+ and CD8+ therapeutic CAR+ T cell compositions after engineering by the process described above was assessed. To assess T cell clonality, the cells were subject to single-cell αβ-paired TCR sequencing, generally as described in WO2016044227, WO2016176322 and WO2012048340. Based on barcoded single-cell sequencing of TCR genes, T cell clonality and diversity of the identified clones in a cell population were determined. In some cases, the Shannon index was used as a threshold to filter clones ("Shannon-adjusted clonality"), which preserves inter-sample relationships while eliminating sample noise. See, Chaara et al. (2018) Front Immunol 9:1038).

Figure 26:
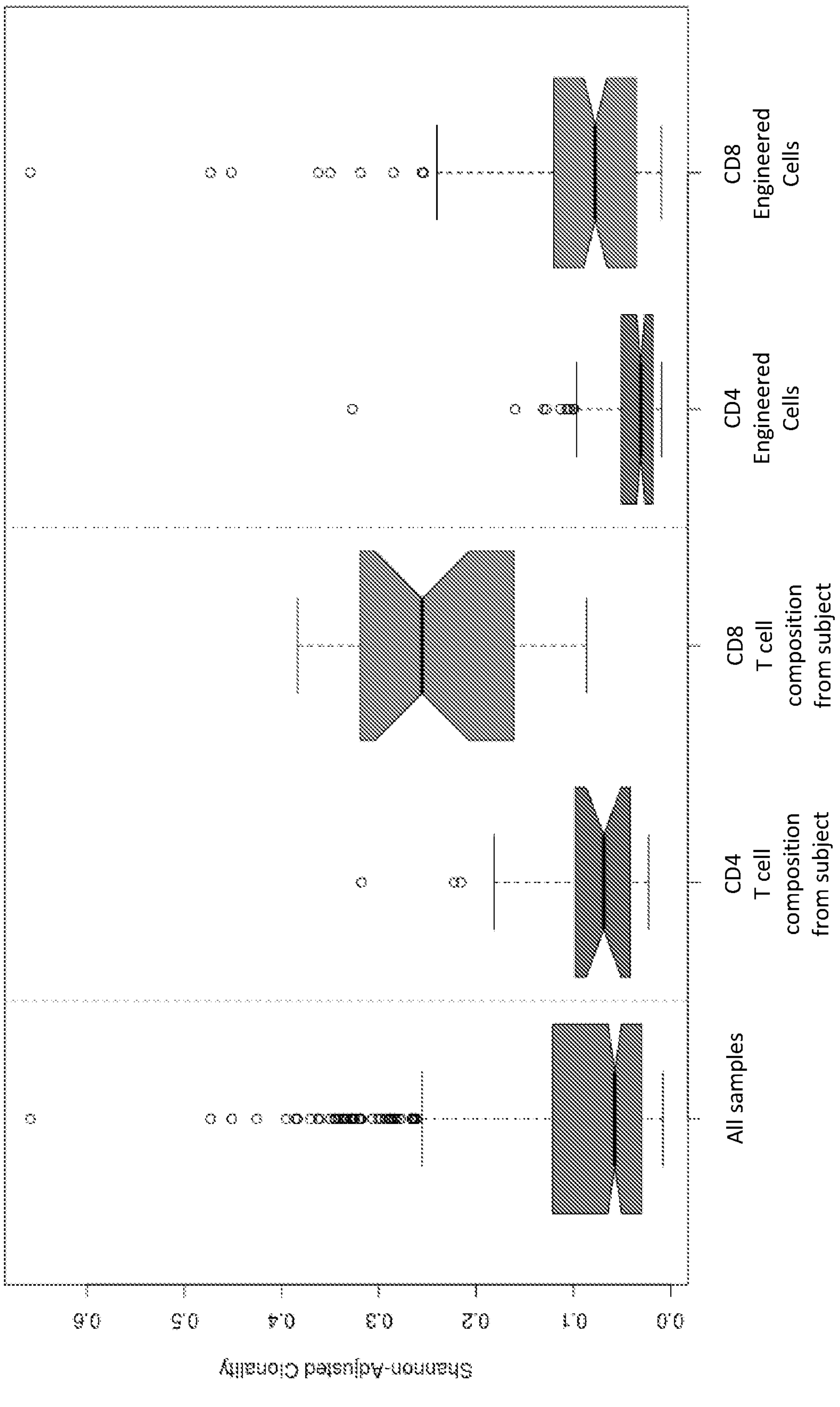
FIG. 26 shows the T cell clonality of the isolated CD4+ and CD8+ T cell compositions before engineering (CMAT) and of the CD4+ and CD8+ therapeutic CAR+ T cell compositions after engineering (Shannon index applied).

FIG. 26 shows the clonality of each sample after applying the Shannon index. As shown in FIG. 26, the clonality of CD4 and CD8 cells differed among T cell compositions before and after the genetic engineering, with the engineered CAR+ T cell compositions exhibiting a reduced clonality compared to the T cells in the compositions prior to initiation of the process for engineering the cells.

CD4+ and CD8+ therapeutic CAR+ T cell compositions after genetic engineering were sorted by flow cytometry expression of a factor indicative of apoptosis, such as surface staining with Annexin V (Annexin V-) or caspase 3 cleavage (indicating non-apoptotic cells), and for expression of various surface markers including CD45RA, CCR7, CD27, CD4 and CD8. The phenotype of the cells was correlated to the degree of clonality of the cells. It was observed that, in both the CD4+ and CD8+ therapeutic CAR+ T cell compositions, the presence of apoptotic marker-negative cells that were $CCR7^-/CD27^-$ positively correlated highly with the clonality of the cells in the composition. Likewise, the presence of apoptotic marker-negative cells that were CCR7+ or CCR7+/CD27+ negatively correlated with the clonality of cells in each of the CD4+ and CD8+ therapeutic CAR+ T cell compositions. These results are consistent with an observation that clonality of cells may be inversely correlated with less differentiated, naïve-like cells, such as determined by CCR7 and/or CD27 positivity.

Example 18: Comparison of Phenotype of Cells Generated from a Non-Expanded Process for Producing an Engineered T Cell Composition Under Different Concentrations of the Oligomeric Streptavidin Mutein Reagent and Media Compositions A process for producing T cell compositions was assessed by incubating T cell compositions with different concentrations of the oligomeric streptavidin mutein reagent and with different media compositions, and assessing engineered cells.

T cell compositions were generated from a non-expanded engineering process using an anti-CD3/anti-CD28 Fab conjugated oligomeric streptavidin mutein reagent, substantially as described in Example 8 except using various titers of the anti-CD3/anti-CD28 Fab conjugated oligomeric streptavidin mutein reagent. In general, cells were transduced 24 hours after stimulation with the oligomeric streptavidin mutein reagent, D-biotin was added 48 hours after initiation of the stimulation, and cells were harvested 96 hours after the initiation of the stimulation. Specifically, CD4+ and CD8+ T cells from the mixed input cell composition were stimulated by incubation with 0.4 μg per $1\times10^6$ cells, 0.24 μg per $1\times10^6$ cells or 0.08 μg per $1\times10^6$ cells of the oligomeric streptavidin mutein reagent.

Following the stimulation, the cells were washed and resuspended in serum free media containing recombinant IL-2, IL-7 and IL-15. The cells were then transduced with a lentiviral vector encoding the anti-BCMA CAR described in Example 1 by spinoculation at 693 g for 30 minutes. After the spinoculation, the cells were washed and resuspended in the following media compositions for further incubation until harvest 96 hours after the initiation of the stimulation:

(i) basal media (e.g. CTS OpTmizer basal media, Thermofisher) without any additional additives or recombinant cytokines ("Basal");
(ii) basal media with 2 mM glutamine ("Basal+Gln");
(iii) basal media with 2 mM glutamine and with the addition of 100 IU/mLIL-2, 600 IU/mL IL-7, and 100 IU/mL IL-15 cytokines (Cyt) ("Basal+Gln+Cyt");
(iv) basal media with 2 mM glutamine, 100 IU/mL IL-2, 600 IU/mL IL-7, and 100 IU/mL IL-15 cytokines (Cyt), and a T cell supplement (e.g., 2.5% OpTmizer® supplement, Thermofisher) (Opt) ("Basal+Gln+Cyt+Opt"); or
(v) complete media ("Complete"), which contains basal media with 2 mM glutamine, 100 IU/mL IL-2, 600 IU/mL IL-7, and 100 IU/mL IL-15 cytokines, T cell supplement (e.g., 2.5% OpTmizer® supplement, Thermofisher), and serum-substituting proteins.

The cells were incubated at about 37.0° C. in an incubator. After 48 hours after initiation of the stimulation, D-biotin was added to dissociate anti-CD3 and anti-CD28 Fab reagents from oligomeric streptavidin reagents. The cells were then collected, washed and formulated in the presence of a cryoprotectant.

Figure 27:
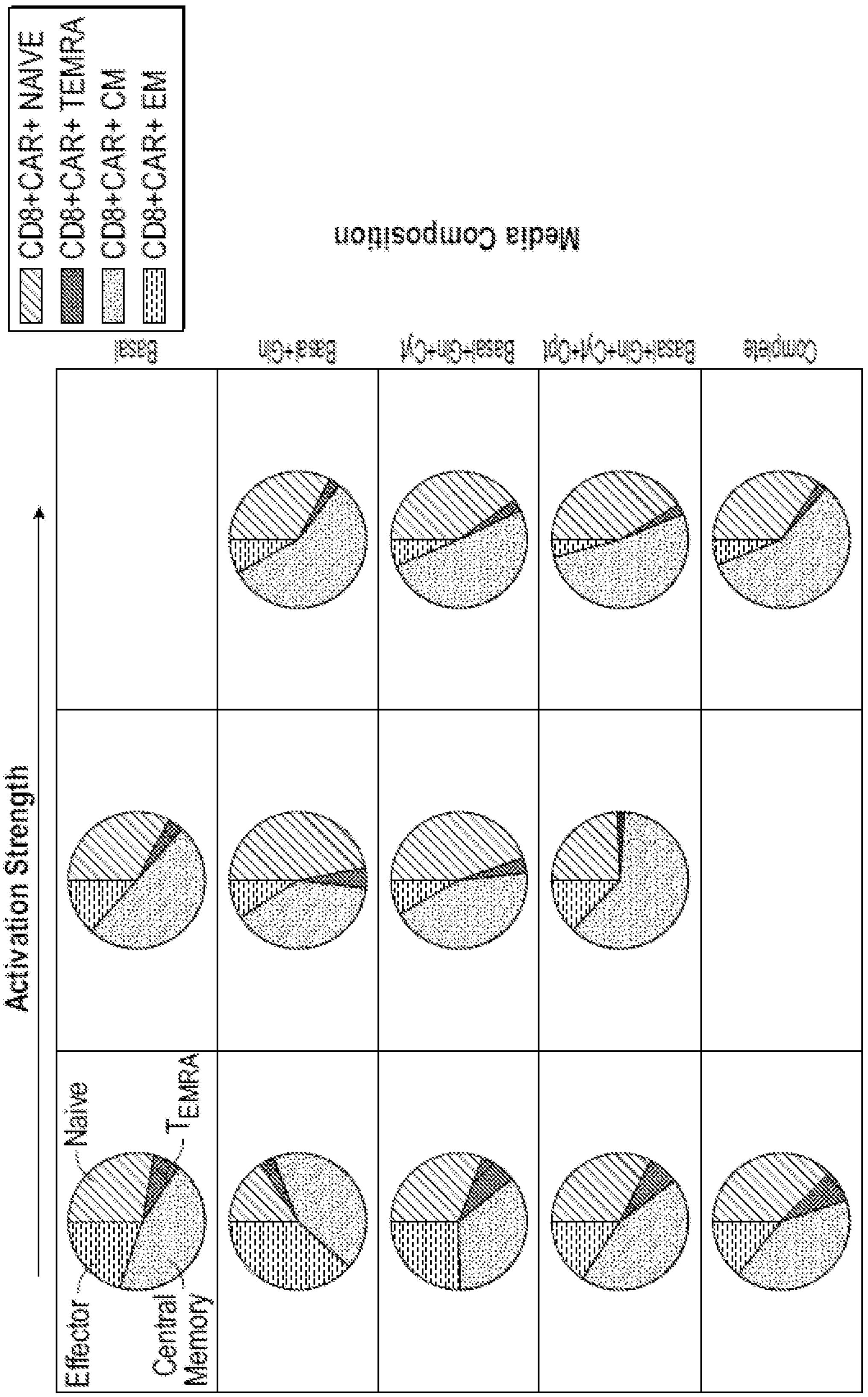
FIG. 27 shows differences in the phenotype of the generated cell composition in the presence of different concentrations of the anti-CD3/anti-CD28 Fab conjugated oligomeric streptavidin mutein reagent and/or in the presence of different media compositions. The percentage of CD8+ CAR+T cells that were indicative of effector memory CD45RA+ cells (CCR7−CD45RA+; EMRA), naïve-like T cells (CCR7+CD45RA+; NAIVE), effector memory (CCR7−CD45RA−; EM), and central memory (CCR7+ CD45RA−; CM), at various combinations of mutein reagent and media composition, are shown.

T cells from the generated T cell compositions were then stained with antibodies recognizing surface markers including CD4, CD8, CCR7, and CD45RA, and for the CAR, and quantified by flow cytometry. The percentage of CD8+ CAR+ T cells that were indicative of effector memory CD45RA+ cells (CCR7−CD45RA+; EMRA), naïve-like T cells (CCR7+CD45RA+; NAIVE), effector memory (CCR7−CD45RA−; EM) or central memory (CCR7+ CD45RA−; CM), at various combinations of mutein reagent concentration and media composition, are shown in FIG. 27. The results show differences in the phenotype of the generated cell composition in the presence of different concentrations of the anti-CD3/anti-CD28 Fab conjugated oligomeric streptavidin mutein reagent and/or in the presence of different media compositions. These results are consistent with the ability to control phenotypic distribution in a process for producing engineered T cell compositions, such as based on the concentration of the anti-CD3/anti-CD28 Fab conjugated oligomeric streptavidin mutein reagent and/or the type of media composition.

Example 19: Comparison of Engineered T Cells Produced from Different Donors Using a Non-Expanded Process Engineered compositions of primary T cells containing T cells expressing CARs were produced from three different human donors using a non-expanded process from cells from each of three human donors. Cells from donor 1 were generated using processes substantially as described in Example 1, and cells from donor 2 were generated using processes substantially as described in Example 8. Cells from donor 3 were generated using processes similar to that described in Example 8 involving activation using paramagnetic polystyrene-coated beads with attached anti-CD3 and anti-CD28 antibodies (beads) or an anti-CD3/anti-CD28 Fab conjugated oligomeric reagent (oligo) to activate T cells prior to transduction with a viral vector, except that the process was carried out with an input cell number containing $3\times10^8$ CD4 cells and $3\times10^8$ CD8 T cells. Engineered cell compositions also were prepared using an expanded process substantially as described in Example 1 from matched donors.

Figure 28:
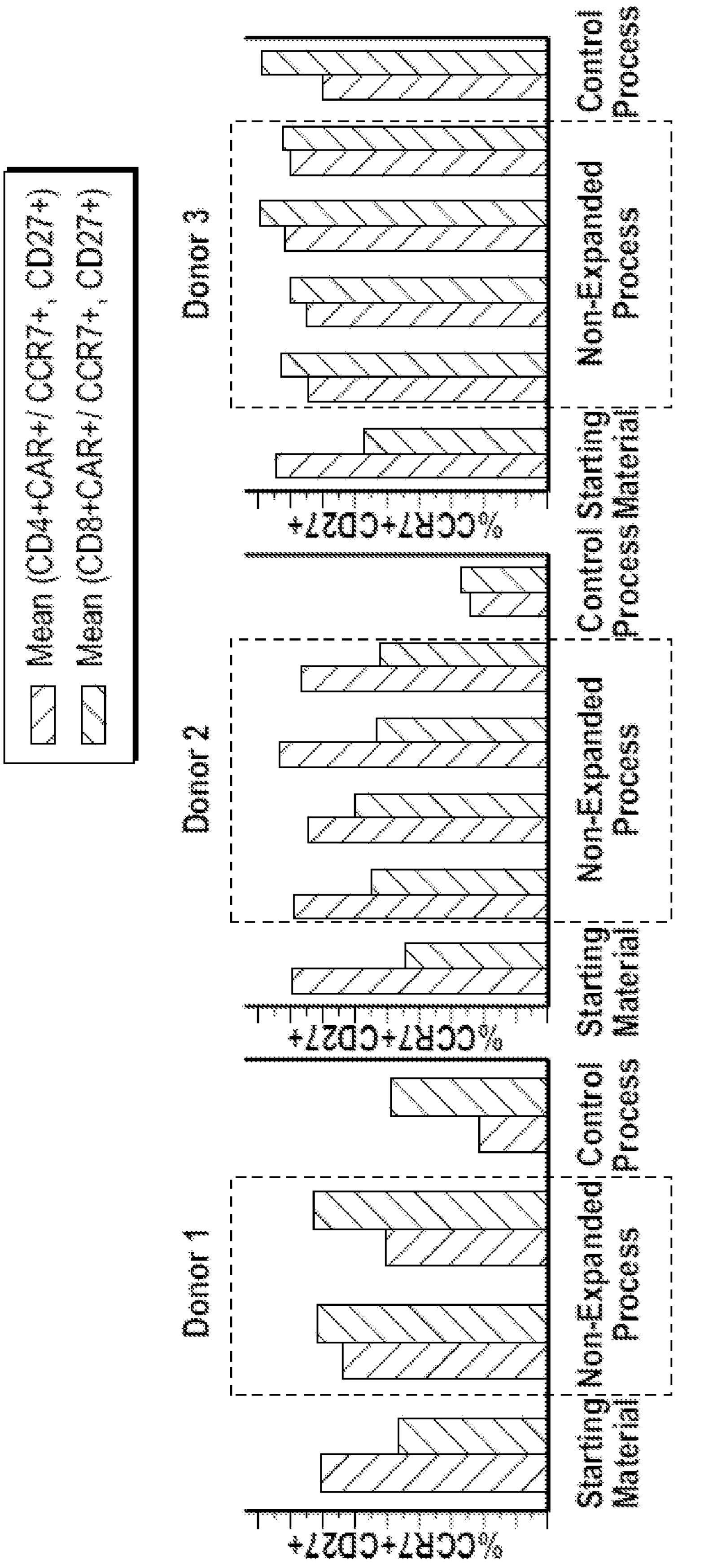
FIG. 28 shows percentages of CD4+CAR+ and CD8+ CAR+ T cells positive for both CCR7 and CD27 staining in engineered compositions of primary T cells from three different donors, using a non-expanded process and an expanded process as control.

T cells produced from the different processes were stained with antibodies recognizing surface markers including CD4, CD8, CCR7, and CD27, and for CAR expression, and quantified by flow cytometry. The percentages of CD4+ CAR+ and CD8+CAR+ T cells positive for both CCR7 and CD27 staining are shown in FIG. 28 for each of the three different donors. The percentages of CCR7+CD27+ cells for CD4+CAR+ T cells or CD8+CAR+ T cells, respectively, in the produced T cell compositions, were compared to the percentages of CCR7+CD27+ cells in the input composition prior to the incubation with the stimulatory reagent ("Starting Material"). For all donors, the results of this experiment indicate that a consistently high percentage of CCR7+ CD27+ were observed in the T cell compositions produced from the non-expanded engineering process, whereas more variability in the percentage of CCR7+CD27+ T cells was observed in engineered T cell compositions produced from the three donors by the expanded process.

Figure 29:
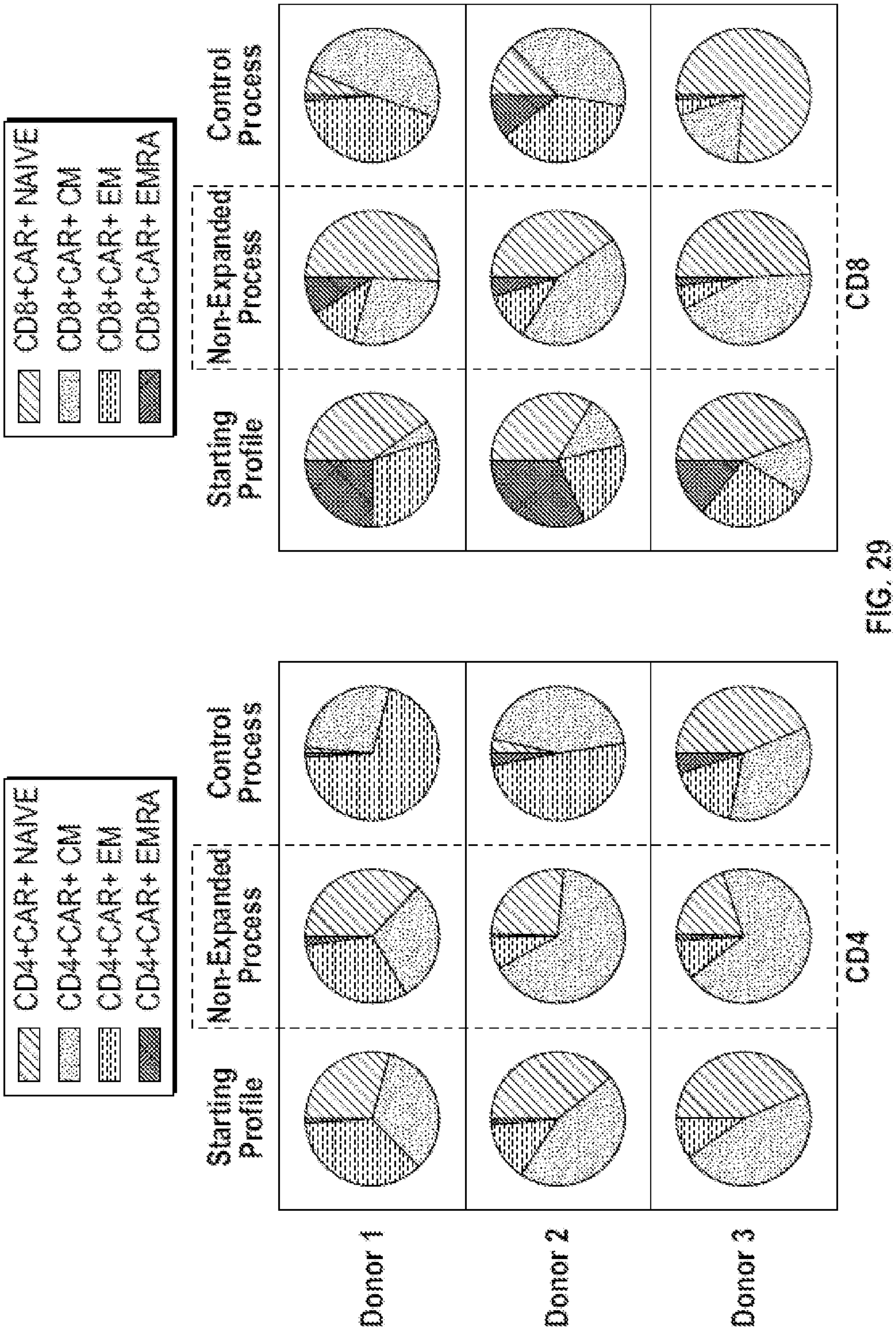
FIG. 29 shows percentages of CD4+CAR+ T cells and CD8+CAR+ T cells that were indicative of effector memory CD45RA+ cells (CCR7−CD45RA+; EMRA), naïve-like T cells (CCR7+CD45RA+; NAIVE), effector memory (CCR7−CD45RA−; EM), and central memory (CCR7+ CD45RA−; CM), in engineered compositions of primary T cells from three different donors, using a non-expanded process and an expanded process as control.

The engineered compositions of primary T cells generated from the three donors were also stained with antibodies recognizing surface markers including CD4, CD8, CCR7, and CD45RA, and for CAR expression, and quantified by flow cytometry. The percentages of CD4+CAR+ T cells and CD8+CAR+ T cells that were indicative of effector memory CD45RA+ cells (CCR7−CD45RA+; EMRA), naïve-like T cells (CCR7+CD45RA+; NAIVE), effector memory (CCR7−CD45RA−; EM) or central memory (CCR7+ CD45RA−; CM) are shown in FIG. 29.

Example 20: Assessment of Features of Selected (Input) Cell Compositions in a Process for Producing a Therapeutic Cell Composition Phenotypic attributes of T cells selected from subjects with Relapsed and Refractory Non-Hodgkin's Lymphoma (NHL), prior to engineering with an anti-CD19 CAR by the process described in Example 10, were assessed. $CD4^+$ and $CD8^+$ T cells were selected by immunoaffinity-based enrichment from leukapheresis of human peripheral blood mononuclear cells (PBMC) from a plurality of subjects. A composition of such selected T cells (before genetic engineering, designated "pre-engineering composition") were assessed for expression of cell surface markers indicative of certain T cell subtypes, such as effector memory or central memory cell subtypes, including C-C chemokine receptor type 7 (CCR7), CD27 and CD45RA, and surface expression of CD4 or CD8 was assessed.

Figure 18F:
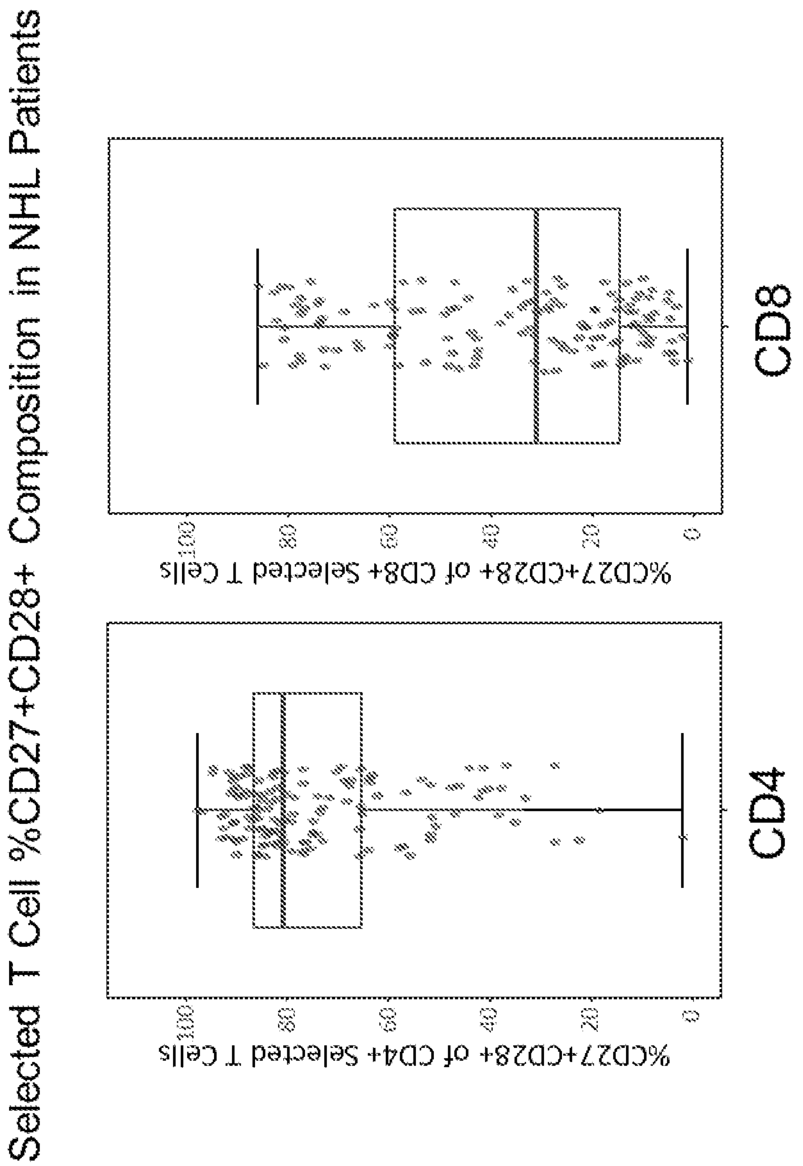
FIG. 18F shows the percentage of CD27+CD28+ T cells in enriched CD4+ (left panel) and CD8+ (right panel) input compositions derived from Non-Hodgkin's lymphoma patients.

Assessment of the enriched CD4+ and CD8+ compositions (e.g., input compositions) revealed that the percentage of T cells positive for naïve-like markers (e.g. CD27+ CD28+ T cells), such as present on central memory T cell subsets, was highly variable between NHL patients (FIG. 18F). This data indicate that interpatient T cell heterogeneity of central memory T cell subsets exists in selected (input) T cell compositions used to generate CAR+ T cell therapeutic T cell compositions.

Figure 18G:
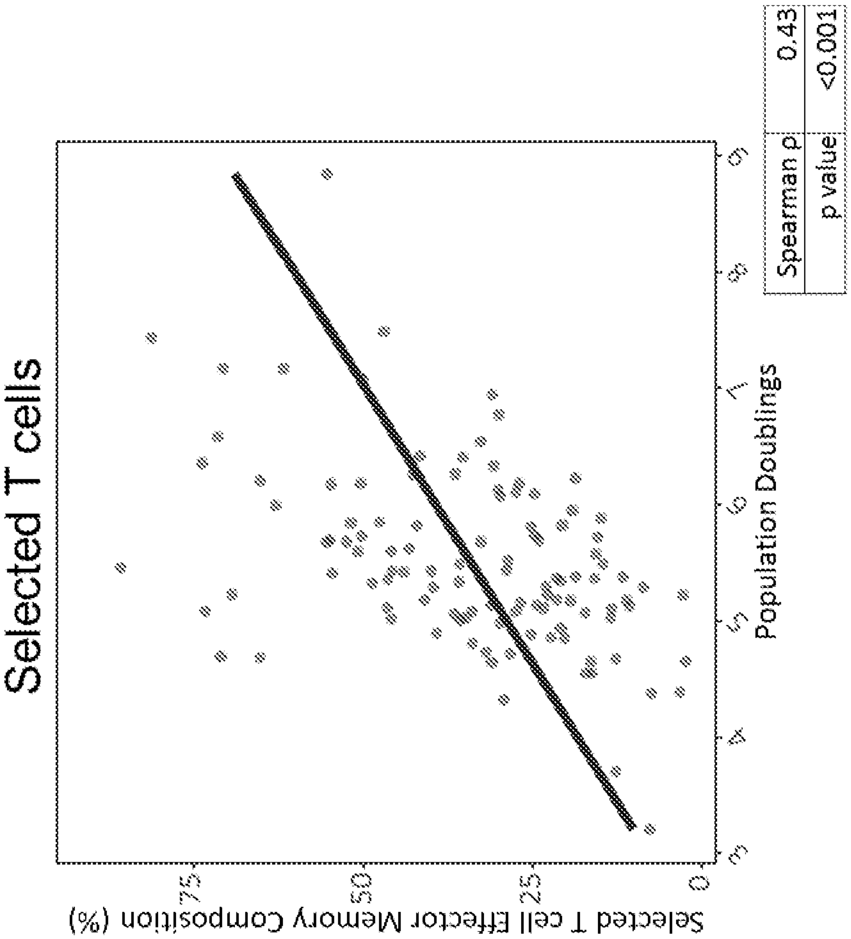
FIG. 18G shows the relationship between the percentage of effector memory T cells in enriched CD4+ input compositions and the number of population doublings needed to achieve harvest criterion (Spearman ρ: 0.43; p-value: <0.001). A similar result was observed for enriched CD8+ input compositions.

The selected (input) T cell compositions were used to generate CD4+ and CD8+ therapeutic T cell compositions substantially as described in Example 10. The number of doublings of the generated cell compositions also was determined based on total nuclear count (TNC) of cells as described in Example 10. The correlation between phenotypic attributes of cells in the selected (input) T cell compositions and the number of doublings in the process for producing the therapeutic composition was determined. As shown in FIG. 18G, a higher percentage of effector memory CD4+ T cells identified by negative staining for CD45RA and CCR7 (CD45RA−CCR7−) in the enriched CD4+ (input) compositions correlated positively with the number of population doublings during production of the therapeutic T cell composition. A similar result was observed for CD8+ T cells.

The above results are supportive of an approach that includes reducing the percentage of effector memory T cells and/or enriching for T cells positive for markers of naïve-like or central memory cell subsets in an input composition used in a process for producing an engineered T cell composition. Consistent with the results above, such an approach may improve one or more feature of an engineered therapeutic T cell composition, such as reducing patient-to-patient variability, lowering the number of population doublings in a process for producing an engineered therapeutic T cell composition and/or increasing the likelihood a subject may exhibit PFS that is durable.

Example 21: Assessment of T Cell Phenotype and Function in Engineered T Cells Produced in the Presence of a Small Molecule mTOR Kinase Inhibitor CD4+ and CD8+ T cells were isolated by immunoaffinity-based enrichment from leukapheresis samples from human donor subjects. At day 1, isolated CD4+ and CD8+ T cells were mixed 1:1 and stimulated with an anti-CD3/anti-CD28 oligomeric stimulatory reagent generated as described in Example 2 in serum-free media supplemented with recombinant IL-2 (100 IU/mL), recombinant IL-7 (600 IU/mL), and recombinant IL-15 (100 IU/mL) with or without 1 μM of 2-(3-hydroxyphenyl)-9-(2-isopropylphenyl)-8-oxo-8,9-dihydro-7H-purine-6-carboxamide (Compound 63). The T cells cultured with our without Compound 63 were incubated overnight (approximately 24 hr) at 37° C., and were then transduced in serum-free culture media with our without Compound 63 (1 mM) with a lentiviral vector encoding an anti-CD19 CAR. The CAR contained an scFv antigen-binding domain specific for CD19 (derived from FMC63), a CD28 transmembrane region, a 4-1BB costimulatory signaling region, and a CD3-zeta derived intracellular signaling domain. Following transduction, the cells were incubated in serum free media without recombinant cytokines (basal media) and with or without Compound 63 (1 mM) and allowed to incubate at about 37.0° C. in an incubator for up to 96 hours after initiation of the stimulation with the anti-CD3/anti-CD28 oligomeric stimulatory reagent (until day 5 of the process). At approximately 24 hours after beginning the incubation (day 3 of the process), 1 mM biotin was added. Following incubation CD4+ and CD8+ T cells from each donor were harvested, formulated, and cryofrozen.

Figure 30A:
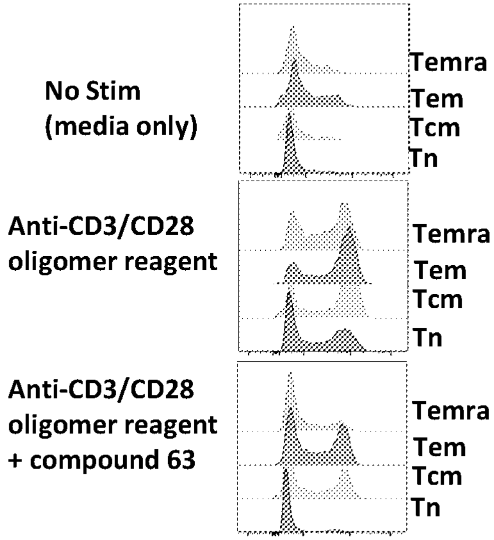
FIGS. 30A-30D show exemplary effects of incubating T cells with an anti-CD3/anti-CD28 oligomeric stimulatory reagent in the presence or absence of Compound 63 on mTor signaling and viability and growth kinetics.
Figure 30B:
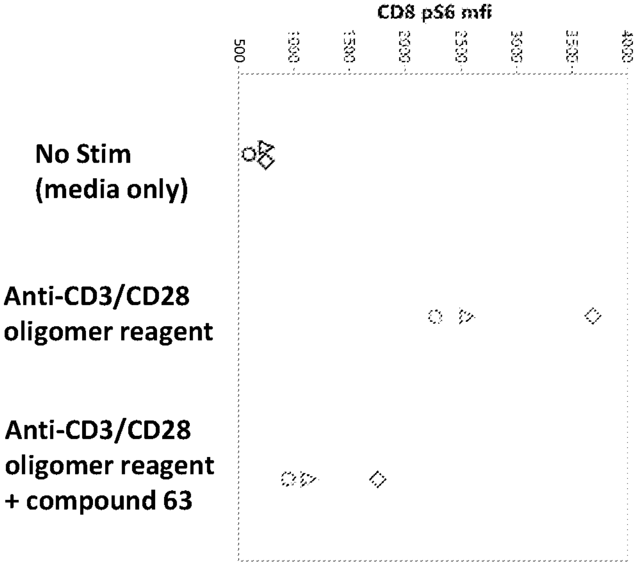
Figure 30C:
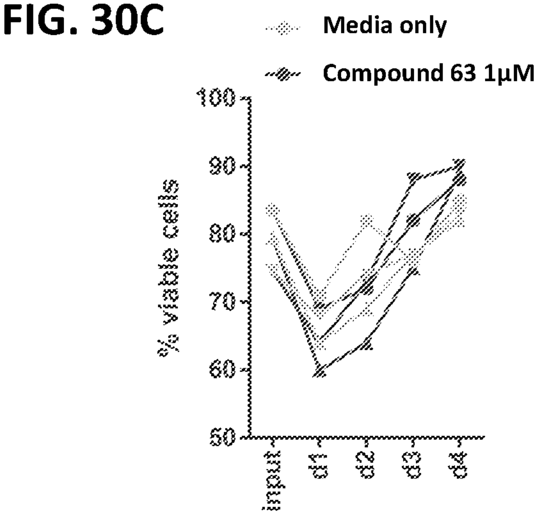
Figure 30D:
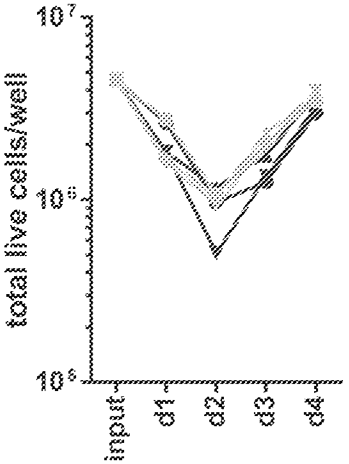

The cryofrozen engineered CD4+ and CD8+ T cells were thawed, and T cells were assessed for intracellular S6 phosphorylation, a ribosomal protein and marker of mTOR inhibition, and co-stained for surface expression of CD4 or CD8 and for CCR7 and CD45RA as markers of memory subsets. pS6 expression in live CD8+ T cells by memory subsets was shown by the expression of CCR7 and CD45RA as shown in FIG. 30A. As shown, incubation with Compound 63 decreased the mean fluorescence intensity of stimulated memory T cell subsets, Temra, Tem, and Tem cells, indicating an inhibition of mTOR, while having no significant effect on the percentage or total number of viable cells over time. Mean fluorescence intensity (MFI) of PS6 in CD8+ T cells is shown in FIG. 30B. As shown in FIG. 30C and FIG. 30D, the presence of compound 63 did not impact the percent viable cells or the total live cells, respectively, in the generated composition.

Figures 31A, 31B, 31C, 31D, 31E, 31F:
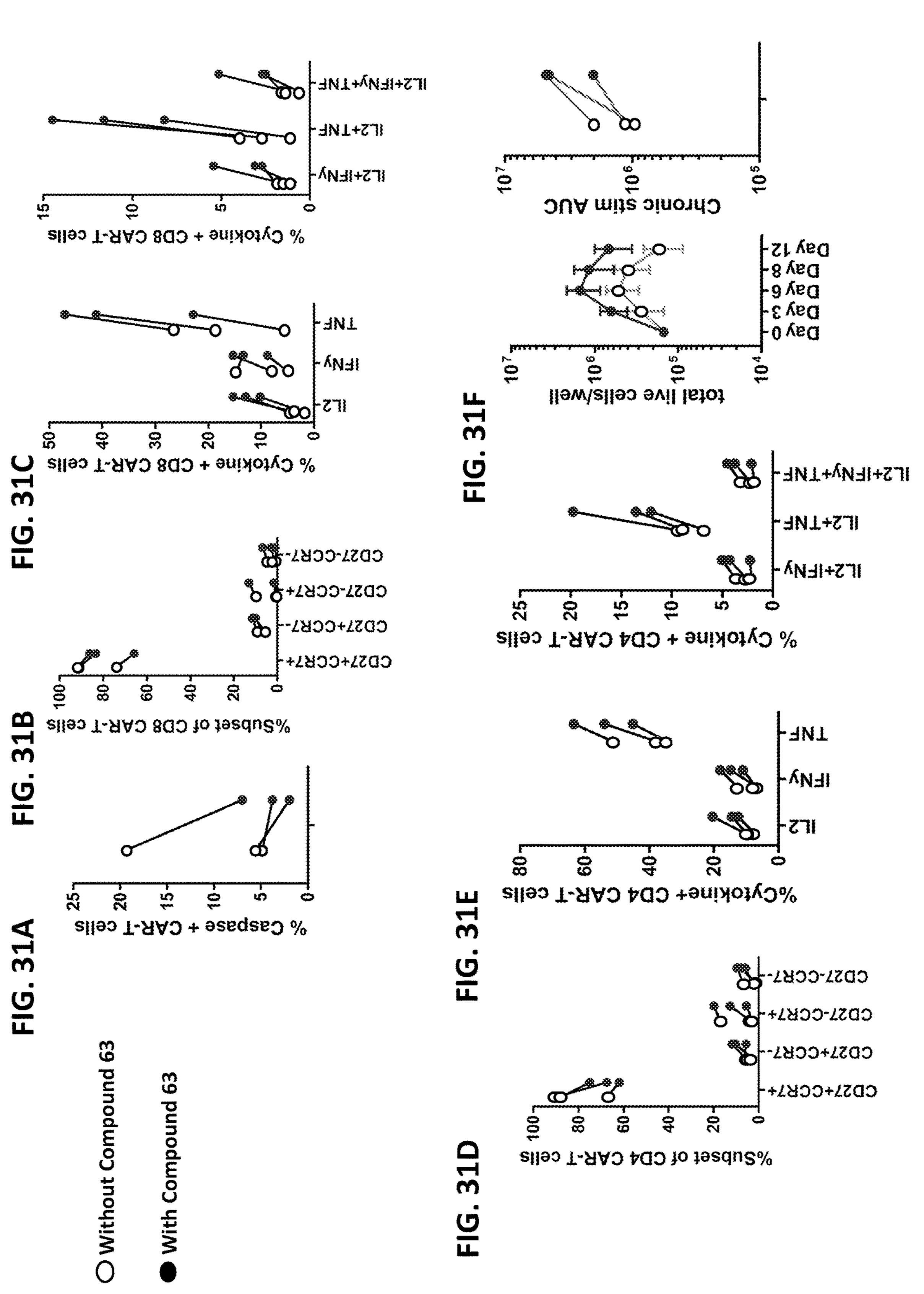
FIGS. 31A-31F show exemplary functional and phenotypic properties of cryopreserved CAR-T cells generated using methods employing incubation with an anti-CD3/anti-CD28 oligomeric stimulatory reagent in the presence or absence of Compound 63.

Thawed cells generated by the process described were assessed for a marker of apoptosis (e.g., percentage of caspase positive CAR-T cells), phenotypic profile, and ability to produce intracellular cytokines following stimulation with PMA/Ionomycin and a Golgi Inhibitor. As shown in FIG. 31A, T cells from samples incubated with compound 63 exhibited less intracellular caspase expression than those not incubated with compound 63, indicating that the presence of compound 63 during the process for generating the engineered cells improved overall cell heath of the T cell composition. Thawed cells also were stained for surface expression of CD27 and CCR7 by flow cytometry. As shown in FIG. 31B (CD8+ T cells) and FIG. 31D (CD4+ T cells), incubation with compound 63 did not substantially alter the phenotypic subset profile of the cells as assessed by expression of CD27 and/or CCR7. The functional activity of CD4+ and CD8+ T cells produced in the presence of compound 63, as evidenced by the level of intracellular cytokines IL2, IFNg, or TNF, was substantially improved in both the engineered CD8+ T cells (FIG. 31C) and CD4+ T cells (FIG. 31E) that had been produced in the presence of Compound 63.

To further assess the functional activity of the cells, the generated T cell compositions were stimulated long-term over 12 days with beads conjugated with an anti-idiotype (ID) antibody against the anti-CD19 CAR, and expansion and survival of the cells were monitored (FIG. 31F, left panel) and total expansion metric calculated by area under the curve (FIG. 31F, right panel). As shown, stimulation of the cells in the absence of compound 63 resulted in a decreased expansion of the cells over time consistent with chronic stimulation of the CAR and loss of sustained function following the long-term stimulation. The results show that improved function of the T cells was observed following long-term CAR-specific stimulation in engineered cells that had been produced in the presence of compound 63.

Example 22: Effect of Sample Cryopreservation in a Non-Expanded Process for Producing an Engineered T Cell Composition In a process for producing engineered compositions of primary T cells containing T cells expressing a chimeric antigen receptor (CAR), different processes were carried out on cells that had been cryopreserved, either by cryopreservation of the starting leukapheresis sample or by cryopreservation of CD4+ and CD8+ T cells that had been isolated from a fresh leukapheresis sample. Leukapheresis samples were collected from three healthy human donors and washed. An aliquot of the leukapheresis sample for each donor was cryopreserved, while another aliquot of each leukapheresis sample was not cryopreserved and was used immediately for selection of CD4+ and CD8+ T cells as described below.

In one process (cryopreserved apheresis), engineered T cell compositions were individually manufactured from the three donor aliquots of cryopreserved leukapheresis samples. The cryopreserved leukapheresis samples were thawed, and separate compositions of CD4+ and CD8+ cells were selected from each sample by immunoaffinity-based selection. The selected CD4+ and CD8+ T cells were used immediately in the downstream steps for engineering the cells.

In the other process (cryopreserved T cell material), CD4+ and CD8+ cells were selected directly by immunoaffinity-based selection from the three aliquots of leukapheresis samples which had not been cryofrozen. After selection, the separate CD4+ and CD8+ T cell compositions were cryofrozen and then were thawed prior to subsequent downstream steps for engineering the cells.

In both processes, the downstream steps of the process included mixing the selected CD4+ and CD8+ T cells at a ratio of 1:1 of viable CD4+ T cells to viable CD8+ T cells to produce an input composition. Cells from the mixed input cell composition were stimulated by incubation with 0.2× (0.8 μg per $1\times10^6$ cells) anti-CD3/anti-CD28 Fab conjugated oligomeric streptavidin mutein reagents generated as described in Example 2, in serum free media containing recombinant IL-2, IL-7 and IL-15 for between 18-30 hours. After stimulation, the cells were transduced by spinoculation with a lentiviral vector encoding a CAR, in this case the exemplary anti-CD19 CAR described in Example 6. After the spinoculation, the cells were washed and resuspended in serum free media without recombinant cytokines (basal media) at a density of about $0.75\times10^6$ cells/mL, and incubated at about 37.0° C. in an incubator. After 48 hours after initiation of the stimulation (about 24 hours after beginning the incubation), 1.0 mM D-biotin was added and mixed with the cells to dissociate anti-CD3 and anti-CD28 Fab reagents from oligomeric streptavidin reagent. The cells were further incubated for an additional about 48 hours (about 96 hours±6 hours after initiation of stimulation or until day 5 of the process), and then were formulated with a cryoprotectant.

Table E10 summarizes features of the process for each assessed sample.

| Donor | Upstream process source | Activation reagent | Cell number | Transduction | Removal of Stimulatory Reagent | Harvest |
|---|---|---|---|---|---|---|
| 1 | Crypreserved T cell material | 0.8 μg per $1 \times 10^6$ cells Oligo | $1.2 \times 10^6$ CD4 and $1.2 \times 10^6$ CD8 | Spinoculation & incubation for about 72 hours in basal media | Biotin added during incubation about 48 hours after stimulation | 96 hours after initiation of stimulation |
| | Cryopreserved apheresis | 0.8 μg per $1 \times 10^6$ cells Oligo | $1.2 \times 10^6$ CD4 and $1.2 \times 10^6$ CD8 | Spinoculation & incubation for about 72 hours in basal media | Biotin added during incubation about 48 hours after stimulation | 96 hours after initiation of stimulation |
| 2 | Crypreserved T cell material | 0.8 μg per $1 \times 10^6$ cells Oligo | $1.25 \times 10^6$ CD4 and $1.25 \times 10^6$ CD8 | Spinoculation & incubation for about 72 hours in basal media | Biotin added during incubation about 48 hours after stimulation | 96 hours after initiation of stimulation |
| | Cryopreserved apheresis | 0.8 μg per $1 \times 10^6$ cells Oligo | $1.25 \times 10^6$ CD4 and $1.25 \times 10^6$ CD8 | Spinoculation & incubation for about 72 hours in basal media | Biotin added during incubation about 48 hours after stimulation | 96 hours after initiation of stimulation |
| 3 | Crypreserved T cell material | 0.8 μg per $1 \times 10^6$ cells Oligo | $1.5 \times 10^6$ CD4 and $1.5 \times 10^6$ CD8 | Spinoculation & incubation for about 72 hours in basal media | Biotin added during incubation about 48 hours after stimulation | 96 hours after initiation of stimulation |
| | Cryopreserved apheresis | 0.8 μg per $1 \times 10^6$ cells Oligo | $1.5 \times 10^6$ CD4 and $1.5 \times 10^6$ CD8 | Spinoculation & incubation for about 72 hours in basal media | Biotin added during incubation about 48 hours after stimulation | 96 hours after initiation of stimulation |

The two processes were compared for attributes of cells (viability, total viable nucleated cells, yield), including during downstream process steps and in the harvested manufactured cell compositions. Cells at harvest also were assessed by flow cytometry staining for expression of the CAR using an anti-idiotype antibody, activated caspase 3 (aCas3) as a measure of cell health, and for expression of various surface markers including CD25, CD45RA, CCR7, CD27, CD28, CD62L, CD4 and CD8. The ability to produce cytokines also was assessed.

Figure 32A:
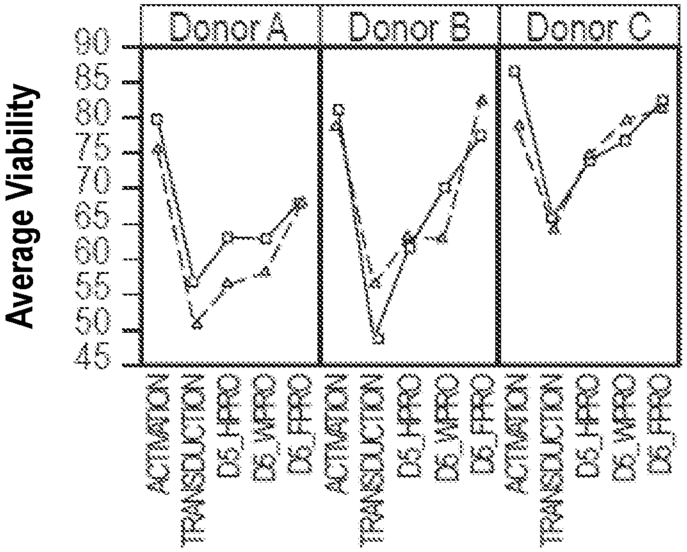
FIGS. 32A-32C show exemplary viability (FIG. 32A), total viable nucleated cells (FIG. 32B), and cumulative downstream yield (FIG. 32C) at each processing step for processes using cryopreserved apheresis (CrAPH) or cryopreserved T cell selected material (CMAT) taken from 3 donors. D5_HRPO, D5_WPRO, D5_FPRO refer to day 5 harvested cellular product, day 5 washed cellular product, and day 5 formulated cellular product (e.g., formulated drug product), respectively.
Figure 32B:
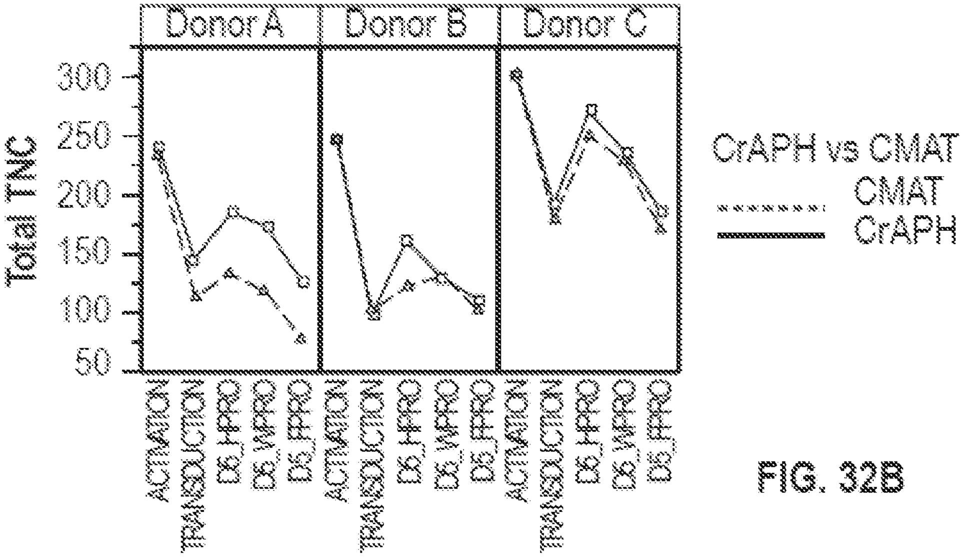
Figure 32C:
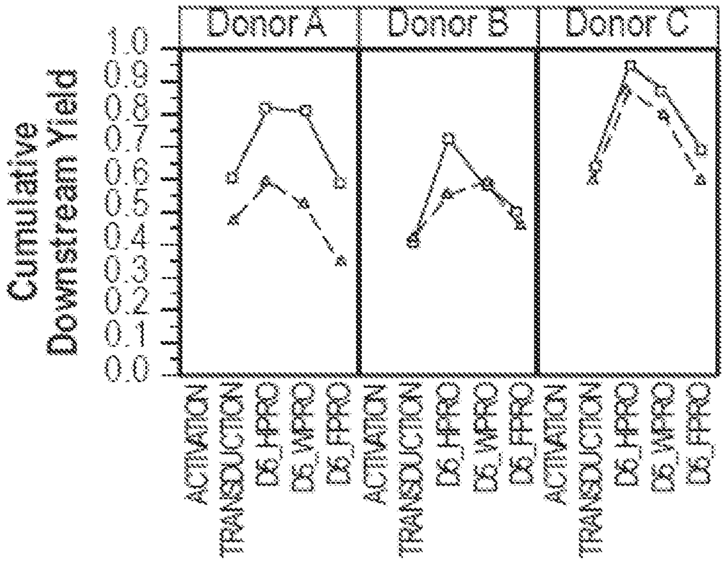

Results demonstrated that there was some initial decrease in viability of selected CD4+ T cells and CD8+ T cells from cryopreserved apheresis samples compared to cells selected from fresh apheresis. However, comparison of the cells after downstream process steps, such as after stimulation, transduction and at harvest, showed that the process using cryopreserved apheresis (CrAPH) resulted in similar or improved attributes compared to cells in the process using cryopreserved T cell selected material (CMAT). For example, cryopreservation of the leukapheresis sample prior to selection resulted in similar or better cell viability (FIG. 32A), similar or better numbers of total viable nucleated cells (FIG. 32B), and similar or better cumulative yield (FIG. 32C).

Figure 32D:
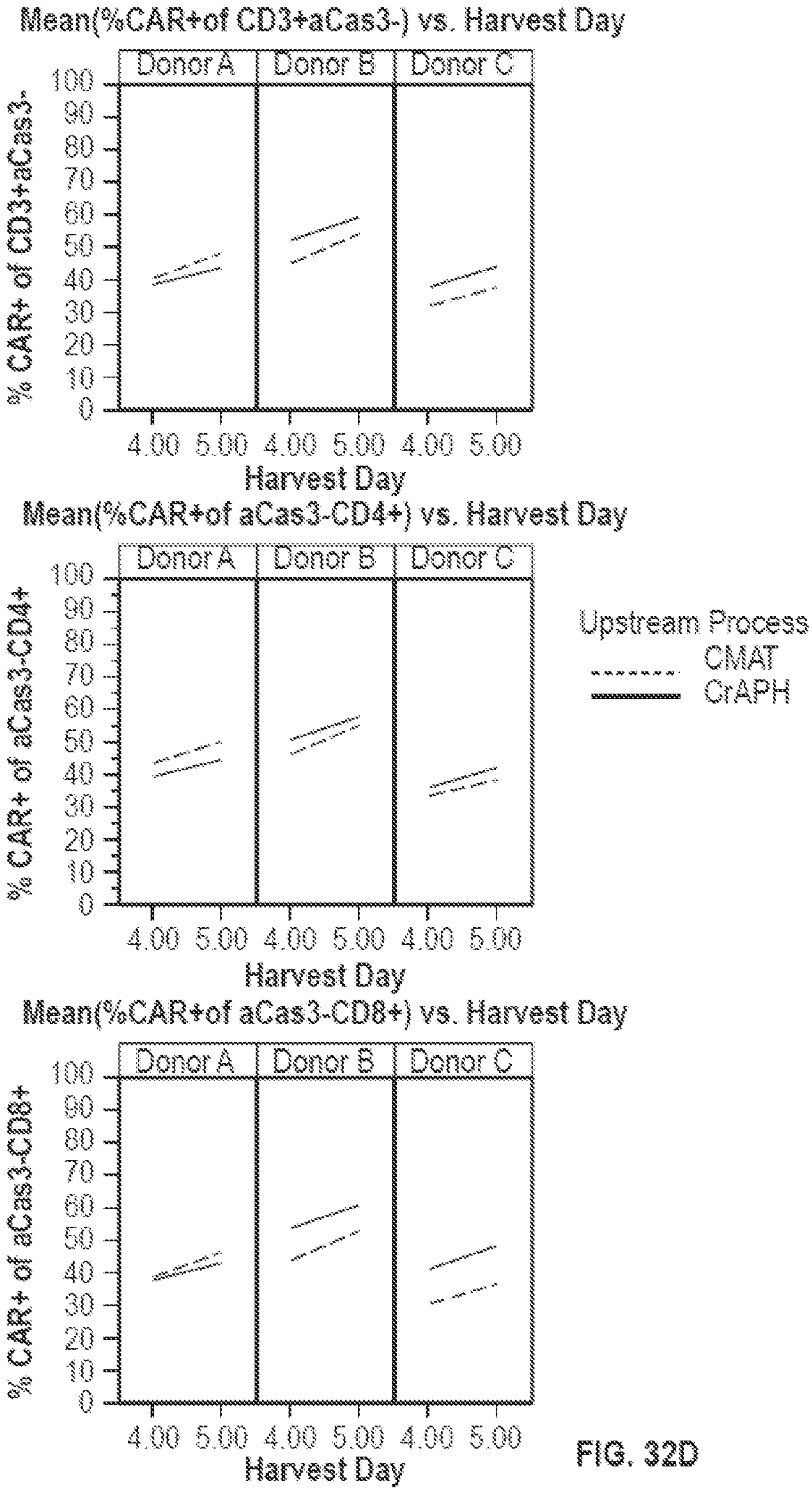
FIGS. 32D-32F show exemplary mean percentages of cell phenotypes at harvest (day 4 or day 5) from processed cryopreserved (CrAPH) or fresh apheresis (CMAT) samples from 3 donors.
Figure 32E:
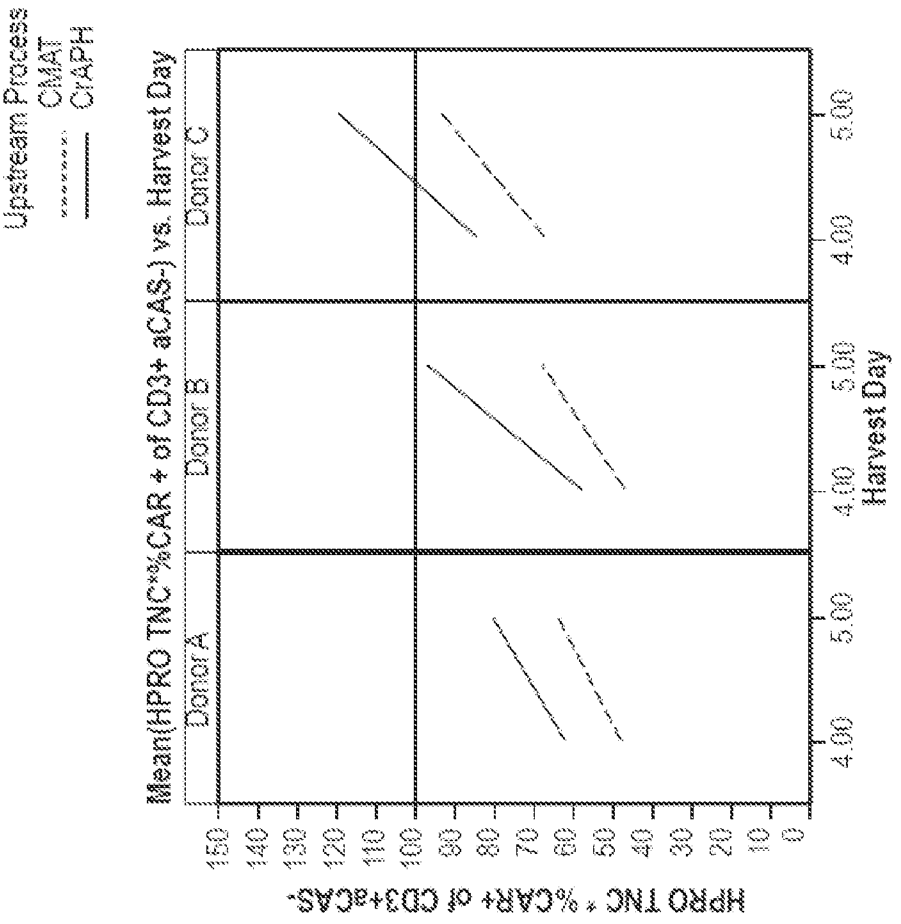
Figure 32F:
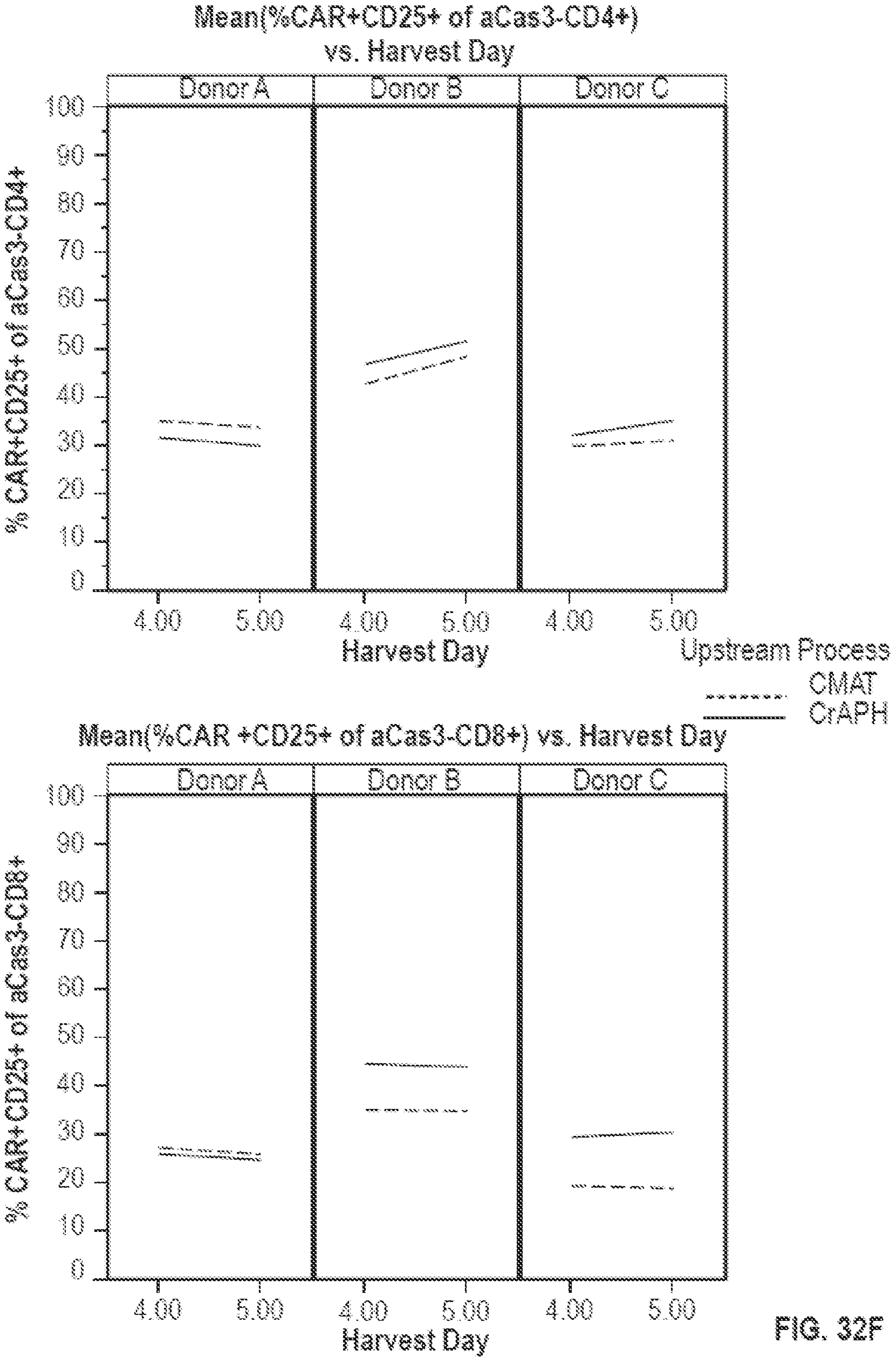

At harvest, comparison of cell phenotype showed that cell compositions manufactured using a cryopreserved apheresis sample prior to selection, compared to using cryopreserved T cell selected material, exhibited similar or higher percentages of CAR+ cells (FIG. 32D), higher percentages of Cas-CAR+ cells (FIG. 32E), and similar or higher percentages of CD25+ cells (FIG. 32F). The cell compositions from the two processes also exhibited a similar ability to produce cytokines and a similar differentiation phenotype with no increase in Tem and Temra between cells produced by the two processes (data not shown).

Example 23: Assessment of Effects of Stimulation Incubation Length on T Cell Phenotype Separate compositions of CD4+ and CD8+ T cells were selected from a leukapheresis sample and then were cyrofrozen. The selected cells were thawed and were subsequently mixed at a ratio of 1:1 of viable CD4+ T cells to viable CD8+ T cells to produce an input composition. The input compositions were stimulated by incubation with 0.2× (0.8 μg per $1\times10^6$ cells) anti-CD3/anti-CD28 Fab conjugated oligomeric streptavidin mutein reagents generated as described in Example 2 for various stimulation incubation times, including 0, 16, 24, and 48 hours, prior to transduction.

In one arm, the cells were transduced immediately followed by stimulation with the oligomeric stimulatory reagent (0 h), whereas the other arms included stimulation with the oligomeric stimulatory reagent for 16 hours, 24 hours or 48 hours prior to transduction. Transduction was carried out by spinoculation with a lentiviral vector encoding a CAR, in this case the exemplary anti-CD19 CAR described in Example 6. After the spinoculation, the cells were washed and resuspended in serum free media without recombinant cytokines (basal media) at a density of about $0.75\times10^6$ cells/mL, and incubated at about 37.0° C. in an incubator for approximately 72 hours. For example, for the 16 h and 24 h samples, the cells were incubated until about 96 hours±6 hours after initiation of the stimulation. About 48 hours after beginning the incubation, 1.0 mM D-biotin was added and mixed with the cells to dissociate anti-CD3 and anti-CD28 Fab reagents from oligomeric streptavidin reagent. Due the differences in time for the stimulation, the cells were harvested either at day 4 (0 h stimulation), day 5 (16 h or 24 h stimulation) or day 6 (48 h stimulation); the harvest time was staggered so that each arm had about the same 72 hour post-transduction incubation. Phenotypes of the engineered cells were assessed by flow cytometry for expression of the CAR using an anti-idiotype antibody, activated caspase 3 (aCas3) as a measure of cell health, and for various surface markers including CD45RA, CCR7, CD4 and CD8.

Figure 33:
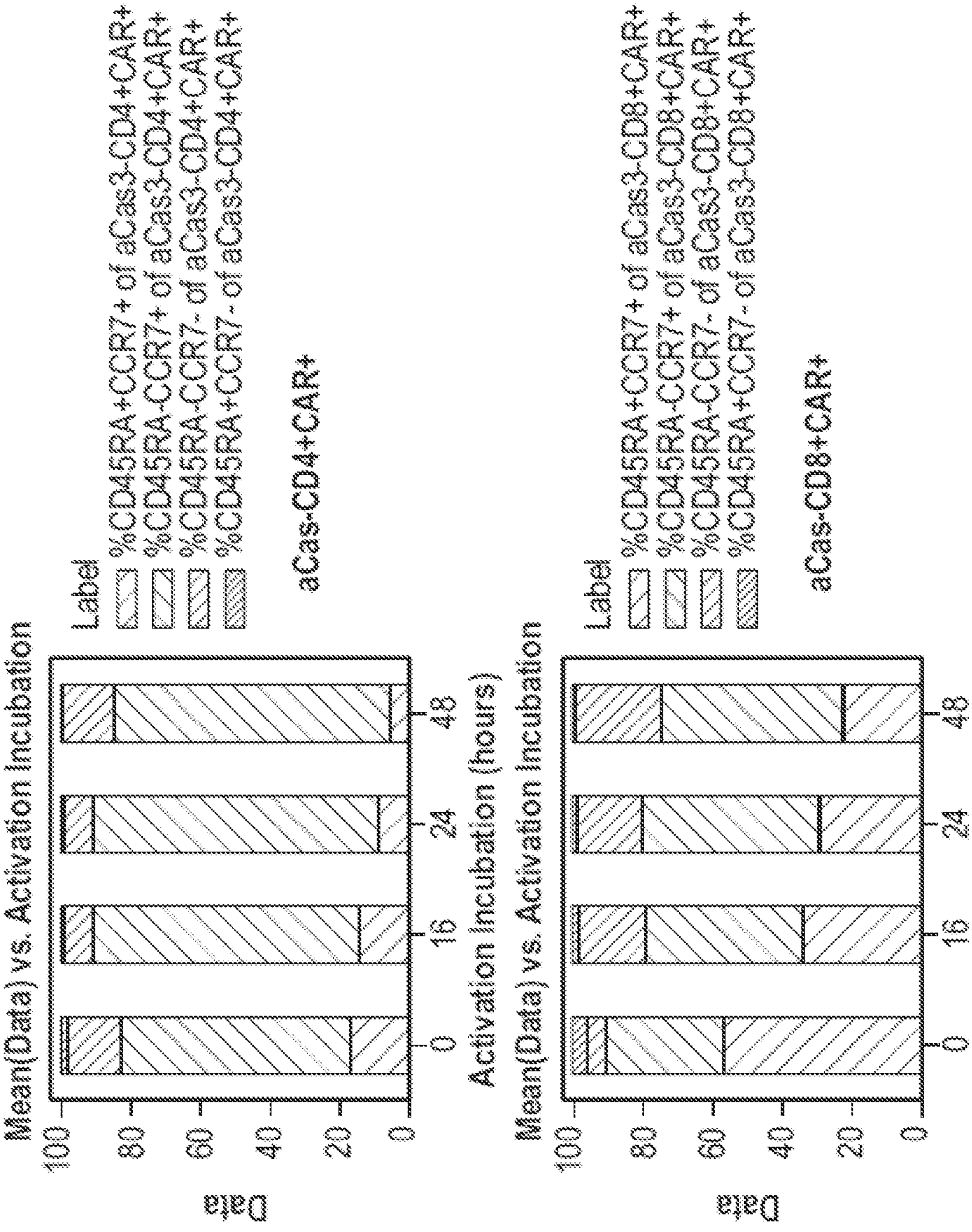
FIG. 33 shows exemplary memory phenotype profiles of aCas3−CD4+CAR+ cells (top panel) and aCas3−CD8+ CAR+ cells (bottom panel) generated with stimulation incubation times of 0, 16, 24, or 48 hours from the initiation of stimulation.

FIG. 33 shows the memory phenotype profiles of aCas3−CD4+CAR+ cells and aCas3−CD8+CAR+ cells generated with stimulation incubation time of 0, 16, 24, or 48 hours from the initiation of stimulation. Longer stimulation incubation led to decreased percentages of cells of the naive phenotype (CD45RA+CCR7+) in both CD4 and CD8 cells, with particular differences evident among Cas3-CD8+ CAR+ cells.

Example 24: Characteristics of T Cell Compositions Across Different Manufacturing Processes T cell compositions produced using different non-expanded processes that differed in various features, including the starting source of cells (cryopreserved apheresis or fresh apheresis), concentration of oligomeric stimulatory reagent, and number of cells used for stimulation, were compared. The two processes were compared to two different exemplary processes in which cells were cultivated for expansion. The processes were carried out on healthy donors or on patient donors.

A. Non-Expanded Process

Two different non-expanded processes, designated non-expanded Process A and non-expanded process B, were compared.

In non-expanded Process A, leukapheresis samples were collected from human donors and washed. CD4+ and CD8+ cells were selected directly by immunoaffinity-based selection from the leukapheresis samples which had not been cryofrozen. After selection, the separate CD4+ and CD8+ T cell compositions were cryofrozen and then were thawed, and then the selected CD4+ and CD8+ T cells were mixed at a ratio of 1:1 of viable CD4+ T cells to viable CD8+ T cells to produce an input composition. About $600\times10^6$ cells from the mixed input cell composition (about $300\times10^6$ CD4+ and $300\times10^6$ CD8+) were stimulated by incubation with 0.8 μg per $1\times10^6$ cells anti-CD3/anti-CD28 Fab conjugated oligomeric streptavidin mutein reagents generated as described in Example 2. The stimulation was carried out for between 18-30 hours (24±6 hours) in serum-free complete media containing basal media (e.g., CTS™ OpTmizer basal media, Thermo Fisher), a T cell supplement (e.g., 2.6% OpTmizer® T-cell Expansion Supplement, Thermo Fisher), an immune cell serum replacement (e.g., 2.5% CTS™ Immune Cell Serum Replacement), 2 mM L-glutamine, a dipeptide form of L-glutamine (e.g., 1.0% Glutamax™, Thermo Fisher), recombinant 100 IU/mL IL-2, recombinant 600 IU/mL IL-7, and recombinant 100 IU/mL IL-15. After stimulation, up to $300\times10^6$ cells were transduced by spinoculation with a lentiviral vector encoding a CAR, in this case either the exemplary anti-BCMA CAR described in Example 1 or the exemplary anti-CD19 CAR described in Example 6. After the spinoculation, the cells were washed and resuspended at a density of up to about $0.75\times10^6$ cells/mL in basal media (e.g., CTS™ OpTmizer basal media, Thermo Fisher) with 2 mM glutamine but without the addition of recombinant cytokines, and incubated at about 37.0° C. in an incubator. After about 48 hours±6 hours after initiation of the stimulation (about 24 hours after beginning the incubation), 1.0 mM D-biotin was added and mixed with the cells to dissociate anti-CD3 and anti-CD28 Fab reagents from oligomeric streptavidin reagent. The cells were further incubated for an additional about 48 hours (about 96 hours±6 hours after initiation of stimulation or until day 5 of the process), and then were formulated with a cryoprotectant.

In non-expanded Process B, leukapheresis samples were collected from human donors, washed and cryopreserved. The cryopreserved leukapheresis samples were thawed, and separate compositions of CD4+ and CD8+ cells were selected from each sample by immunoaffinity-based selection, and then the CD4+ and CD8+ T cells were mixed with the goal to produce an input composition of up to about $900\times10^6$ viable CD4+ and CD8+ T cells, and the ratio of viable CD4+ T cells to viable CD8+ T cells might vary. The mixed input cell composition were stimulated by incubation with 1.2 μg per $1\times10^6$ cells anti-CD3/anti-CD28 Fab conjugated oligomeric streptavidin mutein reagents generated as described in Example 2 (where 1.2 μg of the oligomeric stimulatory reagent includes 0.9 μg of oligomeric particles and 0.15 μg of anti-CD3 Fabs and 0.15 μg of anti-CD28 Fabs). The stimulation was carried out for between 16-24 hours (20±4 hours) in the same serum-fee complete media described for Process A. After stimulation, up to about $600\times10^6$ cells were transduced by spinoculation with a lentiviral vector encoding a CAR, in this case the same exemplary anti-BCMA CAR or exemplary anti-CD19 CAR described in Examples 1 and Example 6. In this study, the cells that were incubated with the higher concentration of the oligomeric streptavidin mutein reagents exhibited an improved transaction efficiency (data not shown). After the spinoculation, the cells were washed and resuspended at a density of $0.75\times10^6$ cells/mL in basal media ((e.g., CTS™ OpTmizer basal media, Thermo Fisher) with 2 mM glutamine and 2.6% T cell supplement (e.g. 2.6% OpTmizer® supplement, Thermofisher) without the addition of recombinant cytokines, and incubated at about 37.0° C. in an incubator. After about 48 hours±6 hours after initiation of the stimulation (about 24 hours after beginning the incubation), 1.0 mM D-biotin was added and mixed with the cells to dissociate anti-CD3 and anti-CD28 Fab reagents from oligomeric streptavidin reagent. The cells were further incubated for an additional about 48 hours (about 96 hours±6 hours after initiation of stimulation or until day 5 of the process), and then were formulated with a cryoprotectant.

B. Expanded Process

Two different expanded processes, designated expanded Process X and non-expanded process Y, were compared.

In Expanded Process X, engineered CD4+ T cells and engineered CD8+ T cells each expressing the same chimeric antigen receptor (CAR) (anti-CD19 or anti-BCMA) were produced by a process involving subjecting enriched CD4+ and enriched CD8+ cell populations, separately, to process steps, including separate selection, cryopreservation, stimulation, transduction, expansion, and harvesting steps. Leukapheresis samples were washed and used for isolation of CD4+ and CD8+ T cells by immunoaffinity-based selection, resulting in a composition enriched in CD4+ T cells and a composition enriched in CD8+ T cells. Cells of the enriched CD4+ and CD8+ compositions were activated with anti-CD3/anti-CD28 paramagnetic beads and then were separately subjected to lentiviral transduction with a vector encoding the exemplary anti-CD19 CAR described in Example 6. Paramagnetic beads were removed, and then transduced populations were separately incubated in the presence of recombinant IL-2 and IL-15 cytokines (and additionally recombinant IL-7 for the CD4+ T cell composition) and were cultivated in a rocking motion bioreactor for cell expansion until reaching a threshold of about 4-fold expansion, such as between 9 and 13 days from start of expansion. The cells were then separately harvested, formulated and cryofrozen.

In Expanded Process Y, separate compositions of CD4+ and CD8+ cells were selected from human leukapheresis samples and were cryofrozen. The selected cell compositions were subsequently thawed and mixed at a ratio of 1:1 of viable CD4+ T cells to viable CD8+ T cells. Approximately $300\times10^6$ T cells ($150\times10^6$ CD4 and $150\times10^6$ CD8+ T cells) of the mixed composition were stimulated in the presence of paramagnetic polystyrene-coated beads with attached anti-CD3 and anti-CD28 antibodies at a 1:1 bead to cell ratio in serum free media containing recombinant IL-2, IL-7 and IL-15 for between 18 to 30 hours. Following the incubation, approximately 100×106 viable cells from the stimulated cell composition were concentrated in the serum free media containing recombinant IL-2, IL-7 and IL-15 The cells were transduced, by spinoculation at approximately 1600 g for 60 minutes, with a lentiviral vector encoding an exemplary CAR, in this case an anti-BCMA CAR as described in Example 1. After spinoculation, the cells were resuspended in the serum free media containing recombinant IL-2, IL-7 and IL-15, and incubated for about 18 to 30 hours at about 37° C. The cells were then cultivated for expansion by transfer to a bioreactor (e.g. a rocking motion bioreactor) in about 500 mL of the exemplary serum free media containing twice the concentration of IL-2, IL-7 and IL-15 as used during the incubation and transduction steps. When a set viable cell density was achieved, perfusion was initiated, where media was replaced by semi-continuous perfusion with continual mixing. The cells were cultivated the next day in the bioreactor until a threshold cell density of about 3x16 cells/mL was achieved, which typically occurred in a process involving 6-7 days of expansion. The anti-CD3 and anti-CD28 antibody conjugated paramagnetic beads were removed from the cell composition by exposure to a magnetic field. The cells where then collected, formulated and cryoprotected.

C. Features of Engineered T Cell Compositions a) CD4/CD8 Frequencies and CD4/CD8 Ratio.

Figure 34A:
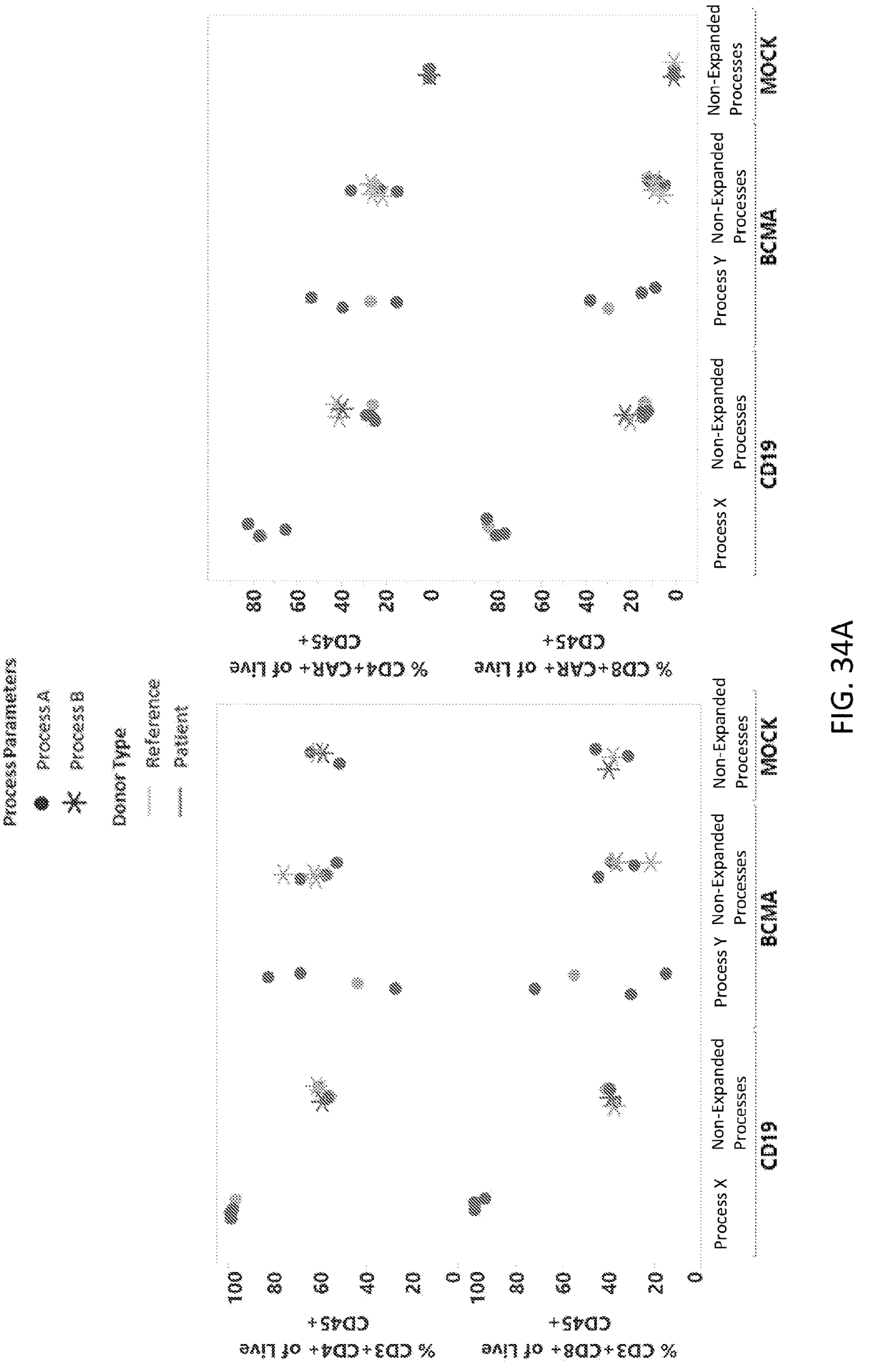
FIGS. 34A-34B show exemplary quantifications of cell phenotypes determined by flow cytometry for expanded and non-expanded engineering processes using different donor types (Reference, Patient). Cells were engineered to express exemplary anti-CD19 CARs (CD19), exemplary anti-BCMA CARs (BCMA), or were mock transduced (mock).
Figure 34B:
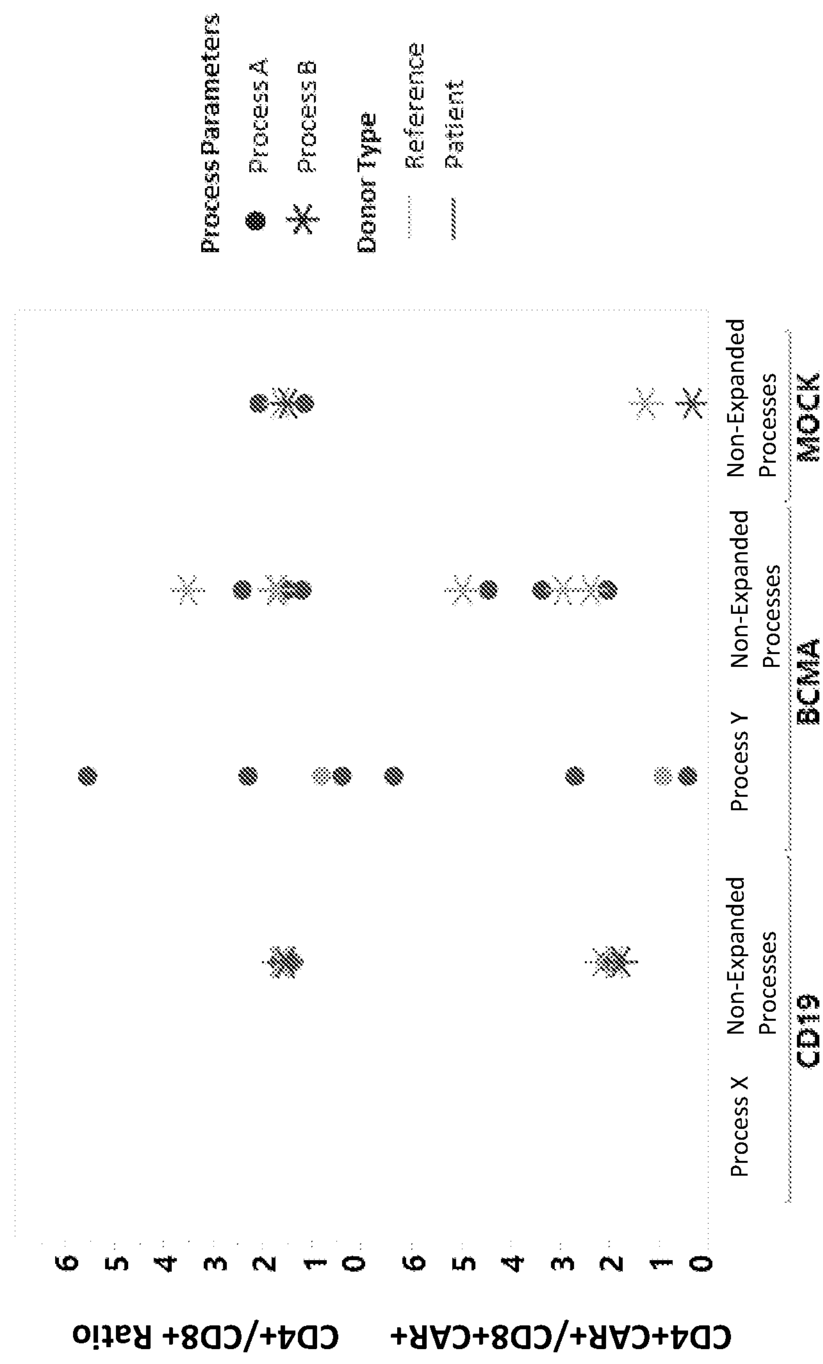

T cell compositions produced from expanded and non-expanded engineering processes were stained with antibodies recognizing surface markers including CD3, CD4, and CD8, and quantified by flow cytometry as shown in FIGS. 34A & B. Mock transduced T cell compositions were generated and used as controls. Cell compositions generated using either non-expanded process exhibited reduced variability among samples with regard to percentages of CD4+ and CD8+ T cells and CD4/CD8 T cell ratios, as compared to T cell compositions produced from the expanded process Y. Because the expanded process X produces separate CD4 and CD8 compositions, each of the CD4+ or CD8+ T cells are reported as being present at 100% in the respective generated compositions by that process.

b) Fold Expansion/Population Doubling.

For each generated therapeutic composition, the number of doublings of the generated cell compositions also was determined based on total nuclear count (TNC) of cells, by dual-fluorescence staining with acridine orange (AO) and either propridum iodide (PI) or DAPI, using the following formula:

$$\text{Cell doublings} = \frac{\ln\left(\frac{TNC \text{ at harvest}}{TNC \text{ 3 days post-activation}}\right)}{\ln 2} \quad 1)$$

Figure 35:
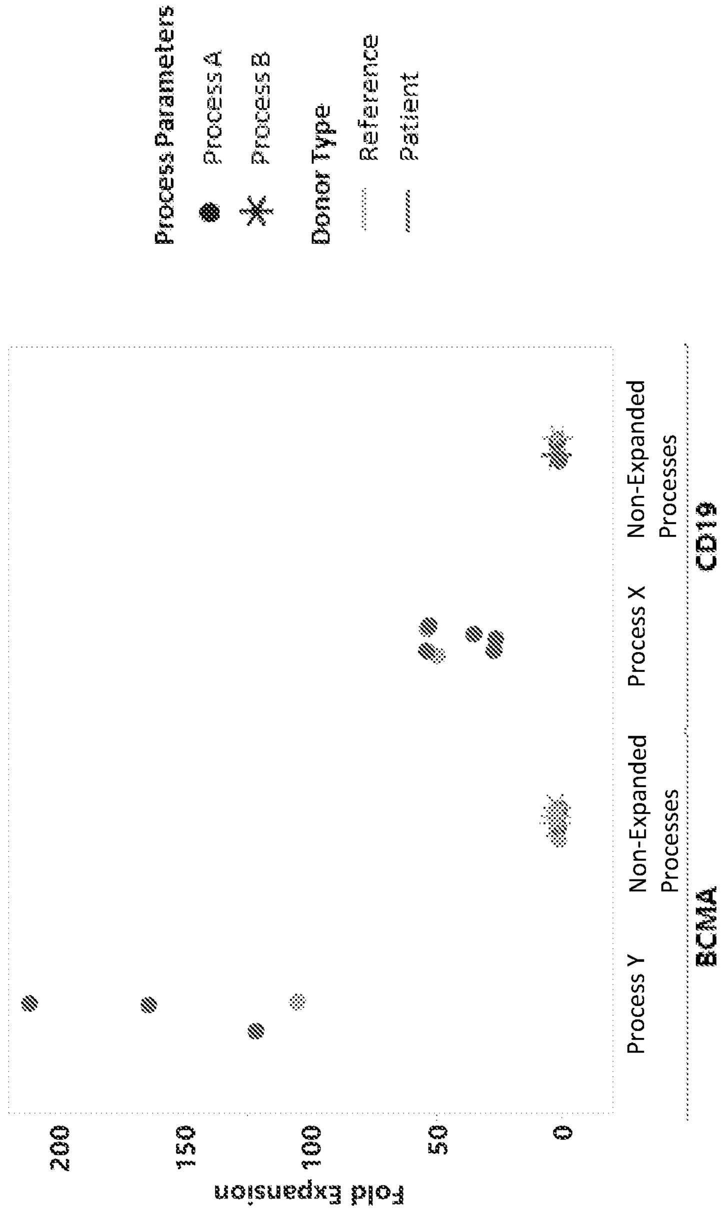
FIG. 35 shows fold expansion of cell compositions from different donor types (Reference, Patient) generated by expanded or non-expanded engineering processes. Cells were engineered to express exemplary anti-CD19 CARs (CD19) or exemplary anti-BCMA CARs (BCMA).

FIG. 35 shows that cell compositions generated using either non-expanded process exhibited not only reduced fold expansion.

c) Memory Profiles

Figure 36A:
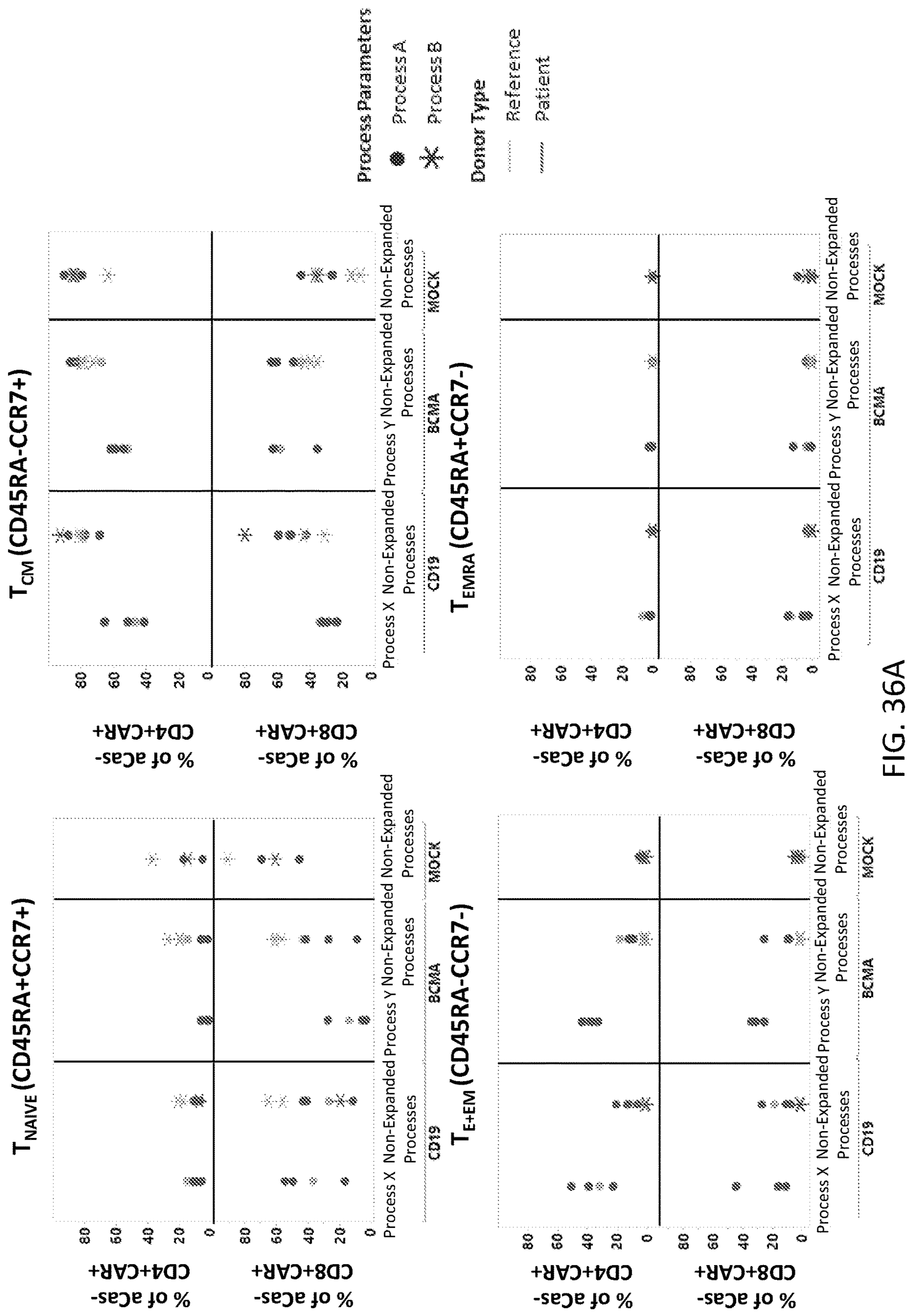
FIGS. 36A-36B show exemplary percentages of cell phenotypes resulting from expanded and non-expanded engineering processes using different donor types (Reference, Patient). Cells were engineered to express exemplary anti-CD19 CARs (CD19), exemplary anti-BCMA CARs (BCMA), or were mock transduced (mock).

T cell compositions produced from expanded and non-expanded engineering processes were stained for activated caspase 3 (aCas3) and with antibodies recognizing surface markers including CD4, CD8, CCR7, CD27 and CD45RA. The percentage of T cells that were indicative of naïve/naïve-like T cells (CD45RA+CCR7+), central memory (CD45RA−CCR7+), effector memory (CD45RA−CCR7−; $T_{E+EM}$) and effector memory CD45RA+ cells (CCR7−CD45RA+; $T_{EMRA}$) was determined. As shown in FIG. 36A, compared to the expanded processes, the non-expanded processes consistently enriched in central memory/naïve-like T cells and minimized the percentage of $T_{E+EM}$ and $T_{EMRA}$ in the final product.

Figure 36B:
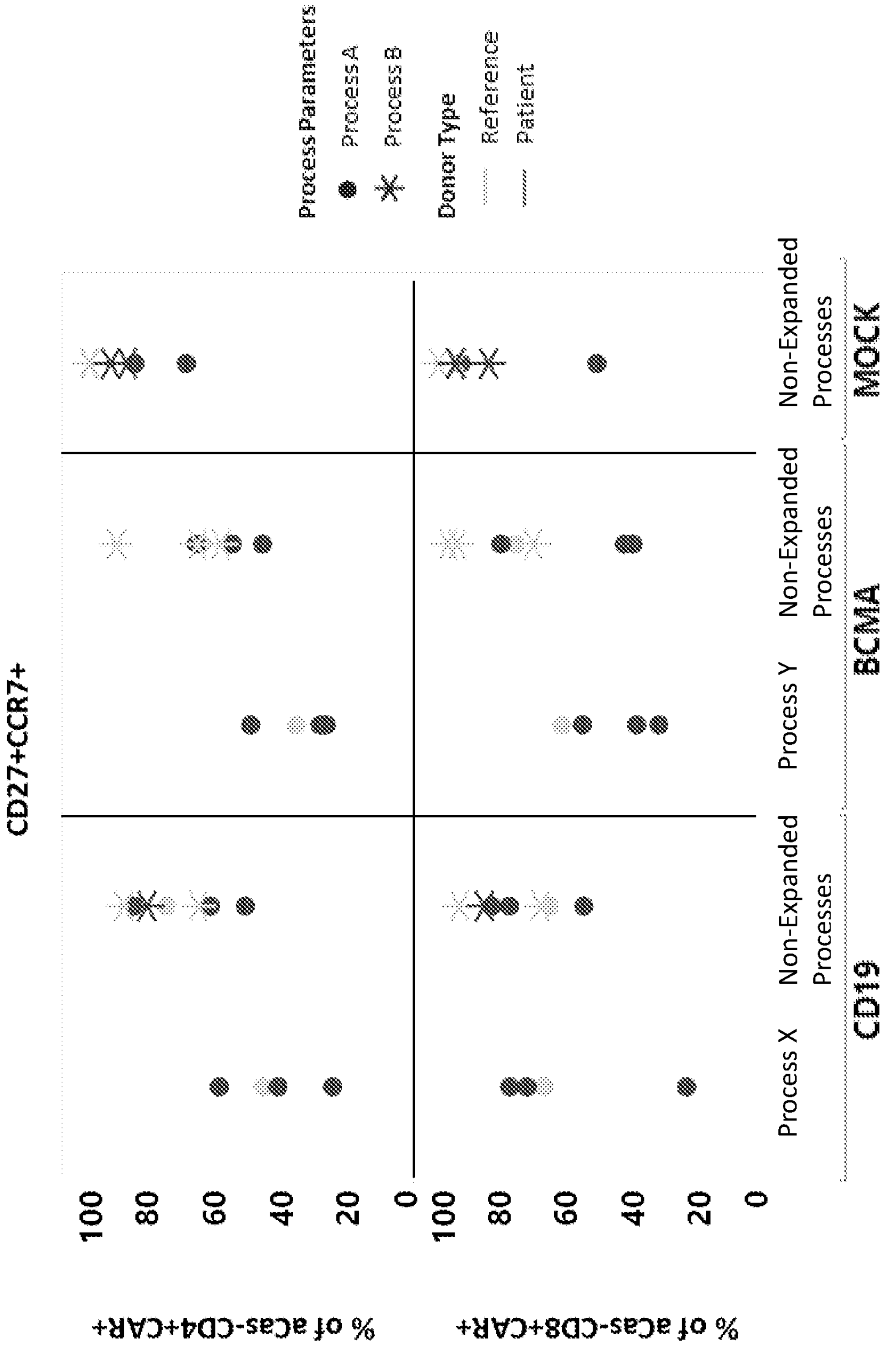

The percentage of CD4+CAR+ and CD8+CAR+ T cells among aCas-T cells positive for both CCR7 and CD27 staining are shown in FIG. 36B. As shown, the non-expanded processes were consistently enriched for CCR7+CD27+ cells compared to the expanded processes.

These results further support the consistent generation of engineered cell compositions generated from the non-expanded processes that have a greater portion of cells with a naïve-like, less differentiated phenotype than cell compositions generated from expanded processes.

Example 25: Comparison of Non-Expanded and Expanded Processes from Matched Donor Material Engineered T cell compositions of primary T cells containing T cells expressing a chimeric antigen receptor (CAR) were produced from eight matched donors using a non-expanded and expanded process for manufacturing the T cells ex vivo, and attributes of the cell compositions were compared.

A. Engineered Cell Compositions

Leukapheresis samples from 1 healthy donor and three patients with Non-Hodgkin Lymphoma (NHL) (two patients with diffuse large B-cell lymphoma, DLBCL; and one patient with mantel cell lymphoma, MCL) were collected and manufacturing runs were carried out to engineer T cells with an anti-CD19 CAR using the non-expanded Process A as described in Example 24. The engineered T cell compositions were compared to T cell compositions produced from donor-matched process runs using an expanded process substantially as described in Process X as set forth in Example 24. The anti-CD19 CAR contained an anti-CD19 scFv derived from a murine antibody (variable region derived from FMC63, $V_L$-linker-$V_H$ orientation), an immunoglobulin-derived spacer, a transmembrane domain derived from CD28, a costimulatory region derived from 4-1BB, and a CD3-zeta intracellular signaling domain. The viral vector further contained sequences encoding a truncated receptor, which served as a surrogate marker for CAR expression; separated from the CAR sequence by a T2A ribosome skip sequence.

Leukapheresis samples from 1 healthy donor and three patients (with multiple myeloma) were collected and manufacturing runs were carried out to engineer T cells with an anti-BCMA CAR using the non-expanded Process B as described in Example 24. The engineered T cell compositions were compared to T cell compositions produced from donor-matched process runs using an expanded process substantially as described in Process Y as set forth in Example 24. The anti-BCMA CAR contained an scFv antigen-binding domain specific for BCMA, a CD28 transmembrane region, a 4-1BB costimulatory signaling region, and a CD3-zeta derived intracellular signaling domain. The viral vector further contained sequences encoding a truncated receptor, which served as a surrogate marker for CAR expression; separated from the CAR sequence by a T2A ribosome skip sequence.

Figure 37A:
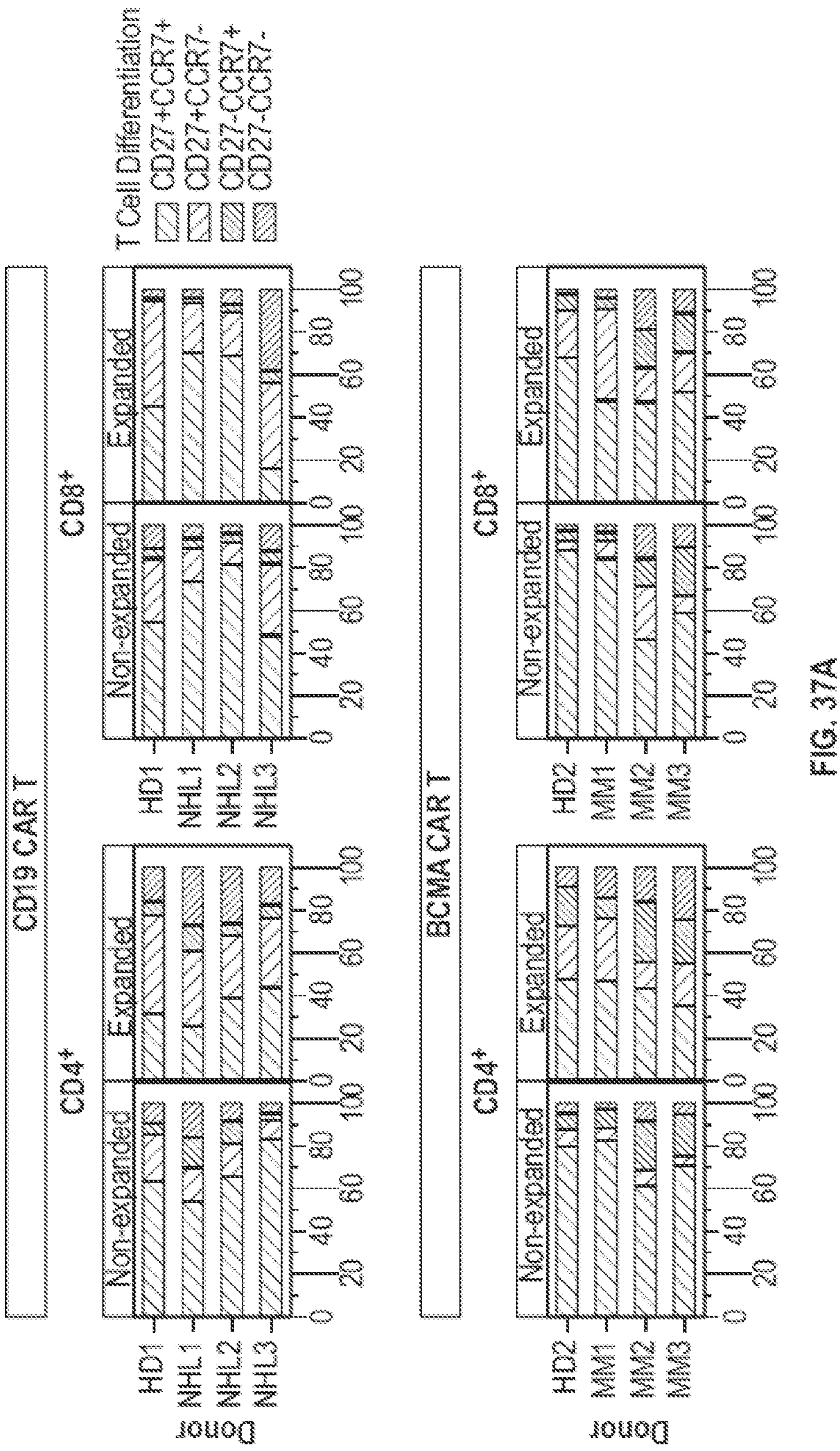
FIGS. 37A-37B show exemplary quantifications of cell phenotypes as indicated determined by flow cytometry for donor-matched expanded and non-expanded engineering processes where cells were engineered to express exemplary anti-CD19 CARs (CD19 CAR T) or exemplary anti-BCMA CARs (BCMA CAR T).

The generated cell compositions were stained with antibodies recognizing surface markers including CD4, CD8, CCR7, CD27, and CD45RA and quantified by flow cytometry. The results in FIG. 37A show a significantly higher percentage of CD27+CCR7+ cells were observed in both CD4+ arm ($p<0.01$) and CD8+ arm ($p<0.05$) in the T cell compositions produced from each non-expanded engineering process as compared to the donor-matched expanded engineering process. In addition, a significantly lower percentage of CD27+CCR7-cells were observed in both CD4+ arm ($p<0.01$) and CD8+ arm ($p<0.05$) in the T cell compositions produced from each non-expanded engineering process as compared to the donor-matched expanded engineering process. A significantly lower percentage of CD27-CCR7-cells were also observed CD4+ arm ($p<0.01$) in the T cell compositions produced from each non-expanded engineering process as compared to the donor-matched expanded engineering process.

Figure 37B:
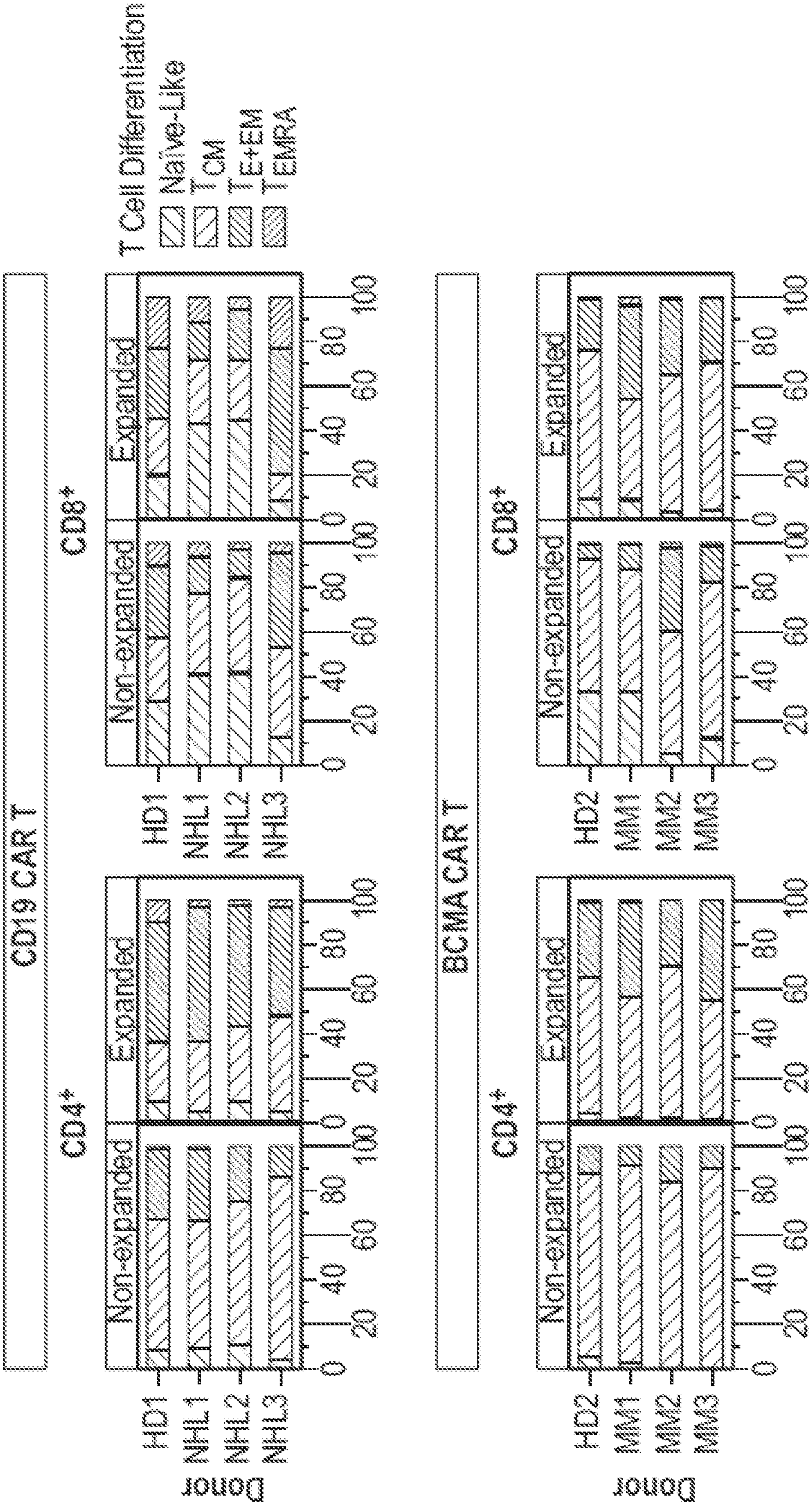

The results in FIG. 37B show the T cell compositions produced from each non-expanded engineering process are enriched in CCR7+ cells (CCR7+CD45RA− cells and CCR7+CD45RA+ cells), with fewer CCR7− cells (CCR7−CD45RA− cells and CCR7−CD45RA+ cells) in both the CD4 and CD8 arms.

B. Activity Following Long-Term CAR-Dependent Stimulation

The activity of cells from the engineered T cell compositions generated from matched donors by the different processes were assessed in a long-term stimulation assay involving continuous incubation for 9 to 14 days in the presence of paramagnetic beads conjugated with an agonistic anti-idiotypic antibody against the CAR to provide a CAR-dependent stimulus, which mimics the fitness and ability of cells to survive upon long-term exposure to antigen as may occur in vivo up administration.

1. Proliferative Capacity

Figure 38:
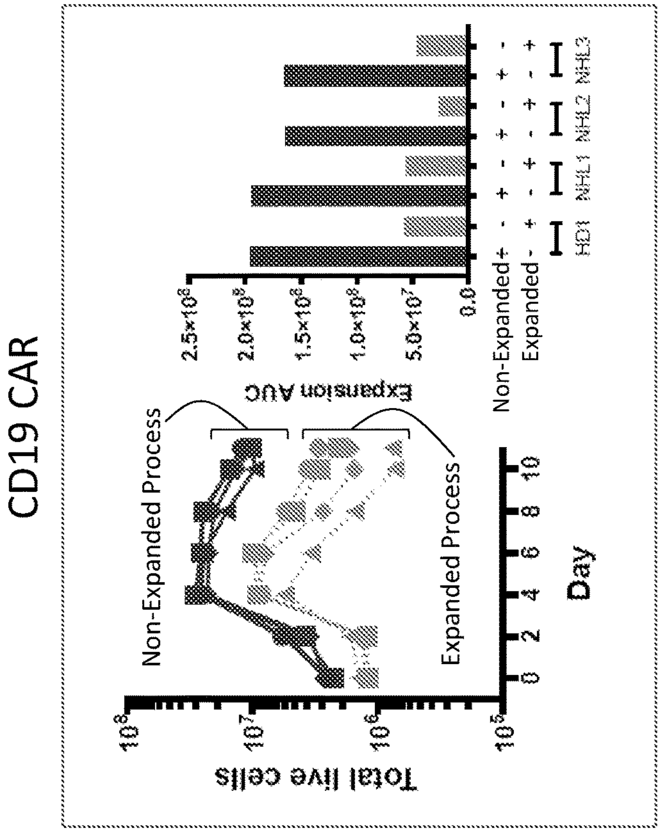
FIGS. 38-39 show numbers of total live cells over time and area under the curve (AUC) for cells generated from either non-expanded or expended processes following long-term CAR-dependent stimulation with an anti-ID antibody.
Figure 39:
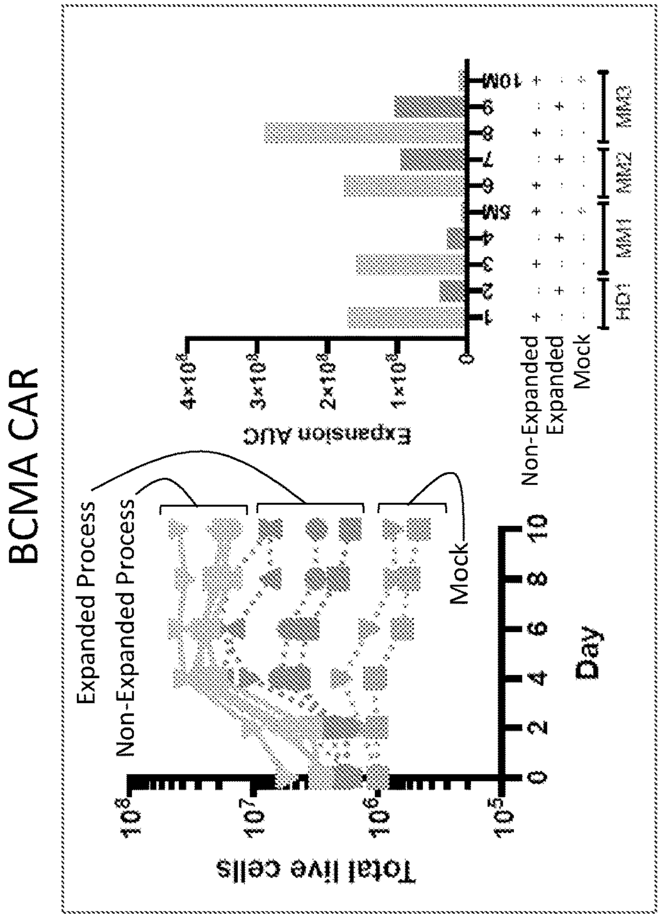

Proliferative capacity was assessed following long-term CAR-dependent stimulation with an anti-ID antibody specific for the CAR for 10 days as described above. After the long-term stimulation, the numbers of total live cells was measured, to assess the potency and expansion potential of cells generated from non-expanded processes compared to cells generated from matched donors in an expanded process. As shown in FIG. 38 and FIG. 39, cells from the anti-CD19 or anti-BCMA non-expanded cell products, respectively, exhibited substantially enhanced proliferative capacity compared to engineered cells in a donor-matched expanded cell product. These results are consistent with the observation that non-expanded cell products contains a higher relative proportion of less-differentiated T cells, including cells that maintain characteristics similar to central memory and stem cell memory T cells, and thus may have the ability to undergo additional rounds of division in response to signaling through their CAR.

2. Cytolytic Activity

For assessment of cytolytic potential, anti-CD19 CAR T cells engineered as described above in a non-expanded or expanded process were stimulated for 10-14 days with an anti-ID antibody specific for the CAR and expansion data were summarized based on the proliferation observed through day 10. K562 cells transduced to express CD19 (K562-CD19) were labeled with NucLight Red (NLR) to permit their tracking by microscopy. Engineered CAR-T cell compositions from the non-expanded or expanded process before or after the long term stimulation were co-cultured with K562-CD19 at an effector to target cell (E:T) ratio of 1:1 and 0.5:1. Cytolytic activity was assessed by measuring the loss of viable target cells over a period of 96 hours as determined by red fluorescent signal (using the IncuCyte® Live Cell Analysis System, Essen Bioscience). Data were transformed into an area under the curve (AUC) for comparison either for individual donors/process or by manufacturing process.

Figure 40A:
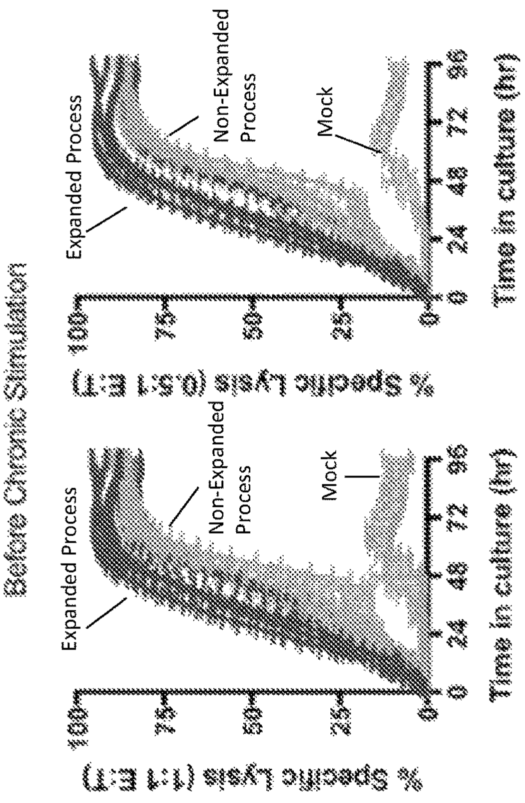
FIGS. 40A-40B show the cytolytic potential of anti-CD19 CAR T cells engineered by non-expanded or expanded processes before (FIG. 40A) and after chronic stimulation (FIG. 40B) at different effector to target ratios.
Figure 40B:
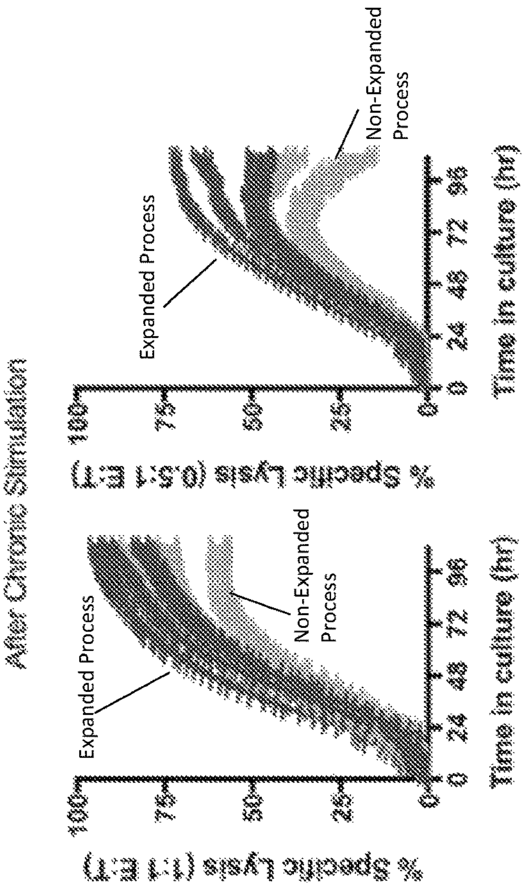

As shown in FIG. 40A, engineered CAR-T cell compositions generated using a non-expanded process exhibited similar cytolytic activity as compared to T cell compositions generated using an expanded process, indicating that after manufacturing all cells appeared highly potent in their ability to kill target cells. However, after long-term stimulation, CAR-T cells generated using the non-expanded process exhibited the ability to retain functional cytolytic activity better than matched-donor cells generated using the expanded process at low effector to target ratios (FIG. 40B).

3. Cytokine Production

For assessment of cytokine production, anti-CD19 CAR T cells engineered as described above in a non-expanded or expanded process were stimulated for 9 to 14 days with an anti-ID antibody specific for the CAR. Engineered CAR-T cell compositions from the non-expanded or expanded process before or after the long term stimulation were incubated on plate-bound anti-ID for 5 hours. Intracellular IL-2, IFNγ or TNF cytokine production was measured by flow cytometry. Frequency of CAR+ cells expressing a single cytokine was determined within the CD4+CAR+ or CD8+CAR+ populations. A polyfunctional score based on simultaneous production of the three cytokines in CD4+CAR+ and CD8+ CAR+ cells also was determined by Boolean logic gating of triple-positive cells. Statistical significance was assessed by Mann-Whitney, * $p<0.05$.

Figure 41:
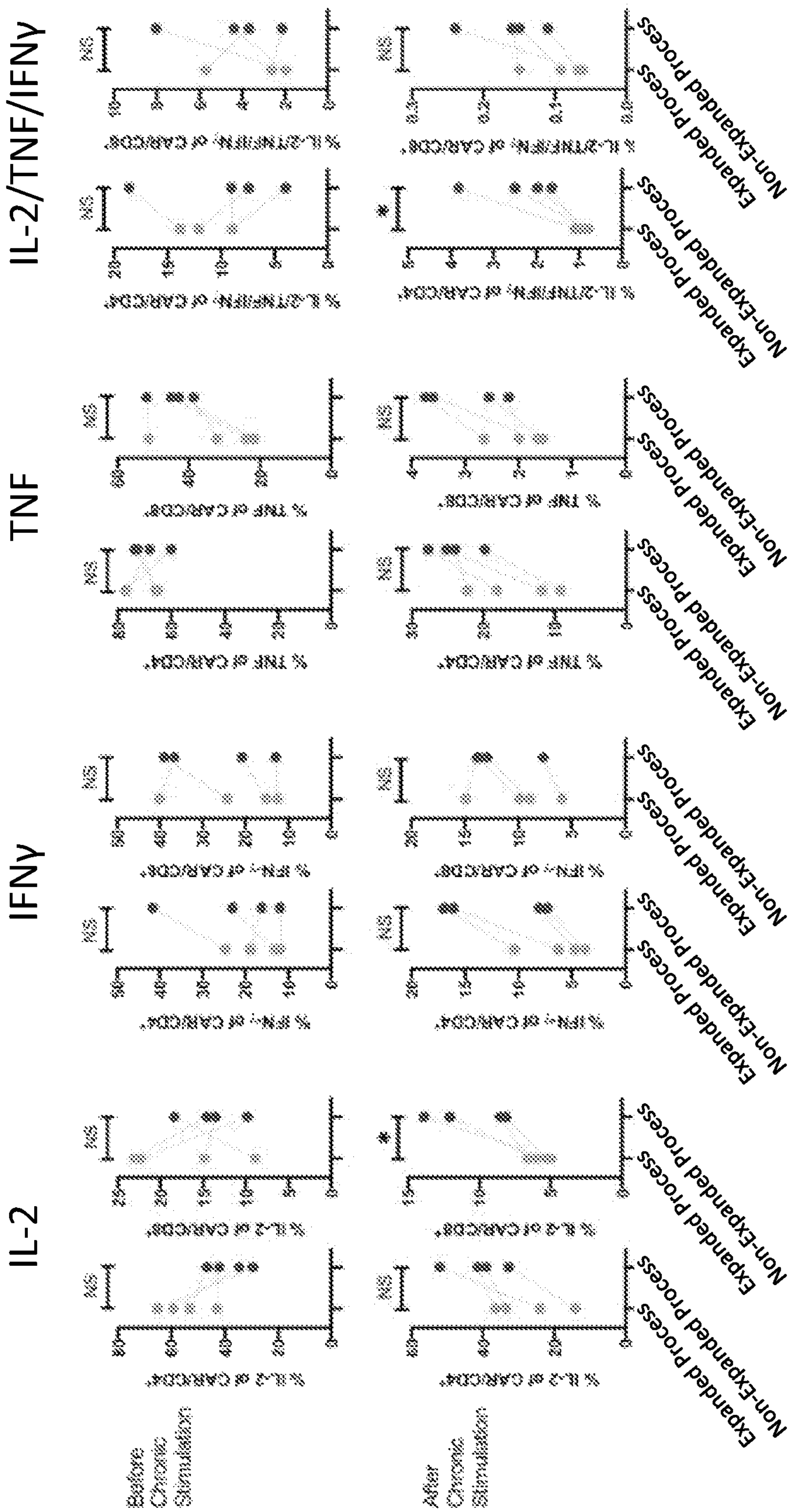
FIG. 41 shows exemplary percentages of CAR+CD4+ and CAR+CD8+ cells engineered by non-expanded or expanded processes expressing IL-2, IFNγ, TNF, and IL-2/IFNγ/TNF, measured by flow cytometry, before and after chronic stimulation.

Before long-term stimulation, cytokine production of anti-CD19 CAR-T cells produced from both the non-expanded and expanded processes was robust and did not significantly differ between the two processes. Both generated cell compositions exhibited the ability to generate a polyfunctional drug product as shown by secretion of IL-2, IFNγ and TNF (FIG. 41. After the long-term stimulation, secretion of these cytokines, particularly polyfunctional secretion, was generally greater in CAR-T cells generated using the non-expanded process compared to the expanded process (FIG. 41B).

C. In Vivo Activity

1. BCMA+OPM-2 Myeloma Model

Anti-BCMA CAR-T cell compositions generated from non-expanded and expanded matched-donor engineering processes were evaluated in the OPM-2 mouse xenograft Myeloma tumor model. Immunocompromised NOD-Scid-IL-2 Gamma receptor deficient (NSG) mice were engrafted with $2\times10^6$ OPM2 cells engineered to express Firefly luciferase to facilitate detection by bioluminescence imaging. About 12 days after tumor engraftment when mice had a moderate tumor burden, mice were randomized into groups to balance tumor burden. Approximately $1\times10^6$ CAR-T cells per mouse (n=8 mice per group) were intravenously administered to mice. Tumor growth was assessed by imaging FfLuc-positive bioluminescence (BLI).

Figure 42A:
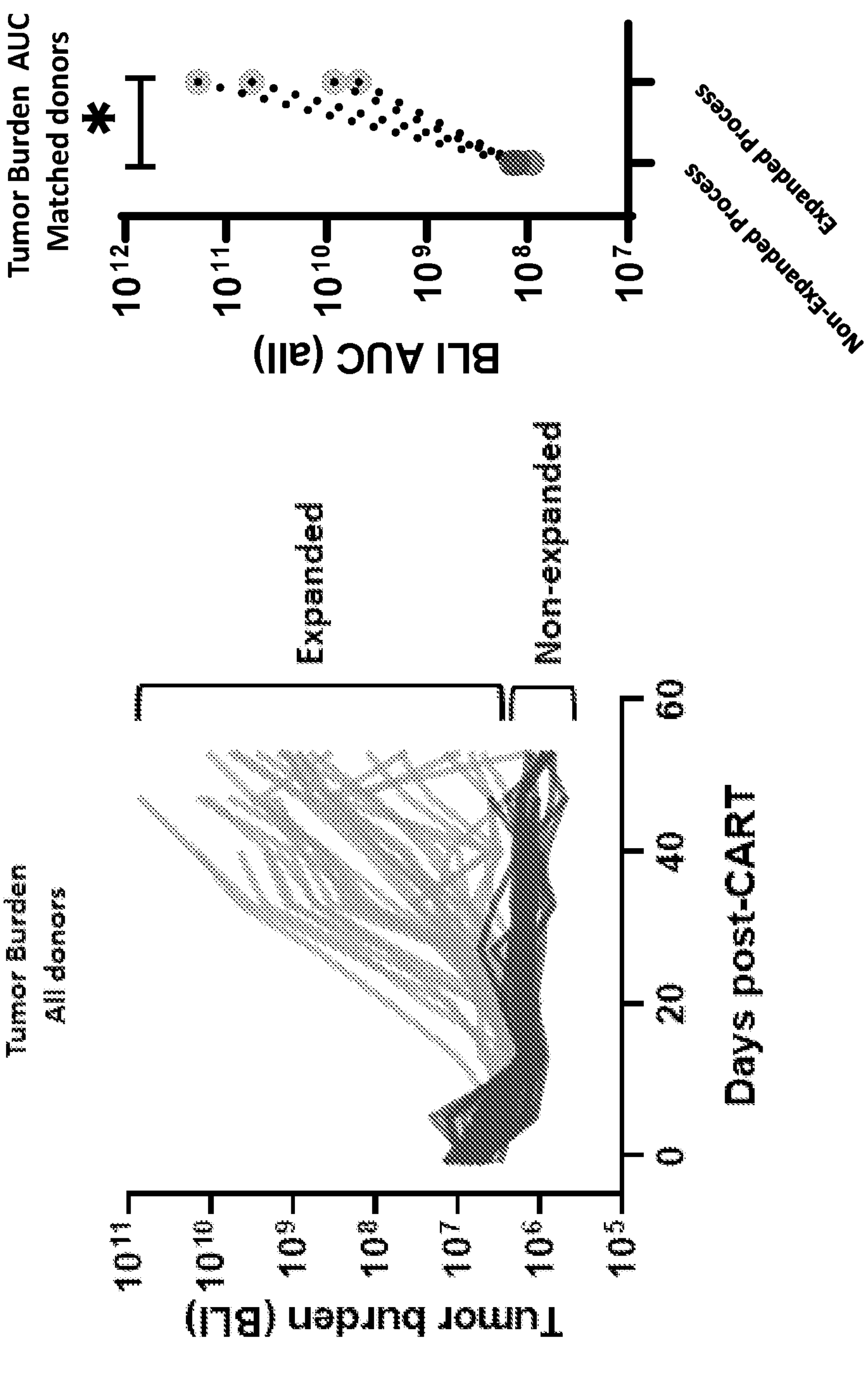
FIG. 42A (left panel) shows tumor burden over time following treatment with anti-BCMA CAR-T cell compositions generated from non-expanded and expanded matched-donor engineering processes.

FIG. 42A (left panel) shows changes in bioluminescence radiance (phtotons/second [p/s]; y-axis) for all groups (tumor burden) and FIG. 42A (right panel) shows tumor growth from Day-1 (before treatment) to Day 50 post-treatment calculated from area under the curve (AUC) of BLI for each group. As shown, CAR-T cells generated from the non-expanded process demonstrated superior anti-tumor activity at equivalent dose compared to matched-donor CAR-T cells generated by the expanded process.

Figure 42B:
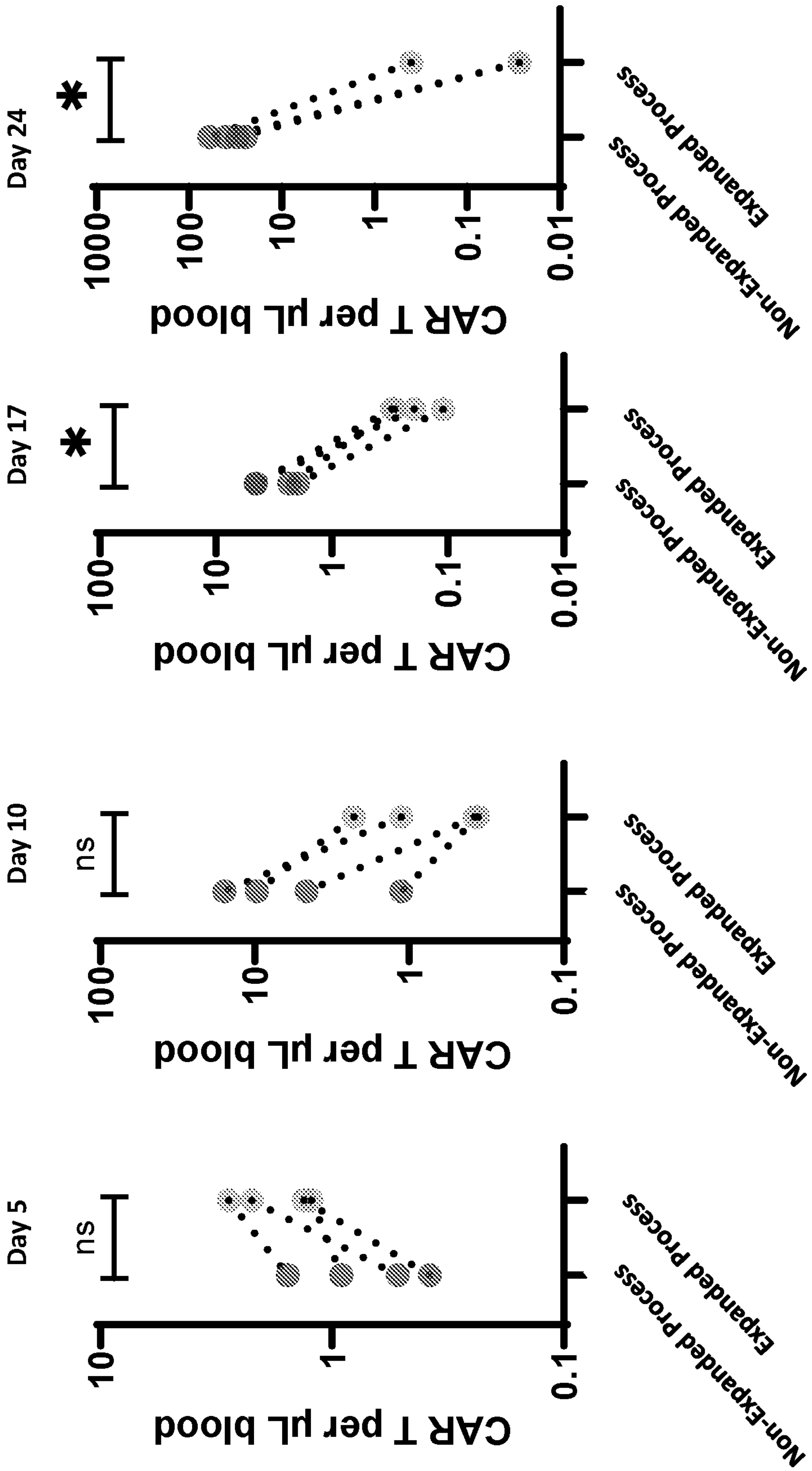
FIG. 42B shows absolute counts of anti-BCMA CAR-T cells per μL of blood over days for cells generated from non-expanded and expanded matched-donor engineering processes.

Circulating CAR-T cells in the blood were monitored at various days post-treatment. As shown in FIG. 42B, absolute counts of CAR-T cells per μL in the blood were higher for CAR-T cells that had been produced by the expanded process compared to the non-expanded process at Day 5 post-treatment. However, beyond Day 5, mice treated with CAR-T cells from the non-expanded process showed greater expansion of CAR-T cells compared to mice treated with CAR-T cells from the expanded process. Following an initial lag, CAR-T cell expansion of cells generated from the non-expanded process exhibited superior proliferative capacity with about 5-10 fold greater expansion than cells generated using the expanded process.

2. CD19+ Nalm6 Leukemia Model

Anti-CD19 CAR-T cell compositions generated from non-expanded and expanded matched-donor engineering processes were evaluated in the Nalm-6 acute lymphocytic leukemia (ALL) tumor model. NOD.Cg-Prkdc$^{scid}$IL-2rg$^{tm1\,Wjl}$/SzJ mice were injected intravenously with $5.0\times10^5$ Nalm-6 firefly luciferase-green fluorescent protein (FfLuc-GFP) lymphocytic leukemia cells, and 3 days later, mice were randomized into groups to balance tumor burden. This model is a slow-growing tumor model with mice reaching end-stage disease by approximately Day 24 to Day 26 in mice that were not administered CAR-T cells. At day 4 after engraftment, approximately $1\times10^6$ or $2.5\times10^5$ CAR-T cells per mouse (n=8 mice per group) were intravenously administered to mice. Disseminated tumor growth was assessed by imaging Nalm-6 FfLuc-positive bioluminescence (BLI).

Figures 43A, 43B:
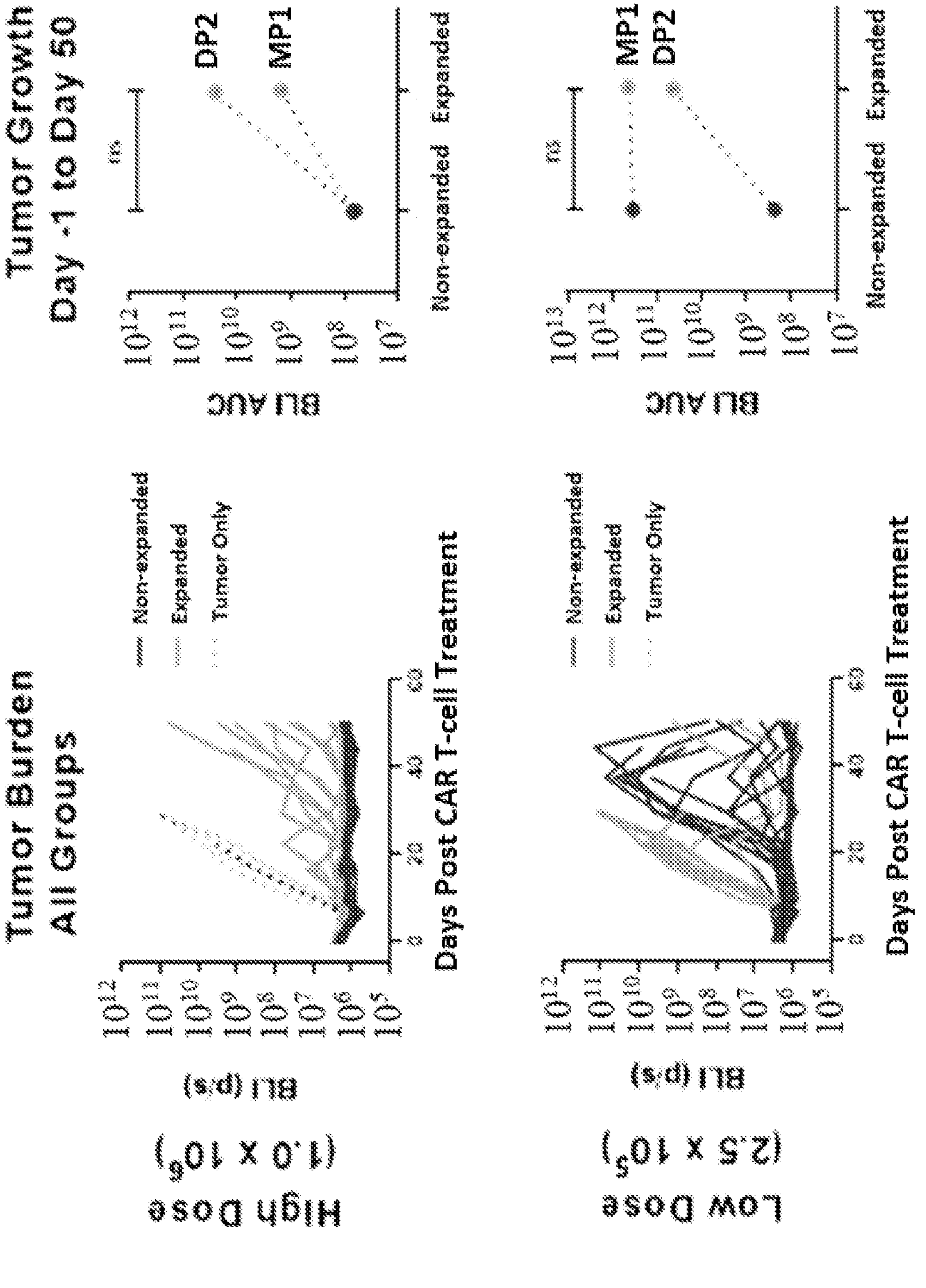
FIG. 43A shows tumor burden over days following treatment with higher (top panel) and lower (bottom panel) doses of anti-CD19 CAR-T cell compositions generated from non-expanded and expanded matched-donor engineering processes.
FIG. 43B shows tumor growth from Day-1 (before treatment) to Day 50 post-treatment calculated from area under the curve (AUC) of BLI for each group treated with the higher (top panel) and lower dose (bottom panel) doses of anti-CD19 CAR-T cell.

FIG. 43A shows changes in bioluminescence radiance (photons/second [p/s]; y-axis) for all groups treated with the higher $1.0\times10^6$ (top panel) and lower $2.5\times10^5$ dose (bottom panel). FIG. 43B (right panel) shows tumor growth from Day-1 (before treatment) to Day 50 post-treatment calculated from area under the curve (AUC) of BLI for each group treated with the higher $1.0\times10^6$ (top panel) and lower $2.5\times10^5$ dose (bottom panel). As shown, complete tumor regression occurred without delay up to Day 50 in mice treated with CAR-T cells generated from the non-expanded process, whereas mice treated with CAR-T cells generated using the expanded process showed initial regression of tumor growth that was not maintained in many of the animals.

Figure 43C:
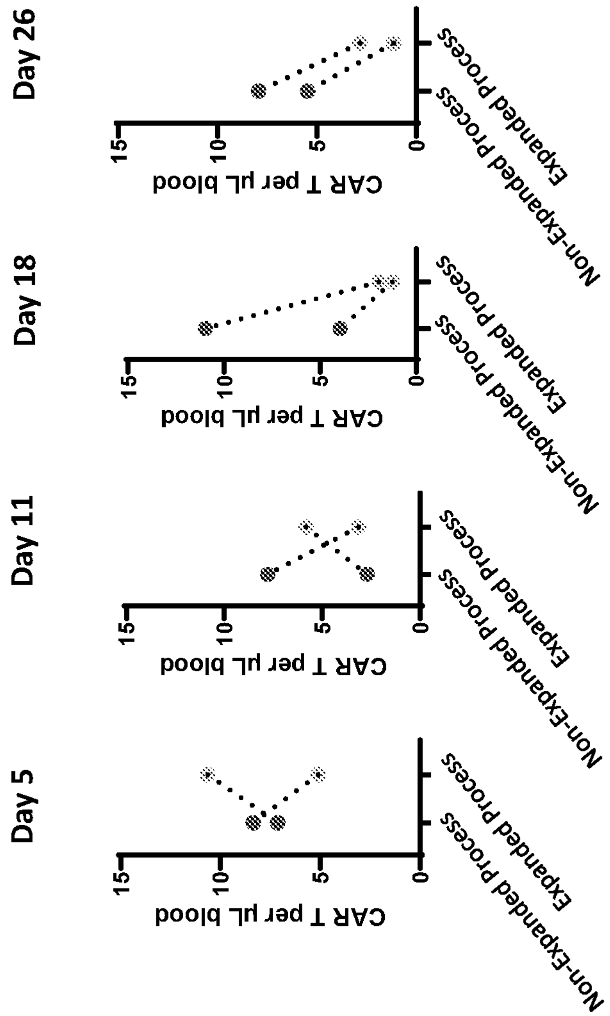
FIG. 43C shows absolute counts of anti-CD19 CAR-T cells per μL of blood over days for cells generated from non-expanded and expanded matched-donor engineering processes.

Circulating CAR-T cells in the blood were monitored at various days post-treatment. As shown in FIG. 43C, very low expansion of CAR-T cells, as determined by absolute counts of CAR-T cells per μL in the blood, was observed consistent with the lower tumor burden in this model. Improved proliferative capacity of CAR-T cells was observed in mice treated with CAR-T cells from the non-expanded process compared to the expanded process after Day 11.

D. Conclusion

Together, the results support that CAR-T cells produced by the non-expanded process have a less-differentiated phenotype enriched for naïve-like and central memory T cells compared to CAR-T cells produced by an expanded process. The CAR-T cells produced from the non-expanded process exhibit the ability to retain substantial functional activity following long-term or repeat stimulation with antigen. Further, while exhibiting a slower rate of initial expansion in vivo, the results are consistent with a finding that CAR-T cells produced from the non-expanded process exhibit long-term persistence and are able to mediate long-term anti-tumor activity.

Example 26; Kinetics of Non-Expanded and Expanded Engineering Processes

A composite analysis of cells during and after manufacturing runs by a variety of non-expanded or expanded processes carried out substantially as described in the above examples was undertaken. The manufacturing runs included at-scale runs similar to those described in Example 24. The manufacturing runs also included scale-down models (SDMs) in which a lower number of cells were used in the process for engineering cells. In general, the scale-down manufacturing runs shared the process activities described in Table E11.

| Day of Process | Summary of Activity |
|---|---|
| Day 1 | Cells are stimulated with stimulatory reagent (e.g. anti-CD3/anti-CD28 paramagnetic beads or anti-CD3/anti-CD28 Fab conjugated oligomeric streptavidin mutein reagents) |
| Day 2 | Cells are transduced by spinoculation with lentivirus encoding a CAR (e.g. anti-CD19 CAR or anti-BCMA CAR) |
| Day 3 | For non-expansion cohort, biotin is added for cells stimulated with anti-CD3/anti-CD28 Fab conjugated oligomeric streptavidin mutein reagents |
| Day 4 | Cells are in recovery |
| Day 5 | For non-expansion cohort, cells activated with anti-CD3/anti-CD28 paramagnetic beads, cells are debeaded Cells are harvested as a non-expanded cohort; cells are washed in formulation buffer and cryopreserved |
| Day 5 | For expansion cohort, cells are transferred to a shaking incubator |
| Day 7 | For cells in expansion cohort activated with anti-CD3/anti-CD28 Fab conjugatedoligomeric streptavidin mutein reagents, biotin is added |
| Day 9 | For expansion cohort, cells activated with anti-CD3/anti-CD28 paramagnetic beads, cells are debeaded Cells are harvested as a expanded cohort; cells are washed in formulation buffer and cryopreserved |

Cells were collected at various times during and at the end of the manufacturing runs, and were counted, and assessed for viability and by flow cytometry following staining with antibodies recognizing surface markers including CD4, CD8, CCR7, CD27, and CD45RA.

Figure 44B:
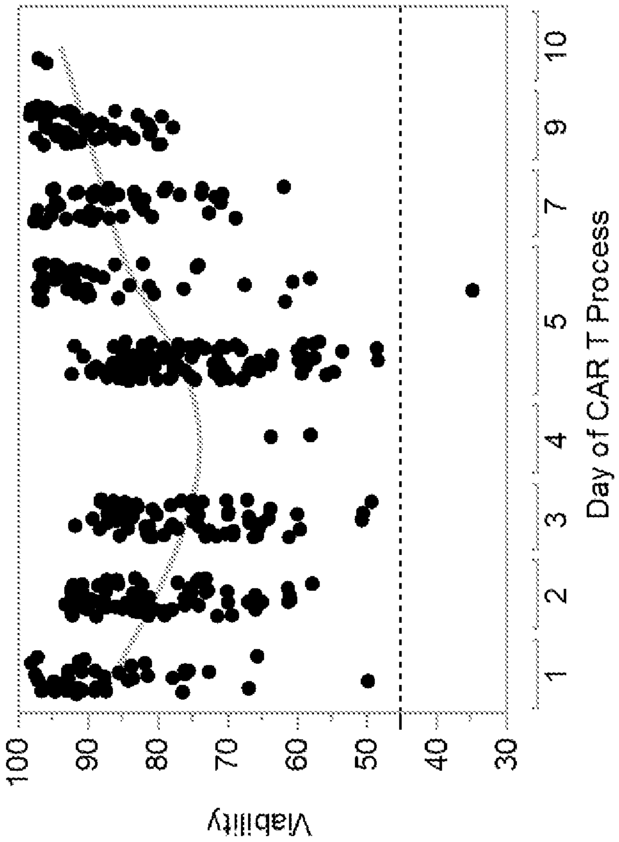
FIGS. 44A-44D show total live cells (FIG. 44A), viability (FIG. 44B), and phenotype (FIGS. 44C and 44D) during and after manufacturing runs including a variety of non-expanded and expanded engineering processes.
Figure 44A:
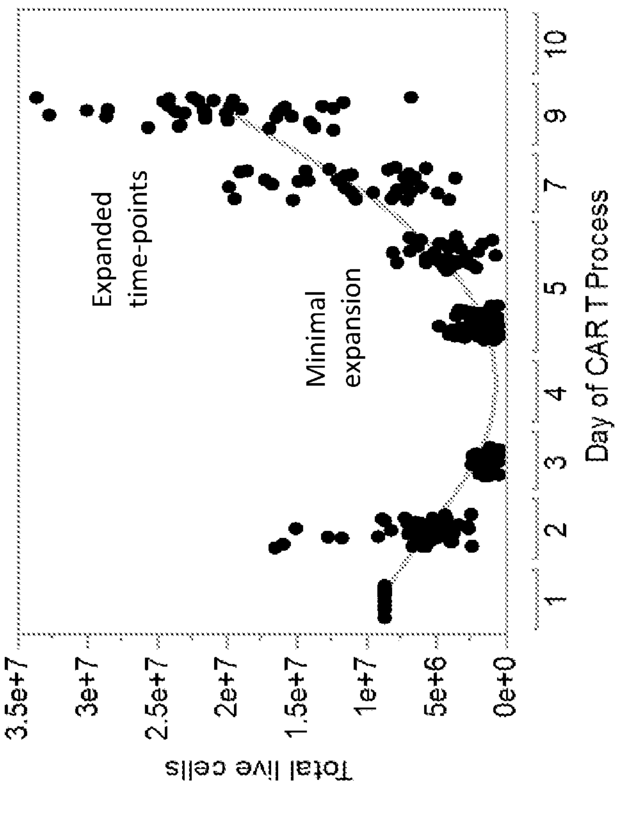
Figure 44C:
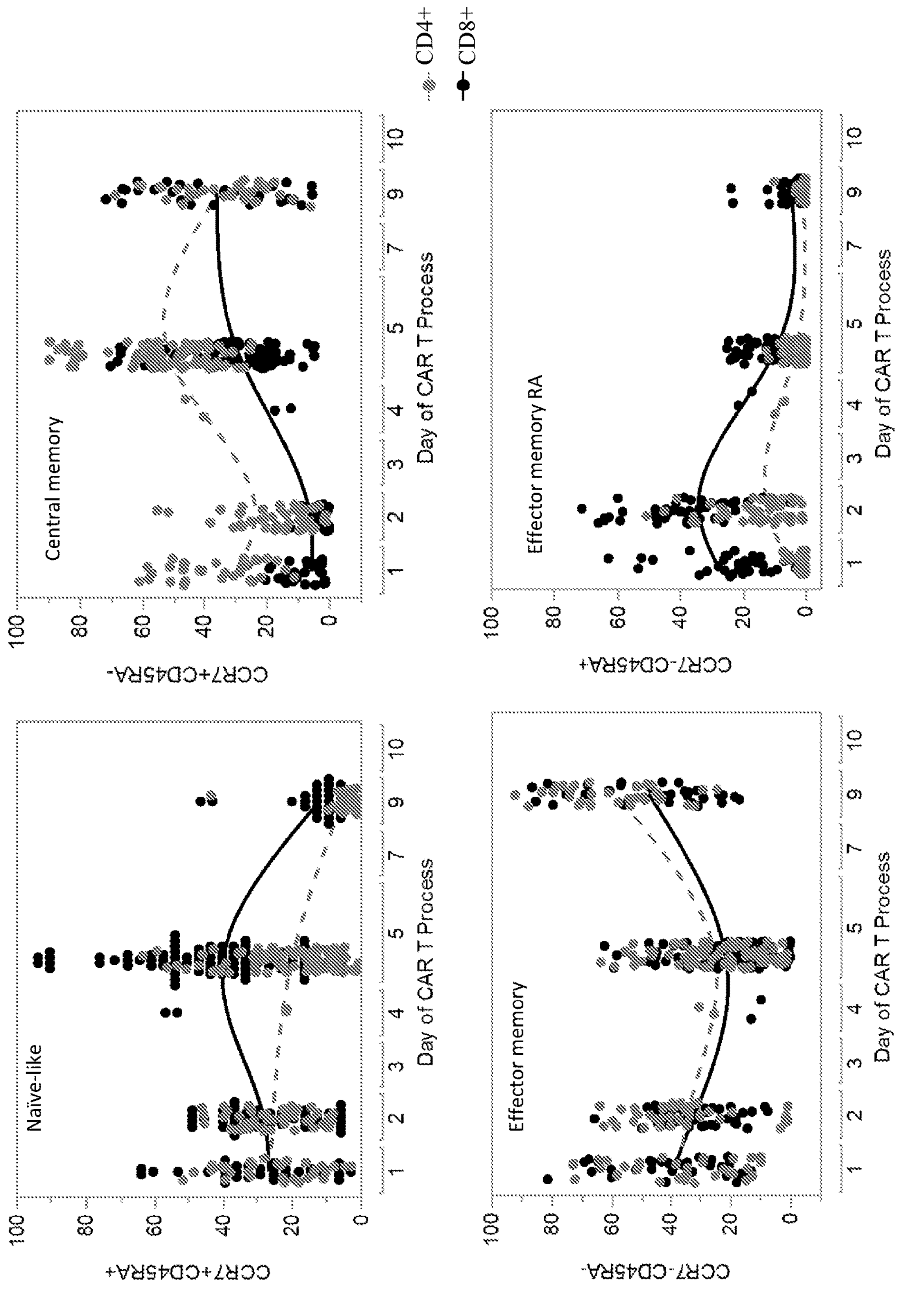
Figure 44D:
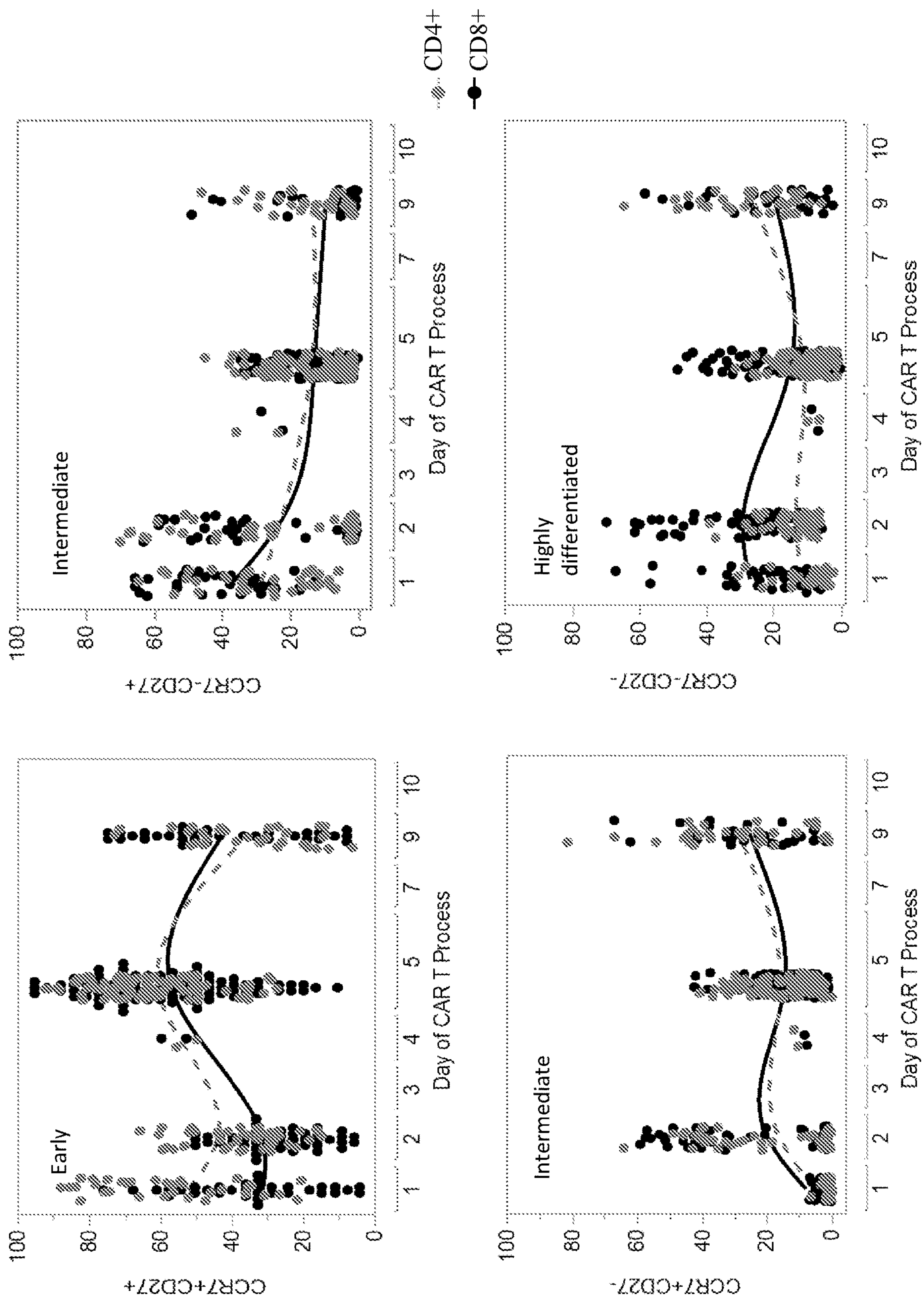

Process metrics such as total live cells (FIG. 44A) and viability (FIG. 44B) were monitored during the manufacturing runs. As shown in FIG. 44A, minimal expansion of cells was observed at the day 5 time point, with robust expansion beginning after Day 5. FIG. 44B shows an initial decrease in viability of cells in the manufacturing runs which begins to increase as the cells start to expand after Day 5 of the processes. Results of comparison of memory/differentiation phenotype at different time points in the manufacturing runs are shown in FIG. 44CA (by CD5RA and CCR7 expression) and FIG. 44D (by CD27 and CCR7 expression). As shown, assessment of cells early during the manufacturing runs show that cells at about day 5 are substantially more enriched for less differentiated cell types, such as CCR7+CD45RA− or CCR7+CD27+ cells, compared to cells both at earlier times in the process (e.g. Day 1 or Day 2) or later times in the process (e.g. Day 9).

Without wishing to be bound by theory, these results are consistent with an observation that stimulation of cells with an anti-CD3/anti-CD28 stimulatory reagent may result in activation-induced cell death (AICD) of more differentiated cells, such as effector-like cells (CCR7−CD45RA−) and TEMRA (CCR7−CD45RA+), in cell compositions early in the process, resulting in decreased cell viability and an enrichment of less differentiated cells. In some aspects, completing the process at about Day 5 maximizes recovery of the enriched population before expansion of cells may result in further differentiation. Moreover, as shown in Example 16 and FIG. 25, Day 5 also is a time point at which CAR expression is stable in the engineered cells, as evidenced by differences in vector copy number determined by a standard VCN assay or an iVCN assay. Together, these results support utility of a shortened manufacturing process for engineering CAR-T cells.

Example 27: Correlation of Standard VCN Assay and iVCN Assay to Surface Expression of Recombinant Receptor During Cell Manufacturing Processes Vector copy number (VCN) and iVCN assays described above were used to determine copy number of a transgene encoding a recombinant receptor, e.g. chimeric antigen receptor (CAR), introduced into T cells by lentiviral transduction, and the results were correlated to surface expression of the CAR. In this study, the assays were carried out on cell compositions produced from primary T cells from different human donors that had been engineered to express a CAR using either an expanded process, generally as described in Example 2.B, or a non-expanded process generally as described in Example 4.A.3, with a modification in which the cells were activated with an anti-CD3/anti-CD28 Fab conjugated oligomeric streptavidin mutein reagent followed by transduction and a short incubation in basal media that does not include addition of recombinant cytokines (cytokine-free media) before harvesting.

Genomic DNA was prepared from the cell samples at the end of the process for engineering in the shortened, non-expanded process or in the expanded process. The VCN and iVCN assays were carried out as described in Examples 1 using a threshold value for separation of >15 kb ("iVCN") and the PippinHT (Sage Science, Beverly, MA) device, or (2) a standard VCN method in which genomic DNA was not first separated by PFGE ("VCN").

Figure 45A:
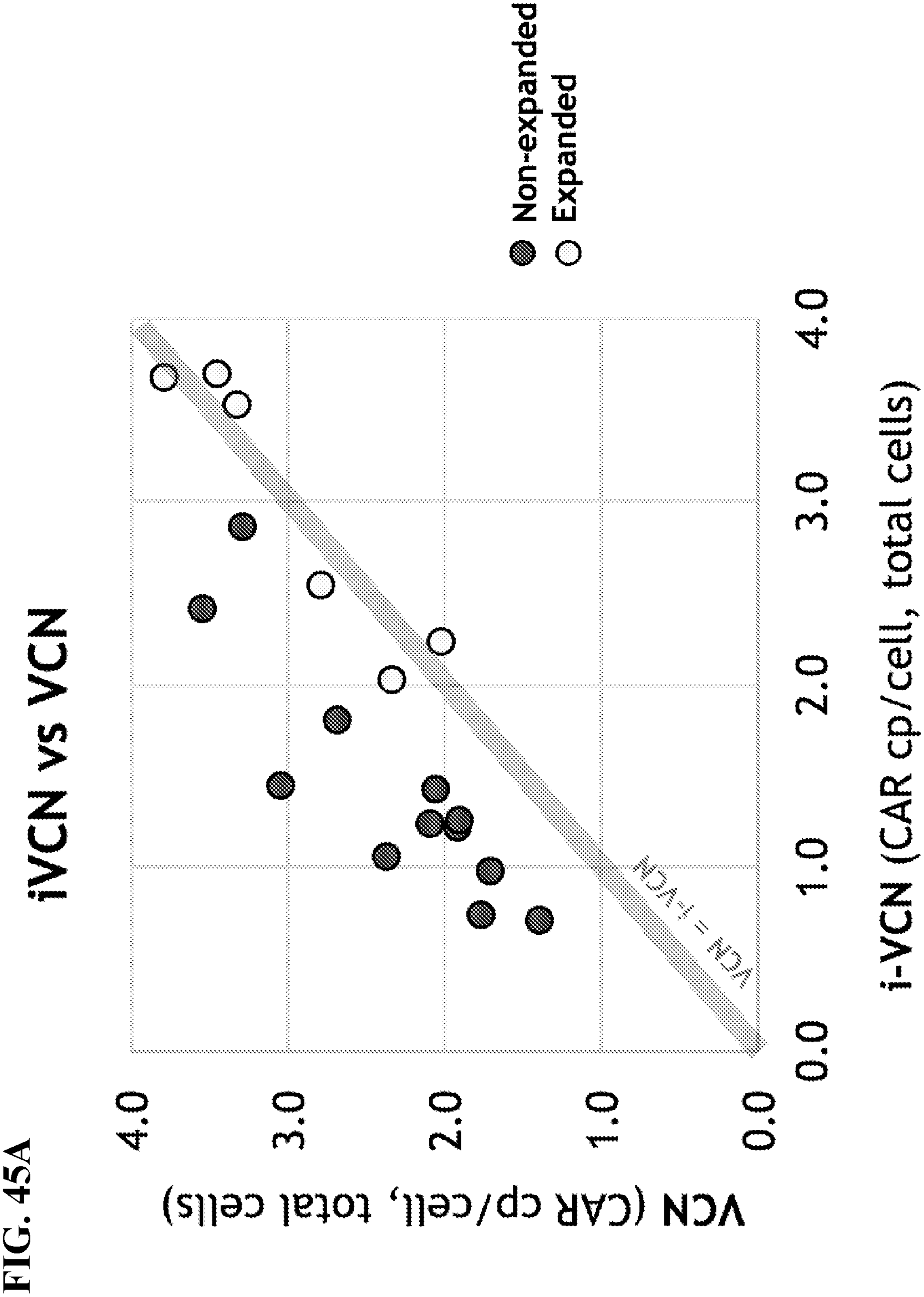
FIG. 45A shows the relationship between copy number per cell among total cells as assessed by standard VCN (without PFGE) and iVCN (with PFGE), in cell compositions produced from primary T cells from different human donors that had been engineered to express a CAR using an expanded process (○) or a non-expanded process (●).

The results showed that transgene copy number assessed using the VCN assay generally correlated with the transgene copy number assessed by iVCN (FIG. 45A). However, for cells manufactured using the non-expanded process, the values obtained by VCN were higher than the values obtained by iVCN, consistent with the VCN assay detecting non-integrated transgene sequences that could be present in samples containing cells generated using the non-expanded process. In contrast, for cells manufactured using the expanded process, the value obtained by VCN and iVCN were nearly identical (near the VCN=iVCN line). These differences are likely due to the presence of a greater amount of free, non-integrated copies of transgene sequences in samples in the shorter non-expanded process compared to the expanded process. These results are consistent with the observation that a standard VCN assay that is able to detect both high and low molecular weight DNA has limitations compared to an iVCN assay, particularly when used to assess cells early after transgene introduction, such as in a shortened process for engineering T cells, where free, non-integrated copies of transgene sequences may still be present in the sample.

Figure 45B:
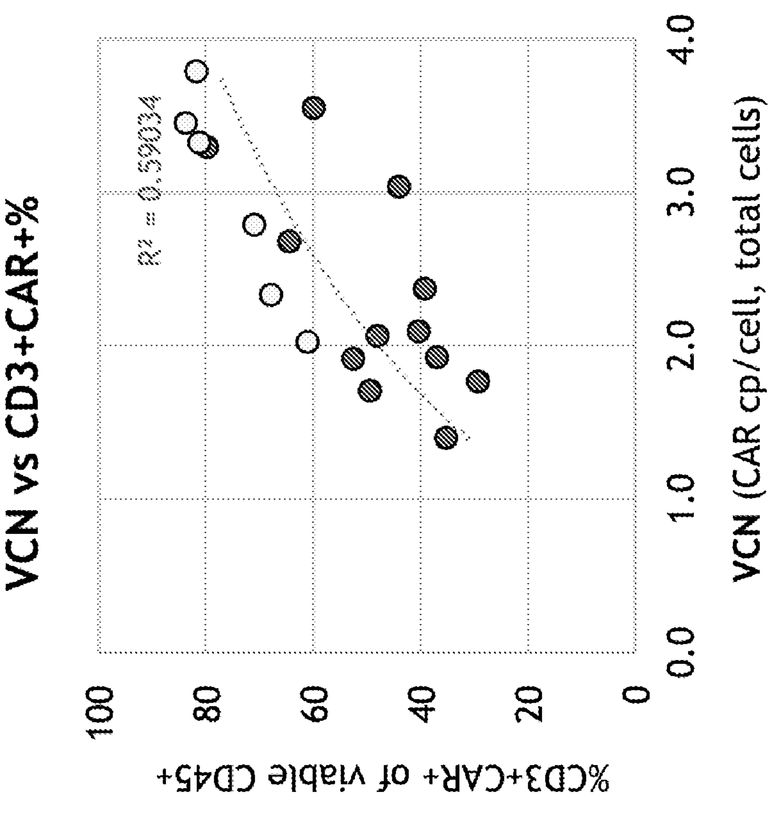
FIGS. 45B-45C show the relationship between the copy number per cell in the cell compositions as assessed by standard VCN (FIG. 45B) or iVCN (FIG. 45C) and the surface expression of the CAR, as indicated by the percentage of CAR-expressing CD3+ cells (% CD3+CAR+) among viable CD45+ cells assessed by flow cytometry.
Figure 45C:
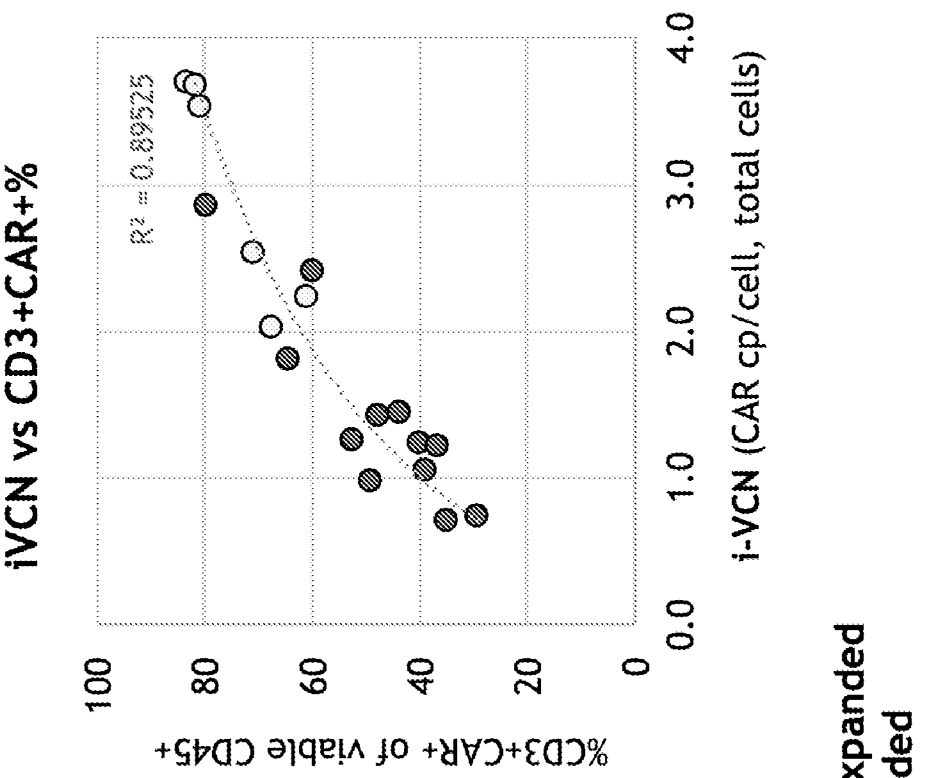

To assess the degree of correlation of the iVCN or VCN assay to surface expression of the CAR, cell samples from the non-expanded or expanded process were assessed by flow cytometry for expression of CD3, CD45 and the CAR to determine the percentage of CD3+CAR+ cells among viable CD45+ cells. As shown in FIGS. 45B, the VCN assay exhibited better correlation to the percentage of CAR+ cells for samples engineered by the expanded process than by the non-expanded process, likely due to the presence of non-integrated CAR DNA sequences that did not contribute to surface CAR expression. As shown in FIG. 45C, the iVCN showed similar correlation to expression of the CAR among cells that had been engineered by either the non-expanded or expanded process. For all samples, the correlation of CAR expression with the copy number per cell was higher by the iVCN assay ($R^2$=0.8952) compared to the copy number per cell as determined by the VCN assay ($R^2$=0.5903).

The results support the utility of the iVCN assay for accurately determining the copy number of stably integrated transgene sequence, particularly for cells generated using a non-expanded process which may retain free, non-integrated copies of transgene sequences. The VCN assay, which does not distinguish integrated vs. non-integrated transgene sequences, is limited in accurately determining the number of stably integrated transgene sequences, especially during and after a shorter, non-expanded process.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | ESKYGPPCPPCP | spacer (IgG4hinge) (aa) |
| 2 | GAATCTAAGTACGGACCGCCCTGCCCCCCTTGCCCT | spacer (IgG4hinge) (nt) |
| 3 | ESKYGPPCPPCPGQPREPQVYTLPPSQEEMTKNQVSLTCLVKGFYPSDIAVEW ESNGQPENNYKTTPPVLDSDGSFFLYSRLTVDKSRWQEGNVFSCSVMHEALH NHYTQKSLSLSLGK | Hinge-CH3 spacer |
| 4 | ESKYGPPCPPCPAPEFLGGPSVFLFPPKPKDTLMISRTPEVTCVVVDVSQEDPEV QFNWYVDGVEVHNAKTKPREEQFNSTYRVVSVLTVLHQDWLNGKEYKCKVS NKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEA LHNHYTQKSLSLSLGK | Hinge-CH2-CH3 spacer |
| 5 | RWPESPKAQASSVPTAQPQAEGSLAKATTAPATTRNTGRGGEEKKKEKEKEE QEERETKTPECPSHTQPLGVYLLTPAVQDLWLRDKATFTCFVVGSDLKDAHLT WEVAGKVPTGGVEEGLLERHSNGSQSQHSRLTLPRSLWNAGTSVTCTLNHPS LPPQRLMALREPAAQAPVKLSLNLLASSDPPEAASWLLCEVSGFSPPNILLMWL EDQREVNTSGFAPARPPPQPGSTTFWAWSVLRVPAPPSPQPATYTCVVSHED SRTLLNASRSLEVSYVTDH | IgD-hinge-Fc |
| 6 | LEGGGEGRGSLLTCGDVEENPGPR | T2A |
| 7 | MLLLVTSLLLCELPHPAFLLIPRKVCNGIGIGEFKDSLSINATNIKHFKNCTSISGDL HILPVAFRGDSFTHTPPLDPQELDILKTVKEITGFLLIQAWPENRTDLHAFENLEII RGRTKQHGQFSLAVVSLNITSLGLRSLKEISDGDVIISGNKNLCYANTINWKKLF GTSGQKTKIISNRGENSCKATGQVCHALCSPEGCWGPEPRDCVSCRNVSRGRE CVDKCNLLEGEPREFVENSECIQCHPECLPQAMNITCTGRGPDNCIQCAHYID GPHCVKTCPAGVMGENNTLVWKYADAGHVCHLCHPNCTYGCTGPGLEGCPT NGPKIPSIATGMVGALLLLLVVALGIGLFM | tEGFR |
| 8 | FWVLVVVGGVLACYSLLVTVAFIIFWV | CD28 (amino acids 153-179 of Accession No. P10747) |
| 9 | IEVMYPPPYLDNEKSNGTIIHVKGKHLCPSPLFPGPSKP FWVLVVVGGVLACYSLLVTVAFIIFWV | CD28 (amino acids 114-179 of |

-continued

Sequences

| # | SEQUENCE | ANNOTATION |
|---|---|---|
| | | Accession No. P10747) |
| 10 | RSKRSRLLHSDYMNMTPRRPGPTRKHYQPYAPPRDFAAYRS | CD28 (amino acids 180-220 of P10747) |
| 11 | RSKRSRGGHSDYMNMTPRRPGPTRKHYQPYAPPRDFAAYRS | CD28 (LL to GG) |
| 12 | KRGRKKLLYIFKQPFMRPVQTTQEEDGCSCRFPEEEEGGCEL | 4-1BB (amino acids 214-255 of Q07011.1) |
| 13 | RVKFSRSADAPAYQQGQNQLYNELNLGRREEYDVLDKRRGRDPEMGGKPRR KNPQEGLYNELQKDKMAEAYSEIGMKGERRRGKGHDGLYQGLSTATKDTYDA LHMQALPPR | CD3 zeta |
| 14 | RVKFSRSAEPPAYQQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR | CD3 zeta |
| 15 | RVKFSRSADAPAYKQGQNQLYNELNLGRREEYDVLDKRRGRDPEMGGKPRRK NPQEGLYNELQKDKMAEAYSEIGMKGERRRGKGHDGLYQGLSTATKDTYDAL HMQALPPR | CD3 zeta |
| 16 | RKVCNGIGIGEFKDSLSINATNIKHFKNCTSISGDLHILPVAFRGDSFTHTPPLDP QELDILKTVKEITGFLLIQAWPENRTDLHAFENLEIIRGRTKQHGQFSLAVVSLNI TSLGLRSLKEISDGDVIISGNKNLCYANTINWKKLFGTSGQKTKIISNRGENSCKA TGQVCHALCSPEGCWGPEPRDCVSCRNVSRGRECVDKCNLLEGEPREFVENS ECIQCHPECLPQAMNITCTGRGPDNCIQCAHYIDGPHCVKTCPAGVMGENNT LVWKYADAGHVCHLCHPNCTYGCTGPGLEGCPTNGPKIPSIATGMVGALLLLL VVALGIGLFM | tEGFR |
| 17 | EGRGSLLTCGDVEENPGP | T2A |
| 18 | GSGATNFSLLKQAGDVEENPGP | P2A |
| 19 | ATNFSLLKQAGDVEENPGP | P2A |
| 20 | QCTNYALLKLAGDVESNPGP | E2A |
| 21 | VKQTLNFDLLKLAGDVESNPGP | F2A |
| 22 | -PGGG-(SGGGG)5-P- wherein P is proline, G is glycine and S is serine | Linker |
| 23 | GSADDAKKDAAKKDGKS | Linker |
| 24 | atgcttctcctggtgacaagccttctgctctgtgagttaccacacccagcattcctcctgatccca | GMCSFR alpha chain signal sequence |
| 25 | MLLLVTSLLLCELPHPAFLLIP | GMCSFR alpha chain signal sequence |
| 26 | MALPVTALLLPLALLLHA | CD8 alpha signal peptide |
| 27 | EPKSCDKTHTCPPCP | Hinge |
| 28 | ERKCCVECPPCP | Hinge |
| 29 | ELKTPLGDTHTCPRCPEPKSCDTPPPCPRCPEPKSCDTPPPCPRCPEPKSCDTPP PCPRCP | Hinge |
| 30 | ESKYGPPCPSCP | Hinge |
| 31 | $X_1PPX_2P$ X1 is glycine, cysteine or arginine X2 is cysteine or threonine | Hinge |
| 32 | YGPPCPPCP | Hinge |
| 33 | KYGPPCPPCP | Hinge |
| 34 | EVVVKYGPPCPPCP | Hinge |

-continued

Sequences

| # | SEQUENCE | ANNOTATION |
|---|---|---|
| 35 | RASQDISKYLN | FMC63 CDR L1 |
| 36 | SRLHSGV | FMC63 CDR L2 |
| 37 | GNTLPYTFG | FMC63 CDR L3 |
| 38 | DYGVS | FMC63 CDR H1 |
| 39 | VIWGSETTYYNSALKS | FMC63 CDR H2 |
| 40 | YAMDYWG | FMC63 CDR H3 |
| 41 | EVKLQESGPGLVAPSQSLSVTCTVSGVSLPDYGVSWIRQPPRKGLEWLGVIWG<br>SETTYYNSALKSRLTIIKDNSKSQVFLKMNSLQTDDTAIYYCAKHYYYGGSYAMD<br>YWGQGTSVTVSS | FMC63 VH |
| 42 | DIQMTQTTSSLSASLGDRVTISCRASQDISKYLNWYQQKPDGTVKLLIYHTSRLH<br>SGVPSRFSGSGSGTDYSLTISNLEQEDIATYFCQQGNTLPYTFGGGTKLEIT | FMC63 VL |
| 43 | DIQMTQTTSSLSASLGDRVTISCRASQDISKYLNWYQQKPDGTVKLLIYHTSRLH<br>SGVPSRFSGSGSGTDYSLTISNLEQEDIATYFCQQGNTLPYTFGGGTKLEITGSTS<br>GSGKPGSGEGSTKGEVKLQESGPGLVAPSQSLSVTCTVSGVSLPDYGVSWIRQ<br>PPRKGLEWLGVIWGSETTYYNSALKSRLTIIKDNSKSQVFLKMNSLQTDDTAIYY<br>CAKHYYYGGSYAMDYWGQGTSVTVSS | FMC63 scFv |
| 44 | KASQNVGTNVA | SJ25C1 CDR L1 |
| 45 | SATYRNS | SJ25C1 CDR L2 |
| 46 | QQYNRYPYT | SJ25C1 CDR L3 |
| 47 | SYWMN | SJ25C1 CDR H1 |
| 48 | QIYPGDGDTNYNGKFKG | SJ25C1 CDR H2 |
| 49 | KTISSVVDFYFDY | SJ25C1 CDR H3 |
| 50 | EVKLQQSGAELVRPGSSVKISCKASGYAFSSYWMNWVKQRPGQGLEWIGQIY<br>PGDGDTNYNGKFKGQATLTADKSSSTAYMQLSGLTSEDSAVYFCARKTISSVV<br>DFYFDYWGQGTTVTVSS | SJ25C1 VH |
| 51 | DIELTQSPKFMSTSVGDRVSVTCKASQNVGTNVAWYQQKPGQSPKPLIYSATY<br>RNSGVPDRFTGSGSGTDFTLTITNVQSKDLADYFCQQYNRYPYTSGGGTKLEIK<br>R | SJ25C1 VL |
| 52 | GGGGSGGGGSGGGGS | Linker |
| 53 | EVKLQQSGAELVRPGSSVKISCKASGYAFSSYWMNWVKQRPGQGLEWIGQIY<br>PGDGDTNYNGKFKGQATLTADKSSSTAYMQLSGLTSEDSAVYFCARKTISSVV<br>DFYFDYWGQGTTVTVSSGGGGSGGGGSGGGGSDIELTQSPKFMSTSVGDRV<br>SVTCKASQNVGTNVAWYQQKPGQSPKPLIYSATYRNSGVPDRFTGSGSGTDF<br>TLTITNVQSKDLADYFCQQYNRYPYTSGGGTKLEIKR | SJ25C1 scFv |
| 54 | HYYYGGSYAMDY | FMC63 HC-CDR3 |
| 55 | HTSRLHS | FMC63 LC-CDR2 |
| 56 | QQGNTLPYT | FMC63 LC-CDR3 |
| 57 | gacatccagatgacccagaccacctccagcctgagcgccagcctgggcgaccgggtgaccatcag<br>ctgccgggccagccaggacatcagcaagtacctgaactggtatcagcagaagcccgacggcaccg<br>tcaagctgctgatctaccacaccagccggctgcacagcggcgtgcccagccggtttagcggcagcg<br>gctccggcaccgactacagcctgaccatctccaacctggaacaggaagatatcgccacctactttg<br>ccagcagggcaacacactgccctacacctttggcggcggaacaaagctggaaatcaccggcagca<br>cctccggcagcggcaagcctggcagcggcgagggcagcaccaagggcgaggtgaagctgcagga<br>aagcggccctggcctggtggcccccagccagagcctgagcgtgacctgcaccgtgagcggcgtga<br>gcctgcccgactacggcgtgagctggatccggcagcccccccaggaagggcctggaatggctgggc<br>gtgatctggggcagcgagaccacctactacaacagcgccctgaagagccggctgaccatcatcaa<br>ggacaacagcaagagccaggtgttcctgaagatgaacagcctgcagaccgacgacaccgccatct<br>actactgcgccaagcactactactacggcggcagctacgccatggactactggggccagggcacc<br>agcgtgaccgtgagcagc | Sequence encoding<br>scFv |
| 58 | GSTSGSGKPGSGEGSTKG | Linker |

-continued

Sequences

| # | SEQUENCE | ANNOTATION |
|---|---|---|
| 59 | ASTKGPSVFPLAPCSRSTSESTAALGCLVKDYFPEPVTVSWNSGALTSGVHTFP AVLQSSGLYSLSSVVTVPSSNFGTQTYTCNVDHKPSNTKVDKTVERKCCVECPP CPAPPVAGPSVFLFPPKPKDTLMISRTPEVTCVVVDVSHEDPEVQFNWYVDGV EVHNAKTKPREEQFNSTFRVVSVLTVVHQDWLNGKEYKCKVSNKGLPAPIEKTI SKTKGQPREPQVYTLPPSREEMTKNQVSLTCLVKGFYPSDISVEWESNGQPEN NYKTTPPMLDSDGSFFLYSKLTVDKSRWQQGNVFSCSVMHEALHNHYTQKSL SLSPGK | Human IgG2 Fc (Uniprot P01859) |
| 60 | ASTKGPSVFPLAPCSRSTSESTAALGCLVKDYFPEPVTVSWNSGALTSGVHTFP AVLQSSGLYSLSSVVTVPSSSLGTKTYTCNVDHKPSNTKVDKRVESKYGPPCPSC PAPEFLGGPSVFLFPPKPKDTLMISRTPEVTCVVVDVSQEDPEVQFNWYVDGV EVHNAKTKPREEQFNSTYRVVSVLTVLHQDWLNGKEYKCKVSNKGLPSSIEKTI SKAKGQPREPQVYTLPPSQEEMTKNQVSLTCLVKGFYPSDIAVEWESNGQPE NNYKTTPPVLDSDGSFFLYSRLTVDKSRWQEGNVFSCSVMHEALHNHYTQKSL SLSLGK | Human IgG4 Fc (Uniprot P01861) |
| 61 | DPSKDSKAQVSAAEAGITGTWYNQLGSTFIVTAGADGALTGTYESAVGNAESR YVLTGRYDSAPATDGSGTALGWTVAWKNNYRNAHSATTWSGQYVGGAEARI NTQWLLTSGTTEANAWKSTLVGHDTFTKVKPSAASIDAAKKAGVNNGNPLDA VQQ | Streptavidin Species: *Streptomyces avidinii* UniProt No. P22629 |
| 62 | EAGITGTWYNQLGSTFIVTAGADGALTGTYESAVGNAESRYVLTGRYDSAPAT DGSGTALGWTVAWKNNYRNAHSATTWSGQYVGGAEARINTQWLLTSGTTE ANAWKSTLVGHDTFTKVKPSAAS | Minimal streptavidin Species: *Streptomyces avidinii* |
| 63 | EAGITGTWYNQLGSTFIVTAGADGALTGTYIGARGNAESRYVLTGRYDSAPAT DGSGTALGWTVAWKNNYRNAHSATTWSGQYVGGAEARINTQWLLTSGTTE ANAWKSTLVGHDTFTKVKPSAAS | Mutein Streptavidin Ile44-Gly45-Ala-46-Arg47 Species: *Streptomyces avidinii* |
| 64 | WSHPQFEK | Strep-tag® II |
| 65 | WSHPQFEKGGGSGGGSGGGSWSHPQFEK | Twin-Strep-tag |
| 66 | WSHPQFEKGGGSGGGSWSHPQFEK | Twin-Strep-tag |
| 67 | WSHPQFEKGGGSGGGSGGSAWSHPQFEK | Twin-Strep-tag |
| 68 | MEAGITGTWYNQLGSTFIVTAGADGALTGTY**IGAR**GNAESRYVLTGRYDSAPA TDGSGTALGWTVAWKNNYRNAHSATTWSGQYVGGAEARINTQWLLTSGTT EANAWKSTLVGHDTFTKVKPSAAS | Mutein Streptavidinlle44-Gly45-Ala-46-Arg47 Species: *Streptomyces avidinii* |
| 69 | -Trp-Xaa-His-Pro-Gln-Phe-Yaa-Zaa- | Streptavidin-binding peptide Xaa is any amino acid; Yaa is Gly or Glu Zaa is Gly, Lys or Arg |
| 70 | Trp-Arg-His-Pro-Gln-Phe-Gly-Gly | Streptavidin binding peptide, Strep-tag® |
| 71 | Trp-Ser-His-Pro-Gln-Phe-Glu-Lys-(Xaa)n-Trp-Ser-His-Pro-Gln-Phe-Glu-Lys- | Sequential modules of streptavidin-binding peptide Xaa is any amino acid; n is either 8 or 12 |

-continued

Sequences

| # | SEQUENCE | ANNOTATION |
|---|---|---|
| 72 | Trp-Ser-His-Pro-Gln-Phe-Glu-Lys-(GlyGlyGlySer)n-Trp-Ser-His-Pro-Gln-Phe-Glu-Lys | Sequential modules of streptavidin-binding peptide n is 2 or 3 |
| 73 | SAWSHPQFEKGGGSGGGSGGGSWSHPQFEK | Twin-Strep-tag |
| 74 | SAWSHPQFEKGGGSGGGSGGSAWSHPQFEK | Twin-Strep-tag |
| 75 | DPSKDSKAQVSAAEAGITGTWYNQLGSTFIVTAGADGALTGTY**VTAR**GNAES RYVLTGRYDSAPATDGSGTALGWTVAWKNNYRNAHSATTWSGQYVGGAEA RINTQWLLTSGTTEANAWKSTLVGHDTFTKVKPSAASIDAAKKAGVNNGNPL DAVQQ | Mutein Streptavidin Val44-Thr45-Ala46-Arg47 Species: *Streptomyces avidinii* |
| 76 | EAGITGTWYNQLGSTFIVTAGADGALTGTY**VTAR**GNAESRYVLTGRYDSAPAT DGSGTALGWTVAWKNNYRNAHSATTWSGQYVGGAEARINTQWLLTSGTTE ANAWKSTLVGHDTFTKVKPSAAS | Mutein Streptavidin Val44-Thr45-Ala46-Arg47 Species: *Streptomyces avidinii* |
| 77 | MEAGITGTWYNQLGSTFIVTAGADGALTGTY**VTAR**GNAESRYVLTGRYDSAP ATDGSGTALGWTVAWKNNYRNAHSATTWSGQYVGGAEARINTQWLLTSGT TEANAWKSTLVGHDTFTKVKPSAAS | Mutein Streptavidin Val44-Thr45-Ala46-Arg47 Species: *Streptomyces avidinii* |
| 78 | His-Pro-Gln-Phe | Streptavidin-binding peptide |
| 79 | Oaa-Xaa-His-Pro-Gln-Phe-Yaa-Zaa | Streptavidin-binding peptide Oaa is Trp, Lys or Arg; Xaa is any amino acid; Yaa is Gly or Glu Zaa is Gly, Lys or Arg |
| 80 | DPSKDSKAQVSAAEAGITGTWYNQLGSTFIVTAGADGALTGTY**IGAR**GNAESR YVLTGRYDSAPATDGSGTALGWTVAWKNNYRNAHSATTWSGQYVGGAEARI NTQWLLTSGTTEANAWKSTLVGHDTFTKVKPSAASIDAAKKAGVNNGNPLDA VQQ | Mutein Streptavidin Ile44-Gly45-Ala-46-Arg47 Species: *Streptomyces avidinii* |
| 81 | EAGITGTWYNQLGSTFIVTAGADGALTGTY**VTAR**GNAESRYVLTGRYDSAPAT DGSGTALGWTVAWKNNYRNAHSATTWSGQYVGGAEARINTQWLLTSGTTE ENAGYSTLVGHDTFTKVKPSAAS | Mutein Streptavidin Val44-Thr45-Ala46-Arg47 and Glu117, Gly120, Try121 (mutein m1-9) Species: *Streptomyces avidinii* |
| 82 | DPSKDSKAQVSAAEAGITGTWYNQLGSTFIVTAGADGALTGTY**VTAR**GNAES RYVLTGRYDSAPATDGSGTALGWTVAWKNNYRNAHSATTWSGQYVGGAEA RINTQWLLTSGTTEENAGYSTLVGHDTFTKVKPSAAS | Mutein Streptavidin Val44-Thr45-Ala46-Arg47 and Glu117, Gly120, Try121 (mutein m1-9) Species: *Streptomyces avidinii* |
| 83 | MEAGITGTWYNQLGSTFIVTAGADGALTGTYESAVGNAESRYVLTGRYDSAPA TDGSGTALGWTVAWKNNYRNAHSATTWSGQYVGGAEARINTQWLLTSGTT EANAWKSTLVGHDTFTKVKPSAAS | Minimal streptavidin Species: |

-continued

| # | SEQUENCE | ANNOTATION |
|---|---|---|
| | | *Streptomyces avidinii* |
| 84 | GVQVETISPGDGRTFPKRGQTCVVHYTGMLEDGKKMDSSRDRNKPFKFMLG KQEVIRGWEEGVAQMSVGQRAKLTISPDYAYGATGHPGIIPPHATLVFDVELL KLE | FKBP |
| 85 | GVQVETISPGDGRTFPKRGQTCVVHYTGMLEDGKKVDSSRDRNKPFKFMLGK QEVIRGWEEGVAQMSVGQRAKLTISPDYAYGATGHPGIIPPHATLVFDVELLKL E | FKBP12v36 |
| 86 | MGSNKSKPKDASQRRR | Modified acylation motif |
| 87 | Met-Gly-Cys-Xaa-Cys | dual acylation motif |
| 88 | Cys-Ala-Ala-Xaa | acylation region |
| 89 | Gln Val Gln Leu Gln Gln Ser Gly Ala Glu Leu Ala Arg Pro Gly Ala Ser Val Lys Met Ser Cys Lys Ala Ser Gly Tyr Thr Phe Thr Arg Tyr Thr Met His Trp Val Lys Gln Arg Pro Gly Gln Gly Leu Glu Trp Ile Gly Tyr Ile Asn Pro Ser Arg Gly Tyr Thr Asn Tyr Asn Gln Lys Phe Lys Asp Lys Ala Thr Leu Thr Thr Asp Lys Ser Ser Ser Thr Ala Tyr Met Gln Leu Ser Ser Leu Thr Ser Glu Asp Ser Ala Val Tyr Tyr Cys Ala Arg Tyr Tyr Asp Asp His Tyr Cys Leu Asp Tyr Trp Gly Gln Gly Thr Thr Leu Thr Val Ser Ser | Variable Heavy chain of anti-CD3 antibody OKT3 |
| 90 | Gln Ile Val Leu Thr Gln Ser Pro Ala Ile Met Ser Ala Ser Pro Gly Glu Lys Val Thr Met Thr Cys Ser Ala Ser Ser Ser Val Ser Tyr Met Asn Trp Tyr Gln Gln Lys Ser Gly Thr Ser Pro Lys Arg Trp Ile Tyr Asp Thr Ser Lys Leu Ala Ser Gly Val Pro Ala His Phe Arg Gly Ser Gly Ser Gly Thr Ser Tyr Ser Leu Thr Ile Ser Gly Met Glu Ala Glu Asp Ala Ala Thr Tyr Tyr Cys Gln Gln Trp Ser Ser Asn Pro Phe Thr Phe Gly Ser Gly Thr Lys Leu Glu Ile Asn | Variable Light chain of anti-CD3 antibody OKT3 |
| 91 | Leu Gln Gln Ser Gly Ala Glu Leu Val Lys Pro Gly Ala Ser Val Arg Leu Ser Cys Lys Ala Ser Gly Tyr Thr Phe Thr Glu Tyr Ile Ile His Trp Ile Lys Leu Arg Ser Gly Gln Gly Leu Glu Trp Ile Gly Trp Phe Tyr Pro Gly Ser Asn Asp Ile Gln Tyr Asn Ala Lys Phe Lys Gly Lys Ala Thr Leu Thr Ala Asp Lys Ser Ser Ser Thr Val Tyr Met Glu Leu Thr Gly Leu Thr Ser Glu Asp Ser Ala Val Tyr Phe Cys Ala Arg Arg Asp Asp Phe Ser Gly Tyr Asp Ala Leu Pro Tyr Trp Gly Gln Gly Thr Met Val Thr Val | Variable Heavy chain of anti-CD28 antibody CD28.3 |
| 92 | Asp Ile Gln Met Thr Gln Ser Pro Ala Ser Leu Ser Val Ser Val Gly Glu Thr Val Thr Ile Thr Cys Arg Thr Asn Glu Asn Ile Tyr Ser Asn Leu Ala Trp Tyr Gln Gln Lys Gln Gly Lys Ser Pro Gln Leu Leu Ile Tyr Ala Ala Thr His Leu Val Glu Gly Val Pro Ser Arg Phe Ser Gly Ser Gly Ser Gly Thr Gln Tyr Ser Leu Lys Ile Thr Ser Leu Gln Ser Glu Asp Phe Gly Asn Tyr Tyr Cys Gln His Phe Trp Gly Thr Pro Cys Thr Phe Gly Gly Gly Thr Lys Leu Glu Ile Lys Arg | Variable Light chain of anti-CD28 antibody CD28.3 |
| 93 | His-Pro-Xaa | Streptavidin Binding peptide Xaa is selected from Gln, Asp, and Met |
| 94 | Tyr-Pro-Tyr-Asp-Val-Pro-Asp-Tyr-Ala | HA-tag |
| 95 | Tyr-Thr-Asp-Ile-Glu-Met-Asn-Arg-Leu-Gly-Lys | VSV-G-tag |
| 96 | Gln-Pro-Glu-Leu-Ala-Pro-Glu-Asp-Pro-Glu-Asp | HSV-tag |
| 97 | Ala-Ser-Met-Thr-Gly-Gly-Gln-Gln-Met-Gly | T7 epitope |
| 98 | Gln-Pro-Glu-Leu-Ala-Pro-Glu-Asp-Pro-Glu-Asp | HSV epitope |
| 99 | Glu-Gln-Lys-Leu-Ile-Ser-Glu-Glu-Asp-Leu | Myc epitope |
| 100 | Gly-Lys-Pro-lle-Pro-Asn-Pro-Leu-Leu-Gly-Leu-Asp-Ser-Thr | V5-tag |
| 101 | AMQVQLKQSG PGLVQPSQSL SITCTVSGFS LTTFGVHWVR QSPGKGLEWL GVIWASGITD YNVPFMSRLS ITKDNSKSQV FFKLNSLQPD DTAIYYCAKN DPGTGFAYWG QGTLVTVSAG STKGPSVFPL APSSKSTSGG TAALGCLVKD YFPEPVTVSW NSGALTSGVH TFPAVLQSSG LYSLSSVVTV PSSSLGTQTY ICNVNHKPSN TKVDKKVEPK SCGSAWSHPQ FEKGGGSGGG SGGSAWSHPQ FEK | Variable Heavy chain of Fab fragment m13B8.2 |

-continued

Sequences

| # | SEQUENCE | ANNOTATION |
|---|---|---|
| 102 | AMDIQMTQSP ASLSASVGET VTFTCRASEM IYSYLAWYQQ KQGKSPQLLV HDAKTLAEGV PSRFSGGGSG TQFSLKINTL QPEDFGTYYC QAHYGNPPTF GGGTKLEIKR GIAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGECGS | Variable Light chain of Fab Fragment m13B8.2 |
| 103 | His-Asn-His-Arg-His-Lys-His-Gly-Gly-Gly-Cys | MAT tag |
| 104 | Gln Val Gln Leu Val Gln Ser Gly Ala Glu Val Lys Lys Pro Gly Ala1 Thr Val Lys Ile Ser Cys Lys Val Ser Gly Phe Asn Ile Lys Asp Thr Tyr Ile His Trp Val Gln Gln Ala Pro Gly Lys Gly Leu Glu Trp Met Gly Arg Ile Asp Pro Ala Asn Asp Asn Thr Leu Tyr Ala Ser Lys Phe Gln Gly Arg Val Thr Ile Thr Ala Asp Thr Ser Thr Asp Thr Ala Tyr65 Met Glu Leu Ser Ser Leu Arg Ser Glu Asp Thr Ala Val Tyr Tyr Cys Ala Arg Gly Tyr Gly Tyr Tyr Val Phe Asp His Trp Gly Gln Gly Thr Leu Val Thr Val Ser Ser | Variable Heavy chain of huOKT8 |
| 105 | Asp Val Gln Ile Thr Gln Ser Pro Ser Ser Leu Ser Ala Ser Val Gly Asp Arg Val Thr Ile Thr Cys Arg Thr Ser Arg Ser Ile Ser Gln Tyr Leu Ala Trp Tyr Gln Gln Lys Pro Gly Lys Val Pro Lys Leu Leu Ile Tyr Ser Gly Ser Thr Leu Gln Ser Gly Val Pro Ser Arg Phe Ser Gly Ser Gly Ser Gly Thr Asp Phe Thr Leu Thr Ile Ser Ser Leu Gln Pro Glu Asp Val Ala Thr Tyr Tyr Cys Gln Gln His Asn Glu Asn Pro Leu Thr Phe Gly Gly Gly Thr Lys Val Glu Ile Lys | Variable Light chain of huOKT8 |
| 106 | EVQLVQSGAEMKKPGASLKLSCKASGYTFIDYYVYWMRQAPGQGLESMGWI NPNSGGTNYAQKFQGRVTMTRDTSISTAYMELSRLRSDDTAMYYCARSQRD GYMDYWGQGTLVTVSS | Variable heavy ($V_H$) Anti-BCMA |
| 107 | QSALTQPASVSASPGQSIAISCTGTSSDVGWYQQHPGKAPKLMIYEDSKRPSG VSNRFSGSKSGNTASLTISGLQAEDEADYYCSSNTRSSTLVFGGGTKLTVLG | Variable light ($V_L$) Anti-BCMA |
| 108 | ESKYGPPCPPCPAPPVAGPSVFLFPPKPKDTLMISRTPEVTCVVVDVSQEDPEV QFNWYVDGVEVHNAKTKPREEQFQSTYRVVSVLTVLHQDWLNGKEYKCKVS NKGLPSSIEKTISKAKGQPREPQVYTLPPSQEEMTKNQVSLTCLVKGFYPSDIAV EWESNGQPENNYKTTPPVLDSDGSFFLYSRLTVDKSRWQEGNVFSCSVMHEA LHNHYTQKSLSLSLGK | Hinge-$C_H2$-$C_H3$ spacer *Homo sapiens* |
| 109 | QIQLVQSGPELKKPGETVKISCKASGYTFTDYSINWVKRAPGKGLKWMGWINT ETREPAYAYDFRGRFAFSLETSASTAYLQINNLKYEDTATYFCALDYSYAMDYW GQGTSVTVSS | Variable heavy ($V_H$) Anti-BCMA |
| 110 | DIVLTQSPPSLAMSLGKRATISCRASESVTILGSHLIHWYQQKPGQPPTLLIQLAS NVQTGVPARFSGSGSRTDFTLTIDPVEEDDVAVYYCLQSRTIPRTFGGGTKLEIK | Variable light ($V_L$) Anti-BCMA |
| 111 | QIQLVQSGPDLKKPGETVKLSCKASGYTFTNFGMNWVKQAPGKGFKWMAW INTYTGESYFADDFKGRFAFSVETSATTAYLQINNLKTEDTATYFCARGEIYYGYD GGFAYWGQGTLVTVSA | Variable heavy ($V_H$) Anti-BCMA |
| 112 | DVVMTQSHRFMSTSVGDRVSITCRASQDVNTAVSWYQQKPGQSPKLLIFSAS YRYTGVPDRFTGSGSGADFTLTISSVQAEDLAVYYCQQHYSTPWTFGGGTKLDI K | Variable light ($V_L$) Anti-BCMA |
| 113 | EVQLVQSGAEVKKPGESLKISCKGSGYSFTSYWIGWVRQMPGKGLEWMGIIY PGDSDTRYSPSFQGHVTISADKSISTAYLQWSSLKASDTAMYYCARYSGSFDN WGQGTLVTVSS | Variable heavy ($V_H$) Anti-BCMA |
| 114 | SYELTQPPSASGTPGQRVTMSCSGTSSNIGSHSVNWYQQLPGTAPKLLIYTNN QRPSGVPDRFSGSKSGTSASLAISGLQSEDEADYYCAAWDGSLNGLVFGGGTK LTVLG | Variable light ($V_L$) Anti-BCMA |
| 115 | GGGGS | Linker |
| 116 | GGGS | Linker |
| 117 | SRGGGGSGGGGSGGGGSLEMA | Linker |
| 118 | EVQLVQSGAEVKKPGSSVKVSCKASGGTFSSYAISWVRQAPGQGLEWMGRII PILGIANYAQKFQGRVTMTEDTSTDTAYMELSSLRSEDTAVYYCARSGYSKSIVS YMDYWGQGTLVTVSS | Variable heavy ($V_H$) Anti-BCMA |
| 119 | LPVLTQPPSTSGTPGQRVTVSCSGSSSNIGSNVVFWYQQLPGTAPKLVIYRNN QRPSGVPDRFSVSKSGTSASLAISGLRSEDEADYYCAAWDDSLSGYVFGTGTKV TVLG | Variable light ($V_L$) Anti-BCMA |

-continued

Sequences

| # | SEQUENCE | ANNOTATION |
|---|---|---|
| 120 | QVQLVQSGAEVKKPGSSVKVSCKASGGTFSSYAISWVRQAPGQGLEWMGRII PILGTANYAQKFQGRVTITADESTSTAYMELSSLRSEDTAVYYCARSGYGSYRW EDSWGQGTLVTVSS | Variable heavy ($V_H$) Anti-BCMA |
| 121 | QAVLTQPPSASGTPGQRVTISCSGSSSNIGSNYVFWYQQLPGTAPKLLIYSNNQ RPSGVPDRFSGSKSGTSASLAISGLRSEDEADYYCAAWDDSLSASYVFGTGTKV TVLG | Variable light ($V_L$) Anti-BCMA |
| 122 | QVQLVQSGAEVKKPGASVKVSCKASGYTFTDYYMHWVRQAPGQRLEWMG WINPNSGGTNYAQKFQDRITVTRDTSSNTGYMELTRLRSDDTAVYYCARSPYS GVLDKWGQGTLVTVSS | Variable heavy ($V_H$) Anti-BCMA |
| 123 | QSVLTQPPSVSGAPGQRVTISCTGSSSNIGAGFDVHWYQQLPGTAPKLLIYGN SNRPSGVPDRFSGSKSGTSASLAITGLQAEDEADYYCQSYDSSLSGYVFGTGTK VTVLG | Variable light ($V_L$) Anti-BCMA |

What is claimed:

1. A method for producing a composition of engineered T cells, the method comprising:

(a) exposing an input composition comprising primary T cells with a stimulatory reagent under conditions to stimulate T cells, wherein the stimulatory reagent comprises (i) an anti-CD3 antibody or antigen-binding fragment thereof and (ii) an anti-CD28 antibody or an antigen-binding fragment thereof, each bound to a bead, thereby generating a stimulated population;

(b) introducing into T cells of the stimulated population a viral vector comprising a heterologous polynucleotide encoding a recombinant protein, thereby generating a population of transformed T cells;

(c) incubating the population of transformed T cells in a serum-free medium, thereby generating an incubated population of transformed T cells, wherein the serum-free medium comprises 50 IU/mL to 200 IU/mL recombinant IL-2, 50 IU/mL to 200 IU/mL recombinant IL-15, and 500 IU/mL to 1,000 IU/mL recombinant IL-7, and wherein the heterologous polynucleotide becomes integrated into the genome of T cells of the incubated population;

(d) harvesting cells of the incubated population of transformed T cells, wherein the harvesting is carried out at a time between 48 and 120 hours, inclusive, after the exposing to the stimulatory reagent is initiated; and (e) formulating the harvested cells in a composition for cryopreservation, wherein the formulated composition is suitable for use as a cell therapy for administration to a subject.

2. The method of claim 1, wherein the incubating is carried out for up to 96 hours.

3. The method of claim 1, wherein the incubating is carried out for between 60 hours to 120 hours.

4. The method of claim 1, wherein the incubating is carried out under static conditions.

5. The method of claim 1, wherein one or both of the exposing in (a) and the introducing in (b) is carried out in the presence of one or more recombinant cytokines, wherein the one or more recombinant cytokines comprise recombinant IL-2, recombinant IL-7, and recombinant IL-15.

6. The method of claim 5, wherein one or both of the exposing in (a) and the introducing in (b) is carried out in the presence of recombinant IL-2, recombinant IL-7 and recombinant IL-15.

7. The method of claim 1, wherein one or both of the exposing in (a) and the introducing in (b) is carried out in a serum-free medium.

8. The method of claim 7, wherein the serum-free medium in which one or both of the exposing in (a) and the introducing in (b) is carried out comprises recombinant IL-2, recombinant IL-7, recombinant IL-15, or any combination thereof.

9. The method of claim 7, wherein the serum-free medium in which one or both of the exposing in (a) and the introducing in (b) is carried out comprises recombinant IL-2, recombinant IL-7 and recombinant IL-15.

10. The method of claim 9, wherein the serum-free medium in which one or both of the exposing in (a) and the introducing in (b) is carried out comprises (a) 50 IU/mL to 200 IU/mL recombinant IL-2, (b) 500 IU/mL to 1000 IU/mL recombinant IL-7, and (c) 50 IU/mL to 200 IU/mL recombinant IL-15.

11. The method of claim 1, wherein the input composition comprises at least about $300\times10^6$ viable primary T cells.

12. The method of claim 11, wherein the incubating is carried out for up to 96 hours.

13. The method of claim 11, wherein the incubating is carried out for between 60 hours to 120 hours.

14. The method of claim 1, wherein at least about 80% of the cells in the input composition are CD3+ T cells or are CD4+ T cells and CD8+ T cells.

15. The method of claim 1, wherein the input composition comprises a ratio of between 1.5:1 and 2.0:1 CD4+ to CD8+ T cells.

16. The method of claim 1, wherein the input composition comprises a ratio of about 1:1 CD4+ to CD8+ T cells.

17. The method of claim 1, wherein the method comprises prior to the exposing to the stimulatory reagent, enriching CD3+ T cells or CD4+ T cells and CD8+ T cells from a biological sample to produce the input composition and wherein the biological sample:

comprises primary T cells obtained from a subject;

comprises a whole blood sample, a buffy coat sample, a peripheral blood mononuclear cells (PBMC) sample, an unfractionated T cell sample, a lymphocyte sample, a white blood cell sample, an apheresis product, or a leukapheresis product; or is an apheresis or leukapheresis product that has been previously cryofrozen prior to the enriching.

18. The method of claim 1, wherein the incubated population of transformed T cells is harvested as an output composition in one or more containers, wherein the output composition comprises at least about $5\times10^6$ total cells.

19. The method of claim 1, wherein the introducing is carried out in the presence of a transduction adjuvant.

20. The method of claim 1, wherein the recombinant protein comprises a TCR or antigen-binding fragment thereof.

21. The method of claim 1, wherein the recombinant protein is a chimeric antigen receptor (CAR).

22. The method of claim 1, comprising during or subsequent to the incubation adding an agent to reduce the binding between the stimulatory reagent and the T cells.

23. The method of claim 1, wherein the bead is a magnetic bead particle.

24. The method of claim 23, comprising during or subsequent to the incubation adding an agent to reduce the binding between the stimulatory reagent and the T cells.

25. The method of claim 1, wherein:

the stimulatory reagent comprises a magnetic bead bound to the anti-CD3 antibody or antigen-binding fragment thereof and the anti-CD28 antibody or antigen-binding fragment thereof;

the exposing and the introducing are carried out in the presence of serum free medium that includes recombinant IL-2, IL-7, and IL-15;

the incubating is carried out for between 24 hours and 96 hours; and the harvesting is carried out at a time between 72 and 120 hours, inclusive, after the exposing to the stimulatory reagent is initiated.

26. The method of claim 1, the method further comprising adding a substance to the cells either subsequent to or during at least a portion of the incubating, wherein the substance terminates or lessens stimulation of the T cells by the stimulatory reagent.

27. The method of claim 1, wherein the serum-free medium comprises 0.5 mM to 5 mM of a dipeptide form of L-glutamine and 0.5 mM to 5 mM L-glutamine.

28. A method for producing a composition comprising engineered T cells, the method comprising:

(a) stimulating a cell composition comprising CD4+ and CD8+ T cells obtained from a biological sample from a human subject, by exposing the cell composition to an anti-CD3 antibody or an antigen-binding fragment thereof and an anti-CD28 antibody or an antigen-binding fragment thereof, each bound to a bead, in a first serum-free medium, wherein the first serum-free medium comprises: (1) recombinant interleukin-2 (IL-2) at a concentration of 50 IU/mL to 200 IU/mL, (2) recombinant IL-7 at a concentration of 500 IU/mL to 1000 IU/mL; (3) recombinant IL-15 at a concentration of 50 IU/mL to 200 IU/mL, (4) a dipeptide form of L-glutamine at a concentration of 0.5 mM to 5 mM, and (5) L-glutamine at a concentration of 0.5 mM to 5 mM, thereby producing a population of stimulated T cells;

(b) introducing a lentiviral vector into the T cells of the population of stimulated T cells and incubating the T cells, wherein:

(i) the introducing and incubating is in a second serum-free medium that comprises: (1) recombinant IL-2 at a concentration of 50 IU/mL to 200 IU/mL, (2) recombinant IL-7 at a concentration of 500 IU/mL to 1000 IU/mL; (3) recombinant IL-15 at a concentration of 50 IU/mL to 200 IU/mL, (4) a dipeptide form of L-glutamine at a concentration of 0.5 mM to 5 mM, and (5) L-glutamine at a concentration of 0.5 mM to 5 mM, (ii) the lentiviral vector comprises a heterologous polynucleotide encoding a chimeric antigen receptor (CAR), and (iii) the heterologous polynucleotide becomes integrated into the genome of T cells of the population;

(c) harvesting the T cells from step (b) between 48 hours and 120 hours, inclusive, after initiation of the stimulation in step (a); and (d) formulating the harvested cells in a composition for cryopreservation, wherein the formulated composition is suitable for use as a cell therapy for administration to a subject.

29. The method of claim 28, wherein the first serum-free medium and the second serum-free medium each comprise:

(a) recombinant IL-2 at a concentration of 100 IU/mL to 200 IU/mL;

(b) recombinant IL-7 at a concentration of 500 IU/mL to 750 IU/mL; and (c) recombinant IL-15 at a concentration of 100 IU/mL to 200 IU/mL.

30. The method of claim 28, wherein the total duration of the incubation is between 24 hours and 72 hours, inclusive.

31. The method of claim 28, wherein the harvesting is carried out at a time between 72 and 120 hours, inclusive, after the exposing to the stimulatory reagent is initiated.

32. The method of claim 28, wherein the biological sample is an apheresis product or a leukapheresis product.

33. The method of claim 28, wherein the cell composition comprising CD4+ and CD8+ T cells comprises at least about $300\times10^6$ viable primary T cells.

34. The method of claim 28, wherein at least about 80% of the cells in the cell composition comprising CD4+ and CD8+ T cells are CD4+ T cells or CD8+ T cells.

* * * * *